(12) United States Patent
Booker et al.

(10) Patent No.: US 7,928,140 B2
(45) Date of Patent: Apr. 19, 2011

(54) BENZOTHIAZOLE PI3 KINASE MODULATORS FOR CANCER TREATMENT

(75) Inventors: Shon Booker, Thousand Oaks, CA (US); Noel D'Angelo, Thousand Oaks, CA (US); Derin C. D'Amico, Newbury Park, CA (US); Tae-Seong Kim, Thousand Oaks, CA (US); Longbin Liu, Thousand Oaks, CA (US); Kristin Meagher, Thousand Oaks, CA (US); Mark H. Norman, Thousand Oaks, CA (US); Kathleen Panter, Cambridge, MA (US); Laurie B. Schenkel, Boston, MA (US); Adrian L. Smith, Simi Valley, CA (US); Nuria A. Tamayo, Newbury Park, CA (US); Douglas A. Whittington, Waltham, MA (US); Ning Xi, Thousand Oaks, CA (US); Kevin Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 19 days.

(21) Appl. No.: 12/221,416

(22) Filed: Aug. 1, 2008

(65) Prior Publication Data
US 2009/0054405 A1 Feb. 26, 2009

Related U.S. Application Data

(60) Provisional application No. 60/963,263, filed on Aug. 2, 2007.

(51) Int. Cl.
*A61K 31/38* (2006.01)
(52) U.S. Cl. ..... 514/514; 544/333; 544/405; 546/281.1; 548/143; 548/161; 548/346.1
(58) Field of Classification Search .................. 514/443; 544/333, 405; 546/281.1; 548/143, 161, 548/346.1
See application file for complete search history.

(56) References Cited

U.S. PATENT DOCUMENTS
| 3,725,428 A | 4/1973 | Janiak |
| 2003/0153568 A1 | 8/2003 | Cusack |

FOREIGN PATENT DOCUMENTS
| WO | WO 2004/007491 A1 | 1/2004 |
| WO | WO 2004/010995 A1 | 2/2004 |
| WO | WO 2004/098494 A2 | 11/2004 |
| WO | WO 2005/003127 A1 | 1/2005 |
| WO | WO 2005/009389 A2 | 2/2005 |
| WO | WO 2005/070920 A1 | 8/2005 |
| WO | WO 2006/039718 A2 | 4/2006 |
| WO | WO 2006/040318 A2 | 4/2006 |
| WO | WO 2006/044732 A2 | 4/2006 |
| WO | WO 2006/051270 A1 | 5/2006 |
| WO | WO 2007/016392 A2 | 2/2007 |
| WO | WO 2008/133192 A1 | 4/2007 |
| WO | WO 2007/076092 A2 | 7/2007 |
| WO | WO 2007/095588 A1 | 8/2007 |
| WO | WO 2007/129044 A1 | 11/2007 |
| WO | WO 2007/129052 A1 | 11/2007 |
| WO | WO 2007/134828 A1 | 11/2007 |
| WO | WO 2007/135398 A1 | 11/2007 |
| WO | WO 2008/003856 A1 | 1/2008 |
| WO | WO 2008/012326 A1 | 1/2008 |
| WO | WO 2008/016131 A1 | 2/2008 |
| WO | WO 2008/025821 A1 | 3/2008 |
| WO | WO 2008/037477 A1 | 4/2008 |
| WO | WO 2008/052733 A1 | 5/2008 |
| WO | WO 2008/116129 A2 | 9/2008 |
| WO | WO 2008/138834 A1 | 11/2008 |
| WO | WO 2008/138889 A2 | 11/2008 |
| WO | WO 2008/144463 A1 | 11/2008 |
| WO | WO 2008/144464 A1 | 11/2008 |
| WO | WO 2008/144465 A1 | 11/2008 |
| WO | WO 2008/150827 A1 | 12/2008 |
| WO | WO 2008/152387 A2 | 12/2008 |
| WO | WO 2008/157191 A2 | 12/2008 |
| WO | WO 2009/000832 A2 | 12/2008 |
| WO | WO 2009/010530 A1 | 1/2009 |
| WO | WO 2009/055418 A1 | 4/2009 |
| WO | WO 2009/129211 A1 | 10/2009 |
| WO | WO 2009/133127 A1 | 11/2009 |

OTHER PUBLICATIONS

Altland H.W., et al., A Facile Synthesis of 2-Aminothiazolo[5,4-b]- and 2-Aminothiazolo [4,5-c] pyridines, Journal of Heterocyclic Chemistry, Jan. 1, 1977, pp. 129-134, vol. 14, Heterocorporation. Provo, US.

P. Garay et al., Synthese et etude des activites antiparasitaires et molliscicides de derives polycycliques de la pyridine, European Journal Medicinal Chemistry, 1978, pp. 171-175, vol. 13, No. 2.

P. Garay et al., Synthese et etude des activites antiparasitaires et molliscicides de derives polycycliques de la pyridine, European Journal Medicinal Chemistry, 1978, pp. 171-175, vol. 13, No. 2. (English_Translation).

(Continued)

*Primary Examiner* — James O Wilson
*Assistant Examiner* — Douglas M Willis
(74) *Attorney, Agent, or Firm* — Todd M. Crissey

(57) ABSTRACT

The present invention comprises a new class of compounds capable of modulating the activity of PI3 kinase and, accordingly, useful for treatment of PI3 kinase mediated diseases, including melanomas, carcinomas and other cancer-related conditions. The compounds have a general Formula I

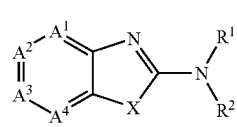

wherein each of $A^1$, $A^2$, $A^3$, $A^4$, X, $R^1$ and $R^2$ are defined herein. The invention further comprises pharmaceutical compositions, methods for treatment of PI3 kinase mediated diseases, and intermediates and processes useful for the preparation of compounds of the invention.

17 Claims, No Drawings

OTHER PUBLICATIONS

Patil V.H., et al., Synthesis of some sulphanilamido-benzothiazolyl thiazole derivatives as antibacterial agents, Journal of the Indian Chemical Society, Dec. 1, 1979, pp. 1243-1245, vol. 56, No. 12, The Indian Chemical Society, Calcutta. IN.

Patil V.H., et al., Synthesis of 2-arylamino-4- not 2'-(P-Acetamido-Benzenesulphonamido)-6'-Benzothiazolyl 3/4 Thiazoles & 2-Arylamino-4-(2'-Sulphanilamido-6'-Benzothiazolyl)Thiazoles, Indian Journal of Chemistry, Section B: Organic, Incl. Medicinal, Jan. 1, 1979, pp. 519-521, vol. 17B, No. 5, Publications & Informations Directorate, New Delhi, IN.

Cosulich et al., New Thiazole Pyridine Sulfonamides as Orally Bioavailable Highly Potent PI3 Kinase Inhibitors, Cancer and Infection Research Area, AstraZeneca, Alderley Park, Cheshire, UK. Keystone Conference Presentation, New Mexico, Feb. 15-20, 2007.

Camps et al., Blockade of PI3K gamma Suppresses Joint Inflammation and Damage in Mouse Models of Rheumatoid Arthritis, Nature Medicine, Sep. 2005, pp. 936-943, vol. 11, No. 9.

Hayakawa, et al., Synthesis and Biological Evaluation of Imidazo[1,2-alpha]pyridine derivatives as novel PI3 kinase p110alpha Inhibitors, Bioorganic and Medical Chemistry, 2007, pp. 403-412, vol. 15.

Knight, et al., A Pharmacological Map of the PI3-K Family Defines a Role for p110alpha in Insulin Signaling, Cell, May 19, 2006, pp. 733-747, vol. 125.

Knight, et al., Supplemental Data—A Pharmacological Map of the PI3-K Family Defines a Role for p110alpha in Insulin Signaling, Cell, May 19, 2006, pp. 733-747, vol. 125.

BENZOTHIAZOLE PI3 KINASE MODULATORS FOR CANCER TREATMENT

This application claims the benefit of U.S. Provisional Application No. 60/963,263, filed Aug. 2, 2007, which is hereby incorporated by reference.

FIELD OF THE INVENTION

The invention generally relates to the field of pharmaceutical agents and, specifically to compounds, intermediates and pharmaceutical compositions capable of modulating Phosphoinositide 3-kinase (PI3K) activity and useful for treating PI3K mediated diseases, such as cancer.

BACKGROUND OF THE INVENTION

PI3 Kinases are a family of lipid kinases that have been found to play a key role in the regulation of many cellular processes including proliferation, survival, carbohydrate metabolism, and motility. Recent evidence suggests that some members of the PI3K family have an important role in cancer. For example, emerging evidence for functional specialization of PI3K isoforms has suggested that isoform selective inhibitors may prove to be useful anticancer drugs. (*Endocrine-Related Cancer*, Stein, R. C., Soc. For Endocrinology, (2001) 8, 237-248.)

PI3Ks are considered to have an important role in intracellular signal transduction in health and disease. In particular, the PI3Ks generate and convey signals that have an important role in cancer. PI3Ks are ubiquitously expressed, are activated by a high proportion of cell surface receptors, especially those linked to tyrosine kinases, and influence a variety of cellular functions and events. Although some PI3K activity is likely to be essential for cellular health, the PI3Ks are a rather diverse group of enzymes for which there is increasing evidence of functional specialization. This opens up the possibility of developing isoform-selective inhibitors that could be used to treat cancer with limited toxicity.

The primary enzymatic activity of the PI3K is the phosphorylation of inositol lipids (phosphoinositides) on the 3-position of the inositol headgroup. PI3 kinases catalyse the addition of phosphate to the 3'-OH position of the inositol ring of inositol lipids generating phosphatidyl inositol monophosphate, phosphatidyl inositol diphosphate and phosphatidyl inositol triphosphate (Whitman et al, 1988, Stephens et al 1989 and 1991).

There are a total of eight mammalian PI3Ks, which have been divided into three main classes on the basis of sequence homology, in vitro substrate preference and method of activation and regulation. Enzymes of a first class have a broad substrate specificity and phosphorylate PtdIns, PtdIns(4)P and PtdIns(4,5)P$_2$. Class I PI3Ks include mammalian p110α, p110β, p110δ and p110γ. (Hiles et al, 1192; Hu et al, 1993; Stephens et al, 1994; Stoyanov et al, 1995). Different members of the PI3K family generate different lipid products. To date, four 3-phosphorylated inositol lipids have been identified in vivo. These lipids are bound by proteins that contain the appropriate lipid recognition module and that act to transmit the PI3K signal onwards.

The most familiar form of PI3K is the PI3Kα heterodimer, which consists of a 110 kDa catalytic subunit and an 85 kDa regulatory/adapter subunit, p85α. (*Endocrine-Related Cancer* (2001) 8, 237-248.)

The catalytic subunit contains a kinase domain that uses ATP to phosphorylate PtdIns, PtdIns4P and PtdIns (4,5)P$_2$. The major product of class I PI3Ks is PtdIns(3,4,5)P$_3$, or PIP3, which is required for translocation of protein kinase B (PKB, AKT1) to the cell membrane where it is phosphorylated and activated by upstream kinases. PTEN, a tumor suppressor, dephosphorylates PIP3. The effect of PTEN on cell death is mediated through the PI3K/AKT1 pathway.

PI3Kα has been implicated in the control of cytoskeletal reorganization, apoptosis, vesicular trafficking and proliferation and differentiation processes. Increased copy number and expression of the p110alpha gene (PIK3CA) is associated with a number of malignancies such as ovarian cancer (Campbell et al., Cancer Res 2004, 64, 7678-7681; Levine et al., Clin Cancer Res 2005, 11, 2875-2878; Wang et al., Hum Mutat 2005, 25, 322; Lee et al., Gynecol Oncol 2005, 97, 26-34), cervical cancer, breast cancer (Bachman, et al. Cancer Biol Ther 2004, 3, 112-115; Levine, et al., supra; Li et al., Breast Cancer Res Treat 2006, 96, 91-95; Saal et al., Cancer Res 2005, 65, 2554-2559; Samuels and Velculescu, Cell Cycle 2004, 3, 1221-1224), colorectal cancer (Samuels, et al. Science 2004, 304, 554; Velho et al. Eur J Cancer 2005, 41, 1649-1654), endometrial cancer (Oda et al. Cancer Res. 2005, 65, 10669-10673), gastric carcinomas (Byun et al., Int J Cancer 2003, 104, 318-327; Li et al., supra; Velho et al., supra; Lee et al., Oncogene 2005, 24, 1477-1480), hepatocellular carcinoma (Lee et al., id.), small and non-small cell lung cancer (Tang et al., Lung Cancer 2006, 51, 181-191; Massion et al., Am J Respir Crit. Care Med 2004, 17 ft 1088-1094), thyroid carcinoma (Wu et al., J Clin Endocrinol Metab 2005, 90, 46884693), acute myelogenous leukemia (AML) (Sujobert et al., Blood 1997, 106, 1063-1066), chronic myelogenous leukemia (CML) (Hickey and Cotter J Biol Chem 2006, 281, 2441-2450), and glioblastomas (Hartmann et al. Acta Neuropathol (Berl) 2005, 109, 639-642; Samuels et al., supra). In view of the important role of PI3Kα in biological processes and disease states, inhibitors of this protein kinase are desirable.

BRIEF DESCRIPTION OF THE INVENTION

The present invention provides a new class of nitrogen-containing bicyclic heteroaryl compounds useful for modulating the activity of PI3Kα and, thereby, useful for treating PI3Kα-mediated diseases and conditions. Particularly, the compounds are useful for treating carcinomas, leukemias, glioblastomas and other forms of cancer. The compounds provided by the invention, including stereoisomers, tautomers, solvates, pharmaceutically acceptable salts, derivatives or prodrugs thereof.

In one embodiment, the compounds of the present invention are defined by general Formula I

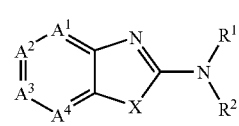

I wherein each of the variables are as defined and described below.

In another embodiment, the invention provides compounds defined generally by Formula II

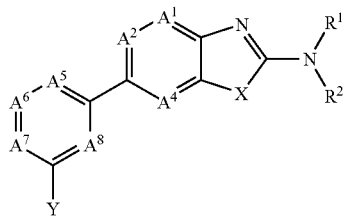

II wherein each of the variables are as defined and described below.

In another embodiment, the invention provides compounds defined generally by Formula III

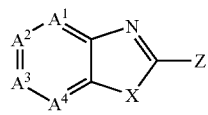

III wherein each of the variables are as defined and described below.

In another embodiment, the invention provides compounds defined generally by Formula IV

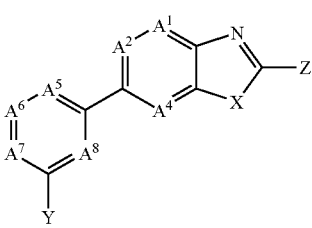

IV wherein each of the variables are as defined and described below.

In another embodiment, the invention provides compounds defined generally by Formula V

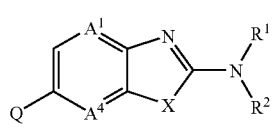

V wherein each of the variables are as defined and described below.

In another embodiment, the invention provides compounds defined generally by Formula VI

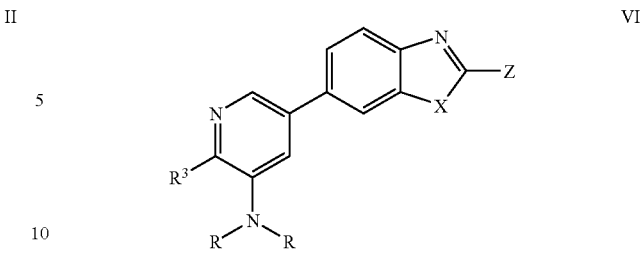

VI wherein each of the variables are as defined and described below.

The invention also provides procedures for making compounds of Formulas I, II, III, IV, V, and VI, as well as intermediates useful in such procedures.

The compounds provided by the invention are capable of modulating PI3K activity, and more particularly of modulating PI3Kα activity. To this end, the invention further provides for the use of these compounds for therapeutic, prophylactic, acute and/or chronic treatment of PI3Kα-mediated diseases, such as those described herein. For example, the invention provides the use and preparation of a pharmaceutical composition, also referred to herein as a medicament, containing one or more of the compounds, useful to attenuate, alleviate, or treat disorders through inhibition of PI3Kα. These compounds are further useful in the treatment of a variety of associated cancerous diseases and/or conditions.

DETAILED DESCRIPTION OF THE INVENTION

The invention provides compounds, optionally including one or two nitrogen atoms in the fused benzene ring, which are useful for treating cell proliferation and cell survival related disorders, including cancer. In one embodiment of the invention, the compounds, including stereoisomers, tautomers, solvates or pharmaceutically acceptable salts thereof, are defined by general Formula I:

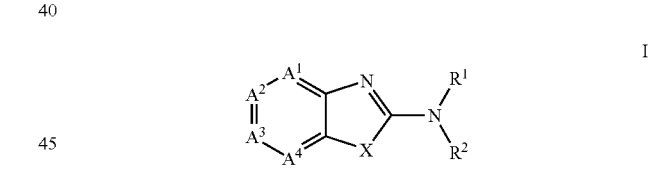

I wherein
$A^1$ is $CR^3$ or N;
$A^2$ is $CR^4$ or N;
$A^3$ is $CR^5$ or N; and
$A^4$ is $CR^6$ or N;
provided that no more than two of $A^1, A^2, A^3$ and $A^4$ are N;
X is O or S;
$R^1$ is H, $C_{1-6}$-alkyl, $C_{2-6}$-alkenyl, $C_{2-6}$-alkynyl or $C_{3-6}$-cycloalkyl;
$R^2$ is $C_{1-6}$-alkyl-$R^7$, $C_{2-6}$-alkenyl-$R^7$, $C_{2-6}$-alkynyl-$R^7$, $C_{3-6}$-cycloalkyl-$R^7$, $C(O)R^7$, $C(=O)NHR^7$, $COOR^7$, $S(O)_2R^7$ or a partially or fully saturated or fully unsaturated 5- or 6-membered monocyclic ring formed of carbon atoms and including 1-3 heteroatoms selected from N, O and S, wherein the, $C_{1-6}$-alkyl-$R^7$, $C_{2-6}$-alkenyl-$R^7$, $C_{2-6}$-alkynyl-$R^7$ and $C_{3-6}$-cycloalkyl is optionally substituted with 1-5 substituents of $R^9$;
$R^3$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$- alkyl, —N-di-$C_{1-8}$-alkyl, —$C_{1-6}$-alkyl-NH—$C_{1-6}$-alkyl, —$C_{1-4}$-alkyl-OH, $C_{1-6}$-alkyl-NH$_2$, $C_{1-6}$-alkyl-N-di-$C_{1-8}$-alkyl, $C_{2-8}$-alkenyl, $C_{2-8}$-alkynyl or $C_{3-6}$-cycloalkyl;

$R^4$ is H, halo, haloalkyl, OH, NH$_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl or a partially or fully saturated 5-membered or a partially or fully saturated or unsaturated 6-membered monocyclic ring or a partially or fully saturated or unsaturated 8-10-membered bicyclic ring, said ring(s) formed of carbon atoms optionally including 1-3 heteroatoms per ring selected from N, O and S, wherein each of said $C_{1-6}$-alkyl, $C_{2-8}$-alkenyl, $C_{2-8}$-alkynyl and ring is optionally substituted independently with 1-5 substituents of $R^7$, $R^8$ or $R^9$;

$R^5$ is H, halo, haloalkyl, OH, NH$_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl or a partially or fully saturated 5-membered or a partially or fully saturated or unsaturated 6-membered monocyclic ring or a partially or fully saturated or unsaturated 8-10-membered bicyclic ring, said ring(s) formed of carbon atoms optionally including 1-3 heteroatoms per ring selected from N, O and S, wherein each of said $C_{1-6}$-alkyl, $C_{2-8}$-alkenyl, $C_{2-8}$-alkynyl and ring is optionally substituted independently with 1-5 substituents of $R^7$, $R^8$ or $R^9$; provided that both of $R^4$ and $R^5$ are not each, independently, a partially or fully saturated 5-membered or a partially or fully saturated or unsaturated 6-membered monocyclic ring or a partially or fully saturated or unsaturated, 8-10-membered bicyclic ring formed of carbon atoms optionally including 1-3 heteroatoms;

$R^6$ is H, halo, haloalkyl, OH, NH$_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, —$C_{1-4}$-alkyl-OH, $C_{1-6}$-alkyl-NH$_2$, $C_{1-6}$-alkyl-N-di-$C_{1-8}$-alkyl, $C_{2-8}$-alkenyl, $C_{2-8}$-alkynyl or $C_{3-6}$-cycloalkyl;

each $R^7$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, NR$^8$R$^9$, NR$^9$R$^9$, OR$^8$, SR$^8$, OR$^9$, SR$^9$, C(O)R$^8$, OC(O)R$^9$, COOR$^9$, C(O)R$^9$, C(O)NR$^8$R$^9$, NR$^9$C(O)R$^9$, C(O)NR$^9$R$^9$, NR$^9$C(O)NR$^9$R$^9$, S(O)$_2$R$^8$, S(O)$_2$R$^9$, S(O)$_2$NR$^8$R$^9$, S(O)$_2$NR$^9$R$^9$, NR$^9$S(O)$_2$NR$^9$R$^9$, NR$^9$S(O)$_2$R$^8$ or NR$^9$S(O)$_2$R$^9$, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of R$^8$, R$^9$, NR$^8$R$^9$, NR$^9$R$^9$, OR$^8$, SR$^8$, OR$^9$, SR$^9$, C(O)R$^8$, OC(O)R$^9$, COOR$^9$, C(O)R$^9$, C(O)NR$^9$R$^9$, NR$^9$C(O)R$^9$, C(O)NR$^9$R$^9$, NR$^9$C(O)NR$^9$R$^9$, S(O)$_2$R$^8$, S(O)$_2$R$^9$, S(O)$_2$NR$^9$R$^9$, NR$^9$S(O)$_2$NR$^9$R$^9$, NR$^9$S(O)$_2$R$^8$ or NR$^9$S(O)$_2$R$^9$;

$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of R$^9$;

each R$^9$, independently, is H, F, Cl, Br, I, haloalkyl, CN, OH, NH$_2$, $C_{1-8}$-alkyl, —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds of Formula I include compounds wherein $A^2$ is CR$^4$ and R$^4$ is a ring selected from phenyl, naphthyl, pyridyl, pyrimidyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, benzoxazolyl, benzisoxazolyl, benzothiazolyl, benzoisothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of R$^7$, R$^8$ or R$^9$, in conjunction with any of the above or below embodiments.

In another embodiment, the compounds of Formula I include compounds wherein $A^2$ is CR$^4$ and R$^4$ is a phenyl, pyridyl, pyrimidyl, triazinyl, pyridazinyl, thiophenyl, furyl, pyrazolyl, oxazolyl, isoxazolyl, thiazolyl, isothiazolyl, oxadiazolyl or imidazolyl, each of which is substituted independently with 1-5 substituents of R$^7$, R$^8$ or R$^9$, in conjunction with any of the above or below embodiments.

In another embodiment, the compounds of Formula I include compounds wherein $A^3$ is CR$^5$, in conjunction with any of the above or below embodiments.

In another embodiment, the compounds of Formula I include compounds wherein $A^3$ is CR$^5$ and R$^5$ is a ring selected from phenyl, naphthyl, pyridyl, pyrimidyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, benzoxazolyl, benzisoxazolyl, benzothiazolyl, benzoisothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of R$^7$, R$^8$ or R$^9$, in conjunction with any of the above or below embodiments.

In another embodiment, the compounds of Formula I include compounds wherein $A^1$ is CR$^3$, $A^2$ is CR$^4$, $A^3$ is CR$^5$, $A^4$ is CH, X is S, $R^1$ is H, $R^1$ is $C_{1-6}$-alkyl- optionally substituted with 1-5 substituents of R$^9$, and R$^5$ is a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, optionally substituted independently with 1-5 substituents of R$^7$, R$^8$ or R$^9$, in conjunction with any of the above or below embodiments.

In another embodiment, the compounds of Formula I include compounds wherein $A^1$ is CR$^3$, $A^2$ is CR$^4$, $A^3$ is CR$^5$, $A^4$ is CH, X is S, $R^1$ is H, $R^2$ is $C_{1-6}$-alkyl$^-$ optionally substituted with 1-5 substituents of R$^9$, and R$^5$ is a ring selected from phenyl, naphthyl, pyridyl, pyrimidyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, benzoxazolyl, benzisoxazolyl, benzothiazolyl, benzoisothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, optionally substituted independently with 1-5 substituents of $R^7$, $R^8$ or $R^9$, in conjunction with any of the above or below embodiments.

In another embodiment, the compounds of Formula I include compounds wherein $A^3$ is $CR^5$ and $R^5$ is a phenyl, pyridyl, pyrimidyl, triazinyl, pyridazinyl, thiophenyl, furyl, pyrazolyl, oxazolyl, isoxazolyl, thiazolyl, isothiazolyl, oxadiazolyl or imidazolyl, each of which is substituted independently with 1-5 substituents of $R^7$, $R^8$ or $R^9$, in conjunction with any of the above or below embodiments.

In another embodiment, the compounds of Formula I include compounds wherein $A^2$ is $CR^4$ and $R^4$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl; and $A^3$ is $CR^5$ and $R^5$ is a partially or fully saturated 5-membered or a partially or fully saturated or unsaturated 6-membered monocyclic ring formed of carbon atoms optionally including 1-3 heteroatoms, wherein said ring is optionally substituted independently with 1-5 substituents of $R^9$, in conjunction with any of the above or below embodiments.

In another embodiment, the compounds of Formula I include compounds wherein $A^1$ is $CR^3$ and $R^3$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl;

$A^2$ is $CR^4$ and $R^4$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl;

$A^3$ is $CR^5$ and $R^5$ is a ring selected from phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, benzoxazolyl, benzisoxazolyl, benzothiazolyl, benzoisothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$, $R^8$ and $R^9$; and $A^4$ is $CR^6$ and $R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl, in conjunction with any of the above or below embodiments.

In another embodiment, the compounds or a stereoisomer, tautomer or pharmaceutically acceptable salt thereof, are defined by a general Formula II

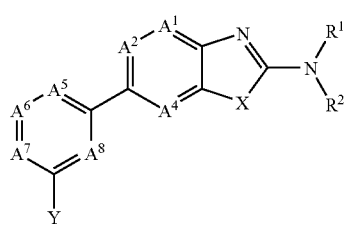

II wherein
$A^1$ is $CR^3$ or N;
$A^2$ is $CR^4$ or N; and
$A^4$ is $CR^6$ or N; provided that no more than two of $A^1$, $A^2$ and $A^4$ is N;
$A^5$ is $CR^3$ or N;
$A^6$ is $CR^3$ or N;
$A^7$ is $CR^3$ or N; and
$A^8$ is $CR^3$ or N; provided that no more than three of $A^5$, $A^6$, $A^7$, and $A^8$ is N;
X is O or S;
Y is $R^7$, $R^8$ or $R^9$;
$R^1$ is H, $C_{1-6}$-alkyl, $C_{2-6}$-alkenyl, $C_{2-6}$-alkynyl or $C_{3-6}$-cycloalkyl;
$R^2$ is $C_{1-6}$-alkyl-$R^7$, $C_{2-6}$-alkenyl-$R^7$, $C_{2-6}$-alkynyl-$R^7$, $C_{3-6}$-cycloalkyl-$R^7$, $C(O)R^7$, $C(=O)NHR^7$, $COOR^7$, $S(O)_2R^7$ or a partially or fully saturated or fully unsaturated 5- or 6-membered monocyclic ring formed of carbon atoms and including 1-3 heteroatoms selected from N, O and S, wherein the $C_{1-6}$-alkyl-$R^7$, $C_{2-6}$-alkenyl-$R^7$, $C_{2-6}$-alkynyl-$R^7$ and $C_{3-6}$-cycloalkyl is optionally substituted with 1-5 substituents of $R^9$;

$R^3$ is H, halo, haloalkyl, OH, $NH_2$, $C_{1-4}$-alkyl, —O—$C_{1-4}$-alkyl, —O—$C_{1-4}$-haloalkyl, —S—$C_{1-4}$-alkyl, —NH—$C_{1-4}$-alkyl, —N-di-$C_{1-4}$-alkyl, —$C_{1-4}$-alkyl-OH or —$C_{1-6}$-alkyl-$NH_2$;

$R^4$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, wherein each of said $C_{1-6}$-alkyl, $C_{2-8}$-alkenyl, $C_{2-8}$-alkynyl is optionally substituted independently with 1-5 substituents of $R^9$;

$R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl or $C_{3-6}$-cycloalkyl;

each $R^7$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $NR^9R^9$, $OR^5$, $SR^8$, $OR^9$, $SR^9$, $C(O)R^5$, $OC(O)R^9$, $COOR^9$, $C(O)R^9$, $C(O)NR^5R^9$, $NR^9C(O)R^9$, $C(O)NR^9R^9$, $NR^9C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^5$ or $NR^9S(O)_2R^9$, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$;

each $R^9$, independently, is H, F, Cl, Br, I, haloalkyl, CN, OH, $NH_2$, $C_{1-8}$-alkyl, —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds of Formula II include compounds wherein $A^5$ is N, in conjunction with any of the above or below embodiments.

In another embodiment, the compounds of Formula II include compounds wherein $A^5$ is $CR^3$, in conjunction with any of the above or below embodiments.

In another embodiment, the compounds of Formula II include compounds wherein $A^6$ is N, in conjunction with any of the above or below embodiments.

In another embodiment, the compounds of Formula II include compounds wherein $A^6$ is $CR^3$, in conjunction with any of the above or below embodiments.

In another embodiment, the compounds of Formula II include compounds wherein $A^7$ is N, in conjunction with any of the above or below embodiments.

In another embodiment, the compounds of Formula II include compounds wherein $A^7$ is $CR^3$, in conjunction with any of the above or below embodiments.

In another embodiment, the compounds of Formula II include compounds wherein $A^8$ is N, in conjunction with any of the above or below embodiments.

In another embodiment, the compounds of Formula II include compounds wherein $A^8$ is $CR^3$, in conjunction with any of the above or below embodiments.

In another embodiment, the compounds of Formula II include compounds wherein each of $A^7$ and $A^8$ independently, is N, in conjunction with any of the above or below embodiments.

In another embodiment, the compounds of Formula II include compounds wherein $A^5$ is $CR^3$, $A^6$ is $CR^3$, $A^7$ is $CR^3$ and $A^8$ is $CR^3$, in conjunction with any of the above or below embodiments.

In another embodiment, the compounds of Formula II include compounds wherein one of $A^5$, $A^6$, $A^7$ and $A^8$ is N, in conjunction with any of the above or below embodiments.

In another embodiment, the compounds of Formula II include compounds wherein two of $A^5$, $A^6$, $A^7$ and $A^8$ is N, in conjunction with any of the above or below embodiments.

In another embodiment, the compounds of Formula II include compounds wherein $A^5$ is $CR^3$, $A^6$ is $CR^3$, $A^7$ is N, and $A^8$ is N, in conjunction with any of the above or below embodiments.

In another embodiment, the compounds of Formula II include compounds wherein $A^5$ is $CR^3$, $A^6$ is $CR^3$, $A^7$ is N, and $A^8$ is N, in conjunction with any of the above or below embodiments.

In another embodiment, the compounds of Formula II include compounds wherein Y is $R^7$, in conjunction with any of the above or below embodiments.

In another embodiment, the compounds of Formula II include compounds wherein Y is $R^7$, in conjunction with any of the above or below embodiments.

In another embodiment, the compounds of Formula II include compounds wherein Y is $R^9$, in conjunction with any of the above or below embodiments.

In another embodiment, the compounds of Formula II include compounds wherein $A^1$ is $CR^3$;
$A^2$ is $CR^4$;
$A^4$ is $CR^6$;
$A^5$ is $CR^3$;
$A^6$ is $CR^3$;
$A^7$ is N;
$A^8$ is N;
X is S; and
Y is $R^7$ or $R^9$;
each $R^3$, independently, is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl or $C_{3-6}$-cycloalkyl;

$R^4$ is H, halo, haloalkyl, $C_{1-8}$-alkyl, —O—$C_{1-8}$-alkyl, —O—$C_{1-8}$-haloalkyl- or —S—$C_{1-6}$-alkyl; and $R^6$ is H, halo, haloalkyl, $C_{1-8}$-alkyl, —O—$C_{1-8}$-alkyl, —O—$C_{1-8}$-haloalkyl- or —S—$C_{1-6}$-alkyl, in conjunction with any of the above or below embodiments.

In another embodiment, the compounds of Formula I or II include compounds wherein $A^1$ is $CR^3$, in conjunction with any of the above or below embodiments.

In another embodiment, the compounds of Formula I or II include compounds wherein $A^1$ is N, in conjunction with any of the above or below embodiments.

In another embodiment, the compounds of Formula I or II include compounds wherein $A^2$ is $CR^4$, in conjunction with any of the above or below embodiments.

In another embodiment, the compounds of Formula I or II include compounds wherein $A^2$ is N, in conjunction with any of the above or below embodiments.

In another embodiment, the compounds of Formula I or II include compounds wherein $A^4$ is $CR^6$, in conjunction with any of the above or below embodiments.

In another embodiment, the compounds of Formula I or II include compounds wherein $A^4$ is N, in conjunction with any of the above or below embodiments.

In another embodiment, the compounds of Formula I or II include compounds wherein $A^1$ is $CR^3$, $A^2$ is $CR^4$, $A^3$ is $CR^5$ and $A^4$ is $CR^6$, in conjunction with any of the above or below embodiments.

In another embodiment, the compounds of Formula I or II include compounds wherein one of $A^1$, $A^2$, $A^3$ and $A^4$ is N, in conjunction with any of the above or below embodiments.

In another embodiment, the compounds of Formula I or II include compounds wherein two of $A^1$, $A^2$, $A^3$ and $A^4$ is N, in conjunction with any of the above or below embodiments.

In another embodiment, the compounds of Formula I or II include compounds wherein $A^1$ is $CR^3$ and $A^4$ is $CR^6$, in conjunction with any of the above or below embodiments.

In another embodiment, the compounds of Formula I or II include compounds wherein $A^1$ is N and $A^4$ is $CR^6$, in conjunction with any of the above or below embodiments.

In another embodiment, the compounds of Formula I or II include compounds wherein X is O, in conjunction with any of the above or below embodiments.

In another embodiment, the compounds of Formula I or II include compounds wherein X is S, in conjunction with any of the above or below embodiments.

In another embodiment, the compounds of Formula I or II include compounds wherein X is S, $A^1$ is $CR^3$, $A^2$ is $CR^4$, $A^3$ is $CR^5$ and $A^4$ is $CR^6$, in conjunction with any of the above or below embodiments.

In another embodiment, the compounds of Formula I or II include compounds wherein $R^1$ is H or $C_{1-6}$-alkyl and $R^2$ is $C_{1-6}$-alkyl-$R^7$, $C(O)R^7$ or $S(O)_2R^7$, in conjunction with any of the above or below embodiments.

In another embodiment, the compounds of Formula I or II include each exemplary compound, and pharmaceutically acceptable salt form thereof, which are described in the examples herein below.

The invention also provides methods of synthesizing compounds of the present invention. For example, in one embodiment, a process for synthesizing a compound of Formula I comprises the step of reacting a compound of Formula A

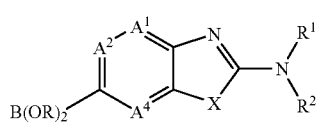

A wherein $B(OR)_2$ is a boronate ester or cyclic boronate as described herein and wherein $A^1, A^2, A^4, X$, and $R^1$ and $R^2$ are as defined herein, with a compound of Formula B

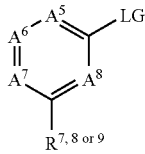

B wherein LG is a leaving group selected from a halogen and $A^5, A^6, A^7, A^8, R^7, R^8$ and $R^9$ are as defined herein, to synthesize the compound of Formulas I or II. The boronic acid in Formula A may be a boronate ester species, such as those shown and/or described herein.

In another embodiment (embodiment 3), the present invention provides compounds of Formula I:

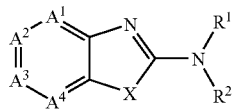

I or a pharmaceutically acceptable salt thereof, wherein
$A^1$ is $CR^3$ or N;
$A^2$ is $CR^4$ or N;
$A^3$ is $CR^5$ or N; and
$A^4$ is $CR^6$ or N;
provided that no more than two of $A^1, A^2, A^3$ and $A^4$ is N;
X is O or S;
$R^1$ is H, $C_{1-6}$-alkyl, $C_{2-6}$-alkenyl, $C_{2-6}$-alkynyl or $C_{3-6}$-cycloalkyl;
$R^2$ is $C_{1-6}$-alkyl-$R^{7a}$, $C_{2-6}$-alkenyl-$R^{7a}$, $C_{2-6}$-alkynyl-$R^{7a}$, $C_{3-6}$-cycloalkyl-$R^{7a}$, $C(O)R^{7a}$, $C(=O)NHR^{7a}$, $COOR^{7a}$, $S(O)_2R^{7a}$ or a partially or fully saturated or fully unsaturated 5- or 6-membered monocyclic ring formed of carbon atoms and including 1-3 heteroatoms selected from N, O and S, wherein the $C_{1-6}$-alkyl-$R^{7a}$, $C_{2-6}$-alkenyl-$R^{7a}$, $C_{2-6}$-alkynyl-$R^{7a}$ and $C_{3-6}$-cycloalkyl-$R^{7a}$ is optionally substituted with 1-5 substituents of $R^9$;
$R^3$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, —$C_{1-4}$-alkyl-OH, $C_{1-6}$-alkyl-$NH_2$, $C_{1-6}$-alkyl-N-di-$C_{1-8}$-alkyl, $C_{2-8}$-alkenyl, $C_{2-8}$-alkynyl or $C_{3-6}$-cycloalkyl;
$R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl or a partially or fully saturated 5-membered or a partially or fully saturated or unsaturated 6-membered monocyclic ring or a partially or fully saturated or unsaturated 8-10-membered bicyclic ring, said ring(s) formed of carbon atoms optionally including 1-3 heteroatoms per ring selected from N, O and S, wherein each of said $C_{1-6}$-alkyl, $C_{2-8}$-alkenyl, $C_{2-8}$-alkynyl and ring is optionally substituted independently with 1-5 substituents of $R^7, R^8$ or $R^9$;
$R^5$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl or a partially or fully saturated 5-membered or a partially or fully saturated or unsaturated 6-membered monocyclic ring or a partially or fully saturated or unsaturated 8-10-membered bicyclic ring, said ring(s) formed of carbon atoms optionally including 1-3 heteroatoms per ring selected from N, O and S, wherein each of said $C_{1-6}$-alkyl, $C_{2-8}$-alkenyl, $C_{2-8}$-alkynyl and ring is optionally substituted independently with 1-5 substituents of $R^7, R^8$ or $R^9$; provided that both of $R^4$ and $R^5$ are not each, independently, a partially or fully saturated 5-membered or a partially or fully saturated or unsaturated 6-membered monocyclic ring or a partially or fully saturated or unsaturated 8-10-membered bicyclic ring formed of carbon atoms optionally including 1-3 heteroatoms;
$R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, —$C_{1-4}$-alkyl-OH, $C_{1-6}$-alkyl-$NH_2$, $C_{1-6}$-alkyl-N-di-$C_{1-8}$-alkyl, $C_{2-8}$-alkenyl, $C_{2-8}$-alkynyl or $C_{3-6}$-cycloalkyl;
each $R^7$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $OR^8$, $SR^8$, $OR^9$, $SR^9$, $C(O)R^8$, $OC(O)R^9$, $COOR^9$, $C(O)R^9$, $C(O)NR^8R^9$, $C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8, R^9, NR^8R^9, NR^9R^9, OR^8, SR^8, OR^9, SR^9, C(O)R^8, OC(O)R^9, COOR^9, C(O)R^9, C(O)NR^9R^9, NR^9C(O)R^9, C(O)NR^9R^9, NR^9C(O)NR^9R^9, S(O)_2R^8, S(O)_2R^9, S(O)_2NR^9R^9, NR^9S(O)_2NR^9R^9, NR^9S(O)_2R^8$ or $NR^9S(O)_2R^9$;
each $R^{7a}$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^8R^9$, $NR^9C(O)R^9$, $C(O)NR^9R^9$, $NR^9C(O) NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8, R^9, NR^8R^9, NR^9R^9, OR^8, SR^8, OR^9, SR^9, C(O)R^8, OC(O)R^9, COOR^9, C(O)R^9, C(O)NR^9R^9, NR^9C(O) R^9, C(O)NR^9R^9, NR^9C(O)NR^9R^9, S(O)_2R^8, S(O)_2R^9, S(O)_2 NR^9R^9, NR^9S(O)_2NR^9R^9, NR^9S(O)_2R^8$ or $NR^9S(O)_2R^9$;
$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$;

each $R^9$, independently, is H, F, Cl, Br, I, haloalkyl, CN, OH, $C_{1-6}$-alkyl, —O—$C_{1-6}$-alkyl, —$C_{1-6}$-alkyl-O—$C_{1-6}$-alkyl, —S—$C_{1-6}$-alkyl, —$C_{1-6}$-alkyl-S—$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-6}$-alkyl, $C_{2-8}$-alkenyl, $C_{2-8}$-alkynyl and ring of said ring system is optionally substituted independently with 1-5 substituents of halo, haloalkyl, CN, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In an embodiment of the compounds of Formula I (embodiment 3), or a pharmaceutically acceptable salt thereof, either separately or in combination with any of the above or below embodiments, X is O.

In an embodiment of the compounds of Formula I (embodiment 3), or a pharmaceutically acceptable salt thereof, either separately or in combination with any of the above or below embodiments, X is S.

In an embodiment of the compounds of Formula I (embodiment 3), or a pharmaceutically acceptable salt thereof, either separately or in combination with any of the above or below embodiments, $A^1$ is $CR^3$, $A^2$ is $CR^4$, $A^3$ is $CR^5$ and $A^4$ is $CR^6$.

In an embodiment of the compounds of Formula I (embodiment 3), or a pharmaceutically acceptable salt thereof, either separately or in combination with any of the above or below embodiments, one of $A^1$, $A^2$, $A^3$ and $A^4$ is N.

In an embodiment of the compounds of Formula I (embodiment 3), or a pharmaceutically acceptable salt thereof, either separately or in combination with any of the above or below embodiments, X is S, $A^1$ is $CR^3$, $A^2$ is $CR^4$, $A^3$ is $CR^5$ and $A^4$ is $CR^6$ In an embodiment of the compounds of Formula I (embodiment 3), or a pharmaceutically acceptable salt thereof, either separately or in combination with any of the above or below embodiments, $A^2$ is $CR^4$ and $R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl; and $A^3$ is $CR^5$ and $R^5$ is a partially or fully saturated 5-membered or a partially or fully saturated or unsaturated 6-membered monocyclic ring formed of carbon atoms optionally including 1-3 heteroatoms, wherein said ring is optionally substituted independently with 1-5 substituents of $R^7$, $R^8$ or $R^9$.

In an embodiment of the compounds of Formula I (embodiment 3), or a pharmaceutically acceptable salt thereof, either separately or in combination with any of the above or below embodiments, $A^1$ is $CR^3$ and $R^3$ is H, halo, haloalkyl, OH, $NO_2$, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl;

$A^2$ is $CR^4$ and $R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl;

$A^3$ is $CR^5$ and $R^5$ is a ring selected from phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, benzoxazolyl, benzisoxazolyl, benzothiazolyl, benzoisothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$, $R^8$ or $R^9$; and $A^4$ is $CR^6$ and $R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl.

In an embodiment of the compounds of Formula I (embodiment 3), or a pharmaceutically acceptable salt thereof, either separately or in combination with any of the above or below embodiments, $R^1$ is H or $C_{1-6}$-alkyl and $R^2$ is $C_{1-6}$-alkyl-$R^{7a}$ $C(O)R^{7a}$ or $S(O)_2R^{7a}$.

In another embodiment (embodiment 4), the present invention provides compounds of Formula II:

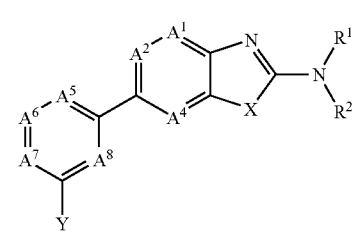

II or a pharmaceutically acceptable salt thereof, wherein $A^1$ is $CR^3$ or N;

$A^2$ is $CR^4$ or N; and $A^4$ is $CR^6$ or N; provided that no more than two of $A^1$, $A^2$ and $A^4$ is N;

$A^5$ is $CR^3$ or N;

$A^6$ is $CR^3$ or N;

$A^7$ is $CR^3$ or N; and $A^8$ is $CR^3$ or N; provided that no more than three of $A^5$, $A^6$, $A^7$, and $A^8$ is N;

X is O or S;

Y is $R^7$, $R^8$ or $R^9$;

$R^1$ is H, $C_{1-6}$-alkyl, $C_{2-6}$-alkenyl, $C_{2-6}$-alkynyl or $C_{3-6}$-cycloalkyl;

$R^2$ is $C_{1-6}$-alkyl-$R^{7a}$, $C_{2-6}$-alkenyl-$R^{7a}$, $C_{2-6}$-alkynyl-$R^{7a}$, $C_{3-6}$-cycloalkyl-$R^{7a}$, $C(O)R^{7a}$, $C(=O)NHR^{7a}$, $COOR^{7a}$, $S(O)_2R^{7a}$ or a partially or fully saturated or fully unsaturated 5- or 6-membered monocyclic ring formed of carbon atoms and including 1-3 heteroatoms selected from N, O and S, wherein the $C_{1-6}$-alkyl-$R^{7a}$, $C_{2-6}$-alkenyl-$R^{7a}$, $C_{2-6}$-alkynyl-$R^{7a}$ and $C_{3-6}$-cycloalkyl-$R^{7a}$ is optionally substituted with 1-5 substituents of $R^9$;

$R^3$ is H, halo, haloalkyl, OH, $NH_2$, $C_{1-4}$-alkyl, —O—$C_{1-4}$-alkyl, —O—$C_{1-4}$-haloalkyl, —S—$C_{1-4}$-alkyl, —NH—$C_{1-4}$-alkyl, —N-di-$C_{1-4}$-alkyl, —$C_{1-4}$-alkyl-OH or —$C_{1-6}$-alkyl-$NH_2$;

$R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, wherein each of said $C_{1-6}$-alkyl, $C_{2-8}$-alkenyl, $C_{2-8}$-alkynyl is optionally substituted independently with 1-5 substituents of $R^9$;

$R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl or $C_{3-6}$-cycloalkyl;

each $R^7$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $OR^8$, $SR^8$, $OR^9$, $SR^9$, $C(O)R^8$, $OC(O)R^9$, $COOR^9$, $C(O)R^9$, $C(O)NR^8R^9$, $C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

each $R^{7a}$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^8R^9$, $NR^9C(O)R^9$, $C(O)NR^9R^9$, $NR^9C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$;

each $R^9$, independently, is H, F, Cl, Br, I, haloalkyl, CN, OH, $C_{1-8}$-alkyl, —O—$C_{1-8}$-alkyl, —$C_{1-6}$-alkyl-O—$C_{1-6}$-alkyl, —S—$C_{1-6}$-alkyl, —$C_{1-6}$-alkyl-S—$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{2-8}$-alkenyl, $C_{2-8}$-alkynyl and ring of said ring system is optionally substituted independently with 1-5 substituents of halo, haloalkyl, CN, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In an embodiment of the compounds of Formula II (embodiment 4), or a pharmaceutically acceptable salt thereof, either separately or in combination with any of the above or below embodiments, $A^1$ is $CR^3$;
$A^2$ is $CR^4$;
$A^4$ is $CR^6$;
$A^5$ is $CR^3$;
$A^6$ is $CR^3$;
$A^7$ is N;
$A^8$ is N;
X is S; and
Y is $R^7$ or $R^9$;

each $R^3$, independently, is H, halo, haloalkyl, OH, $NH_2$, $C_{1-4}$-alkyl, —O—$C_{1-4}$-alkyl, —O—$C_{1-4}$-haloalkyl, —S—$C_{1-4}$-alkyl, —NH—$C_{1-4}$-alkyl, or —N-di-$C_{1-4}$-alkyl;
$R^4$ is H, halo, haloalkyl, $C_{1-6}$-alkyl, —O—$C_{1-6}$-alkyl, —O—$C_{1-8}$-haloalkyl- or —S—$C_{1-6}$-alkyl; and
$R^6$ is H, halo, haloalkyl, $C_{1-8}$-alkyl, —O—$C_{1-8}$-alkyl, —O—$C_{1-8}$-haloalkyl- or —S—$C_{1-8}$-alkyl.

In another embodiment (embodiment 5), the present invention provides compounds of Formula III:

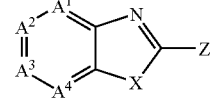

or a pharmaceutically acceptable salt thereof, wherein
$A^1$ is $CR^3$ or N;
$A^2$ is $CR^4$ or N;
$A^3$ is $CR^5$ or N; and
$A^4$ is $CR^6$ or N;
provided that no more than two of $A^1$, $A^2$, $A^3$ and $A^4$ is N;
X is O or S;
Z is H, —$NR^1R^2$, $C_1$-$C_6$alkyl, $C_1$-$C_6$haloalkyl, —$SO_2R^{7a}$, —$SR^{7a}$, or —$OR^{7a}$;
$R^1$ is H, $C_{1-6}$-alkyl, $C_{2-6}$-alkenyl, $C_{2-6}$-alkynyl or $C_{3-6}$-cycloalkyl;
$R^2$ is H, $C_{1-6}$-alkyl-$R^{7a}$, $C_{2-6}$-alkenyl-$R^{7a}$, $C_{2-6}$-alkynyl-$R^{7a}$, $C_{3-6}$-cycloalkyl-$R^{7a}$, $C(O)R^{7a}$, $C(=O)NHR^{7a}$, $COOR^{7a}$, $S(O)_2R^{7a}$ or a partially or fully saturated or fully unsaturated 5- or 6-membered monocyclic ring formed of carbon atoms and including 1-3 heteroatoms selected from N, O and S, wherein the 7, $C_{2-6}$-alkynyl-$R^{7a}$ and $C_{2-6}$-cycloalkyl-$R^{7a}$ is optionally substituted with 1-5 substituents of $R^9$, or $R^1$ and $R^2$ together with the nitrogen atom to which they are attached form a 5 to 8 membered ring containing from 1 to 3 heteroatoms independently selected from N, O or S;

$R^3$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, —$C_{1-4}$-alkyl-OH, $C_{1-6}$-alkyl-$NH_2$, $C_{1-6}$-alkyl-N-di-$C_{1-8}$-alkyl, $C_{2-8}$-alkenyl, $C_{2-8}$-alkynyl or $C_{3-6}$-cycloalkyl;

$R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl or a partially or fully saturated 5-membered or a partially or fully saturated or unsaturated 6-membered monocyclic ring or a partially or fully saturated or unsaturated 8-10-membered bicyclic ring, said ring(s) formed of carbon atoms optionally including 1-3 heteroatoms per ring selected from N, O and S, wherein each of said $C_{1-6}$-alkyl, $C_{2-8}$-alkenyl, $C_{2-8}$-alkynyl and ring is optionally substituted independently with 1-5 substituents of $R^7$, $R^8$ or $R^9$;

$R^5$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl or a partially or fully saturated 5-membered or a partially or fully saturated or unsaturated 6-membered monocyclic ring or a partially or fully saturated or unsaturated 8-10-membered bicyclic ring, said ring(s) formed of carbon atoms optionally including 1-3 heteroatoms per ring selected from N, O and S, wherein each of said $C_{1-6}$-alkyl, $C_{2-8}$-alkenyl, $C_{2-8}$-alkynyl and ring is optionally substituted independently with 1-5 substituents of $R^7$, $R^8$ or $R^9$; provided that both of $R^4$ and $R^5$ are not each, independently, a partially or fully saturated 5-membered or a partially or fully saturated or unsaturated 6-membered monocyclic ring or a partially or fully saturated or unsaturated 8-10-membered bicyclic ring formed of carbon atoms optionally including 1-3 heteroatoms;

$R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, —$C_{1-4}$-alkyl-OH, $C_{1-6}$-alkyl-$NH_2$, $C_{1-6}$-alkyl-N-di-$C_{1-8}$-alkyl, $C_{2-8}$-alkenyl, $C_{2-8}$-alkynyl or $C_{3-6}$-cycloalkyl;

each $R^7$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $OR^8$, $SR^8$, $OR^9$, $SR^9$, $C(O)R^8$, $OC(O)R^9$, $COOR^9$, $C(O)R^9$, $C(O)NR^8R^9$, $C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

each $R^{7a}$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^8R^9$, $NR^9C(O)R^9$, $C(O)NR^9R^9$, $NR^9C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$;

each $R^9$, independently, is H, F, Cl, Br, I, haloalkyl, CN, OH, $C_{1-6}$-alkyl, —O—$C_{1-6}$-alkyl, —$C_{1-6}$-alkyl-O—$C_{1-6}$-alkyl, —S—$C_{1-6}$-alkyl, —$C_{1-6}$-alkyl-S—$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-6}$-alkyl, $C_{2-8}$-alkenyl, $C_{2-8}$-alkynyl and ring of said ring system is optionally substituted independently with 1-5 substituents of halo, haloalkyl, CN, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In an embodiment of the compounds of Formula III (embodiment 5), or a pharmaceutically acceptable salt thereof, either separately or in combination with any of the above or below embodiments, X is S.

In an embodiment of the compounds of Formula III (embodiment 5), or a pharmaceutically acceptable salt thereof, either separately or in combination with any of the above or below embodiments, $A^1$ is $CR^3$, $A^2$ is $CR^4$, $A^3$ is $CR^5$ and $A^4$ is $CR^6$.

In an embodiment of the compounds of Formula III (embodiment 5), or a pharmaceutically acceptable salt thereof, either separately or in combination with any of the above or below embodiments, one of $A^1$, $A^2$, $A^3$ and $A^4$ is N.

In an embodiment of the compounds of Formula III (embodiment 5), or a pharmaceutically acceptable salt thereof, either separately or in combination with any of the above or below embodiments, X is S, $A^1$ is $CR^3$, $A^2$ is $CR^4$, $A^3$ is $CR^5$ and $A^4$ is $CR^6$ In an embodiment of the compounds of Formula III (embodiment 5), or a pharmaceutically acceptable salt thereof, either separately or in combination with any of the above or below embodiments, $A^2$ is $CR^4$ and $R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl; and $A^3$ is $CR^5$ and $R^5$ is a partially or fully saturated 5-membered or a partially or fully saturated or unsaturated 6-membered monocyclic ring formed of carbon atoms optionally including 1-3 heteroatoms, wherein said ring is optionally substituted independently with 1-5 substituents of $R^7$, $R^8$ or $R^9$.

In an embodiment of the compounds of Formula III (embodiment 5), or a pharmaceutically acceptable salt thereof, either separately or in combination with any of the above or below embodiments, $A^1$ is $CR^3$ and $R^3$ is H, halo, haloalkyl, OH, $NO_2$, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl;

$A^2$ is $CR^4$ and $R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl;

$A^3$ is $CR^5$ and $R^5$ is a ring selected from phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, benzoxazolyl, benzisoxazolyl, benzothiazolyl, benzoisothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$, $R^8$ or $R^9$; and $A^4$ is $CR^6$ and $R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl.

In an embodiment of the compounds of Formula III (embodiment 5), or a pharmaceutically acceptable salt thereof, either separately or in combination with any of the above or below embodiments, Z is —$NR^1R^2$, $R^1$ is H or $C_{1-6}$-alkyl and $R^2$ is H, $C_{1-6}$-alkyl-$R^{7a}$, $C(O)R^{7a}$ or $S(O)_2R^{7a}$.

In another embodiment (embodiment 6), the present invention provides compounds of Formula IV:

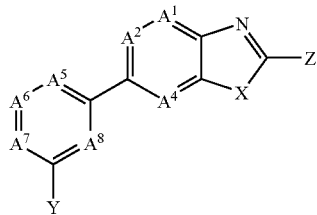

or a pharmaceutically acceptable salt thereof, wherein
A¹ is CR³ or N;
A² is CR⁴ or N; and
A⁴ is CR⁶ or N; provided that no more than two of A¹, A² and A⁴ is N;
A⁵ is CR³ or N;
A⁶ is CR³ or N;
A⁷ is CR³ or N; and
A⁸ is CR³ or N; provided that no more than three of A⁵, A⁶, A⁷, and A⁸ is N;
X is O or S;
Y is R⁷, R⁸ or R⁹;
Z is H, —NR¹R², C₁-C₆alkyl, C₁-C₆haloalkyl, —SO₂R⁷ᵃ, —SR⁷ᵃ, or —OR⁷ᵃ;
R¹ is H, C₁₋₆-alkyl, C₂₋₆-alkenyl, C₂₋₆-alkynyl or C₃₋₆-cycloalkyl;
R² is H, C₁₋₆-alkyl-R⁷ᵃ, C₂₋₆-alkenyl-R⁷ᵃ, C₂₋₆-alkynyl-R⁷ᵃ, C₃₋₆-cycloalkyl-R⁷ᵃ, C(O)R⁷ᵃ, C(=O)NHR⁷ᵃ, COOR⁷ᵃ, S(O)₂R⁷ᵃ or a partially or fully saturated or fully unsaturated 5- or 6-membered monocyclic ring formed of carbon atoms and including 1-3 heteroatoms selected from N, O and S, wherein the C₁₋₆-alkyl-R⁷ᵃ, C₂₋₆-alkenyl-R⁷ᵃ, C₂₋₆-alkynyl-R⁷ᵃ and C₃₋₆-cycloalkyl-R⁷ᵃ is optionally substituted with 1-5 substituents of R⁹, or R¹ and R² together with the nitrogen atom to which they are attached form a 5 to 8 membered ring containing from 1 to 3 heteroatoms independently selected from N, O or S;
R³ is H, halo, haloalkyl, OH, NH₂, C₁₋₄-alkyl, —O—C₁₋₄-alkyl, —O—C₁₋₄-haloalkyl, —S—C₁₋₄-alkyl, —NH—C₁₋₄-alkyl, —N-di-C₁₋₄-alkyl, —C₁₋₄-alkyl-OH or —C₁₋₆-alkyl-NH₂;
R⁴ is H, halo, haloalkyl, OH, NH₂, C₁₋₆-alkyl, —O—C₁₋₆-alkyl, —O—C₁₋₈-haloalkyl, —C₁₋₆-alkyl-O—C₁₋₆-alkyl, —S—C₁₋₆-alkyl, —C₁₋₆-alkyl-S—C₁₋₆-alkyl, —NH—C₁₋₆-alkyl, —N-di-C₁₋₆-alkyl, —C₁₋₆-alkyl-NH—C₁₋₆-alkyl, C₂₋₈-alkenyl, C₂₋₈-alkynyl, C₃₋₆-cycloalkyl, wherein each of said C₁₋₆-alkyl, C₂₋₈-alkenyl, C₂₋₈-alkynyl is optionally substituted independently with 1-5 substituents of R⁹;
R⁶ is H, halo, haloalkyl, OH, NH₂, C₁₋₈-alkyl, —O—C₁₋₈-alkyl, —O—C₁₋₈-haloalkyl, —C₁₋₆-alkyl-O—C₁₋₆-alkyl, —S—C₁₋₈-alkyl, —C₁₋₆-alkyl-S—C₁₋₆-alkyl, —NH—C₁₋₈-alkyl, —N-di-C₁₋₈-alkyl, —C₁₋₆-alkyl-NH—C₁₋₆-alkyl, C₂₋₈-alkenyl, C₂₋₈-alkynyl or C₃₋₆-cycloalkyl;
each R⁷ independently, is H, C₁₋₈-alkyl, C₂₋₈-alkenyl, C₂₋₈-alkynyl, C₃₋₆cycloalkyl, C₄₋₈-cycloalkenyl, NR⁸R⁹, OR⁸, SR⁸, OR⁹, SR⁹, C(O)R⁸, OC(O)R⁹, COOR⁹, C(O)R⁹, C(O)NR⁸R⁹, C(O)NR⁹R⁹, S(O)₂R⁸, S(O)₂R⁹, S(O)₂NR⁸R⁹, S(O)₂NR⁹R⁹, NR⁹S(O)₂NR⁹R⁹, NR⁹S(O)₂R⁸ or NR⁹S(O)₂R⁹, each of the C₁₋₈-alkyl, C₂₋₈-alkenyl, C₂₋₈-alkynyl, C₃₋₆-cycloalkyl and C₄₋₈-cycloalkenyl is optionally substituted with one or more substituents of R⁸, R⁹, NR⁸R⁹, NR⁹R⁹, OR⁸, SR⁸, OR⁹, SR⁹, C(O)R⁸, OC(O)R⁹, COOR⁹, C(O)R⁹, C(O)NR⁹R⁹, NR⁹C(O)R⁹, C(O)NR⁹R⁹, NR⁹C(O)NR⁹R⁹, S(O)₂R⁸, S(O)₂R⁹, S(O)₂NR⁹R⁹, NR⁹S(O)₂NR⁹R⁹, NR⁹S(O)₂R⁸ or NR⁹S(O)₂R⁹;

each R⁷ᵃ independently, is H, C₁₋₈-alkyl, C₂₋₈-alkenyl, C₂₋₈-alkynyl, C₃₋₆cycloalkyl, C₄₋₈-cycloalkenyl, NR⁸R⁹, NR⁹R⁹, OR⁸, SR⁸, OR⁹, SR⁹, C(O)R⁸, OC(O)R⁹, COOR⁹, C(O)R⁹, C(O)NR⁸R⁹, NR⁹C(O)R⁹, C(O)NR⁹R⁹, NR⁹C(O) NR⁹R⁹, S(O)₂R⁸, S(O)₂R⁹, S(O)₂NR⁸R⁹, S(O)₂NR⁹R⁹, NR⁹S(O)₂NR⁹R⁹, NR⁹S(O)₂R⁸ or NR⁹S(O)₂R⁹, each of the C₁₋₈-alkyl, C₂₋₈-alkenyl, C₂₋₈-alkynyl, C₃₋₆-cycloalkyl and C₄₋₈-cycloalkenyl is optionally substituted with one or more substituents of R⁸, R⁹, NR⁸R⁹, NR⁹R⁹, OR⁸, SR⁸, OR⁹, SR⁹, C(O)R⁸, OC(O)R⁹, COOR⁹, C(O)R⁹, C(O)NR⁹R⁹, NR⁹C(O) R⁹, C(O)NR⁹R⁹, NR⁹C(O)NR⁹R⁹, S(O)₂R⁸, S(O)₂R⁹, S(O)₂ NR⁹R⁹, NR⁹S(O)₂NR⁹R⁹, NR⁹S(O)₂R⁸ or NR⁹S(O)₂R⁹;
R⁸ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of R⁹;
each R⁹, independently, is H, F, Cl, Br, I, haloalkyl, CN, OH, C₁₋₈-alkyl, —O—C₁₋₈-alkyl, —C₁₋₆-alkyl-O—C₁₋₆-alkyl, —S—C₁₋₆-alkyl, —C₁₋₆-alkyl-S—C₁₋₆-alkyl, —C₁₋₆-alkyl-NH—C₁₋₆-alkyl, C₂₋₈-alkenyl, C₂₋₈-alkynyl, C₃₋₆-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said C₁₋₈-alkyl, C₂₋₈-alkenyl, C₂₋₈-alkynyl and ring of said ring system is optionally substituted independently with 1-5 substituents of halo, haloalkyl, CN, NH₂, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In an embodiment of the compounds of Formula IV (embodiment 6), or a pharmaceutically acceptable salt thereof, either separately or in combination with any of the above or below embodiments,
A¹ is CR³;
A² is CR⁴;
A⁴ is CR⁶;
A⁵ is CR³;
A⁶ is CR³;
A⁷ is N;
A⁸ is N;
X is S; and
Y is R⁷ or R⁹;
each R³, independently, is H, halo, haloalkyl, OH, NH₂, C₁₋₄-alkyl, —O—C₁₋₄-alkyl, —O—C₁₋₄-haloalkyl, —S—C₁₋₄-alkyl, —NH—C₁₋₄-alkyl, or —N-di-C₁₋₄-alkyl;
R⁴ is H, halo, haloalkyl, C₁₋₆-alkyl, —O—C₁₋₆-alkyl, —O—C₁₋₈-haloalkyl- or —S—C₁₋₆-alkyl; and
R⁶ is H, halo, haloalkyl, C₁₋₈-alkyl, —O—C₁₋₈-alkyl, —O—C₁₋₈-haloalkyl- or —S—C₁₋₈-alkyl.

The present invention also provides pharmaceutical compositions comprising a pharmaceutically acceptable excipient and a compound according to Formula I, II, III, IV, V, or VI, or a pharmaceutically acceptable salt thereof.

The present invention also provides methods of treating a disease or condition resulting from the unregulated activity of PI3Kα in a subject, the methods comprising administering to the subject a therapeutically effective amount of a compound according to Formula I, II, III, IV, V, or VI, or a pharmaceutically acceptable salt thereof.

The present invention also provides methods of treating melanoma, a solid tumor, ovarian cancer, cervical cancer, breast cancer, colon cancer, endometrial cancer, pancreatic cancer, lung cancer, gastric carcinoma, glioblastoma, hepatocellular carcinoma, prostate carcinoma, rectal cancer, acute lyelogeous leukemia, chronic lyelogenous leukemia, small cell lung cancer, non-small-cell lung cancer, thyroid cancer or a combination thereof, the methods comprising administering to the subject a therapeutically effective amount of a compound according to Formula I, II, III, IV, V, or VI, or a pharmaceutically acceptable salt thereof.

In a further embodiment of the methods of treatment above, the subject is administered a compound according to Formula I, II, III, IV, V, or VI, or, or a pharmaceutically acceptable salt thereof, in combination with one or more compounds selected from the group consisting of antineoplastic agents, anti-angiogenic agents, chemotherapeutic agents and peptidal cancer therapy agents.

In a further embodiment of the combination treatment above, the antineoplastic agents are selected from the group consisting of antibiotic-type agents, alkylating agents, antimetabolite agents, hormonal agents, immunological agents, interferon-type agents, kinase inhibitors, miscellaneous agents and combinations thereof.

In another embodiment (embodiment 7), the present invention provides compounds of Formula V:

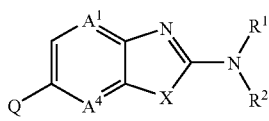

V or a pharmaceutically acceptable salt thereof, wherein Q is

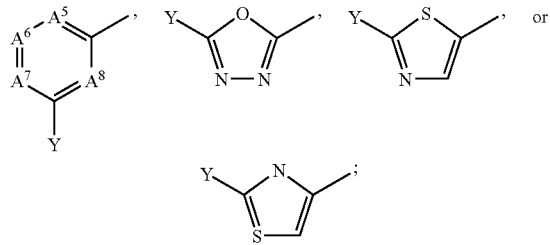

X is O or S;
$A^1$ is CH, N or C-halo;
$A^4$ is CH, N or C-halo;
$A^5$ is $CR^3$ or N;
$A^6$ is $CR^3$ or N;
$A^7$ is $CR^3$ or N;
$A^8$ is $CR^3$ or N; provided that no more than three of $A^5$, $A^6$, $A^7$ and $A^8$ is N;
each $R^3$ is independently H, $C_1$-$C_6$alkyl, halo, —$OC_1$-$C_6$alkyl, —Ohaloalkyl, —CN, or —$CF_3$;
$R^1$ is H;
$R^2$ is H, or $C(O)R^{7a}$,
$R^{7a}$, is $C_1$-$C_6$alkyl, —$(CRR)_nNR^xR^y$, —$(CRR)_n$aryl, —$(CRR)_n$heteroaryl, —$(CRR)_nOR$ —$(CRR)_n$heterocycloalkyl, —$(CRR)_n$Ophenyl, —$NR(CRR)_nR^xR^y$, or —$S(O)_2R$;
each R is independently H or $C_1$-$C_6$ alkyl;
each $R^X$ and $R^Y$ are independently hydrogen, or $C_1$-$C_6$alkyl, or $R^X$ and $R^Y$ together with the nitrogen atom to which they are attached form a 5 to 8 membered ring containing from 1 to 3 heteroatoms independently selected from N, O or S;
each n is independently 0, 1, 2, 3 or 4;
Y is —$NRSO_2(CRR)_n$aryl,
—S—$(CRR)_n$aryl,
—$O(CRR)_n$aryl,
—$SO_2$aryl,
halo,
—$(CRR)_n$OH,
—$NRSO_2C_1$-$C_6$alkyl,
—$NRSO_2$heteroaryl,
—$OC_1$-$C_6$alkyl,
—$OC_1$-$C_6$haloalkyl
—$O(CRR)_n$CN
—$O(CRR)_nO(CRR)_nOC_1$-$C_6$alkyl,
—$SC_1$-$C_6$alkyl,
—$O(CRR)_nNR^xR^y$,
—$O(CRR)_n$—OR,
—$O(CRR)$nheteroaryl,
—OR, or
—$(CRR)_n$aryl;
wherein aryl or heteroaryl can be optionally substituted with from 1 to 4 substitutents selected from halo, $C_1$-$C_6$alkyl, —$CF_3$, —CN, —$OC_1$-$C_6$haloalkyl, —$OC_1$-$C_6$alkyl, or $C(O)$ $C_1$-$C_6$alkyl.

In an embodiment of the compounds of Formula V (embodiment 7), or a pharmaceutically acceptable salt thereof, either separately or in combination with any of the above or below embodiments, Q is

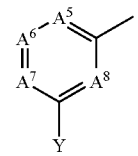

In an embodiment of the compounds of Formula V (embodiment 7), or a pharmaceutically acceptable salt thereof, either separately or in combination with any of the above or below embodiments, X is S; Y is —$NRSO_2$phenyl; and R is H or $CH_3$, wherein phenyl can be optionally substituted with from 1 to 4 substitutents selected from halo, $C_1$-$C_6$alkyl, —$CF_3$, —CN, —$OC_1$-$C_6$haloalkyl, —$OC_1$-$C_6$alkyl, or $C(O)$ $C_1$-$C_6$alkyl.

In an embodiment of the compounds of Formula V (embodiment 7), or a pharmaceutically acceptable salt thereof, either separately or in combination with any of the above or below embodiments, Q is

23

-continued

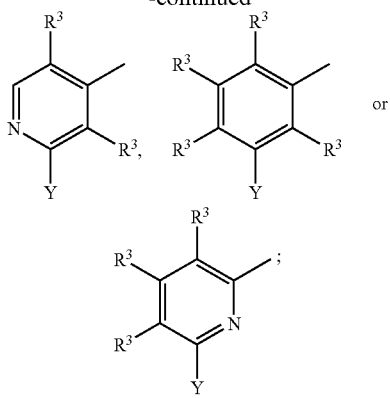

and each $R^3$ is independently H, halo, $C_1$-$C_6$alkyl, —$OC_1$-$C_6$alkyl, —CN or —$CF_3$.

In an embodiment of the compounds of Formula V (embodiment 7), or a pharmaceutically acceptable salt thereof, either separately or in combination with any of the above or below embodiments, $R^1$ is H and $R^2$ is $C(O)CH_3$.

In an embodiment of the compounds of Formula V (embodiment 7), or a pharmaceutically acceptable salt thereof, either separately or in combination with any of the above or below embodiments, $A^1$ is CH or C-halo In an embodiment of the compounds of Formula V (embodiment 7), or a pharmaceutically acceptable salt thereof, either separately or in combination with any of the above or below embodiments, $A^4$ is CH or N In an embodiment of the compounds of Formula V (embodiment 7), or a pharmaceutically acceptable salt thereof, either separately or in combination with any of the above or below embodiments, Q is

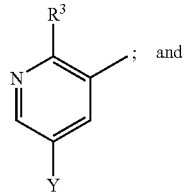

$R^3$ is halo, $C_1$-$C_6$alkyl, —$OC_1$-$C_6$alkyl, —CN or —$CF_3$.

In an embodiment of the compounds of Formula V (embodiment 7), or a pharmaceutically acceptable salt thereof, either separately or in combination with any of the above or below embodiments, $R^1$ is H;

$R^2$ is $C(O)CH_3$;
$A^1$ and $A^4$ are CH;
Q is

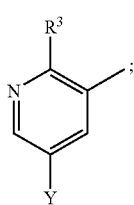

24

$R^3$ is halo; and
Y is —$NHSO_2$-phenyl, wherein the phenyl is optionally substituted with from 1 to 4 substituents selected from halo, $C_1$-$C_6$ alkyl, —$CF_3$, —CN, —$OC_1$-$C_6$haloalkyl, —$OC_1$-$C_6$alkyl, or $C(O)C_1$-$C_6$alkyl.

In another embodiment (embodiment 8), the present invention provides compounds of Formula VI:

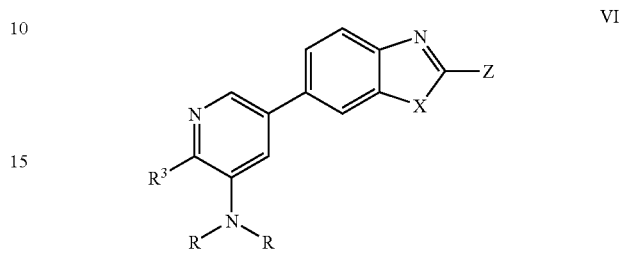

VI or a pharmaceutically acceptable salt thereof, wherein
X is O or S;
Z is H, —$NR^1R^2$, $C_1$-$C_6$alkyl, $C_1$-$C_6$haloalkyl, —$SO_2R^{7a}$, —$SR^{7a}$, or —$OR^{7a}$;
$R^1$ is H, $C_{1-6}$-alkyl, $C_{2-6}$-alkenyl, $C_{2-6}$-alkynyl or $C_{3-6}$-cycloalkyl;
$R^2$ is H, $C_{1-6}$-alkyl-$R^{7a}$, $C_{2-6}$-alkenyl-$R^{7a}$, $C_{2-6}$-alkynyl-$R^{7a}$, $C_{3-6}$-cycloalkyl-$R^{7a}$, $C(O)R^{7a}$, $C(=O)NHR^{7a}$, $COOR^{7a}$, $S(O)_2R^{7a}$ or a partially or fully saturated or fully unsaturated 5- or 6-membered monocyclic ring formed of carbon atoms and including 1-3 heteroatoms selected from N, O and S, wherein the $C_{1-6}$-alkyl-$R^{7a}$, $C_{2-6}$-alkenyl-$R^{7a}$, $C_{2-6}$-alkynyl-$R^{7a}$ and $C_{3-6}$-cycloalkyl-$R^{7a}$ is optionally substituted with 1-5 substituents of $R^9$, or $R^1$ and $R^2$ together with the nitrogen atom to which they are attached form a 5 to 8 membered ring containing from 1 to 3 heteroatoms independently selected from N, O or S;

each $R^{7a}$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^8R^9$, $NR^9C(O)R^9$, $C(O)NR^9R^9$, $NR^9C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$;

each $R^9$, independently, is H, F, Cl, Br, I, haloalkyl, CN, OH, $C_{1-8}$-alkyl, —O—$C_{1-8}$-alkyl, —$C_{1-6}$-alkyl-O—$C_{1-6}$-alkyl, —S—$C_{1-6}$-alkyl, —$C_{1-6}$-alkyl-S—$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{2-8}$-alkenyl, $C_{2-8}$-alkynyl and ring of said ring system is optionally substituted independently with 1-5 substituents of halo, haloalkyl, CN, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

each R$^3$ is independently —(CR$^q$R$^q$)$_n$OC$_1$-C$_6$alkyl, halo, C$_1$-C$_6$alkyl, —CN, —CF$_3$,
—O(CR$^q$R$^q$)$_n$NR$^q$R$^q$, —NR$^q$(CR$^q$R$^q$)$_n$aryl;

each n is independently 0, 1, 2, 3, or 4;

each R$^q$ is independently H or C$_1$-C$_6$alkyl; and each R is independently H, C$_1$-C$_6$alkyl, aryl, heteroaryl, cycloalkyl or R and R taken together with the nitrogen atom to which they are attached form a ring that contains the nitrogen atom and one or two additional heteroatoms selected from O, N, or S; and each aryl, heteroaryl, cycloalkyl or heterocycloalkyl group is optionally substituted with from one to four substituents selected from halo, C$_1$-C$_6$ alkyl, —CF$_3$, —CN, —OC$_1$-C$_6$haloalkyl, —OC$_1$-C$_6$alkyl, or C(O)C$_1$-C$_6$alkyl.

Also provided by the present invention, either collectively, independently or in groups, are the compounds:

N-(6-(2-(3-(3-pyridinyl)propoxy)-4-pyrimidinyl)-1,3-benzothiazol-2-yl)acetamide;
N-(6-(2-(3-pyridinylmethoxy)-4-pyrimidinyl)-1,3-benzothiazol-2-yl)acetamide;
N-(6-(2-(benzyloxy)-4-pyrimidinyl)-1,3-benzothiazol-2-yl)acetamide;
N-(6-(2-(3-phenylpropoxy)-4-pyrimidinyl)-1,3-benzothiazol-2-yl)acetamide;
N-(6-(2-(3-methoxypropoxy)-4-pyrimidinyl)-1,3-benzothiazol-2-yl)acetamide;
N-(6-(2-(1-methylethoxy)-4-pyrimidinyl)-1,3-benzothiazol-2-yl)acetamide;
N-(6-(2-(2-phenylethoxy)-4-pyrimidinyl)-1,3-benzothiazol-2-yl)acetamide;
N-(6-(2-(3-dimethylamino)propoxy)-4-pyrimidinyl)-1,3-benzothiazol-2-yl)acetamide;
N-(6-(2-(2-dimethylamino)ethoxy)-4-pyrimidinyl)-1,3-benzothiazol-2-yl)acetamide;
N-(6-(2-(3-morpholino)propoxy)-4-pyrimidinyl)-1,3-benzothiazol-2-yl)acetamide
N-(6-(2-(2-morpholino)ethoxy)-4-pyrimidinyl)-1,3-benzothiazol-2-yl)acetamide;
N-(6-(2-((3-fluorobenzyl)oxy)-4-pyrimidinyl)-1,3-benzothiazol-2-yl)acetamide;
N-(6-(2-benzyl-4-pyrimidinyl)-1,3-benzothiazol-2-yl)acetamide;
N-(6-(2-(3-phenylpropyl)-4-pyrimidinyl)-1,3-benzothiazol-2-yl)acetamide;
N-(6-(2-(2-phenylethyl)-4-pyrimidinyl)-1,3-benzothiazol-2-yl)acetamide;
N-(6-(2-((4-methoxyphenyl)sulfanyl)-4-pyrimidinyl)-1,3-benzothiazol-2-yl)acetamide;
N-(6-(2-(4-pyridinylmethoxy)-4-pyrimidinyl)-1,3-benzothiazol-2-yl)acetamide;
N-(6-(2-(2-(3-pyridinyl)ethoxy)-4-pyrimidinyl)-1,3-benzothiazol-2-yl)acetamide;
N-(6-(2-(benzylsulfanyl)-4-pyrimidinyl)-1,3-benzothiazol-2-yl)acetamide;
N-(6-(2-(3-(1H-1,2,3-triazol-1-yl)propoxy)-4-pyrimidinyl)-1,3-benzothiazol-2-yl)acetamide;
N-(6-(2-(phenylsulfanyl)-4-pyrimidinyl)-1,3-benzothiazol-2-yl)acetamide;
N-(6-(2-(6-quinolinylmethoxy)-4-pyrimidinyl)-1,3-benzothiazol-2-yl)acetamide;
N-(6-(2-((2-fluorophenyl)sulfanyl)-4-pyrimidinyl)-1,3-benzothiazol-2-yl)acetamide;
N-(6-(2-(1H-indol-5-ylmethoxy)-4-pyrimidinyl)-1,3-benzothiazol-2-yl)acetamide;
N-(6-(2-((1-methyl-4-piperidinyl)methoxy)-4-pyrimidinyl)-1,3-benzothiazol-2-yl)acetamide;
N-(6-(2-((4-fluorophenyl)sulfanyl)-4-pyrimidinyl)-1,3-benzothiazol-2-yl)acetamide;
N-(6-(2-((4-methoxy-2-methylphenyl)sulfanyl)-4-pyrimidinyl)-1,3-benzothiazol-2-yl)acetamide;
N-(6-(2-((2-methoxyphenyl)sulfanyl)-4-pyrimidinyl)-1,3-benzothiazol-2-yl)acetamide;
N-(4-((4-(2-(acetylamino)-1,3-benzothiazol-6-yl)-2-pyrimidinyl)sulfanyl)phenyl)acetamide;
N-(6-(2-((2-tert-butylphenyl)sulfanyl)-4-pyrimidinyl)-1,3-benzothiazol-2-yl)acetamide;
N-(6-(2-((1-methyl-4-piperidinyl)oxy)-4-pyrimidinyl)-1,3-benzothiazol-2-yl)acetamide
N-(6-(2-(3-(2-oxo-1,3-oxazolidin-3-yl)propoxy)-4-pyrimidinyl)-1,3-benzothiazol-2-yl)acetamide;
N-(6-(2-phenoxy-4-pyrimidinyl)-1,3-benzothiazol-2-yl)acetamide;
N-(6-(2-((2-methylphenyl)sulfanyl)-4-pyrimidinyl)-1,3-benzothiazol-2-yl)acetamide;
N-(6-(2-((3-methylphenyl)sulfanyl)-4-pyrimidinyl)-1,3-benzothiazol-2-yl)acetamide;
N-(6-(2-((4-methylphenyl)sulfanyl)-4-pyrimidinyl)-1,3-benzothiazol-2-yl)acetamide;
N-(6-(2-((2-methylbenzyl)sulfanyl)-4-pyrimidinyl)-1,3-benzothiazol-2-yl)acetamide;
N-(6-(2-((4-methoxybenzyl)oxy)-4-pyrimidinyl)-1,3-benzothiazol-2-yl)acetamide;
N-(6-(2-((4-fluorobenzyl)oxy)-4-pyrimidinyl)-1,3-benzothiazol-2-yl)acetamide;
N-(6-(2-(1,3-benzodioxol-5-ylmethoxy)-4-pyrimidinyl)-1,3-benzothiazol-2-yl)acetamide;
N-(6-(2-((3-methoxyphenyl)sulfanyl)-4-pyrimidinyl)-1,3-benzothiazol-2-yl)acetamide;
N-(6-(2-(2,2-dimethylpropoxy)-4-pyrimidinyl)-1,3-benzothiazol-2-yl)acetamide;
N-(6-(2-((1R)-1-phenylethoxy)-4-pyrimidinyl)-1,3-benzothiazol-2-yl)acetamide;
N-(6-(2-(3-(4-pyridinyl)propoxy)-4-pyrimidinyl)-1,3-benzothiazol-2-yl)acetamide;
6-(2-((3-phenylpropyl)amino)-4-pyrimidinyl)-1,3-benzothiazol-2-amine;
N-(6-(2-((3-methoxypropyl)amino)-4-pyrimidinyl)-1,3-benzothiazol-2-yl)acetamide;
N-(6-(2-((2-methoxyethyl)amino)-4-pyrimidinyl)-1,3-benzothiazol-2-yl)acetamide;
6-(2-((2-methoxyethyl)amino)-4-pyrimidinyl)-1,3-benzothiazol-2-amine;
N-(6-(2-(benzylamino)-4-pyrimidinyl)-1,3-benzothiazol-2-yl)acetamide;
N-(6-(2-(methylsulfanyl)-4-pyrimidinyl)-1,3-benzothiazol-2-yl)acetamide;
N-(6-(2-methoxy-4-pyrimidinyl)-1,3-benzothiazol-2-yl)acetamide;
N-(6-(2-(dimethylamino)-4-pyrimidinyl)-1,3-benzothiazol-2-yl)acetamide;
N-(6-(2-hydroxy-4-pyrimidinyl)-1,3-benzothiazol-2-yl)acetamide;
N-(6-(2-(benzyloxy)-4-pyrimidinyl)-1,3-benzothiazol-2-yl)-2-(4-morpholinyl)acetamide;
N-(6-(2-(benzyloxy)-4-pyrimidinyl)-1,3-benzothiazol-2-yl)-2-hydroxy-2-methylpropanamide;
1-(6-(2-(benzyloxy)-4-pyrimidinyl)-1,3-benzothiazol-2-yl)-3-methylurea;

N-(6-(2-(benzyloxy)-4-pyrimidinyl)-1,3-benzothiazol-2-yl)
propanamide;
N-(6-(2-(benzyloxy)-4-pyrimidinyl)-1,3-benzothiazol-2-yl)
benzamide;
N-(6-(2-(benzyloxy)-4-pyrimidinyl)-1,3-benzothiazol-2-
yl)-N~2~,N~2~-dimethylglycinamide;
N-(6-(2-((4-methoxyphenyl)sulfonyl)-1,3-thiazol-5-yl)-1,3-
benzothiazol-2-yl)acetamide;
N-(6-(2-((4-methoxyphenyl)sulfanyl)-1,3-thiazol-5-yl)-1,3-
benzothiazol-2-yl)acetamide;
N-(6-(2-((2-fluorophenyl)sulfonyl)-1,3-thiazol-4-yl)-1,3-
benzothiazol-2-yl)acetamide;
N-(6-(2-(phenylsulfonyl)-1,3-thiazol-4-yl)-1,3-benzothia-
zol-2-yl)acetamide;
N-(6-(6-(phenylsulfonyl)-2-pyridinyl)-1,3-benzothiazol-2-
yl)acetamide;
N-(6-(6-((4-fluorophenyl)sulfonyl)-2-pyridinyl)-1,3-ben-
zothiazol-2-yl)acetamide;
N-(6-(6-((3-fluorophenyl)sulfonyl)-2-pyridinyl)-1,3-ben-
zothiazol-2-yl)acetamide;
N-(6-(6-((4-methoxyphenyl)sulfonyl)-2-pyridinyl)-1,3-ben-
zothiazol-2-yl)acetamide;
N-(6-(6-((3-methoxyphenyl)sulfonyl)-2-pyridinyl)-1,3-ben-
zothiazol-2-yl)acetamide;
N-(6-(6-((2-methoxyphenyl)sulfonyl)-2-pyridinyl)-1,3-ben-
zothiazol-2-yl)acetamide;
N-(6-(2-amino-1,3-benzothiazol-6-yl)-2-pyridinyl)benzene-
sulfonamide;
N-(6-(2-amino-1,3-benzothiazol-6-yl)-2-pyridinyl)-2-fluo-
robenzenesulfonamide;
N-(6-(6-(((2-fluorophenyl)sulfonyl)amino)-2-pyridinyl)-1,
3-benzothiazol-2-yl)acetamide;
N-(6-(6-(methyl((4-methylphenyl)sulfonyl)amino)-2-py-
ridinyl)-1,3-benzothiazol-2-yl)acetamide;
N-(6-(6-(methyl(phenylsulfonyl)amino)-2-pyridinyl)-1,3-
benzothiazol-2-yl)acetamide;
N-(6-(2-((phenylsulfonyl)amino)-4-pyrimidinyl)-1,3-ben-
zothiazol-2-yl)acetamide;
N-(6-(2-(((4-methoxyphenyl)sulfonyl)amino)-4-pyrimidi-
nyl)-1,3-benzothiazol-2-yl)acetamide;
N-(6-(2-((3-pyridinylsulfonyl)amino)-4-pyrimidinyl)-1,3-
benzothiazol-2-yl)acetamide;
N-(6-(2-(((4-fluorophenyl)sulfonyl)amino)-4-pyrimidinyl)-
1,3-benzothiazol-2-yl)acetamide;
N-(6-(2-(((2-fluorophenyl)sulfonyl)amino)-4-pyrimidinyl)-
1,3-benzothiazol-2-yl)acetamide;
N-(6-(2-(((3-fluorophenyl)sulfonyl)amino)-4-pyrimidinyl)-
1,3-benzothiazol-2-yl)acetamide;
N-(6-(2-(((4-methylphenyl)sulfonyl)amino)-4-pyrimidinyl)-
1,3-benzothiazol-2-yl)acetamide;
N-(6-(2-(((4-ethylphenyl)sulfonyl)amino)-4-pyrimidinyl)-1,
3-benzothiazol-2-yl)acetamide;
N-(6-(2-(((3-methoxyphenyl)sulfonyl)amino)-4-pyrimidi-
nyl)-1,3-benzothiazol-2-yl)acetamide;
N-(4-((4-(2-(acetylamino)-1,3-benzothiazol-6-yl)-2-pyrim-
idinyl)sulfamoyl)phenyl)acetamide;
N-(6-(2-(((3,4-dimethoxyphenyl)sulfonyl)amino)-4-pyrim-
idinyl)-1,3-benzothiazol-2-yl)acetamide;
N-(6-(2-(((4-methoxyphenyl)sulfonyl)(methyl)amino)-4-
pyrimidinyl)-1,3-benzothiazol-2-yl)acetamide;
N-(6-(2-(ethyl((4-methoxyphenyl)sulfonyl)amino)-4-pyri-
midinyl)-1,3-benzothiazol-2-yl)acetamide;
N-(6-(2-(methyl((4-methylphenyl)sulfonyl)amino)-4-pyri-
midinyl)-1,3-benzothiazol-2-yl)acetamide;
N-(6-(2-(methyl(phenylsulfonyl)amino)-4-pyrimidinyl)-1,
3-benzothiazol-2-yl)acetamide;
N-(6-(2-(((2-fluorophenyl)sulfonyl)(methyl)amino)-4-pyri-
midinyl)-1,3-benzothiazol-2-yl)acetamide;
N-(6-(2-(methyl((3-methylphenyl)sulfonyl)amino)-4-pyri-
midinyl)-1,3-benzothiazol-2-yl)acetamide;
N-(7-(3-fluoro-4-methoxyphenyl)-1,3-benzothiazol-2-yl)
acetamide;
N-(7-(4-methoxyphenyl)-1,3-benzothiazol-2-yl)acetamide;
N-(7-(3-methoxyphenyl)-1,3-benzothiazol-2-yl)acetamide;
N-(6-(2-((4-fluorophenyl)sulfonyl)-1,3-thiazol-4-yl)-1,3-
benzothiazol-2-yl)acetamide;
N-(2-oxo-2,3-dihydro-4,6'-bi-1,3-benzothiazol-2'-yl)aceta-
mide;
N-(6-(1H-indazol-4-yl)-1,3-benzothiazol-2-yl)acetamide;
N-(6-(2-((1-methyl-1-phenylethyl)amino)-4-pyrimidinyl)-1,
3-benzothiazol-2-yl)acetamide;
N-(6-(2-amino-6-methyl-4-pyrimidinyl)-1,3-benzothiazol-
2-yl)acetamide;
N-(6-(2-(3-hydroxypropoxy)-4-pyrimidinyl)-1,3-benzothia-
zol-2-yl)acetamide;
N-(6-(2-(4-hydroxybutoxy)-4-pyrimidinyl)-1,3-benzothia-
zol-2-yl)acetamide;
N-(6-(2-(2-hydroxyethoxy)-4-pyrimidinyl)-1,3-benzothia-
zol-2-yl)acetamide;
N-(6-(2-chloro-4-pyrimidinyl)-1,3-benzothiazol-2-yl)aceta-
mide;
N-(6-(2-((4-methylbenzyl)oxy)-4-pyrimidinyl)-1,3-ben-
zothiazol-2-yl)acetamide;
N-(6-(2-((3-methylbenzyl)oxy)-4-pyrimidinyl)-1,3-ben-
zothiazol-2-yl)acetamide;
N-(6-(2-((3-methoxybenzyl)oxy)-4-pyrimidinyl)-1,3-ben-
zothiazol-2-yl)acetamide;
N-(6-(2-((3-fluorophenyl)sulfanyl)-4-pyrimidinyl)-1,3-ben-
zothiazol-2-yl)acetamide;
N-(6-(6-methyl-5-((phenylsulfonyl)amino)-3-pyridinyl)-1,
3-benzothiazol-2-yl)acetamide;
N-(6-(5-(((4-fluorophenyl)sulfonyl)amino)-6-methyl-3-py-
ridinyl)-1,3-benzothiazol-2-yl)acetamide;
N-(6-(5-(((2-fluorophenyl)sulfonyl)amino)-6-methyl-3-py-
ridinyl)-1,3-benzothiazol-2-yl)acetamide;
N-(6-(6-methyl-5-(((3-(trifluoromethyl)phenyl)sulfonyl)
amino)-3-pyridinyl)-1,3-benzothiazol-2-yl)acetamide;
N-(6-(5-(((4-tert-butylphenyl)sulfonyl)amino)-6-methyl-3-
pyridinyl)-1,3-benzothiazol-2-yl)acetamide;
N-(6-(5-(((3-(difluoromethoxy)phenyl)sulfonyl)amino)-6-
methyl-3-pyridinyl)-1,3-benzothiazol-2-yl)acetamide;
N-(6-(5-(((4-methoxyphenyl)sulfonyl)amino)-6-methyl-3-
pyridinyl)-1,3-benzothiazol-2-yl)acetamide;
N-(4-fluoro-6-(5-(((4-(trifluoromethyl)phenyl)sulfonyl)
amino)-3-pyridinyl)-1,3-benzothiazol-2-yl)acetamide;
N-(6-(6-(((4-methoxyphenyl)sulfonyl)amino)-2-pyrazinyl)-
1,3-benzothiazol-2-yl)acetamide;
N-(6-(5-(((4-acetylphenyl)sulfonyl)amino)-6-chloro-3-py-
ridinyl)-1,3-benzothiazol-2-yl)acetamide;
N-(6-(6-((4-methoxyphenyl)sulfonyl)-2-pyrazinyl)-1,3-ben-
zothiazol-2-yl)acetamide;
N-(6-(6-((2-fluorophenyl)sulfonyl)-2-pyrazinyl)-1,3-ben-
zothiazol-2-yl)acetamide;
N-(6-(2-((2,4-dimethylphenyl)sulfanyl)-4-pyrimidinyl)-1,3-
benzothiazol-2-yl)acetamide;
N-(6-(2-((2,5-dimethylphenyl)sulfanyl)-4-pyrimidinyl)-1,3-
benzothiazol-2-yl)acetamide;
N-(6-(5-(dimethylamino)-6-methoxy-3-pyridinyl)-1,3-ben-
zothiazol-2-yl)acetamide;
N-(6-(2-((2-chlorophenyl)sulfanyl)-4-pyrimidinyl)-1,3-ben-
zothiazol-2-yl)acetamide;
N-(6-(6-(((4-methoxyphenyl)sulfonyl)(methyl)amino)-2-
pyrazinyl)-1,3-benzothiazol-2-yl)acetamide;

N-(6-(6-(methyl((4-methylphenyl)sulfonyl)amino)-2-pyrazinyl)-1,3-benzothiazol-2-yl)acetamide;
N-(6-(2-((3,4-dimethylphenyl)sulfanyl)-4-pyrimidinyl)-1,3-benzothiazol-2-yl)acetamide;
N-(6-(2-((2,6-dimethylphenyl)sulfanyl)-4-pyrimidinyl)-1,3-benzothiazol-2-yl)acetamide;
N-(6-(6-((2-fluorophenyl)sulfanyl)-2-pyrazinyl)-1,3-benzothiazol-2-yl)acetamide;
N-(4-fluoro-6-(2-(((4-methoxyphenyl)sulfonyl)amino)-4-pyrimidinyl)-1,3-benzothiazol-2-yl)acetamide;
N-(6-(6-chloro-5-((1-methylethyl)amino)-3-pyridinyl)-1,3-benzothiazol-2-yl)acetamide;
N-(6-(6-((4-methoxyphenyl)sulfanyl)-2-pyrazinyl)-1,3-benzothiazol-2-yl)acetamide;
N-(6-(2-((2-bromophenyl)sulfanyl)-4-pyrimidinyl)-1,3-benzothiazol-2-yl)acetamide;
N-(6-(6-(benzyloxy)-2-pyrazinyl)-1,3-benzothiazol-2-yl)acetamide;
N-(5-(3-(((4-methylphenyl)sulfonyl)amino)phenyl)[1,3]thiazolo[5,4-b]pyridin-2-yl)acetamide;
N-(4-fluoro-6-(6-((2-fluorophenyl)sulfonyl)-2-pyridinyl)-1,3-benzothiazol-2-yl)acetamide;
N-(6-(2-((4-chlorophenyl)sulfanyl)-4-pyrimidinyl)-1,3-benzothiazol-2-yl)acetamide;
N-(6-(2-((4-bromophenyl)sulfanyl)-4-pyrimidinyl)-1,3-benzothiazol-2-yl)acetamide;
N-(6-(2-((3-chlorophenyl)sulfanyl)-4-pyrimidinyl)-1,3-benzothiazol-2-yl)acetamide;
N-(6-(6-chloro-5-((1-methylethyl)amino)-3-pyridinyl)-1,3-benzothiazol-2-yl)-2-(2-pyridinyl)acetamide;
N-(6-(5-amino-6-methyl-3-pyridinyl)-1,3-benzothiazol-2-yl)acetamide;
N-(4-fluoro-6-(2-(((4-methoxyphenyl)sulfonyl)(methyl)amino)-4-pyrimidinyl)-1,3-benzothiazol-2-yl)acetamide;
N-(6-(6-chloro-5-((1-methylethyl)amino)-3-pyridinyl)-1,3-benzothiazol-2-yl)-2-methoxyacetamide;
N-(6-(6-methoxy-5-((1-methylethyl)amino)-3-pyridinyl)-1,3-benzothiazol-2-yl)acetamide;
N-(5-(3-(((4-methoxyphenyl)sulfonyl)amino)phenyl) [1,3]thiazolo[5,4-b]pyridin-2-yl)acetamide;
N-(4-fluoro-6-(6-((4-methoxyphenyl)sulfonyl)-2-pyridinyl)-1,3-benzothiazol-2-yl)acetamide;
N-(6-(2-((3,5-dimethylphenyl)sulfanyl)-4-pyrimidinyl)-1,3-benzothiazol-2-yl)acetamide;
N-(6-(6-chloro-2-pyrazinyl)-1,3-benzothiazol-2-yl)acetamide;
N-(6-(6-chloro-5-((1-methylethyl)amino)-3-pyridinyl)-1,3-benzothiazol-2-yl)-2-((2S)-tetrahydro-2-furanyl)acetamide;
N-(6-(6-(3-(dimethylamino)propoxy)-5-((1-methylethyl)amino)-3-pyridinyl)-1,3-benzothiazol-2-yl)acetamide;
N-(6-(2-((2-(1-methylethyl)phenyl)sulfanyl)-4-pyrimidinyl)-1,3-benzothiazol-2-yl)acetamide;
6-(6-chloro-5-((1-methylethyl)amino)-3-pyridinyl)-1,3-benzothiazol-2-amine;
N-(6-(2,2,3-trimethyl-2,3-dihydro-1H-imidazo[4,5-b]pyridin-6-yl)-1,3-benzothiazol-2-yl)acetamide;
N-(6-(2-((2,5-dimethoxyphenyl)sulfanyl)-4-pyrimidinyl)-1,3-benzothiazol-2-yl)acetamide;
N-(6-(6-(2-(dimethylamino)ethoxy)-5-((1-methylethyl)amino)-3-pyridinyl)-1,3-benzothiazol-2-yl)acetamide;
N-(6-(2-(4-morpholinyl)-4-pyrimidinyl)-1,3-benzothiazol-2-yl)acetamide;
N-(6-(6-chloro-5-(((4-(1-hydroxy-1-methylethyl)phenyl)sulfonyl)amino)-3-pyridinyl)-1,3-benzothiazol-2-yl)acetamide;
N-(6-(6-chloro-5-(((4-fluorophenyl)sulfonyl)amino)-3-pyridinyl)-1,3-benzothiazol-2-yl)acetamide;
N-(6-(6-chloro-5-(((4-methoxyphenyl)sulfonyl)amino)-3-pyridinyl)-1,3-benzothiazol-2-yl)acetamide;
N-(6-(5-(((4-fluorophenyl)sulfonyl)amino)-1,3,4-oxadiazol-2-yl)-1,3-benzothiazol-2-yl)acetamide;
N-(5-(2-amino-1,3-benzothiazol-6-yl)-1,3,4-oxadiazol-2-yl)-4-methylbenzenesulfonamide;
tert-butyl (6-(5-(((4-methylphenyl)sulfonyl)amino)-1,3,4-oxadiazol-2-yl)-1,3-benzothiazol-2-yl)carbamate;
tert-butyl (6-(5-(((4-fluorophenyl)sulfonyl)amino)-1,3,4-oxadiazol-2-yl)-1,3-benzothiazol-2-yl)carbamate;
N-(5-(2-amino-1,3-benzothiazol-6-yl)-1,3,4-oxadiazol-2-yl)-4-fluorobenzenesulfonamide;
tert-butyl (6-(5-(benzylamino)-1,3,4-oxadiazol-2-yl)-1,3-benzothiazol-2-yl)carbamate;
tert-butyl (6-(5-(benzyl(methylsulfonyl)amino)-1,3,4-oxadiazol-2-yl)-1,3-benzothiazol-2-yl)carbamate;
N-(6-(6-chloro-5-((cyclohexylsulfonyl)amino)-3-pyridinyl)-1,3-benzothiazol-2-yl)acetamide;
N-(6-(6-chloro-5-(((3-(trifluoromethyl)phenyl)sulfonyl)amino)-3-pyridinyl)-1,3-benzothiazol-2-yl)acetamide;
N-(6-(5-(((3-tert-butylphenyl)sulfonyl)amino)-6-chloro-3-pyridinyl)-1,3-benzothiazol-2-yl)acetamide;
N-(6-(6-chloro-5-(((4-hydroxyphenyl)sulfonyl)amino)-3-pyridinyl)-1,3-benzothiazol-2-yl)acetamide;
N-(6-(6-chloro-5-(((3,5-dichlorophenyl)sulfonyl)amino)-3-pyridinyl)-1,3-benzothiazol-2-yl)acetamide;
N-(6-(6-chloro-5-(((3,5-difluorophenyl)sulfonyl)amino)-3-pyridinyl)-1,3-benzothiazol-2-yl)acetamide;
N-(6-(6-chloro-5-((propylsulfonyl)amino)-3-pyridinyl)-1,3-benzothiazol-2-yl)acetamide;
N-(6-(5-((butylsulfonyl)amino)-6-chloro-3-pyridinyl)-1,3-benzothiazol-2-yl)acetamide;
N-(6-(6-chloro-5-(((1-methylethyl)sulfonyl)amino)-3-pyridinyl)-1,3-benzothiazol-2-yl)acetamide;
N-(6-(6-chloro-5-(((4-chlorophenyl)sulfonyl)amino)-3-pyridinyl)-1,3-benzothiazol-2-yl)acetamide;
N-(6-(6-chloro-5-((phenylsulfonyl)amino)-3-pyridinyl)-1,3-benzothiazol-2-yl)acetamide;
N-(6-(6-chloro-5-(((4-(difluoromethoxy)phenyl)sulfonyl)amino)-3-pyridinyl)-1,3-benzothiazol-2-yl)acetamide;
N-(6-(6-chloro-5-(((3-fluorophenyl)sulfonyl)amino)-3-pyridinyl)-1,3-benzothiazol-2-yl)acetamide;
N-(6-(6-chloro-5-(((3-(difluoromethoxy)phenyl)sulfonyl)amino)-3-pyridinyl)-1,3-benzothiazol-2-yl)acetamide;
N-(6-(6-chloro-5-(((3-chlorophenyl)sulfonyl)amino)-3-pyridinyl)-1,3-benzothiazol-2-yl)acetamide;
N-(6-(6-chloro-5-((2-thiophenylsulfonyl)amino)-3-pyridinyl)-1,3-benzothiazol-2-yl)acetamide;
N-(6-(6-chloro-5-((3-thiophenylsulfonyl)amino)-3-pyridinyl)-1,3-benzothiazol-2-yl)acetamide;
N-(6-(5-((benzylsulfonyl)amino)-6-chloro-3-pyridinyl)-1,3-benzothiazol-2-yl)acetamide;
N-(6-(6-chloro-5-(((4-methylphenyl)sulfonyl)amino)-3-pyridinyl)-1,3-benzothiazol-2-yl)acetamide;
N-(6-(6-chloro-5-(((4-(trifluoromethyl)phenyl)sulfonyl)amino)-3-pyridinyl)-1,3-benzothiazol-2-yl)acetamide;
N-(6-(5-(((4-tert-butylphenyl)sulfonyl)amino)-6-chloro-3-pyridinyl)-1,3-benzothiazol-2-yl)acetamide;
N-(5-(2-amino-1,3-benzothiazol-6-yl)-2-chloro-3-pyridinyl)-4-fluorobenzenesulfonamide;
N-(6-(6-chloro-5-(((5-chloro-2-thiophenyl)sulfonyl)amino)-3-pyridinyl)-1,3-benzothiazol-2-yl)acetamide;
N-(6-(5-(((4-methylphenyl)sulfonyl)amino)-3-pyridinyl)-1,3-benzothiazol-2-yl)acetamide;

N-(6-(5-(((4-methoxyphenyl)sulfonyl)amino)-3-pyridinyl)-1,3-benzothiazol-2-yl)acetamide;
N-(6-(5-(((4-(trifluoromethyl)phenyl)sulfonyl)amino)-3-pyridinyl)-1,3-benzothiazol-2-yl)acetamide;
N-(6-(5-(((3-(trifluoromethyl)phenyl)sulfonyl)amino)-3-pyridinyl)-1,3-benzothiazol-2-yl)acetamide;
N-(6-(5-(((4-fluorophenyl)sulfonyl)amino)-3-pyridinyl)-1,3-benzothiazol-2-yl)acetamide;
N-(6-(5-(((3-fluorophenyl)sulfonyl)amino)-3-pyridinyl)-1,3-benzothiazol-2-yl)acetamide;
N-(6-(5-(((3,4-dichlorophenyl)sulfonyl)amino)-3-pyridinyl)-1,3-benzothiazol-2-yl)acetamide;
N-(6-(5-(((4-tert-butylphenyl)sulfonyl)amino)-3-pyridinyl)-1,3-benzothiazol-2-yl)acetamide;
N-(6-(5-((phenylsulfonyl)amino)-3-pyridinyl)-1,3-benzothiazol-2-yl)acetamide;
N-(6-(2-(((4-fluorophenyl)sulfonyl)(methyl)amino)-4-pyrimidinyl)-1,3-benzothiazol-2-yl)acetamide;
N-(6-(2-(methyl(6-quinolinylsulfonyl)amino)-4-pyrimidinyl)-1,3-benzothiazol-2-yl)acetamide;
N-(6-(2-(((4-tert-butylphenyl)sulfonyl)(methyl)amino)-4-pyrimidinyl)-1,3-benzothiazol-2-yl)acetamide;
N-(6-(2-(methyl(2-thiophenylsulfonyl)amino)-4-pyrimidinyl)-1,3-benzothiazol-2-yl)acetamide;
N-(6-(2-(methyl(1-naphthalenylsulfonyl)amino)-4-pyrimidinyl)-1,3-benzothiazol-2-yl)acetamide;
N-(6-(2-((5-isoquinolinylsulfonyl)(methyl)amino)-4-pyrimidinyl)-1,3-benzothiazol-2-yl)acetamide;
N-(6-(2-(methyl(3-thiophenylsulfonyl)amino)-4-pyrimidinyl)-1,3-benzothiazol-2-yl)acetamide;
N-(6-(2-(((3,4-dimethylphenyl)sulfonyl)(methyl)amino)-4-pyrimidinyl)-1,3-benzothiazol-2-yl)acetamide;
N-(6-(2-(methyl((1-methyl-1H-imidazol-4-yl)sulfonyl)amino)-4-pyrimidinyl)-1,3-benzothiazol-2-yl)acetamide;
N-(6-(2-(((2,4-dimethylphenyl)sulfonyl)(methyl)amino)-4-pyrimidinyl)-1,3-benzothiazol-2-yl)acetamide;
N-(6-(2-(methyl((4-(trifluoromethyl)phenyl)sulfonyl)amino)-4-pyrimidinyl)-1,3-benzothiazol-2-yl)acetamide;
N-(6-(2-(methyl(2-naphthalenylsulfonyl)amino)-4-pyrimidinyl)-1,3-benzothiazol-2-yl)acetamide;
N-(6-(2-(methyl((4-methylphenyl)sulfonyl)amino)-4-pyridinyl)-1,3-benzothiazol-2-yl)acetamide;
N-(6-(2-(((4-methylphenyl)sulfonyl)amino)-4-pyridinyl)-1,3-benzothiazol-2-yl)acetamide;
N-(6-(2-(((4-methoxyphenyl)sulfonyl)amino)-4-pyridinyl)-1,3-benzothiazol-2-yl)acetamide;
N-(6-(5-(methyl((4-(trifluoromethyl)phenyl)sulfonyl)amino)-3-pyridinyl)-1,3-benzothiazol-2-yl)acetamide;
N-(6-(5-(((4-fluorophenyl)sulfonyl)(methyl)amino)-3-pyridinyl)-1,3-benzothiazol-2-yl)acetamide;
N-(6-(5-(((4-chlorophenyl)sulfonyl)(methyl)amino)-3-pyridinyl)-1,3-benzothiazol-2-yl)acetamide;
N-(6-(5-(((3,4-dichlorophenyl)sulfonyl)(methyl)amino)-3-pyridinyl)-1,3-benzothiazol-2-yl)acetamide;
N-(6-(5-(((3,4-difluorophenyl)sulfonyl)(methyl)amino)-3-pyridinyl)-1,3-benzothiazol-2-yl)acetamide;
N-(6-(5-(((4-tert-butylphenyl)sulfonyl)(methyl)amino)-3-pyridinyl)-1,3-benzothiazol-2-yl)acetamide;
N-(6-(5-(methyl(phenylsulfonyl)amino)-3-pyridinyl)-1,3-benzothiazol-2-yl)acetamide;
N-(6-(6-(methyl((3-methylphenyl)sulfonyl)amino)-2-pyridinyl)-1,3-benzothiazol-2-yl)acetamide;
N-(6-(6-(((2-fluorophenyl)sulfonyl)(methyl)amino)-2-pyridinyl)-1,3-benzothiazol-2-yl)acetamide;
N-(6-(6-(tert-butylamino)-2-pyrazinyl)-1,3-benzothiazol-2-yl)acetamide;
N-(5-(5-(((4-fluorophenyl)sulfonyl)amino)-3-pyridinyl)[1,3]thiazolo[5,4-b]pyridin-2-yl)acetamide;
N-(6-(5-(2-(2-oxo-1-pyrrolidinyl)ethoxy)-3-pyridinyl)-1,3-benzothiazol-2-yl)acetamide;
N-(6-(5-(2-(4-morpholinyl)ethoxy)-3-pyridinyl)-1,3-benzothiazol-2-yl)acetamide;
N-(6-(5-(1-methyl-2-(4-morpholinyl)ethoxy)-3-pyridinyl)-1,3-benzothiazol-2-yl)acetamide;
N-(6-(5-(2-(2-oxo-1,3-oxazolidin-3-yl)ethoxy)-3-pyridinyl)-1,3-benzothiazol-2-yl)acetamide;
N-(6-(5-(2-(1-piperidinyl)ethoxy)-3-pyridinyl)-1,3-benzothiazol-2-yl)acetamide;
N-(6-(5-(2-(1-azepanyl)ethoxy)-3-pyridinyl)-1,3-benzothiazol-2-yl)acetamide;
N-(6-(6-chloro-5-(tetrahydro-3-furanyloxy)-3-pyridinyl)-1,3-benzothiazol-2-yl)acetamide;
N-(6-(6-chloro-5-(1-methylethoxy)-3-pyridinyl)-1,3-benzothiazol-2-yl)acetamide;
N-(6-(6-chloro-5-((3S)-tetrahydro-3-furanyloxy)-3-pyridinyl)-1,3-benzothiazol-2-yl)acetamide;
N-(6-(6-bromo-5-methoxy-3-pyridinyl)-1,3-benzothiazol-2-yl)acetamide;
N-(6-(6-chloro-5-fluoro-3-pyridinyl)-1,3-benzothiazol-2-yl)acetamide;
N-(6-(6-chloro-5-ethoxy-3-pyridinyl)-1,3-benzothiazol-2-yl)acetamide;
N-(6-(6-chloro-5-methoxy-3-pyridinyl)-1,3-benzothiazol-2-yl)acetamide;
N-(6-(4-methoxy-3-pyridinyl)-1,3-benzothiazol-2-yl)acetamide;
N-(6-(6-methoxy-3-pyridinyl)-1,3-benzothiazol-2-yl)acetamide;
N-(6-(6-ethoxy-3-pyridinyl)-1,3-benzothiazol-2-yl)acetamide;
N-(6-(6-methoxy-4-methyl-3-pyridinyl)-1,3-benzothiazol-2-yl)acetamide;
N-(6-(4-methyl-3-pyridinyl)-1,3-benzothiazol-2-yl)acetamide;
N-(6-(6-chloro-4-methoxy-3-pyridinyl)-1,3-benzothiazol-2-yl)acetamide;
N-(6-(6-chloro-5-(difluoromethoxy)-3-pyridinyl)-1,3-benzothiazol-2-yl)acetamide;
N-(6-(4-(difluoromethoxy)-3-pyridinyl)-1,3-benzothiazol-2-yl)acetamide;
N-(6-(6-(difluoromethoxy)-3-pyridinyl)-1,3-benzothiazol-2-yl)acetamide;
N-(6-(6-(difluoromethoxy)-4-methyl-3-pyridinyl)-1,3-benzothiazol-2-yl)acetamide;
N-(6-(4-(hydroxymethyl)-3-pyridinyl)-1,3-benzothiazol-2-yl)acetamide;
N-(6-(5-(2-(3,3-dimethyl-2-oxo-1-pyrrolidinyl)ethoxy)-3-pyridinyl)-1,3-benzothiazol-2-yl)acetamide;
N-(6-(5-(2-(3-methyl-2-oxo-1-pyrrolidinyl)ethoxy)-3-pyridinyl)-1,3-benzothiazol-2-yl)acetamide;
N-(6-(5-(2-(3,3-difluoro-2-oxo-1-pyrrolidinyl)ethoxy)-3-pyridinyl)-1,3-benzothiazol-2-yl)acetamide;
N-(6-(5-(2-(3-fluoro-2-oxo-1-pyrrolidinyl)ethoxy)-3-pyridinyl)-1,3-benzothiazol-2-yl)acetamide;
N-(6-(6-chloro-5-(((4-(1-hydroxyethyl)phenyl)sulfonyl)amino)-3-pyridinyl)-1,3-benzothiazol-2-yl)acetamide;
N-(6-(6-chloro-5-(((4-(1-hydroxyethyl)phenyl)sulfonyl)amino)-3-pyridinyl)-1,3-benzothiazol-2-yl)acetamide (enantiomer A);
N-(6-(6-chloro-5-(((4-(1-hydroxyethyl)phenyl)sulfonyl)amino)-3-pyridinyl)-1,3-benzothiazol-2-yl)acetamide (entantiomer B);

N-(6-(5-(((4-(1-hydroxyethyl)phenyl)sulfonyl)amino)-3-pyridinyl)-1,3-benzothiazol-2-yl)acetamide;
N-(6-(3-(((4-methoxyphenyl)sulfonyl)amino)phenyl)-1,3-benzothiazol-2-yl)acetamide;
N-(6-(2-(tetrahydro-2H-pyran-4-ylamino)-4-pyrimidinyl)-1,3-benzothiazol-2-yl)acetamide;
N-(6-(2-((2R)-2-(2-methylphenyl)-1-pyrrolidinyl)-4-pyrimidinyl)-1,3-benzothiazol-2-yl)acetamide;
N-(6-(2-(1-piperidinyl)-4-pyrimidinyl)-1,3-benzothiazol-2-yl)acetamide;
N-(6-(2-(2-pyridinylamino)-4-pyrimidinyl)-1,3-benzothiazol-2-yl)acetamide;
N-(6-(2-(1-piperidinylamino)-4-pyrimidinyl)-1,3-benzothiazol-2-yl)acetamide;
N-(6-(2-((2R)-2-phenyl-1-pyrrolidinyl)-4-pyrimidinyl)-1,3-benzothiazol-2-yl)acetamide;
N-(6-(6-cyano-5-(((4-methoxyphenyl)sulfonyl)amino)-3-pyridinyl)-1,3-benzothiazol-2-yl)acetamide;
N-(6-(5-amino-6-cyano-3-pyridinyl)-1,3-benzothiazol-2-yl)acetamide;
N-(6-(6-chloro-5-(dimethylamino)-3-pyridinyl)-1,3-benzothiazol-2-yl)acetamide;
phenyl (6-(6-chloro-5-(dimethylamino)-3-pyridinyl)-1,3-benzothiazol-2-yl)carbamate;
N-(6-(6-chloro-5-(dimethylamino)-3-pyridinyl)-1,3-benzothiazol-2-yl)-2-methoxyacetamide;
N-(6-(6-chloro-5-(dimethylamino)-3-pyridinyl)-1,3-benzothiazol-2-yl)-2-phenoxyacetamide;
1-(6-(6-chloro-5-(dimethylamino)-3-pyridinyl)-1,3-benzothiazol-2-yl)-3-(2-(4-morpholinyl)ethyl)urea;
6-(6-chloro-5-(dimethylamino)-3-pyridinyl)-1,3-benzothiazol-2-amine;
N-(6-(6-chloro-5-(dimethylamino)-3-pyridinyl)-1,3-benzothiazol-2-yl)-N~2~,N~2~-dimethylglycinamide;
N-(6-(6-chloro-5-(dimethylamino)-3-pyridinyl)-1,3-benzothiazol-2-yl)methanesulfonamide; di-tert-butyl (5-(2-(acetylamino)-1,3-benzothiazol-6-yl)-2-chloro-3-pyridinyl)imidodicarbonate;
N-(6-(5-(cyanomethoxy)-3-pyridinyl)-1,3-benzothiazol-2-yl)acetamide;
N-(6-(5-fluoro-3-pyridinyl)-1,3-benzothiazol-2-yl)acetamide;
N-(6-(6-chloro-5-(1-cyanoethoxy)-3-pyridinyl)-1,3-benzothiazol-2-yl)acetamide;
N-(6-(2-chloro-5-(1-cyanoethoxy)-3-pyridinyl)-1,3-benzothiazol-2-yl)acetamide;
N-(6-(6-chloro-5-((2-methoxyethoxy)methoxy)-3-pyridinyl)-1,3-benzothiazol-2-yl)acetamide;
N-(6-(5-((2-methoxyethoxy)methoxy)-6-(trifluoromethyl)-3-pyridinyl)-1,3-benzothiazol-2-yl)acetamide;
N-(6-(5-(((2R)-5-oxo-2-pyrrolidinyl)methoxy)-3-pyridinyl)-1,3-benzothiazol-2-yl)acetamide;
N-(6-(5-((1-aminocyclopropyl)methoxy)-3-pyridinyl)-1,3-benzothiazol-2-yl)acetamide;
N-(6-(5-hydroxy-3-pyridinyl)-1,3-benzothiazol-2-yl)acetamide;
N-(6-(6-chloro-3-pyridinyl)-1,3-benzothiazol-2-yl)acetamide;
N-(2-((5-(2-(acetylamino)-1,3-benzothiazol-6-yl)-3-pyridinyl)oxy)ethyl)-2-methoxyacetamide;
N-(6-(6-(3-azabicyclo[322]non-3-yl)-2-pyrazinyl)-1,3-benzothiazol-2-yl)acetamide;
N-(6-(6-chloro-5-hydroxy-3-pyridinyl)-1,3-benzothiazol-2-yl)acetamide;
N-(6-(5-hydroxy-6-(trifluoromethyl)-3-pyridinyl)-1,3-benzothiazol-2-yl)acetamide;
5-(2-(acetylamino)-1,3-benzothiazol-6-yl)-2-chloro-3-pyridinyl acetate;
N-(6-(6-chloro-5-(((4-methoxyphenyl)sulfonyl)amino)-3-pyridinyl)-1,3-benzothiazol-2-yl)cyclohexanecarboxamide;
N-(2-chloro-5-(2-((1-methylethyl)amino)-1,3-benzothiazol-6-yl)-3-pyridinyl)-4-methoxybenzenesulfonamide;
N-(2-chloro-5-(2-((cyclohexylmethyl)amino)-1,3-benzothiazol-6-yl)-3-pyridinyl)-4-methoxybenzenesulfonamide;
N-(5-(2-amino-1,3-benzothiazol-6-yl)-2-chloro-3-pyridinyl)-3-(difluoromethoxy)benzenesulfonamide;
N-(5-(2-amino-1,3-benzothiazol-6-yl)-2-chloro-3-pyridinyl)-2-chloro-4-(trifluoromethyl)benzenesulfonamide;
N-(5-(2-amino-1,3-benzothiazol-6-yl)-2-chloro-3-pyridinyl)-2-chloro-4-fluorobenzenesulfonamide;
N-(5-(2-amino-1,3-benzothiazol-6-yl)-2-chloro-3-pyridinyl)-2,4-dichlorobenzenesulfonamide;
N-(5-(2-amino-1,3-benzothiazol-6-yl)-2-chloro-3-pyridinyl)-2,4-difluorobenzenesulfonamide;
N-(5-(2-amino-1,3-benzothiazol-6-yl)-2-chloro-3-pyridinyl)-4-fluoro-2-methylbenzenesulfonamide;
N-(5-(2-amino-1,3-benzothiazol-6-yl)-2-chloro-3-pyridinyl)-4-chloro-2-fluorobenzenesulfonamide;
N-(5-(2-amino-1,3-benzothiazol-6-yl)-2-chloro-3-pyridinyl)-2-(trifluoromethyl)benzenesulfonamide;
6-(5-(tert-butylamino)-6-chloro-3-pyridinyl)-1,3-benzothiazol-2-amine;
N-(6-(6-chloro-5-((1-piperidinylsulfonyl)amino)-3-pyridinyl)-1,3-benzothiazol-2-yl)acetamide;
N-(2-chloro-5-(2-(methylamino)-1,3-benzothiazol-6-yl)-3-pyridinyl)-4-fluorobenzenesulfonamide;
2-chloro-N-(2-chloro-5-(2-(methylamino)-1,3-benzothiazol-6-yl)-3-pyridinyl)-6-methylbenzenesulfonamide;
2,6-dichloro-N-(2-chloro-5-(2-(methylamino)-1,3-benzothiazol-6-yl)-3-pyridinyl)benzenesulfonamide;
N-(2-chloro-5-(2-(methylamino)-1,3-benzothiazol-6-yl)-3-pyridinyl)-2-fluorobenzenesulfonamide;
4-acetyl-N-(2-chloro-5-(2-(methylamino)-1,3-benzothiazol-6-yl)-3-pyridinyl)benzenesulfonamide;
N-(1-(4-((2-chloro-5-(2-(methylamino)-1,3-benzothiazol-6-yl)-3-pyridinyl)sulfamoyl)phenyl)-1-methylethyl)acetamide;
N-(1-(4-((5-(2-amino-1,3-benzothiazol-6-yl)-2-chloro-3-pyridinyl)sulfamoyl)phenyl)-1-methylethyl)acetamide;
N-(5-(2-amino-1,3-benzothiazol-6-yl)-2-chloro-3-pyridinyl)-4-(1-hydroxy-1-methylethyl)benzenesulfonamide;
4-acetyl-N-(5-(2-amino-1,3-benzothiazol-6-yl)-2-chloro-3-pyridinyl)benzenesulfonamide;
N-(5-(1,3-benzoxazol-6-yl)-2-chloro-3-pyridinyl)-4-fluorobenzenesulfonamide;
N-(2-chloro-5-(2-(methylsulfanyl)-1,3-benzothiazol-6-yl)-3-pyridinyl)-4-methoxybenzenesulfonamide;
5-(1,3-benzothiazol-6-yl)-2-chloro-3-pyridinol;
5-(1,3-benzothiazol-6-yl)-2-chloro-3-pyridinyl acetate;
1-(5-(1,3-benzothiazol-6-yl)-3-pyridinyl)ethanone; or
6-fluoro-5-(2-methyl-1,3-benzothiazol-6-yl)-2-(trifluoromethyl)-3-pyridinol,
or a pharmaceutically acceptable salt thereof.

DEFINITIONS

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$alkyl" or "$C_\alpha$-$C_\beta$alkyl", when used either alone or within other terms such as "haloalkyl" and "alkylamino", means a linear or branched hydrocarbon chain ("alkyl") having a specified range ($\alpha$ to $\beta$) of carbon atoms (such as $C_1$-$C_{10}$). The term "lower alkyl" means having one to six carbon atoms. Examples of "lower alkyl" radicals include methyl, ethyl, n-propyl, isopropyl, n-butyl, isobutyl, sec-butyl, tert-butyl, pentyl, isoamyl, hexyl and the like. The term "alkylenyl", when used alone or in combination, means divalent alkyl radicals such as methylenyl and ethylenyl.

The term "alkenyl", when used alone or in combination, means a linear or branched hydrocarbon chain having at least one carbon-carbon double bond. The hydrocarbon chain can have from two and ten carbon atoms. The term "lower alkenyl" means radicals having two to six carbon atoms. Examples of lower alkenyl include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, means linear or branched hydrocarbon chains having at least one carbon-carbon triple bond and having two to ten carbon atoms. The term "lower alkynyl" means hydrocarbon chains having two to six carbon atoms. Examples of lower alkynyl radicals include, without limitation, ethynyl, propynyl (propargyl), butynyl, and the like.

The term "alkoxy", when used alone or in combination, means linear or branched oxygen-containing hydrocarbon chains, each having alkyl portions of one or more carbon atoms. For example, the term includes both —OR and —ROR radicals wherein R is an alkyl group. The term "lower alkoxy" means oxygen-containing hydrocarbon chains having one to six carbon atoms. Examples of lower alkoxy include methoxy, ethoxy, propoxy, butoxy, tert-butoxy and dimethylether. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means an aromatic (fully unsaturated) carbocyclic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. However, the point of attachment of an aryl group to the group in question will be on the aromatic ring. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a fully saturated ring moiety formed from carbon atoms and containing one ("monocyclic"), two ("bicyclic") or even three ("tricyclic") rings attached together in a fused manner. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. The ring itself, as well as any substitutents thereon, may be attached at any atom that allows a stable compound to be formed.

The term "cycloalkenyl", when used alone or in combination, means a partially saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, means an alkyl radical having one or more of the hydrogen atoms of the hydrocarbon chain substituted with halogen atom. Thus, the term includes monohaloalkyl, dihaloalkyl and polyhaloalkyl radicals such as a perhaloalkyl. A monohaloalkyl radical, for example, may have a single iodo, bromo, chloro or fluoro halogen atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means an aromatic ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. However, the point of attachment of a heteroaryl group to the group in question will be on the aromatic ring. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocycle", when used alone or in combination, means a partially or fully saturated ring moiety formed from carbon atoms and including one or more heteroatoms selected from N, O or S. The ring moiety may contain one, two or even three rings wherein such rings may be attached together in a fused manner. The point of attachment of a heterocycle to the group in question will be on a partially of fully saturated ring. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also includes radicals which are fused/condensed with aryl groups or heteroaryl groups containing 1 to 5 nitrogen atoms, for example, indolinyl, isoindolinyl, indolizinyl, pyridyl, pyrimidyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

Examples of heterocycles include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "oxo", whether used alone or with other terms, means a carbonyl radical —(C=O)—.

The term "aminocarbonyl" denotes an amide group of the formula —C(=O)NH$_2$.

The term "alkylthio" embraces radicals containing a linear or branched alkyl radical, of one to ten carbon atoms, attached to a divalent sulfur atom. An example of "alkylthio" is methylthio, (CH$_3$S—).

The term "haloalkylthio" embraces radicals containing a haloalkyl radical, of one to ten carbon atoms, attached to a divalent sulfur atom. An example of "haloalkylthio" is trifluoromethylthio.

The term "aminoalkyl" embraces linear or branched alkyl radicals having one to about ten carbon atoms any one of which may be substituted with one or more amino radicals. Examples of aminoalkyl radicals include "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "pharmaceutically acceptable" when used with reference to a compound of Formula I, II, III, IV, V or VI is intended to refer to a form of the compound that is acceptable for use or administration. For example, a salt form, a solvate, a hydrate or derivative form of a compound of the present invention, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I, II, III, IV, V and VI are the pharmaceutically acceptable salt forms of the free-base compounds. The term "pharmaceutically acceptable salts" includes salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I, II, III, IV, V or VI may be prepared from an inorganic acid or from an organic acid. Examples of such inorganic acids are hydrochloric (HCl), hydrobromic (HBr), hydroiodic (HI), hydrofluoric (HF), nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, trifluoroacetic (TFA), undecanoic, stearic, algenic, β-hydroxybutyric, salicylic, galactaric and galacturonic acid.

Other examples include salts with alkali metals or alkaline earth metals such as sodium, potassium, calcium or magnesium, or with organic bases.

Suitable pharmaceutically-acceptable base addition salts of compounds of Formulas I, II, III, IV, V or VI include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, diisopropylethylamine and trimethylamine.

Also, basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. water or oil-soluble or dispersible products are thereby obtained.

All of these salts may be prepared by conventional means from the corresponding compound of the invention by reacting, for example, the appropriate acid or base with the a compound of Formula I, II, III, IV, V, or VI. Examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein.

Similarly, hemi-, mono-, di, tri- and poly-hydrated forms and solvated forms of the compounds of Formulas I, II, III, IV, V and VI are also contemplated herein.

The compound(s) of Formulas I, II, III, IV, V, or VI may be used to treat a subject by administering the compound(s) as a pharmaceutical composition. To this end, the compound(s) can be combined with one or more carriers, diluents or adjuvants to form a suitable composition, which is described in more detail herein.

The term "excipient", as used herein, denotes any pharmaceutically acceptable additive, carrier, diluent, adjuvant, or other suitable ingredient, other than the active pharmaceutical ingredient (API), which is typically included for formulation and/or administration purposes.

"Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "therapeutically effective amount" is intended to quantify the amount of each compound or agent, which can be used to treat the disorder. This amount may reduce the severity and frequency of incidence of such disorder. For example, effective neoplastic therapeutic agents prolong the survivability of the patient, inhibit the rapidly-proliferating cell growth associated with the neoplasm, or effect a regression of the neoplasm.

The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer.

General Synthetic Procedures

The present invention further comprises procedures for the preparation of a compound of Formulas I, II, III, IV, V or VI. The compounds of Formulas I, II, III, IV, V or VI can be synthesized according to the procedures described in the following exemplary schematic methods 1-4, wherein the substituents are as defined in Formulas I, II, III, IV, V or VI herein, except where further noted. The synthetic methods described below are merely exemplary, and the compounds of the invention may be synthesized by alternate routes as appreciated by persons of ordinary skill in the art.

Below is a list of abbreviations used in the specification:

| | |
|---|---|
| ACN | acetonitrile |
| BSA | bovine serum albumin |
| $Cs_2CO_3$ | cesium carbonate |
| $CHCl_3$ | chloroform |
| DCM | dichloromethane, methylene chloride |
| mCPBA | meta-chloro peroxybenzoic acid |
| DIBAL | diisobutylaluminum hydride |
| DIC | 1,3-diisopropylcarbodiimide |
| DIEA | diisopropylethylamine |
| DME | dimethoxyethane |
| DMF | dimethylformamide |
| DMSO | dimethylsulfoxide |
| EDC | 1-(3-dimethylaminopropyl)-3-ethylcarbodiimide |
| $Et_2O$ | diethyl ether |
| EtOAc | ethyl acetate |
| FBS | fetal bovine serum |
| gm | gram |
| hr | hour |

| | |
|---|---|
| HATU | O-(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HPLC | high pressure liquid chromatography |
| IPA | isopropyl alcohol |
| K$_2$CO$_3$ | potassium carbonate |
| KI | potassium iodide |
| MgSO$_4$ | magnesium sulfate |
| MeOH | methanol |
| NaBH$_4$ | sodium borohydride |
| NaHCO$_3$ | sodium bicarbonate |
| NaOCH$_3$ | sodium methoxide |
| NaOH | sodium hydroxide |
| Na$_2$SO$_4$ | sodium sulfate |
| PBS | phospate buffered saline |
| Pd/C | palladium on carbon |
| Pd(PPh$_3$)$_4$ | palladium(0)triphenylphosphine tetrakis |
| Pd(dppf)Cl$_2$ | palladium(1,1-bisdiphenylphosphinoferrocene) II chloride |
| Pd$_2$(dba)$_3$ | bis(dibenzylideneacetone) palladium |
| POCl$_3$ | phosphorus oxychloride |
| PyBop | benzotriazol-1-yl-oxy-tripyrrolidino-phosphonium hexafluorophosphate |
| RBF | round bottom flask |
| RT | room temperature |
| TBTU | O-benzotriazol-1-yl-N,N,N',N'-tetramethyluronium tetrafluoroborate |
| TEA | triethylamine |
| TFA | trifluoroacetic acid |
| THF | tetrahydrofuran |

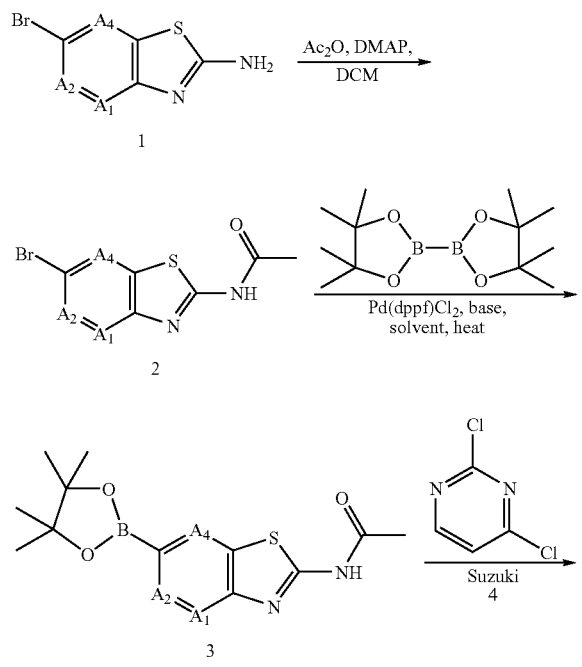

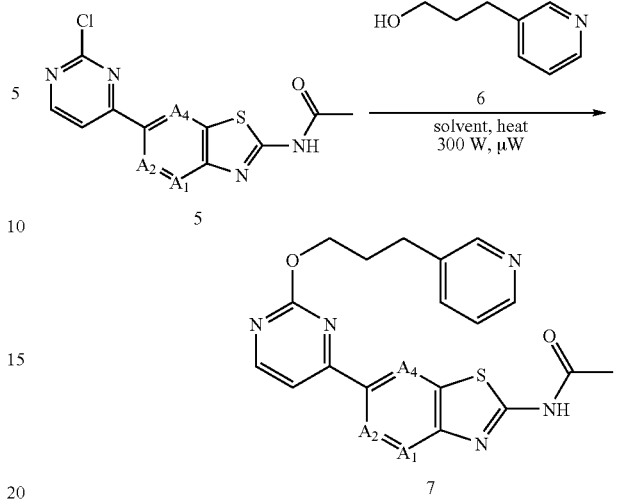

A method for making compounds of Formula 7 is described in Scheme 1. As shown, a desirably substituted fused bromo-amino-thiazole 1 can be acetylated with acetic anhydride in the presence of a suitable base, such dimethylaminopyridine (DMAP) in a suitable solvent, such as DCM, as shown, to form the acetyl adduct 2. The bromide of compound 2 may then be converted to the corresponding boronate using known, conventional methods, such as the cyclic boronate shown in the presence of a palladium catalyst, base such as potassium acetate in a suitable solvent such as DMSO to form the corresponding boronic acid intermediate 3. Heat may or may not be required to efficiently prepare intermediate 3. Intermediate 3 can be reacted with a desired halogen substituted R$^5$ ring or Y group in Formula II, such as a chloro-substituted pyrimidine ring 4 as shown, under suitable Suzuki or Suzuki-like conditions to provide the corresponding pyrimidine-substituted adduct 5. Suzuki conditions are described herein below. The chloride functionality of compound 5 may be further functionalized as desired. For example, as shown above in Scheme 1, the chloride may be displaced with a suitable nucleophilic intermediate, such as the alcohol 6 as shown in Scheme 1, under suitable conditions such as in pyridine with heat under a microwave UV, to afford the corresponding compound 7. Other suitable nucleophiles include without limitation, sulfur and amino nucleophiles, as appreciated by those of ordinary skill in the art.

The Suzuki method of forming compound 5 is a reaction using a borane reagent, such as a dioxaborolane intermediate (not shown) or a boronic acid 3 and a suitable leaving group containing reagent, such as the halo-substituted compound 4. As appreciated by one of ordinary skill in the art, Suzuki reactions also use palladium as a catalyst, in the presence of a suitable base, such as a carbonate base, bicarbonate or an acetate base, in a suitable solvent, such as toluene, acetonitrile, DMF or an aqueous-organic solvent combination (such as dioxanes/water) or a biphasic system of solvents (such as toluene/aq. NaCO$_3$). Suitable palladium reagents include Pd(PPh$_3$)$_4$, Pd(OAc)$_2$ or Pd(dppf)Cl$_2$. Where LG is a halide, the halide may be an iodide, a bromide or even a chloride (chloro-pyridyl or chloro-picolinyl B rings undergo suzuki reactions in the presence of Pd(OAc)$_2$). In addition, a corresponding halo intermediate, the C-D ring piece or the B-A ring piece, may be converted to the borane, such as the dioxaborolane as described in Scheme 6. Other LGs are also suitable. For example, Suzuki couplings are known to occur with a sulfonate, such as trifluoromethanesulfonate, as the leaving group.

Scheme 2 (Method D)

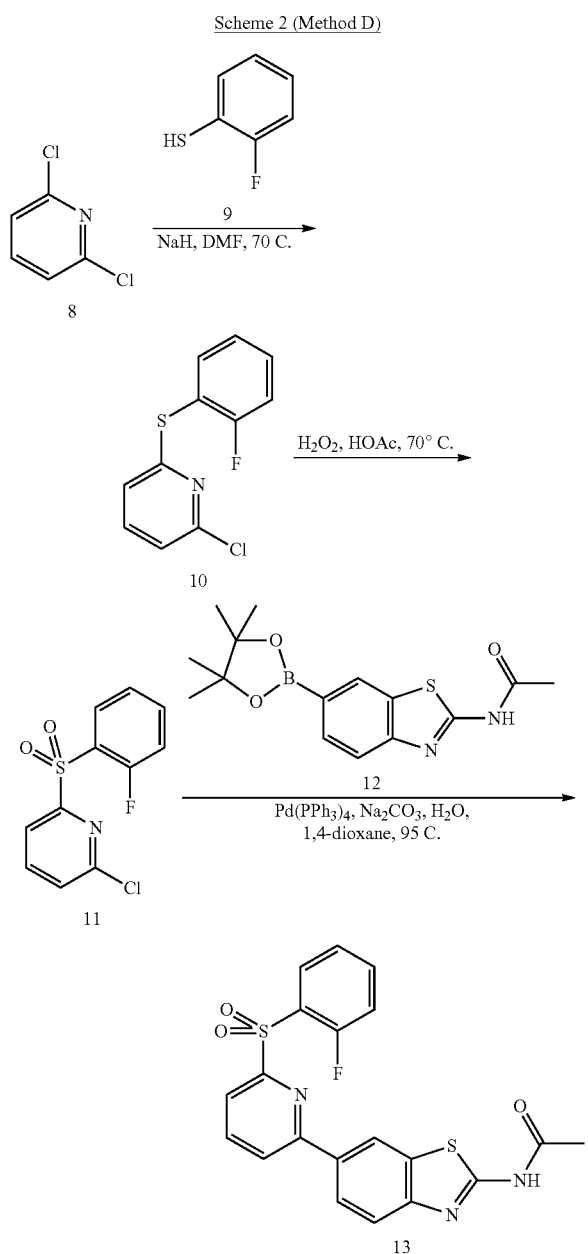

Scheme 2 illustrates a method for making compounds of Formula 13. As shown, a dichloro pyridine 8 may be reacted with a suitable substituted thiophenol 9 in the presence of a suitable base capable of deprotonating the thiol proton, such as NaH to afford the corresponding thioether adduct 10. The sulfide may be oxidized to the corresponding sulfone 11 using known, conventional methods, such as with peroxide as shown, in the presence of suitable conditions, such as HOAc as shown in scheme 2. The corresponding chloro-pyridyl-sulfone 11 can then be reacted with a desired boronic acid, such as intermediate 12 shown above, in a Suzuki-type reaction (see scheme 1) to afford the corresponding desired compound of Formula 13. Note that the method described in scheme 2 to prepare specific compound 13 is an exemplary method and merely representative of one method which may be utilized to prepare compounds of the present invention.

Scheme 3 (Method E)

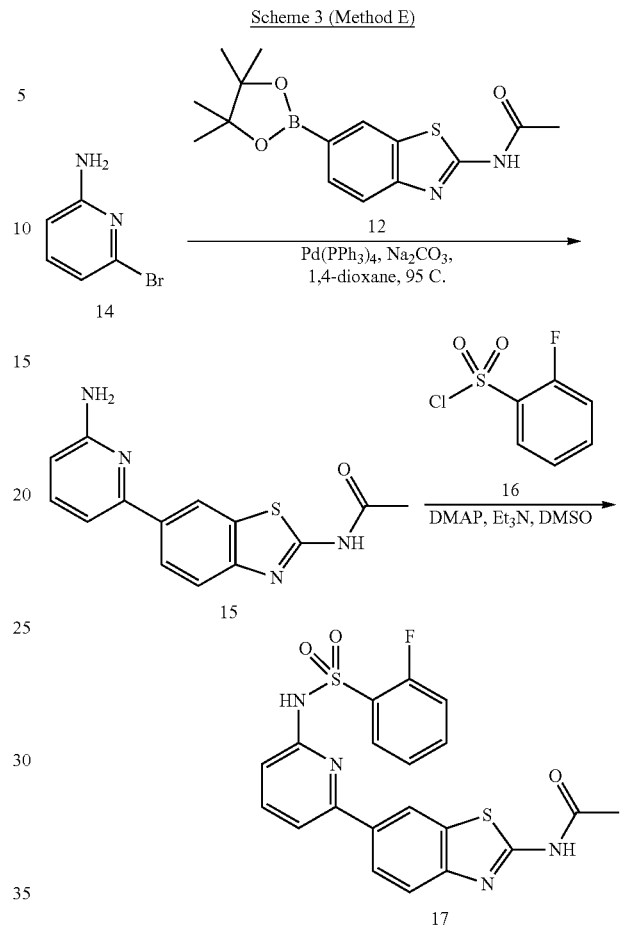

Scheme 3 illustrates a method for making compounds of Formula 17. As shown, a bromo amino-pyridine 14 may be reacted with a suitably substituted boronic acid 12 in the presence of conventional Suzuki conditions to afford the corresponding amino-pyridyl benzothiazole adduct 15. The free amine group of compound 15 may be functionalized by reaction with a sulfonylchloride 16 to afford the corresponding sulfonamide 17 using known, conventional methods, as shown in scheme 3. Note that the method described in scheme 3 to prepare specific compound 17 is an exemplary method and merely representative of one method which may be utilized to prepare compounds of the present invention.

Similarly, $R^7$ groups may be amide linked groups, urea-linked groups and others, as defined herein. Amides may be made from the chloride or other LG pre-cursor (not shown). The LG can be displaced by a carbon nucleophile and then oxidized up to the corresponding carboxylic acid. The acid functional group can be activated with known activating groups, such as an acid chloride, and reacted with desired species to form the desired compounds of the present invention. For example, to form an amide bond, an ester, a carbamate, a urea, and the like, each of the two starting materials must possess one or the other of an electrophilic ($E^+$) and a nucleophile ($Nu^-$). The acid may be the $E^+$ by activating it with a component "X". X in this context refers generally to a "leaving group" such as a halide (bromine, chlorine, iodine or fluorine), alkylsulfonate and other known groups (also see definitions herein). $Nu^-$ refers generally to a nucleophilic species such as a primary or secondary amine, an oxygen, a sulfur or a anionic carbon species. Examples of nucleophiles include, without limitation, amines, hydroxides, alkoxides and the like. E+ refers generally to an electrophilic species, such as the carbon atom of a carbonyl, which is susceptible to nucleophilic attack or readily eliminates. Examples of suitable electrophilic carbonyl species include, without limitation, acid halides, mixed anhydrides, aldehydes, carbamoylchlorides, sulfonyl chlorides, acids activated with activating reagents such as TBTU, HBTU, HATU, HOBT, BOP, PyBOP and carbodiimides (DCC, EDC and the like), and other electrophilic species including halides, isocyanates, daizonium ions and the like.

For example, an amide or a sulfonamide linkage where the Nu– is an amine can be made utilizing an amine on either the B or A rings and an acid chloride or sulfonyl chloride on the other of either the B or A rings. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates where Nu– is an amine, anhydrides where Nu– is an oxygen, reverse amides where Nu– is an amine and E+ is an acid chloride, ureas, thioamides and thioureas where the respective carbonyl oxygen is a sulfur, thiocarbamates where the respective carbonyl oxygen and/or carbamate oxygen is a sulfur, and the like, can be made utilizing similar methods as described for the amide or sulfonamide bond above. While the above methods are so described, they are not exhaustive, and other methods for linking rings A and B together may be utilized as appreciated by those skilled in the art.

The amide may be converted to the corresponding thioamide with a suitable reagent, such as Lawesson's Reagent, as appreciated by those skilled in the art.

Scheme 4 (Method G)

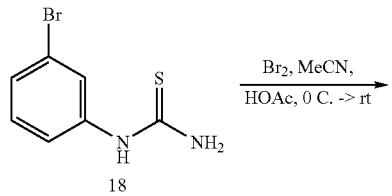

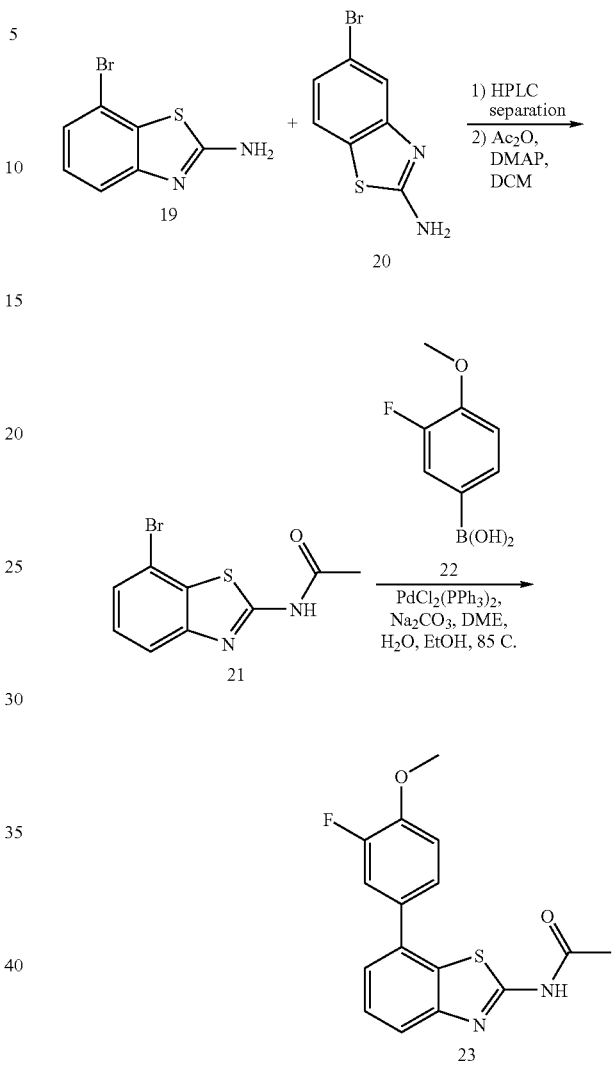

Scheme 4 illustrates an exemplary method for preparing compounds of Formula 23. As shown, a bromo sulfonamidophenyl 18 may be cyclized in the presence of bromine and acid to afford the corresponding ring closed benzothiazole 19. Compound 19 can be acetylated using conventional methods such as that shown above, to provide the acetyl adduct 21. The bromide of compound 21 now can serve as a handle for coupling desired boronic acids, such as compound 22 to afford the final compounds 23. Note that the method described in scheme 4 to prepare specific compound 23 is an exemplary method and merely representative of one method which may be utilized to prepare compounds of the present invention.

While the above Schemes 1, 2, 3 and 4 describe methods of making compounds as shown, the strategy employed may be utilized to make other compounds of the present invention, as appreciated by those of ordinary skill in the art. For example, while the schemes describe methods for making a benzothiazole compound, the methods used may also be applied to make benzoxazole compounds. Similarly, while the schemes generally describe benzothiazole rings, the methods may be used to prepare aza- and diaza-benzothiazole rings, such as those described herein. Similarly, while the schemes generally describe pyrimidine and pyridine $R^5$ rings, the methods may be used to prepare 5-membered and other 6-membered $R^5$ rings, such as those described herein. It is appreciated and understood by persons of ordinary skill in the art that certain conditions will not be universal and may not be used to make every ring or compound contemplated herein. Similarly, the methods teaching how to make the $R^3$, $R^4$ and $R^5$ groups above, may be applicable in making other $R^3$, $R^4$ and $R^5$ groups contemplated herein. Further, while many compounds illustrated in schemes 1-4 show one $R^2$ group (acetyl), similar compounds with other $R^2$ groups may also be made using similar methods.

The following analytical methods were used, unless otherwise noted, to identify the intermediates and compounds exemplified herein.

Analytical Methods:

Unless otherwise indicated, HPLC analyses and liquid chromatography-mass spectroscopy (LC-MS) procedures were run on an Agilent Model 1100 system utilizing one of the following two columns and methods:

(A) Using an Agilent Technologies Zorbax SB-$C_8$ (5µ) reverse phase column (4.6×150 mm; Part no. 883975-906, Santa Clara, Calif.) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

(B) Using a Synergi MAX-RP (Phenomenex, Torrance, Calif.)$_{5µ,\ 50×2.0}$ mm column with the same solvent system, a flow rate of 0.8 ml/min, and a gradient of 10%->100% B for the first two minutes, then 100% B for 1.8 minutes, and then a return to 10% B over 0.2 minutes.

LC-MS Method:

Samples were run on an Agilent model-1100 LC-MSD system with an Agilent Technologies XDB-$C_8$ (3.5µ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation (Gilson, Middleton, Wis.) utilizing one of the following three columns and methods:

(A) Using a 50×100 mm column (Waters, Exterra, C18, 5µ, Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 min gradient from 40% to 100% solvent B followed by a 5 min flow of 100% solvent B. The gradient was followed by a 2 min return to 40% solvent B.

(B) Using a 20×50 mm column at 20 mL/min. The mobile phase used was a mixture of solvent A ($H_2O$/0.1% TFA) and solvent B (ACN/0.11% TFA) with a 10 min gradient from 5% to 100% solvent B. The gradient is followed by a 2 min return to 5% ACN.

(C) Using a 150×30 mm column (Gemini, 5µ, C18, Phenomenex, Torrance, Calif.) at 20 ml/min. The mobile phase and solvent systems used were the same as in method B. The time gradient was 10%->100% solvent B over 28 minutes, followed by a 2 min return to 10% solvent B.

Proton NMR Spectra:

Unless otherwise indicated, all $^1H$ NMR spectra were run on a Varian (Palo Alto, Calif.) series Mercury 300 MHz instrument or a Bruker (Madison, Wis.) series 400 MHz instrument. Where so characterized, all observed protons are reported as parts-per-million (ppm) downfield from tetramethylsilane (TMS) or other internal reference in the appropriate solvent indicated.

Mass Spectra (MS):

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

Various experimental methods have been employed to synthesize the compounds of the present invention, as more generally described in Schemes 1-4 above, and further described in more detail by the representative examples 1-341 below. Table I following the written examples provides biological data relating to the examples.

Example 1

(Method A)

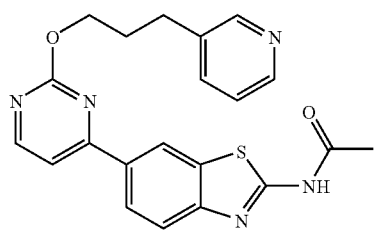

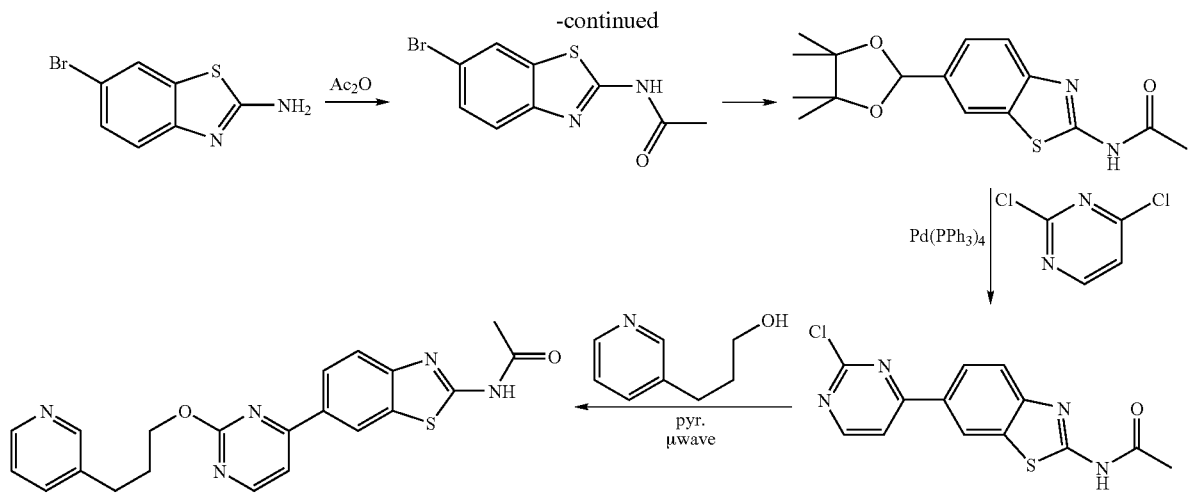

N-(6-(2-(3-(pyridin-3-yl)propoxy)pyrimidin-4-yl)benzo[d]thiazol-2-yl)acetamide

Step 3. N-(6-(2-Chloropyrimidin-4-yl)benzo[d]thiazol-2-yl)acetamide

Step 1. N-(6-bromobenzo[d]thiazol-2-yl)acetamide

6-Bromobenzo[d]thiazol-2-amine (Aldrich, St. Louis, Mo.; 10.02 g, 43.7 mmol) was suspended in DCM (175 mL) to which DMAP (6.107 g, 50.0 mmol) was added. The flask was cooled in an ice water bath under argon, and acetic anhydride (4.60 mL, 48.8 mmol) was added, and the reaction was warmed to RT and stirred overnight. The reaction was washed with 10% HCl and water. The precipitate in the organic phase was filtered. The aqueous washings were extracted with DCM and 10:1 DCM/MeOH. These extracts were concentrated, combined with the filtrate from the above filtration, and concentrated again. The solid was collected (from the filtration as well as the aqueous workup), concentrated, and dried under vacuum to afford the desired N-(6-bromobenzo[d]thiazol-2-yl)acetamide (12.30 g, 45.39 mmol, 88% purity, 91% yield). MS (ESI pos. ion) m/z: 271 (MH+, $^{79}$Br), 273 (MH+, $^{81}$Br). Calculated exact mass for $C_9H_7BrN_2OS$: 270 ($^{79}$Br), 272 ($^{81}$Br).

Step 2. N-(6-(4,4,5,5-tetramethyl-1,3,2-dioxaborolan-2-yl)benzo[d]thiazol-2-yl)acetamide N-(6-Bromobenzo[d]thiazol-2-yl)acetamide (10.29 g, 38.0 mmol), 4,4,5,5-tetramethyl-2-(4,4,5,5-tetramethyl-1,3,2-dioxaborolan-2-yl)-1,3,2-dioxaborolane (13.34 g, 52.53 mmol), and potassium acetate (14.9 g, 152 mmol) were suspended in DMSO (140 mL) to which 1,1'-bis(diphenylphosphino)ferrocene]dichloride palladium(ii) (2.81 g, 3.84 mmol) (a 1:1 complex with DCM, 3.44 mmol) was added. Argon was bubbled through the suspension for about 1 minute, and the reaction flask was placed in a preheated oil bath (100° C.) and heated while stirring under argon overnight. The reaction was then cooled to RT and filtered through Celite® (diatomaceous earth), which was washed with MeOH. The filtrate was partially concentrated, and poured into water (500 mL), and extracted repeatedly with DCM. The organic extracts were combined, concentrated, and purified on a silica gel filter (~3 inches; DCM to 50:1 to 30:1 DCM/MeOH). The fractions containing product were collected, concentrated, and dried under vacuum to afford the desired boronic ester (14.22 g). MS (ESI pos. ion) m/z: 319. Calculated exact mass for $C_{15}H_{19}BN_2O_3S$: 318.

2,4-Dichloropyrimidine (1.060 g, 7115 μmol) and N-(6-(4,4,5,5-tetramethyl-1,3,2-dioxaborolan-2-yl)benzo[d]thiazol-2-yl)acetamide (2.86 g, 8988 μmol) were suspended in 1,4-dioxane (40 mL) to which palladium tetrakis (triphenylphosphine) (782 mg, 677 μmol) was added, followed by 2 mL of 1,4-dioxane and sodium carbonate (7.1 mL, 2.0 M in water, 14200 μmol). Argon was bubbled through the solution for about 1 minute, and the flask was fit with a reflux condenser and placed in a preheated oil bath (95 C) and heated while stirring under argon. When LCMS indicated a complete reaction, the reaction flask was cooled to RT and filtered through Celite® (diatomaceous earth). The Celite® (diatomaceous earth) pad was washed with 1,4-dioxane, and 1:1 DCM/MeOH. The filtrate was concentrated, treated with DCM, and filtered. The solid was washed with DCM, collected, and dried under vacuum to afford the desired product (1.28 g, 4.20 mmol, 95% purity, 56% yield). MS (ESI pos. ion) m/z: 305. Calculated exact mass for $C_{13}H_9ClN_4OS$: 304.

Step 4. N-(6-(2-(3-(pyridin-3-yl)propoxy)pyrimidin-4-yl)benzo[d]thiazol-2-yl)acetamide N-(6-(2-Chloropyrimidin-4-yl)benzo[d]thiazol-2-yl)acetamide (59.4 mg, 195 μmol) and 3-pyridinepropanol (0.25 mL, 1.9 mmol) were suspended in pyridine (0.80 mL) in a microwave vial, which was then sealed and heated in a microwave (CEM brand) at 120° C. and 300 watts using a ramp time of 5 minutes and a run time of 20 minutes. The reaction was cooled to RT, concentrated, and purified on HPLC (10% to >95% MeCN/water with 0.1% TFA over 40 minutes) to afford N-(6-(2-(3-(pyridin-3-yl)propoxy)pyrimidin-4-yl)benzo[d]thiazol-2-yl)acetamide. MS (ESI pos. ion) m/z: 406. Calculated exact mass for $C_{21}H_{19}N_5O_2S$: 405. $^1$H NMR (400 MHz, DMSO-$d_6$): 12.51 (s, 1H), 8.83 (d, J=5.5 Hz, 2H), 8.71 (d, J=5.0 Hz, 1H), 8.64 (d, J=5.5 Hz, 1H), 8.39 (d, J=8.0 Hz, 1H), 8.25 (d, J=8.5 Hz, 1H), 7.84-7.89 (m, 2H), 7.75 (d, J=5.0 Hz, 1H), 4.47 (t, J=7.5 Hz, 2H), 2.98 (t, J=7.5 Hz, 2H), 2.23 (s, 3H), 2.17-2.22 (m, 2H).

Compound Examples 2-12 in Table I were made by a method analogous to that described in Example 1, Method A above.

Example 13

Method B

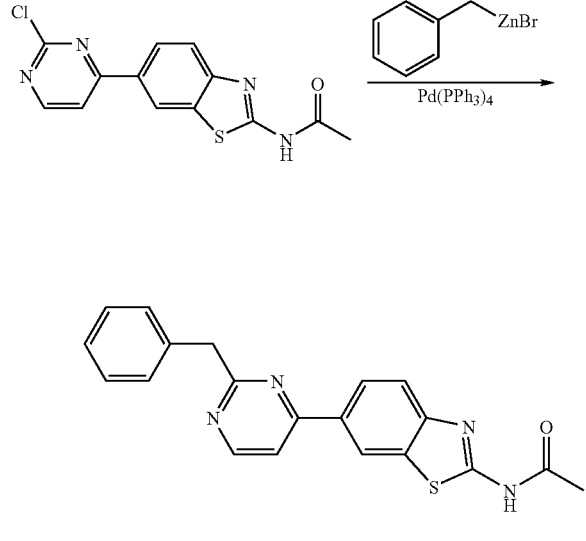

N-(6-(2-Benzylpyrimidin-4-yl)benzo[d]thiazol-2-yl)acetamide

Step 1: N-(6-(2-Chloropyrimidin-4-yl)benzo[d]thiazol-2-yl)acetamide (59.0 mg, 194 μmol) was suspended in THF (1.8 mL) to which tetrakis(triphenylphosphine)palladium (25.6 mg, 22 μmol) and benzylzinc bromide, 0.5 m solution in THF (0.55 mL, 275 μmol) were added under argon, and the reaction solution was stirred at RT. After about 2 hours, the reaction was heated to 80° C., and stirring was continued under argon. After about 100 minutes, additional Pd(PPh$_3$)$_4$ (21 mg) and benzylzinc bromide (0.57 mL) were added, and the reaction was stirred. After another hour or so, additional benzylzinc bromide (0.73 mL) was added, and stirring was continued at 80° C. The reaction was stirred overnight and quenched with saturated ammonium chloride (1.5 mL) and 0.5 M EDTA (2.5 mL), extracted with 10:1 DCM/MeOH, and the organic phases were dried over sodium sulfate, filtered through Celite®(diatomaceous earth), and concentrated. The crude concentrate was purified on a silica gel column (20:1 to >5:1 DCM/MeOH), and the product-containing fractions were collected, concentrated, and washed with Et$_2$O and MeOH and filtered. The solid was collected and purified on HPLC (10% to >95% MeCN/water with 0.1% TFA over 40 minutes), to provide N-(6-(2-benzylpyrimidin-4-yl)benzo[d]thiazol-2-yl)acetamide (8 mg, 11% yield). MS (ESI pos. ion) m/z: 361. Calculated exact mass for C$_{20}$H$_{16}$N$_4$OS: 360. $^1$H NMR (400 MHz, DMSO-d$_6$): 12.50 (s, 1H), 8.85 (s, 1H), 8.78 (d, J=5.5 Hz, 1H), 8.29 (d, J=8.0 Hz, 1H), 7.95 (d, J=5.5 Hz, 1H), 7.85 (d, J=8.5 Hz, 1H), 7.38 (m, 2H), 7.31 (m, 2H), 7.21 (m, 1H), 4.28 (s, 2H), 2.23 (s, 3H).

Compound Examples 14-15 in Table I were made by a method analogous to that described in Example 13, Method B above.

Example 16

Method C

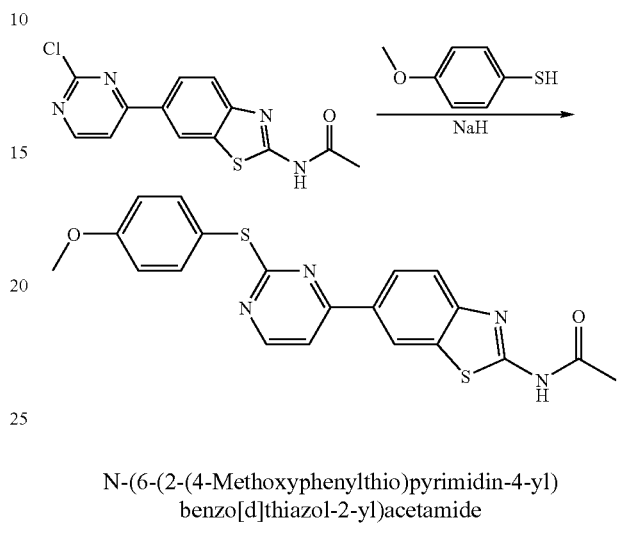

N-(6-(2-(4-Methoxyphenylthio)pyrimidin-4-yl)benzo[d]thiazol-2-yl)acetamide

Step 1: 4-Methoxythiophenol (0.168 ml, 1.36 mmol) was dissolved in DMF (1.0 mL) and NaH (60% in mineral oil), 66.8 mg, 1.67 mmol) was added. The reaction was stirred under nitrogen at RT for 65 minutes, then N-(6-(2-chloropyrimidin-4-yl)benzo[d]thiazol-2-yl)acetamide (48.0 mg, 158 μmol) was added, and the reaction solution was stirred overnight under nitrogen at RT and quenched with water. The suspension was filtered, and the solid was washed with water, MeOH, and Et$_2$O, then collected. The layers of the biphasic filtrate were separated, and the aqueous phase was extracted with 10:1 DCM/MeOH (2×25 mL; 10 mL; 2×25 mL). Organic extracts were combined with the solid, concentrated, and purified on HPLC (10% to 95% MeCN/water with 0.1% TFA over 30 minutes) to afford N-(6-(2-(4-methoxyphenylthio)pyrimidin-4-yl)benzo[d]thiazol-2-yl)acetamide (24 mg, 38% yield). MS (ESI pos. ion) m/z: 409. Calculated exact mass for C$_{20}$H$_{16}$N$_4$O$_2$S$_2$: 408. $^1$H NMR (400 MHz, DMSO-d$_6$): 12.52 (s, 1H), 8.65 (s, 1H), 8.61 (d, J=8.5 Hz, 1H), 7.80 (m, 2H), 7.58 (d, J=8.5 Hz, 2H), 7.09 (d, J=8.5 Hz, 2H), 4.85 (s, 3H), 2.23 (s, 3H).

Compound Examples 17-44 and 50-52 in Table I were made by a method analogous to that described in Example 16, Method C above.

Example 45

Similar to Method A

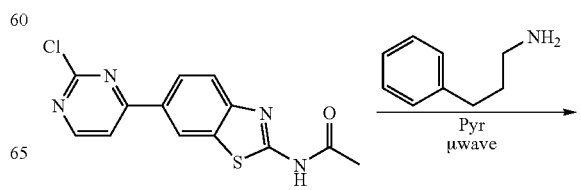

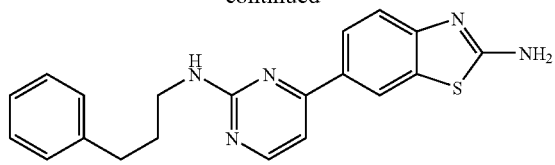

6-(2-(3-Phenylpropylamino)pyrimidin-4-yl)benzo[d]thiazol-2-amine

Step 1: N-(6-(2-chloropyrimidin-4-yl)benzo[d]thiazol-2-yl)acetamide (54.1 mg, 178 µmol) and 3-phenylpropylamine (25.2 µl, 178 µmol) were suspended in pyridine (0.80 mL) and sealed in a microwave vial and heated in the CEM microwave (CEM Corporation, Matthews, N.C.) at 120° C. and 300 watts with a 5 minute ramp time and 20-minute run time. The reaction was cooled to RT, concentrated, and the resulting crude material was purified on HPLC (10% to 95% MeCN/water with 0.1% TFA over 30 minutes) to afford 6-(2-(3-phenylpropylamino) pyrimidin-4-yl)benzo[d]thiazol-2-amine. MS (ESI pos. ion) m/z: 362. Calculated exact mass for $C_{20}H_{19}N_5S$: 361.

Compound Examples 46-49 in Table I were made by a method analogous to that described in Example 45, Method A above.

Compound Examples 53-59 in Table I were made by a method analogous to that described in Examples 1 and 45, Methods A and C above.

Example 60

Method D

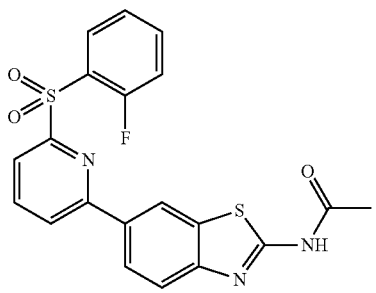

N-(6-(6-(2-fluorophenylsulfonyl)pyridin-2-yl)benzo[d]thiazol-2-yl)acetamide

Step 1. 2-Chloro-6-(2-fluorophenylthio)pyridine

2-Fluorothiophenol (Aldrich, St. Louis, Mo., Cat. No. 275379; 1.6 mL, 15 mmol) was dissolved in DMF (10 mL), and then NaH (0.45 g, 19 mmol) was added slowly to the mixture. After 1 hour, 2,6-dichloropyridine (Aldrich, St. Louis, Mo., Cat. No. 073707; 2.00 g, 14 mmol) was added and the mixture was heated in a pre-heated (70° C.) bath, and allowed to stir under inert atmosphere for 3 hours. The mixture was quenched with 1N NaOH and diluted with DCM. The organic layer was extracted with 4:1 DCM/MeOH (3×25 mL). The combined organic layers were dried over $Na_2SO_4$, filtered and concentrated in vacuo. The crude residue was purified by ISCO Silica-Gel Chromatography (Teledyne ISCO, Lincoln, Nebr.) on a 120 gm column eluting with a solvent gradient of 1-30% DCM/Hexanes over 35 minutes to give 2-chloro-6-(2-fluorophenylthio)pyridine (1.13 g, 35% yield) as colorless oil. MS (ESI pos. ion) m/z: 240 (MH+). Calculated exact mass for $C_{11}H_7ClFNS$: 239.

Step 2. 2-Chloro-6-(2-fluorophenylsulfonyl)pyridine

2-Chloro-6-(2-fluorophenylthio)pyridine (1.13 g, 4.71 mmol) was dissolved in HOAc (10 mL) and hydrogen peroxide, (30% in water, 10 mL, 294 mmol) was added slowly to the mixture. The flask was fit with a reflux condenser and heated in a pre-heated (70° C.) bath and stirred under inert atmosphere for 2 hours. The mixture was quenched with saturated $NaHCO_3$ and diluted with DCM. The mixture was allowed to stir an additional 30 minutes, and then 1N NaOH was added to make the solution basic. The organic layer was extracted with DCM (3×50 mL), and the combined organic layers were dried over sodium sulfate, filtered and concentrated in vacuo to give 2-chloro-6-(2-fluorophenyl sulfonyl) pyridine (1.050 g, 82% yield) as white solids. MS (ESI pos. ion) m/z: 272 (MH+). Calculated exact mass for $C_{11}H_7ClFNO_2S$: 271.

Step 3. N-(6-(6-(2-fluorophenylsulfonyl)pyridin-2-yl)benzo[d]thiazol-2-yl)acetamide A RBF was charged with N-(6-(4,4,5,5-tetramethyl-1,3,2-dioxaborolan-2-yl)benzo[d]thiazol-2-yl)acetamide (0.6 g, 2 mmol), 2-chloro-6-(2-fluorophenylsulfonyl)pyridine (0.400 g, 1 mmol), 2M sodium carbonate (1 mL, 2 mmol), tetrakis (triphenyl phosphine)palladium(0) (0.2 g, 0.2 mmol), and dioxane (8 mL). The flask was heated in a pre-heated (95° C.) heat bath while stirring under inert atmosphere overnight. The mixture was cooled, diluted with DMSO and filtered. The crude was purified by reverse-phase HPLC to provide N-(6-(6-(2-fluorophenylsulfonyl)pyridin-2-yl)benzo[d]thiazol-2-yl)acetamide as an off-white solid. MS (ESI pos. ion) m/z: 428. Calculated exact mass for $C_{20}H_{14}FN_3O_3S_3$: 427. $^1$H NMR (400 MHz, DMSO-$d_6$): 8.49 (s, 1H), 8.20-8.36 (m, 2H), 8.08-8.19 (m, 2H), 7.95 (d, J=7.5 Hz, 1H), 7.79-7.88 (m, 1H), 7.75 (d, J=8.5 Hz, 1H), 7.56 (m, 1H), 7.44 (m, 1H), 2.21 (s, 3H).

Compound Examples 61-72 in Table I were made by a method analogous to that described in Example 60 Method D above or as described below.

Example 61

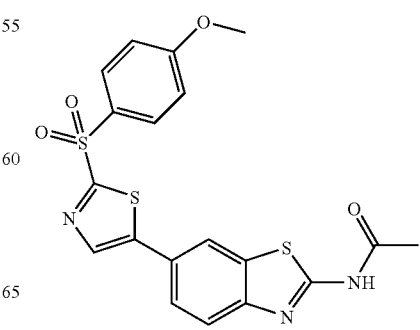

(s, 1H), 7.99 (d, J=9.0 Hz, 2H), 7.81 (m, 2H), 7.22 (d, J=8.5 Hz, 2H), 3.87 (s, 3H), 2.22 (s, 3H).

Example 62

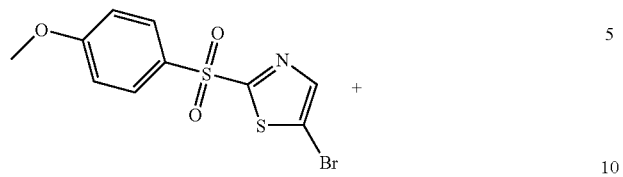

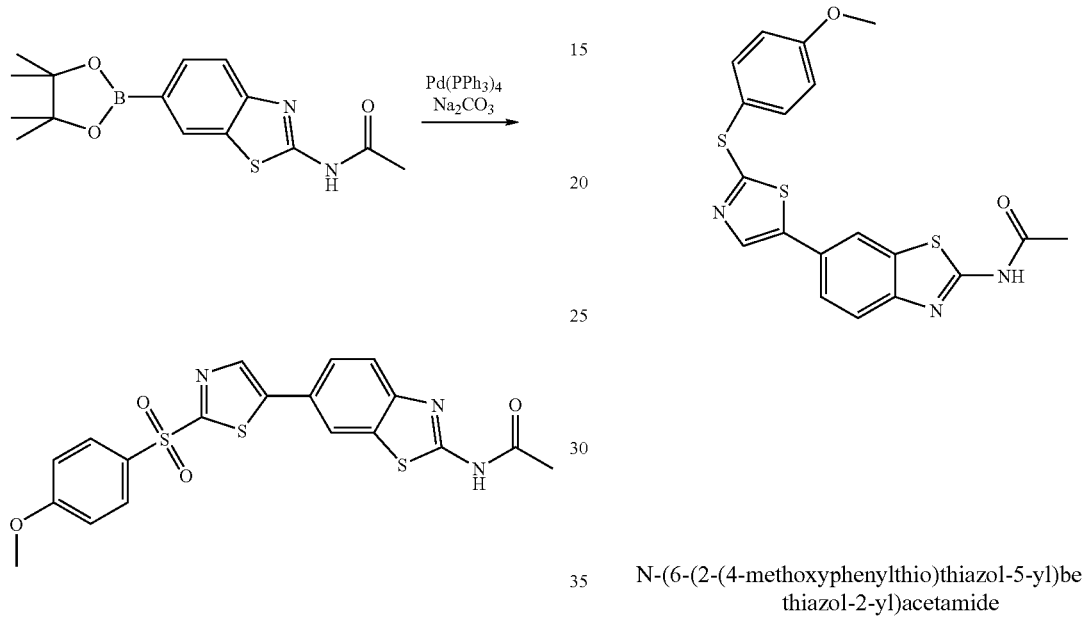

N-(6-(2-(4-methoxyphenylthio)thiazol-5-yl)benzo[d]thiazol-2-yl)acetamide

MS (ESI pos. ion) m/z: 414 (MH+). Calculated exact mass for $C_{19}H_{15}N_3O_2S_3$: 413. $^1$H NMR (400 MHz, DMSO-$d_6$): 12.40 (s, 1H), 8.16 (s, 1H), 8.11 (s, 1H), 7.69 (d, J=8.5 Hz, 3H), 7.60 (m, 1H), 7.12 (d, J=9.0 Hz, 2H), 3.84 (s, 3H), 2.20 (s, 3H).

Example 63

N-(6-(2-(4-methoxyphenylsulfonyl)thiazol-5-yl)benzo[d]thiazol-2-yl)acetamide

5-Bromo-2-(4-methoxyphenylsulfonyl)thiazole (134.8 mg, 4.034 mmol), N-(6-(4,4,5,5-tetramethyl-1,3,2-dioxaborolan-2-yl)benzo[d]thiazol-2-yl)acetamide (163.6 mg, 0.5141 mmol), sodium carbonate (0.40 mL, 2.0 M in water, 0.80 mmol), and palladiumtetrakis(triphenyl phosphine) (59.5 mg, 51.5 µmol) were suspended in 1,4-dioxane (3.2 mL) and the reaction mixture was stirred and heated at 80° C. for 1.5 hours. Additional Pd(PPh$_3$)$_4$ (78 mg) was added to the mixture and stirring and heating were continued at 90° C. for another 90 minutes, at which time the reaction was cooled to RT. The organic phase was decanted, and the residual solid was washed with DCM and MeOH and filtered through a Celite® (diatomaceous earth) pad. This pad was washed with DCM and MeOH, and the filtrate was combined with the decanted suspension and concentrated. The solid was treated with Et$_2$O and filtered. Solid washed with Et$_2$O and purified on HPLC (10% to 95% MeCN/water with 0.1% TFA over 40 minutes) to afford N-(6-(2-(4-methoxyphenylsulfonyl)thiazol-5-yl)benzo[d]thiazol-2-yl)acetamide. MS (ESI pos. ion) m/z: 446. Calculated exact mass for $C_{19}H_{15}N_3O_4S_3$: 445. $^1$H NMR (400 MHz, DMSO-$d_6$): 12.51 (s, 1H), 8.48 (s, 1H), 8.45

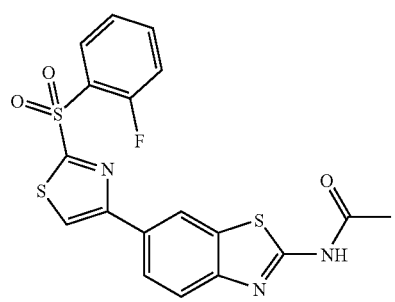

N-(6-(2-(2-fluorophenylsulfonyl)thiazol-4-yl)benzo[d]thiazol-2-yl)acetamide

MS (ESI pos. ion) m/z: 434 (MH+). Calculated exact mass for $C_{18}H_{12}FN_3O_3S_3$: 433.

Example 64

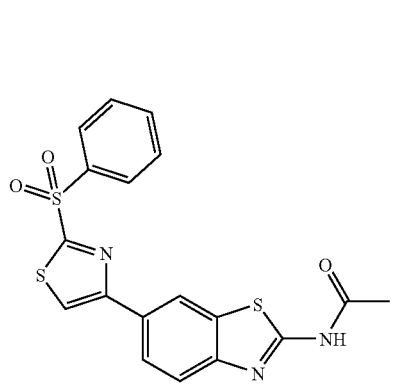

N-(6-(2-(phenylsulfonyl)thiazol-4-yl)benzo[d]thiazol-2-yl)acetamide

MS (ESI pos. ion) m/z: 416 (MH+). Calculated exact mass for $C_{18}H_{13}N_3O_3S_3$: 415. $^1$H NMR (400 MHz, DMSO-d6): 8.53 (s, 1H), 8.30 (s, 1H), 8.12 (d, J=7.0 Hz, 2H), 7.82 (d, J=7.0 Hz, 2H), 7.73 (d, J=7.0 Hz, 2H), 7.55 (d, J=8.0 Hz, 1H), 2.06 (s, 3H).

Example 65

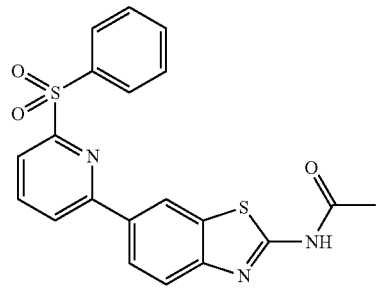

N-(6-(6-(phenylsulfonyl)pyridin-2-yl)benzo[d]thiazol-2-yl)acetamide

MS (ESI pos. ion) m/z: 410 (MH+). Calculated exact mass for $C_{20}H_{15}N_3O_3S_2$: 409.

Example 66

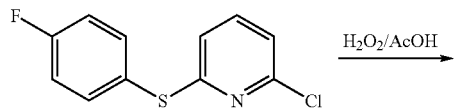

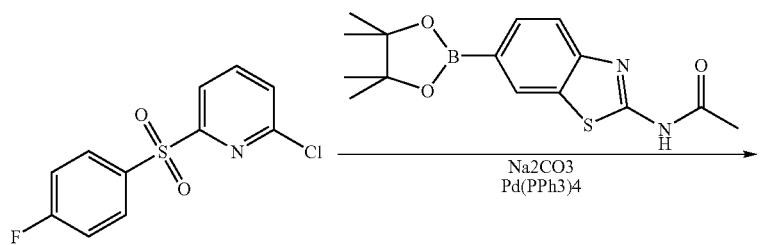

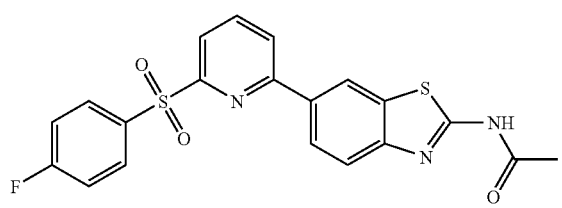

N-(6-(6-(4-Fluorophenylsulfonyl)pyridin-2-yl)benzo[d]thiazol-2-yl)acetamide

Step 1. 2-Chloro-6-(4-fluorophenylsulfonyl)pyridine

2-Chloro-6-(4-fluorophenylthio)pyridine (0.220 g, 0.9 mmol) was dissolved in acetic acid (2.5 mL, 44 mmol) and then hydrogen peroxide (2.5 mL, 30%, 73 mmol) was added slowly into the mixture. The flask was fit with a reflux condensor and placed into a pre-heated (70° C.) bath and allowed to stir under an inert atmosphere for 2 hours. The mixture was quenched with saturated sodium bicarbonate and diluted with DCM. The mixture was allowed to stir an additional 30 minutes and was treated with 1N NaOH to raise the pH above 7. The aqueous layer was extracted with DCM three times, and the combined extracts were dried over sodium sulfate, filtered, and concentrated in vacuo to give 2-chloro-6-(4-fluorophenylsulfonyl)pyridine as a white solid. MS (ESI pos. ion) m/z: 272 (MH+). Calculated exact mass for $C_{11}H_7ClFNO_2S$: 271.

Step 2. N-(6-(6-(4-Fluorophenylsulfonyl)pyridin-2-yl)benzo[d]thiazol-2-yl)acetamide A RBF was charged with N-(6-(4,4,5,5-tetramethyl-1,3,2-dioxaborolan-2-yl)benzo[d]thiazol-2-yl)acetamide (0.3 g, 1 mmol), 2-chloro-6-(4-fluorophenylsulfonyl)pyridine (0.230 g, 0.8 mmol), 2M $Na_2CO_3$ (0.8 mL, 2 mmol), tetrakis(triphenylphosphine)palladium(0) (0.1 g, 0.1 mmol), and dioxane (6 mL). The flask was heated in a pre-heated (95° C.) bath and allowed to stir under an inert atmosphere for 2.5 hours. The mixture was allowed to cool to ambient temperature and diluted with DMSO and filtered. The crude material was purified by reverse-phase HPLC to give N-(6-(6-(4-fluorophenylsulfonyl)pyridin-2-yl)benzo[d]thiazol-2-yl)acetamide as an off-white solid. MS (ESI pos. ion) m/z: 428 (MH+). Calculated exact mass for $C_{20}H_{14}FN_3O_3S_2$: 427. $^1$H NMR (400 MHz, DMSO-$d_6$): 8.06-8.27 (m, 5H), 7.97-7.99 (m, 1H), 7.82-7.84 (m, 1H), 7.52-7.54 (m, 2H), 7.37-7.40 (m, 1H), 1.96 (s, 3H).

Example 68

N-(6-(6-(4-Methoxyphenylsulfonyl)pyridin-2-yl)benzo[d]thiazol-2-yl)acetamide

Step 1. 2-Chloro-6-(4-methoxyphenylthio) pyridine

4-Methoxythiophenol (Aldrich, St. Louis, Mo., Cat. No. 109525; 0.91 mL, 7.4 mmol) was dissolved in DMF (10 mL) and chilled to 0° C. in an ice bath. NaH (0.227 g, 9.5 mmol) was added slowly and the mixture was allowed to stir under an inert atmosphere. After 1 hour, 2,6-dichloropyridine (1.000 g, 6.8 mmol) was added to the mixture and the ice bath was removed. The resulting mixture was allowed to stir under inert atmosphere overnight. The mixture was quenched with 1N NaOH and diluted with DCM. The aqueous layer was extracted with 4:1 DCM/MeOH three times, and the combined organic layers were dried over $Na_2SO_4$, filtered, and concentrated in vacuo. The crude material was purified by silica gel chromatography (1-30% DCM/hexanes) to give 2-chloro-6-(4-methoxyphenylthio) pyridine (0.950 g, 56% yield) as a yellow oil. MS (ESI pos. ion) m/z: 252 (MH+). Calculated exact mass for $Cl_2H_{10}ClNOS$: 251.

Step 2. 2-Chloro-6-(4-methoxyphenylsulfonyl)pyridine

2-Chloro-6-(4-methoxyphenylthio)pyridine (0.950 g, 3.78 mmol) was dissolved in acetic acid (10 mL) and then hydrogen peroxide (10 mL, 30%, 294 mmol) was added slowly into the mixture. The flask was fit with a reflux condensor and placed into a pre-heated (70° C.) bath and allowed to stir under inert atmosphere for 1 hour. The mixture was quenched with satd $NaHCO_3$ and diluted with DCM. The mixture was allowed to stir an additional 30 minutes and then was treated with 1N NaOH to raise the pH above 7. The aqueous layer was extracted with DCM three times, and the combined extracts were dried over sodium sulfate, filtered, and concentrated in vacuo to give 2-chloro-6-(4-methoxyphenylsulfonyl)pyridine (0.730 g, 68% yield) as a white solid. MS (ESI pos. ion) m/z: 284 (MH+). Calculated exact mass for $C_{12}H_{10}ClNO_3S$: 283.

Step 3. N-(6-(6-(4-Methoxyphenylsulfonyl)pyridin-2-yl)benzo[d]thiazol-2-yl)acetamide 2-Chloro-6-(4-methoxyphenylsulfonyl)pyridine (0.300 g, 1.06 mmol) was dissolved in 1,4-dioxane (6 mL) and then

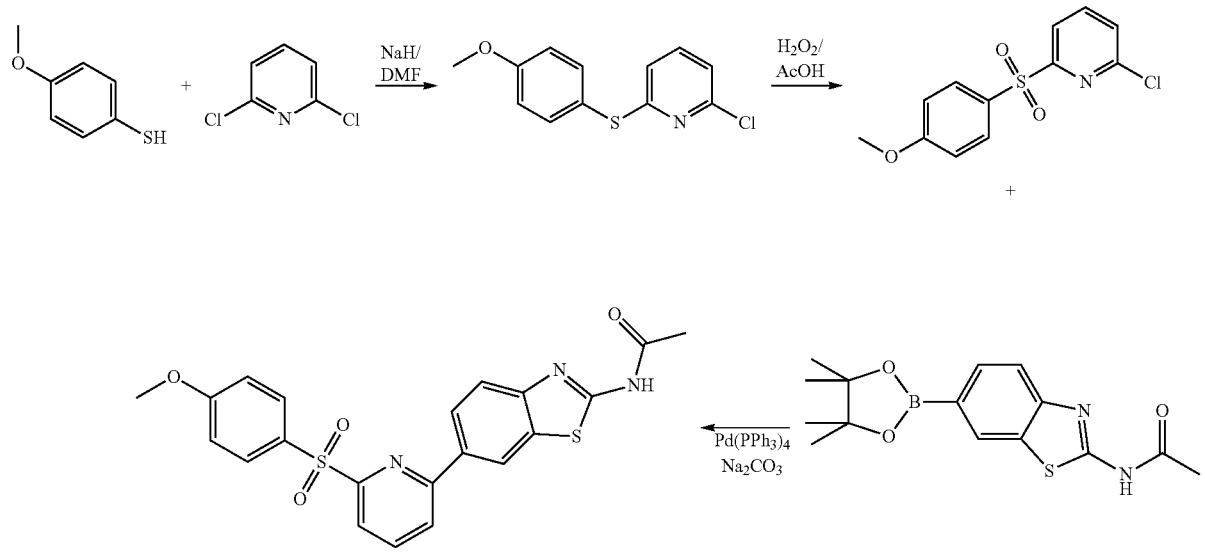

N-(6-(4,4,5,5-tetramethyl-1,3,2-dioxaborolan-2-yl)benzo[d]thiazol-2-yl)acetamide (0.4 g, 1 mmol), tetrakis(triphenylphosphine)palladium (0) (0.2 g, 0.1 mmol) and 2M sodium carbonate (1 mL, 2 mmol) were added to it. The flask was fit with a reflux condensor and placed into a pre-heated (95° C.) bath. The mixture was allowed to stir under inert atmosphere overnight. The mixture was allowed to cool to ambient temperature and diluted with DMSO. The crude was filtered and purified by reverse-phase HPLC. This gave N-(6-(6-(4-methoxyphenylsulfonyl)pyridin-2-yl)benzo[d]thiazol-2-yl)acetamide as an off-white solid. MS (ESI pos. ion) m/z: 440 (MH+). Calculated exact mass for $C_{21}H_{17}N_3O_4S_2$: 439. $^1$H NMR (400 MHz, DMSO-$d_6$): 8.53 (s, 1H), 8.15-8.24 (m, 2H), 8.02 (br s, 4H), 7.70 (d, J=7.53 Hz, 1H), 7.7.19 (d, J=7.53 Hz, 2H), 3.83 (s, 3H), 2.15 (s, 3H).

Example 71

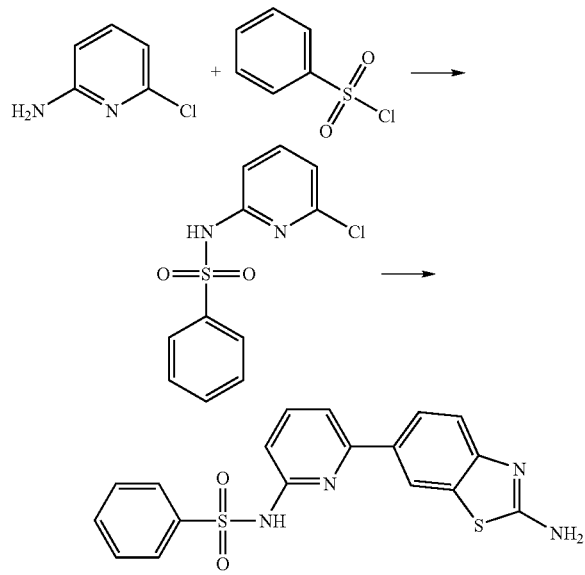

N-(6-(2-Aminobenzo[d]thiazol-6-yl)pyridin-2-yl)benzenesulfonamide

Step 1.
N-(6-Chloropyridin-2-yl)benzenesulfonamide

6-Chloropyridin-2-amine (0.3 g, 2 mmol) was dissolved in DCM (20 mL) and then pyridine (0.57 mL, 7.0 mmol) was added to the mixture with stirring. Then, benzenesulfonyl chloride (0.36 mL, 2.8 mmol) was added into the mixture. The mixture was allowed to stir under inert atmosphere for 2 hours. The mixture was diluted with DCM and saturated NaHCO$_3$, and then the aqueous layer was extracted with DCM three times. The combined organic layers were dried over Na$_2$SO$_4$, filtered, and concentrated in vacuo. The crude material was purified by silica gel chromatography (10-100% EtOAc/hexanes) to provide N-(6-chloropyridin-2-yl)benzenesulfonamide (0.5 g, 80% yield) as a colorless oil. MS (ESI pos. ion) m/z: 254 (MH+). Calculated exact mass for $C_{11}H_8ClNO_2S$: 253.

Step 2. N-(6-(2-Aminobenzo[d]thiazol-6-yl)pyridin-2-yl)benzenesulfonamide

N-(6-Chloropyridin-2-yl)benzenesulfonamide (0.480 g, 1.90 mmol) was dissolved in 1,4-dioxane (6 mL). Then N-(6-(4,4,5,5-tetramethyl-1,3-dioxolan-2-yl)benzo[d]thiazol-2-yl)acetamide (0.7 g, 2 mmol), 2M Na$_2$CO$_3$ (2 mL, 4 mmol), and tetrakis(triphenylphosphine)palladium (0) (0.3 g, 0.2 mmol) was added to the mixture. The flask was fit with a reflux condensor, then placed into a pre-heated (95° C.) bath and allowed to stir under inert atmosphere overnight. The flask was removed from the heat bath and allowed to cool to ambient temperature. The mixture was filtered through a fritted funnel and the crude filtrate was purified by reverse-phase HPLC. This gave N-(6-(2-aminobenzo[d]thiazol-6-yl)pyridin-2-yl)benzenesulfonamide. MS (ESI pos. ion) m/z: 383 (MH+). Calculated exact mass for $C_{18}H_{14}N_4O_2S_2$: 382. $^1$H NMR (400 MHz, acetone-$d_6$): 8.19 (s, 1H), 8.08 (d, J=8.0 Hz, 2H), 7.86 (d, J=8.0 Hz, 1H), 7.74 (t, J=8.0 Hz, 1H), 7.53-7.64 (m, 4H), 7.44 (d, J=8.5 Hz, 1H), 7.13 (d, J=8.0 Hz, 1H), 6.98 (br s, 1H).

Example 73

Method E

N-(6-(6-(2-Fluorophenylsulfonamido)pyridin-2-yl)benzo[d]thiazol-2-yl)acetamide

Step 1. N-(6-(6-aminopyridin-2-yl)benzo[d]thiazol-2-yl)acetamide

6-Bromopyridin-2-amine (0.5 g, 3 mmol) was dissolved in 1,4-dioxane (6 mL). Then N-(6-(4,4,5,5-tetramethyl-1,3-dioxolan-2-yl)benzo[d]thiazol-2-yl)acetamide (1.0 g, 3.1 mmol), 2M Na$_2$CO$_3$ (3 mL, 6 mmol), and tetrakis(triphenylphosphine)palladium (0) (0.4 g, 0.4 mmol) were added to the mixture. The flask was fitted with a reflux condenser, placed into a pre-heated (95° C.) bath, and allowed to stir under an inert atmosphere overnight. The flask was removed from the heat bath and allowed to cool to ambient temperature. The mixture was diluted with 5:1 DCM/MeOH and saturated NaHCO$_3$. The aqueous layer was extracted with 5:1 DCM/MeOH three times, and the combined organic layers were dried over sodium sulfate, filtered, and concentrated in vacuo. The crude residue was purified by silica gel chromatography (1-5% MeOH/DCM) to give N-(6-(6-aminopyridin-2-yl)benzo[d]thiazol-2-yl)acetamide (0.23 g, 28% yield) as a light yellow solid. MS (ESI pos. ion) m/z: 285 (MH+). Calculated exact mass for $C_{14}H_{12}N_4OS$: 284.

Step 2. N-(6-(6-(2-Fluorophenylsulfonamido)pyridin-2-yl)benzo[d]thiazol-2-yl)acetamide N-(6-(6-Aminopyridin-2-yl)benzo[d]thiazol-2-yl)acetamide (0.220 g, 0.775 mmol) was dissolved in DMSO (3 mL). TEA (0.3 mL, 2 mmol), DMAP (0.020 g, 0.16 mmol), and 2-fluorobenzene-1-sulfonyl chloride (0.4 mL, 3 mmol) were added to the mixture while stirring. The mixture was allowed to stir under inert atmosphere overnight and then it was diluted with DMSO and purified by reverse phase HPLC to give N-(6-(6-(2-fluorophenylsulfonamido)pyridin-2-yl)benzo[d]thiazol-2-yl)acetamide as a yellow solid. MS (ESI pos. ion) m/z: 443 (MH+). Calculated exact mass for $C_{21}H_{15}FN_4O_3S_2$: 442. $^1$H NMR (400 MHz, DMSO-$d_6$): 7.99 (s, 1H), 7.94 (t, J=7.3 Hz, 1H), 7.68 (d, J=8.5 Hz, 1H), 7.32-7.47 (m, 3H), 7.28 (t, J=7.5 Hz, 1H), 7.21 (t, J=7.8 Hz, 1H), 7.10 (d, J=7.5 Hz, 1H), 6.41 (d, J=8.5 Hz, 1H), 2.10 (s, 3H).

Compound Examples 74-75 in Table I were made by a method analogous to that described in Example 73 Method E above or as described below.

Example 74

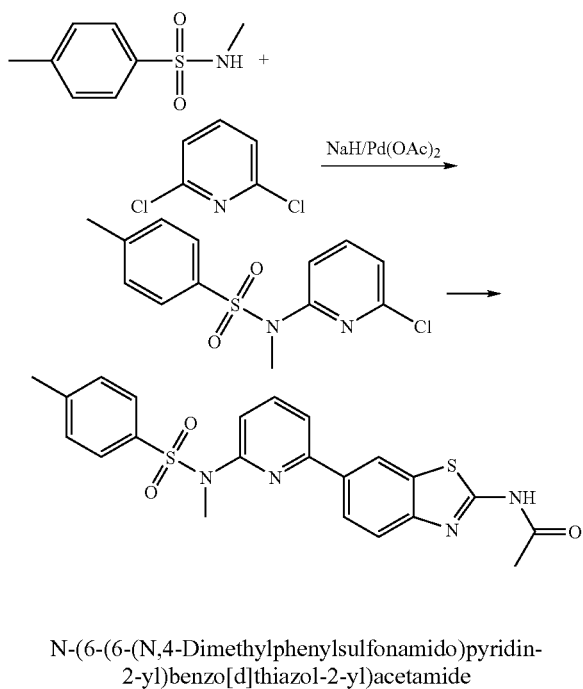

N-(6-(6-(N,4-Dimethylphenylsulfonamido)pyridin-2-yl)benzo[d]thiazol-2-yl)acetamide Step 1. N-(6-Chloropyridin-2-yl)-N,4-dimethylbenzenesulfonamide N-Methyl-p-toluenesulfonamide (0.2 g, 1 mmol) was added to a microwave vial equipped with a stir bar. DMF (3 mL) was added to the mixture, followed by NaH (0.13 g, 5.40 mmol), and the reaction solution was allowed to stir for 20 minutes. Then 2,6-dichloropyridine (0.24 g, 1.6 mmol), palladium(II) acetate (0.0242 g, 0.108 mmol) and Xantphos (0.024 g) were added to the mixture. The vial was capped and placed in the CEM microwave and heated for 10 minutes at 100° C. The mixture was diluted with DCM and saturated NaHCO$_3$. The aqueous layer was extracted with 4:1 DCM/MeOH three times, and the combined organic layers were dried over Na$_2$SO$_4$, filtered, and concentrated in vacuo. The crude was purified by silica gel chromatography (1-10% EtOAc/hexanes) to give N-(6-chloropyridin-2-yl)-N,4-dimethylbenzenesulfonamide (0.1 g, 31.2% yield) as a colorless oil. MS (ESI pos. ion) m/z: 297 (MH+). Calculated exact mass for C$_{13}$H$_{13}$ClN$_2$O$_2$S: 296.

Step 2. N-(6-(6-(N,4-dimethylphenylsulfonamido)pyridin-2-yl)benzo[d]thiazol-2-yl)acetamide N-(6-Chloropyridin-2-yl)-N,4-dimethylbenzenesulfonamide (0.080 g, 0.27 mmol) was dissolved in 1,4-dioxane (6 mL), and N-(6-(4,4,5,5-tetramethyl-1,3,2-dioxaborolan-2-yl)benzo[d]thiazol-2-yl)acetamide (0.1 g, 0.3 mmol), tetrakis(triphenylphosphine)palladium (0) (0.04 g, 0.04 mmol) and 2M Na$_2$CO$_3$ (0.3 mL, 0.6 mmol) were added to the mixture. The flask was fit with a reflux condensor and placed into a pre-heated (95° C.) bath and stirred under an inert atmosphere overnight. The mixture was then allowed to cool to ambient temperature and diluted with DCM and saturated NaHCO$_3$. The organic layers were collected by extracting with DCM three times, and the combined organic extracts were dried over sodium sulfate, filtered, and concentrated in vacuo. The crude was purified by silica gel chromatography (1-10% IPA/DCM) to give N-(6-(6-(N,4-dimethylphenylsulfonamido)pyridin-2-yl)benzo[d]thiazol-2-yl)acetamide as a tan solid. MS (ESI pos. ion) m/z: 453 (MH+). Calculated exact mass for C$_{22}$H$_{20}$N$_4$O$_3$S$_2$: 452. $^1$H NMR (400 MHz, DMSO-d$_6$): 8.35 (s, 1H), 7.93 (t, J=8.0 Hz, 2H), 7.83 (d, J=7.5 Hz, 1H), 7.74 (d, J=8.5 Hz, 1H), 7.58 (d, J=8.0 Hz, 2H), 7.48 (d, J=8.0 Hz, 1H), 7.37 (d, J=7.5 Hz, 2H), 3.38 (s, 3H), 2.36 (s, 3H), 2.22 (s, 3H).

Example 76

N-(6-(6-(N-Methylphenylsulfonamido)pyridin-2-yl)benzo[d]thiazol-2-yl)acetamide

The title compound was a yellow crystalline solid. MS (ESI pos. ion) m/z: 453 (MH+). Calculated exact mass for C$_{22}$H$_{20}$N$_4$O$_3$S$_2$: 452.

Example 77

Similar to Method C

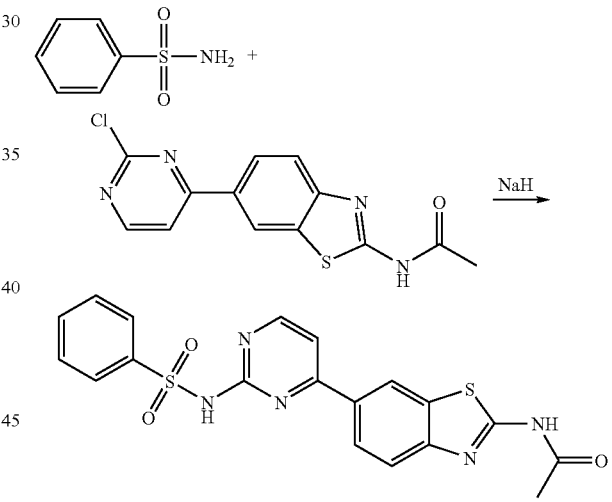

N-(6-(2-(Phenylsulfonamido)pyrimidin-4-yl)benzo[d]thiazol-2-yl)acetamide

Benzenesulfonamide (150 mg, 0.954 mmol) was dissolved in DMSO (1.5 mL) and NaH (56.1 mg, 1.40 mmol, 60% in mineral oil) was added, and the reaction mixture was stirred at RT for 1 hour. N-(6-(2-Chloropyrimidin-4-yl)benzo[d]thiazol-2-yl)acetamide (50.2 mg, 0.165 mmol) was added, and the reaction flask was placed in a preheated oil bath (125° C.) and stirred under nitrogen. The reaction was stirred for 21 hours, and then cooled to RT and quenched with MeOH. The suspension was filtered through a pad of Celite® (diatomaceous earth), which was washed with DCM and MeOH, and the filtrate was concentrated, and purified on an HPLC system (10-95% MeCN/water with 0.1% TFA over 30 minutes) to provide N-(6-(2-(phenylsulfonamido)pyrimidin-4-yl)benzo[d]thiazol-2-yl)acetamide (29 mg, 41%). MS (ESI pos. ion)

m/z: 426 (MH+). Calculated exact mass for $C_{19}H_5N_5O_3S_2$: 425. $^1$H NMR (400 MHz, DMSO-d$_6$): 12.53 (s, 1H), 8.54-8.56 (m, 2H), 8.09 (d, J=9.0 Hz, 1H), 8.05 (d, J=7.5 Hz, 2H), 7.83 (d, J=8.5 Hz, 1H), 7.58-7.63 (m, 4H), 2.24 (s, 3H).

Example 79

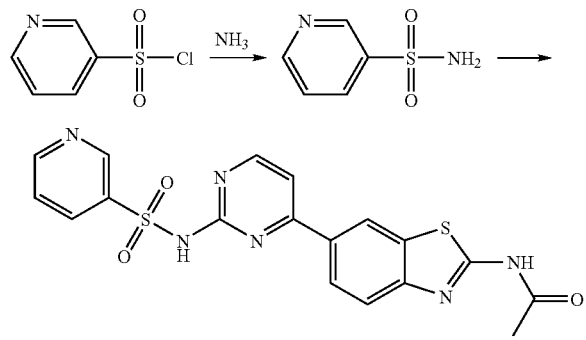

N-(6-(2-(pyridine-5-sulfonamido)pyrimidin-4-yl)benzo[d]thiazol-2-yl)acetamide

Step 1. Pyridine-3-sulfonamide

Pyridine-3-sulfonyl chloride HCl (647.2 mg, 3.023 mmol) was suspended in DCM (9.0 mL) and NH$_3$ (5 mL, 7N in MeOH, 35 mmol) was added. The reaction was stirred at RT under nitrogen for 50 minutes and then filtered, and the solid was washed with DCM. The filtrate was concentrated and dried under high vacuum to provide pyridine-3-sulfonamide (477 mg, 91% yield). MS (ESI pos. ion) m/z: 159 (MH+). Calculated exact mass for $C_5H_6N_2O_2S$: 158.

Step 2. N-(6-(2-(Pyridine-5-sulfonamido)pyrimidin-4-yl)benzo[d]thiazol-2-yl)acetamide The title compound was prepared in a manner analogous to the procedure described for Example 77 above. MS (ESI pos. ion) m/z: 427 (MH+). Calculated exact mass for $C_{18}H_{14}N_6O_3S_2$: 426.

Example 88

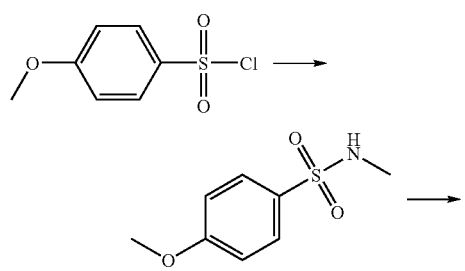

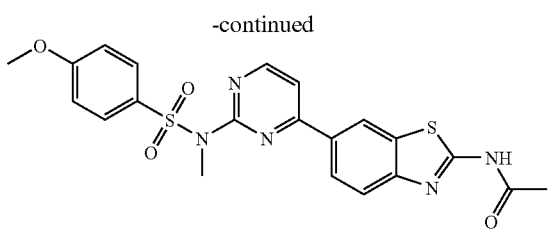

N-(6-(2-(4-Methoxy-N-methylphenylsulfonamido)pyrimidin-4-yl)benzo[d]thiazol-2-yl)acetamide Step 1. 4-Methoxy-N-methylbenzenesulfonamide 4-Methoxybenzene-1-sulfonyl chloride (688.1 mg, 3.331 mmol) was suspended in DCM (10 mL) and methylamine (6.5 mL, 2.0 M in THF, 13 mmol) was added. The reaction was stirred under nitrogen for about 80 minutes. The mixture was filtered, and the solid was washed with DCM. The filtrate was concentrated and dried under high vacuum to provide 4-methoxy-N-methylbenzenesulfonamide (497 mg, 74% yield). MS (ESI pos. ion) m/z: 202 (MH+). Calculated exact mass for $C_8H, NO_3S$: 201.

Step 2. N-(6-(2-(4-Methoxy-N-methylphenylsulfonamido)pyrimidin-4-yl)benzo[d]thiazol-2-yl)acetamide 4-Methoxy-N-methylbenzenesulfonamide (228 mg, 1.13 mmol) was dissolved in DMSO (1.6 mL) and NaH (57.5 mg, 60% in mineral oil, 1.44 mmol) was added and the reaction was stirred under nitrogen at RT. After 1 hour, N-(6-(2-chloropyrimidin-4-yl)benzo[d]thiazol-2-yl)acetamide (82.3 mg, 0.270 mmol) was added, and the reaction flask was heated in a preheated oil bath (125° C.) and stirred under nitrogen overnight. The reaction was cooled to RT and filtered through a pad of Celite®(diatomaceous earth). Filtrate was concentrated and the crude material was purified on HPLC (10-95% MeCN/water with 0.1% TFA over 30 minutes) to provide N-(6-(2-(4-methoxy-N-methylphenylsulfonamido)pyrimidin-4-yl)benzo[d]thiazol-2-yl)acetamide. MS (ESI pos. ion) m/z: 470 (MH+). Calculated exact mass for $C_{21}H_{19}N_5O_4S_2$: 469. $^1$H NMR (400 MHz, DMSO-d$_6$): 12.52 (s, 1H), 8.64 (d, J=5.0 Hz, 1H), 8.56 (s, 1H), 8.14 (d, J=8.5 Hz, 1H), 7.99 (d, J=8.5 Hz, 2H), 7.84 (d, J=8.5 Hz, 1H), 7.72 (d, J=5.0 Hz, 1H), 7.10 (d, J=9.0 Hz, 2H), 3.82 (s, 3H), 3.69 (s, 3H), 2.23 (s, 3H).

Example 89

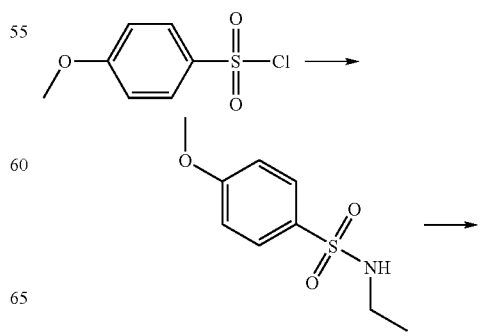

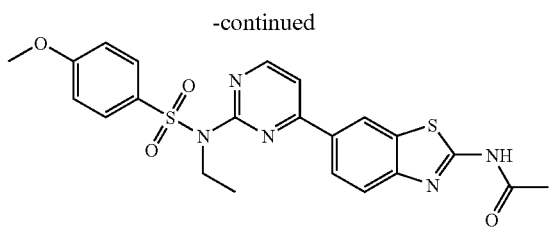

N-(6-(2-(N-Ethyl-4-methoxyphenylsulfonamido)
pyrimidin-4-yl)benzo[d]thiazol-2-yl)acetamide Step 1. N-Ethyl-4-methoxybenzenesulfonamide 4-Methoxybenzene-1-sulfonyl chloride (619.5 mg, 2.999 mmol) was dissolved in DCM (10 mL) and ethylamine (4.6 mL, 2.0 M in THF, 9.2 mmol) was added, and the reaction flask was put in a water bath and stirred under nitrogen. After stirring at RT over the weekend, the suspension was filtered, and the solid was washed with DCM. The filtrate was concentrated and dried under high vacuum to provide N-ethyl-4-methoxybenzenesulfonamide (723 mg, 89% yield). MS (ESI pos. ion) m/z: 216 (MH+). Calculated exact mass for $C_9H_{13}NO_3S$: 215.

Step 2. N-(6-(2-(N-Ethyl-4-methoxyphenylsulfonamido)pyrimidin-4-yl)benzo[d]thiazol-2-yl)acetamide The title compound was prepared in a manner analogous to the procedure described for Example 88 above. MS (ESI pos. ion) m/z: 484 (MH+). Calculated exact mass for $C_{22}H_{21}N_5O_4S_2$: 483.

Example 90

Method F

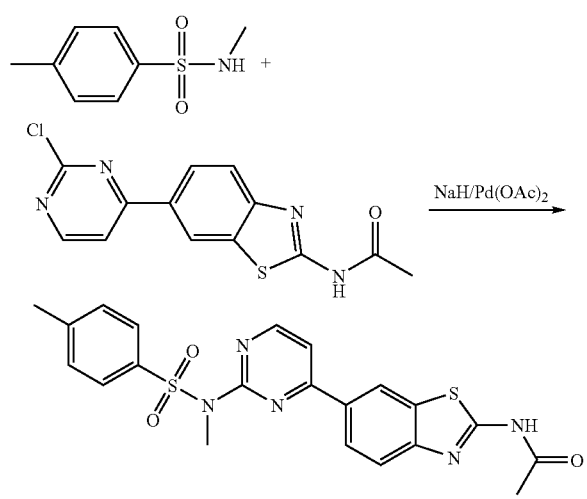

N-(6-(2-(N,4-Dimethylphenylsulfonamido)pyrimidin-4-yl)benzo[d]thiazol-2-yl)acetamide Step 1: A microwave vial equipped with a stir bar was charged with N-methyl-p-toluenesulfonamide (0.23 g, 1.2 mmol) in DMF (3 mL). NaH (0.12 g, 4.9 mmol) was added to the mixture and allowed to stir for 30 minutes. Then, palladium (II) acetate (0.011 g, 0.049 mmol), N-(6-(2-chloropyrimidin-4-yl)benzo[d]thiazol-2-yl)acetamide (0.150 g, 0.492 mmol), and Xantphos (0.010 g) were added to the mixture. The vial was capped and placed into a microwave for 10 minutes at 100° C. The mixture was then added to a RBF, diluted with water (150 mL), and allowed to stir overnight. The resulting precipitate was collected by filtration and washed with hexane and 1:1 hexanes/ethyl ether to provide N-(6-(2-(N,4-dimethylphenylsulfonamido)pyrimidin-4-yl)benzo[d]thiazol-2-yl)acetamide as a tan solid. MS (ESI pos. ion) m/z: 454 (MH+). Calculated exact mass for $C_{21}H_{19}N_5O_3S_2$: 453. $^1$H NMR (400 MHz, DMSO-d$_6$): 12.52 (s, 1H), 8.64 (s, 1H), 8.48 (s, 1H), 8.10 (d, J=5.0 Hz, 1H), 7.93 (s, 2H), 7.83 (s, 1H), 7.71 (s, 1H), 7.40 (s, 2H), 3.70 (s, 3H), 2.37 (s, 3H), 2.24 (s, 3H).

Compound Examples 91 was prepared in a manner analogous to the procedure described for Example 90, Method F above Example 92

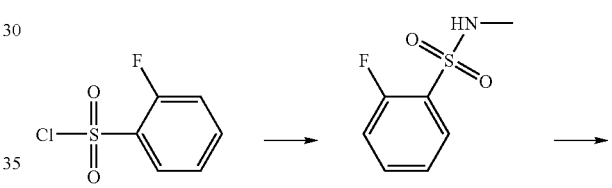

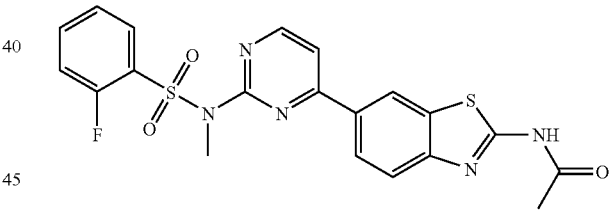

N-(6-(2-(2-Fluoro-N-methylphenylsulfonamido)
pyrimidin-4-yl)benzo[d]thiazol-2-yl)acetamide Step 1. 2-Fluoro-N-methylbenzenesulfonamide A RBF was charged with methylamine (0.5 mL, 40%, 14 mmol) in ethanol (2 mL). The mixture was chilled to 0° C. in an ice bath while being stirred under an inert atmosphere. 2-Fluorobenzenesulfonyl chloride (0.6 mL, 3 mmol) was added dropwise into the mixture. The resulting mixture was allowed to stir at 0° C. for 30 minutes. The mixture was diluted with EtOAc and water. The aqueous layer was extracted with EtOAc three times, and the combined organic layers were washed with brine, dried over sodium sulfate, filtered, and concentrated in vacuo to give 2-fluoro-N-methylbenzenesulfonamide (0.530 g, 99% yield) as a colorless oil. MS (ESI pos. ion) m/z: 190 (MH+). Calculated exact mass for $C_7H_8FNO_2S$: 189.

Step 2. N-(6-(2-(2-Fluoro-N-methylphenylsulfonamido)pyrimidin-4-yl)benzo[d]thiazol-2-yl)acetamide The title compound was prepared in a manner analogous to the procedure described for Example 90 above. MS (ESI pos. ion) m/z: 458 (MH+). Calculated exact mass for $C_{20}H_{16}FN_5O_3S_2$: 457.

Example 93

N-(6-(2-(N,3-Dimethylphenylsulfonamido)pyrimidin-4-yl)benzo[d]thiazol-2-yl)acetamide was prepared by Step 1. N,3-Dimethylbenzenesulfonamide A RBF was charged with methylamine (0.9 mL, 40%, 28 mmol) in ethanol (2 mL). The mixture was chilled to 0° C. in an ice bath while stirred under an inert atmosphere. Then, m-toluenesulfonyl chloride (0.8 mL, 6 mmol) was added dropwise into the mixture. The resulting mixture was allowed to stir at 0° C. under an inert atmosphere for 30 minutes. The mixture was diluted with EtOAc and water and then the aqueous layer was extracted three times with EtOAc. The combined organic layers were washed with brine, dried over sodium sulfate, filtered, and concentrated in vacuo to give N,3-dimethylbenzenesulfonamide (1.0 g, 98% yield) as a colorless oil. MS (ESI pos. ion) m/z: 173 (MH+). Calculated exact mass for $C_7H_{10}NO_2S$: 172.

Step 2. N-(6-(2-(N,3-Dimethylphenylsulfonamido)pyrimidin-4-yl)benzo[d]thiazol-2-yl)acetamide The title compound was prepared in a manner analogous to the procedure described for Example 90 above. MS (ESI pos. ion) m/z: 454 (MH+). Calculated exact mass for $C_{21}H_{19}N_5O_3S_2$: 453.

Example 94

Method G

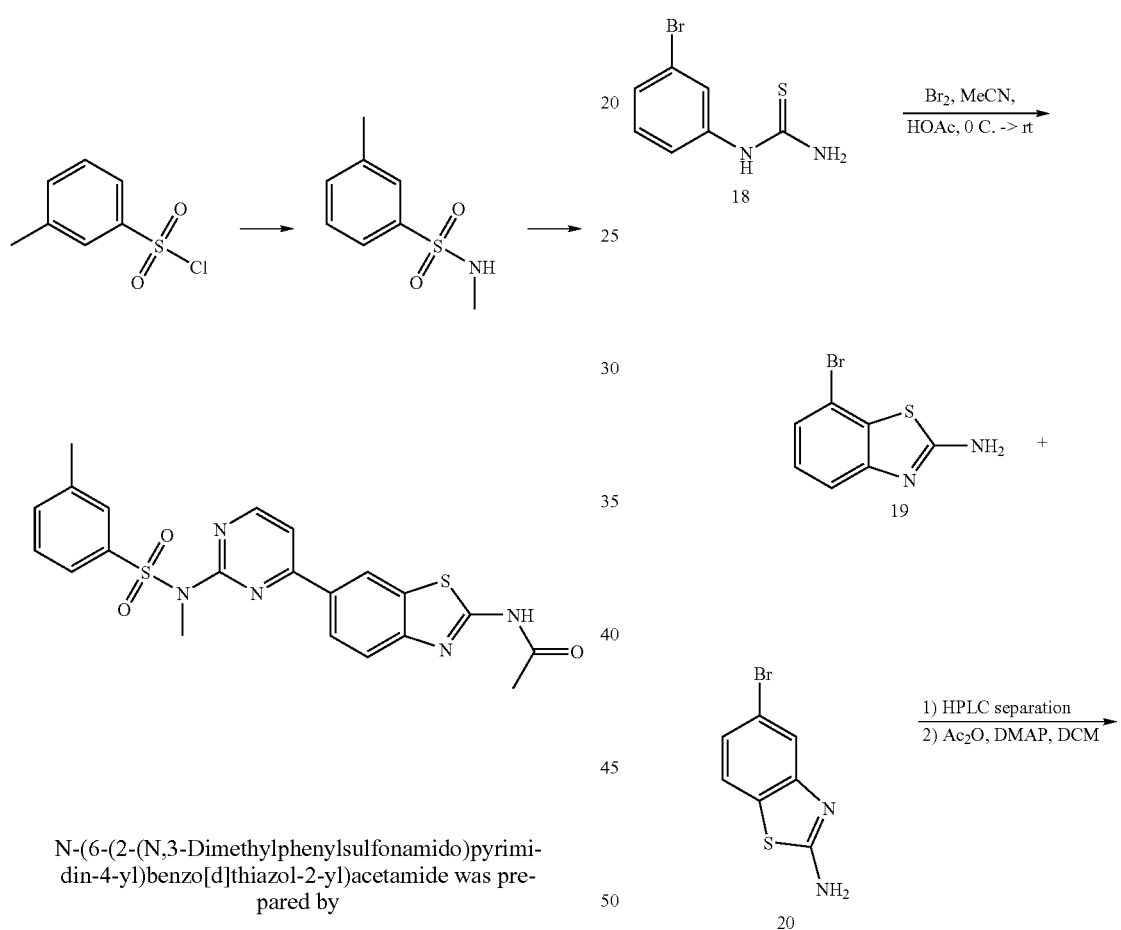

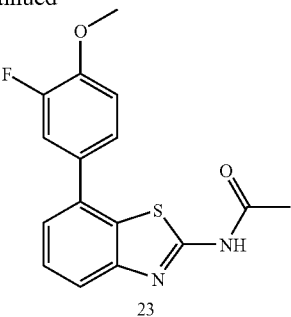

N-(7-(3-Fluoro-4-methoxyphenyl)benzo[d]thiazol-2-yl)acetamide and N-(6-(3-Fluoro-4-methoxyphenyl)benzo[d]thiazol-2-yl)acetamide Step 1. 7-Bromobenzo[d]thiazol-2-amine and 6-Bromobenzo[d]thiazol-2-amine 1-(3-Bromophenyl)-2-thiourea (Oakwood Products, Inc., West Columbia, S.C.; 2.479 g, 10.73 mmol) was suspended in MeCN (200 mL) and cooled in an ice water bath under nitrogen. Then, a solution of bromine (1.1 mL, 21 mmol) in acetic acid (10 mL) was added dropwise over 15 minutes. The reaction was stirred while being cooled in an ice water bath for 30 minutes, then allowed to warm to RT while stirring over the weekend. The resulting precipitate was filtered and the solid was washed with $Et_2O$ to afford the mixture (2.5 g, 100% yield) of 7-bromobenzo[d]thiazol-2-amine and 6-bromobenzo[d]thiazol-2-amine in a 1:2 ratio. MS (ESI pos. ion) m/z: 229 (MH+, $^{79}$Br), 231 (MH+, $^{81}$Br). Calculated exact mass for $C_7H_5BrN_2S$: 228 ($^{79}$Br), 230 ($^{81}$Br).

Step 2. N-(7-Bromobenzo[d]thiazol-2-yl)acetamide and N-(6-Bromobenzo[d]thiazol-2-yl)acetamide The mixture (1.02 g, 4.45 mmol) of 7-bromobenzo[d]thiazol-2-amine and 6-bromobenzo[d]thiazol-2-amine and DMAP (620.6 mg, 5.079 mmol) were suspended in DCM (40 mL) and acetic anhydride (0.46 mL, 4.9 mmol) was added. The reaction was stirred under nitrogen at RT for 2 hours and was then quenched with 1 N HCl (25 mL). The layers were separated, and the aqueous phase was extracted with DCM, and the organic extracts were washed with 1 N HCl, dried over sodium sulfate, filtered, and concentrated to provide the mixture (865 mg, 72% yield) of N-(7-bromobenzo[d]thiazol-2-yl)acetamide and N-(6-bromobenzo[d]thiazol-2-yl)acetamide. MS (ESI pos. ion) m/z: 271 (MH+, $^{79}$Br), 273 (MH+, $^{81}$Br). Calculated exact mass for $C_9H_7BrN_2S$: 270 ($^{79}$Br), 272 ($^{81}$Br).

Step 3. N-(7-(3-Fluoro-4-methoxyphenyl)benzo[d]thiazol-2-yl)acetamide and N-(6-(3-Fluoro-4-methoxyphenyl)benzo[d]thiazol-2-yl)acetamide The mixture (302.6 mg, 1.116 mmol) of N-(7-bromobenzo[d]thiazol-2-yl)acetamide and N-(6-bromobenzo[d]thiazol-2-yl)acetamide, 3-fluoro-4-methoxyphenylboronic acid (298 mg, 1.75 mmol), sodium carbonate monohydrate (0.247 mL, 4.48 mmol), and dichlorobis(triphenylphosphine)palladium(II) (168 mg, 0.239 mmol) were suspended in 1,2-dimethoxyethane (3.5 mL), water (1.5 mL) and EtOH (1.0 mL). The reaction flask was fit with a reflux condensor and placed in a preheated oil bath (85° C.) and stirred under argon for 1 hour. The reaction was cooled to room temperature and allowed to stand overnight. It was then filtered through a Celite® (diatomaceous earth) pad, and the solid was washed with MeOH, DCM, and DME. The filtrate was concentrated and treated with DCM. The resulting precipitate was collected by filtration and the crude was further purified by HPLC to provide N-(7-(3-Fluoro-4-methoxyphenyl)benzo[d]thiazol-2-yl)acetamide and N-(6-(3-Fluoro-4-methoxyphenyl)benzo[d]thiazol-2-yl)acetamide.

Step 4: N-(7-(3-Fluoro-4-methoxyphenyl)benzo[d]thiazol-2-yl)acetamide

The title compound was isolated, by purifying the mixture of compounds from step 3, as a white solid (LCMS 10-minute run shows peak at 6.5 minutes). MS (ESI pos. ion) m/z: 317 (MH+). Calculated exact mass for $C_{16}H_{13}FN_2O_2S$: 316. $^1$H NMR (400 MHz, DMSO-$d_6$): 12.32 (s, 1H), 7.73 (d, J=8.0 Hz, 1H), 7.52-7.55 (m, 3H), 7.36 (t, J=7.8 Hz, 2H), 3.92 (s, 3H), 2.20 (s, 3H).

Step 5: N-(6-(3-Fluoro-4-methoxyphenyl)benzo[d]thiazol-2-yl)acetamide

The title compound was isolated, by purifying the mixture of compounds from step 3, as a white solid (LCMS 10-minute run shows peak at 6.5 minutes). MS (ESI pos. ion) m/z: 317 (MH+). Calculated exact mass for $C_{16}H_{13}FN_2O_2S$: 316. $^1$H NMR (400 MHz, DMSO-$d_6$): 12.36 (s, 1H), 8.01 (d, J=8.0 Hz, 1H), 7.97 (s, 1H), 7.56-7.67 (m, 3H), 7.26 (t, J=8.8 Hz, 1H), 3.89 (s, 3H), 2.21 (s, 3H).

Example 95

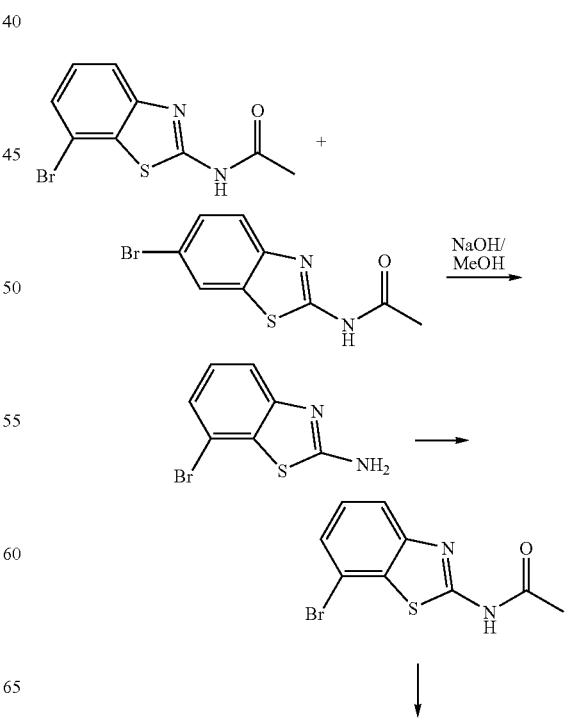

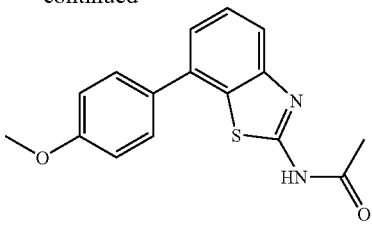

N-(7-(4-Methoxyphenyl)benzo[d]thiazol-2-yl)acetamide

Step 1. 7-Bromobenzo[d]thiazol-2-amine

The mixture (562 mg, 2.07 mmol) of N-(7-bromobenzo[d]thiazol-2-yl)acetamide and N-(6-bromobenzo[d]thiazol-2-yl)acetamide were suspended in MeOH (10 mL) and water (2 mL), sodium hydroxide (468.1 mg, 11.70 mmol) were added. The flask was fit with a reflux condenser and placed in a preheated oil bath (78° C.-80° C.) and stirred under nitrogen for 90 minutes. The reaction was cooled to RT and treated with 5N HCl to lower the pH to about 2. The suspension was filtered, and the solid was washed with water. The filtrate was treated with saturated sodium bicarbonate to adjust pH to about 7, and it was filtered again. The solid was collected and purified on an HPLC (10-95% MeCN/water with 0.1% TFA over 40 minutes) to provide 7-bromobenzo[d]thiazol-2-amine (550.3 mg).

MS (ESI pos. ion) m/z: 229 (MH+, [79]Br), 231 (MH+, [81]Br). Calculated exact mass for $C_7H_5BrN_2S$: 228 ([79]Br), 230 ([81]Br). $^1$H NMR (400 MHz, DMSO-$d_6$): 7.83 (br s, 2H), 7.32 (d, J=7.0 Hz, 1H), 7.16-7.22 (m, 2H).

Step 2. N-(7-Bromobenzo[d]thiazol-2-yl)acetamide

7-Bromobenzo[d]thiazol-2-amine (550 mg, 2.40 mmol) and DMAP (330 mg, 2.70 mmol) were suspended in DCM (12 mL) and acetic anhydride (0.25 mL, 2.7 mmol) was added. The reaction was stirred under nitrogen at RT for 6 hours, the suspension was filtered, and the solid was washed with DCM. The solid was collected, and the filtrate was concentrated and treated with MeOH. This batch of solid was also collected by filtration. The filtrate was concentrated, and filtered through silica gel (40:1 DCM/MeOH) to provide additional products. The collected solids were combined to afford N-(7-bromobenzo[d]thiazol-2-yl)acetamide (433 mg, 67% yield) as a white solid. MS (ESI pos. ion) m/z: 271 (MH+, [79]Br), 273 (MH+, [81]Br). Calculated exact mass for $C_9H_7BrN_2S$: 270 ([79]Br), 272 ([81]Br).

Step 3. N-(7-(4-Methoxyphenyl)benzo[d]thiazol-2-yl)acetamide

N-(7-Bromobenzo[d]thiazol-2-yl)acetamide (56.5 mg, 0.208 mmol), 4-methoxybenzeneboronic acid (47.8 mg, 0.315 mmol), dichlorobis(triphenyl-phosphine)palladium (II) (30.7 mg, 43.7 μmol), and sodium carbonate (0.31 mL, 2 M, 0.62 mmol) were suspended in EtOH (0.25 mL) and 1,2-dimethoxyethane (0.9 mL). The flask was fit with a reflux condenser and placed in a preheated oil bath (85° C.) and stirred under nitrogen for 50 minutes. The reaction was cooled to RT, and filtered through a pad of Celite® (diatomaceous earth). This pad was washed with DCM and MeOH, and the filtrate was concentrated and filtered through a silica gel pad with 10:1 DCM/MeOH. The filtrate was concentrated and purified on HPLC (10-95% MeCN/water with 0.1% TFA over 30 minutes) to provide N-(7-(4-methoxyphenyl)benzo[d]thiazol-2-yl)acetamide. MS (ESI pos. ion) m/z: 299 (MH+). Calculated exact mass for $C_{16}H_{14}N_2O_2S$: 298. $^1$H NMR (400 MHz, DMSO-$d_6$): 12.34 (s, 1H), 7.70 (d, J=8.0 Hz, 1H), 7.63 (d, J=8.5 Hz, 5H), 7.51 (t, J=7.8 Hz, 1H), 7.34 (d, J=7.5 Hz, 1H), 7.12 (d, J=8.5 Hz, 2H), 3.81 (s, 3H), 2.20 (s, 3H).

Compound Example 96 was prepared in a manner analogous to the procedure described for Example 94, Method G above Example 97

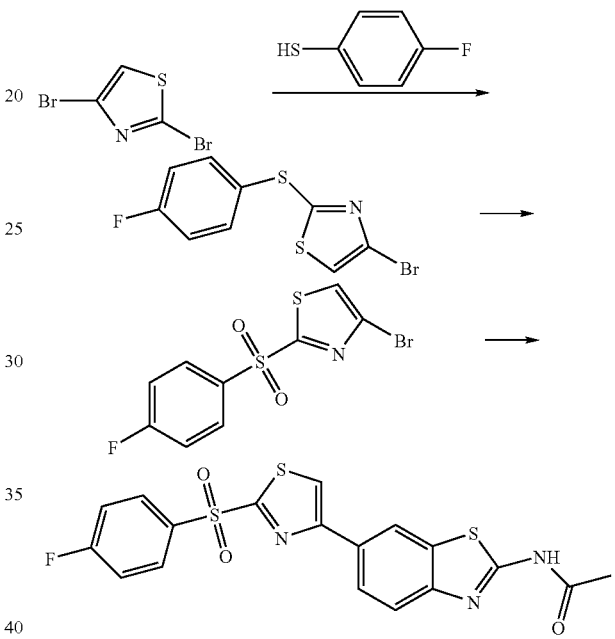

N-(6-(2-(4-Fluorophenylsulfonyl)thiazol-4-yl)benzo[d]thiazol-2-yl)acetamide

Step 1. 4-Bromo-2-(4-fluorophenylthio)thiazole

4-Fluorothiophenol (0.48 mL, 4.5 mmol) was dissolved in DMF (10 mL) and then chilled to 0° C. in an ice bath. NaH (0.14 g, 5.8 mmol) was added slowly to the mixture and it was allowed to stir under inert atmosphere. After 1 hour, 2,4-dibromothiazole (1.0 g, 4.1 mmol) was added to the mixture and the ice bath was removed. The resulting mixture was allowed to stir 3 hours under an inert atmosphere. The mixture was quenched with 1N NaOH and diluted with DCM. The aqueous layer was extracted three times with 4:1 DCM/MeOH, and the combined organic extracts were dried over $Na_2SO_4$, filtered, and concentrated in vacuo. The crude material was purified by silica gel chromatography (1-10% EtOAc/hexanes) to give 4-bromo-2-(4-fluorophenylthio)thiazole (1.0 g, 84% yield) as a white solid. MS (ESI pos. ion) m/z: 290 (MH+, [79]Br), 292 (MH+, [81]Br). Calculated exact mass for $C_9H_5BrFNS_2$: 289 ([79]Br), 291 ([81]Br).

Step 2. 4-Bromo-2-(4-fluorophenylsulfonyl)thiazole

4-Bromo-2-(4-fluorophenylthio)thiazole (0.448 g, 1.54 mmol) was dissolved in acetic acid (3 mL) and then hydrogen peroxide (3 mL, 30%, 88 mmol) was added slowly into the mixture. The flask was fit with a reflux condensor and placed into a pre-heated (70° C.) bath and allowed to stir under an inert atmosphere for 2 hours. The mixture was quenched with saturated sodium bicarbonate and diluted with DCM. The mixture was allowed to stir an additional 30 minutes, and then 1N NaOH (50 mL) was added. The aqueous layer was extracted with DCM three times, and the combined organic extracts were dried over sodium sulfate, filtered, and concentrated in vacuo to give 4-bromo-2-(4-fluorophenylsulfonyl) thiazole (0.42 g, 84% yield) as a white solid. MS (ESI pos. ion) m/z: 322 (MH+, $^{79}$Br), 324 (MH+, $^{81}$Br). Calculated exact mass for $C_9H_5BrFNO_2S_2$: 321 ($^{79}$Br), 323 ($^{81}$Br).

Step 3. N-(6-(2-(4-Fluorophenylsulfonyl)thiazol-4-yl)benzo[d]thiazol-2-yl)acetamide A RBF was charged with N-(6-(4,4,5,5-tetramethyl-1,3,2-dioxaborolan-2-yl)benzo[d]thiazol-2-yl)acetamide (0.5 g, 1 mmol), 4-bromo-2-(4-fluorophenylsulfonyl)thiazole (0.4 g, 1 mmol), 2 M $Na_2CO_3$ (1 mL, 2 mmol), tetrakis(triphenylphosphine)palladium(0) (0.2 g, 0.2 mmol), and dioxane (6 mL). The flask was placed into a pre-heated (95° C.) bath and allowed to stir under an inert atmosphere overnight. The mixture was diluted with DMSO and filtered. The crude was purified by reverse-phase HPLC to give N-(6-(2-(4-fluorophenylsulfonyl)thiazol-4-yl)benzo[d]thiazol-2-yl)acetamide as an off-white solid. MS (ESI pos. ion) m/z: 434 (MH+). Calculated exact mass for $C_{18}H_{12}FN_3O_3S_3$: 433. $^1$H NMR (400 MHz, DMSO-$d_6$): 8.53 (s, 1H), 8.30 (s, 1H), 8.21 (s, 2H), 7.81 (s, 1H), 7.56 (s, 3H), 2.07 (s, 3H).

Example 98

Method H

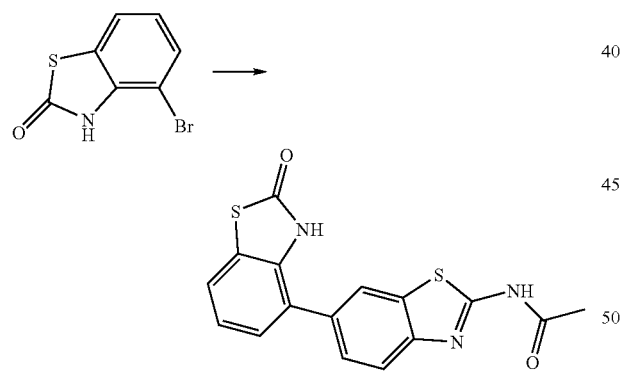

N-(6-(2-oxo-2,3-Dihydrobenzo[d]thiazol-4-yl)benzo[d]thiazol-2-yl)acetamide

Step 1: 4-Bromobenzo[d]thiazol-2(3H)-one (69.9 mg, 0.304 mmol), N-(6-(4,4,5,5-tetramethyl-1,3,2-dioxaborolan-2-yl)benzo[d]thiazol-2-yl)acetamide (124.9 mg, 3.925 mmol), dichlorobis(triphenyl-phosphine)palladium (II) (39.7 mg, 56.6 μmol), and sodium carbonate (0.30 mL, 2.0 M in water, 0.60 mmol) were suspended in 1,2-dimethoxyethane (1.4 mL) and ethanol (0.39 mL). The reaction flask was fit with a reflux condensor and the solution was heated in a preheated oil bath (85° C.) and stirred under nitrogen for 7 hours, at which time the reaction was slowly allowed to cool to RT. After sitting at RT for 4 days, more $PdCl_2(PPh_3)_2$ (37.3 mg) was added, and stirring was resumed at 85° C. for 4 hours. Then, the reaction was cooled to RT and filtered through a silica gel plug with 10:1 DCM/MeOH. The filtrate was concentrated and purified on HPLC (10-95% MeCN/water with 0.1% TFA over 40 minutes) to provide N-(6-(2-oxo-2,3-dihydrobenzo[d]thiazol-4-yl)benzo[d]thiazol-2-yl)acetamide. MS (ESI pos. ion) m/z: 342 (MH+). Calculated exact mass for $C_{16}H_{11}N_3O_2S_2$: 341.

Example 99

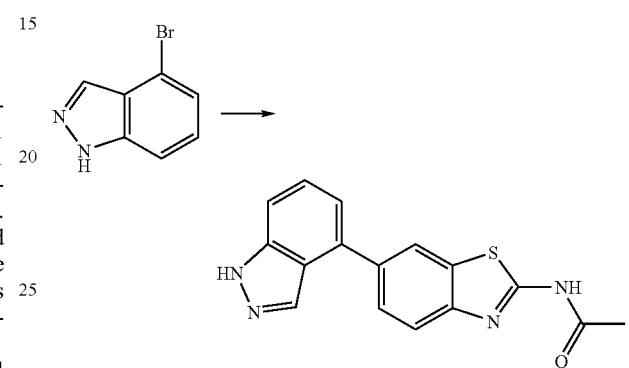

N-(6-(1H-Indazol-4-yl)benzo[d]thiazol-2-yl)acetamide

4-Bromo-1H-indazole (96.8 mg, 0.491 mmol), N-(6-(4,4,5,5-tetramethyl-1,3,2-dioxaborolan-2-yl)benzo[d]thiazol-2-yl)acetamide (193.2 mg, 6.072 mmol), and tetrakis(triphenylphosphine)palladium(0) (51.5 mg, 44.6 μmol) were suspended in 1,4-dioxane (2.0 mL) and sodium carbonate (0.50 mL, 2M in water, 1.0 mmol) was added. The flask was fit with a reflux condensor and placed in a preheated oil bath (95° C.) and stirred under nitrogen overnight. The mixture was then cooled to RT and filtered through a pad of Celite® (diatomaceous earth). The filtrate was concentrated and purified on HPLC (10-95% MeCN/water with 0.1% TFA over 40 minutes) to give N-(6-(1H-indazol-4-yl)benzo[d]thiazol-2-yl)acetamide. MS (ESI pos. ion) m/z: 309 (MH+). Calculated exact mass for $C_{16}H_{12}N_4OS$: 308.

Example 100

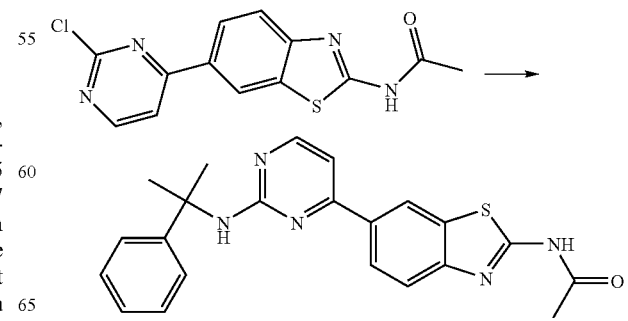

N-(6-(6-Methyl-2-(2-phenylpropan-2-ylamino)pyrimidin-4-yl)benzo[d]thiazol-2-yl)acetamide A solution of N-(6-(2-chloropyrimidin-4-yl)benzo[d]thiazol-2-yl)acetamide (0.1 g, 0.3 mmol), cumylamine (0.05 mL, 0.4 mmol), cesium carbonate (0.05 g, 0.7 mmol) in N,N-DMF was heated under microwave (CEM) at 180° C. for 20 min. The mixture was diluted with DCM and washed with water, dried over sodium sulfate, and concentrated. The residue was purified by HPLC (5-100% $CH_3CN$ in water with 0.05% TFA) to give N-(6-(2-(2-phenylpropan-2-ylamino)pyrimidin-4-yl)benzo[d]thiazol-2-yl)acetamide as an off-white solid. MS (ESI pos. ion) m/z: 404 (MH+). Calculated exact mass for $C_{22}H_{21}N_5OS$: 403.

Example 101

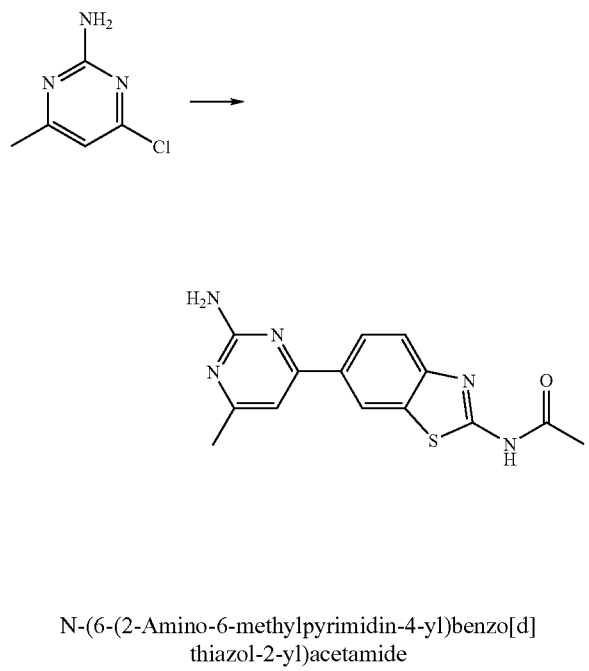

N-(6-(2-Amino-6-methylpyrimidin-4-yl)benzo[d]thiazol-2-yl)acetamide

To a suspension of tetrakis(triphenylphosphine)palladium (0) (0.115 g, 0.0999 mmol), 4-chloro-6-methylpyrimidin-2-amine (0.142 g, 0.999 mmol), N-(6-(4,4,5,5-tetramethyl-1,3,2-dioxaborolan-2-yl)benzo[d]thiazol-2-yl)acetamide (0.318 g, 0.999 mmol) under nitrogen was added sodium carbonate (1 mL, 2M in water, 2 mmol) and then 1,4-dioxane (6 mL). The flask was heated in a pre-heated (90° C.) bath and stirred under an inert atmosphere overnight. The mixture was allowed to cool to ambient temperature and concentrated. The crude material was diluted with DCM and washed with brine. The organic layer was dried over sodium sulfate, concentrated, and purified by silica gel chromatography (0-10% MeOH in DCM) to give N-(6-(2-amino-6-methylpyrimidin-4-yl)benzo[d]thiazol-2-yl)acetamide (200 mg, 67%) as a brown solid. MS (ESI pos. ion) m/z: 300 (MH+). Calculated exact mass for $C_{14}H_{13}N_5OS$: 299.

Compound Examples 102-105 and 150 (Table I) were prepared in an analogous manner to Compound Example 1, Method A.

Compound Examples 106-109, 118, 122-123, 125-130, 133-135, 138-140, 149, 154, 158 and 160 (Table I) were prepared in an analogous manner to compound Example 16, Method C.

Example 110

Method I

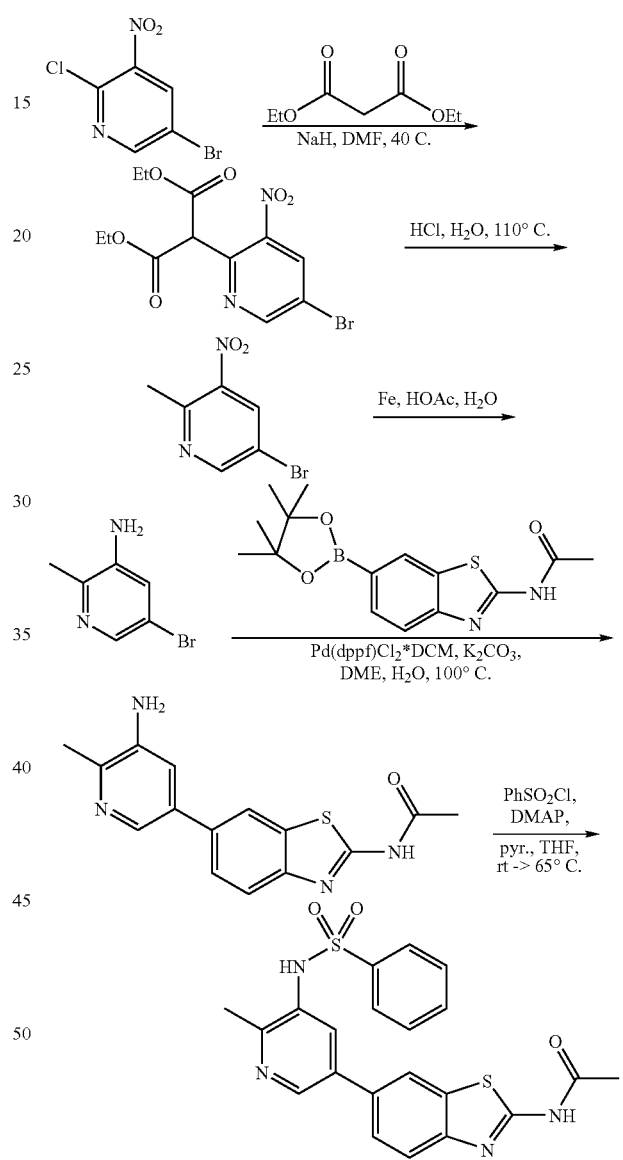

N-(6-(6-methyl-5-(phenylsulfonamido)pyridin-3-yl)benzo[d]thiazol-2-yl)acetamide

Step 1. Diethyl 2-(5-bromo-3-nitropyridin-2-yl)malonate

Sodium hydride (60% in mineral oil, 1.28 g, 0.032 mol) was suspended in DMF (25 ml) and diethyl malonate (4.0 ml, 26 mmol) was added via syringe slowly over 20 minutes, and more DMF (5 ml) was added as a rinse. The reaction stirred at room temperature for 20 minutes, and then 5-bromo-2-chloro-3-nitropyridine (3.2 g, 14 mmol) was added as a solution in DMF. The reaction was placed in a preheated oil bath (40° C.) and stirred under nitrogen for 1 hour. The reaction was cooled to room temperature, quenched with water (50 ml) and allowed to stand at room temperature overnight. The aqueous phase was extracted with $Et_2O$ (3×100 ml, 50 ml), then EtOAC (100 ml) and $Et_2O$ (50 ml, 2×100 ml). The organic extracts were combined, dried over magnesium sulfate, filtered, and concentrated, and taken to the next step. MS (ESI pos. ion) m/z: 361 ($MH^+$, $^{79}Br$), 363 ($MH^+$, $^{81}Br$). Calculated exact mass for $C_{12}H_{13}BrN_2O_6$: 360 ($^{79}Br$), 362 ($^{81}Br$).

Step 2. 5-bromo-2-methyl-3-nitropyridine

The crude material was suspended in hydrochloric acid (5 N, 35 ml, 175 mmol) and the flask was fit with a reflux condensor and placed in a preheated oil bath (110° C.) and stirred for 5 hours. The reaction was cooled to room temperature, and allowed to stand over the weekend, and then treated with concentrated HCl (10 ml). Stirring was continued at 115° C.-120° C. for 2.5 hours, and then the reaction was cooled to room temperature and extracted with $Et_2O$ (4×100 ml). The organic extracts were combined, dried over magnesium sulfate, filtered, concentrated, and filtered through a pad of silica gel with 20:1 hexanes/EtOAc. DCM and MeOH were used to help load the crude material on the column. The fractions with product were collected, concentrated, and dried under high vacuum to afford 5-bromo-2-methyl-3-nitropyridine (1.808 g, 88% purity, 62% yield over two steps. MS (ESI pos. ion) m/z: 217 ($MH^+$, $^{79}Br$), 219 ($MH^+$, $^{81}Br$). Calculated exact mass for $C_6H_5BrN_2O_2$: 216 ($^{79}Br$), 218 ($^{81}Br$).

Step 3. 5-bromo-2-methylpyridin-3-amine 5-bromo-2-methyl-3-nitropyridine (1.808 g, 8.33 mmol) was suspended in glacial acetic acid (16 ml) and water (4 ml) and iron powder (1.411 g, 25.3 mmol) was added in portions over 5 minutes. The reaction was stirred under nitrogen at room temperature for 70 minutes, using a water bath to cool the reaction flask. Then, the reaction was diluted with EtOAc (20 ml) and the suspension was poured into 5 N NaOH (50 ml). The emulsion was filtered through a pad of Celite® (diatomaceous earth), which was washed with water and EtOAc. Layers separated, and the aqueous phase was extracted with EtOAc (2×50 ml). The organic extracts and phases were combined, dried over sodium sulfate, filtered, concentrated, and dried under high vacuum to afford 5-bromo-2-methylpyridin-3-amine.
MS (ESI pos. ion) m/z: 187 ($MH^+$, $^{79}Br$), 189 ($MH^+$, $^{81}Br$). Calculated exact mass for $C_6H_7BrN_2$: 186 ($^{79}Br$), 188 ($^{81}Br$).

Step 4. N-(6-(5-amino-6-methylpyridin-3-yl)benzo[d]thiazol-2-yl)acetamide 5-bromo-2-methylpyridin-3-amine (224.9 mg, 1.202 mmol), N-(6-(4,4,5,5-tetramethyl-1,3,2-dioxaborolan-2-yl)benzo[d]thiazol-2-yl)acetamide (413.7 mg, 1.300 mmol), potassium carbonate (549.4 mg, 3.975 mmol), and Pd(dppf)$Cl_2$*DCM complex (108.7 mg, 0.133 mmol) were suspended in DME (5.0 ml) and water (1.25 ml), and the flask was fit with a reflux condensor and argon was bubbled through for about 15 seconds. Then, the flask was placed in a preheated oil bath (100° C.) and stirred under argon for 80 minutes. The reaction was cooled to room temperature, and the aqueous phase was removed via pipette. The reaction was then concentrated, treated with MeOH, and filtered. Solid washed with MeOH, water, MeOH, and $Et_2O$. Solid then collected and dried under high vacuum to afford N-(6-(5-amino-6-methylpyridin-3-yl)benzo[d]thiazol-2-yl)acetamide (179.7 mg, 50% yield). MS (ESI pos. ion) m/z: 299. Calculated exact mass for $C_{15}H_{14}N_4OS$: 298.

Step 5. N-(6-(6-methyl-5-(phenylsulfonamido)pyridin-3-yl)benzo[d]thiazol-2-yl)acetamide N-(6-(5-amino-6-methylpyridin-3-yl)benzo[d]thiazol-2-yl)acetamide (101.9 mg, 0.342 mmol) and 4-dimethylaminopyridine (4.2 mg, 0.034 mmol) were suspended in pyridine (2.0 ml) and THF (2.0 ml) and benzenesulfonyl chloride (0.21 ml, 1.637 mmol) was added. The reaction was stirred under nitrogen at room temperature. After 1 day, more DMAP (21.3 mg) was added and stirring was continued. After about 2 hours, more benzenesulfonyl chloride (0.18 ml) was added, and stirring was continued. After 3.5 hours, flask put in preheated oil bath (65° C.) and stirring continued. After 45 minutes, LCMS shows mostly product, so reaction cooled to room temperature, concentrated and purified on a silica gel column (20:1 to 10:1 DCM/MeOH to 10:1 DCM/2 N ammonia in MeOH). Fractions with product collected, concentrated, treated with DCM, and filtered. Solid washed with DCM and $Et_2O$, collected, and dried under high vacuum to afford N-(6-(6-methyl-5-(phenylsulfonamido)pyridin-3-yl)benzo[d]thiazol-2-yl)acetamide (38.0 mg, 25% yield). MS (ESI pos. ion) m/z: 439. Calculated exact mass for $C_{21}H_{18}N_4O_3S_2$: 438.

Compound Examples 111-116 and 142 (Table I) were prepared in an analogous manner to Compound Example 110, Method I.

Example 117

Method J

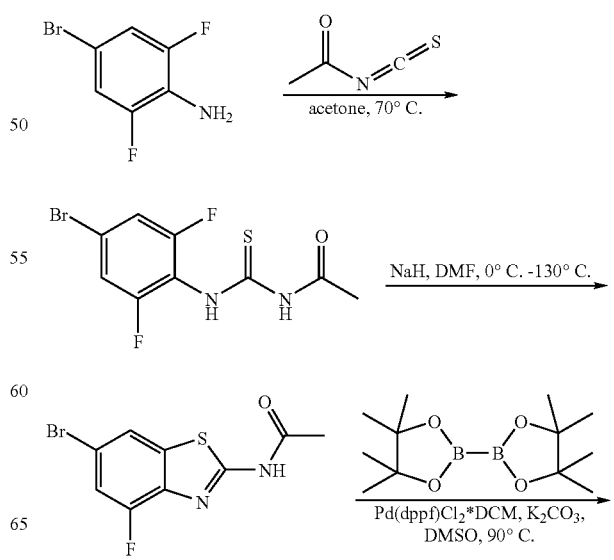

-continued

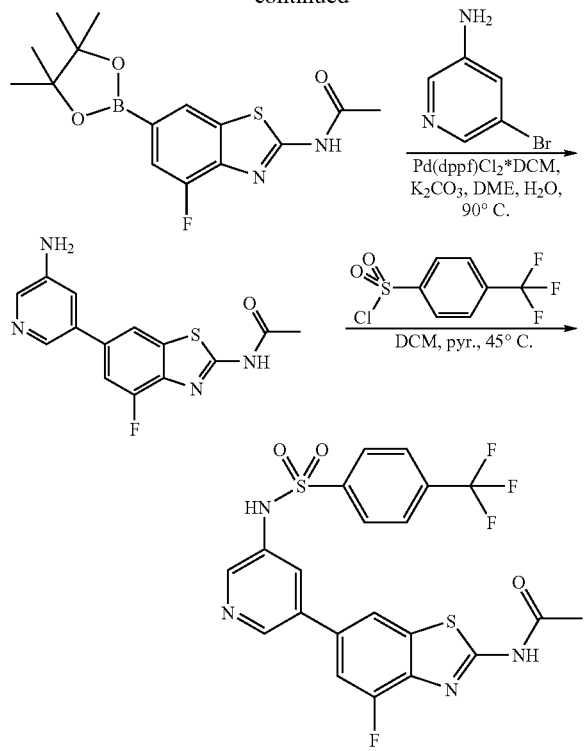

N-(4-fluoro-6-(5-(4-(trifluoromethyl)phenylsulfonamido)pyridin-3-yl)benzo[d]thiazol-2-yl)acetamide Step 1.
1-acetyl-3-(4-bromo-2,6-difluorophenyl)thiourea 4-bromo-2,6-difluorobenzenamine (2.514 g, 12.1 mmol) was dissolved in acetone (75 ml) and ethanoyl isothiocyanate (1.30 ml, 14.8 mmol) was added. The reaction flask was fit with a reflux condensor and placed in a preheated oil bath (70-74° C.) and the reaction was stirred under nitrogen for 90 minutes. The reaction was then cooled to room temperature and poured into water (200 ml), and the resultant suspension was filtered. The solid was washed with water, collected, and dried under high vacuum in water bath (60° C.) to afford 1-acetyl-3-(4-bromo-2,6-difluorophenyl)thiourea (3.435 g, 93% purity, 85% yield). MS (ESI pos. ion) m/z: 309 (MH+, $^{79}$Br), 311 (MH+, $^{81}$Br). Calculated exact mass for $C_9H_7BrF_2N_2OS$ 308 ($^{79}$Br), 310 ($^{81}$Br).

Step 2.
N-(6-bromo-4-fluorobenzo[d]thiazol-2-yl)acetamide 1-acetyl-3-(4-bromo-2,6-difluorophenyl)thiourea (3.356 g, 10.86 mmol) was dissolved in DMF (100 ml) and the flask was cooled under nitrogen in an ice water bath. Then, sodium hydride (60% in mineral oil, 512.6 mg, 12.82 mmol) was added, and the reaction was warmed to room temperature and stirred for 1 hour. Then, the reaction flask was put in a preheated oil bath (130° C.) and stirred under nitrogen for an additional hour. The reaction was cooled to room temperature, poured into deionized water (300 ml), and filtered. The solid was washed with water and then dried by suction overnight to afford N-(6-bromo-4-fluorobenzo[d]thiazol-2-yl)acetamide (3.205 g, ~100%). MS (ESI pos. ion) m/z: 289 (MH+, $^{79}$Br), 291 (MH+, $^{81}$Br). Calculated exact mass for $C_9H_6BrFN_2OS$ 288 (79Br), 290 (81Br).

Step 3. N-(4-fluoro-6-(4,4,5,5-tetramethyl-1,3,2-dioxaborolan-2-yl)benzo[d]thiazol-2-yl)acetamide N-(6-bromo-4-fluorobenzo[d]thiazol-2-yl)acetamide (2.935 g, 10.15 mmol), 4,4,5,5-tetramethyl-2-(4,4,5,5-tetramethyl-1,3,2-dioxaborolan-2-yl)-1,3,2-dioxaborolane (3.102 g, 12.22 mmol), dichloro[1,1'-bis(diphenylphosphino)ferrocene]palladium (ii) dichloromethane adduct (765.1 mg, 1.046 mmol), and potassium acetate (3.038 g, 30.96 mmol) were suspended in DMSO (40 ml) and argon was bubbled through for about 30 seconds. Then, the flask was put in a preheated oil bath (90° C.) and stirred under argon for 7 hours and 15 minutes, and the reaction was then cooled to room temperature and allowed to stand overnight. The reaction was filtered through a Celite® (diatomaceous earth) pad, which was washed with DCM and MeOH. The filtrate was concentrated, treated with DCM, and filtered. The solid was washed with DCM, and the filtrate was concentrated. The solid was discarded, while the filtrate was purified on silica gel (~3 inches, 20:1 to 10:1 DCM/MeOH). The fractions with product were collected, concentrated, treated with $Et_2O$, and filtered. Both solid and filtrate contain product by LCMS, so they were combined, concentrated, and treated with hexanes. The hexanes wash was decanted and precipitation occurred. This hexanes suspension was filtered. The filtrate precipitated, and the liquid was decanted and discarded. The remaining solid, plus the solid collected by the filtration were combined with the original solid and dried under high vacuum, first in a water bath (~60° C.) with a kugelrohr bulb to collect residual DMSO, and then at room temperature overnight. Material again purified on silica gel (~3 inches, 20:1 DCM/MeOH to 15:1 DCM/MeOH) to afford N-(4-fluoro-6-(4,4,5,5-tetramethyl-1,3,2-dioxaborolan-2-yl)benzo[d]thiazol-2-yl)acetamide (4.237 g, 65% purity, 81% yield). MS (ESI pos. ion) m/z: 337. Calculated exact mass for $C_{15}H_{18}BFN_2O_3S$ 336.

Steps 4 and 5. N-(4-fluoro-6-(5-(4-(trifluoromethyl)phenylsulfonamido)pyridin-3-yl)benzo[d]thiazol-2-yl)acetamide See Method E for procedure on how to accomplish steps 4 and 5.

For the final compound: MS (ESI pos. ion) m/z: 511. Calculated exact mass for $C_{21}H_{14}F_4N_4O_3S_2$ 510.

Compound Examples 131, 137, 143, and 148 (Table I) were prepared in an analogous manner to Compound Example 117, Method J in combination with one or more of Methods A, C and D.

Example 141

Method K

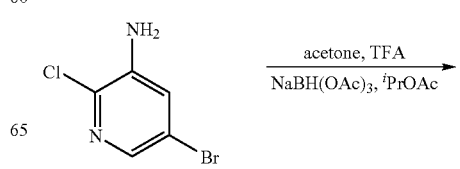

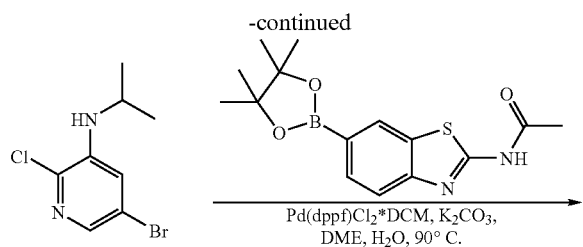

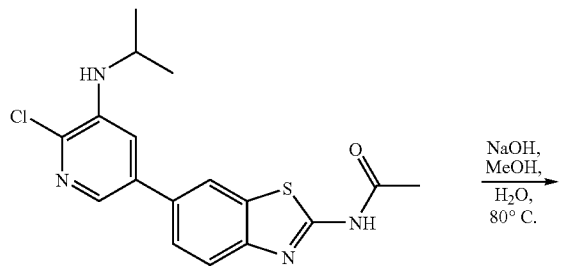

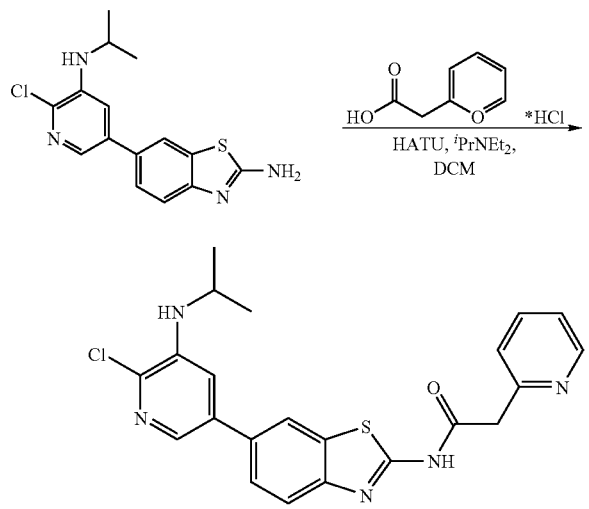

N-(6-(6-chloro-5-(isopropylamino)pyridin-3-yl)
benzo[d]thiazol-2-yl)-2-(pyridin-2-yl)acetamide

Step 1. 5-bromo-2-chloro-N-isopropylpyridin-3-amine 5-bromo-2-chloropyridin-3-amine (1.889 g, 9.1 mmol) was dissolved in isopropyl acetate (20 ml) and acetone (0.81 ml, 11 mmol), trifluoroacetic acid (1.40 ml, 18 mmol), and sodium triacetoxyborohydride (2.34 g, 11 mmol) were added. The reaction was stirred under nitrogen at room temperature for almost 4.5 hours and then quenched with 10% sodium hydroxide in water (~20 ml) to raise the pH to about 9. The layers were separated, and the aqueous phase was extracted with EtOAc. The organic extracts were combined, dried over sodium sulfate, filtered, concentrated, and dried under high vacuum to afford 5-bromo-2-chloro-N-isopropylpyridin-3-amine (2.33 g, 89% purity, 100% yield). MS (ESI pos. ion) m/z: 249 (MH+, $^{79}$Br), 251 (MH+, $^{81}$Br). Calculated exact mass for $C_8H_{10}BrClN_2$ 248 ($^{79}$Br), 250 ($^{81}$Br).

Step 2. N-(6-(6-chloro-5-(isopropylamino)pyridin-3-yl)benzo[d]thiazol-2-yl)acetamide 5-bromo-2-chloro-N-isopropylpyridin-3-amine (127.6 mg, 0.511 mmol), N-(6-(4,4,5,5-tetramethyl-1,3,2-dioxaborolan-2-yl)benzo[d]thiazol-2-yl)acetamide (191.5 mg, 0.602 mmol), potassium carbonate (317.8 mg, 2.299 mmol), and Pd(dppf)$C_{12}$-DCM complex (42.9 mg, 0.0526 mmol) were suspended in 1,2-dimethoxyethane (2.0 ml) and water (0.5 ml). Argon was bubbled through the suspension for about 15 seconds, and then the flask was fit with a reflux condensor and placed in a preheated oil bath (100° C.) and stirred under argon for 100 minutes. The reaction was cooled to room temperature, concentrated, and treated with DCM and MeOH. These organic washings were decanted, concentrated, treated with water, and filtered. The solid was washed with water and the filtrate was discarded. Solid also washed with MeOH and $Et_2O$, but the filtrate and solid contain product. The solid and filtrate were combined, concentrated, and purified on a silica gel column (25:1 to 20:1 DCM/MeOH to 15:1 DCM/2 N ammonia in MeOH) to afford N-(6-(6-chloro-5-(isopropylamino)pyridin-3-yl)benzo[d]thiazol-2-yl)acetamide (64.5 mg, 35% yield). MS (ESI pos. ion) m/z: 361. Calculated exact mass for $C_{17}H_{17}ClN_4OS$ 360.

Step 3. 6-(6-chloro-5-(isopropylamino)pyridin-3-yl)benzo[d]thiazol-2-amine

N-(6-(6-chloro-5-(isopropylamino)pyridin-3-yl)benzo[d]thiazol-2-yl)acetamide (123.6 mg, 342.5 µmol) was suspended in MeOH (2.2 ml) and sodium hydroxide (89.90 mg, 2248 µmol) and water (0.44 ml) were added. The reaction flask was fit with a reflux condenser and placed in a preheated oil bath (80° C.), and the reaction was stirred for 1 hour. The reaction was cooled to room temperature, treated with 5 N HCl to neutralize the solution, and allowed to stand overnight. It was then extracted with 10:1 DCM/MeOH, and the organic extracts were combined, concentrated, and purified on a silica gel column (20:1 DCM/MeOH to 15:1 DCM/2 N ammonia in MeOH). Fractions with product collected, concentrated, and treated with $Et_2O$ and MeOH. The MeOH washings were decanted, and the solid was collected and dried under high vacuum to afford 6-(6-chloro-5-(isopropylamino)pyridin-3-yl)benzo[d]thiazol-2-amine (18.2 mg, 17% yield). MS (ESI pos. ion) m/z: 319. Calculated exact mass for $C_{15}H_{15}ClN_4S$ 318.

Step 4. N-(6-(6-chloro-5-(isopropylamino)pyridin-3-yl)benzo[d]thiazol-2-yl)-2-(pyridin-2-yl)acetamide 6-(6-chloro-5-(isopropylamino)pyridin-3-yl)benzo[d]thiazol-2-amine (121.8 mg, 0.382 mmol) and HATU (215.9 mg, 0.568 mmol) were suspended in DCM (2.9 ml) and diisopropylethylamine (0.21 ml, 1.2 mmol) and 2-pyridylacetic acid hydrochloride (94.3 mg, 0.543 mmol) were added. The reaction was stirred under nitrogen at room temperature overnight, concentrated and purified on a silica gel column (20:1 DCM/MeOH). Fractions with product were collected, concentrated, and purified on HPLC (10% to 100% MeCN/water with 0.1% TFA over 30 minutes). Fractions with product were collected, concentrated, and dried under high vacuum in a water bath (~50° C.), then at room temperature overnight to afford N-(6-(6-chloro-5-(isopropylamino)pyridin-3-yl)benzo[d]thiazol-2-yl)-2-(pyridin-2-yl)acetamide (57.5 mg, 34% yield). MS (ESI pos. ion) m/z: 438. Calculated exact mass for $C_{22}H_{20}ClN_5OS$ 437.

Compound Examples 132, 144, 151, and 155 (Table I) were prepared in an analogous manner to Compound Example 141, Method K.

Example 159

Method L

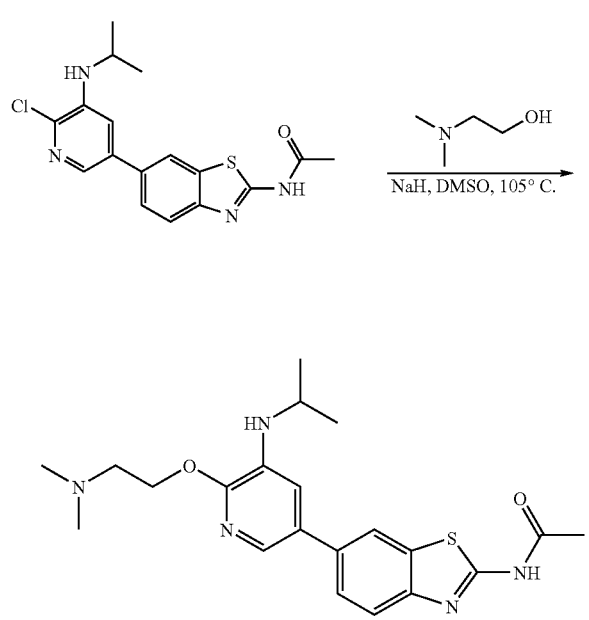

N-(6-(6-(2-(dimethylamino)ethoxy)-5-(isopropylamino)pyridin-3-yl)benzo[d]thiazol-2-yl)acetamide 2-(dimethylamino)ethanol (140.2 mg, 1.573 mmol) was dissolved in DMSO (1.5 ml) and sodium hydride (85.8 mg, 60% in mineral oil, 2.15 mmol) was added. The reaction was stirred under nitrogen at room temperature for almost 2 hours, and then N-(6-(6-chloro-5-(isopropylamino)pyridin-3-yl) benzo[d]thiazol-2-yl)acetamide (102.5 mg, 0.2840 mmol) was added. The flask was put in a preheated oil bath (105° C.) and stirred under nitrogen (a reflux condenser was added after about 5 minutes). After 90 minutes, the reaction was cooled to room temperature and quenched with water. The reaction was extracted with 10:1 DCM/MeOH, but the product is water soluble, so the organic and aqueous phases were combined, concentrated, and filtered through a pad of Celite® (diatomaceous earth), which was washed with DCM and MeOH. This filtrate was concentrated and purified on a silica gel column (20:1 DCM/MeOH to 15:1 DCM/2 N ammonia in MeOH to 10:1 DCM/2 N ammonia in MeOH) to afford N-(6-(6-(2-(dimethylamino)ethoxy)-5-(isopropylamino)pyridin-3-yl) benzo[d]thiazol-2-yl)acetamide (39.4 mg, 34% yield). MS (ESI pos. ion) m/z: 414. Calculated exact mass for $C_{21}H_{27}N_5O_2S$ 413.

Compound Examples 124, 145, and 153 (Table I) were prepared in an analogous manner to Compound Example 159, Method L.

EXAMPLES 147 AND 157

Method M

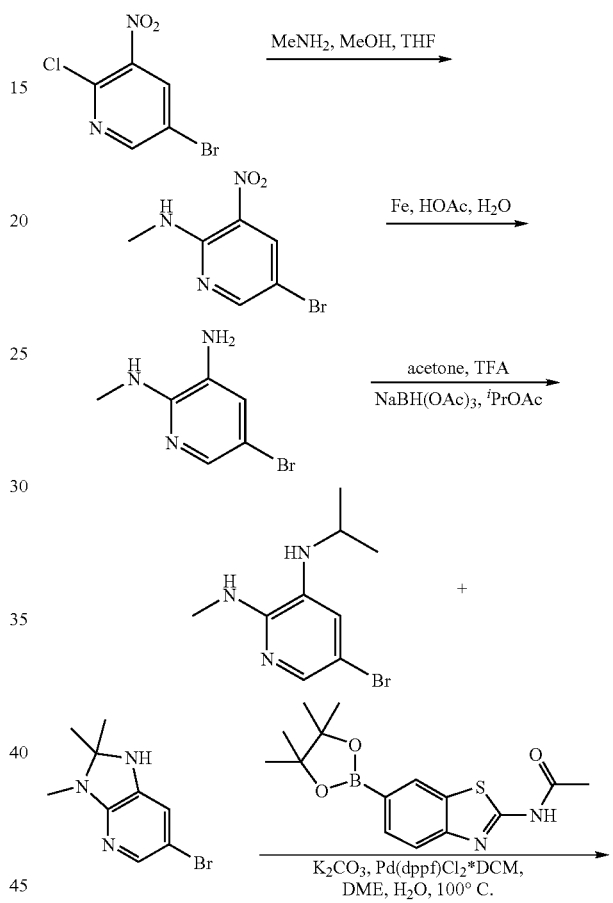

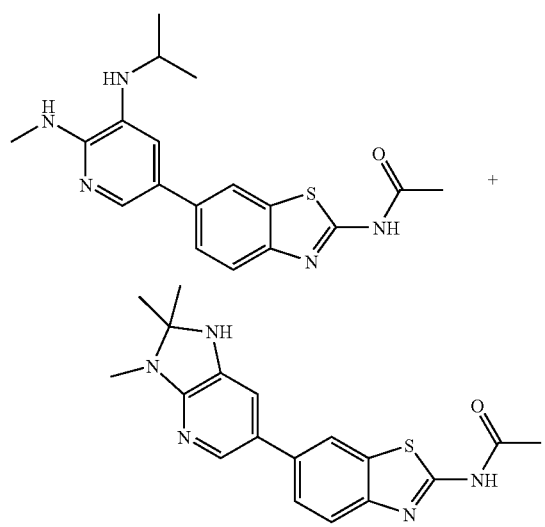

N-(6-(5-(isopropylamino)-6-(methylamino)pyridin-3-yl)benzo[d]thiazol-2-yl)acetamide (Example 147) and N-(6-(2,2,3-trimethyl-2,3-dihydro-1H-imidazo[4,5-b]pyridin-6-yl)benzo[d]thiazol-2-yl)acetamide (Example 157)

Step 1. 5-bromo-N-methyl-3-nitropyridin-2-amine 5-bromo-2-chloro-3-nitropyridine (456 mg, 1920 μmol) was dissolved in MeOH (6.0 ml) and methylamine, 2.0 M solution in tetrahydrofuran (2.5 ml, 5.0 mmol) was added. The reaction was stirred at room temperature for 6 hours, allowed to stand at room temperature overnight, and then concentrated. material was taken directly to the next step.

Step 2. 5-bromo-N2-methylpyridine-2,3-diamine

The crude material was dissolved in acetic acid (10 ml) and water (2.5 ml) and iron (445 mg, 7.97 mmol) was added. The reaction was stirred at room temperature for 40 minutes and then poured into 5 N NaOH (40 ml), and the suspension was cooled briefly in an ice water bath. Then, the suspension was filtered through a Celite® (diatomaceous earth), pad, which was washed with water, EtOAC, and 10:1 DCM/MeOH. The biphasic solution was separated, and the aqueous phase was extracted with 10:1 DCM/MeOH. The Celite® (diatomaceous earth), pads were washed again with MeOH, and this filtrate was combined with the organic extracts, concentrated, and dried under high vacuum in water bath (~60° C.) to afford 5-bromo-N2-methylpyridine-2,3-diamine (427 mg, ~100%).

LCMS supports structure of compound (peak at 0.7 minutes with m/e of 202 and 204). Compound isolated in ~100% yield over 2 steps. MS (ESI pos. ion) m/z: 202 (MH+, $^{79}$Br), 204 (MH+, $^{81}$Br). Calculated exact mass for $C_6H_8BrN_3$ 201 ($^{79}$Br), 203 ($^{81}$Br).

Step 3. 5-bromo-N-3-isopropyl-N2-methylpyridine-2,3-diamine and 6-bromo-2,2,3-trimethyl-2,3-dihydro-1H-imidazo[4,5-b]pyridine 5-bromo-N2-methylpyridine-2,3-diamine (54.4 mg, 0.269 mmol) was dissolved in isopropyl acetate (1.5 ml) and acetone (23 μl, 0.31 mmol), trifluoroacetic acid (0.045 ml, 0.58 mmol), and sodium triacetoxyborohydride (64 mg, 0.30 mmol) were added. The reaction was stirred under nitrogen at room temperature for 4 hours, and then more acetone was added (0.040 ml) along with TFA (0.090 ml) and isopropyl acetate (0.5 ml). The reaction was then stirred overnight. This reaction was repeated on a larger scale using 5-bromo-N2-methylpyridine-2,3-diamine (288 mg, 1.43 mmol), 2,2,2-trifluoroacetic acid (0.30 ml, 3.9 mmol), acetone (0.13 ml, 1.8 mmol), and sodium triacetoxyborohydride (352 mg, 1.66 mmol). Then, both reactions were poured into water (25 ml), and solid sodium hydroxide was added to raise the pH to about 10. The layers were separated, and the aqueous phase was extracted with EtOAc. The organic extracts were combined, dried over sodium sulfate, filtered, concentrated, and dried under high vacuum. To afford 5-bromo-N3-isopropyl-N2-methylpyridine-2,3-diamine and 6-bromo-2,2,3-trimethyl-2,3-dihydro-1H-imidazo[4,5-b]pyridine (399 mg, 97% combined yield).

5-bromo-N3-isopropyl-N2-methylpyridine-2,3-diamine: MS (ESI pos. ion) m/z: 244 (MH+, $^{79}$Br), 246 (MH+, $^{81}$Br). Calculated exact mass for $C_9H_{14}BrN_3$ 243 ($^{79}$Br), 245 ($^{81}$Br).

6-bromo-2,2,3-trimethyl-2,3-dihydro-1H-imidazo[4,5-b]pyridine: MS (ESI pos. ion) m/z: 242 (MH+, $^{79}$Br), 244 (MH+, $^{81}$Br). Calculated exact mass for $C_9H_{12}BrN_3$ 241 ($^{79}$Br), 243 ($^{81}$Br).

Step 4. N-(6-(5-(isopropylamino)-6-(methylamino)pyridin-3-yl)benzo[d]thiazol-2-yl)acetamide and N-(6-(2,2,3-trimethyl-2,3-dihydro-1H-imidazo[4,5-b]pyridin-6-yl)benzo[d]thiazol-2-yl)acetamide These compounds were made following the procedure described in Example 141, Method K, step 2. N-(6-(5-(isopropylamino)-6-(methylamino)pyridin-3-yl)benzo[d]thiazol-2-yl)acetamide was isolated in 1% yield. MS (ESI pos. ion) m/z: 356. Calculated exact mass for $C_{18}H_{21}N_5OS$ 355.

N-(6-(2,2,3-trimethyl-2,3-dihydro-1H-imidazo[4,5-b]pyridin-6-yl)benzo[d]thiazol-2-yl)acetamide was isolated in 1% yield. MS (ESI pos. ion) m/z: 354. Calculated exact mass for $C_{18}H_{19}N_5OS$ 353.

Example 152

N-(6-(5-amino-6-(methylamino)pyridin-3-yl)benzo[d]thiazol-2-yl)acetamide

This compound was made using 5-bromo-N2-methylpyridine-2,3-diamine and following the procedure outlined in Method M, step 2 above. MS (ESI pos. ion) m/z: 314. Calculated exact mass for $C_{15}H_{15}N_5OS$ 313.

Example 146

Method N

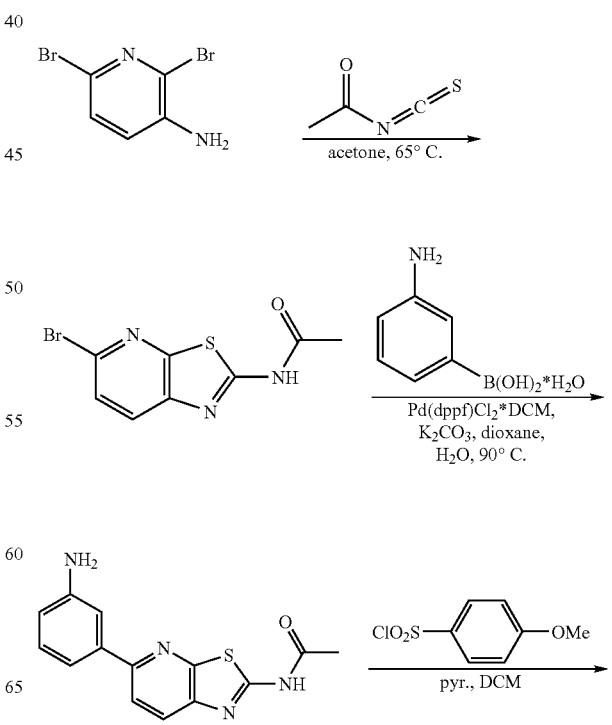

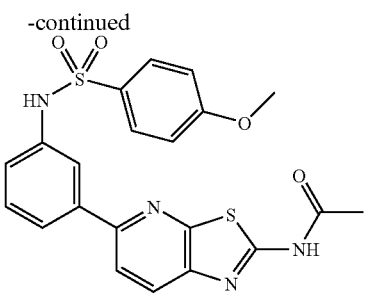

N-(5-(3-(4-methoxyphenylsulfonamido)phenyl)thiazolo[5,4-b]pyridin-2-yl)acetamide Step 1.
N-(5-bromothiazolo[5,4-b]pyridin-2-yl)acetamide 2,6-dibromopyridin-3-amine (4.235 g, 16.8 mmol) was dissolved in acetone and acetyl isothiocyanate (1.85 ml, 21.0 mmol) was added. The flask was fit with a reflux condensor and placed in a preheated oil bath (65-70° C.) and stirred under nitrogen for 2.5 hours. Then, the reaction was cooled to room temperature, poured into water, and filtered. The solid was washed with water, saturated sodium bicarbonate, and water again, and then collected and dried under high vacuum to afford N-(5-bromothiazolo[5,4-b]pyridin-2-yl)acetamide (5.54 g, Yield >100%).

MS (ESI pos. ion) m/z: 272 (MH+, $^{79}$Br), 274 (MH+, $^{81}$Br). Calculated exact mass for $C_8H_6BrN_3OS$ 271 ($^{79}$Br), 273 ($^{81}$Br).

Step 2. N-(5-(3-aminophenyl)thiazolo[5,4-b]pyridin-2-yl)acetamide (Example 156)

N-(5-bromothiazolo[5,4-b]pyridin-2-yl)acetamide (1.504 g, 5.527 mmol), 3-aminophenylboronic acid monohydrate (1.316 g, 8.493 mmol), Pd(dppf)C$_{12}$-DCM complex (604.4 mg, 0.7401 mmol), and potassium carbonate (2.292 g, 16.58 mmol) were suspended in 1,4-dioxane (45 ml) and water (15 ml) was added. Argon was bubbled through the solution for about 30 seconds, and then the flask was fit with a reflux condensor and placed in a preheated oil bath (90-99° C.) and stirred under argon for 4 hours. The reaction was cooled to room temperature, filtered, and the solid was washed with DCM and MeOH. The filtrate was concentrated, treated with DCM and MeOH, and filtered. The solid was collected and set aside, and the filtrate was concentrated, treated with Et$_2$O, and filtered. Solid washed with Et$_2$O. This solid was combined with the first batch and dried under high vacuum first at room temperature, and then at ~50° C. This solid was treated with deionized water and filtered, and the solid was washed with water, collected, and dried under high vacuum in water bath (~50° C.) to afford N-(5-(3-aminophenyl)thiazolo[5,4-b]pyridin-2-yl)acetamide (1.22 g, 78% yield). MS (ESI pos. ion) m/z: 285. Calculated exact mass for $C_{14}H_{12}N_4OS$ 284.

Step 3. N-(5-(3-(4-methoxyphenylsulfonamido)phenyl)thiazolo[5,4-b]pyridin-2-yl)acetamide N-(5-(3-aminophenyl)thiazolo[5,4-b]pyridin-2-yl)acetamide (102.6 mg, 0.361 mmol) was suspended in DCM (2.7 ml) and pyridine (0.050 ml, 0.61 mmol) and 4-methoxybenzene-1-sulfonyl chloride (107.2 mg, 0.519 mmol) were added. The reaction was stirred under nitrogen at room temperature for about 100 minutes. The, reaction was treated with Et$_2$O and filtered. Solid washed with Et$_2$O, MeOH, and Et$_2$O, then collected and purified on HPLC (10% to 95% MeCN/water with 0.1% TFA over 30 minutes) to afford N-(5-(3-(4-methoxyphenylsulfonamido)phenyl)thiazolo[5,4-b]pyridin-2-yl)acetamide (62.7 mg, 38% yield). MS (ESI pos. ion) m/z: 455. Calculated exact mass for $C_{21}H_{18}N_4O_4S_2$ 454.

Example 136

N-(5-(3-(4-methylphenylsulfonamido)phenyl)thiazolo[5,4-b]pyridin-2-yl)acetamide

This compound was made using 4-methyl-N-(3-(4,4,5,5-tetramethyl-1,3,2-dioxaborolan-2-yl)phenyl)benzenesulfonamide and N-(5-bromothiazolo[5,4-b]pyridin-2-yl)acetamide and following the procedure in Example 146, Method N, step 2 above. MS (ESI pos. ion) m/z: 439. Calculated exact mass for $C_{21}H_{18}N_4O_3S_2$ 438.

Example 161

Method O

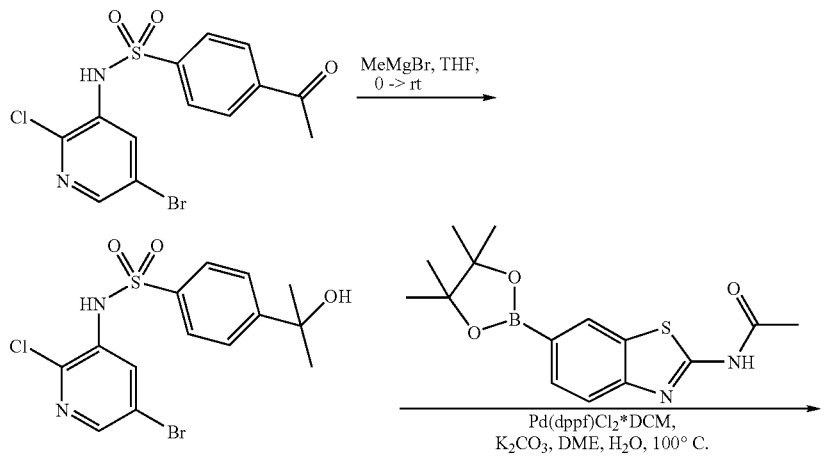

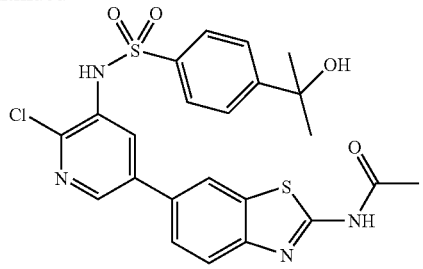

N-(6-(6-chloro-5-(4-(2-hydroxypropan-2-yl)phenyl-sulfonamido)pyridin-3-yl)benzo[d]thiazol-2-yl)acetamide Step 1. N-(5-bromo-2-chloropyridin-3-yl)-4-(2-hydroxypropan-2-yl)benzenesulfonamide 4-acetyl-N-(5-bromo-2-chloropyridin-3-yl)benzenesulfonamide (123.5 mg, 0.317 mmol) was dissolved in THF (2.6 ml) and cooled in an ice water bath under nitrogen. Then, methylmagnesium bromide (0.65 ml, 1.4 M solution in toluene/tetrahydrofuran (75:25), 0.91 mmol) was added via syringe, and the reaction was allowed to slowly warm to room temperature. After 2 hours and 45 minutes, more methylmagnesium bromide (0.50 ml) was added, and stirring was continued at room temperature. After 75 minutes, more methylmagnesium bromide (0.93 ml) was added, and stirring was continued. After another hour, the reaction quenched with saturated ammonium chloride. The layers were separated, and the aqueous phase was extracted with 10:1 DCM/MeOH. Organic extracts combined, concentrated, and taken on to the next step. MS (ESI pos. ion) m/z: 405 (MH+, $^{79}$Br), 407 (MH+, $^{81}$Br). Calculated exact mass for $C_{14}H_{14}BrClN_2O_3S$ 404 ($^{79}$Br), 406 ($^{81}$Br).

Step 2. N-(6-(6-chloro-5-(4-(2-hydroxypropan-2-yl)phenylsulfonamido)pyridin-3-yl)benzo[d]thiazol-2-yl)acetamide This compound was prepared following the procedure outlined in Method K, step 2, above.
MS (ESI pos. ion) m/z: 517. Calculated exact mass for $C_{23}H_{21}ClN_4O_4S_2$ 516.
Compound Example 119 (Table I) was prepared in an analogous manner to Compound Example 161, Method O.

Example 162

N-(6-(6-Chloro-5-(4-fluorophenylsulfonamido)pyridin-3-yl)benzo[d]thiazol-2-yl)acetamide Step 1. 3-[N,N-Bis(4-fluorophenylsulfonyl)amino]-5-bromo-2-chloropyridine A solution of 3-amino-5-bromo-2-chloropyridine (0.94 g, 4.5 mmol) (Oakwood Products, Inc., West Columbia, S.C.) and 4-fluorobenzenesulfonyl chloride (Aldrich, St. Louis, Mo.) (1.73 g, 8.9 mmol) in pyridine (20 mL) was heated in a microwave tube at 100° C. for 15 minutes. The mixture was concentrated in vacuo and the residue was washed with EtOAc containing small amount of MeOH to give the desired product as a white solid (2.0 g).

Step 2. N-(6-(6-Chloro-5-(4-fluorophenylsulfonamido)pyridin-3-yl)benzo[d]thiazol-2-yl)acetamide To a solution of N-(6-(4,4,5,5-tetramethyl-1,3,2-dioxaborolan-2-yl)benzo[d]thiazol-2-yl)acetamide (0.22 g, 0.71 mmol) and 3-[N,N-bis(4-fluorophenylsulfonyl)amino]-5-bromo-2-chloropyridine (0.37 g, 0.71 mmol) in dioxane (3 mL) was added aqueous $Na_2CO_3$ (10%, 1.0 mL) followed by Pd FibreCat® (Anchored homogeneous catalyst, Johnson Matthey, West Deptford, N.J.) (20 mg) in a microwave vial.

The reaction was heated to 100° C. for 12 minutes. The mixture was then filtered. The filtrate was diluted with $NaHCO_3$ (40 mL) and of EtOAc (60 mL). The organic phase was separated, washed with brine (30 mL), dried over $Na_2SO_4$ and concentrated in vacuo. The residue was purified by a prep-HPLC to give the desired product as light yellow solid (0.010 g).

The filtered solid, mainly the bis(sulfonamide), was stirred in a mixture of dioxane (20 mL) and aqueous $Na_2CO_3$ (10%) at rt. After the completion of the reaction, the solid was collected and recrystallized in $MeOH/CHCl_3$ solution to give additional N-(6-(6-chloro-5-(4-fluorophenylsulfonamido)pyridin-3-yl)benzo[d]thiazol-2-yl)acetamide (0.10 g). MS (ESI pos. ion) m/z. calc'd for $C_{20}H_{14}ClFN_4O_3S_2$: 476.0. found: 476.9 (MH+). $^1$H NMR (300 MHz, DMSO-$d_6$) δ ppm 2.23 (s, 3H) 7.44 (t, J=8.77 Hz, 2H) 7.67-7.77 (m, 1H) 7.77-7.89 (m, 3H) 8.04 (d, J=2.05 Hz, 1H) 8.35 (d, J=1.46 Hz, 1H) 8.64 (d, J=2.19 Hz, 1H) 10.50 (s, 1H) 12.46 (s, 1H).

Example 163

N-(6-(6-Chloro-5-(4-methoxyphenylsulfonamido)pyridin-3-yl)benzo[d]thiazol-2-yl)acetamide Step 1. N-(5-Bromo-2-chloropyridin-3-yl)-4-methoxybenzenesulfonamide A solution of 4-methoxybenzenesulfonyl chloride (1 g, 5 mmol) and 3-amino-5-bromo-2-chloropyridine (0.45 g, 2 mmol) in 15 mL of pyridine was heated in a microwave vial at 100° C. for 20 minutes. The mixture was then concentrated in vacuo and the residue was purified by a silica gel column chromatography to give first the di-sulfonamide compound (0.5 g, 42% yield): $^1$H NMR (300 MHz, chloroform-d) δ ppm 3.92 (s, 6H) 6.94-7.09 (m, 4H) 7.59 (d, J=2.34 Hz, 1H) 7.81-7.98 (m, 4H) 8.50 (d, J=2.34 Hz, 1H); and then the mono-sulfonamide compound N-(5-bromo-2-chloropyridin-3-yl)-4-methoxybenzenesulfonamide (0.4 g, 49% yield): $^1$H NMR (300 MHz, chloroform-d) δ ppm 3.86 (s, 3H) 6.84-7.06 (m, 3H) 7.68-7.83 (m, 2H) 8.08-8.21 (m, 2H).

Step 2. N-(6-(6-Chloro-5-(4-methoxyphenylsulfonamido)pyridin-3-yl)benzo[d]thiazol-2-yl)acetamide A mixture of N-(6-(4,4,5,5-tetramethyl-1,3,2-dioxaborolan-2-yl)benzo[d]thiazol-2-yl)acetamide (0.18 g, 0.6 mmol), N-(5-bromo-2-chloropyridin-3-yl)-4-methoxybenzenesulfonamide (0.15 g, 0.4 mmol) and Pd FibreCat® in 1 mL of 10% $Na_2CO_3$ and 3 mL of dioxane was heated at 100° C. for 12 minutes. The mixture was then filtered and the filtrate was concentrated in vacuo, washed with small amount of EtOAc, and recrystallized in MeOH to give white solid N-(6-(6-chloro-5-(4-methoxyphenylsulfonamido)pyridin-3-yl)benzo[d]thiazol-2-yl)acetamide (0.08 g, 41% yield). MS (ESI pos. ion) m/z: calc'd for $C_{21}H_{17}ClN_4O_4S_2$: 488.0. found: 489.0 (MH+). $^1$H NMR (300 MHz, MeOH) δ ppm 2.29 (s, 3H) 3.85 (s, 3H) 6.97-7.07 (m, 2H) 7.66 (dd, J=8.48, 1.90 Hz, 1H) 7.70-7.78 (m, 2H) 7.81-7.90 (m, 2H) 8.11 (d, J=1.61 Hz, 1H) 8.17 (d, J=2.34 Hz, 1H) 8.44 (d, J=2.34 Hz, 1H).

Example 164

N-(6-(5-(4-Fluorophenylsulfonamido)-1,3,4-oxadiazol-2-yl)benzo[d]thiazol-2-yl)acetamide. A mixture of N-(5-(2-aminobenzo[d]thiazol-6-yl)-1,3,4-oxadiazol-2-yl)-4-fluorobenzenesulfonamide, pyridine, $Ac_2O$, and DMAP, was stirred at rt for 4 h. The product was isolated following standard procedures. MS (ESI pos. ion) m/z: calk's for $C_{17}H_{12}FN_5O_4S_2$: 433.0. found: 434.0 (MH+).

Example 165

N-(5-(2-Aminobenzo[d]thiazol-6-yl)-1,3,4-oxadiazol-2-yl)-4-methylbenzenesulfonamide A mixture of tert-butyl 6-(5-(4-methylphenylsulfonamido)-1,3,4-oxadiazol-2-yl)benzo[d]thiazol-2-ylcarbamate (0.40 g, 0.82 mmol) in 1:1 solution of $TFA/CH_2Cl_2$ was stirred at room temperature for 4 hours. The solution was concentrated in vacuo to give the desired product as white solid N-(5-(2-aminobenzo[d]thiazol-6-yl)-1,3,4-oxadiazol-2-yl)-4-methylbenzenesulfonamide (0.30 g, 94% yield). MS (ESI pos. ion) m/z: calc'd for $C_{16}H_{13}N_5O_3S_2$: 387.0. found: 387.9 (MH+). $^1$H NMR (300 MHz, MeOH) δ ppm 2.41 (s, 3H) 7.37 (d, J=8.04 Hz, 2H) 7.54 (d, J=8.48 Hz, 1H) 7.82-7.94 (m, 3H) 8.22 (d, J=1.46 Hz, 1H).

Example 166 tert-Butyl 6-(5-(4-methylphenylsulfonamido)-1,3,4-oxadiazol-2-yl)benzo[d]thiazol-2-ylcarbamate Step 1. 2-N—BOC-amino-4-benzothiazole-6-carbohydrazide To a suspended solution of 2-N—BOC-amino-4-benzothiazole-6-carboxylic acid (2.05 g, 6.97 mmol) and 2,3,4,5,6-pentafluorophenol (1.92 g, 10.4 mmol) in EtOAc (60 mL) was added 1,3-dicyclohexylcarbodiimide (2.16 g, 10.4 mmol). The mixture was heated at 45° C. for 16 hours. Small amount of MeOH was added to the mixture and the solid was removed by filtration. The filtrate was concentrated in vacuo to give pentafluorophenyl 2-(tert-butoxycarbonyl)benzo[d]thiazole-6-carboxylate as a pink material (3.50 g), which was used in the next step without further purification. A solution of pentafluorophenyl 2-(tert-butoxycarbonyl)benzo[d]thiazole-6-carboxylate (1.0 g, 2.2 mmol) and anhydrous hydrazine (0.35 ml, 11 mmol) in THF (30 mL) was stirred at room temperature for 6 hours. The mixture was then concentrated in vacuo and the residue was washed with $CHCl_3$ containing small amount of MeOH. The solid was collected by filtration to give the product as a light yellow solid (0.30 g, 45% yield). MS (ESI pos. ion) m/z: calc'd for: $C_{13}H_{16}N_4O_3S$: 308.0. found: 309.0.

Step 2. 2-N—BOC-amino-4-benzothiazole-6-carbonyl)thiosemicarbazide

To a mixture of 2-N—BOC-amino-4-benzothiazole-6-carbohydrazide (0.76 g, 2.5 mmol) in THF (20 mL) was added trimethylsilyl isothiocyanate (1.4 mL, 9.9 mmol). The reaction mixture was then heated to 45° C. for 16 hours. The mixture was concentrated in vacuo and the residue was washed with MeOH/EtOAc to give the desired product as yellow solid (0.80 g, 88% yield). MS (ESI pos. ion) m/z: calc'd for: $C_{14}H_{17}N_5O_3S_2$: 367.0. found: 368.0.

Step 3. tert-Butyl 6-(5-(4-methylphenylsulfonamido)-1,3,4-oxadiazol-2-yl)benzo[d]thiazol-2-ylcarbamate To a mixture 2-N—BOC-amino-4-benzothiazole-6-carbonyl)thiosemicarbazide (0.20 g, 0.54 mmol) in THF (10 mL) was added pyridine (0.27 mL, 3.3 mmol) and 4-methylbenzene-1-sulfonyl chloride (0.23 mL, 1.6 mmol). The reaction was heated to 70° C. for 5 hours. The mixture was concentrated in vacuo and the residue was washed with MeOH/$CHCl_3$ to give desired product as white solid (0.10 g, 38% yield). MS (ESI neg. ion) m/z: calc'd for $C_{21}H_{21}N_5O_5S_2$: 487.1. found: 486.1 (M−1). $^1$H NMR (300 MHz, DMSO-$d_6$) δ ppm 1.53 (s, 9H) 2.37 (s, 3H) 7.38 (d, J=8.04 Hz, 2H) 7.81 (d, J=1.02 Hz, 2H) 7.85 (d, J=8.33 Hz, 2H) 8.46 (s, 1H) 12.04 (s, 1H)

Example 167 tert-Butyl 6-(5-(4-fluorophenylsulfonamido)-1,3,4-oxadiazol-2-yl)benzo[d]thiazol-2-ylcarbamate Prepared similarly using p-F-phenylsulfonylchloride as described in Example 166. MS (ESI neg. ion) m/z: calc'd for $C_{20}H_{18}FN_5O_5S_2$: 491.0 found: 490.0 (M−1).

Example 168

N-(5-(2-aminobenzo[d]thiazol-6-yl)-1,3,4-oxadiazol-2-yl)-4-fluorobenzenesulfonamide Deprotection of the BOC group from tert-Butyl 6-(5-(4-fluorophenylsulfonamido)-1,3,4-oxadiazol-2-yl)benzo[d]thiazol-2-ylcarbamate (Example 167) as described in Example 165 gave the desired product. MS (ESI neg. ion) m/z: 391.0 found: 390.0 (M−1).

Example 169 tert-Butyl 6-(5-(benzylamino)-1,3,4-oxadiazol-2-yl)benzo[d]thiazol-2-ylcarbamate Step 1. 2-N—BOC-amino-4-benzothiazole-6-carbonyl(4-benzylthiosemicarbazide)

To a solution of 2-N—BOC-amino-4-benzothiazole-6-carbohydrazide (0.50 g, 1.6 mmol) in THF/DMF mixture (15 mL) at room temperature was added benzyl isothiocyanate (0.48 g, 3.2 mmol). The reaction was then heated to 45° C. for 16 hours. The reaction mixture was concentrated in vacuo and the residue was washed with MeOH to give the product as a yellow solid (0.55 g, 74% yield). MS (ESI pos. ion) m/z: calc'd for $C_{21}H_{23}N_5O_3S_2$: 457.0. found: 458.0 (MH+).

Step 2. tert-Butyl 6-(5-(benzylamino)-1,3,4-oxadiazol-2-yl)benzo[d]thiazol-2-ylcarbamate The oxadiazole ring formation was induced with p-F-phenylsulfonylchloride as described in Example 166. MS (ESI pos. ion) m/z: calc'd for $C_{21}H_{21}N_5O_3S$: 423.1 found: 424.1 (MH+).

Example 170 tert-Butyl 6-(5-(N-benzylmethan-9-ylsulfonamido)-1,3,4-oxadiazol-2-yl)benzo[d]thiazol-2-ylcarbamate Prepared from tert-butyl 6-(5-(benzylamino)-1,3,4-oxadiazol-2-yl)benzo[d]thiazol-2-ylcarbamate (Example 169) via mesylation. MS (ESI pos. ion) m/z: calc'd for $C_{22}H_{23}N_5O_5S_2$: 501.0. found: 502.0 (MH+).

Example 171

Method P

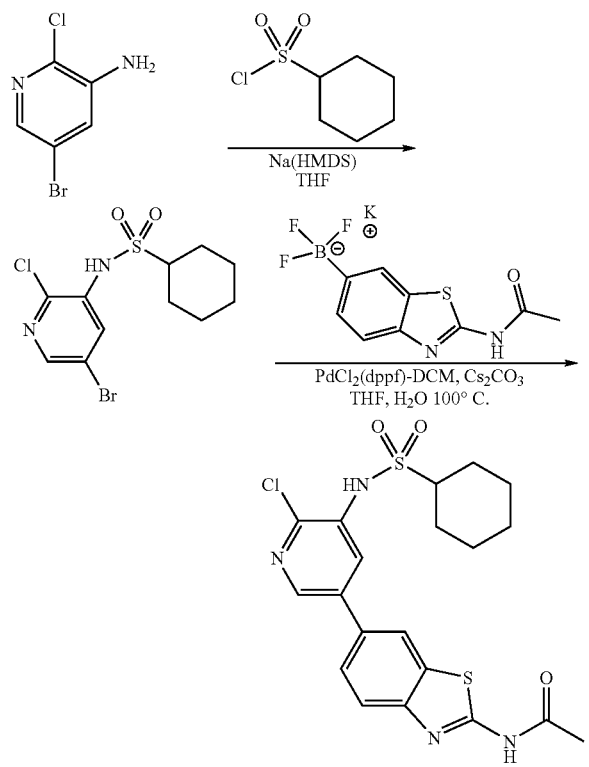

N-(6-(6-chloro-5-(cyclohexanesulfonamido)pyridin-3-yl)benzo[d]thiazol-2-yl)acetamide Step 1. N-(5-bromo-2-chloropyridin-3-yl)cyclohexanesulfonamide To a 50 ml round-bottom flask equipped with a stir bar, was added 5-bromo-2-chloropyridin-3-amine (0.250 g, 1 mmol) while under inert atmosphere. The solid was dissolved in THF (10 ml, 122 mmol), then sodium bis(trimethylsilyl)amide (0.650 g, 3 mmol) was added to the mixture and allowed to stir 5 minutes. Then cyclohexanesulfonyl chloride (0.5 ml, 4 mmol) was added into the mixture. The mixture was allowed to stir overnight, while under inert atmosphere. The progress of the reaction was monitored by LC/MS, which showed product and a small amount of bis-sulfone material in the mixture. The mixture was diluted with DCM and water. The organic layer was extracted with DCM (3×25 ml). Combined organics, dried over sodium sulfate, filtered and concentrated in vacuo. The crude was dissolved in methanol (5 ml), then potassium carbonate (0.250 g) was added to the mixture with stirring. After 20 minutes, the progress of the de-sulfonylation reaction was monitored by LC/MS, which showed mostly desired product. The mixture was filtered and concentrated in vacuo. The crude was purified by ISCO silica-gel chromatography, in a gradient of 1-15% ethyl acetate/hexanes. This gave N-(5-bromo-2-chloropyridin-3-yl)cyclohexanesulfonamide (0.140 g, 33% yield) as an off-white amorphous solid. MS (ESI pos. ion) m/z: 354 (MH+). Calc'd exact mass for $C_{11}H_{14}BrClN_2O_2S$: 353. $^1$H NMR (400 MHz, chloroform-d): 1.15-1.35 (m, 2H), 1.52-1.66 (m, 1H), 1.70 (d, J=4.52 Hz, 1H), 1.73 (s, 1H), 1.76-1.86 (m, 1H), 1.92 (d, J=11.54 Hz, 1H), 2.11-2.22 (m, 2H), 2.96-3.05 (m, 1H), 6.70 (s, 1H), 8.15-8.22 (m, 2H).

Step 2. N-(6-(6-chloro-5-(cyclohexanesulfonamido)pyridin-3-yl)benzo[d]thiazol-2-yl)acetamide To a microwave vial equipped with a stir bar and charged with potassium-6-trifluoroborate-1-yl)benzothiazol-2-yl)acetamide (0.083 g, 0.28 mmol), cesium carbonate (0.190 g, 0.59 mmol), 1,1'-bis(diphenylphosphino)ferrocene palladium(II) chloride-DCM (0.029 g, 0.036 mmol), N-(5-bromo-2-chloropyridin-3-yl)cyclohexanesulfonamide (0.070 g, 0.20 mmol) in THF (2 ml). Then water (0.5 ml) was added to the mixture. The vial was capped and placed into a CEM Microwave for 10 minutes at 100° C., while 100 watts of energy was supplied via Powermax® (Simultaneous heating while cooling technology). The progress of the reaction was monitored by LC/MS, which showed desired material in the material. The organic layer was extracted from the microwave vial by pipette into a round-bottom flask, diluted with acetonitrile and trifluoroacetic acid (0.05 ml). The crude was purified by reverse-phase HPLC. This gave N-(6-(6-chloro-5-(cyclohexanesulfonamido)pyridin-3-yl)benzo[d]thiazol-2-yl)acetamide (0.070 g, 76% yield) as a yellow crystalline solid. MS (ESI pos. ion) m/z: 465 (MH+). Calc'd exact mass for $C_{20}H_{21}ClN_4O_3S_2$: 464. $^1$H NMR (400 MHz, DMSO-$d_6$): 1.16 (s, 1H), 1.28 (d, J=12.05 Hz, 2H), 1.44 (d, J=11.54 Hz, 2H), 1.62 (d, J=11.54 Hz, 1H), 1.78 (s, 2H), 2.14 (d, J=11.04 Hz, 2H), 2.23 (s, 3H), 3.11 (s, 1H), 7.52 (d, J=11.54 Hz, 2H), 7.56 (s, 2H), 7.75 (d, J=7.53 Hz, 1H), 7.85 (d, J=8.03 Hz, 1H), 8.16 (s, 1H), 8.37 (s, 1H), 8.58 (s, 1H), 9.85 (s, 1H), 12.45 9s, 1H).

Compound Examples 172-179 were prepared in an analogous manner to Compound Example 171, Method P.

Example 172

N-(6-(6-chloro-5-(3-(trifluoromethyl)phenylsulfonamido)pyridin-3-yl)benzo[d]thiazol-2-yl)acetamide MS (ESI pos. ion) m/z: 527 (MH+). Calc'd exact mass for $C_{21}H_{14}ClF_3N_4O_3S_2$: 526. $^1$H NMR (400 MHz, DMSO-$d_6$):

2.22 (s, 3H), 7.46 (d, J=7.53 Hz, 1H), 7.64-7.89 (m, 5H), 8.02 (s, 1H), 8.05 (d, J=10.54 Hz, 2H), 12.40 (s, 1H).

Example 173

N-(6-(5-(3-tert-butylphenylsulfonamido)-6-chloropyridin-3-yl)benzo[d]thiazol-2-yl)acetamide MS (ESI pos. ion) m/z: 516 (MH+). Calc'd exact mass for $C_{24}H_{23}ClN_4O_3S_2$: 515. $^1$H NMR (400 MHz, DMSO-$d_6$): 1.22 (s, 9H), 2.23 (s, 3H), 7.51 (s, 1H), 7.58 (s, 1H), 7.62-7.75 (m, 3H), 7.82 (s, 1H), 7.93 (s, 1H), 8.28 (s, 1H), 8.58 (s, 1H), 10.37 (s, 1H), 12.47 (s, 1H).

Example 174

N-(6-(6-chloro-5-(4-hydroxyphenylsulfonamido)pyridin-3-yl)benzo[d]thiazol-2-yl)acetamide MS (ESI pos. ion) m/z: 475 (MH+). Calc'd exact mass for $C_{20}H_{15}ClN_4O_4S_2$: 474. $^1$H NMR (400 MHz, DMSO-$d_6$): 2.21 (s, 3H), 6.74 (s, 2H), 7.40-7.82 (m, 5H), 8.03 (d, 1H), 12.41 (s, 1H).

Example 175

N-(6-(6-chloro-5-(3,5-dichlorophenylsulfonamido)pyridin-3-yl)benzo[d]thiazol-2-yl)acetamide MS (ESI pos. ion) m/z: 528 (MH+). Calc'd exact mass for $C_{20}H_{13}Cl_3N_4O_3S_2$: 527. $^1$H NMR (400 MHz, DMSO-$d_6$): 1.63 (s, 1H), 2.07 (s, 3H), 7.35 (s, 1H), 7.67 (s, 6H), 7.83 (s, 2H).

Example 176

N-(6-(6-chloro-5-(3,5-difluorophenylsulfonamido)pyridin-3-yl)benzo[d]thiazol-2-yl)acetamide MS (ESI pos. ion) m/z: 495 (MH+). Calc'd exact mass for $C_{20}H_{13}ClF_2N_4O_3S_2$: 494. $^1$H NMR (400 MHz, DMSO-$d_6$): 2.16-2.26 (m, 3H), 7.28 (t, J=9.29 Hz, 1H), 7.36 (d, J=5.02 Hz, 2H), 7.49 (d, J=8.53 Hz, 1H), 7.74 (d, J=2.01 Hz, 2H), 7.78 (d, J=8.03 Hz, 1H), 7.86 (s, 1H), 8.08 (s, 1H), 12.40 (s, 1H).

Example 177

N-(6-(6-chloro-5-(propylsulfonamido)pyridin-3-yl)benzo[d]thiazol-2-yl)acetamide

MS (ESI pos. ion) m/z: 425 (MH+). Calc'd exact mass for $C_{17}H_{17}ClN_4O_3S_2$: 424. $^1$H NMR (400 MHz, DMSO-$d_6$): 0.96 (t, J=7.53 Hz, 3H), 1.67-1.78 (m, 2H), 2.22 (s, 3H), 2.97 (s, 2H), 7.67 (d, J=8.03 Hz, 1H), 7.82 (d, J=8.53 Hz, 1H), 7.97 (s, 1H), 8.15 (s, 1H), 8.26 (s, 1H), 12.41 (s, 1H).

Example 178

N-(6-(5-(butylsulfonamido)-6-chloropyridin-3-yl)benzo[d]thiazol-2-yl)acetamide

MS (ESI pos. ion) m/z: 439 (MH+). Calc'd exact mass for $C_{18}H_{19}ClN_4O_3S_2$: 438. $^1$H NMR (400 MHz, DMSO-$d_6$): 0.88 (t, J=7.34 Hz, 3H), 1.41 (d, J=7.43 Hz, 2H), 1.74 (s, 2H), 2.22 (s, 3H), 3.22 (s, 2H), 7.76 (s, 1H), 7.84 (s, 1H), 8.11 (d, J=1.56 Hz, 1H), 8.37 (s, 1H), 8.57 (s, 1H), 9.86 (s, 1H), 12.44 (s, 1H).

Example 179

N-(6-(6-chloro-5-(propan-2-ylsulfonamido)pyridin-3-yl)benzo[d]thiazol-2-yl)acetamide MS (ESI pos. ion) m/z: 425 (MH+). Calc'd exact mass for $C_{17}H_{17}ClN_4O_3S_2$: 424. $^1$H NMR (400 MHz, DMSO-$d_6$): 1.18 (d, J=6.02 Hz, 6H), 2.12 (s, 3H), 2.83-2.94 (m, 1H), 7.47 (d, J=8.03 Hz, 1H), 7.65 (d, J=8.03 Hz, 1H), 7.70 (s, 1H), 7.88 (s, 1H), 7.98 (s, 1H).

Example 180

Method Q

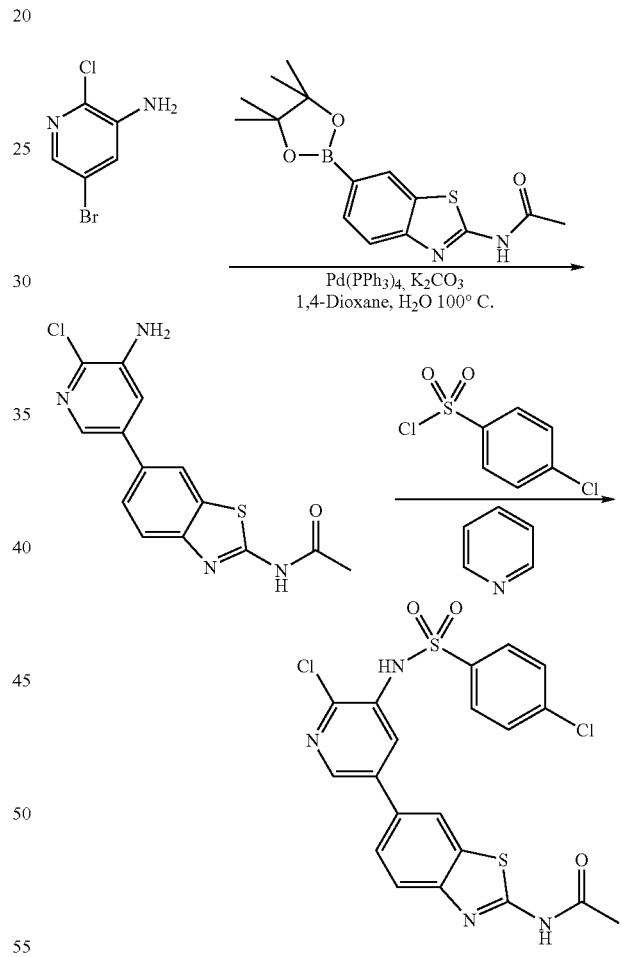

N-(6-(6-chloro-5-(4-chlorophenylsulfonamido)pyridin-3-yl)benzo[d]thiazol-2-yl)acetamide Step 1. N-(6-(5-amino-6-chloropyridin-3-yl)benzo[d]thiazol-2-yl)acetamide 5-bromo-2-chloropyridin-3-amine (1.00 g, 4.82 mmol), N-(6-(4,4,5,5-tetramethyl-1,3,2-dioxaborolan-2-yl)benzo[d]thiazol-2-yl)acetamide (1.73 g, 5.45 mmol), tetrakis(triphenylphosphine)palladium(0) (0.836 g, 0.723 mmol) and potassium carbonate (2.20 g, 15.9 mmol) was suspended in 1,4-dioxane (25 ml) with water (2.5 ml). Argon was bubbled through the suspension for about 30 seconds. The flask was fitted with a reflux condenser and placed into a heat bath (100° C.). The mixture was allowed to stir under inert atmosphere for 3 hours. The progress of the reaction was monitored by LC/MS, which showed desired product. The mixture was allowed to cool to ambient temperature. The mixture was diluted with DCM and saturated sodium bicarbonate solution. The organic layer was extracted with DCM (3×25 ml). Combined organics, dried over sodium sulfate, filtered and concentrated in vacuo. The residue was diluted with ethyl acetate and the precipitate was collected by filtration. The precipitate was washed with hexanes to give N-(6-(5-amino-6-chloropyridin-3-yl)benzo[d]thiazol-2-yl)acetamide (0.500 g, 32.5% yield) as a brown crystalline solid. MS (ESI pos. ion) m/z: 319 (MH+). Calc'd exact mass for $C_{14}H_{11}ClN_4OS$: 318. $^1$H NMR (400 MHz, DMSO-$d_6$): 2.22 (s, 3H), 5.66 (s, 2H), 7.42 (s, 1H), 7.65 (d, J=8.53 Hz, 1H), 7.81 (d, J=8.53 Hz, 1H), 7.94 (s, 1H), 8.24 (s, 1H), 12.41 (s, 1H).

Step 2. N-(6-(6-chloro-5-(4-chlorophenylsulfonamido)pyridin-3-yl)benzo[d]thiazol-2-yl)acetamide N-(6-(5-amino-6-chloropyridin-3-yl)benzo[d]thiazol-2-yl)acetamide (0.040 g, 0.13 mmol) was dissolved in pyridine (1 ml), then 4-chlorobenzene-1-sulfonyl chloride (0.026 g, 0.13 mmol) was added to the mixture while stirring. The mixture was allowed to stir under inert atmosphere for 3 days. The progress of the reaction was monitored by LC/MS, which showed product. The mixture was diluted with DCM and saturated sodium bicarbonate solution. The organic layer was extracted with DCM (3×20 ml). Combined organics, dried over sodium sulfate, filtered and concentrated in vacuo. The crude was purified by ISCO silica-gel chromatography in a gradient of 0-10% Methanol/DCM. The fractions with desired material were combined and concentrated in vacuo. The residue was diluted with ethyl acetate and allowed to stir 10 minutes. The precipitate was collected by filtration and washed with 1:1 ethyl acetate/hexanes to give N-(6-(6-chloro-5-(4-chlorophenylsulfonamido)pyridin-3-yl)benzo[d]thiazol-2-yl)acetamide (0.015 g, 24% yield) as a white crystalline solid. MS (ESI pos. ion) m/z: 494 (MH+). Calc'd exact mass for $C_{20}H_{14}Cl_2N_4O_3S_2$: 493. $^1$H NMR (400 MHz, DMSO-$d_6$): 2.23 (s, 3H), 5.73 (s, 1H), 7.48-8.17 (m, 7H), 8.84 (s, 1H), 8.62 (s, 1H), 12.45 (s, 1H).

Compound Examples 181-193 were prepared by analogous methods to Compound Example 180, Method Q.

Example 181

N-(6-(6-chloro-5-(phenylsulfonamido)pyridin-3-yl)benzo[d]thiazol-2-yl)acetamide

MS (ESI pos. ion) m/z: 459 (MH+). Calc'd exact mass for $C_{20}H_{15}ClN_4O_3S_2$: 458. $^1$H NMR (400 MHz, DMSO-$d_6$): 2.23 (s, 3H), 7.60 (t, J=7.53 Hz, 2H), 7.69 (t, J=7.28 Hz, 2H), 7.75-7.87 (m, 3H), 8.00 (d, J=2.51 Hz, 1H), 8.33 (s, 1H), 8.62 (d, J=2.01 Hz, 1H), 10.45 (s, 1H), 12.46 (s, 1H).

Example 182

N-(6-(6-chloro-5-(4-(difluoromethoxy)phenylsulfonamido)pyridin-3-yl)benzo[d]thiazol-2-yl)acetamide MS (ESI pos. ion) m/z: 525 (MH+). Calc'd exact mass for $C_{21}H_{15}ClF_2N_4O_4S_2$: 524. $^1$H NMR (300 MHz, DMSO-$d_6$): 2.23 (s, 3H), 7.37 (d, J=8.77 Hz, 2H), 7.40 (s, 1H), 7.68-7.73 (m, 1H), 7.80-7.87 (m, 3H), 8.02 (d, J=2.34 Hz, 1H), 8.34 (d, J=1.46 Hz, 1H), 8.63 (d, J=2.19 Hz, 1H), 10.49 (s, 1H), 12.46 (s, 1H).

Example 183

N-(6-(6-chloro-5-(3-fluorophenylsulfonamido)pyridin-3-yl)benzo[d]thiazol-2-yl)acetamide MS (ESI pos. ion) m/z: 477 (MH+). Calc'd exact mass for $C_{20}H_{14}ClFN_4O_3S_2$: 476. $^1$H NMR (400 MHz, DMSO-$d_6$): 2.23 (s, 3H), 7.54-7.64 (m, 3H), 7.65-7.76 (m, 2H), 7.85 (d, J=8.53 Hz, 1H), 8.03 (s, 1H), 8.35 (s, 1H), 8.62 (s, 1H), 10.63 (s, 1H), 12.46 (s, 1H).

Example 184

N-(6-(6-chloro-5-(3-(difluoromethoxy)phenylsulfonamido)pyridin-3-yl)benzo[d]thiazol-2-yl)acetamide MS (ESI pos. ion) m/z: 525 (MH+). Calc'd exact mass for $C_{21}H_{15}ClF_2N_4O_4S_2$: 524. $^1$H NMR (400 MHz, CD$_3$OD): 2.28 (s, 3H), 7.42 (d, 1H), 7.50-7.72 (m, 5H), 7.85 (d, 1H), 8.16 (d, 1H), 8.20 (d, 1H), 8.50 (d, 1H).

Example 185

N-(6-(6-chloro-5-(3-chlorophenylsulfonamido)pyridin-3-yl)benzo[d]thiazol-2-yl)acetamide MS (ESI pos. ion) m/z: 494 (MH+). Calc'd exact mass for $C_{20}H_{14}Cl_2N_4O_3S_2$: 493. $^1$H NMR (400 MHz, DMSO-d6): 2.23 (s, 3H), 7.64 (d, J=7.53 Hz, 1H), 7.70 (s, 1H), 7.73 (d, J=3.51 Hz, 1H), 7.76-7.91 (m, 3H), 8.02 (d, J=2.01 Hz, 1H), 8.35 (s, 1H), 8.65 (s, 1H), 10.63 (s, 1H), 12.47 (s, 1H).

Example 186

N-(6-(6-chloro-5-(thiophene-2-sulfonamido)pyridin-3-yl)benzo[d]thiazol-2-yl)acetamide MS (ESI pos. ion) m/z: 465 (MH+). Calc'd exact mass for $C_{18}H_{13}ClN_4O_3S_3$: 464. $^1$H NMR (400 MHz, DMSO-d6): 2.23 (s, 3H), 7.16-7.22 (m, 1H), 7.56 (d, J=2.51 Hz, 1H), 7.72 (d, J=8.53 Hz, 1H), 7.85 (d, J=8.53 Hz, 1H), 8.00 (d, J=4.02 Hz, 1H), 8.04 (d, J=2.01 Hz, 1H), 8.36 (s, 1H), 8.67 (d, J=2.01 Hz, 1H), 10.61 (s, 1H), 12.46 (s, 1H).

Example 187

N-(6-(6-chloro-5-(thiophene-4-sulfonamido)pyridin-3-yl)benzo[d]thiazol-2-yl)acetamide MS (ESI pos. ion) m/z: 465 (MH+). Calc'd exact mass for $C_{18}H_{13}ClN_4O_3S_3$: 464. $^1$H NMR (400 MHz, DMSO-d6): 2.29 (s, 3H), 7.37 (d, 1H), 7.72 (d, 1H), 7.79 (t, 1H), 7.90 (d, 1H), 7.98 (d, 1H), 8.21 (s, 1H), 8.33 (s, 1H), 8.54 (s, 1H), 12.51 (s, 1H).

Example 188

N-(6-(6-chloro-5-(phenylmethylsulfonamido)pyridin-3-yl)benzo[d]thiazol-2-yl)acetamide MS (ESI pos. ion) m/z: 473 (MH+). Calc'd exact mass for $C_{21}H_{17}ClN_4O_3S_2$: 472. $^1$H NMR (400 MHz, DMSO-d6):

2.23 (s, 3H), 4.69 (s, 2H), 7.26-7.42 (m, 3H), 7.42-7.52 (m, 2H), 7.52-7.63 (m, 2H), 7.85 (d, J=8.53 Hz, 1H), 8.20 (s, 1H), 8.54 (d, J=2.51 Hz, 1H), 9.84 (s, 1H), 12.47 (s, 1H).

Example 189

N-(6-(6-chloro-5-(4-methylphenylsulfonamido)pyridin-3-yl)benzo[d]thiazol-2-yl)acetamide MS (ESI pos. ion) m/z: 473 (MH+). Calc'd exact mass for $C_{21}H_{17}ClN_4O_3S_2$: 472. $^1$H NMR (400 MHz, DMSO-d6): 2.23 (s, 3H), 2.38 (s, 3H), 7.40 (d, J=8.03 Hz, 2H), 7.66 (d, J=8.03 Hz, 3H), 7.84 (d, J=8.53 Hz, 1H), 7.96 (s, 1H), 8.30 (s, 1H), 8.60 (s, 1H), 10.34 (s, 1H), 12.46 (s, 1H).

Example 190

N-(6-(6-chloro-5-(4-(trifluoromethyl)phenylsulfonamido)pyridin-3-yl)benzo[d]thiazol-2-yl)acetamide MS (ESI pos. ion) m/z: 527 (MH+). Calc'd exact mass for $C_{21}H_{14}ClF_3N_4O_3S_2$: 526. $^1$H NMR (400 MHz, DMSO-d6): 2.23 (s, 3H), 7.52-8.11 (m, 7H), 8.27 (s, 1H), 8.55 (s, 1H), 12.45 (s, 1H).

Example 191

N-(6-(5-(4-tert-butylphenylsulfonamido)-6-chloropyridin-3-yl)benzo[d]thiazol-2-yl)acetamide MS (ESI pos. ion) m/z: 516 (MH+). Calc'd exact mass for $C_{24}H_{23}ClN_4O_3S_2$: 515. $^1$H NMR (400 MHz, DMSO-d6): 1.26 (s, 9H), 2.21 (s, 3H), 7.35-7.49 (m, 3H), 7.60-7.80 (m, 5H), 7.94 (s, 1H), 12.39 (s, 1H).

Example 192

N-(5-(2-aminobenzo[d]thiazol-6-yl)-2-chloropyridin-3-yl)-4-fluorobenzenesulfonamide MS (ESI pos. ion) m/z: 435 (MH+). Calc'd exact mass for $C_{18}H_{12}ClFN_4O_2S_2$: 434. $^1$H NMR (400 MHz, DMSO-d6): 1.62 (d, J=3.01 Hz, 1H), 7.21 (s, 3H), 7.56 (s, 3H), 7.70 (s, 3H), 7.77 (s, 2H).

Example 193

N-(6-(6-chloro-5-(2-chlorothiophene-5-sulfonamido)pyridin-3-yl)benzo[d]thiazol-2-yl)acetamide MS (ESI pos. ion) m/z: 500 (MH+). Calc'd exact mass for $C_{18}H_{12}Cl_2N_4O_3S_3$: 499. $^1$H NMR (400 MHz, DMSO-d6): 1.65 (s, 1H), 2.10 (s, 3H), 6.98 (s, 1H), 7.16 (s, 1H), 7.41 (s, 1H), 7.61 (s, 2H), 7.79 (s, 1H), 7.86 (s, 1H), 7.91 (s, 1H).

Example 194

Method R

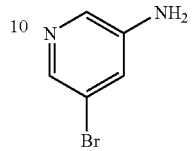
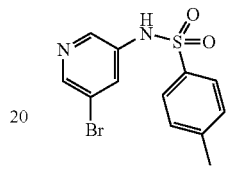
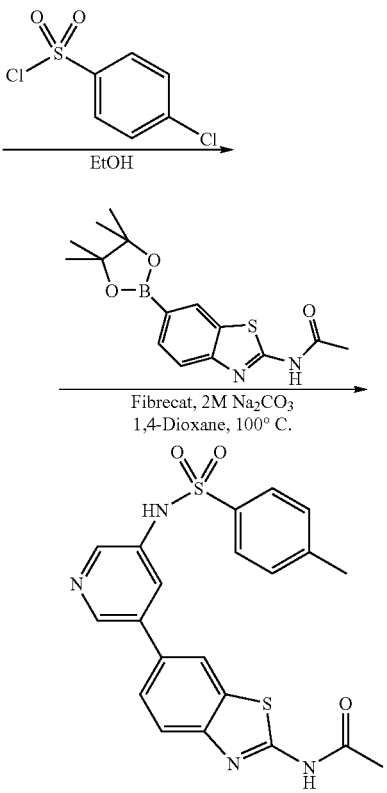

N-(6-(5-(4-methylphenylsulfonamido)pyridin-3-yl)benzo[d]thiazol-2-yl)acetamide

Step 1.
N-(5-bromopyridin-3-yl)-4-methylbenzenesulfonamide

To a round-bottom flask charged with 5-bromopyridin-3-amine (0.400 g, 2.3 mmol) in ethanol (10 ml, 171 mmol), was added 4-methylbenzene-1-sulfonyl chloride (0.880 g, 4.6 mmol) into the mixture. The mixture was allowed to stir at ambient temperature overnight, while under inert atmosphere. The progress of the reaction was monitored by LC/MS, which showed mostly desired product. The mixture was diluted with DCM and saturated sodium bicarbonate solution, then extracted the organic layer with DCM (3×25 ml). The organics were combined, dried over sodium sulfate, filtered and concentrated in vacuo. The crude was purified by ISCO silica-gel chromatography, in a gradient of 10-30% EtOAc/DCM. The fractions with desired product were combined and concentrated. This gave N-(5-bromopyridin-3-yl)-4-methylbenzenesulfonamide (0.350 g, 46% yield) as a light-yellow crystalline solid. MS (ESI pos. ion) m/z: 328 (MH+). Calc'd exact mass for $Cl_2H$, $BrN_2O_2S$: 327. $^1$H NMR (400 MHz, chloroform-d): 2.43 (d, J=18.57 Hz, 3H), 7.35 (d, J=6.53 Hz, 2H), 7.69 (d, J=6.02 Hz, 2H), 7.80 (d, J=5.02 Hz, 2H), 8.13-8.20 (m, 1H), 8.42 (s, 1H).

Step 2. N-(6-(5-(4-methylphenylsulfonamido)pyridin-3-yl)benzo[d]thiazol-2-yl)acetamide To a microwave vial equipped with a stir bar was charged with N-(5-bromopyridin-3-yl)-4-methylbenzenesulfonamide (0.180 g, 0.6 mmol) in 1,4-dioxane (3 ml), was added N-(6-(4,4,5,5-tetramethyl-1,3,2-dioxaborolan-2-yl)benzo[d]thiazol-2-yl)acetamide (0.223 g, 0.7 mmol), Pd FibreCat® (Anchored homogeneous catalyst, Johnson Matthey, West Deptford, N.J.) (0.024 g, 20%) and 2M sodium carbonate (0.7 ml, 1 mmol). The vial was capped and then placed into a CEM Microwave for 10 minutes at 100° C., while 100 watts of energy was supplied via Powermax® (Simultaneous heating while cooling technology). The progress of the reaction was monitored by LC/MS, which showed desired product, N-deacylated material and boronic ester in the mixture. The reaction was stopped at this point, to prevent further de-acylation of product. The mixture was diluted with DCM and saturated sodium bicarbonate solution. The organic layer was collected by extracting with DCM (3×20 ml). Combined organic extracts, dried over sodium sulfate, filtered and concentrated in vacuo. The crude was purified by reverse-phase HPLC. This gave N-(6-(5-(4-methylphenylsulfonamido)pyridin-3-yl)benzo[d]thiazol-2-yl)acetamide (0.016 g, 7% yield) as a white crystalline solid. MS (ESI pos. ion) m/z: 439 (MH+). Calc'd exact mass for $C_{21}H_{18}N_4O_3S_2$: 438. $^1$H NMR (400 MHz, DMSO-d6): 2.19 (s, 3H), 2.27 (s, 3H), 7.16 (d, 2H), 7.37 (s, 1H), 7.49 (s, 1H), 7.62 (d, 2H), 7.73 (d, 1H), 7.90 (s, 1H), 7.94 (s, 1H), 8.02 (s, 1H).

Compound Examples 195-202 were prepared by analogous methods to Compound Example 194, Method R.

Example 195

N-(6-(5-(4-methoxyphenylsulfonamido)pyridin-3-yl)benzo[d]thiazol-2-yl)acetamide

MS (ESI pos. ion) m/z: 455 (MH+). Calc'd exact mass for $C_{21}H_{18}N_4O_4S_2$: 454. $^1$H NMR (400 MHz, DMSO-d6): 2.22 (s, 3H), 3.79 (s, 3H), 7.08 (d, J=5.52 Hz, 2H), 7.63 (s, 1H), 7.75 (s, 3H), 7.82 (s, 1H), 8.24 (s, 2H), 8.59 (s, 1H), 12.42 (s, 1H).

Example 196

N-(6-(5-(4-(trifluoromethyl)phenylsulfonamido)pyridin-3-yl)benzo[d]thiazol-2-yl)acetamide MS (ESI pos. ion) m/z: 493 (MH+). Calc'd exact mass for $C_{21}H_{15}F_3N_4O_3S_2$: 492. $^1$H NMR (400 MHz, DMSO-d6): 2.22 (s, 3H), 7.63 (s, 1H), 7.77 (s, 2H), 8.00 (d, J=12.05 Hz, 4H), 8.25 (s, 3H), 8.64 (s, 1H), 12.43 (s, 1H).

Example 197

N-(6-(5-(3-(trifluoromethyl)phenylsulfonamido)pyridin-3-yl)benzo[d]thiazol-2-yl)acetamide MS (ESI pos. ion) m/z: 493 (MH+). Calc'd exact mass for $C_{21}H_{15}F_3N_4O_3S_2$: 492. $^1$H NMR (400 MHz, DMSO-d6): 2.22 (s, 3H), 7.65 (s, 1H), 7.81 (d, 3H), 8.10 (s, 3H), 8.25 (s, 2H), 8.67 (s, 1H), 12.44 (s, 1H).

Example 198

N-(6-(5-(4-fluorophenylsulfonamido)pyridin-3-yl)benzo[d]thiazol-2-yl)acetamide

MS (ESI pos. ion) m/z: 443 (MH+). Calc'd exact mass for $C_{20}H_{15}FN_4O_3S_2$: 442. $^1$H NMR (400 MHz, DMSO-d6): 2.22 (s, 3H), 7.42 (m, 2H), 7.63 (m, 1H), 7.69-7.96 (m, 4H), 8.25 (d, 2H), 8.62 (s, 1H), 12.43 (s, 1H).

Example 199

N-(6-(5-(3-fluorophenylsulfonamido)pyridin-3-yl)benzo[d]thiazol-2-yl)acetamide

MS (ESI pos. ion) m/z: 443 (MH+). Calc'd exact mass for $C_{20}H_{15}FN_4O_3S_2$: 442. $^1$H NMR (400 MHz, DMSO-d6): 2.21 (s, 3H), 7.19 (d, 1H), 7.42 (m, 3H), 7.56 (m, 2H), 7.76 (d, 1H), 7.94 (s, 1H), 8.01 (s, 1H), 8.10 (s, 1H).

Example 200

N-(6-(5-(3,4-dichlorophenylsulfonamido)pyridin-3-yl)benzo[d]thiazol-2-yl)acetamide MS (ESI pos. ion) m/z: 494 (MH+). Calc'd exact mass for $C_{20}H_{14}Cl_2N_4O_3S_2$: 493. $^1$H NMR (400 MHz, DMSO-d6): 2.22 (s, 3H), 7.77 (s, 2H), 7.85 (s, 2H), 8.26 (d, J=8.53 Hz, 2H).

Example 201

N-(6-(5-(4-tert-butylphenylsulfonamido)pyridin-3-yl)benzo[d]thiazol-2-yl)acetamide MS (ESI pos. ion) m/z: 481 (MH+). Calc'd exact mass for $C_{24}H_{24}N_4O_3S_2$: 480. $^1$H NMR (400 MHz, DMSO-d6): 1.25 (s, 9H), 2.21 (s, 3H), 7.44-7.55 (m, 4H), 7.69 (d, J=8.03 Hz, 2H), 7.77 (d, J=8.03 Hz, 1H), 8.04 (s, 1H), 8.10 (s, 11H), 8.16 (s, 1H).

Example 202

N-(6-(5-(phenylsulfonamido)pyridin-3-yl)benzo[d]thiazol-2-yl)acetamide

MS (ESI pos. ion) m/z: 425 (MH+). Calc'd exact mass for $C_{20}H_{16}N_4O_3S_2$: 424. $^1$H NMR (400 MHz, DMSO-d6): 2.23 (s, 3H), 7.51-7.67 (m, 5H), 7.76 (s, 1H), 7.80-7.86 (m, 3H), 8.25 (s, 2H), 8.61 (s, 1H), 12.43 (s, 1H).

Example 203

N-(6-(2-(4-fluoro-N-methylphenylsulfonamido)pyrimidin-4-yl)benzo[d]thiazol-2-yl)acetamide Step 1. 4-fluoro-N-methylbenzenesulfonamide A round bottom flask was charged with methylamine solution 40% (0.88 ml, 26 mmol) in ethanol (10 ml, 171 mmol). The mixture was chilled to 0° C. in an ice bath, with stirring under inert atmosphere. Then 4-fluorobenzenesulfonyl chloride (1.00 g, 5.1 mmol) was added into the mixture. The resulting mixture was allowed to stir at 0° C., while under inert atmosphere for 30 minutes. The progress of the reaction was monitored by LC/MS, which showed mostly desired product peak. The mixture was diluted with DCM and saturated sodium bicarbonate solution, then extracted the organic layer with DCM (3×25 ml). The organics were combined, dried over sodium sulfate, filtered and concentrated in vacuo. This gave 4-fluoro-N-methylbenzenesulfonamide (0.918 g, 94% yield) as an off-white crystalline solid. MS (ESI pos. ion) m/z: 190 (MH+). Calc'd exact mass for $C_7H_8FNO_2S$:

189. $^1$H NMR (400 MHz, chloroform-d): 2.64-2.71 (m, 3H), 4.63 (s, 1H), 7.18-7.28 (m, 2H), 7.88-7.93 (m, 2H).

Step 2. N-(6-(2-(4-fluoro-N-methylphenylsulfonamido)pyrimidin-4-yl)benzo[d]thiazol-2-yl)acetamide To a microwave vial equipped with a stir bar, was added 4-fluoro-N-methylbenzenesulfonamide (0.23 g, 1.2 mmol) and DMF (3 ml). Then sodium hydride (0.120 g, 4.9 mmol) was added to the mixture and allowed to stir 30 minutes. Then palladium(II) acetate (0.011 g, 0.049 mmol), N-(6-(2-chloropyrimidin-4-yl)benzo[d]thiazol-2-yl)acetamide (0.150 g, 0.49 mmol) and Xantphos (0.010 g) was added to the mixture. The vial was capped and placed into a CEM Microwave for 10 minutes at 100° C., while 100 watts of energy was supplied via Powermax® (Simultaneous heating while cooling technology). The progress of the reaction was monitored by LC/MS, which showed desired product peaks. The mixture was added to a round-bottom flask and diluted with hot water (150 ml). The mixture was allowed to stir overnight. The precipitate was collected by filtration and washed with Hexanes (3×50 ml), then finally with ethyl ether (50 ml). The crude was diluted with DMSO (5 ml) and purified by reverse-phase HPLC. This gave N-(6-(2-(4-fluoro-N-methylphenylsulfonamido)pyrimidin-4-yl)benzo[d]thiazol-2-yl)acetamide (0.030 g, 13% yield) as a light-yellow solid. MS (ESI pos. ion) m/z: 458 (MH+). Calc'd exact mass for $C_{20}H_{16}FN_5O_3S_2$: 457. $^1$H NMR (400 MHz, DMSO-d6): 1.97 (s, 3H), 3.69 (s, 3H), 7.36-7.47 (m, 3H), 7.64 (s, 1H), 7.82 (d, J=8.03 Hz, 1H), 8.11 (s, 2H), 8.19 (s, 1H), 8.51 (d, J=3.51 Hz, 1H).

Compound Examples 204-214 were prepared in an analogous manner to Compound Example 203.

Example 204

N-(6-(2-(N-methylquinoline-6-sulfonamido)pyrimidin-4-yl)benzo[d]thiazol-2-yl)acetamide MS (ESI pos. ion) m/z: 491 (MH+). Calc'd exact mass for $C_{23}H_{18}N_6O_3S_2$: 490. $^1$H NMR (400 MHz, chloroform-d): 2.36 (s, 3H), 3.89 (d, J=2.51 Hz, 3H), 7.56 (m, 1H), 7.76 (d, 1H), 7.96 (d, J=8.03 Hz, 1H), 8.27 (s, 3H), 8.32 (d, J=9.03 Hz, 1H), 8.50 (dd, J=5.27, 2.76 Hz, 1H), 8.76 (s, 1H), 9.04 (s, 1H).

Example 205

N-(6-(2-(4-tert-butyl-N-methylphenylsulfonamido)pyrimidin-4-yl)benzo[d]thiazol-2-yl)acetamide MS (ESI pos. ion) m/z: 496 (MH+). Calc'd exact mass for $C_{24}H_{25}N_5O_3S_2$: 495. $^1$H NMR (400 MHz, DMSO-d6): 2.21 (s, 3H), 3.36 (s, 9H), 3.71 (s, 3H), 7.64 (d, J=7.53 Hz, 2H), 7.72 (s, 1H), 7.76 (d, J=8.53 Hz, 1H), 7.97 (d, J=8.53 Hz, 3H), 8.44 (s, 1H), 8.65 (d, J=4.02 Hz, 1H).

Example 206

N-(6-(2-(N-methylthiophene-2-sulfonamido)pyrimidin-4-yl)benzo[d]thiazol-2-yl)acetamide MS (ESI pos. ion) m/z: 446 (MH+). Calc'd exact mass for $C_{18}H_{15}N_5O_3S_3$: 445. $^1$H NMR (300 MHz, DMSO-d6): 2.17 (s, 3H), 3.64 (s, 3H), 7.17 (s, 1H), 7.78 (s, 2H), 7.92 (s, 2H), 8.19 (s, 1H), 8.69 (s, 2H).

Example 207

N-(6-(2-(N-methylnaphthalene-1-sulfonamido)pyrimidin-4-yl)benzo[d]thiazol-2-yl)acetamide MS (ESI pos. ion) m/z: 490 (MH+). Calc'd exact mass for $C_{24}H_{19}N_5O_3S_2$: 489. $^1$H NMR (400 MHz, DMSO-d6): 2.18 (s, 3H), 3.85 (s, 3H), 7.64 (dd, J=9.54, 4.02 Hz, 3H), 7.75 (d, J=8.03 Hz, 2H), 7.85 (d, J=8.53 Hz, 1H), 8.10 (d, J=7.03 Hz, 1H), 8.25-8.31 (m, 2H), 8.37 (d, J=8.03 Hz, 1H), 8.54 (s, 2H).

Example 208

N-(6-(2-(N-methylisoquinoline-5-sulfonamido)pyrimidin-4-yl)benzo[d]thiazol-2-yl)acetamide MS (ESI pos. ion) m/z: 491 (MH+). Calc'd exact mass for $C_{23}H_{18}N_6O_3S_2$: 490. $^1$H NMR (1.98 (s, 3H), 3.84 (s, 3H), 7.31 (s, 1H), 7.58 (s, 3H), 7.90 (s, 1H), 8.04 (s, 1H), 8.19 (s, 1H), 8.46 (d, J=16.56 Hz, 2H), 8.71 (s, 2H), 9.47 (s, 1H).

Example 209

N-(6-(2-(N-methylthiophene-3-sulfonamido)pyrimidin-4-yl)benzo[d]thiazol-2-yl)acetamide MS (ESI pos. ion) m/z: 446 (MH+). Calc'd exact mass for $C_{18}H_{15}N_5O_3S_3$: 445. $^1$H NMR (400 MHz, DMSO-d6): 2.01 (s, 3H), 3.64 (s, 3H), 7.49 (s, 1H), 7.55 (s, 1H), 7.68 (s, 2H), 7.94 (s, 1H), 8.34 (s, 1H), 8.50 (s, 2H).

Example 210

N-(6-(2-(N,3,4-trimethylphenylsulfonamido)pyrimidin-4-yl)benzo[d]thiazol-2-yl)acetamide MS (ESI pos. ion) m/z: 468 (MH+). Calc'd exact mass for $C_{22}H_{21}N_5O_3S_2$: 467. $^1$H NMR (400 MHz, DMSO-d6): 2.10 (s, 3H), 2.26 (s, 6H), 3.69 (s, 3H), 7.33 (d, J=8.03 Hz, 1H), 7.59 (d, J=8.53 Hz, 1H), 7.65 (d, J=5.52 Hz, 1H), 7.72 (d, J=7.53 Hz, 1H), 7.84 (s, 1H), 7.97 (d, J=8.53 Hz, 1H), 8.32 (s, 1H), 8.57 (d, J=5.02 Hz, 1H).

Example 211

N-(6-(2-(N,1-dimethyl-1H-imidazole-4-sulfonamido)pyrimidin-4-yl)benzo[d]thiazol-2-yl)acetamide MS (ESI pos. ion) m/z: 444 (MH+). Calc'd exact mass for $C_{18}H_{17}N_7O_3S_2$: 443. $^1$H NMR (400 MHz, DMSO-d6): 2.24 (s, 3H), 3.67 (s, 6H), 7.71 (d, J=7.53 Hz, 2H), 7.86 (d, J=6.02 Hz, 1H), 8.17 (s, 2H), 8.64 (s, 1H), 8.73 (s, 1H), 12.52 (s, 1H).

Example 212

N-(6-(2-(N,2,4-trimethylphenylsulfonamido)pyrimidin-4-yl)benzo[d]thiazol-2-yl)acetamide MS (ESI pos. ion) m/z: 468 (MH+). Calc'd exact mass for $C_{22}H_{21}N_5O_3S_2$: 467. $^1$H NMR (400 MHz, DMSO-d6): 2.17

(s, 3H), 2.36 (s, 3H), 2.45 (s, 3H), 3.66 (s, 3H), 7.20-7.32 (s, 2H), 7.66 (s, 2H), 7.91 (s, 1H), 8.04 (s, 1H), 8.21 (s, 1H), 8.59 (s, 1H).

Example 213

N-(6-(2-(N-methyl-4-(trifluoromethyl)phenylsulfonamido)pyrimidin-4-yl)benzo[d]thiazol-2-yl)acetamide MS (ESI pos. ion) m/z: 508 (MH+). Calc'd exact mass for $C_{21}H_{16}F_3N_5O_3S_2$: 507. $^1$H NMR (400 MHz, DMSO-d6): 2.24 (s, 3H), 3.76 (s, 3H), 7.79 (m, 2H), 8.01 (d, J=8.03 Hz, 3H), 8.29 (d, J=7.53 Hz, 2H), 8.51 (s, 1H), 8.66 (d, 1H).

Example 214

N-(6-(2-(N-methylnaphthalene-2-sulfonamido)pyrimidin-4-yl)benzo[d]thiazol-2-yl)acetamide MS (ESI pos. ion) m/z: 490 (MH+). Calc'd exact mass for $C_{24}H_{19}N_5O_3S_2$: 489. $^1$H NMR (400 MHz, DMSO-d6): 2.19 (s, 3H), 3.79 (s, 3H), 7.67 (s, 4H), 8.00 (s, 3H), 8.09 (s, 1H), 8.20 (s, 1H), 8.41 (s, 1H), 8.60 (s, 1H), 8.82 (s, 1H).

Example 215

N-(6-(2-(N,4-dimethylphenylsulfonamido)pyridin-4-yl)benzo[d]thiazol-2-yl)acetamide Step 1. N-(6-(2-chloropyridin-4-yl)benzo[d]thiazol-2-yl)acetamide 2-chloro-4-iodopyridine (0.500 g, 2 mmol) was dissolved in 1,4-dioxane (15 ml), then N-(6-(4,4,5,5-tetramethyl-1,3,2-dioxaborolan-2-yl)benzo[d]thiazol-2-yl)acetamide (0.800 g, 3 mmol), tetrakis(triphenylphosphine)palladium(0) (0.300 g, 0.3 mmol) and 2M sodium carbonate (2 ml, 4 mmol) was added to the mixture. The round-bottom flask was fitted with a reflux condenser and placed into a pre-heated (90° C.) bath. The mixture was allowed to stir under inert atmosphere for 3 hours. The progress of the reaction was monitored by LC/MS, which showed desired product in the mixture. The material was allowed to cool to ambient temperature and diluted with DCM and saturated sodium bicarbonate solution. The organic layer was collected by extracting with DCM (3×20 ml). Combined organics, dried over sodium sulfate, filtered and concentrated in vacuo. The residue was diluted with ethyl ether (50 ml) and allowed to stir 10 minutes. The precipitate was collected by filtration and washed with ethyl ether. This gave N-(6-(2-chloropyridin-4-yl)benzo[d]thiazol-2-yl)acetamide (0.200 g, 32% yield) as a tan crystalline solid. MS (ESI pos. ion) m/z: 304 (MH+). Calc'd exact mass for $C_{14}H_{10}ClN_3OS$: 303. $^1$H NMR (400 MHz, DMSO-d6): 2.23 (s, 3H), 7.80-7.86 (m, 2H), 7.90-7.95 (m, 2H), 8.47 (d, J=5.09 Hz, 1H), 8.54 (s, 1H), 12.49 (s, 1H).

Step 2. N-(6-(2-(N,4-dimethylphenylsulfonamido)pyridin-4-yl)benzo[d]thiazol-2-yl)acetamide A microwave vial equipped with a stir bar was charged with n-methyl-p-toluenesulfonamide (0.26 g, 1.4 mmol) in DMF (3 ml). Then sodium t-butoxide (0.270 g, 2.8 mmol) was added to the mixture and allowed to stir 5 minutes. Then palladium(II) acetate (0.013 g, 0.057 mmol), N-(6-(2-chloropyridin-4-yl)benzo[d]thiazol-2-yl)acetamide (0.173 g, 0.57 mmol) and Xantphos (0.010 g) was added to the mixture. The vial was capped and placed into a CEM Microwave for 20 minutes at 100° C., while 100 watts of energy was supplied via Powermax® (Simultaneous heating while cooling technology). The progress of the reaction was monitored by LC/MS, which showed desired product peaks. The mixture was diluted with DMSO and purified by reverse-phase HPLC. This gave N-(6-(2-(N,4-dimethylphenylsulfonamido)pyridin-4-yl)benzo[d]thiazol-2-yl)acetamide (0.010 g, 3.9% yield) as a tan solid. MS (ESI pos. ion) m/z: 453 (MH+). Calc'd exact mass for $C_{22}H_{20}N_4O_3S_2$: 452. $^1$H NMR (300 MHz, DMSO-d6): 2.03 (s, 3H), 2.37 (s, 3H), 3.24 (s, 3H), 7.32-7.42 (d, 2H), 7.44-7.73 (m, 6H), 7.80 (s, 1H), 8.14 (s, 1H), 8.29 (d, 1H).

Example 216

N-(6-(2-(4-methylphenylsulfonamido)pyridin-4-yl)benzo[d]thiazol-2-yl)acetamide

Step 1. N-(6-(2-(4-methylphenylsulfonamido)pyridin-4-yl)benzo[d]thiazol-2-yl)acetamide A microwave vial equipped with a magnetic stir bar was charged with 4-methylbenzenesulfonamide (0.170 g, 0.99 mmol) in DMF (3 ml). Then sodium hydride (0.047 g, 2.0 mmol) was added into the mixture and allowed to stir an additional 15 minutes. Then N-(6-(2-chloropyridin-4-yl)benzo[d]thiazol-2-yl)acetamide (0.120 g, 0.40 mmol), palladium(II) acetate (0.0089 g, 0.040 mmol) and Xantphos (0.010 g) was added to the mixture. The vial was capped and placed into a CEM Microwave for 20 minutes at 120° C., while 100 watts of energy was supplied via Powermax® (Simultaneous heating while cooling technology). The progress of the reaction was monitored by LC/MS, which showed desired product in the mixture. The mixture was placed into a round-bottom flask, then diluted with ethyl acetate (20 ml) and stirred 20 minutes. The precipitate was collected by filtration and then purified by reverse-phase HPLC. This gave N-(6-(2-(4-methylphenylsulfonamido)pyridin-4-yl)benzo[d]thiazol-2-yl)acetamide (0.012 g, 6.9% yield) as a tan crystalline solid. MS (ESI pos. ion) m/z: 439 (MH+). Calc'd exact mass for $C_{21}H_{18}N_4O_3S_2$: 438. $^1$H NMR (400 MHz, DMSO-d6): 2.07 (s, 3H), 2.28 (s, 3H), 6.69 (s, 1H), 6.91 (s, 1H), 7.15 (d, J=6.53 Hz, 2H), 7.44 (d, J=8.03 Hz, 1H), 7.56 (d, J=7.53 Hz, 1H), 7.68 (d, J=7.03 Hz, 2H), 7.90 (s, 2H).

Example 217

N-(6-(2-(4-methoxyphenylsulfonamido)pyridin-4-yl)benzo[d]thiazol-2-yl)acetamide

MS (ESI pos. ion) m/z: 455 (MH+). Calc'd exact mass for $C_{21}H_{18}N_4O_4S_2$: 454. $^1$H NMR (400 MHz, DMSO-d6): 2.09 (s, 3H), 3.75 (s, 3H), 6.70 (s, 1H), 6.91 (s, 3H), 7.46 (s, 1H), 7.59 (s, 2H), 7.74 (s, 3H), 7.93 (s, 2H).

Example 218

N-(6-(5-(N-methyl-4-(trifluoromethyl)phenylsulfonamido)pyridin-3-yl)benzo[d]thiazol-2-yl)acetamide Step 1. 5-bromo-N-methylpyridin-3-amine 3-amino-5-bromopyridine (5.00 g, 29 mmol) was dissolved in THF (50 ml) and then n-butyl formate (4 ml, 35 mmol) was added into the mixture. Then TFA (0.9 ml, 12 mmol) was added to the mixture. The flask was fitted with a reflux condenser and allowed to stir under reflux at 100° C. overnight. The progress of the reaction was monitored by LC/MS, which showed 50% conversion of starting material. The flask was removed from the heat bath and allowed to cool to ambient temperature. The mixture was chilled to −50° C. in a dry ice/acetone bath. Then lithium aluminum hydride (58 ml, 58 mmol) was added slowly by syringe into the mixture with stirring. After the addition, the mixture was kept cold at −50° C. for 10 additional minutes, then allowed to slowly warm to ambient temperature. The progress of the reaction was monitored by LC/MS, which showed desired N-methylpyridine in the mixture. The mixture was diluted with ethyl ether and chilled to 0° C. Then water (2.2 ml) was added slowly into the mixture with stirring for 5 minutes. Then 2N sodium hydroxide (2.2 ml) was added into the mixture, followed by water (6.6 ml). After 5 minutes of stirring, magnesium sulfate (5 grams) was added to the mixture and allowed to stir an additional 15 minutes. The mixture was filtered through a plug of Celite® (diatomaceous earth).

The filtrate was concentrated in vacuo to give a light yellow oil. The crude was purified by ISCO silica-gel chromatography in a gradient of 1-5% isopropanol/DCM over 30 minutes. The fractions with desired product were combined and concentrated in vacuo. This gave 5-bromo-N-methylpyridin-3-amine (2.368 g, 44% yield) as an off-white solid. MS (ESI pos. ion) m/z: 188 (MH+). Calc'd exact mass for $C_6H_7BrN_2$: 187. $^1$H NMR (400 MHz, DMSO-d6): 2.69 (d, J=5.02 Hz, 3H), 6.24 (d, J=4.02 Hz, 1H), 7.04 (s, 1H), 7.76-7.81 (m, 1H), 7.91 (d, J=2.01 Hz, 1H).

Step 2. N-(5-bromopyridin-3-yl)-N-methyl-4-(trifluoromethyl)benzenesulfonamide

To a microwave vial equipped with a stir bar and charged with 5-bromo-N-methylpyridin-3-amine (0.250 g, 1.3 mmol) in isopropanol (3 ml), was added 4-(trifluoromethyl)benzene-1-sulfonyl chloride (0.820 g, 3.3 mmol) and pyridine (0.32 ml, 4.0 mmol) into the mixture. The vial was capped and placed into a CEM Microwave for 20 minutes at 80° C., while 50 watts of energy was supplied via Powermax® (Simultaneous heating while cooling technology). The progress of the reaction was monitored by LC/MS, which showed mostly desired product. The mixture was diluted with DCM and saturated sodium bicarbonate solution, then extracted the organic layer with DCM (3×25 ml). The organics were combined, dried over sodium sulfate, filtered and concentrated in vacuo. The crude was purified by ISCO silica-gel chromatography in a gradient of 0-5% isopropanol/DCM. The fractions with desired product were combined and concentrated in vacuo. This gave N-(5-bromopyridin-3-yl)-N-methyl-4-(trifluoromethyl)benzenesulfonamide (0.300 g, 57% yield) as an off-white crystalline solid. MS (ESI pos. ion) m/z: 396 (MH+). Calc'd exact mass for $C_{13}H_{10}BrF_3N_2O_2S$: 395. $^1$H NMR (400 MHz, DMSO-d6): 3.24 (s, 3H), 7.79 (s, 2H), 8.01 (s, 3H), 8.46 (s, 1H), 8.66 (s, 1H).

Step 3. N-(6-(5-(N-methyl-4-(trifluoromethyl)phenylsulfonamido)pyridin-3-yl)benzo[d]thiazol-2-yl)acetamide To a microwave vial equipped with a stir bar was charged with N-(5-bromopyridin-3-yl)-N-methyl-4-(trifluoromethyl)benzenesulfonamide (0.250 g, 0.6 mmol) in 1,4-dioxane (3 ml), was added N-(6-(4,4,5,5-tetramethyl-1,3,2-dioxaborolan-2-yl)benzo[d]thiazol-2-yl)acetamide (0.300 g, 0.9 mmol), Pd FibreCat® (0.024 g, 20%) and 2M sodium carbonate (0.8 ml, 2 mmol). The vial was capped and then placed into a CEM Microwave for 15 minutes at 100° C., while 100 watts of energy was supplied via Powermax® (Simultaneous heating while cooling technology). The progress of the reaction was monitored by LC/MS, which showed desired product, N-deacylated material and boronic ester in the mixture. The reaction was stopped at this point, to prevent further de-acylation of product. The mixture was diluted with DCM and saturated sodium bicarbonate solution. The organic layer was collected by extracting with DCM (3×20 ml). Combined organic extracts, dried over sodium sulfate, filtered and concentrated in vacuo. The crude was diluted with ethyl acetate and stirred 10 minutes. The precipitate was collected by filtration and washed with 1:1 ethyl acetate/hexanes. This gave N-(6-(5-(N-methyl-4-(trifluoromethyl)phenylsulfonamido)pyridin-3-yl)benzo[d]thiazol-2-yl)acetamide (0.160 g, 50% yield) as a tan crystalline solid. MS (ESI pos. ion) m/z: 507 (MH+). Calc'd exact mass for $C_{22}H_{17}F_3N_4O_3S_2$: 506. $^1$H NMR (400 MHz, DMSO-d6): 2.23 (s, 3H), 3.31 (s, 3H), 7.71 (d, J=7.53 Hz, 1H), 7.81 (d, J=7.03 Hz, 3H), 7.87 (s, 1H), 8.02 (d, J=6.53 Hz, 2H), 8.26 (s, 1H), 8.42 (s, 1H), 8.91 (s, 1H), 12.44 (s, 1H).

Compound Examples 219-224 were prepared in an analogous manner to Compound Example 218.

Example 219

N-(6-(5-(4-fluoro-N-methylphenylsulfonamido)pyridin-3-yl)benzo[d]thiazol-2-yl)acetamide MS (ESI pos. ion) m/z: 457 (MH+). Calc'd exact mass for $C_{21}H_{17}FN_4O_3S_2$: 456. $^1$H NMR (400 MHz, DMSO-d6): 2.22 (s, 3H), 3.27 (s, 3H), 7.47 (s, 2H), 7.66 (s, 2H), 7.73 (s, 1H), 7.80 (s, 1H), 7.86 (s, 1H), 8.29 (s, 1H), 8.39 (s, 1H), 8.88 (s, 1H).

Example 220

N-(6-(5-(4-chloro-N-methylphenylsulfonamido)pyridin-3-yl)benzo[d]thiazol-2-yl)acetamide MS (ESI pos. ion) m/z: 473 (MH+). Calc'd exact mass for $C_{21}H_{17}ClN_4O_3S_2$: 472. $^1$H NMR (400 MHz, DMSO-d6): 3.22 (s, 3H), 3.28 (s, 3H), 7.06-8.05 (m, 7H), 8.21-8.51 (m, 2H), 8.90 (s, 1H), 12.43 (s, 1H).

Example 221

N-(6-(5-(3,4-dichloro-N-methylphenylsulfonamido)pyridin-3-yl)benzo[d]thiazol-2-yl)acetamide MS (ESI pos. ion) m/z: 508 (MH+). Calc'd exact mass for $C_{21}H_{16}Cl_2N_4O_3S_2$: 507. $^1$H NMR (400 MHz, DMSO-d6): 2.23 (s, 3H), 3.23-3.42 (m, 3H), 7.50 (d, J=7.03 Hz, 1H), 7.72-7.86 (m, 3H), 7.91 (d, J=8.03 Hz, 1H), 7.94 (s, 1H), 8.29 (s, 1H), 8.45 (s, 1H), 8.91 (s, 1), 12.45 (s, 1H).

Example 222

N-(6-(5-(3,4-difluoro-N-methylphenylsulfonamido)pyridin-3-yl)benzo[d]thiazol-2-yl)acetamide MS (ESI pos. ion) m/z: 475 (MH+). Calc'd exact mass for $C_{21}H_{16}F_2N_4O_3S_2$: 474. $^1$H NMR (400 MHz, DMSO-d6): 2.22 (s, 3H), 3.33 (s, 3H), 7.41 (s, 1H), 7.81 (s, 4H), 7.92 (s, 1H), 8.31 (s, 1H), 8.42 (s, 1H), 8.90 (s, 1H).

Example 223

N-(6-(5-(4-tert-butyl-N-methylphenylsulfonamido) pyridin-3-yl)benzo[d]thiazol-2-yl)acetamide MS (ESI pos. ion) m/z: 495 (MH+). Calc'd exact mass for $C_{25}H_{26}N_4O_3S_2$: 494. $^1$H NMR (300 MHz, MeOD): 1.33 (s, 9H), 2.28 (s, 3H), 3.28 (s, 3H), 7.45-7.71 (m, 6H), 7.75-7.86 (d, 1H), 8.05 (s, 1H), 8.36 (s, 1H), 8.77 (s, 1H).

Example 224

N-(6-(5-(N-methylphenylsulfonamido)pyridin-3-yl) benzo[d]thiazol-2-yl)acetamide

MS (ESI pos. ion) m/z: 439 (MH+). Calc'd exact mass for $C_{21}H_{18}N_4O_3S_2$: 438. $^1$H NMR (400 MHz, DMSO-d6): 2.22 (s, 3H), 3.27 (s, 3H), 7.60 (s, 4H), 7.74 (s, 2H), 7.81 (s, 1H), 8.30 (s, 1H), 8.37 (s, 1H), 8.87 (s, 1H), 12.45 (s, 1H).

Example 225

N-(6-(6-(N,3-dimethylphenylsulfonamido)pyridin-2-yl)benzo[d]thiazol-2-yl)acetamide Step 1. N,3-dimethylbenzenesulfonamide A round-bottom flask with methylamine solution 40% (0.9 ml, 28 mmol) in ethanol (2 ml, 34 mmol), was chilled to 0° C. in an ice bath with stirring under inert atmosphere. Then m-toluenesulfonyl chloride (0.8 ml, 6 mmol) was added slowly into the mixture. The mixture was allowed to stir at 0° C., while under inert atmosphere for 30 minutes. The progress of the reaction was monitored by LC/MS, which showed mostly desired product peak. The mixture was diluted with ethyl acetate and water and then extracted the organic layer with EtOAc (3×25 ml) and brine solution. The organics were combined, dried over sodium sulfate, filtered and concentrated in vacuo. This gave N,3-dimethylbenzenesulfonamide (1.00 g, 98% yield) as a colorless oil. MS (ESI pos. ion) m/z: 186 (MH+). Calc'd exact mass for $C_8H_{11}NO_2S$: 185. $^1$H NMR (400 MHz, chloroform-d): 2.35-2.46 (m, 3H), 2.64 (s, 3H), 4.91 (s, 1H), 7.36-7.46 (m, 2H), 7.64-7.73 (m, 2H).

Step 2. N-(6-chloropyridin-2-yl)-N,3-dimethylbenzenesulfonamide

N,3-dimethylbenzenesulfonamide (0.250 g, 1.3 mmol) was added to a microwave vial, equipped with a stir bar. Then DMF (3 ml) was added to the mixture, followed by sodium hydride (0.160 g, 6.7 mmol) and allowed the mixture to stir 20 minutes. Then 2,6-dichloropyridine (0.300 g, 2.0 mmol), palladium(II) acetate (0.030 g, 0.13 mmol) and Xantphos (0.024 g) was added to the mixture. The vial was capped and placed into CEM Microwave for 10 minutes at 100° C., while 100 watts of energy was supplied via Powermax® (Simultaneous heating while cooling technology). The reaction was monitored by LC/MS, which showed desired product in the mixture. The mixture was diluted with DCM and saturated sodium bicarbonate solution. The organic layer was extracted with 4:1 DCM/MeOH (3×25 ml). Combined organics, dried over sodium sulfate, filtered and concentrated in vacuo. The crude was purified by ISCO silica-gel chromatography on a 40 gram column, in a gradient of 1-10% EtOAc/Hexanes over 30 minutes. The fractions with desired product were combined and concentrated to give N-(6-chloropyridin-2-yl)-N,3-dimethylbenzenesulfonamide (0.205 g, 51% yield) as a colorless oil. MS (ESI pos. ion) m/z: 297 (MH+). Calc'd exact mass for $C_{13}H_{13}ClN_2O_2S$: 296. $^1$H NMR (400 MHz, chloroform-d): 2.38 (d, J=2.01 Hz, 3H), 3.31 (d, J=2.51 Hz, 3H), 7.11 (d, J=3.51 Hz, 1H), 7.26-7.48 (m, 4H), 7.57-7.67 (m, 2H).

Step 3. N-(6-(6-(N,3-dimethylphenylsulfonamido) pyridin-2-yl)benzo[d]thiazol-2-yl)acetamide N-(6-chloropyridin-2-yl)-N,3-dimethylbenzenesulfonamide (0.200 g, 0.7 mmol) was dissolved in 1,4-dioxane (6 ml), then N-(6-(4,4,5,5-tetramethyl-1,3,2-dioxaborolan-2-yl)benzo[d]thiazol-2-yl)acetamide (0.300 g, 1 mmol), tetrakis (triphenylphosphine)palladium(0) (0.100 g, 0.1 mmol) and 2M sodium carbonate (1 ml, 2 mmol) was added to the mixture. The flask was fitted with a reflux condenser and placed into a pre-heated (95° C.) bath. The mixture was allowed to stir under inert atmosphere for 3 hours. The progress of the reaction was monitored by LC/MS, which showed desired product. The mixture was allowed to cool to ambient temperature and diluted with DCM and saturated sodium bicarbonate solution. The organic layer was collected by extracting with DCM (3×20 ml). Combined organic extracts, dried over sodium sulfate, filtered and concentrated in vacuo. The crude was filtered and purified by silica-gel chromatography, in a gradient of 1-10% IPA/DCM over 30 minutes. The fractions with desired product were combined and concentrated. The crude was recrystallized from DCM/Hexanes to give N-(6-(6-(N,3-dimethylphenylsulfonamido) pyridin-2-yl)benzo[d]thiazol-2-yl)acetamide (0.175 g, 57% yield) as a yellow crystalline solid. MS (ESI pos. ion) m/z: 453 (MH+). Calc'd exact mass for $C_{22}H_{20}N_4O_3S_2$: 452. $^1$H NMR (400 MHz, DMSO-d6): 2.22 (s, 3H), 2.31 (s, 3H), 3.40 (s, 3H), 7.34-7.56 (m, 5H), 7.75 (d, J=8.53 Hz, 1H), 7.84 (d, J=7.53 Hz, 1H), 7.93 (t, J=6.53 Hz, 2H), 8.40 (s, 1H), 12.42 (s, 1H).

Compound Example 226 was prepared in an analogous manner to Compound Example 225.

Example 226

N-(6-(6-(2-fluoro-N-methylphenylsulfonamido)pyridin-2-yl)benzo[d]thiazol-2-yl)acetamide MS (ESI pos. ion) m/z: 457 (MH+). Calc'd exact mass for $C_{21}H_{17}FN_4O_3S_2$: 456. $^1$H NMR (400 MHz, chloroform-d): 2.26-2.34 (m, 3H), 3.59 (s, 3H), 7.15 (t, J=9.29 Hz, 1H), 7.30 (t, J=7.78 Hz, 1H), 7.40 (d, J=8.03 Hz, 1H), 7.54-7.62 (m, 2H), 7.72-7.78 (m, 2H), 7.89 (d, J=8.53 Hz, 1H), 8.01 (t, J=7.28 Hz, 1H), 8.12 (s, 1H), 10.17 (s, 1H).

Example 227

N-(6-(6-(tert-butylamino)pyrazin-2-yl)benzo[d]thiazol-2-yl)acetamide

A microwave vial equipped with a magnetic stir bar was charged with 2-methylpropan-2-amine (0.100 g, 2 mmol) in DMF (3 ml). Then sodium hydride (0.047 g, 2.0 mmol) was added into the mixture and allowed to stir an additional 15 minutes. Then N-(6-(6-chloropyrazin-2-yl)benzo[d]thiazol-2-yl)acetamide (0.100 g, 0.30 mmol), palladium(II) acetate (0.007 g, 0.03 mmol) and Xantphos (0.010 g) was added to the mixture. The vial was capped and placed into a CEM Microwave for 10 minutes at 100° C., while 100 watts of energy was supplied via Powermax® (Simultaneous heating while cooling technology). The progress of the reaction was monitored by LC/MS, which showed desired product in the mixture. The mixture was placed into a round-bottom flask, then diluted with ethyl acetate (20 ml) and stirred 20 minutes. The precipitate was collected by filtration and then purified by reverse-phase HPLC. This gave N-(6-(6-(tert-butylamino) pyrazin-2-yl)benzo[d]thiazol-2-yl)acetamide (0.005 g, 4% yield) as a tan crystalline solid. MS (ESI pos. ion) m/z: 342 (MH+). Calc'd exact mass for $C_{17}H_{19}N_5OS$: 341. $^1$H NMR 400 MHz, DMSO-d6): 1.49 (s, 9H), 2.09 (s, 3H), 6.80 (s, 1H), 7.62 (d, J=8.03 Hz, 1H), 7.82 (s, 1H), 7.98 (d, J=8.03 Hz, 1H), 8.24 (s, 1H), 8.43 (s, 1H).

Example 228

N-(5-(5-(4-Fluorophenylsulfonamido)pyridin-3-yl) thiazolo[5,4-b]pyridin-2-yl)acetamide (TFA salt)

Step 1.
N-(5-Bromopyridin-3-yl)-4-fluorobenzenesulfonamide

To a round bottom flask was added 5-bromopyridin-3-amine (0.80 g, 4.6 mmol, Matrix Scientific, Columbia S.C.), ethanol (15 mL) and 4-fluorobenzenesulfonyl chloride (2.2 g, 12 mmol, Fluka, St. Louis, Mo.). The mixture was allowed to stir at ambient temperature overnight. The mixture was diluted with $CH_2Cl_2$ and sat. $NaHCO_3$, then the solution was extracted with $CH_2Cl_2$ (3×25 ml). The combined extracts were dried over $Na_2SO_4$, filtered and concentrated. Purification by silica gel chromatography (10-30% EtOAc/$CH_2Cl_2$) afforded the title compound as an off-white crystalline solid (0.35 g, 23% yield). MS (ESI pos. ion) m/z: 333 (M+1). $^1$H NMR (400 MHz, MeOH-d$_4$) δ ppm 8.35 (s, 1H), 8.22 (s, 1H), 7.83-7.89 (m, 2H), 7.76-7.81 (m, 1H), 7.25-7.32 (m, 2H).

Step, 2. N-(5-(5-(4-Fluorophenylsulfonamido)pyridin-3-yl)thiazolo[5,4-b]pyridin-2-yl)acetamide (TFA salt)

To a 25 mL round-bottomed flask was added N-(5-bromopyridin-3-yl)-4-fluorobenzenesulfonamide (0.15 g, 0.45 mmol), bis(pinacolato)diboron (0.17 g, 0.68 mmol, Aldrich, St. Louis. MO), potassium acetate (0.18 g, 1.8 mmol) and 1,4-dioxane (4.0 ml). The mixture was carefully evacuated and backfilled with $N_2$ and then dichloro[1,1'-bis(diphenylphosphino)ferrocene]palladium (II) dichloromethane adduct (0.033 g, 0.045 mmol, Strem, Newburyport, Mass.) was added. The mixture was carefully evacuated and backfilled with $N_2$ again. The mixture was stirred at 90° C. for 19 hours and then allowed to cool to rt. To the mixture was added DMF (4.0 ml), N-(5-chlorothiazolo[5,4-b]pyridin-2-yl)acetamide (0.075 g, 0.33 mmol) and 2 M sodium carbonate (0.82 ml, 1.7 mmol). The mixture was carefully evacuated and backfilled with $N_2$ and then trans-dichlorobis(triphenylphosphine)palladium (II) (0.023 g, 0.033 mmol, Strem) was added. The mixture was carefully evacuated and back-filled with $N_2$ and then stirred at 90° C. for 18 h. The mixture was allowed to cool to room temperature and then poured into water (100 mL) and extracted with 25% iPrOH/$CHCl_3$ (4×50 mL). The combined extracts were dried ($Na_2SO_4$) and concentrated. The residue was taken up in $CH_2Cl_2$/MeOH and concentrated onto silica. Purification by silica gel chromatography (3.0 to 10% MeOH (2 M in $NH_3$)/$CH_2Cl_2$) afforded a brown solid. This was further purified by Prep-HPLC (Phenomenex Synergi 4u MAX-RP 80A 150×21.20 nm n, 00F-4337-P0, 2 to 100% $CH_3CN$ (0.1% TFA)/$H_2O$ (0.1% TFA) over 15 min then 100% $CH_3CN$ for 5 minutes at 20 ml/min) with the fractions containing suspected product concentrated to afford the title compound as a tan solid (0.012 g, 6.3% yield). MS (ESI pos. ion) m/z: 444 (M+1). $^1$H NMR (400 MHz, DMSO-d$_6$) δ ppm 12.55 (s, 1H), 10.71 (s, 1H), 9.00 (d, J=1.8 Hz, 1H), 8.36 (d, J=2.5 Hz, 1H), 8.17-8.22 (m, 2H), 8.07 (d, J=8.6 Hz, 1H), 7.85-7.90 (m, 2H), 7.39-7.45 (m, 2H), 2.24 (s, 3H).

Example 229

N-(6-(5-(2-(2-oxopyrrolidin-1-yl)ethoxy)pyridin-3-yl)benzo[d]thiazol-2-yl)acetamide Step 1. 1-(2-(5-bromopyridin-3-yloxy)ethyl)pyrrolidin-2-one To a solution of triphenylphosphine (3 g, 12 mmol) in THF (20 mL) at 0° C. was added the following reagents in order in 10 minutes interval: diethyl azodicarboxylate (2 ml, 12 mmol), 1-(2-hydroxyethyl)pyrrolidin-2-one (0.9 ml, 8 mmol), and 5-bromopyridin-3-ol (2 g, 12 mmol). After 20 min, ice bath was removed; the reaction mixture was warmed up to rt and stirred for 20 h. The reaction was stopped, and solvent was removed The crude product was purified using $SiO_2$ chromatography with hexanes:acetone (70%:30%) solvent system to afford the product as white solid. Wt: 900 mg. MS (ESI pos. ion) m/z: 286.3. Calc'd exact mass for $C_{11}H_{13}BrN_2O_2$: 285.14. $^1$H NMR (300 MHz, chloroform-d) δ ppm 2.04 (none, 1H) 2.41 (d, J=16.37 Hz, 2H) 3.51-3.62 (m, 2H) 3.71 (t, J=5.19 Hz, 2H) 4.16 (t, J=5.19 Hz, 2H) 7.37 (d, J=1.90 Hz, 1H) 8.23 (s, 1H) 8.31 (s, 1H).

Step 2. N-(6-(5-(2-(2-oxopyrrolidin-1-yl)ethoxy) pyridin-3-yl)benzo[d]thiazol-2-yl)acetamide To a 5 ml CEM microwave tube was added 2-acetamidobenzo[d]thiazol-6-ylboronic acid (0.1 g, 0.4 mmol), 1-(2-(5-bromopyridin-3-yloxy)ethyl)pyrrolidin-2-one (0.2 g, 0.6 mmol), sodium carbonate (0.6 ml, 1 mmol), Pd FibreCat® (Anchored homogeneous catalyst, Johnson Matthey, West Deptford, N.J. (30% wt, 45 mg), and dioxane (3 mL). The vial was sealed and placed into CEM microwave for 20 min. at 100° C., with 100 watts of power via Powermax®. The reaction mixture was partitioned between EtOAc/water. The aqueous layer was extracted with EtOAc (2×10 mL). The combined organic layers were washed with water, brine, dried over $MgSO_4$ and removed solvent. The crude product was purified using $SiO_2$ chromatography with DCM:MeOH (95%:5%) solvent system to afford the product as white solid. Wt: 45.0 mg. MS (ESI pos. ion) m/z: 397.3. Calc'd exact mass for $C_{20}H_{20}N_4O_3S$: 396.46. $^1$H NMR (300 MHz, chloroform-d) δ ppm 1.99-2.14 (m, 2H) 2.33 (s, 3H) 2.42 (t, J=8.11 Hz, 2H) 3.62 (t, J=7.09 Hz, 2H) 3.74 (t, J=5.19 Hz, 2H) 4.25 (t, J=5.19 Hz, 2H) 7.43 (d, J=2.48 Hz, 1H) 7.62 (dd, J=8.48, 1.90 Hz, 1H) 7.81 (d, J=8.33 Hz, 1H) 7.99 (d, J=1.46 Hz, 1H) 8.27 (d, J=2.63 Hz, 1H) 8.50 (s, 1H).

Compound Examples 230-255 were prepared in an analogous manner to Compound Example 229.

Example 230

N-(6-(5-(2-morpholinoethoxy)pyridin-3-yl)benzo[d]thiazol-2-yl)acetamide

MS (ESI pos. ion) m/z: 399.3. Calc'd exact mass for $C_{20}H_{22}N_4O_3S$: 398.48. $^1$H NMR (300 MHz, chloroform-d) δ ppm 2.32 (s, 3H) 2.58-2.66 (m, 4H) 2.86 (t, J=5.55 Hz, 2H) 3.71-3.79 (m, 4H) 4.24 (t, J=5.55 Hz, 2H) 7.43-7.47 (m, 1H)

7.63 (dd, J=8.40, 1.83 Hz, 1H) 7.80 (d, J=8.48 Hz, 1H) 7.99 (d, J=1.46 Hz, 1H) 8.28 (d, J=2.63 Hz, 1H) 8.48 (d, J=1.75 Hz, 1H).

Example 231

N-(6-(5-(1-morpholinopropan-2-yloxy)pyridin-3-yl)benzo[d]thiazol-2-yl)acetamide

MS (ESI pos. ion) m/z: 413.3. Calc'd exact mass for $C_{21}H_{24}N_4O_3S$: 412.16. $^1$H NMR (300 MHz, chloroform-d) δ ppm 1.40 (d, J=6.14 Hz, 3H) 2.35 (s, 3H) 2.51-2.61 (m, 5H) 2.78 (dd, J=13.37, 6.80 Hz, 1H) 3.66-3.74 (m, 4H) 4.70 (dd, J=10.82, 6.43 Hz, 1H) 7.20-7.24 (m, 1H) 7.44-7.49 (m, 1H) 7.66 (dd, J=8.40, 1.83 Hz, 1H) 7.85 (d, J=8.48 Hz, 1H) 8.02 (s, 1H) 8.33 (d, J=2.63 Hz, 1H) 8.51 (d, J=1.75 Hz, 1H).

Example 232

N-(6-(5-(2-(2-oxooxazolidin-3-yl)ethoxy)pyridin-3-yl)benzo[d]thiazol-2-yl)acetamide MS (ESI pos. ion) m/z: 399.3. Calc'd exact mass for $C_{19}H_{18}N_4O_4S$: 398.1. $^1$H NMR (300 MHz, chloroform-d) δ ppm 2.31 (s, 3H) 3.73 (t, J=4.97 Hz, 2H) 3.77-3.86 (m, 2H) 4.29 (t, J=4.97 Hz, 2H) 4.33-4.41 (m, 2H) 7.40-7.46 (m, 1H) 7.62 (dd, J=8.40, 1.83 Hz, 1H) 7.80 (d, J=8.48 Hz, 1H) 7.99 (d, J=1.46 Hz, 1H) 8.26 (d, J=2.78 Hz, 1H) 8.50 (d, J=1.75 Hz, 1H).

Example 233

N-(6-(5-(2-(piperidin-1-yl)ethoxy)pyridin-3-yl)benzo[d]thiazol-2-yl)acetamide

MS (ESI pos. ion) m/z: 399.3. Calc'd exact mass for $C_{19}H_{18}N_4O_4S$: 396.16. $^1$H NMR (300 MHz, chloroform-d) δ ppm 1.37-1.52 (m, 2H) 1.54-1.67 (m, 4H) 2.30 (s, 3H) 2.47-2.58 (m, 4H) 2.81 (t, J=5.92 Hz, 2H) 4.22 (t, J=5.92 Hz, 2H) 7.41-7.48 (m, 1H) 7.62 (dd, J=8.40, 1.83 Hz, 1H) 7.78 (d, J=8.48 Hz, 1H) 7.98 (d, J=1.46 Hz, 1H) 8.25 (d, J=2.78 Hz, 1H) 8.44 (d, J=1.75 Hz, 1H).

Example 234

N-(6-(5-(2-(azepan-1-yl)ethoxy)pyridin-3-yl)benzo[d]thiazol-2-yl)acetamide

MS (ESI pos. ion) m/z: 411.3. Calc'd exact mass for $C_{22}H_{26}N_4O_2S$: 410.18. $^1$H NMR (300 MHz, chloroform-d) δ ppm 1.59-1.72 (m, 8H) 2.32 (s, 3H) 2.76-2.84 (m, 4H) 3.00 (t, J=6.07 Hz, 2H) 4.19 (t, J=5.99 Hz, 2H) 7.43-7.49 (m, 1H) 7.63 (dd, J=8.48, 1.90 Hz, 1H) 7.80 (d, J=8.48 Hz, 1H) 7.99 (d, J=1.46 Hz, 1H) 8.28 (d, J=2.78 Hz, 1H) 8.47 (d, J=1.90 Hz, 1H).

Example 235

N-(6-(6-chloro-5-(tetrahydrofuran-3-yloxy)pyridin-3-yl)benzo[d]thiazol-2-yl)acetamide MS (ESI pos. ion) m/z: 390.3. Calc'd exact mass for $C_{18}H_{16}ClN_3O_3S$: 389.06. $^1$H NMR (300 MHz, chloroform-d) δ ppm 2.19-2.29 (m, 2H) 2.31 (s, 3H) 3.91-4.05 (m, 2H) 4.07 (s, 2H) 5.08 (s, 1H) 7.35 (d, J=1.90 Hz, 1H) 7.57 (d, J=8.48 Hz, 1H) 7.79 (d, J=8.48 Hz, 1H) 7.94 (s, 1H) 8.24 (d, J=1.75 Hz, 1H).

Example 235

N-(6-(6-chloro-5-isopropoxypyridin-3-yl)benzo[d]thiazol-2-yl)acetamide

MS (ESI pos. ion) m/z: 362.3. Calc'd exact mass for $C_{17}H_{16}ClN_3O_2S$: 361.07. $^1$H NMR (300 MHz, chloroform-d) δ ppm 1.44 (d, J=6.14 Hz, 6H) 2.31 (s, 3H) 3.33-3.48 (m, 1H) 4.60-4.76 (m, 1H) 7.41 (d, J=2.05 Hz, 1H) 7.59 (dd, J=8.48, 1.90 Hz, 1H) 7.80 (d, J=8.48 Hz, 1H) 7.95 (s, 1H) 8.21 (s, 1H).

Example 236

N-(6-(6-chloro-5-((S)-tetrahydrofuran-3-yloxy)pyridin-3-yl)benzo[d]thiazol-2-yl)acetamide MS (ESI pos. ion) m/z: 390.3. Calc'd exact mass for $C_{17}H_{16}ClN_3O_2S$: 389.06. $^1$H NMR (300 MHz, chloroform-d) δ ppm 2.21-2.29 (m, 2H) 2.32 (s, 3H) 3.92-4.02 (m, 1H) 4.04-4.14 (m, 3H) 5.09 (d, J=5.85 Hz, 1H) 7.35 (d, J=2.05 Hz, 1H) 7.58 (dd, J=8.48, 1.90 Hz, 1H) 7.81 (d, J=8.33 Hz, 1H) 7.95 (d, J=1.46 Hz, 1H) 8.26 (d, J=2.05 Hz, 1H).

Example 237

N-(6-(6-bromo-5-methoxypyridin-3-yl)benzo[d]thiazol-2-yl)acetamide

MS (ESI pos. ion) m/z: 378.3. Calc'd exact mass for $C_{15}H_{12}BrN_3O_2S$: 376.98. $^1$H NMR (300 MHz, chloroform-d) δ ppm 2.32 (s, 3H) 3.94 (s, 3H) 7.47 (d, J=1.75 Hz, 1H) 7.83 (d, J=8.48 Hz, 1H) 8.05 (dd, J=8.62, 1.75 Hz, 1H) 8.40 (d, J=1.75 Hz, 1H) 8.43 (d, J=1.46 Hz, 1H) 10.71 (s, 1H).

Example 238

N-(6-(6-chloro-5-fluoropyridin-3-yl)benzo[d]thiazol-2-yl)acetamide

MS (ESI pos. ion) m/z: 322.3. Calc'd exact mass for $C_{14}H_9ClFN_3OS$: 321.01. $^1$H NMR (300 MHz, DMSO-$d_6$) δ ppm 2.22 (s, 3H) 7.77-7.92 (m, 2H) 8.36 (d, J=10.08 Hz, 1H) 8.45 (s, 1H) 8.71 (s, 1H) 12.47 (s, 1H).

Example 239

N-(6-(6-chloro-5-ethoxypyridin-3-yl)benzo[d]thiazol-2-yl)acetamide

MS (ESI pos. ion) m/z: 348.3. Calc'd exact mass for $C_{16}H_{14}ClN_3O_2S$: 347.05. $^1$H NMR (300 MHz, DMSO-$d_6$) δ ppm 1.41 (t, J=6.94 Hz, 3H) 2.22 (s, 3H) 4.31 (q, J=6.97 Hz, 2H) 7.83 (s, 3H) 8.33 (d, J=1.90 Hz, 1H) 8.42 (s, 1H) 12.43 (s, 1H).

Example 240

N-(6-(6-chloro-5-methoxypyridin-3-yl)benzo[d]thiazol-2-yl)acetamide

MS (ESI pos. ion) m/z: 334.3. Calc'd exact mass for $C_{15}H_{12}ClN_3O_2S$: 333.03. $^1$H NMR (300 MHz, DMSO-$d_6$) δ ppm 2.22 (s, 3H) 4.02 (s, 3H) 7.85 (s, 3H) 8.35 (s, 1H) 8.44 (s, 1H) 12.44 (s, 1H).

Example 241

N-(6-(4-methoxypyridin-3-yl)benzo[d]thiazol-2-yl)acetamide

MS (ESI pos. ion) m/z: 300.3. Calc'd exact mass for $C_{15}H_{13}N_3O_2S$: 299.07. $^1$H NMR (300 MHz, chloroform-d) δ ppm 2.29 (s, 3H) 3.89 (s, 3H) 6.92 (s, 1H) 7.54 (d, J=8.48 Hz, 1H) 7.75 (d, J=8.48 Hz, 1H) 7.93 (s, 1H) 8.37-8.45 (m, 2H).

Example 242

N-(6-(6-methoxypyridin-3-yl)benzo[d]thiazol-2-yl)acetamide

MS (ESI pos. ion) m/z: 300.3. Calc'd exact mass for $C_{15}H_{13}N_3O_2S$: 299.07. $^1$H NMR (300 MHz, chloroform-d) δ ppm 2.29 (s, 3H) 3.97 (s, 3H) 6.83 (d, J=8.92 Hz, 1H) 7.56 (d, J=8.48 Hz, 1H) 7.75 (d, J=8.48 Hz, 1H) 7.82 (dd, J=8.55, 2.56 Hz, 1H) 7.91 (s, 1H) 8.38 (d, J=2.19 Hz, 1H).

Example 243

N-(6-(6-ethoxypyridin-3-yl)benzo[d]thiazol-2-yl)acetamide

MS (ESI pos. ion) m/z: 314.3. Calc'd exact mass for $C_{16}H_{15}N_3O_2S$: 313.07. $^1$H NMR (300 MHz, chloroform-d) δ ppm 1.38-1.46 (m, 3H) 2.34 (s, 3H) 4.43 (q, J=7.02 Hz, 2H) 6.83 (d, J=9.06 Hz, 1H) 7.62 (d, J=10.23 Hz, 1H) 7.79-7.88 (m, 2H) 7.97 (d, J=1.46 Hz, 1H) 8.43 (d, J=2.05 Hz, 1H) 10.24 (s, 1H).

Example 244

N-(6-(6-methoxy-4-methylpyridin-3-yl)benzo[d]thiazol-2-yl)acetamide

MS (ESI pos. ion) m/z: 314.3. Calc'd exact mass for $C_{16}H_{15}N_3O_2S$: 313.07. $^1$H NMR (300 MHz, chloroform-d) δ ppm 2.27 (s, 3H) 2.35 (s, 3H) 3.98 (s, 3H) 6.69 (s, 1H) 7.37 (d, J=8.48 Hz, 1H) 7.74 (s, 1H) 7.81 (d, J=8.33 Hz, 1H) 8.05 (s, 1H) 10.32 (s, 1H).

Example 245

N-(6-(4-methylpyridin-3-yl)benzo[d]thiazol-2-yl)acetamide

MS (ESI pos. ion) m/z: 284.3. Calc'd exact mass for $C_{15}H_{13}N_3OS$: 283.08. $^1$H NMR (300 MHz, MeOH) δ ppm 2.28 (s, 3H) 2.35 (s, 3H) 7.40 (t, J=7.16 Hz, 2H) 7.78-7.91 (m, 2H) 8.35-8.42 (m, 2H).

Example 246

N-(6-(6-chloro-4-methoxypyridin-3-yl)benzo[d]thiazol-2-yl)acetamide

MS (ESI pos. ion) m/z: 334.3. Calc'd exact mass for $C_{15}H_{12}ClN_3O_2S$: 333.08. $^1$H NMR (300 MHz, chloroform-d) δ ppm 2.30 (s, 3H) 3.90 (s, 3H) 6.94 (s, 1H) 7.50 (dd, J=8.40, 1.68 Hz, 1H) 7.75 (d, J=8.33 Hz, 1H) 7.89 (d, J=1.46 Hz, 1H) 8.21 (s, 1H).

Example 247

N-(6-(6-chloro-5-(difluoromethoxy)pyridin-3-yl)benzo[d]thiazol-2-yl)acetamide

MS (ESI pos. ion) m/z: 370.3. Calc'd exact mass for $C_{15}H_{10}ClF_2N_3O_2S$: 369.02. $^1$H NMR (300 MHz, DMSO-$d_6$) δ ppm 2.22 (s, 3H) 7.49 (t, J=72.71 Hz, 1H) 7.85 (s, 2H) 8.18 (s, 1H) 8.44 (s, 1H) 8.70 (s, 1H).

Example 248

N-(6-(4-(difluoromethoxy)pyridin-3-yl)benzo[d]thiazol-2-yl)acetamide

MS (ESI pos. ion) m/z: 336.3. Calc'd exact mass for $C_{15}H_{11}F_2N_3O_2S$: 335.05. $^1$H NMR (300 MHz, DMSO-$d_6$) δ ppm 2.20 (s, 3H) 6.40 (d, J=7.89 Hz, 1H) 7.37-7.86 (m, 3H) 8.04 (dd, J=7.89, 2.34 Hz, 1H) 8.22 (dd, J=16.81, 1.90 Hz, 2H) 12.37 (s, 1H).

Example 249

N-(6-(6-(difluoromethoxy)pyridin-3-yl)benzo[d]thiazol-2-yl)acetamide

MS (ESI pos. ion) m/z: 336.3. Calc'd exact mass for $C_{15}H_{11}F_2N_3O_2S$: 335.05. $^1$H NMR (300 MHz, chloroform-d) δ ppm 2.32 (s, 3H) 6.69 (d, J=9.50 Hz, 1H) 7.49 (d, J=8.48 Hz, 1H) 7.55-8.00 (m, 5H).

Example 250

N-(6-(6-(difluoromethoxy)-4-methylpyridin-3-yl)benzo[d]thiazol-2-yl)acetamide

MS (ESI pos. ion) m/z: 350.3. Calc'd exact mass for $C_{15}H_{11}F_2N_3O_2S$: 349.05. $^1$H NMR (300 MHz, chloroform-d) δ ppm 2.14 (s, 3H) 2.35 (s, 3H) 6.52 (s, 1H) 7.30-7.39 (m, 2H) 7.53-8.00 (m, 3H) 10.21 (s, 1H).

Example 251

N-(6-(4-(hydroxymethyl)pyridin-3-yl)benzo[d]thiazol-2-yl)acetamide

MS (ESI pos. ion) m/z: 300.3. Calc'd exact mass for $C_{15}H_{13}N_3O_2S$: 299.05. $^1$H NMR (300 MHz, MeOH) δ ppm 2.28 (s, 3H) 4.62 (s, 2H) 7.42 (d, J=6.43 Hz, 1H) 7.72 (d, J=5.12 Hz, 1H) 7.83 (d, J=8.33 Hz, 1H) 7.90 (d, J=1.32 Hz, 1H) 8.42 (s, 1H) 8.45-8.59 (m, 1H).

Example 252

N-(6-(5-(2-(2,2-dimethyl-5-oxopyrrolidin-1-yl)ethoxy)pyridin-3-yl)benzo[d]thiazol-2-yl)acetamide MS (ESI pos. ion) m/z: 425.3. Calc'd exact mass for $C_{22}H_{24}N_4O_3S$: 424.16. $^1$H NMR (300 MHz, chloroform-d) δ ppm 1.17 (s, 6H) 1.87-1.96 (m, 2H) 2.35 (s, 3H) 3.52 (t, J=6.87 Hz, 2H) 3.76 (t, J=5.12 Hz, 2H) 4.27 (t, J=5.12 Hz, 2H) 7.37-7.42 (m, 1H) 7.62 (dd, J=8.40, 1.83 Hz, 1H) 7.82 (d, J=8.48 Hz, 1H) 8.00 (s, 1H) 8.31 (d, J=2.78 Hz, 1H) 8.52 (d, J=1.90 Hz, 1H) 10.24 (s, 1H).

Example 253

N-(6-(5-(2-(2-methyl-5-oxopyrrolidin-1-yl)ethoxy) pyridin-3-yl)benzo[d]thiazol-2-yl)acetamide MS (ESI pos. ion) m/z: 411.02. Calc'd exact mass for $C_{21}H_{22}N_4O_3S$: 410.14. $^1$H NMR (300 MHz, chloroform-d) δ ppm 1.20 (d, J=7.16 Hz, 3H) 1.63-1.75 (m, 1H) 2.19-2.30 (m, 1H) 2.32 (s, 3H) 2.41-2.58 (m, 1H) 3.47-3.58 (m, 2H) 3.73 (q, J=5.16 Hz, 2H) 4.24 (t, J=5.19 Hz, 2H) 7.39-7.46 (m, 1H) 7.62 (d, J=8.48 Hz, 1H) 7.80 (d, J=8.33 Hz, 1H) 7.99 (s, 1H) 8.26 (d, J=2.78 Hz, 1H) 8.49 (s, 1H).

Example 254

N-(6-(5-(2-(2,2-difluoro-5-oxopyrrolidin-1-yl) ethoxy)pyridin-3-yl)benzo[d]thiazol-2-yl)acetamide MS (ESI pos. ion) m/z: 433.3. Calc'd exact mass for $C_{20}H_{18}F_2N_4O_3S$: 432.11. $^1$H NMR (300 MHz, chloroform-d) δ ppm 2.30 (s, 3H) 2.46-2.64 (m, 2H) 3.68 (t, J=6.50 Hz, 2H) 3.82 (t, J=4.90 Hz, 2H) 4.30 (t, J=5.04 Hz, 2H) 7.39-7.44 (m, 1H) 7.61 (dd, J=8.48, 1.90 Hz, 1H) 7.79 (d, J=8.04 Hz, 1H) 7.98 (d, J=1.46 Hz, 1H) 8.23 (d, J=2.63 Hz, 1H) 8.49 (d, J=1.75 Hz, 1H).

Example 255

N-(6-(5-(2-(2-fluoro-5-oxopyrrolidin-1-yl)ethoxy) pyridin-3-yl)benzo[d]thiazol-2-yl)acetamide MS (ESI pos. ion) m/z: 415.3. Calc'd exact mass for $C_{20}H_{19}FN_4O_3S$: 414.11. $^1$H NMR (300 MHz, chloroform-d) δ ppm 2.18-2.27 (m, 1H) 2.31 (s, 3H) 2.40-2.61 (m, 1H) 3.51-3.63 (m, 1H) 3.66-3.91 (m, 3H) 4.27 (t, J=4.60 Hz, 2H) 4.97-5.24 (m, 1H) 7.39-7.44 (m, 1H) 7.61 (dd, J=8.40, 1.83 Hz, 1H) 7.79 (d, J=8.33 Hz, 1H) 7.98 (s, 1H) 8.24 (d, J=2.78 Hz, 1H) 8.49 (d, J=1.75 Hz, 1H).

Example 256

N-(6-(6-chloro-5-(4-(1-hydroxyethyl)phenylsulfonamido)pyridin-3-yl)benzo[d]thiazol-2-yl)acetamide To a solution of N-(6-(5-(4-acetylphenylsulfonamido)-6-chloropyridin-3-yl)benzo[d]thiazol-2-yl)acetamide (0.050 g, 0.10 mmol) in THF (5 mL) and MeOH (5 mL) was added sodium borohydride (0.009 mL, 0.3 mmol) at RT. The resultant was stirred at RT for 1 h, and then diluted with 3 mL of water and 1 mL of DMSO. The resultant was filtered. The filtrate was subjected to reverse phase HPLC (5-60% CH$_3$CN in water) purification to give a white solid (30 mg, 60%). MS (ESI pos. ion) Found m/z: 541, (M+K)$^+$.

Example 257

N-(6-(6-chloro-5-(((4-(1-hydroxyethyl)phenyl)sulfonyl)amino)-3-pyridinyl)-1,3-benzothiazol-2-yl)acetamide (enantiomer A; absolute stereochemistry not determined)

N-(6-(6-chloro-5-(4-(1-hydroxyethyl)phenylsulfonamido)pyridin-3-yl)benzo[d]thiazol-2-yl)acetamide was purified by SFC using OJ column. MS (ESI pos. ion) Found m/z: 503, (M+H)$^+$.

Example 258

N-(6-(6-chloro-5-(((4-((1S)-1-hydroxyethyl)phenyl) sulfonyl)amino)-3-pyridinyl)-1,3-benzothiazol-2-yl) acetamide (enantiomer B; absolute stereochemistry not determined)

N-(6-(6-chloro-5-(4-(1-hydroxyethyl)phenylsulfonamido)pyridin-3-yl)benzo[d]thiazol-2-yl)acetamide was purified by SFC using OJ column. MS (ESI pos. ion) Found m/z: 503, (M+H)$^+$.

Example 259

N-(6-(5-(4-(1-hydroxyethyl)phenylsulfonamido) pyridin-3-yl)benzo[d]thiazol-2-yl)acetamide A mixture of N-(5-bromopyridin-3-yl)-4-(1-hydroxyethyl)benzenesulfonamide (0.120 g, 0.34 mmol), N-(6-(4,4,5,5-tetramethyl-1,3,2-dioxaborolan-2-yl)benzo[d]thiazol-2-yl)acetamide (0.11 g, 0.34 mmol), tetrakis(triphenylphosphine)palladium (0.019 g, 0.017 mmol) in 1 ml of dioxane and 1 ml of aq. 2M sodium carbonate was heated under microwave (CEM) at 120 W, 100° C. for 20 min. Then, the resultant was diluted with DCM and water. The organic layer was separated, dried and concentrated. The residue was purified by HPLC (5-60% CH$_3$CN in water gradient) to give a light yellow solid (25 mg, 16%). MS (ESI pos. ion) Found m/z: 469, (M+H)$^+$.

Example 260

N-(6-(3-(4-methoxyphenylsulfonamido)phenyl) benzo[d]thiazol-2-yl)acetamide

To a mixture of N-(6-(3-aminophenyl)benzo[d]thiazol-2-yl)acetamide (0.030 g, 0.1 mmol), pyridine (0.03 g, 0.3 mmol) in dichloromethane (2 g, 24 mmol) was added 4-methoxybenzene-1-sulfonyl chloride (0.05 g, 0.2 mmol) at RT. The resultant was stirred for 4 h, and then pyrrolidine (0.02 g, 0.3 mmol) was added. The resulting mixture was concentrated and diluted with DMSO (2 ml) and purified by HPLC (5-95% acetonitrile in water). Collected pure solutions were concentrated and diluted with DCM, washed with aq. Na$_2$CO$_3$ solution. The organic layer was dried over sodium sulfate and concentrated to give a white solid (0.035 g, 73%). MS (ESI pos. ion) Found m/z: 454, (M+H)$^+$.

Example 261

N-(6-(2-(tetrahydro-2H-pyran-4-ylamino)pyrimidin-4-yl)benzo[d]thiazol-2-yl)acetamide A mixture of N-(6-(2-chloropyrimidin-4-yl)benzo[d]thiazol-2-yl)acetamide (0.200 g, 0.7 mmol), 4-aminotetrahydropyran (0.07 ml, 0.7 mmol), N-ethyl-N-isopropylpropan-2-amine (0.2 g, 1 mmol) in DMSO (1 g, 13 mmol) was heated under microwave (CEM) at 150° C. and 130 W (Powermax®& off) for 40 min. Then, the mixture was diluted with 1 ml of DMSO and purified by HPLC (5-50% CH$_3$CN in water) to give a light yellow solid (60 mg) as a TFA salt. MS (ESI pos. ion) Found m/z: 370, (M+H)$^+$.

Example 262

N-(6-(2-(2-o-tolylpyrrolidin-1-yl)pyrimidin-4-yl) benzo[d]thiazol-2-yl)acetamide A mixture of N-(6-(2-chloropyrimidin-4-yl)benzo[d]thiazol-2-yl)acetamide (0.100 g, 0.3 mmol), 2-O— tolylpyrrolidine (0.053 g, 0.33 mmol) oxalate, diisopropylethylamine (0.20 ml, 1.2 mmol) in DMSO (1.0 g, 11 mmol) was heated under CEM microwave at 140° C., 130 W (Powermax® off) for 20 min. The resultant was diluted with 5 ml of water and filtered. The solid was dried to give a brown solid (0.065 g, 46%). MS (ESI pos. ion) Found m/z: 430, (M+H)+.

Example 263

N-(6-(2-(piperidin-1-yl)pyrimidin-4-yl)benzo[d]thiazol-2-yl)acetamide

A mixture of N-(6-(2-chloropyrimidin-4-yl)benzo[d]thiazol-2-yl)acetamide (0.100 g, 0.3 mmol) and piperidin-1-amine (0.03 g, 0.3 mmol) in DMSO (0.03 g, 0.3 mmol) was heated under microwave (CEM) at 80° C. and 130 W (Powermax® off) for 20 min. Then, the mixture was diluted with 1 ml of DMSO and purified by HPLC (5-50% CH₃CN in water) to give a light yellow solid (20 mg) as a TFA salt. MS (ESI pos. ion) Found m/z: 354, (M+H)+.

Example 264

N-(6-(2-(pyridin-2-ylamino)pyrimidin-4-yl)benzo[d]thiazol-2-yl)acetamide

A mixture of N-(6-(2-chloropyrimidin-4-yl)benzo[d]thiazol-2-yl)acetamide (0.100 g, 0.3 mmol), pyridin-2-amine (0.03 g, 0.3 mmol), N-ethyl-N-isopropylpropan-2-amine (0.1 g, 1.0 mmol) in DMSO (1 g, 13 mmol) was heated under microwave (CEM) at 180° C. and 200 W (Powermax® off). Then, the mixture was diluted with 1 ml of DMSO and purified by HPLC to give a light yellow solid (10 mg). MS (ESI pos. ion) Found m/z: 363, (M+H)+.

Example 265

N-(6-(2-(piperidin-1-ylamino)pyrimidin-4-yl)benzo[d]thiazol-2-yl)acetamide

A mixture of N-(6-(2-chloropyrimidin-4-yl)benzo[d]thiazol-2-yl)acetamide (0.100 g, 0.3 mmol) and piperidin-1-amine (0.03 g, 0.3 mmol) in DMSO (0.03 g, 0.3 mmol) was heated under microwave (CEM) at 80° C. and 130 W (Powermax® off) for 20 min. Then, the mixture was diluted with 1 ml of DMSO and purified by HPLC (5-50% CH₃CN in water) to give a light yellow solid (10 mg) as a TFA salt. MS (ESI pos. ion) Found m/z: 369, (M+H)+.

Example 266

N-(6-(2-(2-phenylpyrrolidin-1-yl)pyrimidin-4-yl)benzo[d]thiazol-2-yl)acetamide

A mixture of N-(6-(2-chloropyrimidin-4-yl)benzo[d]thiazol-2-yl)acetamide (0.100 g, 0.3 mmol), 2-phenylpyrrolidine (0.05 ml, 0.3 mmol), diisopropylethylamine (0.1 ml, 0.7 mmol) in DMSO (1.0 g, 11 mmol) was heated under CEM microwave at 140° C., 130 W (Powermax® off). The resultant was diluted with 5 ml of water and filtered. The solid was diluted with DCM and filtered. The filterate was recrystallized from DCM to give a brown solid (25 mg). MS (ESI pos. ion) Found m/z: 416, (M+H)+.

Example 267

N-(6-(6-cyano-5-(4-methoxyphenylsulfonamido)pyridin-3-yl)benzo[d]thiazol-2-yl)acetamide To a 100 mL round-bottomed flask was added 3N-(5-bromo-2-cyanopyridin-3-yl)-4-methoxybenzenesulfonamide (100 mg, 272 µmol) and N-(6-(4,4,5,5-tetramethyl-1,3,2-dioxaborolan-2-yl)benzo[d]thiazol-2-yl)acetamide (108 mg, 339 µmol) in 10 mL DME, Ar was bubbled in for 2 minutes. Na₂CO₃ (2M, 5 mL) was mixed, followed by addition of PdCl₂(dppf) (80 mg). The mixture heated at 100° C. for 2 h and cooled to RT. The mixture was diluted by EtOAc (200 mL), solid was formed. Filtration provided 50 mg N-(6-(6-cyano-5-(4-methoxyphenylsulfonamido)pyridin-3-yl)benzo[d]thiazol-2-yl)acetamide as a brown solid with 92% purity. Prep-HPLC couldn't provide the desire product. The filtrate was concentrate in vacuo, ISCO purification (5-20% methanol in DCM) provided N-(6-(6-cyano-5-(4-methoxyphenylsulfonamido)pyridin-3-yl)benzo[d]thiazol-2-yl)acetamide (5 mg, 4% yield) as a brown solid. MS (ESI neg. ion) Found m/z: 478, (M–H)⁻.

Example 268

N-(6-(5-amino-6-cyanopyridin-3-yl)benzo[d]thiazol-2-yl)acetamide

To a 50 mL round-bottomed flask was added 3-amino-5-bromopicolinonitrile (100 mg, 505 µmol) and N-(6-(4,4,5,5-tetramethyl-1,3,2-dioxaborolan-2-yl)benzo[d]thiazol-2-yl)acetamide (193 mg, 606 µmol) in 5 mL DME, Ar was bubbled in for 2 minutes. Na₂CO₃ (2M, 3 mL) was mixed followed by addition of PdCl₂(dppf) (80 mg). The mixture heated at 100° C. for 2 h and cooled to RT. the mixture was diluted by EtOAc (200 mL), washed by water and brine, dried over MgSO₄, concentrated in vacuo to provide 100 mg brown oil, 10% methanol in DCM was added, solid was formed, after filtration, N-(6-(5-amino-6-cyanopyridin-3-yl)benzo[d]thiazol-2-yl)acetamide (20 mg, 13% yield) was obtained as an off-white solid. MS (ESI neg. ion) Found m/z: 308, (M–H)⁻

Example 269

N-(6-(6-Chloro-5-(dimethylamino)pyridin-3-yl)benzo[d]thiazol-2-yl)acetamide

Step 1. N-(6-(5-Amino-6-chloropyridin-3-yl)benzo[d]thiazol-2-yl)acetamide

A mixture of bis(tert-butyl) 5-(2-acetamidobenzo[d]thiazol-6-yl)-2-chloropyridin-3-ylcarbamate (900 mg, 1734 µmol), and TFA (3500 µl, 45429 µmol) in DCM (10 mL) was stirred at rt. After 2 h, the reaction is complete. The mixture was evaporated. MeOH (10 mL) was added and the slurry was concentrated to a film. MS (ESI, pos. ion) m/z: calc'd for $C_{14}H_{11}ClN_4OS$: 318.0. found: 319.0 (M+1). This material was used directly in the next step.

Step 2. N-(6-(6-Chloro-5-(dimethylamino)pyridin-3-yl)benzo[d]thiazol-2-yl)acetamide A suspension of N-(6-(5-amino-6-chloropyridin-3-yl)benzo[d]thiazol-2-yl)acetamide (500 mg, 1568 µmol) and NaBH₄ (500 mg, 13216 µmol) in THF (4 mL) was cooled with an ice bath. A cold mixture of formaldehyde (700 µL, 9325 µmol) and H₂SO₄ (3000 µl, 9000 µmol) was added slowly.

More formaldehyde (700 μL, 9325 μmol) was added followed by the addition of NaCNBH$_3$ (excess). The mixture was neutralized with Na$_2$CO$_3$ and the mixture was aged at 40° C. for 2 h. After standing overnight at rt, the mixture was filtered, washed with H$_2$O, and air dried. The mixture was suspended in pyridine (10 mL) and was treated with HCl (conc., 20 mL). The mixture was filtered, the residue was washed with HCl (5 N). The filtrate was neutralized with NaOH (5N) and Na$_2$CO$_3$. The resulting slurry was aged overnight. The slurry was filtered, washed with H$_2$O, and air dried. The solid was suspended in hot DMSO (10 mL), diluted with hot H$_2$O (10 mL), and filtered. The solid was air dried over the weekend to give the product as a green powder (180 mg). MS (ESI, pos. ion) m/z: calc'd for C$_{16}$H$_{15}$ClN$_4$OS: 346.0. found: 347.0. $^1$H NMR (400 MHz, DMSO-d$_6$) δ ppm 2.22 (s, 3H) 2.86 (s, 6H) 7.74-7.89 (m, 3H) 8.38 (d, J=21.13 Hz, 2H) 12.43 (s, 1H).

Example 270

Phenyl 6-(6-chloro-5-(dimethylamino)pyridin-3-yl)benzo[d]thiazol-2-ylcarbamate

To a mixture of 6-(6-chloro-5-(dimethylamino)pyridin-3-yl)benzo[d]thiazol-2-amine (100 mg, 328 μmol) in pyridine (0.3 mL) and DCM (2 mL) was added phenyl chloroformate (200 μl, 1594 mmol). A clear solution formed. After overnight at rt, the slurry was diluted with EtOAc (10 mL) and filtered. The solid was washed with EtOAc, then H$_2$O (2×3 mL). LCMS indicted that the organic liquid contains most of product and by-product. The small amount of solid remained on the filter was pure product (35 mg). MS (ESI, pos. ion) m/z: calc'd for C$_{21}$H$_{17}$ClN$_4$O$_2$S: 424.1. found: 425.1. $^1$H NMR (400 MHz, DMSO-d$_6$) δ ppm 2.85 (s, 6H) 7.33 (t, J=7.53 Hz, 3H) 7.48 (t, J=7.78 Hz, 2H) 7.76-7.88 (m, 3H) 8.35 (s, 1H) 8.43 (s, 1H) 12.73 (s, 1H).

Example 271

N-(6-(6-Chloro-5-(dimethylamino)pyridin-3-yl)benzo[d]thiazol-2-yl)-2-methoxyacetamide A mixture of 6-(6-chloro-5-(dimethylamino)pyridin-3-yl)benzo[d]thiazol-2-amine (54 mg, 177 μmol) and 2-methoxyacetyl chloride (25 mg, 230 μmol) in DCM-pyridine (0.5 mL each) was stirred at rt. More 2-methoxyacetyl chloride (25 mg, 230 μmol) was added after overnight, resulting in a solution. The reaction was complete after 1 h. The mixture was concentrated, and diluted with NaHCO$_3$ (saturated, 5 mL). After agitating for 30 min, the mixture was filtered, and washed with H$_2$O (3×3 mL) to give a green solid (55 mg, 82%). LCMS: calc'd for C$_{17}$H$_{17}$ClN$_4$O$_2$S:376.0. found: 377.1. $^1$H NMR (400 MHz, DMSO-d$_6$) δ ppm 2.86 (s, 6H) 3.32 (s, 3H) 4.23 (s, 2H) 7.76-7.88 (m, 3H) 8.36 (s, 1H) 8.43 (s, 1H) 12.39 (s, 1H).

Example 272

N-(6-(6-chloro-5-(dimethylamino)pyridin-3-yl)benzo[d]thiazol-2-yl)-2-phenoxyacetamide To a mixture of 6-(6-chloro-5-(dimethylamino)pyridin-3-yl)benzo[d]thiazol-2-amine (100 mg, 328 μmol) in pyridine (0.3 mL) and DCM (2 mL) was added 2-phenoxyacetyl chloride (150 μl, 1086 μmol). A clear solution formed. More 2-phenoxyacetyl chloride (150 μl, 1086 μmol) was added until the reaction was complete. The DCM was evaporated and the mixture was diluted with EtOAc (10 mL). The mixture was filtered, washed with EtOAc, H$_2$O (3×5 mL) and dried in air to give a gray powder. MS (ESI, POS. ION) M/Z: calc'd for C$_{22}$H$_{19}$ClN$_4$O$_2$S: 438.1. found: 439.1. $^1$H NMR (400 MHz, DMSO-d$_6$) δ ppm 2.85 (s, 6H) 4.95 (s, 2H) 6.90-7.08 (m, 3H) 7.33 (t, J=7.78 Hz, 2H) 7.75-7.92 (m, 3H) 8.36 (s, 1H) 8.44 (s, 1H) 12.70 (s, 1H).

Example 273

1-(6-(6-chloro-5-(dimethylamino)pyridin-3-yl)benzo[d]thiazol-2-yl)-3-(2-morpholinoethyl)urea A mixture of 6-(6-chloro-5-(dimethylamino)pyridin-3-yl)benzo[d]thiazol-2-amine (95 mg, 312 μmol) and CDI (110 mg, 678 μmol) in DMF (1 mL) was heated at 60° $^C$. After sitting overnight, more reagent was added and the mixture was heated for 4 h. 2-morpholinoethanamine (300 μL, 2286 μmol) was added to the mixture, a solution formed. After 3 h, the mixture was cooled to rt and diluted with DCM (15 mL). The solution was washed with H$_2$O (15 mL), dried over Na$_2$SO$_4$ and concentrated. The crude oil was purified by silica gel chromatography with 0-5% (2 N NH$_3$-MeOH) in DCM to give the product as a white powder after hexane washing (45 mg, 31%). MS (ESI, POS. ION) M/Z: calc'd for C$_{21}$H$_{25}$ClN$_6$O$_2$S: 460.1. found: 461.1. $^1$H NMR (400 MHz, chloroform-d) δ ppm 2.49-2.70 (m, 6H) 2.92 (s, 6H) 3.49-3.59 (m, 2H) 3.71-3.83 (m, 4H) 7.49 (s, 1H) 7.56 (d, J=8.03 Hz, 1H) 7.79 (d, J=8.53 Hz, 1H) 7.90 (s, 1H) 8.24 (s, 1H).

Example 274

6-(6-Chloro-5-(dimethylamino)pyridin-3-yl)benzo[d]thiazol-2-amine

To a mixture of N-(6-(6-chloro-5-(dimethylamino)pyridin-3-yl)benzo[d]thiazol-2-yl)acetamide (160 mg, 461 μmol) in MeOH (10 mL) was added NaOH (1000 μL, 5000 μmol). The mixture was heated to 60° C. for 5.5 h. The reaction mixture was neutralized with HCl (5 N, 1 mL), filtered and the solid was washed with H$_2$O (3×2 mL) and air dried (140 mg). MS (ESI, POS. ION) M/Z: calc'd for C$_{14}$H$_{13}$ClN$_4$S: 304.5. found: 305.0. $^1$H NMR (400 MHz, DMSO-d$_6$) δ ppm 2.83 (s, 6H) 7.42 (s, 1H) 7.53-7.77 (m, 4H) 8.10 (s, 1H) 8.29 (s, 1H).

Example 275

N-(6-(6-Chloro-5-(dimethylamino)pyridin-3-yl)benzo[d]thiazol-2-yl)-2-(dimethylamino)acetamide A mixture of 6-(6-chloro-5-(dimethylamino)pyridin-3-yl)benzo[d]thiazol-2-amine (70 mg, 230 μmol), HATU (210 mg, 552 μmol), and 2-(dimethylamino)acetic acid (45 mg, 436 μmol) in DMF (2.5 mL) was heated to 60° C. for 2 h. The solution was diluted with H$_2$O (20 mL) until it became cloudy and cooled to rt. The mixture was filtered, washed with H$_2$O (10 mL), Na$_2$HCO$_3$ (saturated, 5 mL), and H$_2$O (5 mL). The filter was dissolved in MeOH (10%) in DCM and dried over MgSO$_4$. The organic was filtered, concentrated to a yellow solid. This was further purified on silica using MeOH in EtOAc (0-5%) to give a light yellow solid. A second purification with 1:1 hexane-acetone removed the less polar impurity (NAc) effectively, affording a white solid (30 mg). MS (ESI, POS. ION) M/Z: calc'd for C$_{18}$H$_{20}$ClN$_5$OS: 389.1. found: 390.1. $^1$H NMR (400 MHz, chloroform-d) δ ppm 2.43 (s, 3H) 2.93 (s, 3H) 3.25 (s, 2H) 7.52 (d, J=2.15 Hz, 1H) 7.63

(dd, J=8.41, 1.76 Hz, 1H) 7.87 (d, J=8.41 Hz, 1H) 7.99 (d, J=1.56 Hz, 1H) 8.27 (d, J=2.15 Hz, 1H).

Example 276

N-(6-(6-chloro-5-(dimethylamino)pyridin-3-yl) benzo[d]thiazol-2-yl)methanesulfonamide To a slurry of 6-(6-chloro-5-(dimethylamino)pyridin-3-yl) benzo[d]thiazol-2-amine (60 mg, 197 μmol) in DCM (2 mL) was added methanesulfonyl chloride (400 μL, 5168 μmol), and pyridine (300 μL). After overnight, Et$_3$N (0.3 mL) was added. After overnight, the mixture was diluted with H$_2$O and stirred for several days. The mixture was filtered, washed with H$_2$O to give a solid that is mostly the product (R$_f$ 2.20), with small amount of Acetamide (R$_f$ 3.39, m/e 347). The solid was washed with EtOAc, and hot EtOAc containing 5% MeOH to give the product as a brown solid (40 mg, 53%). MS (ESI, POS. ION) M/Z: calc'd for C$_{15}$H$_{15}$ClN$_4$O$_2$S$_2$: 382.0. found: 383.0. $^1$H NMR (400 MHz, DMSO-d$_6$) 5 ppm 2.84 (s, 6H) 3.03 (s, 3H) 7.41 (d, J=6.06 Hz, 1H) 7.66-7.87 (m, 2H) 8.26 (d, J=26.21 Hz, 2H) 12.90-13.23 (m, 1H).

Example 277

Bis(tert-butyl) 5-(2-acetamidobenzo[d]thiazol-6-yl)-2-chloropyridin-3-ylcarbamate A mixture of bis(tert-butyl) 5-bromo-2-chloropyridin-3-ylcarbamate (1.70 g, 4.2 mmol), Pd$_2$(dba)$_3$ (0.16 g, 0.17 mmol), N-(6-(4,4,5,5-tetramethyl-1,3,2-dioxaborolan-2-yl) benzo[d]thiazol-2-yl)acetamide (1.3 g, 4.2 mmol), Pd(dppf) Cl$_2$ (160 mg) and Na$_2$CO$_3$ (1.10 g, 10 mmol) in DME (25 mL)-H$_2$O (5 mL) was heated under nitrogen at 85° C. After 5 h, the mixture was concentrated to a sludge. H$_2$O (20 mL) was added and the mixture was heated at 40° C. for 30 min before it was filtered. The solid was triturated with hot THF-hexane (1:3) and filtered. The solid was dissolved in hot EtOAc-DCM and filtered. The filtrate was concentrated. This pink solid was triturated with hot hexane (30 mL) and DCM (15 mL) to give the product as a tan solid (1.05 g, 49%). MS (ESI, pos. ion) m/z: calc'd for C$_{24}$H$_{27}$ClN$_4$O$_5$S: 518.1. found: 519.1 (M+1). $^1$H NMR (400 MHz, chloroform-d) δ ppm 1.46 (s, 18H) 2.32 (s, 3H) 7.55 (dd, J=8.51, 1.27 Hz, 1H) 7.78 (d, J=8.41 Hz, 1H) 7.84 (d, J=2.15 Hz, 1H) 7.95 (s, 1H) 8.61 (d, J=1.96 Hz, 1H) 10.06 (s, 1H).

For Compound Examples 278-303, HPLC-MS refers to the retention time for the described compound acquired using a 3.0×50 mm Agilent custom SB C18 column (Agilient Technologies, supra, PN USGAH01021); 3.5 μm particle; temperature=40° C.; flow=1.5 mL min$^{-1}$; A=0.1% TFA in water, B=0.1% TFA in ACN; initial composition=10% B; gradient: 0) 3 min, linear gradient from 10 to 95% B; 3→3.5 min, isocratic at 95% B; 3.5 min, step to 10% B; 5 min end). Mass spec measurements (m/z) were obtained using APCI ionization which typically affords the parent ion charged by either a proton (M+H$^+$) or sodium (M+Na$^+$).

Example 278

Potassium trifluoro-(2-(N-actyl)amineobenzo[d] thiazol-6-yl)borate

A 5 mL, PTFE flask was charged with N-(6-(4,4,5,5-tetramethyl-1,3,2-dioxaborolan-2-yl)benzo[d]thiazol-2-yl)acetamide (0.300 g, 0.943 mmol), 3 mL MeOH and a stirbar. The solution was treated with acid potassium fluoride (184 mg, 2.36 mmol), and stirred at room temperature for 12 h. The flask was then cooled in a −20° C. refrigerator over night. The solids were collected using a 0.22 μm PTFE filter, and washed with water (3×1 mL). The solids were then dried at 60° C. and <1 mm Hg for 6 h to afford potassium trifluoro-(2-(N-actyl) amineobenzo[d]thiazol-6-yl)borate (0.230 g, 81.8% yield). $^1$H NMR (400 MHz, DMF) δ ppm 2.30 (s, 3H) 7.73 (d, J=8.31 Hz, 1H) 7.91 (dd, J=8.22, 1.17 Hz, 1H) 8.37 (s, 1H). $^{19}$F NMR (376 MHz, 10% D$_2$O in DMF-d$_6$, ref=KF (−125.3)) δ ppm −78.99 (s, 1 F). $^{13}$C NMR (101 MHz, DMF) δ ppm 22.45 (s, 1 C) 117.96 (s, 1 C) 119.34 (s, 1 C) 127.16 (s, 1 C) 131.00 (s, 1 C) 131.78 (s, 1 C) 149.89 (s, 1 C) 160.01-160.13 (m, 1 C) 171.15 (s, 1 C). HPLC-MS: retention time=0.96 min (99.1%@215 nm; 98.6% @254 nm; m/z=259.0, calculated for C$_9$H$_9$BN$_2$OS+Na$^+$=259.0; assumed to arise from in situ hydrolysis of the BF$_3$ moiety to B(OH)$_2$ during ionization).

Example 279

5-Bromo-2-iodopyridin-3-ol

A 500 mL, one neck round bottom flask was charged with 5-bromopyridin-3-ol (10.00 g, 57.5 mmol), 80 mL water and a stirbar. The slurry was treated with sodium carbonate monohydrate crystals (4.80 ml, 115 mmol), and the flask was swept with Ar. After 15 minutes, the slurry was gently heated with a heat gun until the solution became homogenous. The solution was stirred for an additional 15 minutes, and iodine (mallinckrodt) (14.6 g, 57.5 mmol) was added. The reaction was stirred under Ar overnight in a dark hood. The slurry was then carefully treated with 2 N HCl until a pH of 2.5 was observed. The slurry was filtered, and the collected solids were washed with water (2×50 mL). The solids were dried under a stream of nitrogen for 3 h, dissolved in 100 mL hot MeOH, filtered hot, and allowed to cool over 96 h. The crystals that had formed over this time were collected using a pressure filter equipped with a 0.22 μm PTFE membrane. The solids were washed with MeOH (2×25 mL), and DCM (3×30 mL). The solids were dried under a stream of nitrogen for 2 h, and then at 60° C. and <1 mm Hg for 30 minutes to afford 5-bromo-2-iodopyridin-3-ol (7.9197 g, 45.9% yield). $^1$H NMR (400 MHz, THF) δ ppm 7.20 (dd, J=2.10, 0.44 Hz, 1H) 7.98 (dd, J=2.10, 0.44 Hz, 1H) 9.78 (s, 1H). $^{13}$C NMR (101 MHz, THF) δ ppm 109.16 (s, 1 C) 120.77 (s, 1 C) 124.01 (s, 1 C) 143.16 (s, 1 C) 155.87 (s, 1 C). HPLC-MS: retention time=1.69 min (98.6%@215 nm; 95.4% @254 nm; m/z=299.8, calculated for C$_5$H$_3$I$^{79}$BrNO+H$^+$=299.8; m/z=301.8, calculated for C$_5$H$_3$I$^{81}$BrNO+H$^+$=301.8).

Example 280

5-Bromo-2-iodo-3-((2-methoxyethoxy)methoxy) pyridine and 5-bromo-2-chloro-3-((2-methoxyethoxy)methoxy)pyridine A dry, 100 mL one neck round bottom flask was charged with 5-bromo-2-iodopyridin-3-ol (2.30 g, 7.67 mmol), 15 mL dry THF, a stirbar and n,n-diisopropylethylamine, 99.5% (1.74 ml, 9.97 mmol). The flask was fitted with an inert atmosphere inlet, and swept with Ar for several minutes. To the stirring solution was added 2-methoxyethoxymethyl chloride (0.955 ml, 8.44 mmol) over 5 minutes. The reaction was stirred at room temperature for 24 h, and poured onto 100 mL DCE. The solution was washed with 5% NaHCO$_3$ (2×25 mL) and the DCE solution was passed through an unbuffered Varian Chem elute CE1010 (100 mL, PN 12198010). The tube was extracted with DCE (2×40 mL), and the combined DCE solution was concentrated in vacuo. The residue was purified using 80 g of SiO$_2$ wet packed with 5% THF in hexanes and eluted with 500 mL 10% THF, followed by 500 mL 15% THF in hexanes. A band that eluted with R$_f$=0.33 (15% THF in hexanes) was isolated. The solvent was removed in vacuo to afford 5-bromo-2-iodo-3-((2-methoxyethoxy)methoxy)pyridine as the major component of a 70:30 mixture with 5-bromo-2-chloro-3-((2-methoxyethoxy)methoxy)pyridine (2.0846 g). Data for 5-bromo-2-iodo-3-((2-methoxyethoxy)methoxy)pyridine: $^1$H NMR (300 MHz, chloroform-d) δ ppm 3.38 (s, 3H) 3.57 (dd, J=6.43, 2.70 Hz, 1H) 3.57 (t, J=4.46 Hz, 1H) 3.87 (ddd, J=6.34, 2.76, 1.94 Hz, 2H) 5.36 (s, 2H) 7.50 (d, J=2.05 Hz, 1H) 8.14 (d, J=2.05 Hz, 1H). $^{13}$C NMR (75 MHz, chloroform-d) δ ppm 59.04 (s, 1 C) 68.53 (s, 1 C) 71.28 (s, 1 C) 94.17 (s, 1 C) 110.02 (s, 1 C) 120.28 (s, 1 C) 124.12 (s, 1 C) 144.61 (s, 1 C) 153.67 (s, 1 C). NMR data for 5-bromo-2-chloro-3-((2-methoxyethoxy)methoxy)pyridine: $^1$H NMR (300 MHz, chloroform-d) δ ppm 3.38 (s, 3H) 3.57 (dd, J=6.43, 2.70 Hz, 1H) 3.57 (t, J=4.46 Hz, 1H) 3.87 (ddd, J=6.34, 2.76, 1.94 Hz, 2H) 5.36 (s, 2H) 7.71 (d, J=2.12 Hz, 1H) 8.12 (d, J=2.12 Hz, 1H). $^{13}$C NMR (75 MHz, chloroform-d) δ ppm 59.04 (s, 1 C) 68.53 (s, 1 C) 71.28 (s, 1 C) 94.24 (s, 1 C) 118.90 (s, 1 C) 126.44 (s, 1 C) 140.18 (s, 1 C) 142.57 (s, 1 C) 149.75 (s, 1 C).

Example 281

2-(5-bromo-2-chloropyridin-3-yloxy)propanenitrile

A dry 5 mL, one neck round bottom flask was charged with a 95-5 mixture of 5-bromo-2-chloropyridin-3-ol and 3-bromo-2-chloropyridin-5-ol (0.2031 g, 0.9744 mmol), a stirbar, 2 mL dry DMF and 2-chloropropanenitrile (0.4310 ml, 4.872 mmol). To the mixture was added cesium carbonate (CS$_2$CO$_3$) (0.3492 g, 1.072 mmol), and the flask was sealed with a septa. The reaction was heated using a 100° C. oil bath for 4 h, and cooled. The DMF was diluted with 4 mL THF, and the slurry was loaded onto 5 g of SiO$_2$ wet-packed with THF. The silica was eluted with 50 mL THF, and the eluted volume was concentrated in vacuo. A sample was scouted for prep purification using a 2.1×50 mm Xterra MS C18 column with a 3.5 µm particle size (PN 186000400); A=10 mM NH$_4$HCO$_3$ in water, pH adjusted with concentrated NH$_4$OH to 9.6; B=ACN; gradient: initial@1 mL/min, 10% B; 0→5 min@1 mL/min, linear gradient to 100% B; 5→6.9 min@1 mL/min, isocratic at 100% B; 6.9→6.95 min@1 mL/min, linear gradient to 10% B, 8 min end. A major peak was observed at 2.87 minutes. The sample was purified using a 30×100 mm Waters Xterra Prep C18 OBD column (100 Å pore diameter, 5 µm particle size, spherical shape, PN 186001942); Gradient: 0→5 min@35 mL/min, 10% B; 5→20 min@35 mL/min, linear gradient to 40% B; 20→24.9 min@35 mL/min, isocratic at 40% B; 25.0 min→29.9 min@35 mL/min, step to 100% B; 30→40 min@35 mL/min, step to 10% B; 40 min end. A=10 mM NH$_4$HCO$_3$ in water, pH adjusted with concentrated NOH to 9.6; B=ACN. A band that eluted from 23.6 to 25.4 minutes was isolated. The solvent was removed in vacuo to afford 2-(5-bromo-2-chloropyridin-3-yloxy)propanenitrile and 2-(5-bromo-2-chloropyridin-3-yloxy)propanenitrile (0.1316 g).

Data for 2-(5-bromo-2-chloropyridin-3-yloxy)propanenitrile: $^1$H NMR (400 MHz, chloroform-d) δ ppm 1.89 (d, J=6.85 Hz, 3H) 4.91 (q, J=6.75 Hz, 1H) 7.59 (d, J=2.05 Hz, 1H) 8.25 (d, J=1.96 Hz, 1H). $^{13}$C NMR (101 MHz, chloroform-d) δ ppm 19.74 (s, 1 C) 64.43 (s, 1 C) 116.75 (s, 1 C) 118.90 (s, 1 C) 127.53 (s, 1 C) 141.30 (s, 1 C) 144.70 (s, 1 C) 148.81 (s, 1 C). HPLC-MS: retention time=2.11 min (83.2%@215 nm; 82.1% @254 nm; m/z=260.9, calculated for C$_8$H$_6$$^{79}$Br$^{35}$ClN$_2$O+H$^+$=260.9; m/z=262.9, calculated for C$_8$H$_6$$^{81}$Br$^{35}$ClN$_2$O+H$^+$=262.9).

Example 282

2-(5-bromopyridin-3-yloxy)acetonitrile

A dry, 250 mL one neck round bottom flask was charged with 3-bromo-5-hydroxypyridine 3 (4.9470 g, 28.4 mmol), 40 mL dry ACN, cesium carbonate (CS$_2$CO$_3$) (3.41 ml, 42.6 mmol) and a stirbar. The flask was fitted with an Ar inlet, and cooled to 0° C. To the solution was added 2-chloroacetonitrile (2.34 ml, 37.0 mmol) dissolved in 10 mL dry ACN over 15 minutes via an addition funnel. The reaction warmed to room temperature overnight. The slurry was filtered through a 0.22 µm PTFE filter membrane, and concentrated under a stream of nitrogen. The residue was loaded onto 100 g of SiO$_2$ wet-packed with ACN, and eluted with 500 mL ACN. The eluent was concentrated in vacuo, and the residue was sublimed at 0.5 mm Hg in a 90° C. oil bath to afford 2-(5-bromopyridin-3-yloxy)acetonitrile (3.49 g, 57.6% yield). $^1$H NMR (300 MHz, MeOH) δ ppm 5.12 (s, 2H) 7.81 (dd, J=2.63, 1.83 Hz, 1H) 8.35 (d, J=2.63 Hz, 1H) 8.38 (dd, J=1.83, 0.29 Hz, 1H). $^{13}$C NMR (75 MHz, MeOH) δ ppm 55.24 (s, 1 C) 116.18 (s, 1 C) 121.90 (s, 1 C) 126.59 (s, 1 C) 137.86 (s, 1 C) 145.61 (s, 1 C) 155.29 (s, 1 C). HPLC-MS: retention time=1.42 min (99.0%@215 nm; 98.9% @254 nm; m/z=212.8, calculated for C$_7$H$_5$$^{79}$Br$_2$N$_2$O+H$^+$=213.0, m/z=214.8, calculated for C$_7$H$_5$$^{81}$Br$_2$N$_2$O+H$^+$=215.0).

Example 283

2-(5-Bromo-2-chloropyridin-3-yloxy)acetonitrile

A dry 10 mL, one neck round bottom flask was charged with 5-bromo-2-chloropyridin-3-ol (0.0518 g, 0.249 mmol), cesium carbonate (0.0972 g, 0.298 mmol), a stirbar and 2 mL dry DMF. The stirring slurry was treated with 2-chloroacetonitrile (0.0709 ml, 1.12 mmol) and fitted with an inert atmosphere inlet. The reaction was heated to 80° C. using an oil bath for 3 h, and cooled. The slurry was filtered through a 0.22 µm PTFE filter, and concentrated in vacuo. The residue was purified in one injection using a YMC pack diol-120-NP column (PN DN12S05-2520 wt, 250×20 mm, spherical particle, 5 µm particle size, 120 Å pore size, flow=20 mL/min: A=hexanes; B=THF; 15% B isocratic). A fraction that eluted from 10.0 to 11.8 minutes was isolated. The solvent was removed in vacuo to afford 2-(5-bromo-2-chloropyridin-3-yloxy)acetonitrile (0.0375 g, 61.0% yield). $^1$H NMR (300 MHz, chloroform-d) δ ppm 4.88 (s, 2H) 7.52 (d, J=1.97 Hz, 1H) 8.25 (d, J=1.97 Hz, 1H). $^{13}$C NMR (75 MHz, chloroform-d) δ ppm 54.71 (s, 1 C) 113.51 (s, 1 C) 118.90 (s, 1 C) 125.53 (s, 1 C) 140.63 (s, 1 C) 144.40 (s, 1 C) 148.93 (s, 1 C).

Example 284

2-(5-Bromopyridin-3-yloxy)ethanamine hydrochloride

A dry 15 mL, one neck round bottom flask was charged with 2-(5-bromopyridin-3-yloxy)acetonitrile (0.9321 g, 4.38 mmol), 4 mL dry THF and a stirbar. The flask was swept with Ar, and fitted with a reflux condenser. The stirring solution was treated with borane-dimethyl sulfide (1.66 ml, 17.5 mmol), and the solution was heated using a 80° C. oil bath for 3 h. The reaction was cooled using a ice-water bath and carefully quenched with saturated Rochelle's salt. After the addition, the flask was removed from the cooling bath, and 10 mL THF was added. The slurry was stirred at room temperature overnight. The slurry was poured onto 100 mL DCM, and filtered through a 0.22 µm PTFE membrane. The solution was concentrated in vacuo, and dissolved in 20 mL EtOH. The solution was concentrated in vacuo to 5 mL. A stirring bar was added, and the solution was treated with hydrochloric acid 2 µm (7.99 ml, 16.0 mmol). The solution was heated to 80° C. for 10 minutes, and cooled. The solvent was removed in vacuo, and the residue was heated into 5 mL dry EtOH. A precipitate had formed, and was collected using a course glass filter and positive pressure nitrogen. The solid was washed with cold EtOH (2×3 mL). The solid was dried initially under a stream of nitrogen, and then at 60° C. and <1 mm Hg for 1 h to afford 2-(5-bromopyridin-3-yloxy)ethanamine hydrochloride (0.210 g, 18.9% yield) of a white solid. $^1$H NMR (400 MHz, deuterium oxide) δ ppm 3.49 (t, J=4.79 Hz, 2H) 4.45 (dd, J=5.38, 4.50 Hz, 2H) 8.23 (dd, J=2.49, 1.81 Hz, 1H) 8.46 (d, J=2.54 Hz, 1H) 8.54 (d, J=1.76 Hz, 1H) $^{13}$C NMR (101 MHz, deuterium oxide) δ ppm 38.57 (s, 1 C) 65.74 (s, 1 C) 121.89 (s, 1 C) 131.32 (s, 1 C) 131.57 (s, 1 C) 138.27 (s, 1 C) 155.94 (s, 1 C). HPLC-MS: retention time=0.50 min (95.3%@215 nm; 94.1% @254 nm; m/z=216.9, calculated for $C_7H_9{}^{79}BrN_2O+H^+$=217.0; m/z=218.9, calculated for $C_7H_9{}^{79}BrN_2O+H^+$=219.0). Sample was dissolved in 20 mL EtOH, and treated with 0.69 mmol g$^{-1}$ Si carbonate (Silicycle, 2.9 g, 2.0 mmol). The slurry was occasionally swirled by hand, and filtered. The silica was washed with EtOH (3×10 mL), and the combined eluents were concentrated in vacuo to afford 0.192 of 2-(5-bromopyridin-3-yloxy)ethanamine as a freebase.

Example 285

N-(2-(5-bromopyridin-3-yloxy)ethyl)-2-methoxyacetamide

A dry, 25 mL, one neck pear shaped flask was charged with 2-(5-bromopyridin-3-yloxy)ethanamine (0.1951 g, 0.90 mmol), a stir bar and 3 mL dry DCE. The slurry was treated with die (0.23 ml, 1.3 mmol), and briefly sonicated. The flask was fitted with an Ar inlet, and flushed with Ar for 3 minutes. The slurry was cooled using a ice-water bath, and treated with methoxyacetyl chloride (0.090 ml, 0.99 mmol). The reaction was stirred for 2 h, and quenched with 15 mL EtOH. The cooling bath was removed, and 0.69 mmol g$^{-1}$ Si carbonate (Silicycle, 2.6 g, 1.8 mmol) was added. The slurry was stirred for 15 minutes, and filtered. The silica was eluted with EtOH (2×20 mL), and the combined eluents were concentrated in vacuo to afford 0.184 g of material. The residue was taken up in 1 mL dry THF and filtered through a 0.22 µm PTFE filter, and concentrated to 0.5 mL under a stream of nitrogen in a conical microwave reaction vial. The solution was treated with 0.25 mL MTBE, and the vessel was sealed. The cloudy solution was heated with a heat gun until the solution became clear, and allowed to cool over 72 h. Crystals had formed on the bottom of the conical vial. The mother liquor was withdrawn, and the crystals were washed with 0.5 mL MTBE and discarded (Hunig's HCl). The mother liquor was concentrated in vacuo. The residue was purified in one injection using a Waters Spherisorb S5 column (PN PSS830195, 20×250 mm, 60 Å pore, 5 µm particle size); flow=20 mL/min; A=DCE, B=EtOH; isocratic at 5% B. A band that eluted from 3.3 to 3.6 minutes was isolated. The solvent was removed in vacuo to afford N-(2-(5-bromopyridin-3-yloxy)ethyl)-2-methoxyacetamide (0.0302 g, 12% yield). $^1$H NMR (300 MHz, chloroform-d) δ ppm 3.43 (s, 3H) 3.74 (q, J=5.19 Hz, 2H) 3.93 (s, 2H) 4.11 (t, J=5.19 Hz, 2H) 6.95 (br. s., 1H) 7.38 (d, J=4.46 Hz, 1H) 8.25 (d, J=2.34 Hz, 1H) 8.31 (d, J=1.02 Hz, 1H).

Example 286

1-((5-bromopyridin-3-yloxy)methyl)cyclopropanamine

A dry, 10 mL round bottom flask was charged with 2-(5-bromopyridin-3-yloxy)acetonitrile (0.0996 g, 0.47 mmol), 3 mL dry THF, and a stirbar. The flask was fitted with an inert atmosphere inlet, and swept with Ar for several minutes. The solution was treated with titanium isopropoxide (0.15 ml, 0.51 mmol). To the stirring solution was added ethylmagnesium bromide 1.0 m solution in the (0.94 ml, 0.94 mmol) via a syringe pump over 30 minutes. The reaction was stirred at room temperature for 24 h after which time 1 mL of saturated Rochelle's salt was added, followed by 5 mL dry THF. The slurry was stirred/sonicated over the course of 1 h. The solution was then applied to 20 g of SiO$_2$ wet packed with THF. The Silica was eluted with 75 mL dry THF, and the eluent was concentrated in vacuo. The crude was purified using a 19×150 mm Waters Xterra Prep C18 OBD column (100 Å pore diameter, 5 µm particle size, spherical shape, PN 186002381; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end; A=10.7 mM NH$_4$HCO$_3$ in water, pH adjusted to 8.6 with concentrated NH$_4$OH; B acetonitrile). A band that eluted from 16.1 to 18.3 minutes was isolated. The solvent was removed in vacuo to afford 1-((5-bromopyridin-3-yloxy)methyl)cyclopropanamine (0.0214 g, 19% yield). $^1$H NMR (400 MHz, chloroform-d) δ ppm 0.64-0.67 (m, 2H) 0.77-0.81 (m, 2H) 1.78 (br. s., 2H) 3.88 (s, 2H) 7.37 (dd, J=2.54, 1.86 Hz, 1H) 8.26 (d, J=2.54 Hz, 1H) 8.29 (d, J=1.86 Hz, 1H). $^{13}$C NMR (101 MHz, chloroform-d) δ ppm 12.89 (s, 2 C) 33.49 (s, 1 C) 77.00 (s, 1 C) 120.35 (s, 1 C) 124.03 (s, 1 C) 136.43 (s, 1 C) 143.07 (s, 1 C) 155.53 (s, 1 C). HPLC-MS: retention time=0.87 min (>99%@215 nm; >99% @254 nm; m/z=242.9, calculated for $C_9H_{11}{}^{79}BrN_2O+H^+$=243.0; m/z=244.9, calculated for $C_9H_{11}{}^{81}BrN_2O+H^+$=245.0).

Example 287

(R)-5-((5-bromopyridin-3-yloxy)methyl)pyrrolidin-2-one

A 5 mL, one neck round bottom flask was charged with diphenyl-[4-(1h,1h,2h,2h-perfluorodecyl)phenyl]phosphine (Fluorous Technologies, Pittsburgh, Pa., 0.35 g, 0.49 mmol), a stirbar, and 1 mL dry THF. The flask was fitted with an inert atmosphere inlet, and swept with Ar for several minutes. The solution was cooled using a ice-water bath, and treated with fDEAD (Fluorous Technologies, 0.41 g, 0.49 mmol) dissolved in 1 mL dry THF. After 5 minutes, (R)-(−)-5-(hydroxymethyl)-2-pyrrolidinone (0.056 g, 0.49 mmol) and 3-bromo-5-hydroxypyridine (0.0565 g, 0.32 mmol) were added in succession. The reaction warmed to room temperature over 1 h, and was stirred a total of 96 h. The THF was removed using a stream of nitrogen, and the residue was dissolved in 0.5 mL dry DMF. The solution was loaded onto a FluoroFlash® Fluorous SPE cartridge (5 g, 15 mL tube, PN 801-0058S) that had been pre-conditioned with 50 mL MeOH, followed by 50 mL 20% MeOH in water. Two additional 0.5 mL aliquots of DMF were used to quantitate the transfer. The cartridge was eluted with 50 mL of 70% aqueous methanol, 50 mL of 80% aqueous methanol. The combined eluents were concentrated in vacuo. The residue was taken up in 2 mL dry THF, and passed through 250 mg of $SiO_2$ wet-packed with THF. The silica was washed with 5 mL dry THF, and concentrated in vacuo. The residue was dissolved in 3 mL dry THF, and treated with 0.68 mmol g$^{-1}$ Si carbonate (0.48 g, 0.32 mmol). The slurry was stirred at room temperature for 30 minutes, and filtered. The silica was eluted with 5 mL dry THF, and the combined eluents were concentrated in vacuo to afford (R)-5-((5-bromopyridin-3-yloxy)methyl)pyrrolidin-2-one (0.0813 g, 92% yield). HPLC-MS: retention time=1.09 min (94.1%@215 nm; 93.2% @254 nm; m/z=271.0, calculated for $C_{10}H_{11}^{79}BrN_2O_2+H^+$=271.0; m/z=272.9, calculated for $C_{10}H_{11}^{81}BrN_2O_2+H^+$=273.0).

Example 288

N-(6-(5-(Cyanomethoxy)pyridin-3-yl)benzo[d]thiazol-2-yl)acetamide

A dry 15 mL, one neck round bottom flask was charged with 2-(5-bromopyridin-3-yloxy)acetonitrile (0.162 g, 0.762 mmol), N-(6-(4,4,5,5-tetramethyl-1,3,2-dioxaborolan-2-yl)benzo[d]thiazol-2-yl)acetamide (0.2021 g, 0.635 mmol), 5 mL THF and a stirbar. The flask was flushed with Ar for 2 minutes, and fitted with an inert atmosphere inlet. To the stirring solution was added tetrakis(triphenylphosphine)palladium (0.147 g, 0.127 mmol) followed by 2 M sodium carbonate (0.953 ml, 1.91 mmol). The slurry was refluxed overnight, and cooled to room temperature. The mixture was poured onto 15 mL water and extracted with DCM (3×20 mL). The DCM extracts were Loaded onto an unbuffered Varian Chem elute CE1010 (100 mL, PN 12198010). The tube was extracted with DCM (4×20 mL). The combined extracts were concentrated in vacuo, and the residue was taken up in 1 mL DCM. A precipitate formed, which was collected using a course glass filter fitted with a 0.22 μm syringe filter. The solid was dried at 60° C. at <1 mmHg for 1 h to afford N-(6-(5-(Cyanomethoxy)pyridin-3-yl)benzo[d]thiazol-2-yl)acetamide (15 mg, 7.3%). $^1$H NMR (300 MHz, Pyr) δ ppm 2.36 (s, 3H) 4.98 (br. s., 1H) 5.56 (s, 2H) 7.75 (dd, J=8.40, 1.90 Hz, 1H) 7.93 (dd, J=2.81, 1.86 Hz, 1H) 8.02 (dd, J=8.44, 0.48 Hz, 1H) 8.27 (dd, J=1.90, 0.44 Hz, 1H) 8.77 (d, J=2.85 Hz, 1H) 8.93 (d, J=1.83 Hz, 1H). $^{13}$C NMR (75 MHz, Pyr) δ ppm 23.71 (s, 1 C) 55.20 (s, 1 C) 116.92 (s, 1 C) 120.84 (s, 1 C) 121.15 (s, 1 C) 122.27 (s, 1 C) 126.25 (s, 1 C) 133.18 (s, 1 C) 134.41 (s, 1 C) 137.61 (s, 1 C) 138.12 (s, 1 C) 143.50 (s, 1 C) 150.53 (s, 1 C) 154.29 (s, 1 C) 160.70 (s, 1 C) 170.19 (s, 1 C). HPLC-MS: retention time=1.34 min (93.6%@215 nm; 96.7% @254 nm; m/z=325.6, calculated for $C_{16}H_{12}N_2O_4S+H^+$=325.1).

Example 289

N-(6-(5-Fluoropyridin-3-yl)benzo[d]thiazol-2-yl)acetamide

A 5 mL conical vial was charged with cesium carbonate (0.11 ml, 1.4 mmol), 0.2 mL water, and a stirbar. The slurry was stirred until homogenous. To the solution was added 3-bromo-5-fluoropyridine (0.1003 g, 0.57 mmol), 2 mL dry THF, potassium trifluoro-(2-(N-actyl)amineobenzo[d]thiazol-6-yl)borate 2 (0.171 g, 0.57 mmol), and Pd dppf-DCM complex (0.094 g, 0.11 mmol). The vessel was purged with Ar, and sealed. The reaction was irradiated using a Biotage microwave to 100° C. for 20 minutes. The resulting mixture was poured onto 50 mL water, and stirred for 4 h. The precipitate was collected using a glass frit using positive pressure nitrogen. The solids were washed with EtOH (1 mL), and then DCM (3×3 mL). The solids were dried under a stream of nitrogen, and then at 60° C. and <1 mm Hg for 1 h to afford N-(6-(5-fluoropyridin-3-yl)benzo[d]thiazol-2-yl)acetamide (0.084 g, 51% yield). $^1$H NMR (400 MHz, DMF) δ ppm 2.34 (s, 3H) 7.86 (dd, J=8.41, 0.49 Hz, 1H) 7.92 (dd, J=8.51, 1.96 Hz, 1H) 8.14 (ddd, J=10.47, 2.69, 1.91 Hz, 1H) 8.51 (dd, J=1.86, 0.49 Hz, 1H) 8.59 (d, J=2.64 Hz, 1H) 8.93 (t, J=1.81 Hz, 1H) 12.44 (br. s., 1H). $^{13}$C NMR (101 MHz, DMF) δ ppm 22.45-22.88 (m, 1 C) 120.65-120.89 (m, 1 C) 121.10 (d, J=19.07 Hz, 1 C) 121.44 (s, 1 C) 125.78 (s, 1 C) 131.69 (d, J=1.30 Hz, 1 C) 133.53 (s, 1 C) 136.50 (d, J=22.97 Hz, 1 C) 138.11 (d, J=4.34 Hz, 1 C) 144.50 (d, J=3.90 Hz, 1 C) 149.83 (s, 1 C) 160.24 (d, J=254.46 Hz, 1 C) 159.70 (s, 1 C) 169.98 (s, 1 C). $^9$F NMR (377 MHz, DMF ref: $CFCl_3$=0.00) δ ppm –127.89 (s, 1 F). HPLC-MS: retention time=1.57 min (97.0%@215 nm; 97.6% @254 nm; m/z=288.0, calculated for $C_{14}H_{10}FN_3OS+H^+$=288.1).

Example 290 and Example 291

N-(6-(6-chloro-5-(1-cyanoethoxy)pyridin-3-yl)benzo[d]thiazol-2-yl)acetamide (290) and N-(6-(2-chloro-5-(1-cyanoethoxy)pyridin-3-yl)benzo[d]thiazol-2-yl)acetamide (291)

Prepared in an analogous manner to Compound Example 289. The crude was purified using a 19×150 mm Waters Xterra Prep C18 OBD column (100 Å pore diameter, 5 μm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end; File Name=10090701. A=water; B=10% TFE in ACN). A band that eluted from 21.2 to 22.4 minutes was isolated. The solvent was removed in vacuo to afford N-(6-(6-chloro-5-(1-cyanoethoxy)pyridin-3-yl)benzo[d]thiazol-2-yl)acetamide. $^1$H NMR (400 MHz, THF) δ ppm 1.84 (d, J=6.65 Hz, 2H) 2.22 (s, 3H) 2.49 (br. s., 1H) 5.42 (q, J=6.65 Hz, 1H) 7.71 (dd, J=8.41, 1.86 Hz, 1H) 7.78 (d, J=8.41 Hz, 1H) 7.90 (d, J=2.05 Hz, 1H) 8.20 (d, J=1.76 Hz, 1H) 8.45 (d, J=2.05 Hz, 1H) 11.37 (br. s., 1H). $^{13}$C NMR (101 MHz, THF) δ ppm 23.03 (s, 1 C) 30.81 (s, 1 C) 64.90 (s, 1 C) 118.64 (s, 1 C) 120.99 (s, 1 C) 122.24 (s, 1 C) 122.85 (s, 1 C) 126.04 (s, 1 C) 132.52 (s, 1 C) 134.74 (s, 1 C) 138.15 (s, 1 C) 141.13 (s, 1 C) 142.09 (s, 1 C) 149.83 (s, 1 C) 150.79 (s, 1 C) 160.42 (s, 1 C) 169.46 (s, 1 C). HPLC-MS: Retention time=2.08 min (96.3%@215 nm; 97.4% @254 nm; m/z=373.0, calculated for $C_{17}H_{13}ClN_4O_2S+H^+$=373.0).

A band that eluted from 19.8 to 20.7 minutes was isolated. The solvent was removed in vacuo to afford N-(6-(2-chloro-5-(1-cyanoethoxy)pyridin-3-yl)benzo[d]thiazol-2-yl)acetamide. $^1$H NMR (400 MHz, THF) δ ppm 1.76 (d, J=6.75 Hz, 3H) 2.22 (s, 3H) 5.36 (q, J=6.72 Hz, 1H) 7.51 (dd, J=8.41, 1.86 Hz, 1H) 7.59 (d, J=3.03 Hz, 1H) 7.74 (dd, J=8.36, 0.54 Hz, 1H) 7.97 (dd, J=1.81, 0.54 Hz, 1H) 8.21 (d, J=3.03 Hz, 1H) 11.36 (br. s., 1H). $^{13}$C NMR (101 MHz, THF) δ ppm 18.88 (s, 1 C) 21.89 (s, 1 C) 63.18 (s, 1 C) 117.52 (s, 1 C) 120.22 (s, 1 C) 122.08 (s, 1 C) 126.92 (s, 1 C) 127.08 (s, 1 C) 132.29 (s, 1 C) 132.62 (s, 1 C) 136.49 (s, 1 C) 137.29 (s, 1 C) 142.72 (s, 1 C) 149.31 (s, 1 C) 152.26 (s, 1 C) 159.31 (s, 1 C) 168.27 (s, 1 C). HPLC-MS: Retention time=1.95 min (89.0%@215 nm; 86.5% @254 nm; m/z=373.0, calculated for $C_{17}H_{13}ClN_4O_2S+H^+$=373.0).

Example 292

N-(6-(6-chloro-5-((2-methoxyethoxy)methoxy)pyridin-3-yl)benzo[d]thiazol-2-yl)acetamide Prepared in an analogous manner to Compound Example 289. The crude was purified using a 19×150 mm Waters Xterra Prep C18 OBD column (100 Å pore diameter, 5 μm particle size, spherical shape, PN 186002381; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end; A=10.0 mM $NH_4HCO_3$ in water, pH adjusted to 9.6 with concentrated $NH_4OH$; B acetonitrile). A band that eluted from 20.3 to 22.5 minutes was isolated. The solvent was removed in vacuo to afford N-(6-(6-chloro-5-((2-methoxyethoxy)methoxy)pyridin-3-yl)benzo[d]thiazol-2-yl)acetamide (0.0098 g, 21% yield). $^1$H NMR (400 MHz, DMF) δ ppm 2.18 (d, J=0.39 Hz, 3H) 3.12 (s, 3H) 3.41 (dd, J=5.33, 4.06 Hz, 2H) 3.76 (dd, J=5.38, 4.11 Hz, 2H) 5.49 (s, 2H) 7.69-7.72 (m, 2H) 7.95 (dd, J=2.05, 0.29 Hz, 1H) 8.30 (t, J=0.78 Hz, 1H) 8.34 (dd, J=2.15, 0.49 Hz, 1H) 12.24 (br. s., 1H). $^{13}$C NMR (101 MHz, DMF) δ ppm 22.69 (s, 1 C) 58.28 (s, 1 C) 68.65 (s, 1 C) 71.68 (s, 1 C) 94.63 (s, 1 C) 120.64 (s, 1 C) 121.42 (s, 1 C) 122.83 (s, 1 C) 125.71 (s, 1 C) 131.95 (s, 1 C) 133.51 (s, 1 C) 137.08 (s, 1 C) 139.70 (s, 1 C) 140.06 (s, 1 C) 149.61 (s, 1 C) 149.71 (s, 1 C) 159.59 (s, 1 C) 169.98 (s, 1 C). HPLC-MS: retention time=1.96 min (95.1%@215 nm; 97.2% @254 nm; m/z=408.0, calculated for $C_{18}H_{18}ClN_3O_4S+H^+=408.1$).

Example 293

N-(6-(5-((2-methoxyethoxy)methoxy)-6-(trifluoromethyl)pyridin-3-yl)benzo[d]thiazol-2-yl)acetamide Prepared in an analogous manner to Compound Example 289. The crude was purified using a 30×100 mm Waters Xterra Prep C18 OBD column (100 Å pore diameter, 5 μm particle size, spherical shape, PN 186001942); Gradient: 0→5 min@35 mL/min, 25% B; 5→20 min@35 mL/min, linear gradient to 55% B; 20→24.9 min@35 mL/min, isocratic at 55% B; 25.0 min 29.9 min@35 mL/min, step to 100% B; 30→40 min@35 mL/min, step to 25% B; 40 min end. A band that eluted from 16.7 to 17.9 minutes was isolated. The solvent was removed in vacuo to afford N-(6-(5-((2-methoxyethoxy)methoxy)-6-(trifluoromethyl)pyridin-3-yl)benzo[d]thiazol-2-yl)acetamide (0.0137 g, 12.0% yield). $^1$H NMR (400 MHz, chloroform-d) δ ppm 2.11 (s, 3H) 3.14 (s, 3H) 3.39-3.46 (m, 2H) 3.64-3.73 (m, 2H) 5.26 (s, 2H) 7.53 (dd, J=8.51, 1.76 Hz, 1H) 7.67 (d, J=8.61 Hz, 1H) 7.83 (d, J=0.88 Hz, 1H) 7.89 (d, J=1.56 Hz, 1H) 8.25 (d, J=1.57 Hz, 1H). $^{19}$F NMR ($^1$H coupled, 377 MHz, $CF_3CD_2OD$, ref: $CCl_3F$=0.00) δ ppm −65.89 (s, 3 F). $^{13}$C NMR (126 MHz, $CF_3CD_2OD$) δ ppm 21.29 (s, 255 C) 57.40 (s, 1 C) 67.55 (s, 1 C) 70.88 (s, 1 C) 93.17 (s, 1 C) 121.59 (q, J=272.93 Hz, 1 C) 120.10 (s, 1 C) 120.50 (s, 1 C) 120.66 (s, 1 C) 122.67 (s, 1 C) 122.90 (s, 1 C) 125.91 (s, 1 C) 132.28 (s, 1 C) 132.59 (s, 1 C) 134.83 (q, J=34.51 Hz, 1 C) 138.92 (s, 1 C) 141.69 (s, 1 C) 147.85 (s, 1 C) 152.34 (s, 1 C) 160.34 (s, 1 C) 171.68 (s, 1 C). HPLC-MS: retention time=2.14 min (98.6%@215 nm; 99.0% @254 nm; m/z=442.0, calculated for $C_{19}H_{18}F_3N_3O_4S+H^+=442.1$).

Example 294

N-(6-(5-(((R)-5-oxopyrrolidin-2-yl)methoxy)pyridin-3-yl)benzo[d]thiazol-2-yl)acetamide Prepared in an analogous manner to Compound Example 289. The crude was purified using a 19×150 mm Waters Xterra Prep C18 OBD column (100 Å pore diameter, 5 μm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end; File Name=09200701. A=10.0 mM $NH_4HCO_3$ in water, pH adjusted to 9.2 with concentrated $NH_4OH$; B acetonitrile). A band that eluted from 23.5 to 24.6 minutes was isolated. The solvent was removed in vacuo to afford N-(6-(5-(((R)-5-oxopyrrolidin-2-yl)methoxy)pyridin-3-yl)benzo[d]thiazol-2-yl)acetamide (0.0007 g, 1% yield). $^1$H NMR (400 MHz, DMF) δ ppm 1.94-2.06 (m, J=7.24 Hz, 1H) 2.17-2.30 (m, 2H) 2.33 (s, 3H) 4.04-4.11 (m, 1H) 4.18 (dd, J=9.00, 5.87 Hz, 1H) 4.31 (dd, J=9.54, 4.35 Hz, 1H) 7.76-7.91 (m, 4H) 8.33 (d, J=1.66 Hz, 1H) 8.45 (s, 1H) 8.63 (s, 1H). HPLC-MS: retention time=1.06 min (89.8%@215 nm; 94.6% @254 nm; m/z=383.0, calculated for $C_{19}H_{18}N_4O_3S+H^+=383.1$).

Example 295 and Example 296

N-(6-(5-((1-aminocyclopropyl)methoxy)pyridin-3-yl)benzo[d]thiazol-2-yl)acetamide (295) and N-(6-(5-hydroxypyridin-3-yl)benzo[d]thiazol-2-yl)acetamide (296)

Prepared in an analogous manner to Compound Example 289. The crude was purified using a 19×150 mm Waters Xterra Prep C18 OBD column (100 Å pore diameter, 5 μm particle size, spherical shape, PN 186002381; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end; A=10.7 mM $NH_4HCO_3$ in water, pH adjusted to 9.6 with concentrated $NH_4OH$; B acetonitrile). A band that eluted from 24.7 to 26.7 minutes was isolated. The solvent was removed in vacuo to afford N-(6-(5-((1-aminocyclopropyl)methoxy)pyridin-3-yl)benzo[d]thiazol-2-yl)acetamide (0.0027 g, 8.7% yield). $^1$H NMR (400 MHz, DMF) δ ppm 0.60-0.69 (m, 4H) 2.34 (s, 3H) 3.46 (br. s., 2H) 4.14 (s, 2H) 7.77 (dd, J=2.49, 2.01 Hz, 1H) 7.84 (d, J=8.51 Hz, 1H) 7.87 (dd, J=8.41, 1.76 Hz, 1H) 8.34 (d, J=2.54 Hz, 1H) 8.46 (dd, J=1.76, 0.68 Hz, 1H) 8.61 (d, J=1.56 Hz, 1H). $^3$C NMR (101 MHz, DMF) δ ppm 12.78 (s, 2 C) 22.87 (s, 1 C) 34.32 (s, 1 C) 77.13 (s, 1 C) 119.57 (s, 1 C) 120.72 (s, 1 C) 121.52 (s, 1 C) 125.89 (s, 1 C) 133.38 (s, 1 C) 133.66 (s, 1 C) 137.17 (s, 1 C) 137.52 (s, 1 C) 140.58 (s, 1 C) 149.67 (s, 1 C) 156.42 (s, 1 C) 159.57 (s, 1 C) 170.11 (s, 1 C). HPLC-MS: retention time=0.94 min (98.8%@215 nm; >99% @254 nm; m/z=355.1, calculated for $C_{18}H_{18}N_4O_2S+H^+=355.1$).

A band that eluted from 14.8 to 16.8 minutes was isolated. The solvent was removed in vacuo to afford N-(6-(5-hydroxypyridin-3-yl)benzo[d]thiazol-2-yl)acetamide (0.0023 g, 9.2% yield). $^1$H NMR (400 MHz, DMF) δ ppm 2.16 (s, 3H) 3.47 (br. s., 1H) 7.45 (t, J=2.20 Hz, 1H) 7.60 (dd, J=8.31, 1.66 Hz, 1H) 7.65 (d, J=8.51 Hz, 1H) 8.08 (d, J=2.35 Hz, 1H) 8.18 (d, J=1.66 Hz, 1H) 8.28 (d, J=1.56 Hz, 1H) 11.17 (br. s., 1H). $^{13}$C NMR (101 MHz, DMF) δ ppm 23.18 (s, 1 C) 120.36 (s, 1 C) 120.64 (s, 1 C) 121.28 (s, 1 C) 125.59 (s, 1 C) 133.55 (s, 1 C) 133.75 (s, 1 C) 137.26 (s, 1 C) 137.79 (s, 1 C) 138.73 (s, 1 C) 149.72 (s, 1 C) 155.75 (s, 1 C) 160.39 (s, 1 C) 170.66 (s, 1 C). HPLC-MS: retention time=0.94 min (>99%@215 nm; >99% @254 nm; m/z=286.1, calculated for $C_{14}H_{11}N_3O_2S+H^+=286.1$).

Example 297

N-(6-(6-chloropyridin-3-yl)benzo[d]thiazol-2-yl) acetamide

A 5 mL, conical microwave vessel was charged with cesium carbonate ($Cs_2CO_3$) (0.341 g, 1.05 mmol), a spinvane, and 0.25 mL water. The slurry was stirred until homogenous under a stream of nitrogen. To the vessel was added 4-bromo-2-chloropyridine (0.151 g, 0.786 mmol), trifluoride (0.150 g, 0.524 mmol), Pd(dppf)-DCM complex (0.0856 g, 0.105 mmol) and 4 mL dry THF. The vessel was flushed with nitrogen for an additional 30 s, and sealed. The heterogenous mixture was briefly sonicated and shaken. The reaction was irradiated to 100° C. for 20 minutes using a Biotage initiator. The cooled, biphasic mixture was filtered through a 0.22 µm PTFE filter into 30 mL of stirring water (an additional S mL THF was used to quantitate the transfer). The aqueous slurry was stirred at room temperature for 24 h, and filtered. The isolated solids were washed with EtOH (2×5 mL), 10% THF in DCE (2×0.5 mL), then dried initially under a stream of nitrogen, and then at 60° C. and <1.0 mm Hg for 30 minutes to afford N-(6-(6-chloropyridin-3-yl)benzo[d]thiazol-2-yl)acetamide. $^1$H NMR (400 MHz, THF) δ ppm 2.21 (s, 3H) 7.45 (dd, J=8.31, 0.68 Hz, 1H) 7.68 (dd, J=8.41, 1.86 Hz, 1H) 7.76 (dd, J=8.41, 0.49 Hz, 1H) 8.07 (dd, J=8.31, 2.64 Hz, 1H) 8.19 (dd, J=1.86, 0.49 Hz, 1H) 8.71 (dd, J=2.64, 0.68 Hz, 1H) 11.34 (br. s., 1H). $^{13}$C NMR (101 MHz, THF) δ ppm 22.90 (s, 1 C) 120.60 (s, 1 C) 122.09 (s, 1 C) 124.92 (s, 1 C) 125.68 (s, 1 C) 132.71 (s, 1 C) 134.62 (s, 1 C) 136.42 (s, 1 C) 137.94 (s, 1 C) 148.84 (s, 1 C) 150.45 (s, 1 C) 150.87 (s, 1 C) 160.13 (s, 1 C) 169.28 (s, 1 C). HPLC-MS: retention time=1.86 min (95.3%@215 nm; 95.3% @254 nm; m/z=304.0, calculated for $C_{14}H_{10}ClN_3OS+H^+$=304.0).

Example 298

N-(2-(5-(2-(N-actyl)aminobenzo[d]thiazol-6-yl)pyridin-3-yloxy)ethyl)-2-methoxyacetamide A Biotage high recovery microwave vessel was charged with sodium carbonate hydrate (0.048 g, 0.38 mmol), 0.15 mL water and a stirbar. The slurry was sonicated and stirred for 10 minutes. An inert atmosphere inlet was placed over the vessel and the remaining reagents were added under a flow of nitrogen. To the vessel was added N-(6-(4,4,5,5-tetramethyl-1,3,2-dioxaborolan-2-yl)benzo[d]thiazol-2-yl)acetamide (0.043 g, 0.14 mmol), 100 mg Pd FibreCat® palladium catalyst, and N-(2-(5-bromopyridin-3-yloxy)ethyl)-2-methoxyacetamide (0.0247 g, 0.085 mmol) dissolved in 1 mL THF. The vessel was sealed, and irritated using a Biotage personal chemistry microwave reactor to 130° C. for 25 minutes. The cooled reaction was diluted with 5 mL THF, and filtered through a 0.22 µm PTFE membrane. The catalyst was washed with THF (2×5 mL), and the combined filtrates were concentrated in vacuo. The residue was sonicated in 2 mL water, and filtered. The precipitate was then dissolved in 3 mL MeOH, filtered, and concentrated in vacuo. The crude was purified using a 19×150 mm Waters Xterra Prep C18 OBD column (100 Å pore diameter, 5 µm particle size, spherical shape, PN 186002381; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end; A=10.7 mM $NH_4HCO_3$ in water, pH adjusted to 8.6 with concentrated $NH_4OH$; B acetonitrile). A band that eluted from 24.2 to 26.0 minutes was isolated. The solvent was removed in vacuo to afford N-(2-(5-(2-(N-actyl)aminobenzo[d]thiazol-6-yl)pyridin-3-yloxy)ethyl)-2-methoxyacetamide. (0.0090 g, 26% yield). $^1$H NMR (400 MHz, DMF) δ ppm 2.34 (s, 3H) 3.37 (s, 3H) 3.70 (q, J=5.84 Hz, 2H) 3.89 (s, 2H) 4.35 (t, J=5.97 Hz, 2H) 7.81 (dd, J=2.54, 1.96 Hz, 1H) 7.83 (s, 1H) 7.85 (s, 1H) 7.86-7.90 (m, J=8.41, 1.86 Hz, 1H) 8.32 (d, J=2.25 Hz, 1H) 8.47 (d, J=1.47 Hz, 1H) 8.62 (br. s., 1H) 12.35 (br. s., 1H). $^{13}$C NMR (101 MHz, DMF) δ ppm 22.46 (s, 1 C) 38.02 (s, 1 C) 58.54 (s, 1 C) 66.92 (s, 1 C) 71.91 (s, 1 C) 118.91 (s, 1 C) 120.35 (s, 1 C) 121.07 (s, 1 C) 125.49 (s, 1 C) 132.82 (s, 1 C) 133.22 (s, 1 C) 136.79 (s, 1 C) 137.04 (s, 1 C) 140.37 (s, 1 C) 149.26 (s, 1 C) 155.35 (s, 1 C) 159.21 (s, 1 C) 169.69 (s, 1 C) 169.72 (s, 1 C). HPLC-MS: retention time=1.12 min (99.3%@215 nm; 98.1% @254 nm; m/z=401.1, calculated for $C_{19}H_{20}N_4O_4S+H^+$=401.1).

Example 300

6-(6-(3-aza-bicyclo[3.2.2]nonan-3-yl)pyrazin-2-yl)benzo[d]thiazol-2-amine

Step 1.

A 10 mL, CEM microwave vial was charged with N-(6-(6-chloropyrazin-2-yl)benzo[d]thiazol-2-yl)acetamide (0.0657 g, 0.22 mmol), 3-aza-bicyclo[3.2.2]nonane (0.032 g, 0.26 mmol), 1 mL dry TFE and a stirbar. The vessel was flushed with Ar, sealed and heated using a 110° C. heat block for 12 h. The reaction was cooled and 4 mL EtOH was added. The vial was sealed and the slurry was heated to 140° C. using a heat transfer block for 5 minutes and cooled. The slurry was filtered using a course glass filter fitted with a 0.22 µm teflon filter. The solid was dried at 60° C. and <1 mm Hg for 3 h and then dissolved in warm DMF. The turbid solution was filtered through a 0.22 µm teflon filter, and the solvent was removed in vacuo to afford 6-(6-(3-aza-bicyclo[3.2.2]nonan-3-yl)pyrazin-2-yl)benzo[d]thiazol-2-amine (19 mg). $^1$H NMR (400 MHz, Pyr) δ ppm 1.48-1.68 (m, 8H) 2.01 (s, 2H) 3.83 (d, J=4.11 Hz, 4H) 7.92 (dd, J=8.41, 0.39 Hz, 1H) 8.28 (dd, J=8.41, 1.86 Hz, 1H) 8.34 (s, 1H) 8.71 (s, 1H) 8.75 (dd, J=1.37, 0.49 Hz, 1H) 8.89 (s, 2H). $^{13}$C NMR (101 MHz, Pyr) δ ppm 25.05 (s, 4 C) 30.68 (s, 2 C) 53.39 (s, 2 C) 118.92 (s, 1 C) 119.97 (s, 1 C) 125.11 (s, 1 C) 128.54 (s, 1 C) 128.71 (s, 1 C) 131.27 (s, 1 C) 133.33 (s, 1 C) 149.01 (s, 1 C) 155.03 (s, 1 C) 155.42 (s, 1 C) 169.00 (s, 1 C).

N-(6-(6-(3-aza-bicyclo[3.2.2]nonan-3-yl)pyrazin-2-yl)benzo[d]thiazol-2-yl)acetamide Step 2.

6-(6-(3-aza-bicyclo[3.2.2]nonan-3-yl)pyrazin-2-yl)benzo[d]thiazol-2-amine was dissolved in 0.5 mL dry pyridine in a Biotage high recovery microwave vessel with a stirbar and treated with acetic anhydride (0.020 ml, 0.22 mmol). The vessel was swept with Ar, sealed and place into a 60° C. aluminum heat transfer block. The reaction was stirred for 4 h and cooled. The solution was treated with Si Carbonate (0.31 g, 0.22 mmol) (loading=0.69 mmol g$^{-1}$), and the slurry was stirred at room temperature for 30 minutes. The slurry was filtered, and the silica was washed with dry pyridine (3 mL). The solvent was removed in vacuo to afford N-(6-(6-(3-aza-bicyclo[3.2.2]nonan-3-yl)pyrazin-2-yl)benzo[d]thiazol-2-yl)acetamide (0.0024 g, 2.8% yield). $^1$H NMR (400 MHz, Pyr) δ ppm 1.22-1.41 (m, 8H) 1.76 (br. s., 2H) 2.06 (s, 3H) 3.57 (d, J=4.21 Hz, 4H) 7.85 (d, J=8.51 Hz, 1H) 8.12 (dd, J=8.41, 1.86 Hz, 1H) 8.13 (s, 1H) 8.48 (s, 1H) 8.71 (d, J=1.66

Hz, 1H) 13.58 (br. s., 1H). HPLC-MS: retention time=2.18 min (95%@215 nm; 97% @254 nm; m/z=394.2, calculated for $C_{21}H_{23}N_5OS+H^+=394.2$).

Example 301

N-(6-(6-chloro-5-hydroxypyridin-3-yl)benzo[d]thiazol-2-yl)acetamide

A dry 10 mL, round bottom flask was charged with N-(6-(6-chloro-5-((2-methoxyethoxy)methoxy)pyridin-3-yl) benzo[d]thiazol-2-yl)acetamide (0.0050 g, 0.012 mmol), a stirbar, and 1 mL dry TFE. To the stirring solution was added a 1 M solution of hydrochloric acid (0.037 ml, 0.037 mmol). The solution was transferred to a 5 mL, conical vial, purged with Ar, and sealed. The solution was irradiated using a Biotage microwave synthesizer for 5 minutes at 100° C. The cooled solution was concentrated in vacuo, and sonicated in 0.5 mL THF. The precipitate was collected using a glass frit under positive pressure nitrogen. The solids were washed with 0.5 mL dry THF, initially dried using a stream of nitrogen, and then at 60° C. and <1.0 mm Hg for 30 minutes to afford N-(6-(6-chloro-5-hydroxypyridin-3-yl)benzo[d]thiazol-2-yl)acetamide (0.0040 g). $^1$H NMR (400 MHz, DMF) δ ppm 2.33 (s, 3H) 7.77 (dd, J=8.41, 1.86 Hz, 1H) 7.82 (d, J=2.25 Hz, 1H) 7.83 (d, J=8.61 Hz, 1H) 8.30 (d, J=2.15 Hz, 1H) 8.38 (d, J=1.76 Hz, 1H) 11.30 (br. s., 1H) 12.43 (br. s., 1H). $^{13}$C NMR (101 MHz, DMF) δ ppm 22.67 (s, 1 C) 120.44 (s, 1 C) 121.39 (s, 1 C) 122.26 (s, 1 C) 125.57 (s, 1 C) 132.27 (s, 1 C) 133.46 (s, 1 C) 137.13 (s, 1 C) 137.72 (s, 1 C) 137.88 (s, 1 C) 149.53 (s, 1 C) 150.58 (s, 1 C) 159.48 (s, 1 C) 169.92 (s, 1 C). 91741-17-1 HPLC-MS: retention time=1.56 min (96.0%@215 nm; >99% @254 nm; m/z=319.9, calculated for $C_{14}H_{10}ClN_3O_2S+H^+=320.0$).

Example 302

N-(6-(5-hydroxy-6-(trifluoromethyl)pyridin-3-yl) benzo[d]thiazol-2-yl)acetamide

A 5 mL, conical microwave vessel was charged with N-(6-(5-((2-methoxyethoxy)methoxy)-6-(trifluoromethyl)pyridin-3-yl)benzo[d]thiazol-2-yl)acetamide (0.0137 g, 0.031 mmol), 1M HCl (0.093 ml, 0.093 mmol) and 1.5 mL TFE. The vessel was flushed with nitrogen, sealed, and irradiated to 100° C. using a Biotage initiator microwave for 10 minutes. The solution was concentrated in vacuo, and dried at <1.0 mm Hg for 1 h. The residue was treated with 0.5 mL EtOH, briefly sonicated, and set at room temperature for 1 h. The solids were collected using a 0.22 μm PTFE filter under positive pressure nitrogen, and washed with 0.5 mL EtOH. The precipitate was heated into 2 mL TFE, filtered through a 0.22 μm PTFE filter, and concentrated in vacuo. The solids were then dried at 60° C. and <0.5 mm Hg for 1 h to afford N-(6-(5-hydroxy-6-(trifluoromethyl)pyridin-3-yl)benzo[d]thiazol-2-yl)acetamide (0.0068 g, 62% yield). $^1$H NMR (400 MHz, THF) δ ppm 2.22 (s, 3H) 7.53 (d, J=1.37 Hz, 1H) 7.68 (dd, J=8.46, 1.91 Hz, 1H) 7.77 (dd, J=8.41, 0.49 Hz, 1H) 8.18 (d, J=1.76 Hz, 1H) 8.47 (d, J=1.66 Hz, 1H) 9.68 (br. s., 1H) 11.36 (br. s., 1H). $^{19}$F NMR (377 MHz, THF) δ ppm −65.58 (s, 3 F). HPLC-MS: retention time=1.78 min (97.7%@215 nm; 97.8% @254 nm; m/z=354.0, calculated for $C_{15}H_{10}F_3N_3O_2S+H^+=354.0$).

Example 303

5-(2-acetamidobenzo[d]thiazol-6-yl)-2-chloropyridin-3-yl acetate

A 10 mL flask was charged with N-(6-(6-chloro-5-((2-methoxyethoxy)methoxy)pyridin-3-yl)benzo[d]thiazol-2-yl)acetamide (0.0683 g, 0.167 mmol), 5 mL TFE, a stirbar and 2.0 M HCl (0.251 ml, 0.502 mmol). The flask was fitted with a reflux condenser, heated in a 120° C. oil bath for 45 minutes and cooled. The solvent was removed in vacuo, and the residue was suspended in 3 mL EtOH, and heated with a 120° C. oil bath for 5 minutes and cooled. HPLC-MS showed that a significant amount of de-acetylation had occurred. The solvent was removed in vacuo, the residue was dissolved in 3 mL dry pyridine, and stirred under an Ar atmosphere with 100 mg 5 Å activated powdered molecular sieves for 1 h. The slurry was filtered, and the molecular sieves were washed with 1 mL dy pyridine. The filtrate was treated with Ac$_2$O (0.0474 ml, 0.502 mmol) and the flask was heated using a 70° C. oil bath for 3 h. An additional aliquot of Ac$_2$O (0.0474 ml, 0.502 mmol) was added, and heating was continued for 2 h. The solution was cooled, and the solvent was removed in vacuo. The residue was treated with 3 mL dry TFE and concentrated in vacuo, and evacuated to 0.4 mm Hg over night. The solids were suspended in 2 mL 10% aqueous EtOH, and filtered. The solids were collected using a glass frit under position pressure nitrogen, and washed with EtOH (2×1 mL). The precipitate was initially dried under a stream of nitrogen, and then at 60° C. and <1 mm Hg for 1 h to afford 5-(2-acetamidobenzo[d]thiazol-6-yl)-2-chloropyridin-3-yl acetate (0.0314 g, 51.8% yield). $^1$H NMR (400 MHz, CF$_3$CD$_2$OD) δ ppm 2.15 (s, 3H) 2.25 (s, 3H) 7.50 (dd, J=8.51, 1.56 Hz, 1H) 7.67 (d, J=8.51 Hz, 1H) 7.71 (d, J=2.05 Hz, 1H) 7.84 (d, J=1.17 Hz, 1H) 8.31 (d, J=2.05 Hz, 1H). $^{13}$C NMR (101 MHz, CF$_3$CD$_2$OD) δ ppm 20.74 (s, 1 C) 23.29 (s, 1 C) 121.66 (s, 1 C) 122.72 (s, 1 C) 127.52 (s, 1 C) 133.32 (s, 1 C) 133.39 (s, 1 C) 134.61 (s, 1 C) 139.71 (s, 1 C) 144.50 (s, 1 C) 145.96 (s, 1 C) 146.19 (s, 1 C) 149.75 (s, 1 C) 162.07 (s, 1 C) 172.51 (s, 1 C) 173.47 (s, 1 C). HPLC-MS: retention time=1.95 min (97.0%@215 nm; 98.5% @254 nm; m/z=361.9, calculated for $C_{16}H_{12}ClN_3O_3S+H^+=362.0$).

Example 304

N-(6-(6-chloro-5-(4-methoxyphenylsulfonamido) pyridin-3-yl)benzo[d]thiazol-2-yl)cyclohexanecarboxamide Step 1. N-(5-bromo-2-chloropyridin-3-yl)-4-methoxybenzenesulfonamide A round bottom flask was charged with 5-bromo-2-chloropyridin-3-amine (2.50 g, 12.1 mmol) and 24 mL THF and the solution was cooled to −78° C. under nitrogen. 1.0 M LiHMDS (24.1 ml, 24.1 mmol) was added slowly and the solution was stirred for 10 min at −78° C. 4-methoxybenzene-1-sulfonyl chloride (3.49 g, 16.9 mmol) dissolved in a minimum amount of THF (~5 mL) was added slowly, and the cooling bath was removed after 10 min. The reaction was stirred at room temperature overnight and was quenched with saturated NH$_4$Cl. The layers were separated, and the organic portion was diluted with CH$_2$Cl$_2$, washed with 1 N HCl and brine. The organic portion was dried with MgSO$_4$, filtered and concentrated. The crude material was dissolved in CH$_2$Cl$_2$ (~20 mL) and ether was added (~40 mL) in portions over 15 min. After allowing to stand in the freezer for 1 h, the solids were filtered and washed with ether. N-(5-bromo-2-chloropyridin-3-yl)-4-methoxybenzenesulfonamide (3.127 g, 68.7% yield) was isolated as a white crystalline solid. MS (ESI pos. ion) m/z calc'd for $C_{12}H_{10}BrClN_2O_3S$: 377.6. found 378.8.

Step 2. N-(6-bromobenzo[d]thiazol-2-yl)cyclohexanecarboxamide

A mixture of Hunig's base (286 µl, 1637 µmol), HATU (830 mg, 2182 µmol) and cyclohexanecarboxylic acid (147 mg, 1146 µmol) was dissolved in 2.0 mL $CH_2Cl_2$ and stirred at room temperature for 10 min. 6-bromobenzo[d]thiazol-2-amine (250 mg, 1091 µmol) was added, and stirring was continued overnight. The solids were filtered and washed with $CH_2Cl_2$. The filtrate was concentrated, dissolved in $CH_2Cl_2$ and purified by silica gel chromatography using 100% $CH_2Cl_2$ to provide N-(6-bromobenzo[d]thiazol-2-yl)cyclohexanecarboxamide (290 mg, 78% yield) as a white solid. MS (ESI pos. ion) m/z calc'd for $C_{14}H_{15}BrN_2OS$: 339.3/341.3. found 339.0/341.0.

Step 3. N-(6-(4,4,5,5-tetramethyl-1,3,2-dioxaborolan-2-yl)benzo[d]thiazol-2-yl)cyclohexanecarboxamide A reaction tube was charged with $PdCl_2$(dppf)-$CH_2Cl_2$ (24 mg, 29 µmol), potassium acetate (87 mg, 884 µmol), 4,4,5,5-tetramethyl-2-(4,4,5,5-tetramethyl-1,3,2-dioxaborolan-2-yl)-1,3,2-dioxaborolane (112 mg, 442 µmol), N-(6-bromobenzo[d]thiazol-2-yl)cyclohexanecarboxamide (100 mg, 295 µmol) and 0.6 mL dioxane. The tube was sealed and the mixture was heated to 90° C. for 2 h. An additional 0.1 equiv catalyst was added and heating was continued overnight. The mixture was diluted with EtOAc and washed with water. The organic portion was dried with $MgSO_4$, filtered and concentrated. The crude material was passed through a silica gel plug using 50% EtOAc/hexanes, and the filtrate was concentrated to provide product as a tan oil which crystallized upon standing. Hexane was added and the solids were triturated, filtered and dried. N-(6-(4,4,5,5-tetramethyl-1,3,2-dioxaborolan-2-yl)benzo[d]thiazol-2-yl)cyclohexanecarboxamide (75 mg, 66% yield) was isolated as a white solid. MS (ESI pos. ion) m/z calc'd for $C_{20}H_{27}BN_2O_3S$: 386.3. found 387.0.

Step 4. N-(6-(6-chloro-5-(4-methoxyphenylsulfonamido)pyridin-3-yl)benzo[d]thiazol-2-yl)cyclohexanecarboxamide A reaction tube was charged with 2.0 M aqeuous sodium carbonate (199 µL, 397 µmol), $PdCl_2$(dppf)-$CH_2Cl_2$ (11 mg, 13 µmol), N-(5-bromo-2-chloropyridin-3-yl)-4-methoxybenzenesulfonamide (50 mg, 132 µmol), N-(6-(4,4,5,5-tetramethyl-1,3,2-dioxaborolan-2-yl)benzo[d]thiazol-2-yl)cyclohexanecarboxamide (77 mg, 199 µmol) and 0.7 mL dioxane. The tube was purged with argon, sealed and the mixture was heated at 90° C. for 3 h. The reaction mixture was concentrated, dissolved in $CH_2C_2Cl_2$/MeOH, and purified by silica gel chromatography 0-5% MeOH/$CH_2Cl_2$ to provide N-(6-(6-chloro-5-(4-methoxyphenylsulfonamido)pyridin-3-yl)benzo[d]thiazol-2-yl)cyclohexanecarboxamide (16 mg, 22% yield) as a white solid. This material contained a single impurity and was further purified by reverse phase chromatography, Gilson, 20-90% gradient of 0.1% TFA/ACN in water over 15 min to provide N-(6-(6-chloro-5-(4-methoxyphenylsulfonamido)pyridin-3-yl)benzo[d]thiazol-2-yl)cyclohexanecarboxamide (16 mg, 22% yield) as a white solid. MS (ESI pos. ion) m/z calc'd for $C_{26}H_{25}ClN_4O_4S_2$: 557.1/559.1. found 557.0/558.9. $^1$H NMR (400 MHz, DMSO-$d_6$) δ ppm 1.16-1.51 (m, 6H), 1.73-1.83 (m, 2H), 1.83-1.93 (m, 2H), 2.54-2.62 (m, 1H), 3.83 (s, 3H), 7.07-7.15 (m, 2H), 7.65-7.74 (m, 3H), 7.81-7.88 (m, 1H), 7.99 (s, 1H), 8.32 (s, 1H), 8.61 (s, 1H), 10.23 (s, 1H), 12.39 (s, 1H).

Example 305

N-(2-chloro-5-(2-(isopropylamino)benzo[d]thiazol-6-yl)pyridin-3-yl)-4-methoxybenzenesulfonamide

Step 1. N-(2-chloro-5-(4,4,5,5-tetramethyl-1,3,2-dioxaborolan-2-yl)pyridin-3-yl)-4-methoxybenzenesulfonamide A pressure bottle was charged with potassium acetate (2.43 g, 24.8 mmol), bis(pinacaloto)diboron (3.15 g, 12.4 mmol), $PdCl_2$(dppf)-$CH_2Cl_2$ (0.675 g, 0.826 mmol), N-(5-bromo-2-chloropyridin-3-yl)-4-methoxybenzenesulfonamide (3.12 g, 8.26 mmol) and 15.7 mL dioxane. The bottle was flushed with argon and sealed, and the mixture was heated at 90° C. for 4 h. LCMS showed desired as major (mass observed=boronic acid). The mixture was diluted with EtOAc and washed with water. The organic portion was dried with $MgSO_4$, filtered and concentrated. The crude material was purified by silica gel chromatography 0-50% EtOAc/Hex to provide N-(2-chloro-5-(4,4,5,5-tetramethyl-1,3,2-dioxaborolan-2-yl)pyridin-3-yl)-4-methoxybenzenesulfonamide (3.023 g, 86.2% yield) as a white waxy solid after drying in vacuo. MS (ESI pos. ion) m/z calc'd for $C_{18}H_{22}BClN_2O_5S$: 424.7. found 342.9 (M+1 boronic acid).

Step 2. 6-Bromo-N-isopropylbenzo[d]thiazol-2-amine

A microwave reaction vial was charged with 6-bromo-2-chlorobenzo[d]thiazole (300 mg, 1.21 mmol), propan-2-amine (75 mg, 1.27 mmol), triethylamine (183 mg, 1.81 mmol) and 2.4 mL DMF. The vial was sealed, and the mixture was irradiated in the microwave for 20 min at 150° C. The reaction mixture was concentrated twice from toluene and purified by silica gel chromatography (0-50% 90/10 $CH_2Cl_2$/MeOH in $CH_2Cl_2$), which provided 6-bromo-N-isopropylbenzo[d]thiazol-2-amine (210 mg, 64%) as a white solid. MS (ESI pos. ion) m/z calc'd for $C_{10}H_{11}BrN_2S$: 271.2/273.2. found 271.0/273.0.

Step 3. N-(2-chloro-5-(2-(isopropylamino)benzo[d]thiazol-6-yl)pyridin-3-yl)-4-methoxybenzenesulfonamide A reaction tube was charged with Pd(Ph$_3$P)$_4$ (13.6 mg, 11.8 µmol), 2.0 M aqueous sodium carbonate (235 µl, 471 µmol), 6-bromo-N-isopropylbenzo[d]thiazol-2-amine (63.9 mg, 235 µmol), N-(2-chloro-5-(4,4,5,5-tetramethyl-1,3,2-dioxaborolan-2-yl)pyridin-3-yl)-4-methoxybenzenesulfonamide (100 mg, 235 µmol) and 0.9 mL EtOH. The tube was sealed and the mixture was heated at 80° C. for 3 h. The mixture was concentrated and the crude material was purified by silica gel chromatography 0-10% MeOH/$CH_2Cl_2$ and reverse phase chromatography to provide N-(2-chloro-5-(2-(isopropylamino)benzo[d]thiazol-6-yl)pyridin-3-yl)-4-methoxybenzenesulfonamide (26 mg, 23%) as an off-white solid. MS (ESI pos. ion) m/z calc'd for $C_{22}H_{21}ClN_4O_3S_2$: 489.0/491.0. found 488.9/491.0.

Example 306

N-(2-chloro-5-(2-(cyclohexylmethylamino)benzo[d]thiazol-6-yl)pyridin-3-yl)-4-methoxybenzenesulfonamide Step 1. 6-bromo-N-(cyclohexylmethyl)benzo[d]thiazol-2-amine A microwave reaction vial was charged with 6-bromo-2-chlorobenzo[d]thiazole (300 mg, 1.21 mmol), cyclohexylmethanamine (143 mg, 1.27 mmol), triethylamine (183 mg, 1.81 mmol) and 2.4 mL DMF. The vial was sealed, and the mixture was irradiated in the microwave for 20 min at 150° C. The reaction mixture was concentrated twice from toluene and purified by silica gel chromatography (0-50% 90/10 $CH_2Cl_2$/MeOH in $CH_2Cl_2$), which provided 6-bromo-N-(cyclohexylmethyl)benzo[d]thiazol-2-amine (240 mg, 61%) as a white solid. MS (ESI pos. ion) m/z calc'd for $C_{14}H_{17}BrN_2S$: 325.3/327.3. found 325.0/327.0.

Step 2. N-(2-chloro-5-(2-(cyclohexylmethylamino)benzo[d]thiazol-6-yl)pyridin-3-yl)-4-methoxybenzenesulfonamide A reaction tube was charged with N-(2-chloro-5-(4,4,5,5-tetramethyl-1,3,2-dioxaborolan-2-yl)pyridin-3-yl)-4-methoxybenzenesulfonamide (157 mg, 0.369 mmol), 6-bromo-N-(cyclohexylmethyl)benzo[d]thiazol-2-amine (80 mg, 0.246 mmol), $Pd(PPh_3)_4$ (14.2 mg, 0.012 mmol), 2.0 M aqueous sodium bicarbonate (0.246 mL, 0.492 mmol) and 0.98 mL ethanol. The tube was sealed and the mixture was heated at 85° C. for 2.5 h. The reaction was concentrated, dissolved in 90/10 $CH_2Cl_2$/MeOH and passed through a silica plug. The filtrates were concentrated and the crude material was purified by reverse phase chromatography to provide N-(2-chloro-5-(2-(cyclohexylmethylamino)benzo[d]thiazol-6-yl)pyridin-3-yl)-4-methoxybenzenesulfonamide as a slightly yellow solid (7 mg, 5.2%). MS (ESI pos. ion) m/z calc'd for $C_{21}H_{27}ClN_4O_3S_2$: 543.1/545.1. found 543.0/545.0.

Example 307

N-(5-(2-aminobenzo[d]thiazol-6-yl)-2-chloropyridin-3-yl)-3-(difluoromethoxy)benzenesulfonamide Step 1.
To a 100 mL round-bottomed flask was added 3-amino-5-bromo-2-chloropyridine (855 mg, 4122 μmol), pyridine (5 ml), 3-(difluoromethoxy)benzenesulfonyl chloride (1000 μl, 4122 μmol). The reaction mixture was stirred at room temperature for overnight (ca 16 h). The solvent was removed in vacuo and the residue was dissolved in EtOAc (50 mL), washed with water (10 mL), saturated NaCl (10 mL), dried over $Na_2SO_4$, filtered and concentrated in vacuo and the residue was purified by silica gel chromatography, eluting with 20% EtOAc/hexanes to give N-(5-bromo-2-chloropyridin-3-yl)-3-(difluoromethoxy)benzenesulfonamide (566 mg, 33% yield) as a white solid. MS (ESI pos. ion) m/z calc'd for $C_{12}H_8BrClF_2N_2O_3S$: 413.9. found 414.9. $^1$H NMR (300 MHz, chloroform-d) δ ppm 6.53 (t, J=72.27 Hz, 1H) 6.99 (s, 1H) 7.38 (dd, J=8.18, 1.75 Hz, 1H) 7.52 (t, J=8.04 Hz, 1H) 7.58 (s, 1H) 7.62-7.68 (m, J=1.17 Hz, 1H) 8.16 (d, J=2.34 Hz, 1H) 8.21 (d, J=2.19 Hz, 1H)
Step 2.
To a 50 mL round-bottomed flask was added N-(5-bromo-2-chloropyridin-3-yl)-3-(difluoromethoxy)benzenesulfonamide (190 mg, 459 μmol), bis(pinacolato)diboron (175 mg, 689 μmol), dichloro[1,1'-bis(diphenylphosphino)ferrocene]palladium (ii) dichloromethane adduct (33.6 mg, 45.9 μmol), potassium acetate (115 μl, 1837 μmol), dioxane (3 mL). The reaction mixture was stirred at 90° C. for overnight (ca. 25 h). The mixture was cooled down to rt. The reaction mixture was diluted with water (2 mL) and extracted with EtOAc (2×30 mL). The organic extract was washed with saturated NaCl (1 mL), dried over $Na_2SO_4$, filtered and concentrated in vacuo and the residue was purified by silica gel chromatography, eluting with 30% EtOAc/hexanes to give N-(2-chloro-5-(4,4,5,5-tetramethyl-1,3,2-dioxaborolan-2-yl)pyridin-3-yl)-3-(difluoromethoxy)benzenesulfonamide (104 mg, 49.1% yield). $^1$H NMR (300 MHz, chloroform-d) δ ppm 1.36 (s, 12H) 6.50 (t, J=72.57 Hz, 1H) 7.34 (dd, J=8.04, 1.90 Hz, 1H) 7.48 (t, J=7.97 Hz, 1H) 7.56 (s, 1H) 7.59-7.65 (m, J=1.61 Hz, 1H) 8.30 (d, J=1.61 Hz, 1H) 8.45 (d, J=1.61 Hz, 1H)
Step 3.
To a 50 mL round-bottomed flask was added N-(2-chloro-5-(4,4,5,5-tetramethyl-1,3,2-dioxaborolan-2-yl)pyridin-3-yl)-3-(difluoromethoxy)benzenesulfonamide (98 mg, 213 μmol), 2-amino-6-bromobenzothiazole (49 mg, 213 μmol), tetrakis(triphenylphosphine)palladium (25 mg, 21 μmol), sodium carbonate (213 μl, 425 μmol), dioxane (3 mL). The reaction mixture was stirred at 100° C. for 5 h. The mixture was cooled down to room temperature. The reaction mixture was diluted with water (2 mL) and extracted with EtOAc (3×20 mL). The organic extract was washed with saturated NaCl (10 mL), dried over $Na_2SO_4$, filtered and concentrated in vacuo and the residue was purified by silica gel chromatography, eluting with 80% EtOAc/hexanes to give N-(5-(2-aminobenzo[d]thiazol-6-yl)-2-chloropyridin-3-yl)-3-(difluoromethoxy)benzenesulfonamide (48 mg, 47% yield) as a white solid. MS (ESI pos. ion) m/z calc'd for $C_{19}H_{13}ClF_2N_4O_3S_2$: 482.0. found 483.0.1H NMR (300 MHz, MeOH) δ ppm 6.88 (t, J=73.08 Hz, 1H) 7.38-7.71 (m, 5H) 7.91 (d, J=1.17 Hz, 1H) 8.17 (d, J=2.19 Hz, 1H) 8.46 (d, J=2.34 Hz, 1H)

Example 308

N-(5-(2-aminobenzo[d]thiazol-6-yl)-2-chloropyridin-3-yl)-2-chloro-4-(trifluoromethyl)benzenesulfonamide Step 1. N-(6-(5-amino-6-chloropyridin-3-yl)benzo[d]thiazol-2-yl)acetamide To a microwave vial equipped with a stirbar and charged with the trifluoroborate potassium salt (0.460 g, 1.4 mmol), cesium carbonate (0.940 g, 2.9 mmol), $PdCl_2$(dppf)-DCM (0.140 g, 0.17 mmol) and 5-bromo-2-chloropyridin-3-amine (0.200 g, 0.96 mmol) in THF (3.0 ml) was added water (0.5 ml). The vial was capped and then placed into a CEM Microwave for 10 minutes at 100° C., while 100 watts of energy was supplied via Powermax® (Simultaneous heating while cooling technology). The progress of the reaction was monitored by LC/MS, which showed desired material in the mixture. The mixture was transferred into a round-bottom flask and diluted with water (30 ml). The mixture was allowed to stir 10 minutes, then collected the precipitate by filtration. The solid was washed with Hexanes (3×50 ml) and collected. The solid was allowed to dry in a reduced-pressure oven for 3 hours. This gave N-(6-(5-amino-6-chloropyridin-3-yl)benzo[d]thiazol-2-yl)acetamide (0.308 g, 100% yield) as a tan crystalline solid. MS (ESI pos. ion) m/z: 319 (MH+). Calc'd exact mass for $C_{14}H_{11}ClN_4OS$: 318. $^1$H NMR (400 MHz, DMSO-d6): 2.22 (s, 3H), 5.66 (s, 2H), 7.42 (s, 1H), 7.66 (s, 1H), 7.81 (d, J=7.53 Hz, 1H), 7.94 (s, 1H), 8.24 (s, 1H), 12.42 (s, 1H).

Step 2. N-(5-(2-aminobenzo[d]thiazol-6-yl)-2-chloropyridin-3-yl)-2-chloro-4-(trifluoromethyl)benzenesulfonamide To a 50 ml round-bottom flask equipped with a stirbar and charged with N-(6-(5-amino-6-chloropyridin-3-yl)benzo[d]thiazol-2-yl)acetamide (0.300 g, 0.9 mmol) in Pyridine (5 ml), was added DMAP (0.030 g, 0.2 mmol) and 2-chloro-4-(trifluoromethyl)benzene-1-sulfonyl chloride (1 g, 5 mmol). The flask was allowed to stir under inert atmosphere overnight. The progress of the reaction was monitored by LC/MS, which showed desired (N-Acyl, m/z=562) and bis-sulfonated material. The mixture was diluted with water (30 ml) and ethyl acetate and then allowed the mixture to stir 10 minutes. The organic layer was extracted with EtOAc (3×25 ml). Then combined organics, dried over sodium sulfate, filtered and concentrated in vacuo. The residue was diluted with MeOH (6 ml), then added the mixture into two microwave vials equipped with stirbars (with the organics equally distributed). Potassium carbonate (0.300 g) was added to each vial, then capped and placed into a CEM Microwave for 10 minutes at 80° C., while 60 watts of energy was supplied via Powermax® (Simultaneous heating while cooling technology). The progress of the de-sulfonylation/de-acylation reaction was monitored by LC/MS, which showed mostly desired product. The two mixtures were combined and concentrated in vacuo. Water (30 ml) was added to the flask, along with a stirbar and then neutralized the mixture with 1N HCl. The precipitate was collected by filtration and washed with Hexanes. The solid was dissolved in ethyl acetate, and then purified the crude material by ISCO Silica-Gel Chromatography (120 gram column) in a gradient of 1-5% MeOH/DCM over 30 minutes. The fractions with desired product were combined and concentrated in vacuo. The residue was recrystallized from EtOAc/Hexanes to give N-(5-(2-aminobenzo[d]thiazol-6-yl)-2-chloropyridin-3-yl)-2-chloro-4-(trifluoromethyl)benzenesulfonamide (0.040 g, 8% yield) as a tan crystalline solid. MS (ESI pos. ion) m/z: 520 (MH+). Calc'd exact mass for $C_{19}H_{11}Cl_2F_3N_4O_2S_2$: 519. $^1$H NMR (400 MHz, DMSO-d6): 7.38-7.44 (m, 1H), 7.49 (d, J=8.53 Hz, 1H), 7.68 (s, 2H), 7.89 (d, J=8.53 Hz, 1H), 7.99 (d, J=19.07 Hz, 2H), 8.12 (d, J=8.03 Hz, 1H), 8.58 (s, 1H).

Compound Examples 309-315 and 323-325 were prepared in an analogous manner to Compound Example 308.

Example 309

N-(5-(2-aminobenzo[d]thiazol-6-yl)-2-chloropyridin-3-yl)-2-chloro-4-fluorobenzenesulfonamide MS (ESI pos. ion) m/z: 470 (MH+). Calc'd exact mass for $C_{18}H_{11}Cl_2FN_4O_2S_2$: 469. $^1$H NMR (400 MHz, DMSO-d6): 7.34-7.43 (m, 3H), 7.48 (s, 1H), 7.67 (s, 3H), 7.96 (s, 1H), 7.99 (dd, J=9.79, 3.26 Hz, 2H), 8.54 (s, 1H).

Example 310

N-(5-(2-aminobenzo[d]thiazol-6-yl)-2-chloropyridin-3-yl)-2,4-dichlorobenzenesulfonamide MS (ESI pos. ion) m/z: 486 (MH+). Calc'd exact mass for $C_{18}H_{11}Cl_3FN_4O_2S_2$: 485. $^1$H NMR (400 MHz, DMSO-d6): 7.42 (d, 1H), 7.52 (d, 1H), 7.58 (d, 1H), 7.68 (s, 2H), 7.94 (d, J=10.04 Hz, 3H), 8.01 (s, 1H), 8.58 (s, 1H).

Example 311

N-(5-(2-aminobenzo[d]thiazol-6-yl)-2-chloropyridin-3-yl)-2,4-difluorobenzenesulfonamide MS (ESI pos. ion) m/z: 453 (MH+). Calc'd exact mass for $C_{18}H_{11}ClF_2N_4O_2S_2$: 452. $^1$H NMR (400 MHz, DMSO-d6): 7.24 (t, J=7.78 Hz, 1H), 7.43 (d, J=8.53 Hz, 1H), 7.51-7.65 (m, 2H), 7.68 (s, 2H), 7.73-7.84 (m, 1H), 8.04 (d, J=12.55 Hz, 2H), 8.60 (s, 1H), 10.84 (s, 1H).

Example 312

N-(5-(2-aminobenzo[d]thiazol-6-yl)-2-chloropyridin-3-yl)-4-fluoro-2-methylbenzenesulfonamide MS (ESI pos. ion) m/z: 449 (MH+). Calc'd exact mass for $C_{19}H_{14}ClFN_4O_2S_2$: 448. $^1$H NMR (400 MHz, DMSO-d6): 2.66 (s, 3H), 7.16 (t, J=8.53 Hz, 1H), 7.34-7.50 (m, 3H), 7.68 (s, 2H), 7.75 (dd, J=8.53, 6.02 Hz, 1H), 7.93 (s, 1H), 8.00 (s, 1H), 8.55 (s, 1H), 10.53 (s, 1H).

Example 313

N-(5-(2-aminobenzo[d]thiazol-6-yl)-2-chloropyridin-3-yl)-4-chloro-2-fluorobenzenesulfonamide MS (ESI pos. ion) m/z: 470 (MH+). Calc'd exact mass for $C_{18}H_{11}Cl_2FN_4O_2S_2$: 469. $^1$H NMR (400 MHz, DMSO-d6): 7.44 (t, J=9.03 Hz, 2H), 7.54 (d, J=8.53 Hz, 1H), 7.65-7.80 (m, 4H), 8.01 (s, 1H), 8.03 (d, J=12.55 Hz, 2H), 8.59 (s, 1H).

Example 314

N-(5-(2-aminobenzo[d]thiazol-6-yl)-2-chloropyridin-3-yl)-2-(trifluoromethyl)benzenesulfonamide MS (ESI pos. ion) m/z: 485 (MH+). Calc'd exact mass for $C_{19}H_{12}ClF_3N_4O_2S_2$: 484. $^1$H NMR (400 MHz, DMSO-d6): 7.40-7.45 (m, 1H), 7.48-7.52 (m, 1H), 7.68 (s, 2H), 7.82-7.90 (m, 2H), 7.98-8.06 (m, 4H), 8.59 (s, 1H).

Example 315

6-(5-(tert-butylamino)-6-chloropyridin-3-yl)benzo[d]thiazol-2-amine

MS (ESI pos. ion) m/z: 333 (MH+).

Example 316

N-(6-(6-chloro-5-(piperidine-1-sulfonamido)pyridin-3-yl)benzo[d]thiazol-2-yl)acetamide Step 1. N-(5-bromo-2-chloropyridin-3-yl)piperidine-1-sulfonamide To a 50 ml round-bottom flask equipped with a stir bar and charged with 5-bromo-2-chloropyridin-3-amine (0.245 g, 1.2 mmol) in pyridine (1.5 ml), was added DMAP (0.036 g, 0.30 mmol) and piperidine (0.12 ml, 1.2 mmol). The mixture was chilled to 40° C. in a dry ice/acetone bath. Then sulfuryl chloride (0.10 ml, 1.3 mmol) was added dropwise into the mixture while stirring. After the addition, the ice bath was removed and the mixture was allowed to stir under inert atmosphere overnight. The progress of the reaction was monitored by LC/MS, which showed desired product and consumption of starting material. The mixture was diluted with water (10 ml) and DCM (10 ml). The organic layer was collected by extracting with DCM (3×20 ml). Combined organics, dried over sodium sulfate, filtered and concentrated in vacuo. The crude was dissolved in DCM and purified by ISCO Silica-Gel Chromatography (80 gram column) in a gradient of 5-50% EtOAc/DCM over 20 minutes. The fractions with desired material were combined and concentrated. This gave N-(5-bromo-2-chloropyridin-3-yl)piperidine-1-sulfonamide (0.300 g, 72% yield) as a tan solid. MS (ESI pos. ion) m/z: 355 (MH+). Calc'd exact mass for $C_{10}H_{13}BrClN_3O_2S$: 354. $^1$H NMR (400 MHz, DMSO-d6): 1.42-1.58 (m, 8H), 1.71 (qd, J=5.69, 5.52 Hz, 2H), 3.28 (s, 1H), 8.02 (d, J=2.01 Hz, 1H), 8.38 (d, J=2.51 Hz, 1H).

Step 2. N-(6-(6-chloro-5-(piperidine-1-sulfonamido)pyridin-3-yl)benzo[d]thiazol-2-yl)acetamide To a microwave vial equipped with a stirbar and charged with N-(6-(4,4,5,5-tetramethyl-1,3,2-dioxaborolan-2-yl)benzo[d]thiazol-2-yl)acetamide (0.16 g, 0.51 mmol), cesium carbonate (0.41 g, 1.3 mmol), Pd Cl$_2$ (dppf)-DCM (0.062 g, 0.076 mmol), N-(5-bromo-2-chloropyridin-3-yl)piperidine-1-sulfonamide (0.150 g, 0.42 mmol) in THF (3 ml) was added water (0.5 ml). The vial was capped and placed into CEM Microwave for 10 minutes at 100° C., while 100 watts of energy was supplied via Powermax® (Simultaneous heating while cooling technology). The progress of the reaction was monitored by LC/MS, which showed desired material in the mixture. The organic layer was extracted from the microwave vial by pipet and then diluted the organic with acetonitrile (15 ml) and TFA (0.1 ml). The crude was purified by reverse-phase HPLC. The fractions with desired product were combined and concentrated. The crude was recrystallized from 5:1 EtOAc/Methanol and Hexanes to give N-(6-(6-chloro-5-(piperidine-1-sulfonamido)pyridin-3-yl)benzo[d]thiazol-2-yl)acetamide (0.025 g, 13% yield) as a tan crystalline solid. MS (ESI pos. ion) m/z: 466 (MH+). Calc'd exact mass for $C_{19}H_{20}ClN_5O_3S_2$: 465. $^1$H NMR (400 MHz, DMSO-d6): 1.39 (s, 2H), 1.47 (s, 3H), 1.65 (s, 4H), 2.14 (s, 3H), 2.93 (s, 3H), 7.51 (s, 1H), 7.69 (s, 11H), 7.74 (s, 1H), 7.90 (s, 1H), 8.02 (s, 1H).

Example 317

N-(2-chloro-5-(2-(methylamino)benzo[d]thiazol-6-yl)pyridin-3-yl)-4-fluorobenzenesulfonamide Step 1. 6-bromo-N-methylbenzo[d]thiazol-2-amine 6-bromo-2-chlorobenzo[d]thiazole (1.100 g, 4.4 mmol) and ethanol (20 ml, 343 mmol) was added to a microwave vial equipped with a stirbar. Then methylamine solution, 40% (2.3 ml, 66 mmol) was added to the mixture with stirring. Then HCl (0.34 ml, 11 mmol) was added to the mixture. The vial was capped then placed into the CEM Voyager Microwave (large-scale unit) for 15 minutes at 100° C., while 60 watts of energy was supplied via Powermax® (Simultaneous heating while cooling technology). The progress of the reaction was monitored by LC/MS, which showed mostly desired material in the mixture. The mixture was transferred to a round-bottom flask, then made the mixture basic with sat. Na$_2$HCO$_3$. The precipitate was collected by filtration and washed with Hexanes. The solid was allowed dry in a reduced pressure oven overnight. This gave 6-bromo-N-methylbenzo[d]thiazol-2-amine (0.850 g, 79% yield) as a tan crystalline solid. MS (ESI pos. ion) m/z: 244 (MH+). Calc'd exact mass for $C_8H_7BrN_2S$: 243. $^1$H NMR (400 MHz, DMSO-d6): 2.93 (d, J=4.52 Hz, 3H), 7.33 (q, J=8.53 Hz, 2H), 7.90 (s, 1H), 8.06 (d, J=4.52 Hz, 1H).

Step 2. N-methyl-6-(4,4,5,5-tetramethyl-1,3,2-dioxaborolan-2-yl)benzo[d]thiazol-2-amine To a 50 ml round-bottom flask equipped with a stirbar was added 6-bromo-N-methylbenzo[d]thiazol-2-amine (0.620 g, 2.55 mmol), bis(pinacolato)diboron (1.30 g, 5.10 mmol), potassium acetate (1.00 g, 10.2 mmol) and DMSO (5 ml). Then PdCl$_2$(dppf)$_2$ (0.208 g, 0.255 mmol) was added to the mixture. Argon was bubbled through the mixture for about 1 minute and then the flask was placed into a preheated bath (100° C.) and allowed to stir under inert atmosphere for 3 hours. The progress of the reaction was monitored by LCMS, which showed a peak (m/z=291) consistent with product. The reaction was allowed to cool to ambient temperature and filtered through a pad of Celite® (diatomaceous earth). The Celite® (diatomaceous earth), was washed with MeOH. The filtrate was partially concentrated, then poured into water (200 ml) and allowed to stir 30 minutes. The organic layer was extracted with DCM. Organic extracts combined, dried over sodium sulfate, filtered and concentrated in vacuo. The residual DMSO was removed in vacuo, with the water bath at (70 C). The crude was purified by ISCO Silica-Gel Chromatography, in a gradient of 0-5% MeOH/DCM over 30 minutes to give N-methyl-6-(4,4,5,5-tetramethyl-1,3,2-dioxaborolan-2-yl)benzo[d]thiazol-2-amine (0.660 g, 89.2% yield) as a tan crystalline solid. MS (ESI pos. ion) m/z: 291 (MH+). Calc'd exact mass for $C_{14}H_{19}BN_2O_2S$: 290. $^1$H NMR (400 MHz, CDCl$_3$): 1.16-1.23 (m, 6H), 1.25-1.34 (m, 6H), 3.04 (s, 3H), 7.19 (s, 1H), 7.44 (d, J=8.03 Hz, 1H), 7.67 (d, J=8.03 Hz, 1H), 7.99 (s, 1H).

Step 3. N-(2-chloro-5-(2-(methylamino)benzo[d]thiazol-6-yl)pyridin-3-yl)-4-fluorobenzenesulfonamide To a microwave vial equipped with a stirbar and charged with N-methyl-6-(4,4,5,5-tetramethyl-1,3,2-dioxaborolan-2-yl)benzo[d]thiazol-2-amine (0.22 g, 0.75 mmol), cesium carbonate (0.67 g, 2.1 mmol), PdCl$_2$(dppf)*DCM (0.10 g, 0.12 mmol), N-(5-bromo-2-chloropyridin-3-yl)-4-fluorobenzenesulfonamide (0.250 g, 0.68 mmol) was added THF (3 ml). Then water (0.5 ml) was added into the mixture. The vial was capped and then placed into a CEM Microwave for 10 minutes at 100° C., while 100 watts of energy was supplied via Powermax® (Simultaneous heating while cooling technology). The progress of the reaction was monitored by LC/MS, which showed desired material in the mixture. The organic layer was extracted from the microwave vial by pipet and then diluted the organic with acetonitrile (15 ml) and TFA (0.1 ml). The crude was purified by reverse-phase HPLC. This gave N-(2-chloro-5-(2-(methylamino)benzo[d]thiazol-6-yl)pyridin-3-yl)-4-fluorobenzenesulfonamide (0.065 g, 21% yield) as a yellow crystalline solid. MS (ESI pos. ion) m/z: 449 (MH+). Calc'd exact mass for $C_{19}H_{14}ClFN_4O_2S_2$: 448. $^1$H NMR (400 MHz, DMSO-d6): 2.97 (d, J=3.51 Hz, 3H), 7.42 (t, J=8.78 Hz, 2H), 7.46-7.53 (m, 2H), 7.81 (dd, J=8.53, 5.02 Hz, 2H), 7.94 (s, 1H), 8.03 (s, 1H), 8.13 (d, J=4.02 Hz, 1H), 8.54 (s, 1H), 10.45 (s, 1H).

Example 318

2-chloro-N-(2-chloro-5-(2-(methylamino)benzo[d]thiazol-6-yl)pyridin-3-yl)-6-methylbenzenesulfonamide N-(5-bromo-2-chloropyridin-3-yl)-2-chloro-6-methylbenzenesulfonamide (210 mg, 0.530 mmol), N-methyl-6-(4,4,5,5-tetramethyl-1,3,2-dioxaborolan-2-yl)benzo[d]thiazol-2-amine (101.6 mg, 0.350 mmol), potassium carbonate (250 mg, 1.81 mmol), and Pd(dppf) $Cl_2$*DCM complex (62.6 mg, 0.0768 mmol) were suspended in DME (2.0 ml) and water (0.5) ml. The reaction flask was fit with a reflux condensor and placed in a preheated oil bath (100° C.) and stirred under nitrogen for 1 hour. The reaction was cooled to room temperature, and the aqueous phase was removed via pipette. The reaction was then concentrated and filtered through a silica gel plug with 5:1 to 3:1 DCM/2 N ammonia in MeOH. The filtrate was concentrated and purified on HPLC (10% to 100% MeCN/water with 0.1% TFA over 30 minutes) to afford 2-chloro-N-(2-chloro-5-(2-(methylamino)benzo[d]thiazol-6-yl)pyridin-3-yl)-6-methylbenzenesulfonamide (35.6 mg, 21% yield). MS (ESI pos. ion) m/z: 479 (MH+). Calc'd exact mass for $C_{20}H_{16}Cl_2N_4O_2S_2$: 478.

Example 319

2,6-dichloro-N-(2-chloro-5-(2-(methylamino)benzo[d]thiazol-6-yl)pyridin-3-yl)benzenesulfonamide Following the procedure used to prepare 2-chloro-N-(2-chloro-5-(2-(methylamino)benzo[d]thiazol-6-yl)pyridin-3-yl)-6-methylbenzenesulfonamide, 2,6-dichloro-N-(2-chloro-5-(2-(methylamino)benzo[d]thiazol-6-yl)pyridin-3-yl)benzenesulfonamide was synthesized and isolated in 21% yield. MS (ESI pos. ion) m/z: 499 (MH+). Calc'd exact mass for $C_{19}H_{13}Cl_3N_4O_2S_2$: 498.

Example 320

N-(2-chloro-5-(2-(methylamino)benzo[d]thiazol-6-yl)pyridin-3-yl)-2-fluorobenzenesulfonamide Following the procedure used to prepare 2-chloro-N-(2-chloro-5-(2-(methylamino)benzo[d]thiazol-6-yl)pyridin-3-yl)-6-methylbenzenesulfonamide, N-(2-chloro-5-(2-(methylamino)benzo[d]thiazol-6-yl)pyridin-3-yl)-2-fluorobenzenesulfonamide was synthesized and isolated in 16% yield. MS (ESI pos. ion) m/z: 449 (MH+). Calc'd exact mass for $C_{19}H_{14}ClFN_4O_2S_2$: 448.

Example 321

4-acetyl-N-(2-chloro-5-(2-(methylamino)benzo[d]thiazol-6-yl)pyridin-3-yl)benzenesulfonamide Following the procedure used to prepare 2-chloro-N-(2-chloro-5-(2-(methylamino)benzo[d]thiazol-6-yl)pyridin-3-yl)-6-methylbenzenesulfonamide, 4-acetyl-N-(2-chloro-5-(2-(methylamino)benzo[d]thiazol-6-yl)pyridin-3-yl)benzenesulfonamide was synthesized and isolated in 7% yield. MS (ESI pos. ion) m/z: 473 (MH+). Calc'd exact mass for $C_{21}H_{17}ClN_4O_3S_2$: 472.

Example 322

4-(2-acetamidopropan-2-yl)-N-(2-chloro-5-(2-(methylamino)benzo[d]thiazol-6-yl)pyridin-3-yl)benzenesulfonamide Following the procedure used to prepare 2-chloro-N-(2-chloro-5-(2-(methylamino)benzo[d]thiazol-6-yl)pyridin-3-yl)-6-methylbenzenesulfonamide, 4-(2-acetamidopropan-2-yl)-N-(2-chloro-5-(2-(methylamino)benzo[d]thiazol-6-yl)pyridin-3-yl)benzenesulfonamide was synthesized and isolated in 8% yield. MS (ESI pos. ion) m/z: 530 (MH+). Calc'd exact mass for $C_{24}H_{24}ClN_5O_3S_2$: 529.

Example 326

N-(5-(benzo[d]oxazol-6-yl)-2-chloropyridin-3-yl)-4-fluorobenzenesulfonamide

To a microwave vial equipped with a stirbar and charged with 6-bromobenzo[d]oxazole (0.050 g, 0.25 mmol), cesium carbonate (0.25 g, 0.76 mmol), $PdCl_2$(dppf)*DCM (0.037 g, 0.045 mmol), N-(2-chloro-5-(4,4,5,5-tetramethyl-1,3,2-dioxaborolan-2-yl)pyridin-3-yl)-4-fluorobenzenesulfonamide (0.10 g, 0.25 mmol) in THF (3 ml) was added water (0.5 ml). The vial was capped and placed into CEM Microwave for 10 minutes at 100° C., while 100 watts of energy was supplied via Powermax® (Simultaneous heating while cooling technology). The progress of the reaction was monitored by LC/MS, which showed desired material in the mixture. The mixture was diluted with water and the organic layer was extracted with DCM and brine solution. The organics were collected, dried over sodium sulfate, filtered and concentrated in vacuo. The crude was recrystallized from 5:1 DCM/MeOH and Hexanes to give N-(5-(benzo[d]oxazol-6-yl)-2-chloropyridin-3-yl)-4-fluorobenzenesulfonamide (0.040 g, 39% yield) as a tan crystalline solid. MS (ESI pos. ion) m/z: 404 (MH+).

Example 327

N-(2-chloro-5-(2-(methylthio)benzo[d]thiazol-6-yl)pyridin-3-yl)-4-methoxybenzenesulfonamide In a 15 mL sealed-pressure tube was added 6-bromo-2-(methylthio)benzo[d]thiazole (60 mg, 0.231 mmol), N-(2-chloro-5-(3,3,4,4-tetramethylborolan-1-yl)pyridin-3-yl)-4-methoxybenzenesulfonamide (137 mg, 0.323 mmol), sodium carbonate (2M) (73 mg, 0.692 mmol) and 8 mol % $Pd(PPh_3)_4$ in 2.0 ml of EtOH. The tube was purged with argon for 10 minutes, back-filled with argon, sealed and placed in a pre heated oil bath at 90° C. for 2 hours. Analysis of an aliquot by LCMS shows a small amount of desired product (RT=2.66 min.), exhaustion of boronic ester starting material, remaining aryl bromide starting material, and an unidentified byproduct with mw 315. Added an additional 20 mg of $Pd(PPh_3)_4$ and 60 mg of boronic ester starting material. Continued to heat at 90° C. for two more hours. No additional conversion by LCMS. Stopped reaction and cooled to ambient temperature. Concentrated down in vacuo. Crude taken up in equal parts MeOH and DMSO, filtered and purified by Gilson RPHPLC with a 20-95% gradient of ACN in water with 0.1% TFA as a modifier. Following basification with saturated sodium bicarb and extraction with 10 ml DCM (2×), organic layer was dried over $Na_2SO_4$, filtered and concentrated in vacuo to afford N-(2-chloro-5-(2-(methylthio)benzo

[d]thiazol-6-yl)pyridin-3-yl)-4-methoxybenzenesulfonamide (12 mg, 11% yield). MS (ESI pos. ion) m/z: 478 (MH+).

Preparation A 5-bromo-2-chloro-3-((2-methoxyethoxy)methoxy)pyridine

A dry 100 mL one neck round bottom flask was charged with 5-bromo-2-chloropyridin-3-ol (2.1454 g, 10.3 mmol), 40 mL dry DCE, and a stirbar. The slurry was fitted with an inert atmosphere inlet and cooled with an ice-water bath. To the stirring solution was added triethylamine (4.29 ml, 30.9 mmol) followed by 2-methoxyethoxymethyl chloride (1.17 ml, 10.3 mmol). The reaction was stirred at ice bath temperature for 1 h, and then at room temperature for 2 h. The reaction was cooled to 0° C. and treated with 2 mL MeOH. The slurry was filtered cold, and the solids were washed with DCE (2×50 mL). The filtrate was concentrated in vacuo and purified using 200 g $SiO_2$ wet packed with DCE. A fraction that eluted from 500- to 1500 mL was isolated. The solvent was removed in vacuo to afford 5-bromo-2-chloro-3-((2-methoxyethoxy)methoxy)pyridine (1.28 g, 41.9% yield). $^1$H NMR (400 MHz, chloroform-d) δ ppm 3.38 (s, 3H) 3.55-3.59 (m, 2H) 3.86-3.89 (m, 2H) 5.36 (s, 2H) 7.71 (d, J=2.05 Hz, 1H) 8.12 (d, J=2.05 Hz, 1H). HPLC-MS: 2.04 min (>99%@215 nm; >99% @254 nm; m/z=295.9, calculated for $C_9H_{11}^{79}BrClNO_3+H^+$=296.0; m/z=297.9, calculated for $C_9H_{11}^{79}BrClNO_3+H^+$=298.0).

Preparation B 2-amino-5-bromobenzenethiol

A 100 mL, one neck round bottom flask was charged with 6-bromobenzo[d]thiazol-2-amine (2.216 g, 9.67 mmol), 31 mL water and a stirbar. The flask was immersed into an ice-water bath and potassium hydroxide (16.3 g, 290 mmol) was added. The flask was fitted with a reflux condenser affixed with a vacuum/inert atmosphere inlet. The system was carefully evacuated to <5 mm Hg, and refilled with nitrogen (three cycles). The cooling bath was removed, and the reaction was heated via a 120° C. oil bath for 12 h. The solution was cooled in a ice-water bath, and an addition needle was passed through the inert atmosphere inlet and through the reflux condenser. The stirring solution was treated with acetic acid (36.3 ml, 629 mmol), added through the addition needle via a syringe pump over 15 minutes. The slurry was stirred an additional 15 minutes, and then nitrogen-pressure filtered through a glass frit (40 mL Bohdan reaction vessel) fitted with a 0.22 μm PTFE, 25 mm syringe filter unit (Millipore, Billerica, Mass., PN SLFG025NK). The solids were washed with water (3×10 mL), dried under a stream of nitrogen, and then at 60° C. and <1 mm Hg for 2 h to afford 2.3 g of material. The crude was sonicated in 40 mL 1:1 DCE-EtOH, and nitrogen-pressure filtered through a glass frit (40 mL Bohdan reaction vessel) fitted with a 0.22 μm PTFE, 25 mm syringe filter unit (Millipore, PN SLFG025NK). The solids were washed with the same solvent mixture (3×40 mL), and the combined filtrates were concentrated in vacuo to afford 2-amino-5-bromobenzenethiol (1.74 g, 88.1% yield). Product was immediately carried into the next reaction.

Preparation C 6-bromobenzo[d]thiazole

A 100 mL, one neck round bottom flask was charged with 2-amino-5-bromobenzenethiol (1.19 g, 5.83 mmol), triethyl orthoformate (9.70 ml, 58.3 mmol), 10 mL TFE, and a stirbar. A reflux condenser with a vacuum/nitrogen inlet was a fixed to the flask, and the system was degassed by evacuating to 5 mm Hg, and refilling with nitrogen. To the solution was added 200 mg dithiothreitol, and the reaction was heated using a 80° C. oil bath for 12 h. The reaction was cooled, and concentrated in vacuo. The crude was not characterized further.

Preparation D 6-(4,4,5,5-tetramethyl-1,3,2-dioxaborolan-2-yl)benzo[d]thiazole

A 100 mL, pressure vessel was charged with 6-bromobenzo[d]thiazole (1.25 g, 5.84 mmol), 30 mL dry THF, a stirbar, bis(pinacolato)diboron (2.08 g, 8.17 mmol), and 1,1'-bis(diphenylphosphino)ferrocene-palladium dichloride (0.854 g, 1.17 mmol). The flask was swept with Ar, and sealed. The slurry was heated using a 120° C. oil bath for 24 h and cooled. The slurry was filtered through a 0.2 μm PTFE membrane and the solids were washed with THF (3×30 mL). The combined filtrates were concentrated in vacuo, and taken up in 30 mL MeOH. The resulting slurry filtered through a 0.2 μm PTFE membrane. The precipitate was washed with MeOH (2×10 mL), and the filtrate was taken on as crude boron ester. The crude was not characterized further.

Preparation E

Potassium benzo[d]thiazol-6-yltrifluoroborate

A 125 mL PTFE Erlenmeyer was charged with 6-(4,4,5,5-tetramethyl-1,3,2-dioxaborolan-2-yl)benzo[d]thiazole dissolved in 50 mL MeOH. The solution was treated with potassium hydrogen fluoride (khf2) (1.2 ml, 36 mmol). The flask was sealed and stirred at room temperature for 14 h. The solution was concentrated under a stream of nitrogen to 20 mL, and treated with 20 mL water. The solution was filtered through a 0.22 μM PTFE filter, and washed with water (2×20 mL). The solids were discarded, and then a precipitate had formed in the filtrate over a 2 week period. The slurry was filteredm and the solids were discarded. The aqueous layer was lyophilized, washed with EtOH (3×30 mL), and dried at 60 C and <1 mm Hg vacuum to get potassium benzo[d]thiazol-6-yltrifluoroborate (1.44 g, 103% yield). $^1$H NMR (400 MHz, deuterium oxide) 5 ppm 7.70 (d, J=8.22 Hz, 1H) 7.99 (d, J=8.02 Hz, 1H) 8.16 (s, 1H) 9.16 (s, 1H). $^{19}$F NMR (376 MHz, deuterium oxide) δ ppm −138.15 (s, 3 F). $^{13}$C NMR (101 MHz, deuterium oxide) δ ppm 121.27 (q, J=1.30 Hz, 1 C) 121.47 (s, 1 C) 124.55 (q, J=2.46 Hz, 1 C) 129.48 (s, 1 C) 133.01 (s, 1 C) 151.28 (s, 1 C) 156.51 (s, 1 C).

Preparation F 6-(6-chloro-5-((2-methoxyethoxy)methoxy)pyridin-3-yl)benzo[d]thiazole A 50 mL Schlenk flask was charged with potassium benzo[d]thiazol-6-yltrifluoroborate (0.1929 g, 0.800 mmol), Pd(dppf)C$_{12}$-DCM adduct (0.0469 g, 0.0641 mmol) and a stirbar. The flask was evacuated to <1 mm Hg and refilled with nitrogen. A degassed solution of 5-bromo-2-chloro-3-((2-methoxyethoxy)methoxy)pyridine (0.1900 g, 0.641 mmol) in 5 mL 1% aqueous EtOH was added, followed by triethylamine (0.262 ml, 1.92 mmol). The flask was fitted with a cold finger, and was heated using a 110° C. oil bath for 12 h. The solution was cooled, and water (10 mL) was added. The mixture was vigorously stirred for 1 h, and poured onto a glass frit. The oily residue was washed with water (2×10 mL), and then dissolved in MeOH (30 mL). The brownish solution was stirred for 30 minutes, and then filtered through a 0.22 μm PTFE membrane. The filtrate was concentrated in vacuo. The sample was purified in one injection using a 30×100 mm Waters Xterra Prep C18 OBD column (A=water; B=2% TFE in ACN; 100 Å pore diameter, 5 μm particle size, spherical shape, PN 186001942; Gradient: 0→5 min@35 mL/min, 40% B; 5→20 min@35 mL/min, linear gradient to 70% B; 20→24.9@35 mL/min, isocratic at 70% B, 25→29.9 min@35 mL/min, step to 100% B; 30→40 min@35 mL/min, step to 40% B; 40 min end). A fraction that eluted from 14.7 to 15.9 minutes was isolated. The solvent was removed in vacuo to afford 6-(6-chloro-5-((2-methoxyethoxy)methoxy) pyridin-3-yl)benzo[d]thiazole (0.0231 g, 10.3% yield). $^1$H NMR (400 MHz, chloroform-d) δ ppm 3.37 (s, 3H) 3.58-3.61 (m, 2H) 3.91-3.96 (m, 2H) 5.46 (s, 2H) 7.72 (dd, J=8.51, 1.86 Hz, 1H) 7.83 (d, J=2.15 Hz, 1H) 8.15 (dd, J=1.81, 0.44 Hz, 1H) 8.23 (dd, J=8.51, 0.49 Hz, 1H) 8.35 (d, J=2.05 Hz, 1H) 9.06 (br. s., 1H). $^{13}$C NMR (101 MHz, chloroform-d) δ ppm 58.97 (s, 1 C) 68.25 (s, 1 C) 71.34 (s, 1 C) 94.14 (s, 1 C) 120.47 (s, 1 C) 122.57 (s, 1 C) 124.10 (s, 1 C) 125.67 (s, 1 C) 134.15 (s, 1 C) 134.78 (s, 1 C) 136.37 (s, 1 C) 140.24 (s, 1 C) 140.68 (s, 1 C) 149.46 (s, 1 C) 153.22 (s, 1 C) 154.95 (br. s., 1 C). HPLC-MS: 2.06 min (>99%@215 nm; 99.2% @254 nm; m/z=351.1, calculated for $C_{16}H_{15}ClN_2O_3S+H^+$=351.1).

Example 334

5-(Benzo[d]thiazol-6-yl)-2-chloropyridin-3-ol

A 5 mL conical microwave vessel was charged with 6-(6-chloro-5-((2-methoxyethoxy)methoxy)pyridin-3-yl)benzo [d]thiazole (0.0231 g, 0.0658 mmol), 2 mL TFE, 2M HCl (0.0329 ml, 0.0658 mmol), and a stirbar. The vessel was flushed with nitrogen, and then sealed. The reaction was irradiated using a Biotage microwave synthesizer to 100° C. for 15 minutes, and cooled. The solution was concentrated to half volume under a stream of nitrogen, and diluted with 1 mL 10% aqueous EtOH. The slurry was stirred at room temperature overnight, and cooled to −5° C. in a refrigerator. The precipitate was collected using a glass frit with a 0.22 μm PTFE syringe filter attached and positive pressure nitrogen. The solids were washed with 1 mL 10% aqueous EtOH, and then dried under a stream of nitrogen for 2 h. The solids were dissolved in DMF (2×2 mL), and filtered through the PTFE membrane. The solvent was removed in vacuo to afford 5-(benzo[d]thiazol-6-yl)-2-chloropyridin-3-ol (0.0159 g, 91.9% yield). $^1$H NMR (400 MHz, DMF) δ ppm 7.77 (d, J=2.13 Hz, 1H) 7.90 (dd, J=8.53, 1.76 Hz, 1H) 8.22 (d, J=8.41 Hz, 1H) 8.35 (d, J=2.13 Hz, 1H) 8.60 (d, J=1.00 Hz, 1H) 9.52 (s, 1H) 11.20 (s, 1H). $^{13}$C NMR (101 MHz, DMF) δ ppm 121.32 (s, 1 C) 122.52 (s, 1 C) 123.86 (s, 1 C) 125.82 (s, 1 C) 134.31 (s, 1 C) 135.34 (s, 1 C) 136.79 (s, 1 C) 138.14 (s, 1 C) 138.21 (s, 1 C) 150.44 (s, 1 C) 153.79 (s, 1 C) 157.01 (s, 1 C). HPLC-MS: 1.63 min (98.5%@215 nm; 97.9% @254 nm; m/z=262.9, calculated for $C_{12}H_7ClN_2OS+H^+$=263.0).

Example 335

5-(Benzo[d]thiazol-6-yl)-2-chloropyridin-3-yl acetate

A dry 5 mL, one neck round bottom flask was charged with 5-(benzo[d]thiazol-6-yl)-2-chloropyridin-3-ol (0.0120 g, 0.046 mmol), a stirbar, 0.5 mg DMAP and 1 mL anhydrous pyridine. The flask was fitted with an inert atmosphere inlet. The solution was treated with acetic anhydride (0.017 ml, 0.18 mmol), and the inert atmosphere needle was removed. The closed system was heated in a 60° C. oil bath for 60 minutes, and cooled. The solution was concentrated in vacuo, and purified using a 19×150 mm Waters Xterra Prep C18 OBD column (100 Å pore diameter, 5 μm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end; A=water; B=2% TFE in ACN). A band that eluted from 21.3 to 23.3 minutes was isolated. The solvent was removed in vacuo to afford 5-(benzo[d]thiazol-6-yl)-2-chloropyridin-3-yl acetate (0.0052 g, 37% yield). $^1$H NMR (400 MHz, chloroform-d) δ ppm 2.43 (s) 7.71 (dd) 7.78 (d) 8.16 (d) 8.24 (d) 8.58 (d) 9.08 (s). $^{13}$C NMR (101 MHz, chloroform-d) δ ppm 20.79 (s) 120.61 (s) 124.38 (s) 125.67 (s) 130.70 (s) 133.35 (s) 134.97 (s) 136.67 (s) 143.53 (s) 143.81 (s) 144.86 (s) 153.46 (s) 155.23 (s) 168.08 (s). HPLC-MS: 2.09 min (92.8%@215 nm; 95.0% @254 nm; m/z=305.0, calculated for $C_{14}H_9ClNO_2S+H^+$=305.0).

Example 336

1-(5-(benzo[d]thiazol-6-yl)pyridin-3-yl)ethanone

A 15 mL one neck round bottom flask was charged with 1-(5-bromopyridin-3-yl)ethanone (0.0829 g, 0.414 mmol), (0.150 g, 0.622 mmol), palladium(ii) acetate (0.0107 g, 0.0477 mmol), 2-dicyclohexylphosphino-2′,6′-dimethoxy-1,1′-biphenyl (0.0391 g, 0.0953 mmol), freshly powdered potassium carbonate (0.0500 ml, 0.829 mmol) and a stirbar. The flask was fitted with a reflux condenser affixed with an inert atmosphere/vacuum inlet, and the system was evacuated to <1 mm Hg for several minutes. The system was refilled with Ar, and 5 mL of degassed 10% aqueous IPA was added to the flask. The slurry was heated using a 100° C. oil bath for 3 h, and then cooled. The solution was diluted to 10 mL with THF, and filtered through a 10 g plug of SiO$_2$ wet-packed with THF. The silica was eluted with 10% MeOH in THF (75 mL), and the total elution volume was concentrated in vacuo. The crude was purified using a 19×150 mm Waters Xterra Prep C18 OBD column (100 Å pore diameter, 5 μm particle size, spherical shape, PN 186002381; Gradient: 0→5 min@20 mL/min, 10% B; 5.0→35 min@20 mL/min, linear gradient to 40% B; 35→45@20 mL/nm, isocratic at 40% B, 45→55 min@20 mL/min, step to 100% B; 55→60 min@20 mL/min, step to 10% B; 60 min end; A=water; B=2% TFE in ACN). A band that eluted from 23.8 to 30.6 minutes was isolated. The solvent was removed in vacuo to afford 1-(5-(benzo[d]thia-zol-6-yl)pyridin-3-yl)ethanone (0.0214 g, 20.3% yield). $^1$H NMR (400 MHz, chloroform-d) δ ppm 2.73 (s) 7.78 (dd) 8.22 (dd) 8.27 (dd) 8.49 (t) 9.08 (s) 9.10 (d) 9.18 (d). $^{13}$C NMR (101 MHz, chloroform-d) δ ppm 26.92 (s) 120.58 (s) 124.31 (s) 125.66 (s) 132.31 (s) 133.88 (s) 134.36 (s) 134.92 (s) 136.27 (s) 148.67 (s) 152.01 (s) 153.34 (s) 155.09 (s) 196.49 (s). HPLC-MS: 1.38 min (94.6%@215 nm; 96.3% @254 nm; m/z=255.0, calculated for $Cl_4H_{10}N_2O_2S+H^+$=255.0).

Preparation G

6-Fluoro-2-iodopyridin-3-ol

A 125 mL pressure flask was charged with 2-fluoro-5-hydroxypyridine (5.0374 g, 45 mmol), 50 mL water, a stirbar, and sodium carbonate (4 ml, 89 mmol). The slurry was stirred and heated using a heat gun until homogenous. The solution was cooled to room temperature, and treated with iodine (2 ml, 45 mmol). The flask was sealed, and the reaction was stirred overnight at room temperature. The slurry was filtered through a 0.22 μm PTFE membrane, and the precipitate was washed with water (3×30 mL). The precipitate was dried at <1 mm Hg and 60° C. for 12 h, and then heated into 20 mL dry DCE. The cloudy solution was filtered hot, and allowed to cool. The filtrate was acidified to pH 3 with 2 M HCl, during which a precipitate had formed. The precipitate was isolated using a 0.22 μm PTFE membrane, washed with water (3×30 mL), and dried under a stream of nitrogen overnight. The solids were washed with hexanes (3×50 mL), DCM (3×50 mL), and then dried under a stream of nitrogen for 1 h to afford 6-fluoro-2-iodopyridin-3-ol (2.88 g, 27% yield). $^1$H NMR (400 MHz, acetone) δ ppm 6.93 (ddd, J=8.56, 3.57, 0.29 Hz, 1H) 7.38 (ddd, J=8.58, 6.58, 0.39 Hz, 1H) 9.39 (br. s., 1H). $^{19}$F NMR (377 MHz, acetone) δ ppm −78.17 (s, 1 F). $^{13}$C NMR (101 MHz, acetone) δ ppm 103.81 (d, J=15.17 Hz, 1 C) 110.35 (d, J=39.45 Hz, 1 C) 127.81 (d, J=7.37 Hz, 1 C) 154.14 (d, J=4.33 Hz, 1 C) 156.76 (d, J=234.95 Hz, 1 C). HPLC-MS: 1.39 min (>99%@215 nm; >99% @254 nm; m/z=239.9, calculated for $C_5H_3FINO+H^+$=239.9).

Preparation H

6-Fluoro-2-iodo-3-((2-methoxyethoxy)methoxy) pyridine

A dry, 100 mL one neck round bottom flask was charged with 6-fluoro-2-iodopyridin-3-ol (2.59 ml, 11.9 mmol), a stirbar, and 50 mL dry DCE. The flask was fitted with an inert atmosphere/vacuum inlet, and the flask was cooled with a ice-water bath. The solution was carefully evacuated to <5 mm Hg, and refilled with nitrogen. The slurry was treated with triethylamine (2.49 ml, 17.9 mmol). To the stirring solution was added 2-methoxyethoxymethyl chloride (1.93 g, 15.5 mmol) dropwise over 30 minutes via syringe pump. The reaction was stirred for 2 h at 0° C., and then treated with 1 mL MeOH. The slurry was filtered cold, and the precipitate was washed with cold DCE (2×50 mL). The combined filtrates were concentrated in vacuo, and heated into 50 mL toluene. The slurry was cooled to room temperature, and then to −5° C. (refrigerator) overnight. The slurry was filtered, and the precipitate was washed with toluene (2×20 mL). The combined filtrates were concentrated in vacuo to afford 6-fluoro-2-iodo-3-((2-methoxyethoxy)methoxy)pyridine (3.91 g, 100% yield). $^1$H NMR (400 MHz, chloroform-d) δ ppm 3.36 (s, 3H) 3.53-3.57 (m, 2H) 3.85-3.89 (m, 2H) 5.30 (s, 2H) 6.83 (dd, J=8.71, 3.62 Hz, 1H) 7.46 (dd, J=8.71, 6.46 Hz, 1H). $^{19}$F NMR (376 MHz, chloroform-d) δ ppm −74.58 (dd, J=5.85, 3.25 Hz, 1 F). $^{13}$C NMR (101 MHz, chloroform-d) δ ppm 59.01 (s, 1 C) 68.37 (s, 1 C) 71.39 (s, 1 C) 94.74 (s, 1 C) 106.51 (d, J=14.30 Hz, 1 C) 108.53 (d, J=38.15 Hz, 1 C) 126.55 (d, J=7.80 Hz, 1 C) 152.04 (d, J=4.77 Hz, 1 C) 156.71 (d, J=240.59 Hz, 1 C). HPLC-MS: 1.96 min (93.4%@215 nm; 97.2% @254 nm; m/z=327.9, calculated for $C_9H_{11}FINO_3+H^+$=328.1).

Preparation I

6-Fluoro-3-((2-methoxyethoxy)methoxy)-2-(trifluoromethyl)pyridine

A dry 25 mL was charged with potassium fluoride (1.0 g, 18 mmol), copper(I) iodide (3.4 g, 18 mmol) and a stirbar. The flask was evacuated to <1 mm Hg and the solid was heated using a 170° C. oil bath for 2 h. The flask was cooled to room temperature and the vacuum was released with nitrogen. The flask was fitted with a septa/inert atmosphere inlet. The solids were treated with 5 mL freshly distilled DMF, trimethyl(trifluoromethyl)silane (2.7 ml, 18 mmol), and a solution of 6-fluoro-2-iodo-3-((2-methoxyethoxy)methoxy)pyridine (3.90 g, 12 mmol) in 5 mL dry NMP. The reaction was stirred at room temperature for 16 h, and then poured onto 150 mL dry DCE. The slurry was stirred for 1 h, and then filtered through a 0.22 μm PTFE membrane. The solids were washed with DCE (2×50 mL), and the combined DCE filtrates were concentrated in vacuo. The residue was taken up in 250 mL dry EtOH, and cooled using an ice-water bath. The slurry was filtered through a pad of Celite® (diatomaceous earth), and concentrated in vacuo to afford ~7 mL of sample (in NMP). The sample was loaded onto a Waters Xterra Prep C18 MS Packed by Vydac/The Separations Group (50 mm×300 mm, PN PA0000-050730, 10 μm particle size, spherical shape; gradient: 0→4 min@20 mL/min, 40% B; 4→5 min, 20→100 mL/min@ 40% B; 5→25 min@100 mL/min, linear gradient to 70% B; 25→35 min@100 mL/min, isocratic at 70% B; 35 min, step to 100% B @100 mL/min; 35→50 min@100 mL/min, 100% B; 50 min, step to 40% B @ 100 mL/min; 60 min end. A fraction that eluted from 19.3 to 21.7 minutes was isolated. The solvent was removed in vacuo to afford 6-fluoro-3-((2-methoxyethoxy)methoxy)-2-(trifluoromethyl)pyridine (2.0964 g, 65% yield). $^1$H NMR (400 MHz, chloroform-d) δ ppm 3.36 (s, 3H) 3.52-3.59 (m, 2H) 3.84-3.90 (m, 2H) 5.35 (s, 2H) 7.10 (ddd, J=8.95, 3.77, 0.59 Hz, 1H) 7.86 (ddd, J=9.00, 6.06, 0.59 Hz, 1H). $^{19}$F NMR (376 MHz, chloroform-d) δ ppm −75.45 (dd, J=6.50, 3.90 Hz, 1 F) −66.65 (s, 3 F). $^{13}$C NMR (101 MHz, chloroform-d) δ ppm 58.91 (s, 1 C) 68.32 (s, 1 C) 71.30 (s, 1 C) 113.61 (q, J=1.01 Hz, 1 C) 114.00 (d, J=0.87 Hz, 1 C) 120.73 (qd, J=274.47, 1.52 Hz, 1 C) 133.80 (dq, J=35.26, 13.00 Hz, 1 C) 149.84 (d, J=5.20 Hz, 1 C) 156.28 (dq, J=238.58, 1.00, 0.87 Hz, 1 C). HPLC-MS: 2.04 min (>99%@215 nm; >99% @254 nm; m/z=270.0, calculated for $C_{10}H_{11}F_4NO_3+H^+$=270.1).

Preparation J 6-fluoro-4-iodo-3-((2-methoxyethoxy)methoxy)-2-(trifluoromethyl)pyridine, 2-fluoro-3-iodo-5-((2-methoxyethoxy)methoxy)-6-(trifluoromethyl)pyridine and 2-fluoro-3,4-diiodo-5-((2-methoxyethoxy) methoxy)-6-(trifluoromethyl)pyridine A dry 100 mL, 3-neck round bottom flask was fitted with an additional needle/septa, and inert atmosphere inlet, and a septa. The flask was charged with 2,2,6,6-tetramethylpiperidine (0.47 ml, 2.8 mmol), 5 mL dry THF and a stirbar. The flask was immersed in a ice-water bath and treated with a 1.6 M solution of butyllithium in hexanes (1.4 ml, 2.2 mmol) added over 15 minutes via syringe pump. The solution was stirred an additional 5 minutes and the ice-water bath was replaced with a dry ice acetone bath. To the stirring cold solution was added 6-fluoro-3-((2-methoxyethoxy)methoxy)-2-(trifluoromethyl)pyridine (0.5030 g, 1.9 mmol) dissolved in 5 mL dry THF over 2 minutes. The reaction was stirred for 1 h at −78° C. after which time a solution of iodine (0.12 ml, 2.2 mmol) dissolved in 5 mL dry THF was added via cannula over a 3 minute period. The reaction was stirred for 15 minutes, and then the cooling bath was removed. After stirring 5 minutes, the solution was poured onto sodium thiosulfate (1.8 ml, 19 mmol) dissolved in 50 mL water. The mixture was stirred for 10 minutes, and the layers were separated. The aqueous layer was extracted with DCM (2×50 mL). The combined organic layers were washed with water (3×20 mL) and dried over MgSO$_4$. The slurry was filtered and the filtrate was concentrated in vacuo. The sample was purified in one injection using a Waters Xterra Prep C18 MS Packed by Vydac/The Separations Group, 50 mm×300 mm (PN PA0000-050730), 10 μm particle size, spherical shape. 0→4 min@20 mL/min, 40% B; 4→5 min, 20→100 mL/min@ 40% B; 5→25 min@100 mL/min, linear gradient to 70% B; 25→35 min 100 mL/min, isocratic at 70% B; 35 min, step to 100% B @100 mL/min; 35→50 min@ 100 mL/min, 100% B; 50 min, step to 40% B @ 100 mL/min; 60 min end. A fraction that eluted from 24.4 to 26.1 minutes was isolated. The solvent was removed in vacuo to afford 2-fluoro-3-iodo-5-((2-methoxyethoxy)methoxy)-6-(trifluoromethyl)pyridine (0.3253 g, 44% yield). $^1$H NMR (400 MHz, chloroform-d) δ ppm 3.39-3.42 (m, 3H) 3.60-3.65 (m, 2H) 4.00-4.06 (m, 2H) 5.26 (s, 2H) 7.65 (dd, J=4.11, 0.49 Hz, 1H). $^{19}$F NMR (376 MHz, chloroform-d) δ ppm −71.79 (d, J=3.90 Hz, 1 F)-65.02 (s, 3 F). $^{13}$C NMR (101 MHz, chloroform-d) δ ppm 59.09 (s, 1 C) 70.25 (s, 1 C) 71.47 (s, 1 C) 100.53 (dq, J=1.73, 1.59 Hz, 1 C) 109.88 (d, J=8.67 Hz, 1 C) 119.98 (dq, J=275.70, 1.30 Hz, 1 C) 124.54 (dq, J=40.53, 1.08 Hz, 1 C) 137.97 (qd, J=35.04, 14.09 Hz, 1 C) 150.60 (d, J=5.20 Hz, 1 C) 157.42 (dq, J=245.79, 0.87 Hz, 1 C).

HPLC-MS: 2.28 min (98.5%@215 nm; 98.0% @254 nm; m/z=417.8, calculated for $C_{10}H_{10}F_4{}_1NO_3+Na^+$=418.0). $^1$H-$^1$H Noesy: Correlations between aryl H and MEM protecting group were not observed.

A fraction that eluted from 26.3 to 28.4 minutes was isolated. The solvent was removed in vacuo to afford 6-fluoro-4-iodo-3-((2-methoxyethoxy)methoxy)-2-(trifluoromethyl)pyridine (0.2097 g, 28% yield). $^1$H NMR (400 MHz, chloroform-d) δ ppm 3.39 (s, 3H) 3.55-3.60 (m, 2H) 3.83-3.90 (m, 2H) 5.33 (s, 2H) 8.27 (dd, J=6.31, 0.54 Hz, 1H). $^{19}$F NMR (376 MHz, chloroform-d) δ ppm −66.72 (s, 3 F) −63.99 (d, J=5.20 Hz, 1 F). $^{13}$C NMR (101 MHz, chloroform-d) δ ppm 59.03 (s, 1 C) 68.46 (s, 1 C) 71.25 (s, 1 C) 80.53 (dq, J=45.79, 1.20, 1.16 Hz, 1 C) 94.51 (s, 1 C) 120.61 (qd, J=274.40, 1.30 Hz, 1 C) 133.72 (dq, J=35.76, 35.55, 11.70 Hz, 1 C) 139.38 (s, 1 C) 149.54 (d, J=4.77 Hz, 1 C) 155.37 (dd, J=234.30, 1.08 Hz, 1 C). HPLC-MS: 2.39 min (97.7%@215 nm; 97.6% @254 nm; m/z=395.9, calculated for $C_{10}H_{10}F_4{}_1NO_3+H^+$=396.0). $^1$H-$^1$H Noesy: Correlations between aryl H and MEM acetal CH$_2$ was observed.

A fraction that eluted from 29.5 to 30.7 minutes was isolated. The solvent was removed in vacuo to afford 2-fluoro-3,4-diiodo-5-((2-methoxyethoxy)methoxy)-6-(trifluoromethyl)pyridine (0.0605 g, 6.2% yield). HPLC-MS: 2.56 min (>99%@215 nm; >99% @254 nm; m/z=543.7, calculated for $C_{10}H_9F_4I_2NO_3+Na^+$=543.9).

Preparation K 6-(2-Fluoro-5-((2-methoxyethoxy)methoxy)-6-(trifluoromethyl)pyridin-3-yl)-2-methylbenzo[d]thiazole A dry 5 mL, conical pressure vessel was charged with a 100 mg mL$^{-1}$ slurry of Reike® zinc (0.0276 g, 0.422 mmol), a stir bar and 2-fluoro-3-iodo-5-((2-methoxyethoxy)methoxy)-6-(trifluoromethyl)pyridine (0.0834 g, 0.211 mmol). The vial was flushed with Ar and sealed. The vessel was sonicated for 5 minutes and stirred at room temperature for 8 h. The slurry was filtered through a 0.22 μm PTFE membrane into a second dry, conical vessel with a stirbar. The transfer was quantitated with 2 mL dry THF. The filtered zincate solution was treated with tetrakis(triphenylphosphine)palladium (0.0244 g, 0.0211 mmol), 6-iodo-2-methylbenzo[d]thiazole (0.0697 g, 0.253 mmol) and sealed. The reaction was stirred at room temperature for 72 h, and then treated with 2 mL of a 10% EDTA solution (pH adjusted to 6.1 with HCl). The biphasic mixture was stirred for 15 minutes, and partitioned between 40 mL DCM and 10 mL of the EDTA solution. The DCM layer was passed through an unbuffered, 10 mL Varian Chem elut CE 1005 (PN 12198007). The aqueous layer was extracted with DCM, and the resulting extract was passed through the Chem elut tube (3×10 mL). The combined extracts were concentrated in vacuo. The residue was purified in one injection using a YMC pack diol-120-NP column (PN DN12S05-2520 wt, 250×20 mm, spherical particle, 5 μm particle size, 120 Å pore size, flow=20 mL min$^{-1}$: A=6% DCE in Hex, B=THF; 20% B isocratic). A fraction that eluted from 6.2 to 7.1 minutes was isolated. The solvent was removed in vacuo to afford 6-(2-fluoro-5-((2-methoxyethoxy)methoxy)-6-(trifluoromethyl)pyridin-3-yl)-2-methylbenzo[d]thiazole (0.0186 g, 21.2% yield). $^1$H NMR (400 MHz, chloroform-d) δ ppm 2.89 (s, 3H) 3.35 (s, 3H) 3.56-3.60 (m, 2H) 3.89-3.93 (m, 2H) 5.41 (s, 2H)-7.66 (dt, J=8.49, 1.72 Hz, 1H) 8.01-8.10 (m, 3H). $^{19}$F NMR (376 MHz, chloroform-d) δ ppm −78.34 (d, J=6.50 Hz, 1 F) −66.21 (s, 3 F). $^{13}$C NMR (101 MHz, chloroform-d) δ ppm 20.36 (s, 1 C) 59.04 (s, 1 C) 68.31 (s, 1 C) 71.37 (s, 1 C) 94.46 (s, 1 C) 120.84 (qd, J=274.18, 1.52 Hz, 1 C) 122.08 (d, J=3.90 Hz, 1 C) 122.77 (s, 1 C) 126.86 (d, J=3.47 Hz, 1 C) 127.85 (dq, J=29.91, 0.87 Hz, 1 C) 129.10 (d, J=5.63 Hz, 1 C) 130.09 (d, J=4.33 Hz, 1 C) 132.39 (qd, J=35.55, 13.22 Hz, 1 C) 136.47 (s, 1 C) 150.18 (d, J=4.34 Hz, 1 C) 153.18 (qd, J=239.29, 0.87 Hz, 1 C) 153.92 (s, 1 C) 169.08 (s, 1 C). HPLC-MS: 2.52 min (86.3%@215 nm; 89.6% @254 nm; m/z=417.0, calculated for $C_{18}H_{16}F_4N_2O_3S+H^+$=417.1).

Example 341

6-fluoro-5-(2-methylbenzo[d]thiazol-6-yl)-2-(trifluoromethyl)pyridin-3-ol

A 5 mL conical microwave vessel was charged with 6-(2-fluoro-5-((2-methoxyethoxy)methoxy)-6-(trifluoromethyl)pyridin-3-yl)-2-methylbenzo[d]thiazole (0.0186 g, 0.045 mmol), a spin vane and 1 mL TFE. The vessel was swept with Ar, treated with 2M hydrochloric acid (0.022 ml, 0.045 mmol) and sealed. The vessel was irradiated using a Biotage microwave synthesizer to 120° C. for 15 minutes. The solution was concentrated using a stream of nitrogen. The crude was purified using a 19×150 mm Waters Xterra Prep C18 OBD column (100 Å pore diameter, 5 μm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end. A=water; B=2% TFE in ACN. A band that eluted from 26.4 to 28.7 minutes was isolated. The solvent was concentrated under a stream of nitrogen overnight, and then lyophilized to afford 6-fluoro-5-(2-methylbenzo[d]thiazol-6-yl)-2-(trifluoromethyl)pyridin-3-ol (0.0068 g, 46% yield). $^1$H NMR (400 MHz, DMF) δ ppm 2.88 (s, 3H) 7.78 (dt, J=8.46, 1.78 Hz, 1H) 7.89 (d, J=7.92 Hz, 1H) 8.07 (d, J=8.51 Hz, 1H) 8.39 (t, J=1.37 Hz, 1H) 11.89 (br. s., 1H). $^{19}$F NMR (376 MHz, DMF) δ ppm −82.30 (d, J=6.50 Hz, 1 F) −64.69 (s, 3 F). HPLC-MS: 2.14 min (>99%@215 nm; >99% @254 nm; m/z=329.0, calculated for $C_{14}H_8F_4N_2OS+H^+$=328.0).

Table A below shows the chemical structures of the compounds of the examples. The IUPAC names of the compounds of the examples are listed in Table I along with biological data, the general synthetic method used to make the compound, and the molecular ion (typically M+H unless noted otherwise) from a mass spectra. The chemical drawing program used to draw the structures may not show hydrogen atoms, and such representations are common and well understood to one skilled in the art. For example, —N means —NH$_2$ and —O mean —OH. It is also noted that a methyl group in a complete chemical structure can represented by a "–" in the structure, which is a well known short hand. Alternatively, when a fragment or portion of a chemical structure is shown the "–" means a point of attachment for or to another fragment, which is also well known to those skilled in the art.

TABLE A

| Example | Structure |
|---|---|
| 1 | 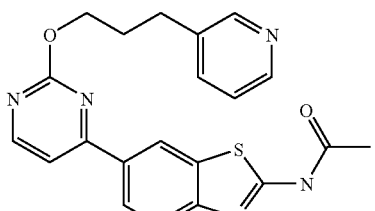 |
| 2 | 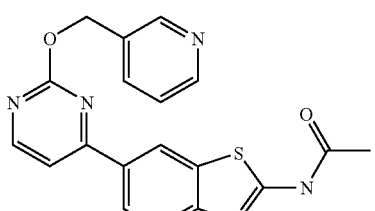 |
| 3 | 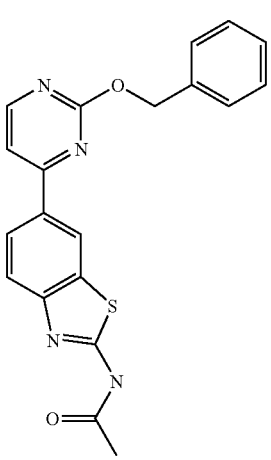 |
| 4 | 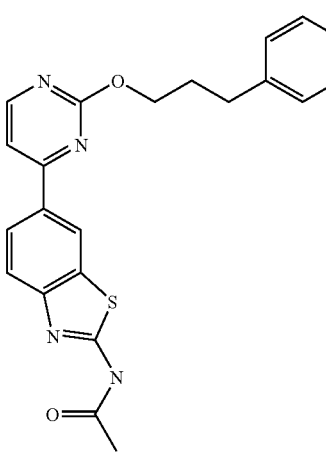 |

TABLE A-continued
| Example | Structure |
|---|---|
| 5 | 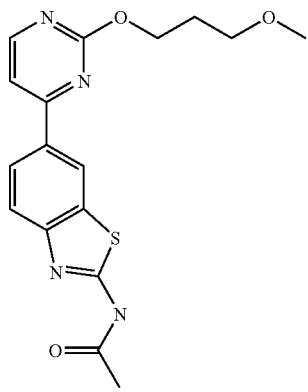 |
| 6 | 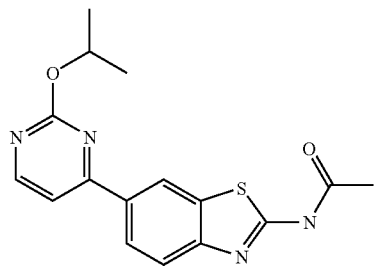 |
| 7 | 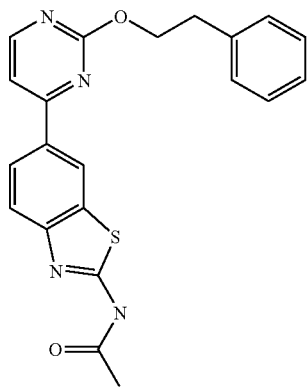 |
| 8 | 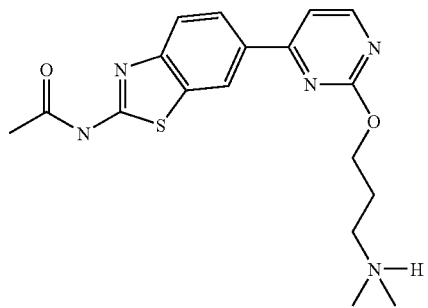 |

TABLE A-continued
| Example | Structure |
|---|---|
| 9 | 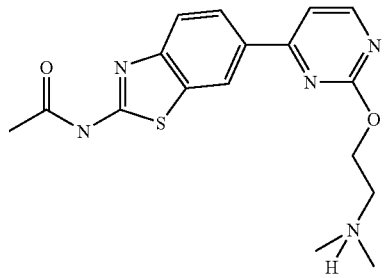 |
| 10 | 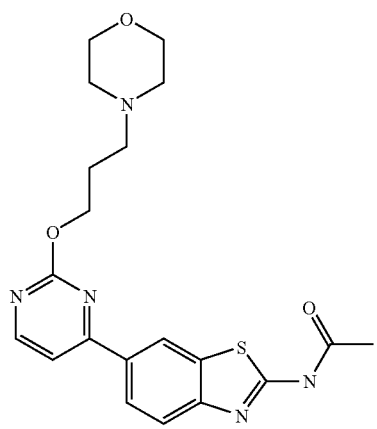 |
| 11 | 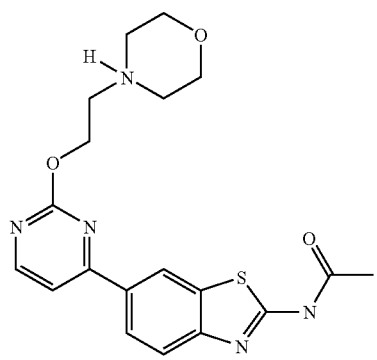 |
| 12 | 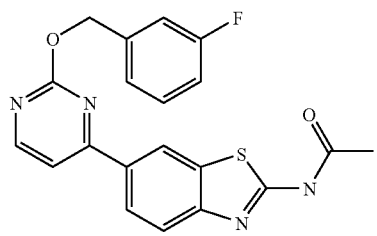 |
| 13 | 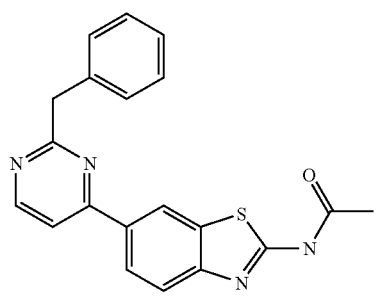 |

TABLE A-continued
| Example | Structure |
|---|---|
| 14 | 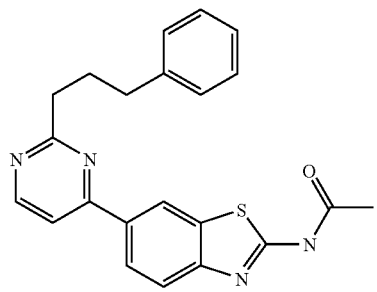 |
| 15 | 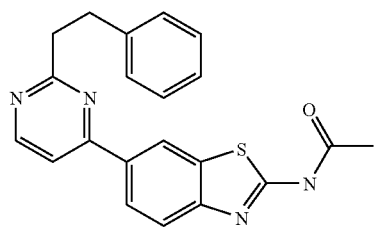 |
| 16 | 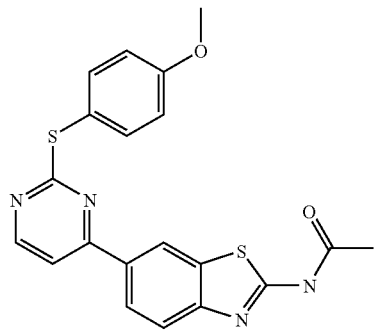 |
| 17 | 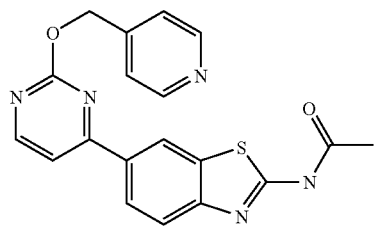 |
| 18 | 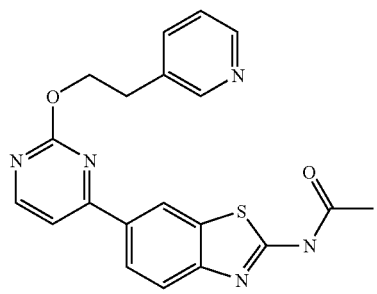 |

TABLE A-continued
| Example | Structure |
|---|---|
| 19 | 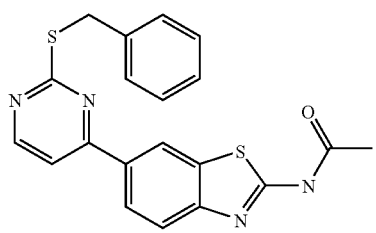 |
| 20 | 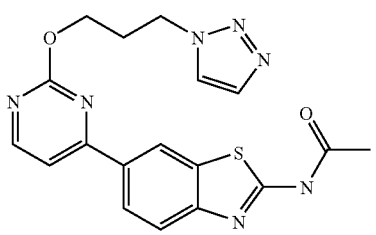 |
| 21 | 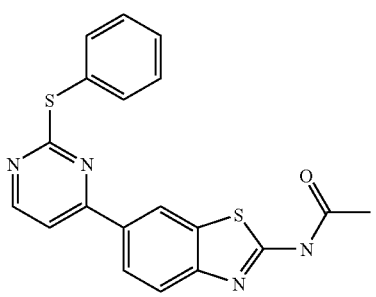 |
| 22 | 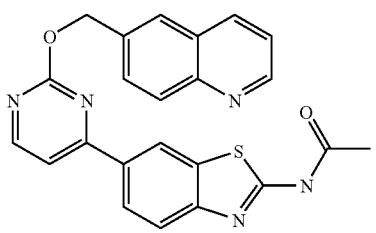 |
| 23 | 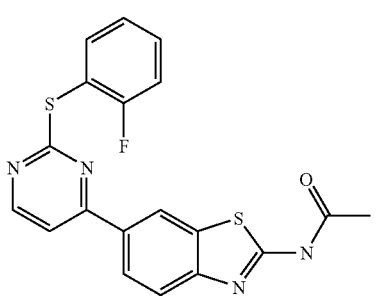 |
| 24 | 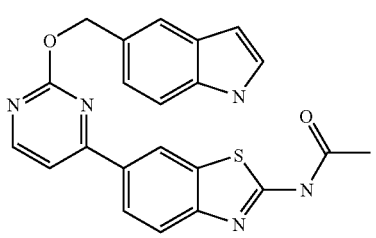 |

TABLE A-continued
| Example | Structure |
|---|---|
| 25 | 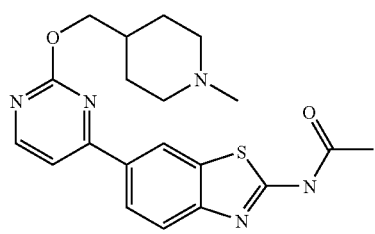 |
| 26 | 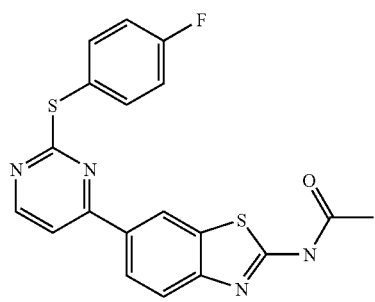 |
| 27 | 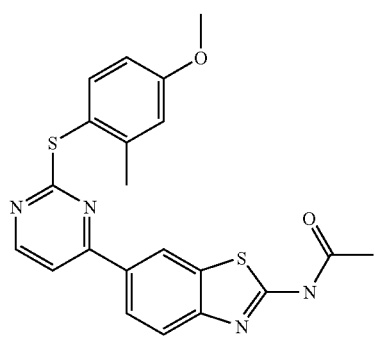 |
| 28 | 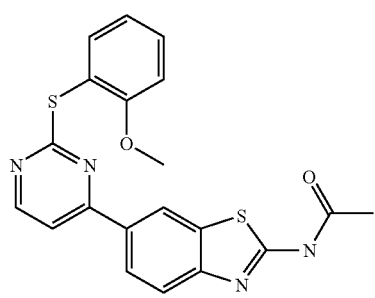 |
| 29 | 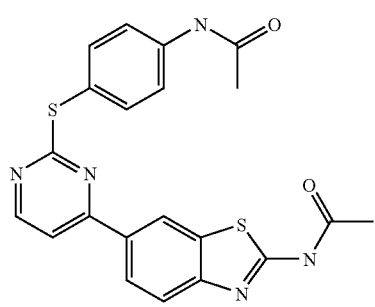 |

TABLE A-continued
| Example | Structure |
|---|---|
| 30 | 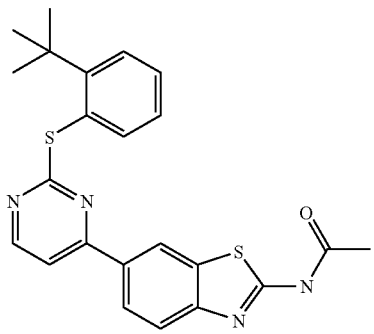 |
| 31 | 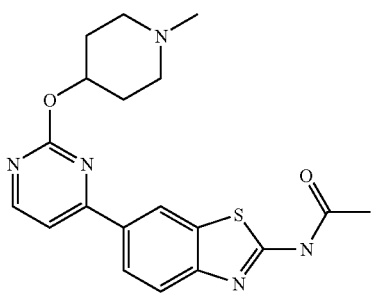 |
| 32 | 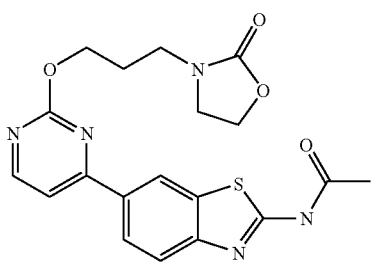 |
| 33 | 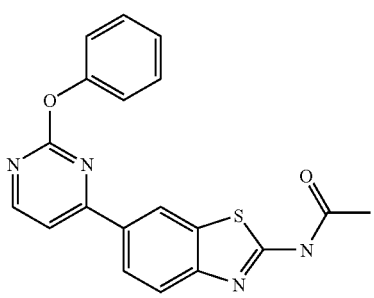 |
| 34 | 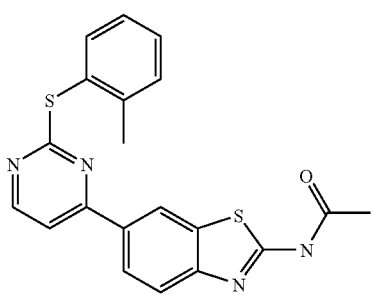 |

TABLE A-continued

| Example | Structure |
|---|---|
| 35 | 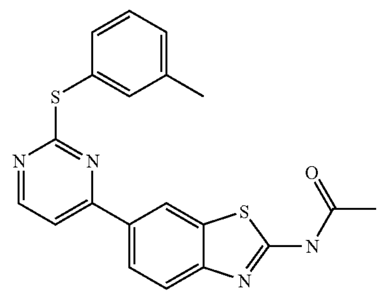 |
| 36 | 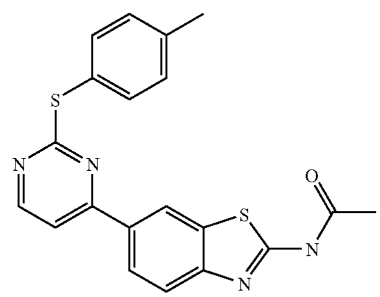 |
| 37 | 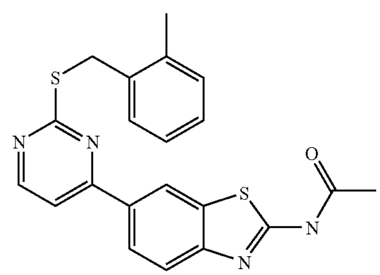 |
| 38 | 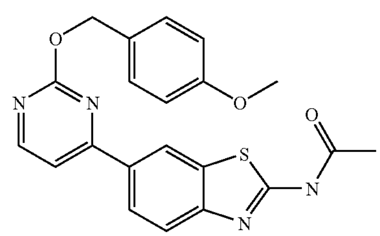 |
| 39 | 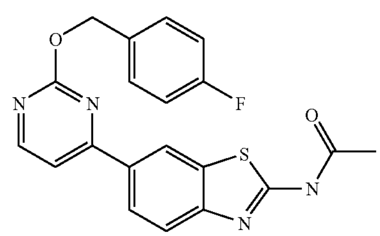 |
| 40 | 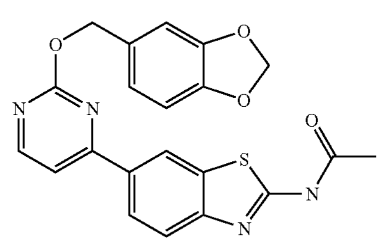 |

TABLE A-continued
| Example | Structure |
|---------|-----------|
| 41 | 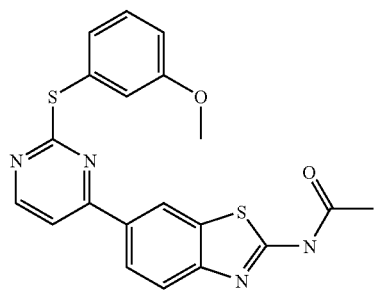 |
| 42 | 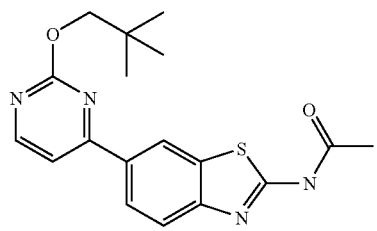 |
| 43 | 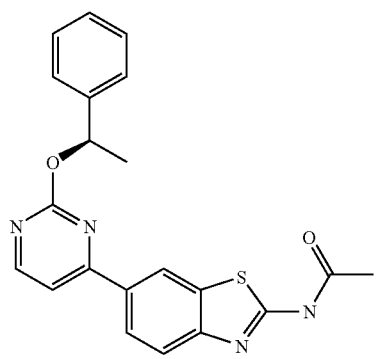 |
| 44 | 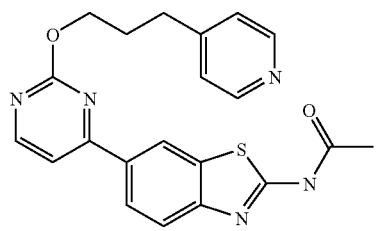 |
| 45 | 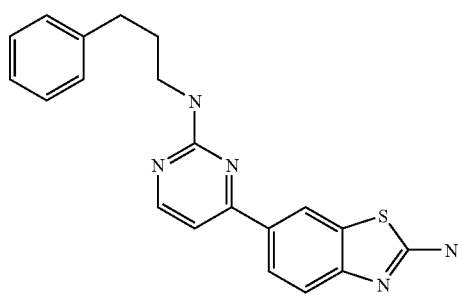 |

TABLE A-continued
| Example | Structure |
|---|---|
| 46 | 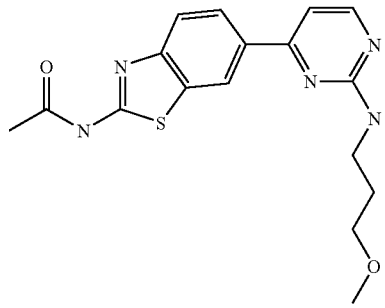 |
| 47 | 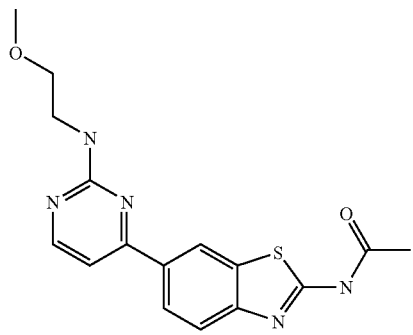 |
| 48 | 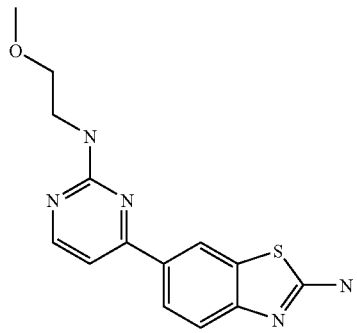 |
| 49 | 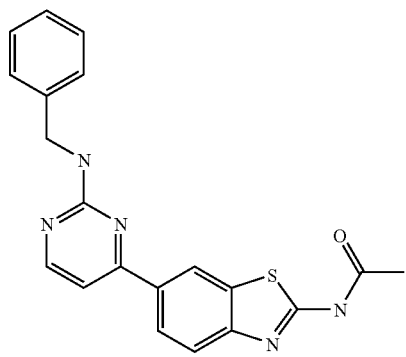 |
| 50 | 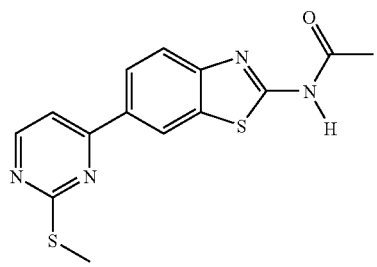 |

TABLE A-continued
| Example | Structure |
|---|---|
| 51 | 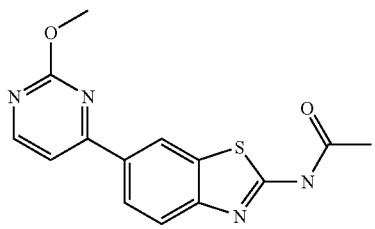 |
| 52 | 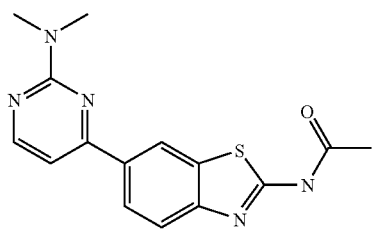 |
| 53 | 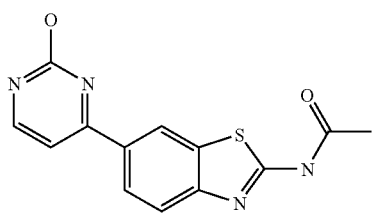 |
| 54 | 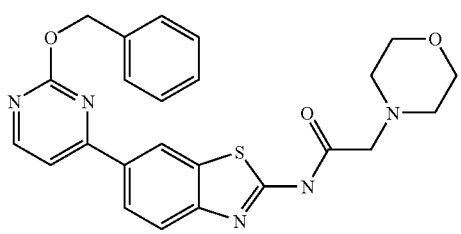 |
| 55 | 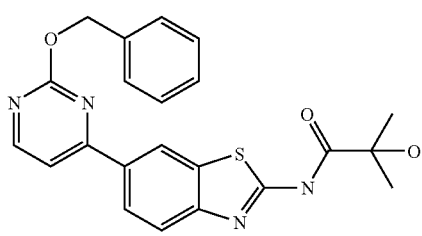 |
| 56 | 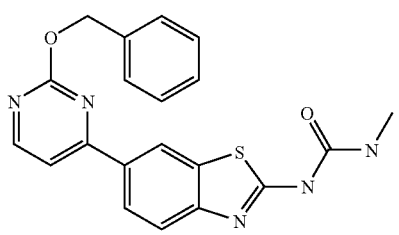 |

TABLE A-continued
| Example | Structure |
|---|---|
| 57 | 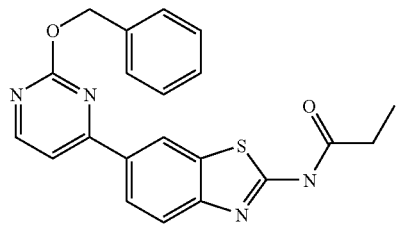 |
| 58 | 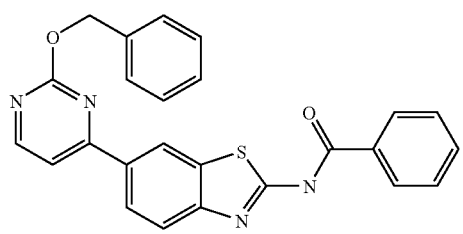 |
| 59 | 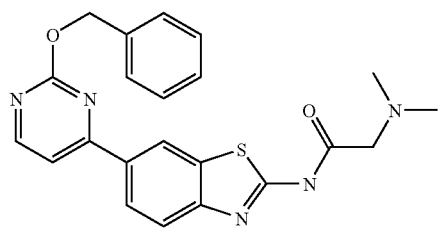 |
| 61 | 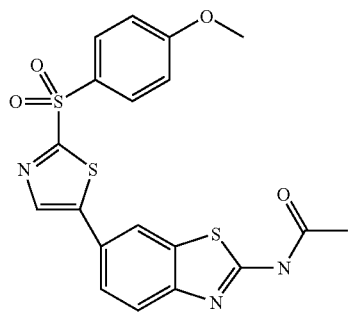 |
| 62 | 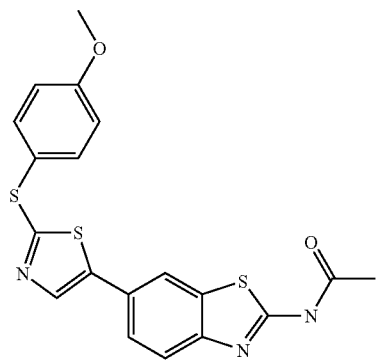 |

TABLE A-continued
| Example | Structure |
|---|---|
| 63 | 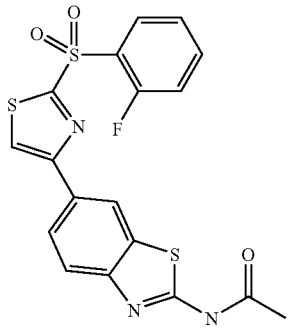 |
| 64 | 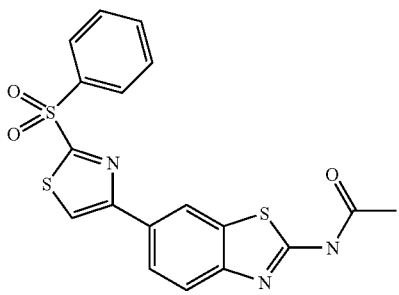 |
| 65 | 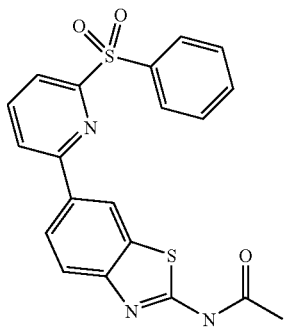 |
| 66 | 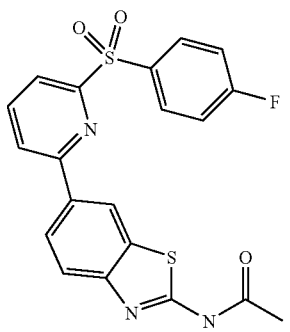 |

TABLE A-continued
| Example | Structure |
|---------|-----------|
| 67 | 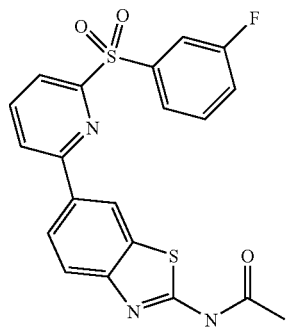 |
| 68 | 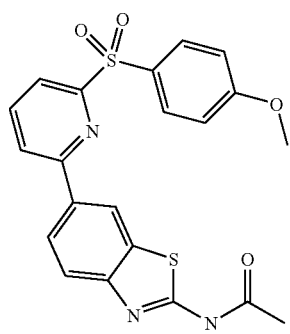 |
| 69 | 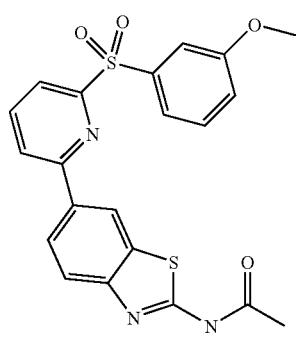 |
| 70 | 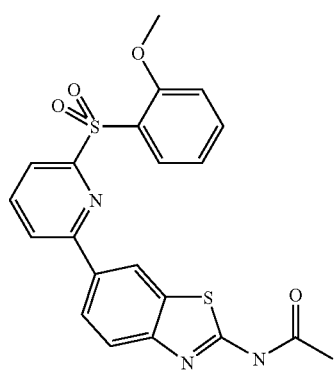 |

TABLE A-continued
| Example | Structure |
|---|---|
| 71 | 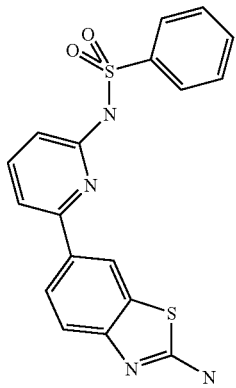 |
| 72 | 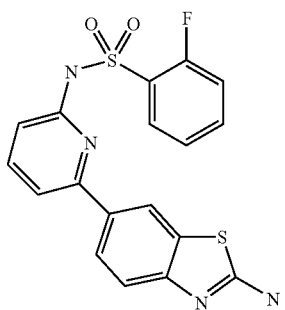 |
| 73 | 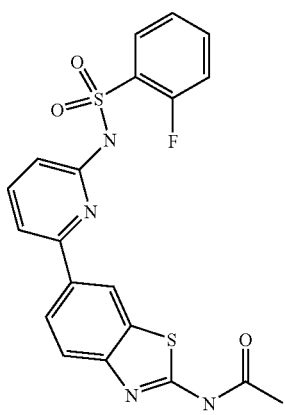 |
| 74 | 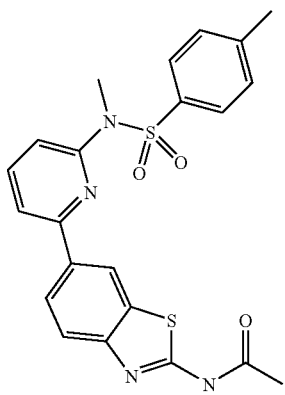 |

TABLE A-continued
| Example | Structure |
|---|---|
| 75 | 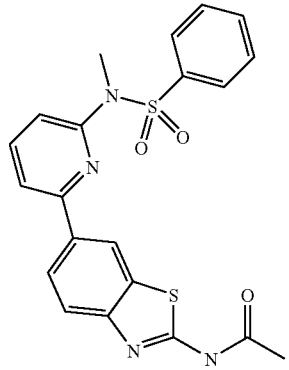 |
| 77 | 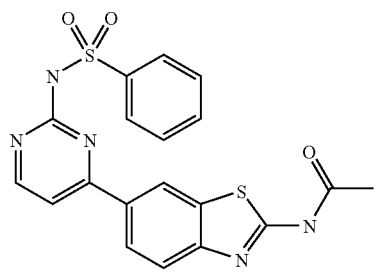 |
| 78 | 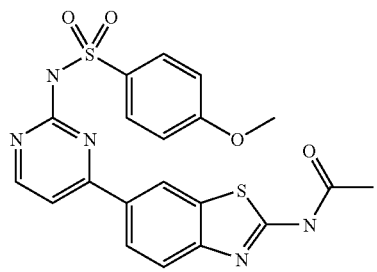 |
| 79 | 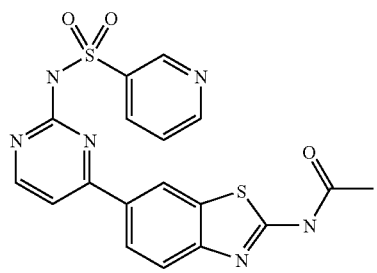 |
| 80 | 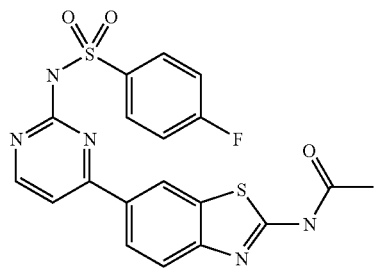 |

TABLE A-continued
| Example | Structure |
|---|---|
| 81 | 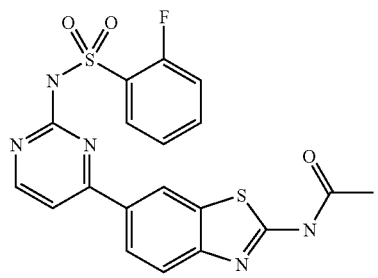 |
| 82 | 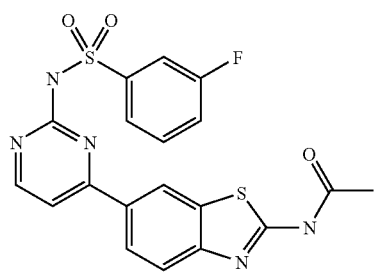 |
| 83 | 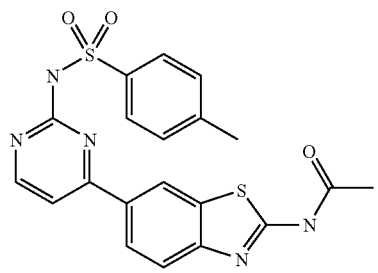 |
| 84 | 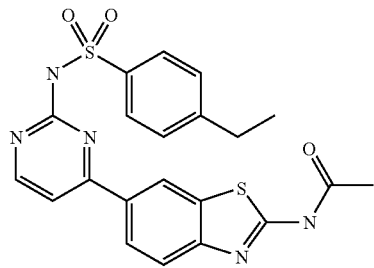 |
| 85 | 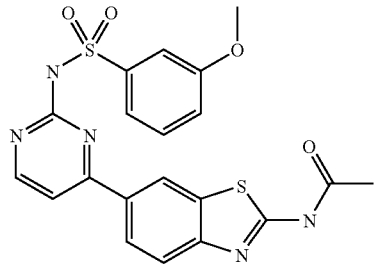 |

TABLE A-continued
| Example | Structure |
|---|---|
| 86 | 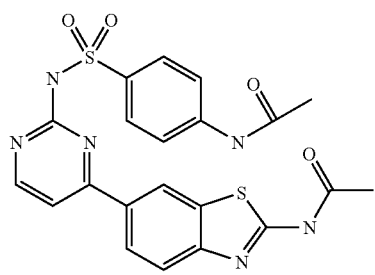 |
| 87 | 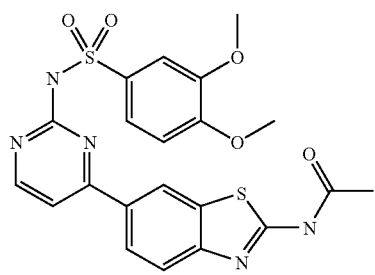 |
| 88 | 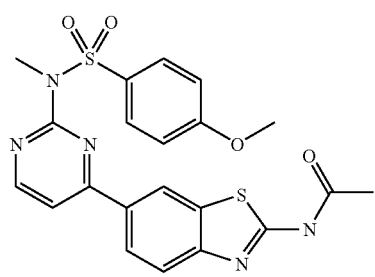 |
| 89 | 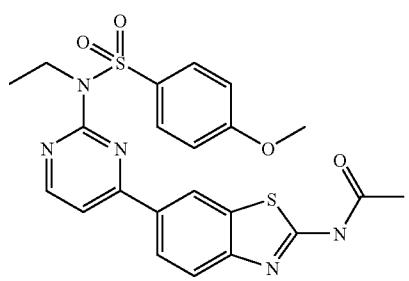 |
| 90 | 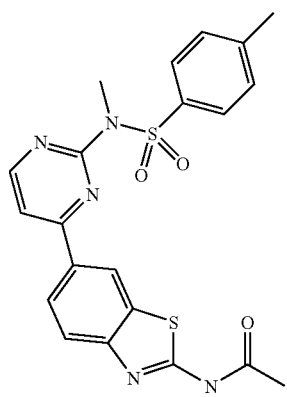 |

TABLE A-continued
| Example | Structure |
|---|---|
| 91 | 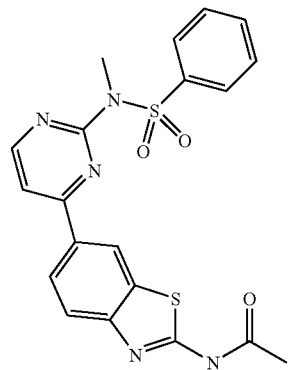 |
| 92 | 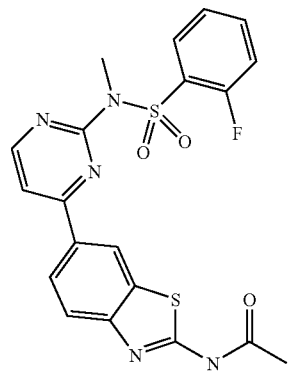 |
| 93 | 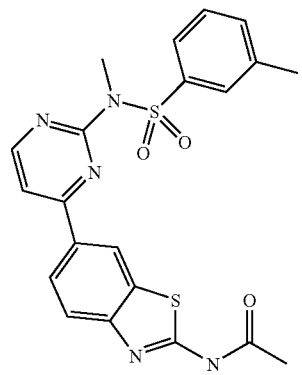 |
| 94 | 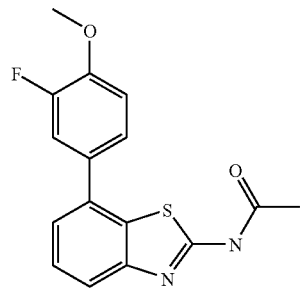 |

TABLE A-continued
| Example | Structure |
|---|---|
| 95 | 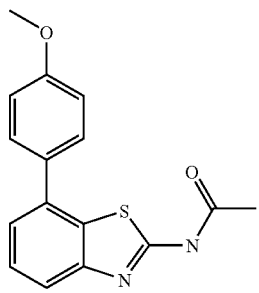 |
| 96 | 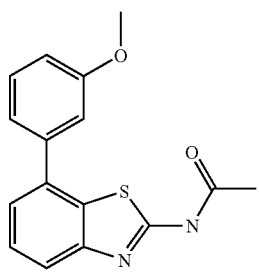 |
| 97 | 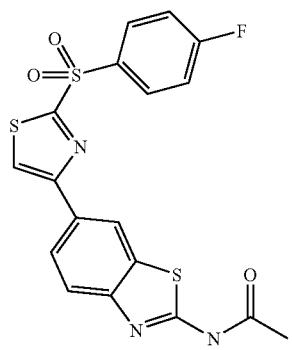 |
| 98 | 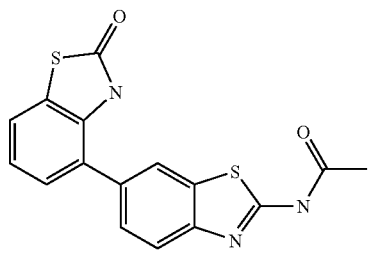 |
| 99 | 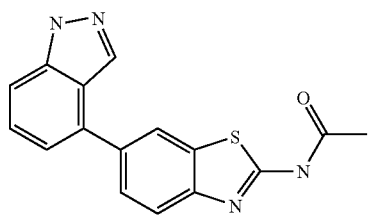 |

TABLE A-continued
| Example | Structure |
|---------|-----------|
| 100 | 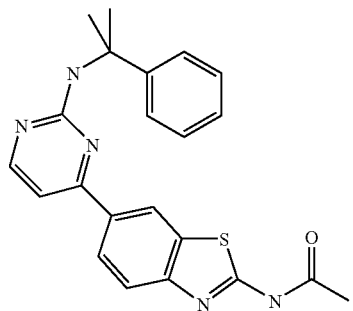 |
| 101 | 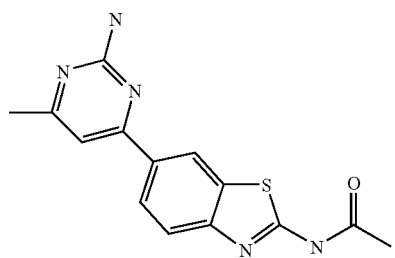 |
| 102 | 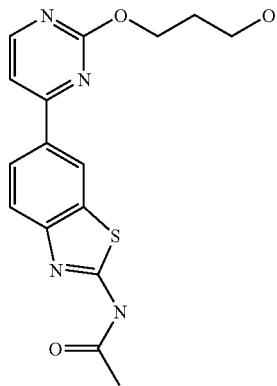 |
| 103 | 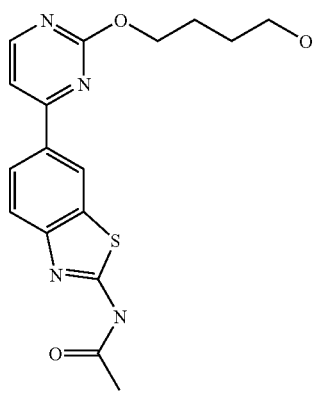 |

TABLE A-continued
| Example | Structure |
|---|---|
| 104 | 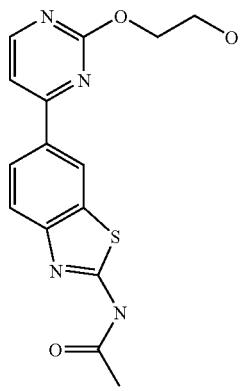 |
| 105 | 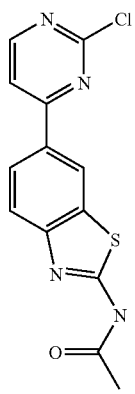 |
| 106 | 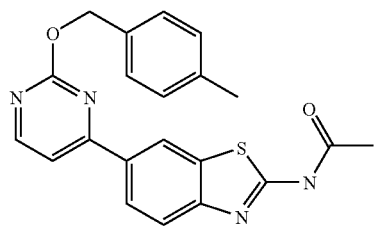 |
| 107 | 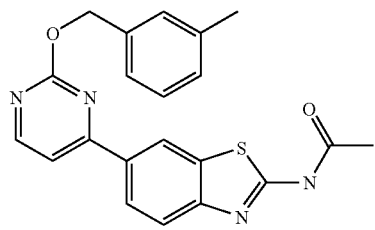 |
| 108 | 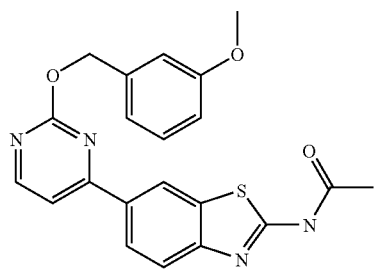 |

TABLE A-continued
| Example | Structure |
|---|---|
| 109 | 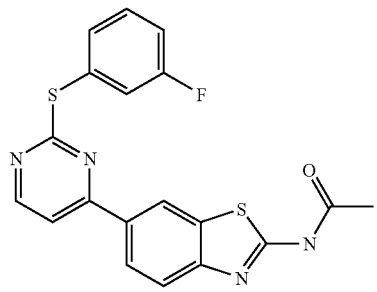 |
| 110 | 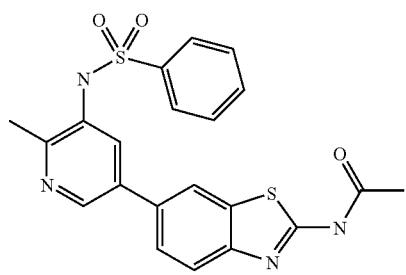 |
| 111 | 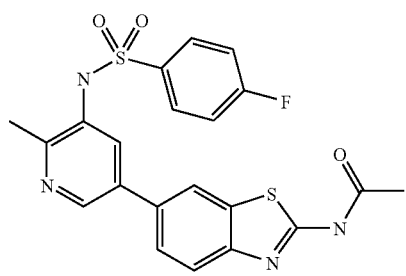 |
| 112 | 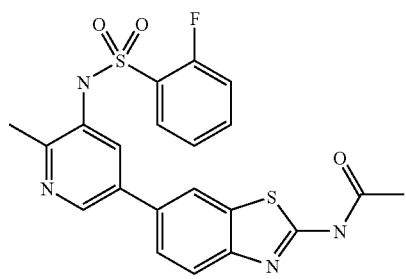 |
| 113 | 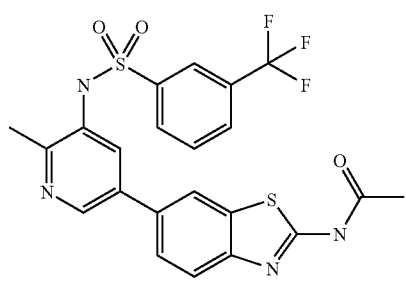 |

TABLE A-continued
| Example | Structure |
|---------|-----------|
| 114 | 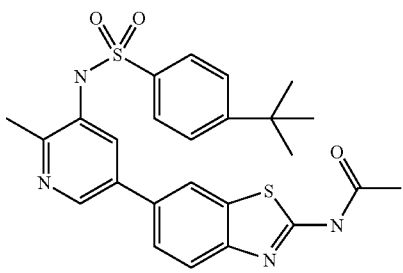 |
| 115 | 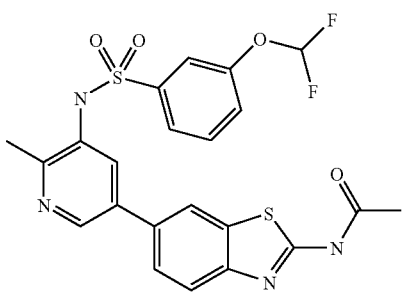 |
| 116 | 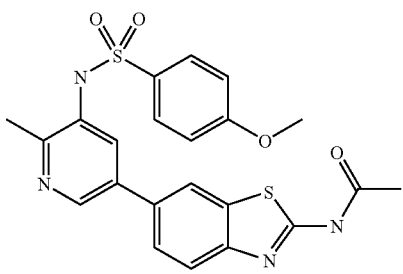 |
| 117 | 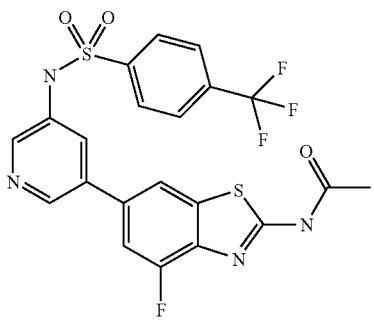 |
| 118 | 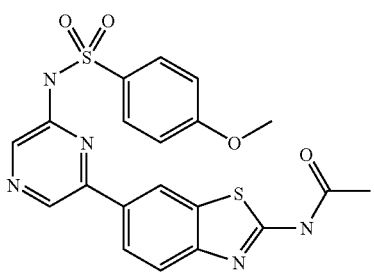 |

TABLE A-continued
| Example | Structure |
|---|---|
| 119 | 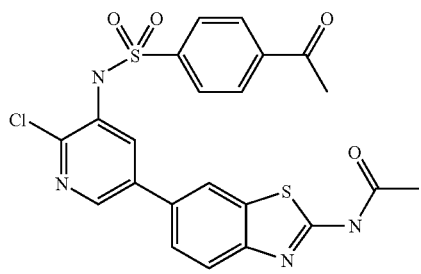 |
| 120 | 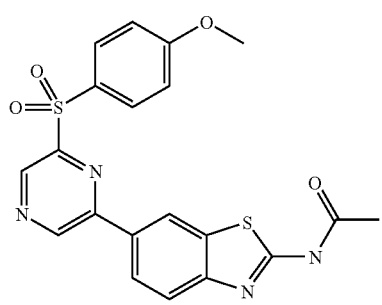 |
| 121 | 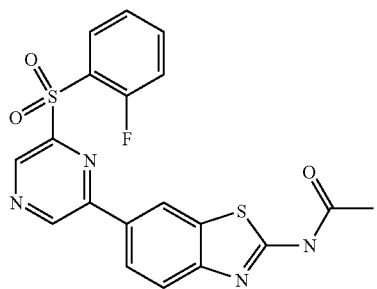 |
| 122 | 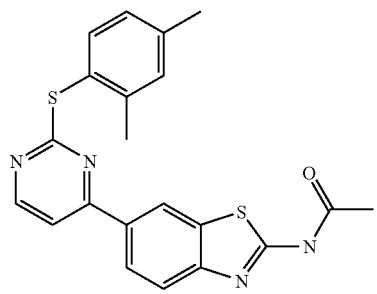 |
| 123 | 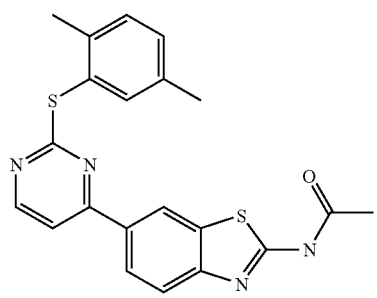 |

TABLE A-continued
| Example | Structure |
|---|---|
| 124 | 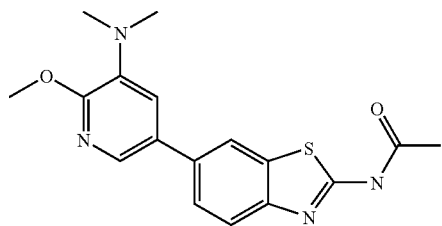 |
| 125 | 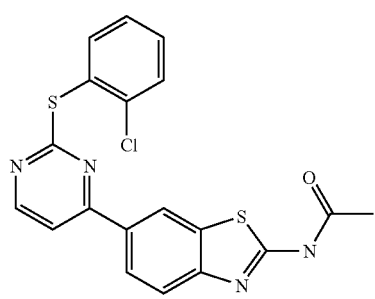 |
| 126 | 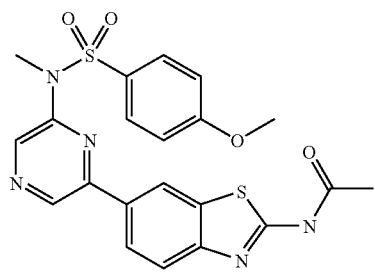 |
| 127 | 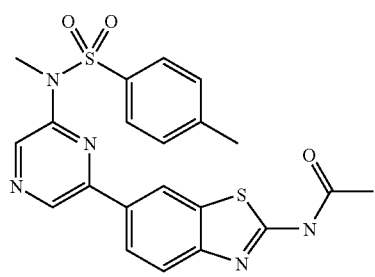 |
| 128 | 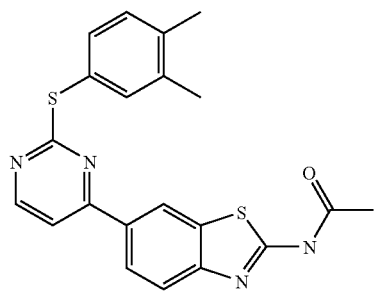 |

TABLE A-continued
| Example | Structure |
|---|---|
| 129 | 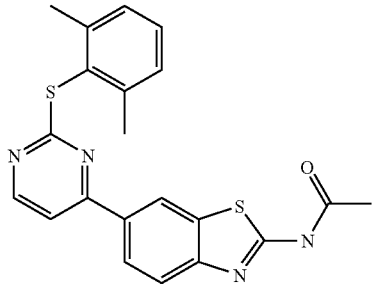 |
| 130 | 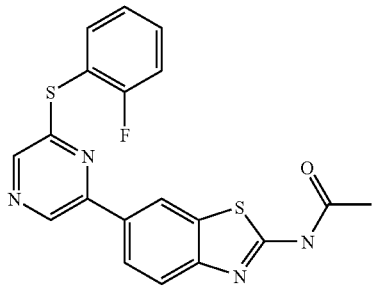 |
| 131 | 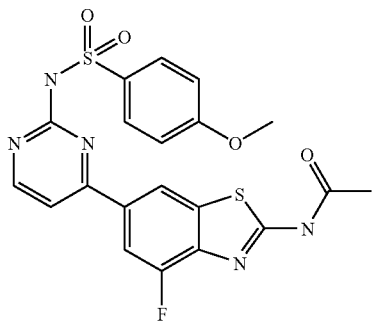 |
| 132 | 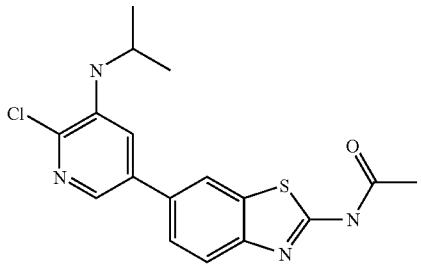 |
| 133 | 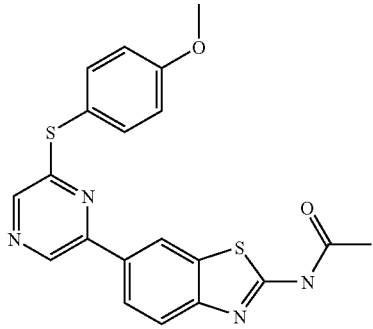 |

TABLE A-continued
| Example | Structure |
|---|---|
| 134 | 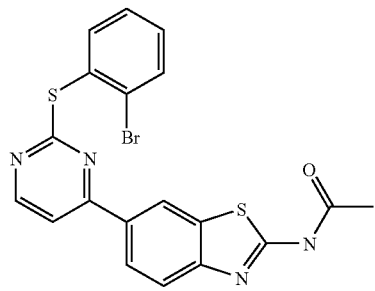 |
| 135 | 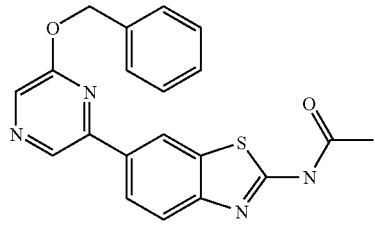 |
| 136 | 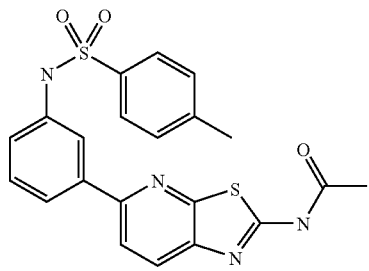 |
| 137 | 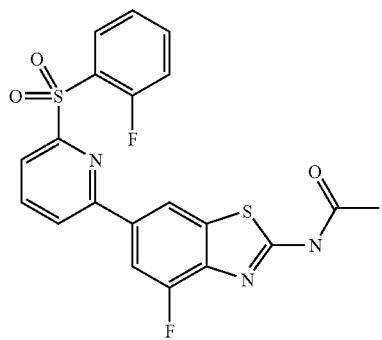 |
| 138 | 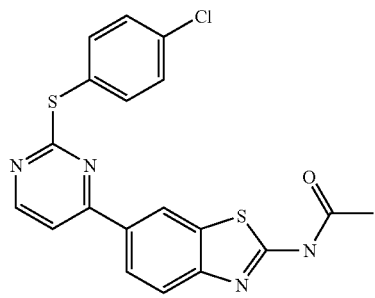 |

TABLE A-continued
| Example | Structure |
|---|---|
| 139 | 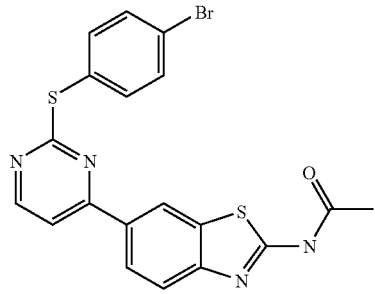 |
| 140 | 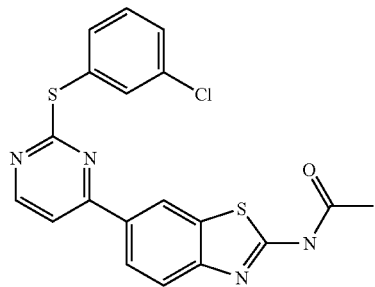 |
| 141 | 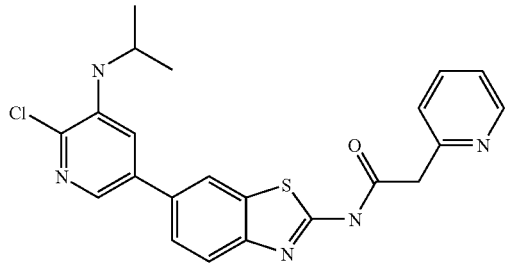 |
| 142 | 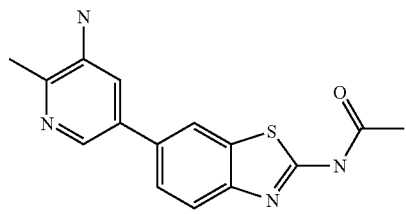 |
| 143 | 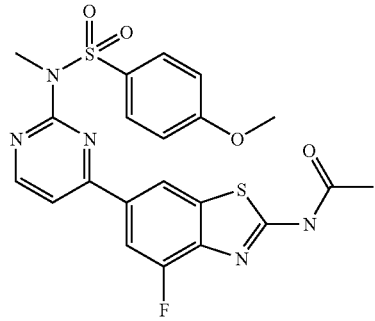 |

TABLE A-continued
| Example | Structure |
|---|---|
| 144 | 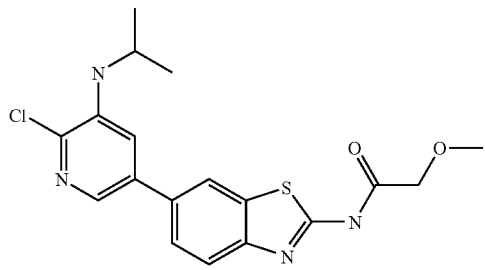 |
| 145 | 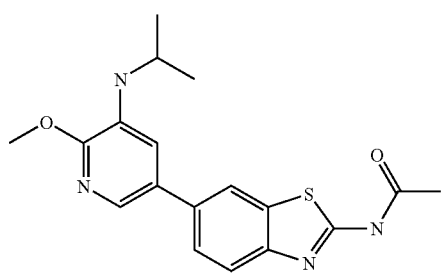 |
| 146 | 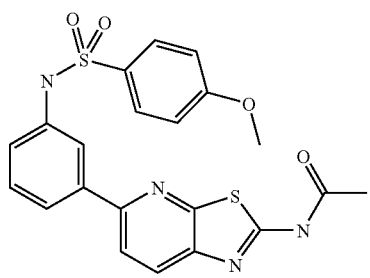 |
| 147 | 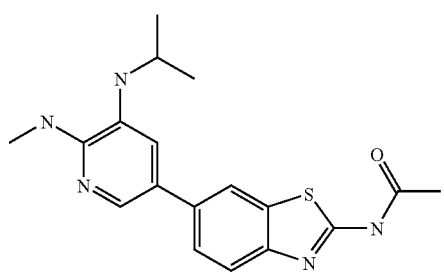 |
| 148 | 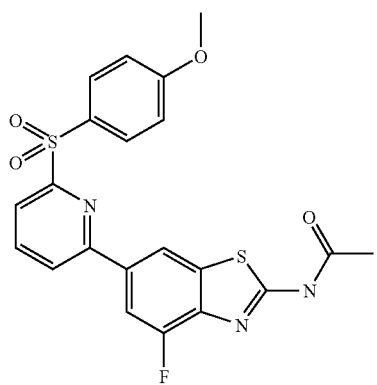 |

218
TABLE A-continued
| Example | Structure |
|---|---|
| 149 | 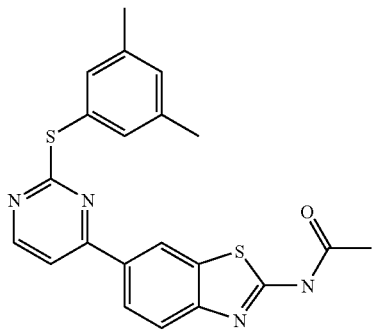 |
| 150 | 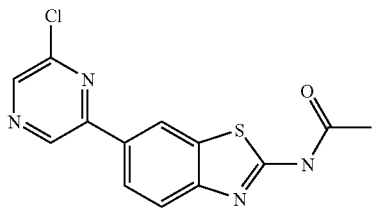 |
| 151 | 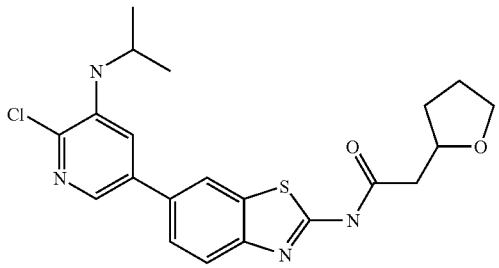 |
| 152 | 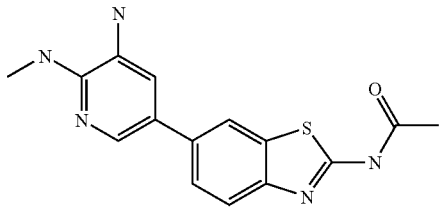 |
| 153 | 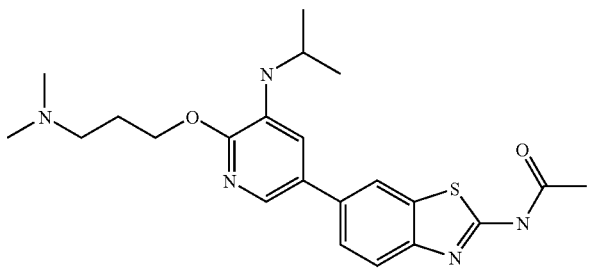 |

TABLE A-continued
| Example | Structure |
|---|---|
| 154 | 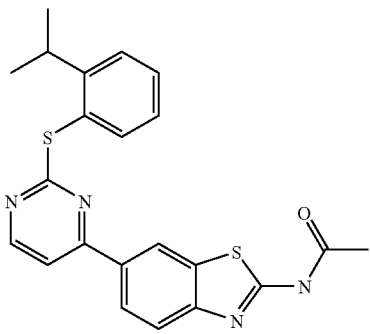 |
| 155 | 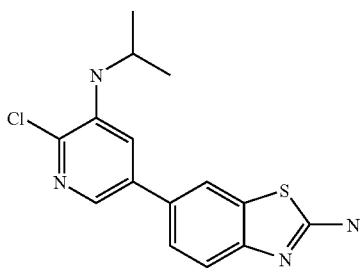 |
| 156 | 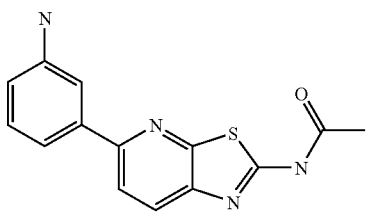 |
| 157 | 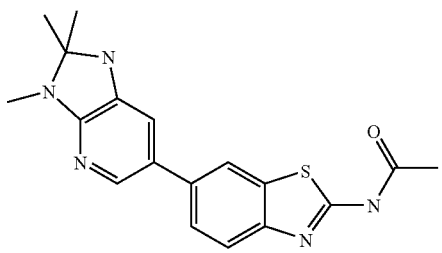 |
| 158 | 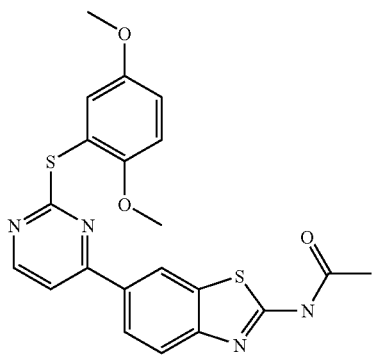 |

TABLE A-continued
| Example | Structure |
|---------|-----------|
| 159 | 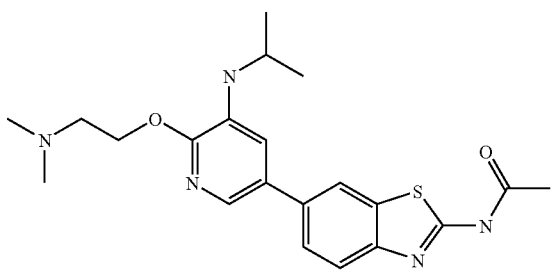 |
| 160 | 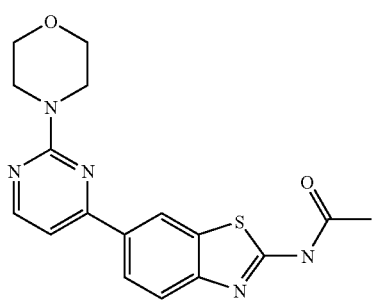 |
| 161 | 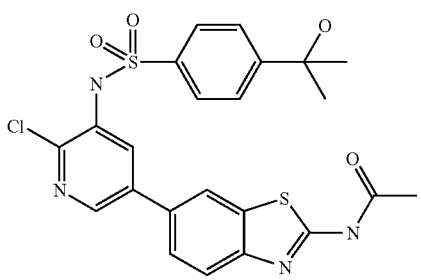 |
| 162 | 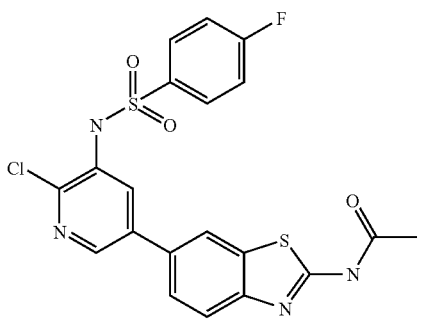 |
| 163 | 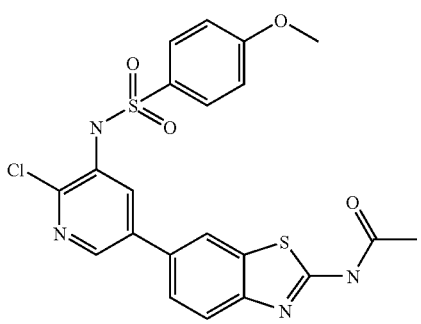 |

TABLE A-continued
| Example | Structure |
|---|---|
| 164 | 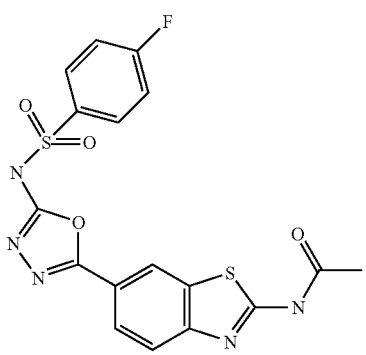 |
| 165 | 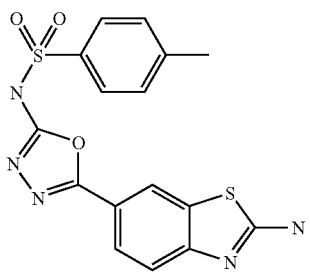 |
| 166 | 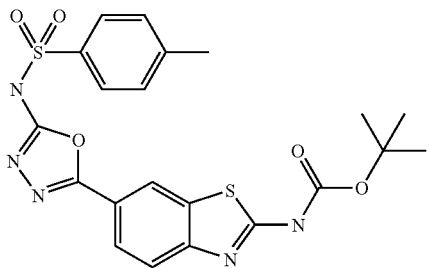 |
| 167 | 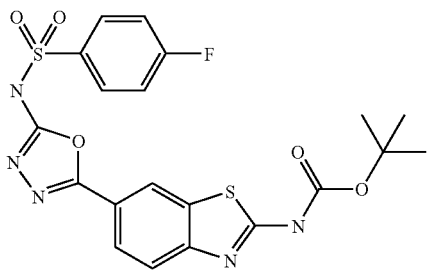 |
| 168 | 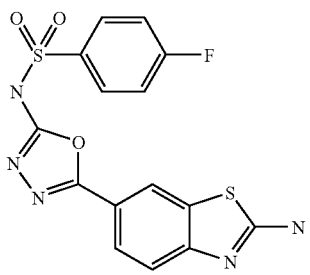 |

TABLE A-continued
| Example | Structure |
|---|---|
| 169 | 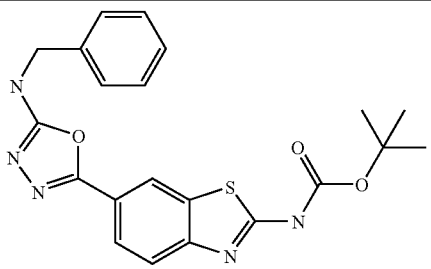 |
| 170 | 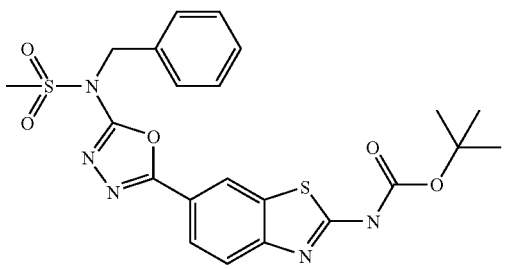 |
| 171 | 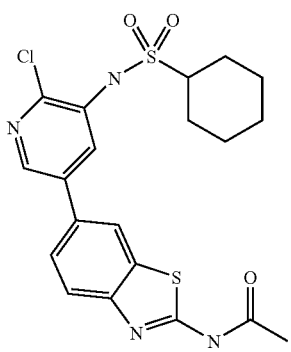 |
| 172 | 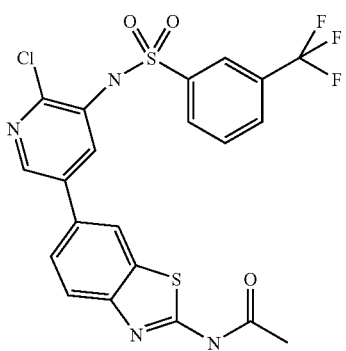 |
| 173 | 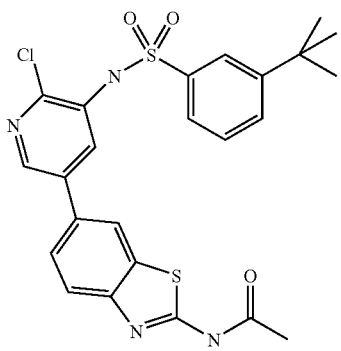 |

TABLE A-continued
| Example | Structure |
|---|---|
| 174 | 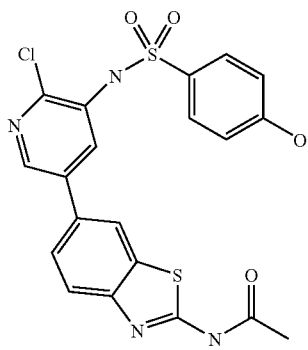 |
| 175 | 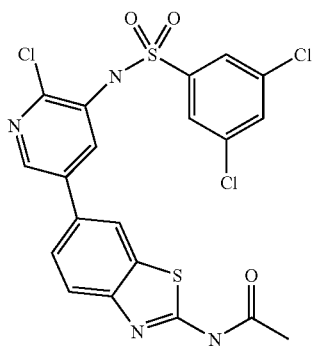 |
| 176 | 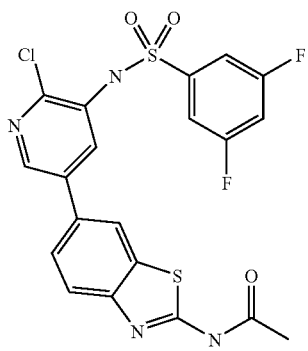 |
| 177 | 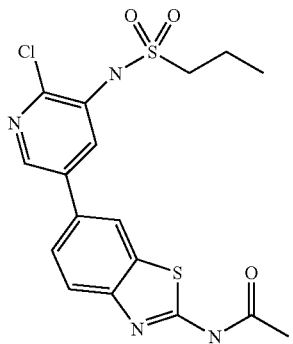 |

TABLE A-continued
| Example | Structure |
|---|---|
| 178 | 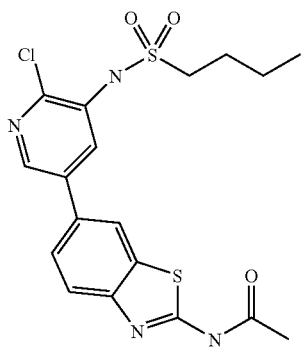 |
| 179 | 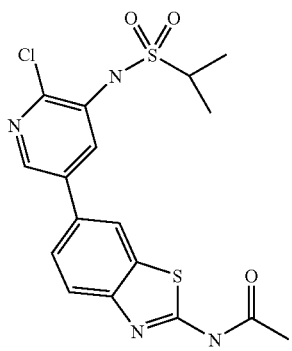 |
| 180 | 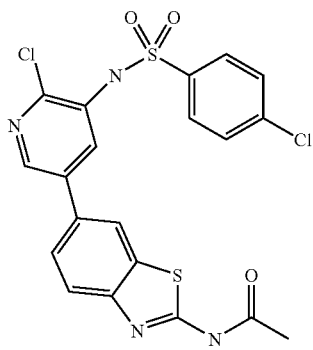 |
| 181 | 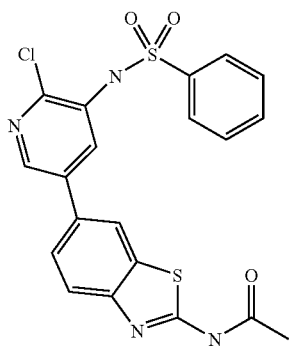 |

TABLE A-continued
| Example | Structure |
|---|---|
| 182 | 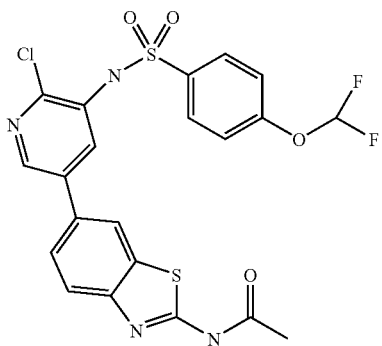 |
| 183 | 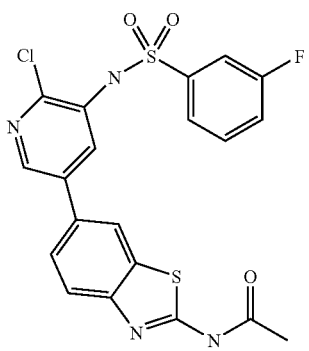 |
| 184 | 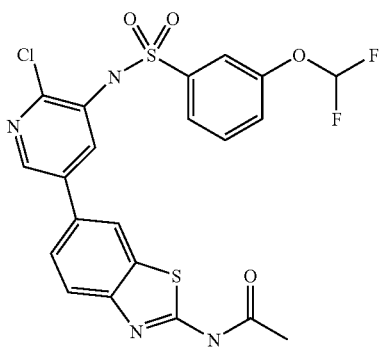 |
| 185 | 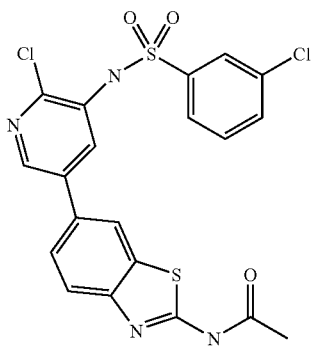 |

TABLE A-continued
| Example | Structure |
|---|---|
| 186 | 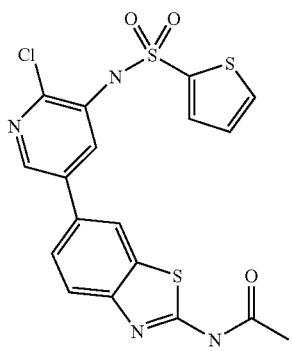 |
| 187 | 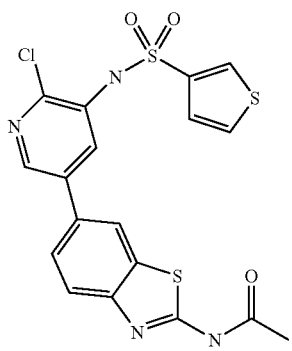 |
| 188 | 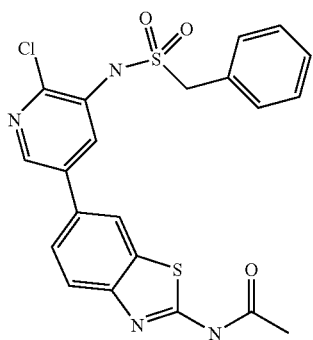 |
| 189 | 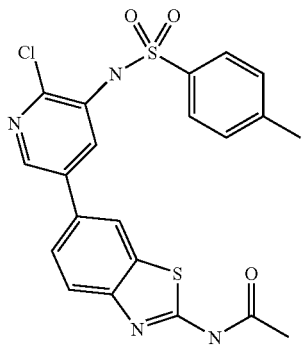 |

TABLE A-continued
| Example | Structure |
|---|---|
| 190 | 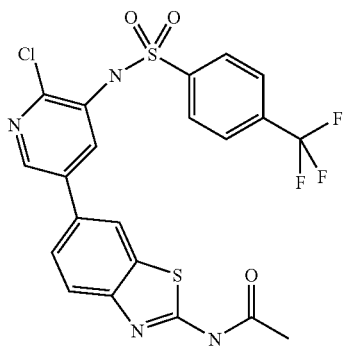 |
| 191 | 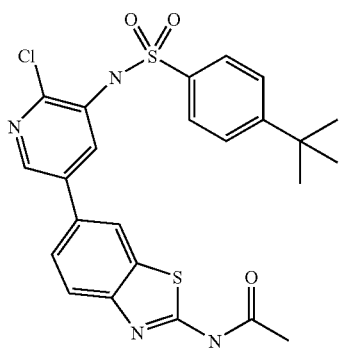 |
| 192 | 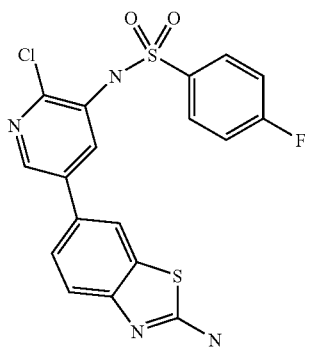 |
| 193 | 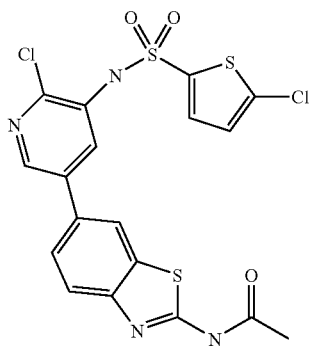 |

TABLE A-continued
| Example | Structure |
|---|---|
| 194 | 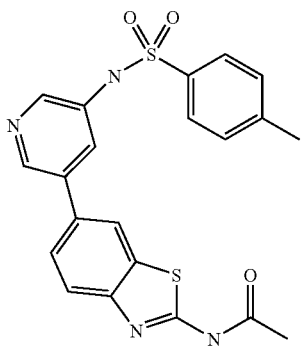 |
| 195 | 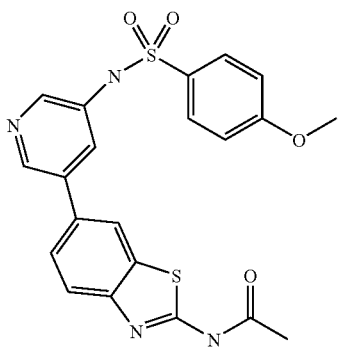 |
| 196 | 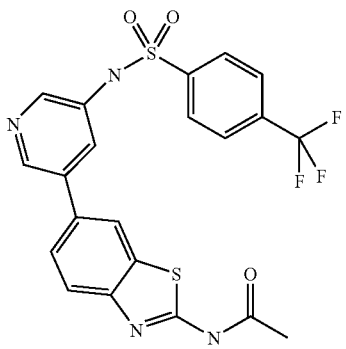 |
| 197 | 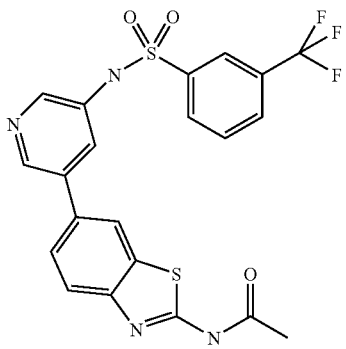 |

TABLE A-continued
| Example | Structure |
|---|---|
| 198 | 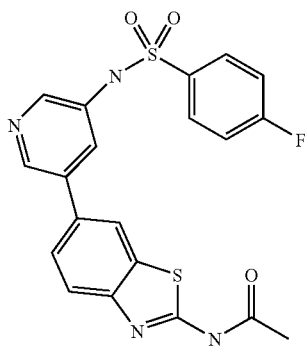 |
| 199 | 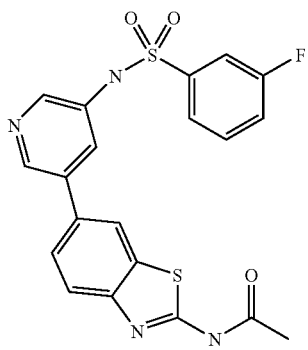 |
| 200 | 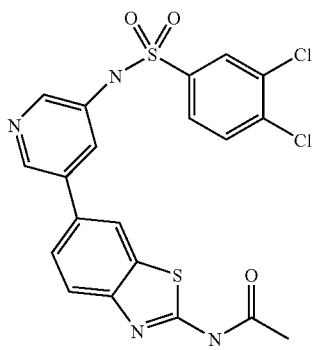 |
| 201 | 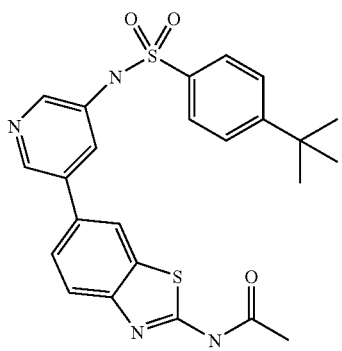 |

TABLE A-continued
| Example | Structure |
|---------|-----------|
| 202 | 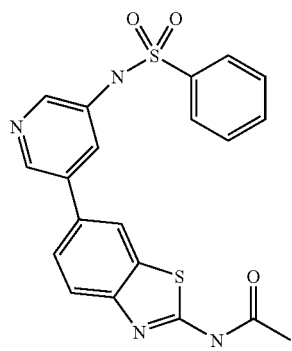 |
| 203 | 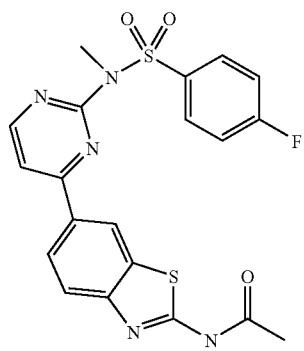 |
| 204 | 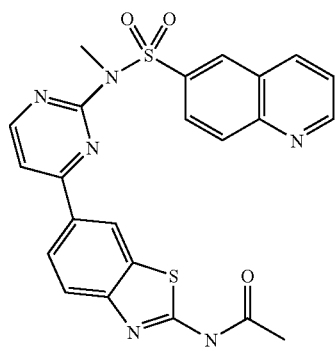 |
| 205 | 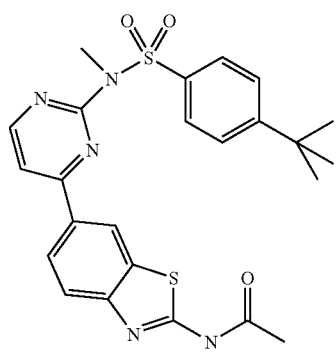 |

TABLE A-continued
| Example | Structure |
|---|---|
| 206 | 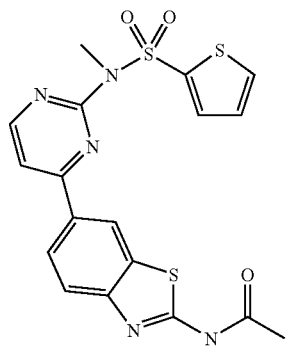 |
| 207 | 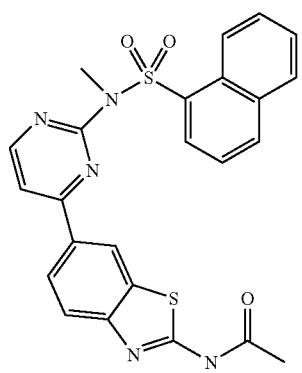 |
| 208 | 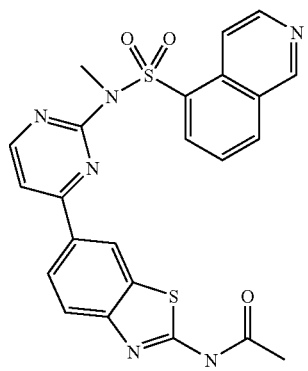 |
| 209 | 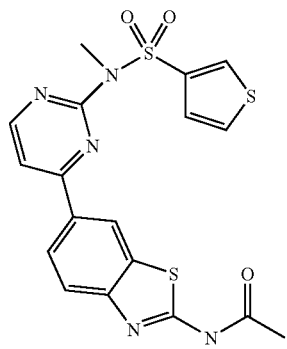 |

TABLE A-continued
| Example | Structure |
|---|---|
| 210 | 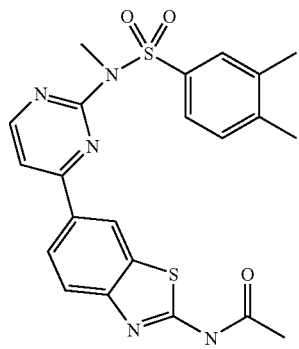 |
| 211 | 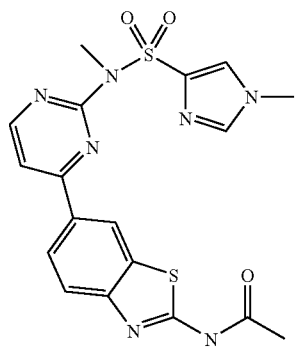 |
| 212 | 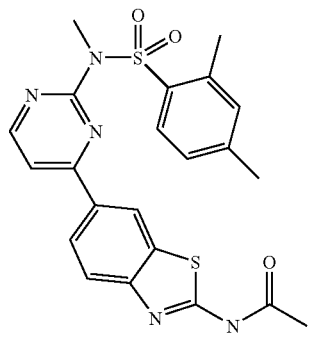 |
| 213 | 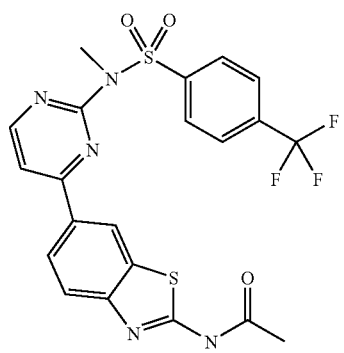 |

TABLE A-continued
| Example | Structure |
|---|---|
| 214 | 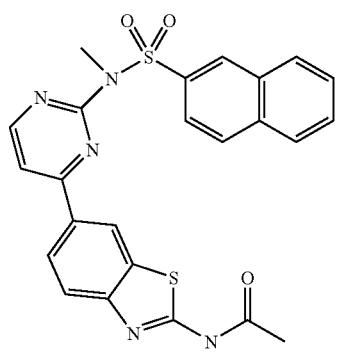 |
| 215 | 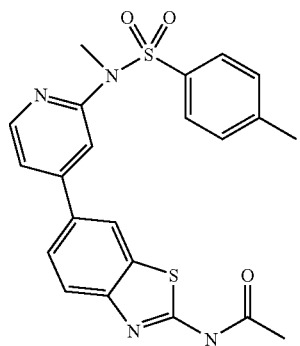 |
| 216 | 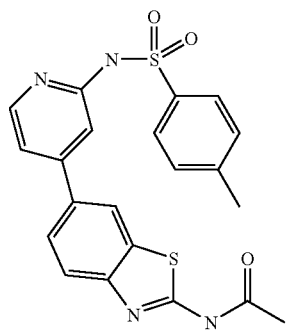 |
| 217 | 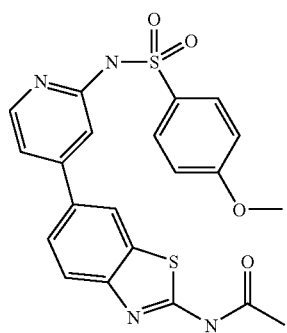 |

TABLE A-continued
| Example | Structure |
|---|---|
| 218 | 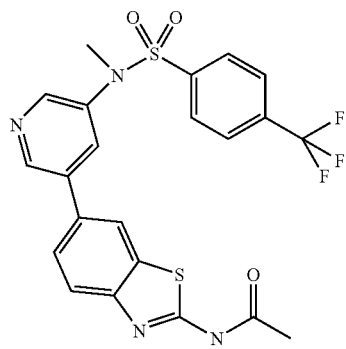 |
| 219 | 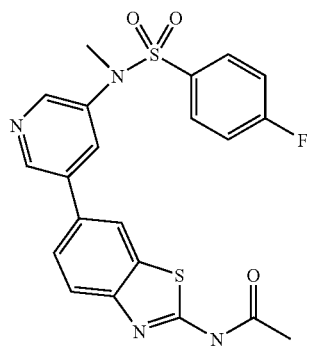 |
| 220 | 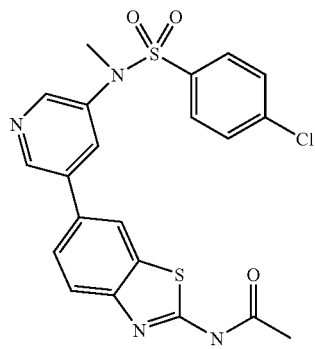 |
| 221 | 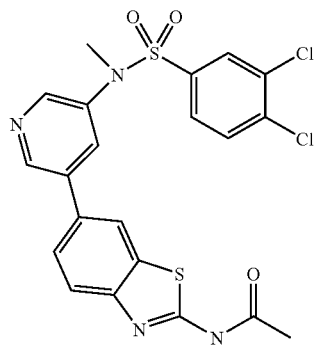 |

TABLE A-continued
| Example | Structure |
|---|---|
| 222 | 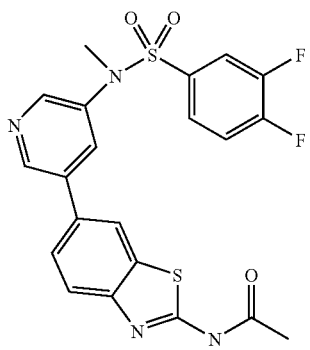 |
| 223 | 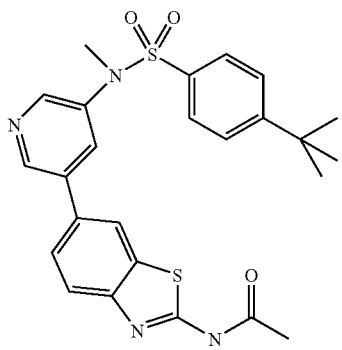 |
| 224 | 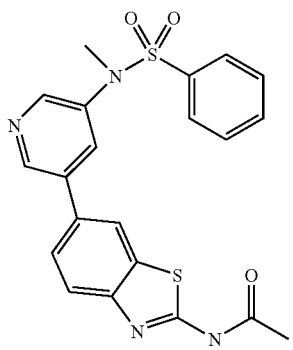 |
| 225 | 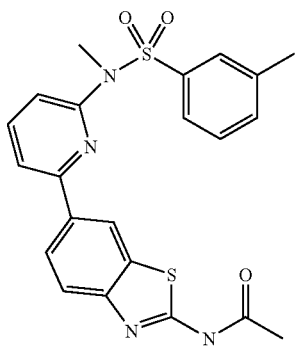 |

TABLE A-continued
| Example | Structure |
|---|---|
| 226 | 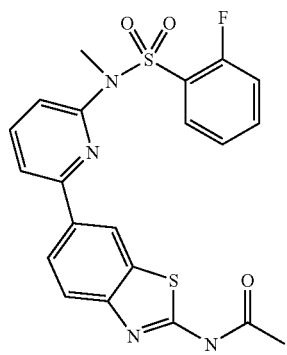 |
| 227 | 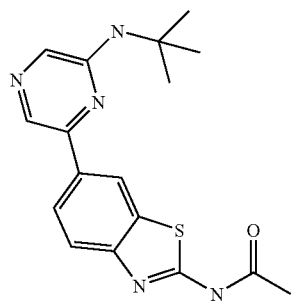 |
| 228 | 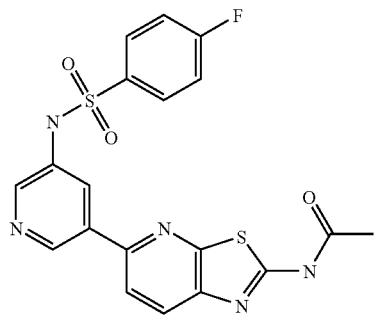 |
| 229 | 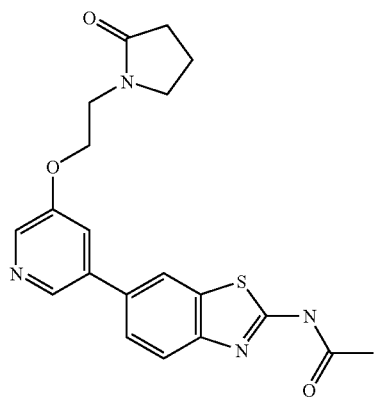 |

TABLE A-continued
| Example | Structure |
|---------|-----------|
| 230 | 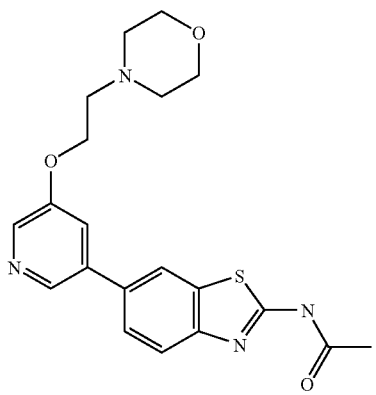 |
| 231 | 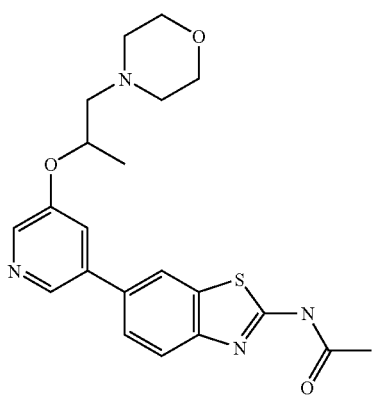 |
| 232 | 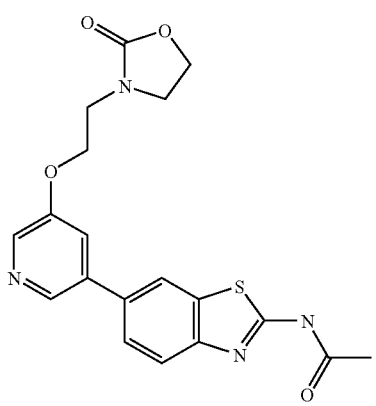 |
| 233 | 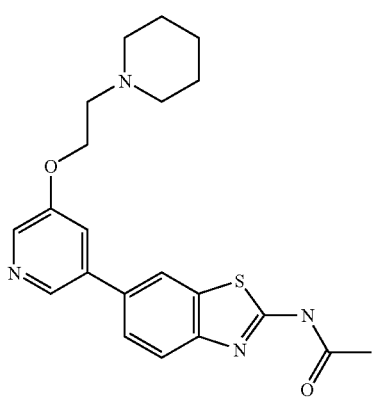 |

TABLE A-continued
| Example | Structure |
|---|---|
| 234 | 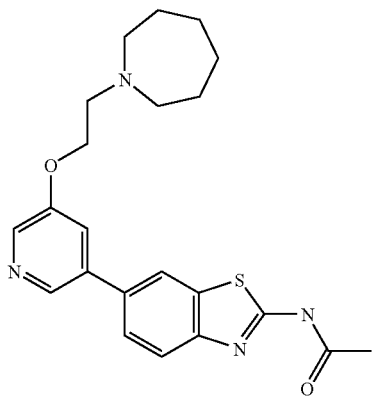 |
| 235 | 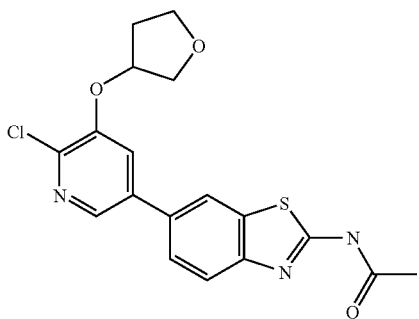 |
| 235 | 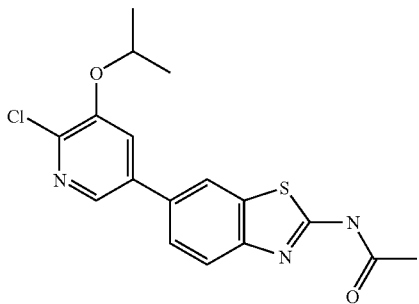 |
| 236 | 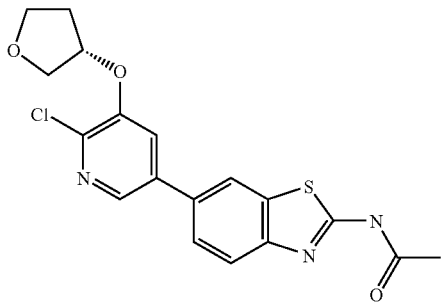 |
| 237 | 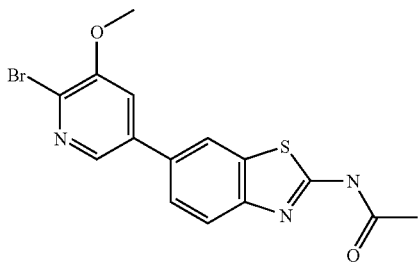 |

TABLE A-continued
| Example | Structure |
|---|---|
| 238 | 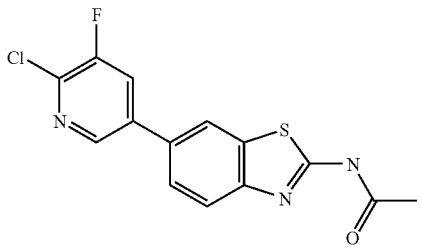 |
| 239 | 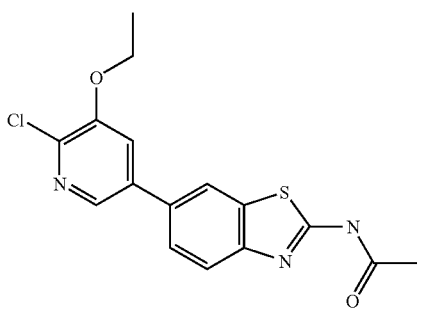 |
| 240 | 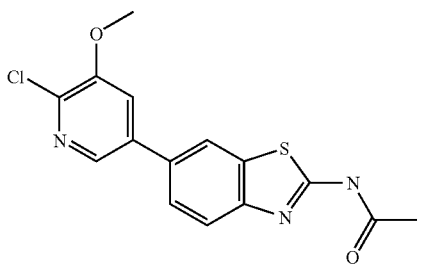 |
| 241 | 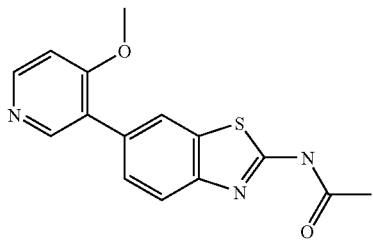 |
| 242 | 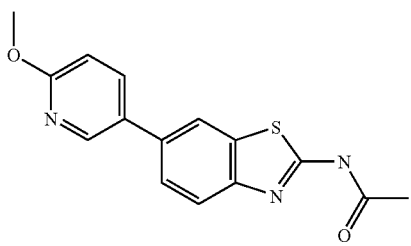 |

TABLE A-continued

| Example | Structure |
|---|---|
| 243 | (6-ethoxypyridin-3-yl)-benzothiazol-2-yl acetamide |
| 244 | (6-methoxy-4-methylpyridin-3-yl)-benzothiazol-2-yl acetamide |
| 245 | (4-methylpyridin-3-yl)-benzothiazol-2-yl acetamide |
| 246 | (6-chloro-4-methoxypyridin-3-yl)-benzothiazol-2-yl acetamide |
| 247 | (6-chloro-5-(difluoromethoxy)pyridin-3-yl)-benzothiazol-2-yl acetamide |
| 248 | (4-(difluoromethoxy)pyridin-3-yl)-benzothiazol-2-yl acetamide |

TABLE A-continued
| Example | Structure |
|---|---|
| 249 | 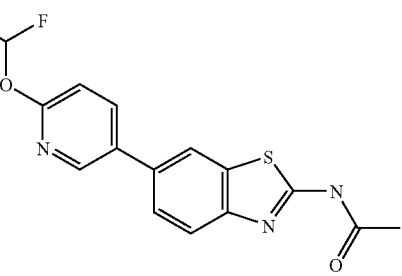 |
| 250 | 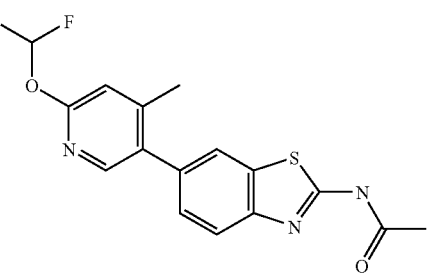 |
| 251 | 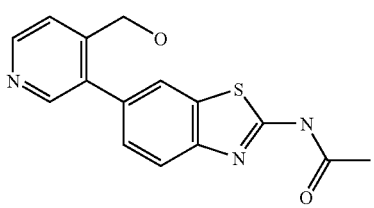 |
| 252 | 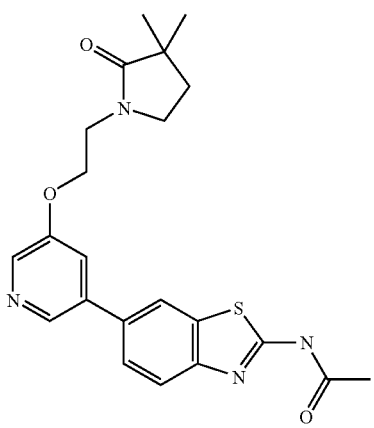 |
| 253 | 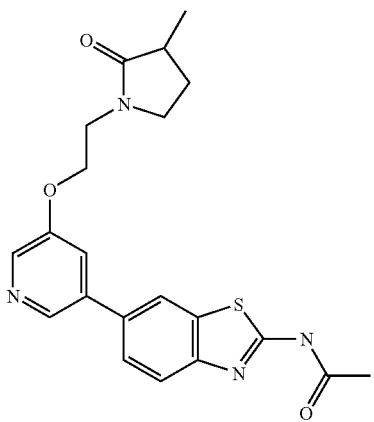 |

TABLE A-continued
| Example | Structure |
|---|---|
| 254 | 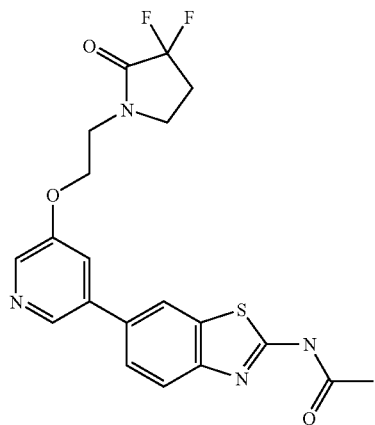 |
| 255 | 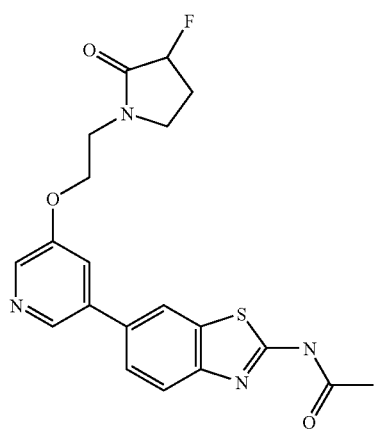 |
| 256 | 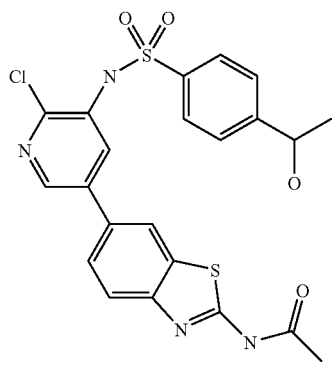 |

TABLE A-continued
| Example | Structure |
|---|---|
| 257 | Enantiomer A 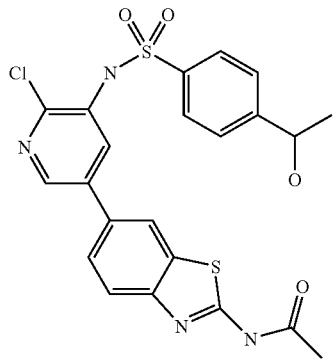 |
| 258 | Enantiomer B 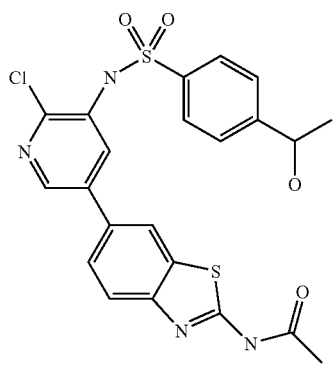 |
| 259 | 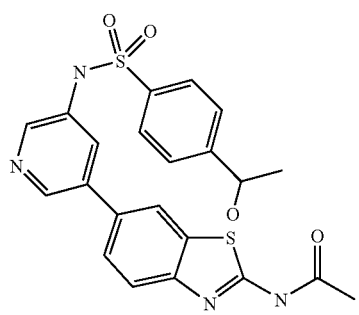 |
| 260 | 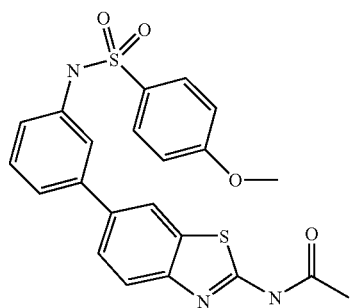 |

TABLE A-continued
| Example | Structure |
|---|---|
| 261 | 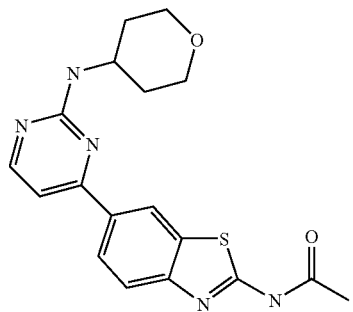 |
| 262 | 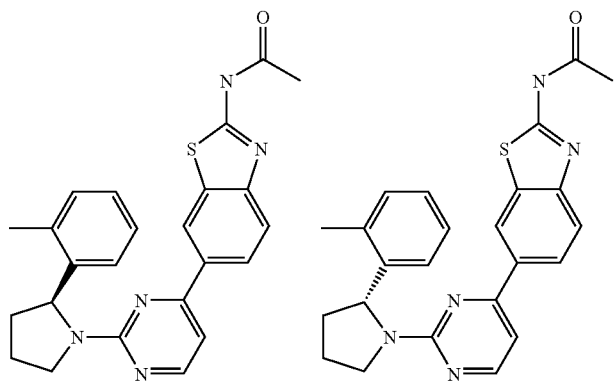 |
| 263 | 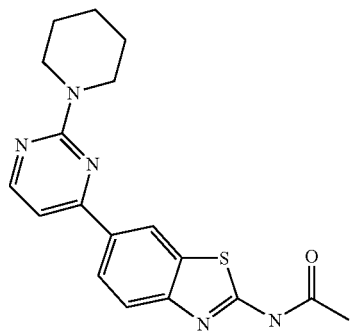 |
| 264 | 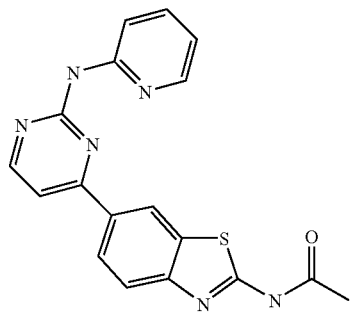 |

TABLE A-continued
| Example | Structure |
|---|---|
| 265 | 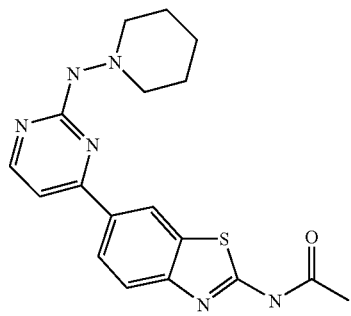 |
| 266 | 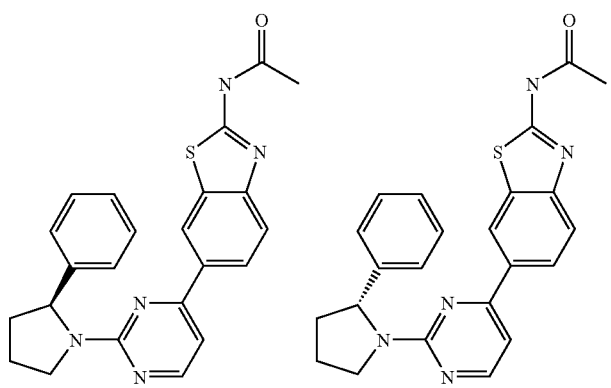 |
| 267 | 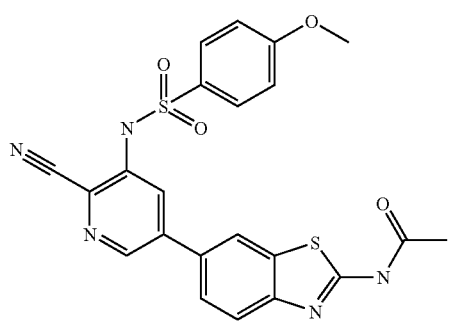 |
| 268 | 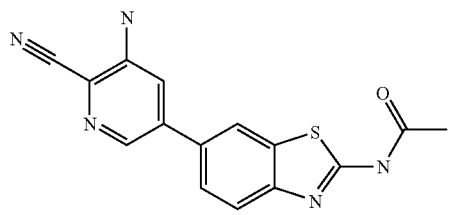 |
| 269 | 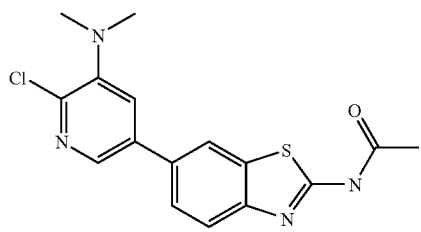 |

TABLE A-continued
| Example | Structure |
|---|---|
| 270 | 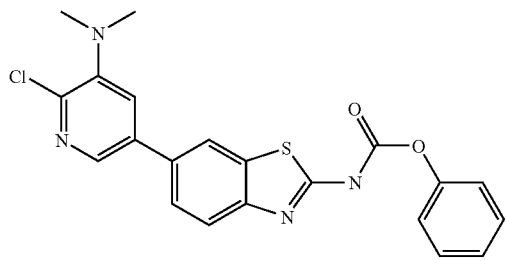 |
| 271 | 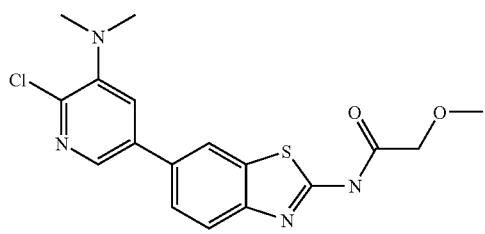 |
| 272 | 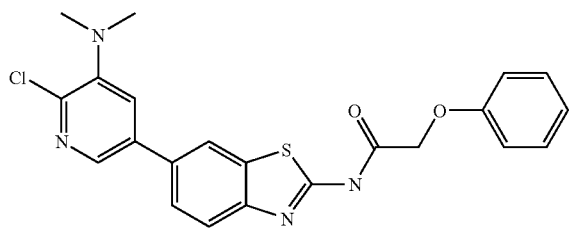 |
| 273 | 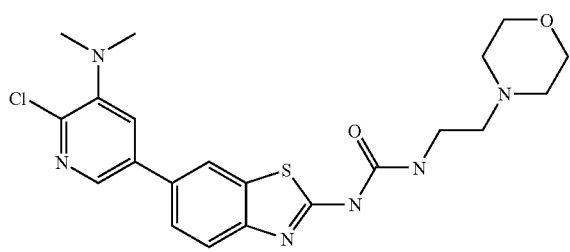 |
| 274 | 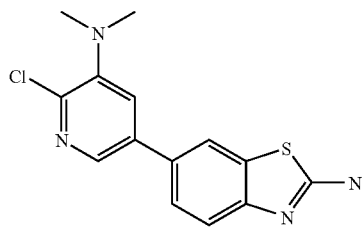 |
| 275 | 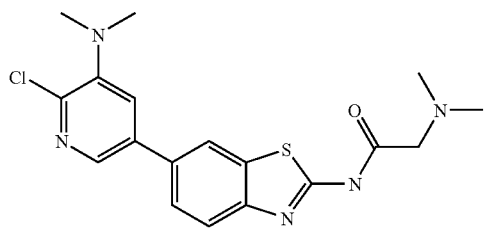 |

TABLE A-continued
| Example | Structure |
|---------|-----------|
| 276 | 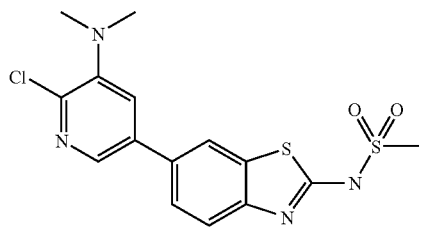 |
| 277 | 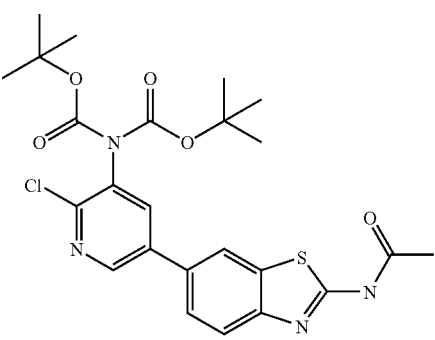 |
| 288 | 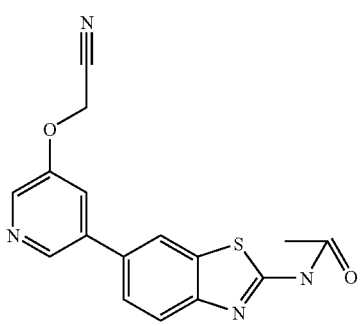 |
| 289 | 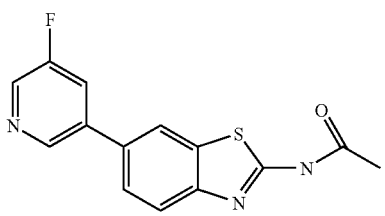 |
| 290 | 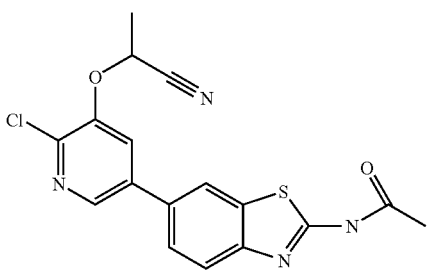 |

TABLE A-continued
| Example | Structure |
|---|---|
| 291 | 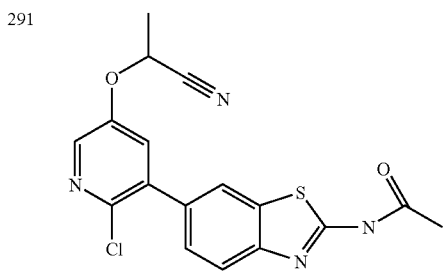 |
| 292 | 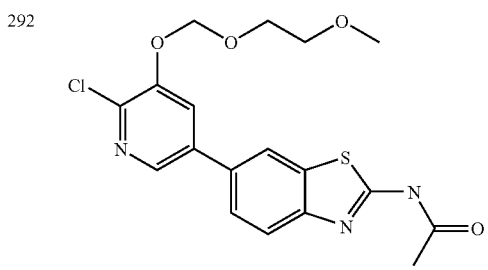 |
| 293 | 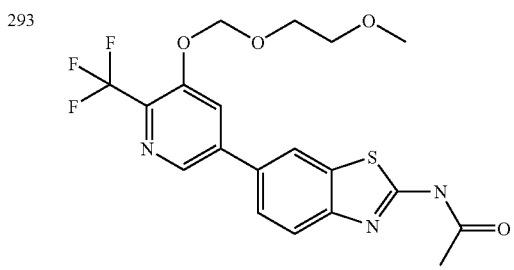 |
| 294 | 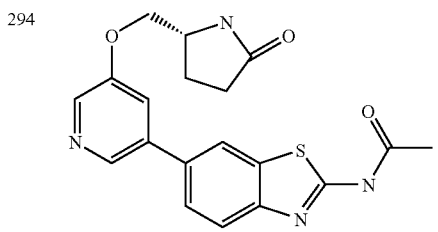 |
| 295 | 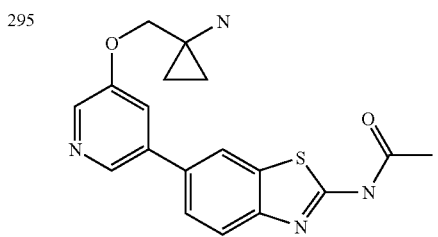 |
| 296 | 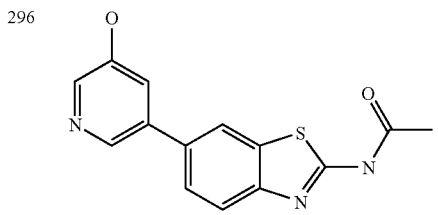 |

TABLE A-continued
| Example | Structure |
|---------|-----------|
| 297 | 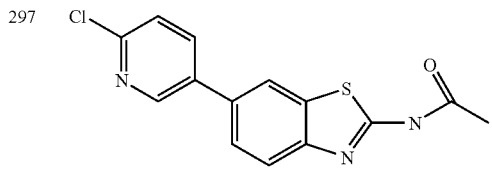 |
| 298 | 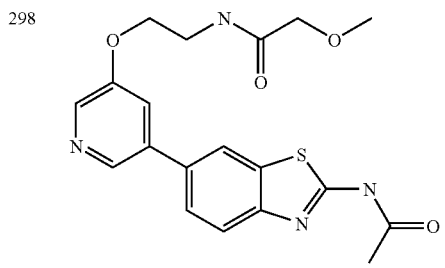 |
| 300 | 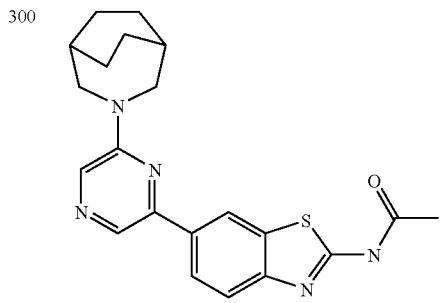 |
| 301 | 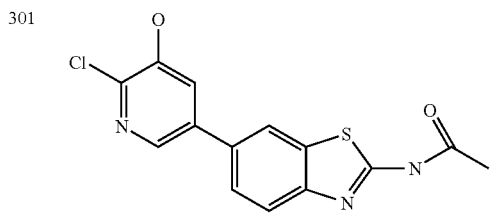 |
| 302 | 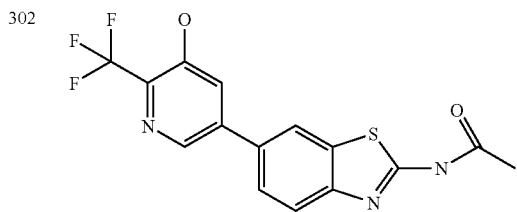 |
| 303 | 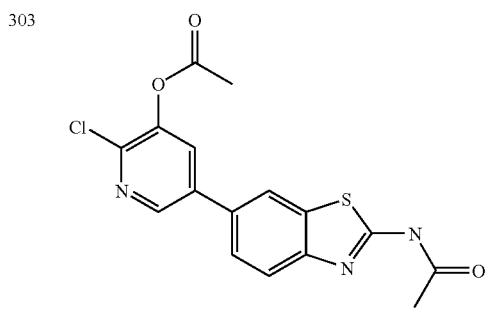 |

TABLE A-continued
| Example | Structure |
|---------|-----------|
| 304 | 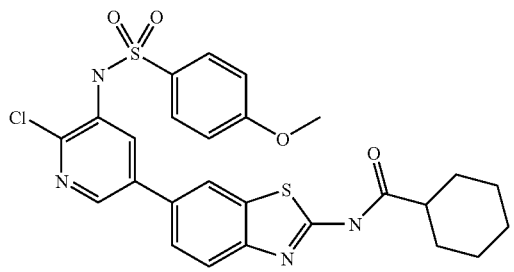 |
| 305 | 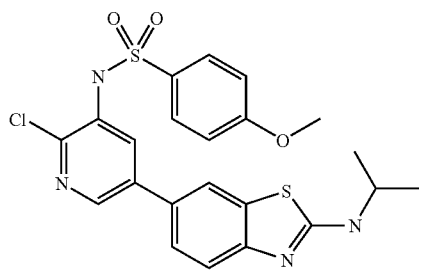 |
| 306 | 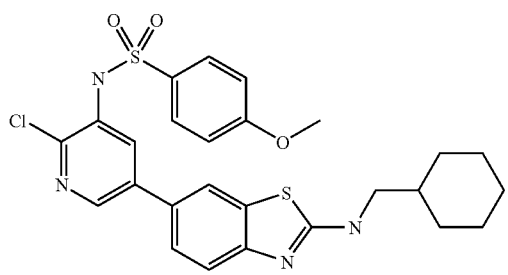 |
| 307 | 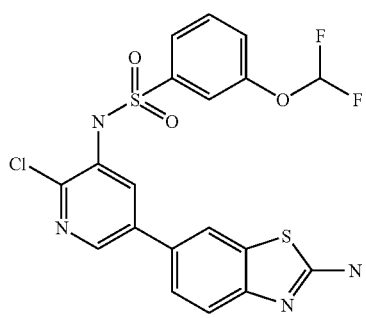 |
| 308 | 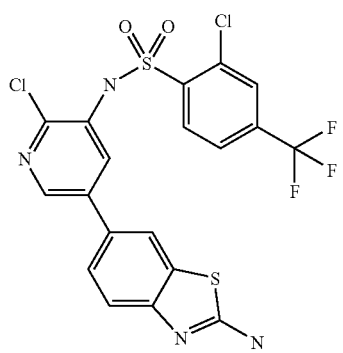 |

TABLE A-continued
| Example | Structure |
|---------|-----------|
| 309 | 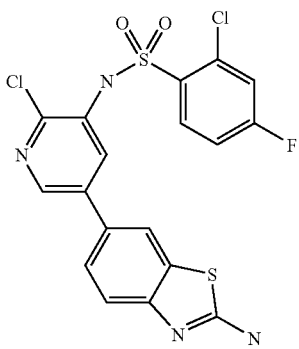 |
| 310 | 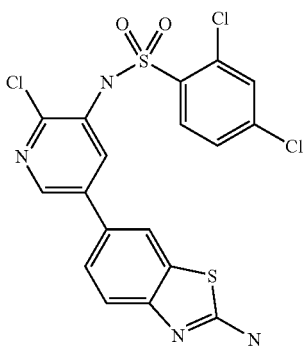 |
| 311 | 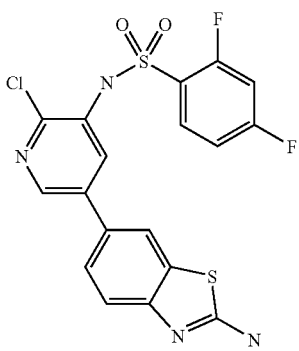 |
| 312 | 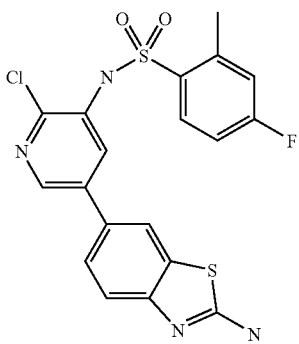 |

TABLE A-continued
| Example | Structure |
|---------|-----------|
| 313 | 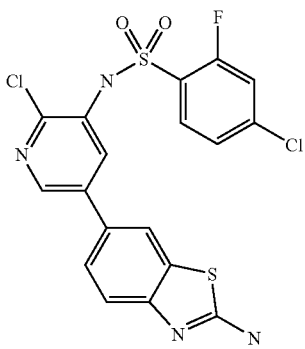 |
| 314 | 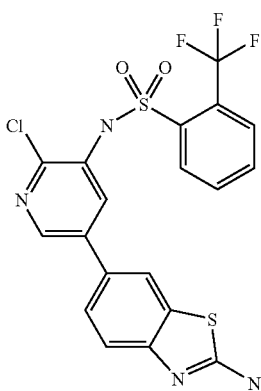 |
| 315 | 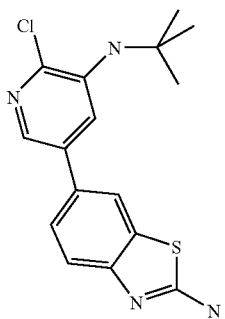 |
| 316 | 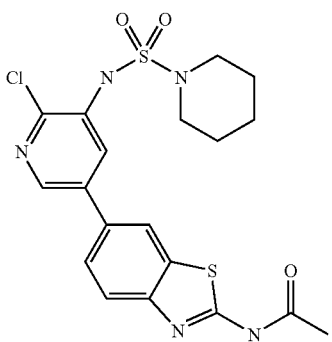 |

TABLE A-continued
| Example | Structure |
|---------|-----------|
| 317 | 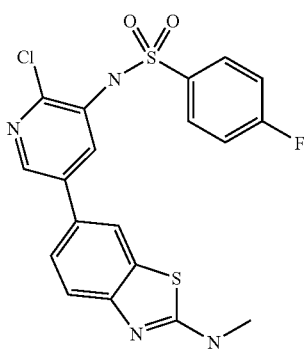 |
| 318 | 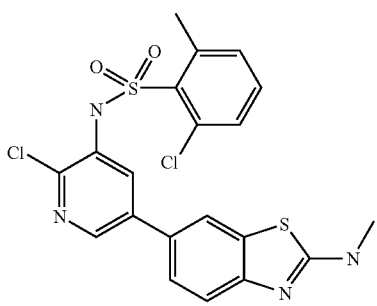 |
| 319 | 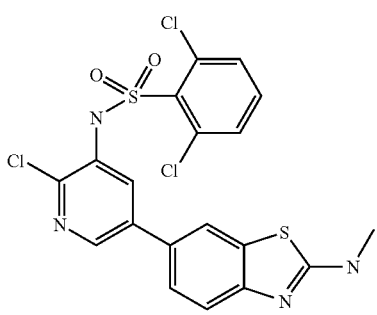 |
| 320 | 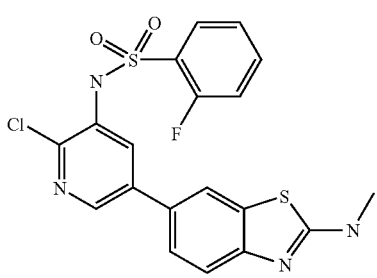 |
| 321 | 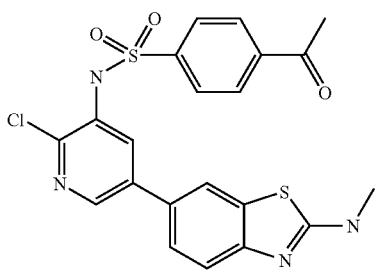 |

TABLE A-continued
| Example | Structure |
|---|---|
| 322 | 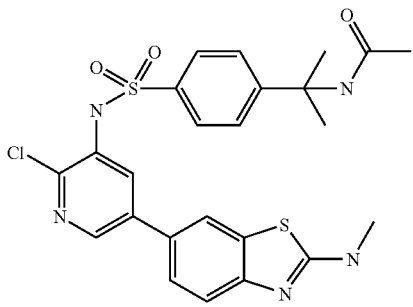 |
| 323 | 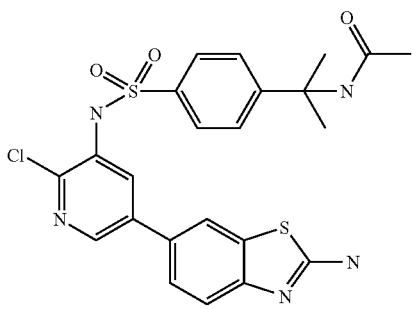 |
| 324 | 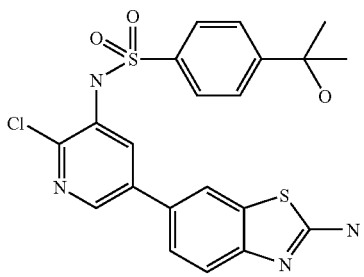 |
| 325 | 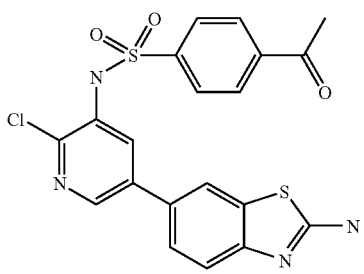 |
| 326 | 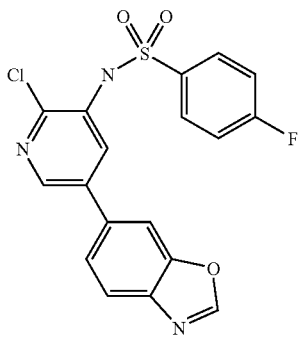 |

TABLE A-continued
| Example | Structure |
|---|---|
| 327 | 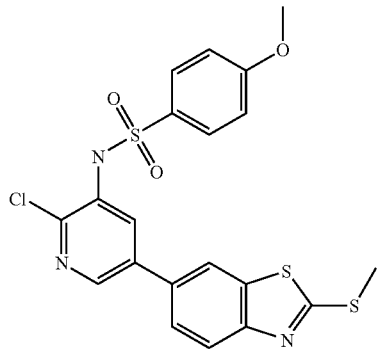 |
| 334 | 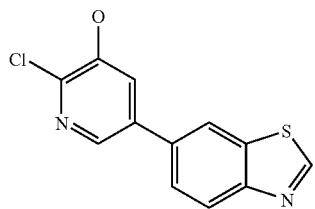 |
| 335 | 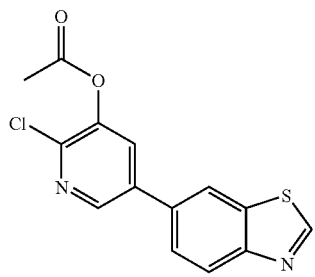 |
| 336 | 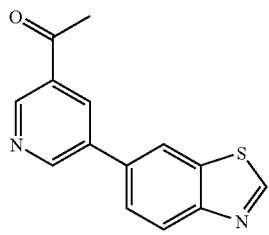 |
| 341 | 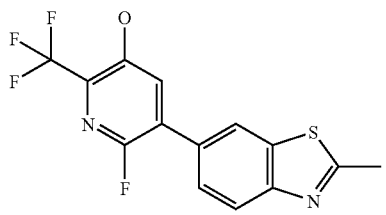 |

TABLE I

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 1 | N-(6-(2-(3-(3-pyridinyl)propoxy)-4-pyrimidinyl)-1,3-benzothiazol-2-yl)acetamide | A | 406 | 0.2584 | 3.6065 | 1.3481 |
| 2 | N-(6-(2-(3-pyridinylmethoxy)-4-pyrimidinyl)-1,3-benzothiazol-2-yl)acetamide | A | 378 | 0.4520 | >40 | 0.7890 |
| 3 | N-(6-(2-(benzyloxy)-4-pyrimidinyl)-1,3-benzothiazol-2-yl)acetamide | A | 377 | 0.0956 | 0.2405 | 3.5141 |
| 4 | N-(6-(2-(3-phenylpropoxy)-4-pyrimidinyl)-1,3-benzothiazol-2-yl)acetamide | A | 405 | 0.1508 | 0.3855 | 2.3670 |
| 5 | N-(6-(2-(3-methoxypropoxy)-4-pyrimidinyl)-1,3-benzothiazol-2-yl)acetamide | A | 359 | 1.0624 | >40 | |
| 6 | N-(6-(2-(1-methylethoxy)-4-pyrimidinyl)-1,3-benzothiazol-2-yl)acetamide | A | 329 | 0.2398 | 2.1405 | 0.9195 |
| 7 | N-(6-(2-(2-phenylethoxy)-4-pyrimidinyl)-1,3-benzothiazol-2-yl)acetamide | A | 391 | 0.2263 | 2.6095 | >25 |
| 8 | N-(6-(2-(3-dimethylamino)propoxy)-4-pyrimidinyl)-1,3-benzothiazol-2-yl)acetamide | A | 374 | 11.0975 | >40 | |
| 9 | N-(6-(2-(2-dimethylamino)ethoxy)-4-pyrimidinyl)-1,3-benzothiazol-2-yl)acetamide | A | 360 | 6.0739 | >40 | |
| 10 | N-(6-(2-(3-morpholino)propoxy)-4-pyrimidinyl)-1,3-benzothiazol-2-yl)acetamide | A | 416 | 0.1994 | 11.0241 | 0.8006 |
| 11 | N-(6-(2-(2-morpholino)ethoxy)-4-pyrimidinyl)-1,3-benzothiazol-2-yl)acetamide | A | 402 | 6.4359 | >40 | |
| 12 | N-(6-(2-((3-fluorobenzyl)oxy)-4-pyrimidinyl)-1,3-benzothiazol-2-yl)acetamide | A | 395 | 0.4268 | 3.9630 | 3.9267 |
| 13 | N-(6-(2-benzyl-4-pyrimidinyl)-1,3-benzothiazol-2-yl)acetamide | B | 361 | 4.4757 | >40 | |
| 14 | N-(6-(2-(3-phenylpropyl)-4-pyrimidinyl)-1,3-benzothiazol-2-yl)acetamide | B | 389 | 2.7528 | 10.6505 | |
| 15 | N-(6-(2-(2-phenylethyl)-4-pyrimidinyl)-1,3-benzothiazol-2-yl)acetamide | B | 375 | 9.1504 | 6.4721 | |
| 16 | N-(6-(2-((4-methoxyphenyl)sulfanyl)-4-pyrimidinyl)-1,3-benzothiazol-2-yl)acetamide | C | 409 | 0.0535 | 0.1064 | 0.8251 |
| 17 | N-(6-(2-(4-pyridinylmethoxy)-4-pyrimidinyl)-1,3-benzothiazol-2-yl)acetamide | C | 378 | 0.5228 | 11.0661 | 1.0627 |
| 18 | N-(6-(2-(2-(3-pyridinyl)ethoxy)-4-pyrimidinyl)-1,3-benzothiazol-2-yl)acetamide | C | 392 | 1.0984 | 32.1646 | |
| 19 | N-(6-(2-(benzylsulfanyl)-4-pyrimidinyl)-1,3-benzothiazol-2-yl)acetamide | C | 393 | 0.0668 | 0.1844 | 0.6695 |
| 20 | N-(6-(2-(3-(1H-1,2,3-triazol-1-yl)propoxy)-4-pyrimidinyl)-1,3-benzothiazol-2-yl)acetamide | C | 396 | 0.2655 | 5.2427 | 1.9332 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 21 | N-(6-(2-(phenylsulfanyl)-4-pyrimidinyl)-1,3-benzothiazol-2-yl)acetamide | C | 379 | 0.0781 | 0.3094 | |
| 22 | N-(6-(2-(6-quinolinylmethoxy)-4-pyrimidinyl)-1,3-benzothiazol-2-yl)acetamide | C | 428 | 0.1242 | >40 | >40 |
| 23 | N-(6-(2-((2-fluorophenyl)sulfanyl)-4-pyrimidinyl)-1,3-benzothiazol-2-yl)acetamide | C | 397 | 0.0623 | 0.3066 | 0.3496 |
| 24 | N-(6-(2-(1H-indol-5-ylmethoxy)-4-pyrimidinyl)-1,3-benzothiazol-2-yl)acetamide | C | 416 | 8.0329 | 8.8640 | |
| 25 | N-(6-(2-((1-methyl-4-piperidinyl)methoxy)-4-pyrimidinyl)-1,3-benzothiazol-2-yl)acetamide | C | 398 | 10.6517 | 26.6679 | |
| 26 | N-(6-(2-((4-fluorophenyl)sulfanyl)-4-pyrimidinyl)-1,3-benzothiazol-2-yl)acetamide | C | 397 | 0.1219 | 0.4071 | 1.0165 |
| 27 | N-(6-(2-((4-methoxy-2-methylphenyl)sulfanyl)-4-pyrimidinyl)-1,3-benzothiazol-2-yl)acetamide | C | 423 | 0.0400 | 0.2008 | 0.5940 |
| 28 | N-(6-(2-((2-methoxyphenyl)sulfanyl)-4-pyrimidinyl)-1,3-benzothiazol-2-yl)acetamide | C | 409 | 0.8094 | 0.4906 | |
| 29 | N-(4-((4-(2-(acetylamino)-1,3-benzothiazol-6-yl)-2-pyrimidinyl)sulfanyl)phenyl)acetamide | C | 436 | 0.3331 | 2.3953 | |
| 30 | N-(6-(2-((2-tert-butylphenyl)sulfanyl)-4-pyrimidinyl)-1,3-benzothiazol-2-yl)acetamide | C | 435 | 0.9084 | 1.4219 | |
| 31 | N-(6-(2-((1-methyl-4-piperidinyl)oxy)-4-pyrimidinyl)-1,3-benzothiazol-2-yl)acetamide | C | 384 | 2.3778 | >40 | |
| 32 | N-(6-(2-(3-(2-oxo-1,3-oxazolidin-3-yl)propoxy)-4-pyrimidinyl)-1,3-benzothiazol-2-yl)acetamide | C | 414 | 0.6012 | >40 | |
| 33 | N-(6-(2-phenoxy-4-pyrimidinyl)-1,3-benzothiazol-2-yl)acetamide | C | 363 | 0.4049 | 5.9731 | |
| 34 | N-(6-(2-((2-methylphenyl)sulfanyl)-4-pyrimidinyl)-1,3-benzothiazol-2-yl)acetamide | C | 393 | 0.0427 | 1.0901 | 2.1592 |
| 35 | N-(6-(2-((3-methylphenyl)sulfanyl)-4-pyrimidinyl)-1,3-benzothiazol-2-yl)acetamide | C | 393 | 0.0576 | 1.0616 | 3.5842 |
| 36 | N-(6-(2-((4-methylphenyl)sulfanyl)-4-pyrimidinyl)-1,3-benzothiazol-2-yl)acetamide | C | 393 | 0.0595 | 0.5537 | 2.3223 |
| 37 | N-(6-(2-((2-methylbenzyl)sulfanyl)-4-pyrimidinyl)-1,3-benzothiazol-2-yl)acetamide | C | 407 | 0.1193 | 4.1244 | |
| 38 | N-(6-(2-((4-methoxybenzyl)oxy)-4-pyrimidinyl)-1,3-benzothiazol-2-yl)acetamide | C | 407 | 0.1260 | 13.3333 | |
| 39 | N-(6-(2-((4-fluorobenzyl)oxy)-4-pyrimidinyl)-1,3-benzothiazol-2-yl)acetamide | C | 395 | 0.1087 | 7.9086 | >40 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 40 | N-(6-(2-(1,3-benzodioxol-5-ylmethoxy)-4-pyrimidinyl)-1,3-benzothiazol-2-yl)acetamide | C | 421 | 0.0834 | 25.1045 | 1.0484 |
| 41 | N-(6-(2-((3-methoxyphenyl)sulfanyl)-4-pyrimidinyl)-1,3-benzothiazol-2-yl)acetamide | C | 409 | 0.1918 | 0.1262 | |
| 42 | N-(6-(2-(2,2-dimethylpropoxy)-4-pyrimidinyl)-1,3-benzothiazol-2-yl)acetamide | C | 357 | 0.5013 | 43.0401 | 6.1777 |
| 43 | N-(6-(2-((1R)-1-phenylethoxy)-4-pyrimidinyl)-1,3-benzothiazol-2-yl)acetamide | C | 391 | 0.1045 | 0.5169 | 1.0595 |
| 44 | N-(6-(2-(3-(4-pyridinyl)propoxy)-4-pyrimidinyl)-1,3-benzothiazol-2-yl)acetamide | C | 406 | 0.0979 | 2.7314 | 0.5766 |
| 45 | 6-(2-((3-phenylpropyl)amino)-4-pyrimidinyl)-1,3-benzothiazol-2-amine | A | 362 | 1.9652 | 0.4552 | |
| 46 | N-(6-(2-((3-methoxypropyl)amino)-4-pyrimidinyl)-1,3-benzothiazol-2-yl)acetamide | A | 358 | 1.2107 | 20.3689 | |
| 47 | N-(6-(2-((2-methoxyethyl)amino)-4-pyrimidinyl)-1,3-benzothiazol-2-yl)acetamide | A | 344 | 0.6955 | 18.3596 | 1.1547 |
| 48 | 6-(2-((2-methoxyethyl)amino)-4-pyrimidinyl)-1,3-benzothiazol-2-amine | A | 302 | 18.0521 | >40 | |
| 49 | N-(6-(2-(benzylamino)-4-pyrimidinyl)-1,3-benzothiazol-2-yl)acetamide | A | 376 | 0.4183 | 1.4506 | 15.2554 |
| 50 | N-(6-(2-(methylsulfanyl)-4-pyrimidinyl)-1,3-benzothiazol-2-yl)acetamide | C | 317 | 0.0758 | 1.1845 | 1.0534 |
| 51 | N-(6-(2-methoxy-4-pyrimidinyl)-1,3-benzothiazol-2-yl)acetamide | C | 301 | 0.5052 | >40 | 0.9518 |
| 52 | N-(6-(2-(dimethylamino)-4-pyrimidinyl)-1,3-benzothiazol-2-yl)acetamide | C | 314 | 2.5836 | >40 | |
| 53 | N-(6-(2-hydroxy-4-pyrimidinyl)-1,3-benzothiazol-2-yl)acetamide | A | 287 | 7.9795 | >40 | |
| 54 | N-(6-(2-(benzyloxy)-4-pyrimidinyl)-1,3-benzothiazol-2-yl)-2-(4-morpholinyl)acetamide | A, C | 462 | 7.3253 | >40 | |
| 55 | N-(6-(2-(benzyloxy)-4-pyrimidinyl)-1,3-benzothiazol-2-yl)-2-hydroxy-2-methylpropanamide | A, C | 421 | 26.6908 | 7.7465 | |
| 56 | 1-(6-(2-(benzyloxy)-4-pyrimidinyl)-1,3-benzothiazol-2-yl)-3-methylurea | A, C | 392 | 0.2538 | 0.4017 | >5 |
| 57 | N-(6-(2-(benzyloxy)-4-pyrimidinyl)-1,3-benzothiazol-2-yl)propanamide | A, C | 391 | 0.2769 | 8.8315 | |
| 58 | N-(6-(2-(benzyloxy)-4-pyrimidinyl)-1,3-benzothiazol-2-yl)benzamide | A, C | 439 | >40 | 3.9340 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 59 | N-(6-(2-(benzyloxy)-4-pyrimidinyl)-1,3-benzothiazol-2-yl)-N~2~,N~2~-dimethylglycinamide | A, C | 420 | 11.2618 | 9.7992 | |
| 61 | N-(6-(2-((4-methoxyphenyl)sulfonyl)-1,3-thiazol-5-yl)-1,3-benzothiazol-2-yl)acetamide | | 446 | 38.8491 | 31.0368 | |
| 62 | N-(6-(2-((4-methoxyphenyl)sulfanyl)-1,3-thiazol-5-yl)-1,3-benzothiazol-2-yl)acetamide | | 414 | 0.0299 | 5.2067 | 2.5800 |
| 63 | N-(6-(2-((2-fluorophenyl)sulfonyl)-1,3-thiazol-4-yl)-1,3-benzothiazol-2-yl)acetamide | | 434 | 0.5556 | 4.6923 | |
| 64 | N-(6-(2-(phenylsulfonyl)-1,3-thiazol-4-yl)-1,3-benzothiazol-2-yl)acetamide | | 416 | 0.8455 | >40 | |
| 65 | N-(6-(6-(phenylsulfonyl)-2-pyridinyl)-1,3-benzothiazol-2-yl)acetamide | | 410 | 0.2212 | >40 | |
| 66 | N-(6-(6-((4-fluorophenyl)sulfonyl)-2-pyridinyl)-1,3-benzothiazol-2-yl)acetamide | D | 428 | 0.2577 | 5.6118 | 2.0195 |
| 67 | N-(6-(6-((3-fluorophenyl)sulfonyl)-2-pyridinyl)-1,3-benzothiazol-2-yl)acetamide | D | 428 | 0.3004 | 3.3465 | |
| 68 | N-(6-(6-((4-methoxyphenyl)sulfonyl)-2-pyridinyl)-1,3-benzothiazol-2-yl)acetamide | D | 440 | 0.0865 | 0.6758 | 0.6639 |
| 69 | N-(6-(6-((3-methoxyphenyl)sulfonyl)-2-pyridinyl)-1,3-benzothiazol-2-yl)acetamide | D | 440 | 0.0465 | 0.2843 | 0.2957 |
| 70 | N-(6-(6-((2-methoxyphenyl)sulfonyl)-2-pyridinyl)-1,3-benzothiazol-2-yl)acetamide | D | 440 | 0.2854 | 1.5449 | |
| 71 | N-(6-(2-amino-1,3-benzothiazol-6-yl)-2-pyridinyl)benzenesulfonamide | D | 383 | 3.8315 | 1.4371 | |
| 72 | N-(6-(2-amino-1,3-benzothiazol-6-yl)-2-pyridinyl)-2-fluorobenzenesulfonamide | D | 401 | 2.2714 | 1.5964 | |
| 73 | N-(6-(6-(((2-fluorophenyl)sulfonyl)amino)-2-pyridinyl)-1,3-benzothiazol-2-yl)acetamide | E | 443 | 0.0606 | 0.1492 | 0.3196 |
| 74 | N-(6-(6-(methyl((4-methylphenyl)sulfonyl)amino)-2-pyridinyl)-1,3-benzothiazol-2-yl)acetamide | D | 453 | 0.0329 | 0.2018 | 0.0859 |
| 75 | N-(6-(6-(methyl(phenylsulfonyl)amino)-2-pyridinyl)-1,3-benzothiazol-2-yl)acetamide | D | 439 | 0.0825 | 0.3383 | 0.2211 |
| 77 | N-(6-(2-((phenylsulfonyl)amino)-4-pyrimidinyl)-1,3-benzothiazol-2-yl)acetamide | C | 426 | 0.0848 | 0.5428 | 2.3493 |
| 78 | N-(6-(2-(((4-methoxyphenyl)sulfonyl)amino)-4-pyrimidinyl)-1,3-benzothiazol-2-yl)acetamide | C | 456 | 0.0155 | 0.0672 | 0.4282 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 79 | N-(6-(2-((3-pyridinylsulfonyl)amino)-4-pyrimidinyl)-1,3-benzothiazol-2-yl)acetamide | C | 427 | 0.0606 | 0.8493 | |
| 80 | N-(6-(2-(((4-fluorophenyl)sulfonyl)amino)-4-pyrimidinyl)-1,3-benzothiazol-2-yl)acetamide | A | 444 | 0.0416 | 0.4053 | 3.2175 |
| 81 | N-(6-(2-(((2-fluorophenyl)sulfonyl)amino)-4-pyrimidinyl)-1,3-benzothiazol-2-yl)acetamide | A | 444 | 0.0365 | 0.1030 | 4.9518 |
| 82 | N-(6-(2-(((3-fluorophenyl)sulfonyl)amino)-4-pyrimidinyl)-1,3-benzothiazol-2-yl)acetamide | A | 444 | 0.0773 | 0.3043 | 3.9037 |
| 83 | N-(6-(2-(((4-methylphenyl)sulfonyl)amino)-4-pyrimidinyl)-1,3-benzothiazol-2-yl)acetamide | A | 440 | 0.0343 | 0.0620 | 0.4084 |
| 84 | N-(6-(2-(((4-ethylphenyl)sulfonyl)amino)-4-pyrimidinyl)-1,3-benzothiazol-2-yl)acetamide | A | 454 | 0.0218 | 0.0793 | 0.1744 |
| 85 | N-(6-(2-(((3-methoxyphenyl)sulfonyl)amino)-4-pyrimidinyl)-1,3-benzothiazol-2-yl)acetamide | A | 456 | 0.0201 | 0.0826 | 0.9172 |
| 86 | N-(4-((4-(2-(acetylamino)-1,3-benzothiazol-6-yl)-2-pyrimidinyl)sulfamoyl)phenyl)acetamide | A | 483 | 0.3193 | 10.2148 | |
| 87 | N-(6-(2-(((3,4-dimethoxyphenyl)sulfonyl)amino)-4-pyrimidinyl)-1,3-benzothiazol-2-yl)acetamide | A | 486 | 0.1528 | 7.1887 | |
| 88 | N-(6-(2-(((4-methoxyphenyl)sulfonyl)(methyl)amino)-4-pyrimidinyl)-1,3-benzothiazol-2-yl)acetamide | C | 470 | 0.0393 | 0.0791 | 0.0688 |
| 89 | N-(6-(2-(ethyl((4-methoxyphenyl)sulfonyl)amino)-4-pyrimidinyl)-1,3-benzothiazol-2-yl)acetamide | C | 484 | 0.2832 | 0.4422 | 0.6916 |
| 90 | N-(6-(2-(methyl((4-methylphenyl)sulfonyl)amino)-4-pyrimidinyl)-1,3-benzothiazol-2-yl)acetamide | F | 454 | 0.0432 | 0.0488 | 0.0516 |
| 91 | N-(6-(2-(methyl(phenylsulfonyl)amino)-4-pyrimidinyl)-1,3-benzothiazol-2-yl)acetamide | F | 440 | 0.1809 | 0.2374 | 0.3099 |
| 92 | N-(6-(2-(((2-fluorophenyl)sulfonyl)(methyl)amino)-4-pyrimidinyl)-1,3-benzothiazol-2-yl)acetamide | F | 458 | 0.3015 | 0.3103 | 0.8884 |
| 93 | N-(6-(2-(methyl((3-methylphenyl)sulfonyl)amino)-4-pyrimidinyl)-1,3-benzothiazol-2-yl)acetamide | F | 454 | 0.1022 | 0.1740 | 0.2184 |
| 94 | N-(7-(3-fluoro-4-methoxyphenyl)-1,3-benzothiazol-2-yl)acetamide | G | 317 | 0.9975 | 24.7822 | |
| 95 | N-(7-(4-methoxyphenyl)-1,3-benzothiazol-2-yl)acetamide | G | 299 | 6.5360 | >40 | |
| 96 | N-(7-(3-methoxyphenyl)-1,3-benzothiazol-2-yl)acetamide | G | 299 | 1.6756 | >40 | |
| 97 | N-(6-(2-((4-fluorophenyl)sulfonyl)-1,3-thiazol-4-yl)-1,3-benzothiazol-2-yl)acetamide | D | 434 | 17.2852 | 27.9945 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 98 | N-(2-oxo-2,3-dihydro-4,6'-bi-1,3-benzothiazol-2'-yl)acetamide | H | 342 | 3.1421 | 10.0390 | |
| 99 | N-(6-(1H-indazol-4-yl)-1,3-benzothiazol-2-yl)acetamide | H | 309 | 0.2882 | >40 | |
| 100 | N-(6-(2-((1-methyl-1-phenylethyl)amino)-4-pyrimidinyl)-1,3-benzothiazol-2-yl)acetamide | A | 404 | 0.0659 | 0.5948 | 0.6978 |
| 101 | N-(6-(2-amino-6-methyl-4-pyrimidinyl)-1,3-benzothiazol-2-yl)acetamide | A | 300 | 4.1879 | 9.9933 | |
| 102 | N-(6-(2-(3-hydroxypropoxy)-4-pyrimidinyl)-1,3-benzothiazol-2-yl)acetamide | A | 345 | 0.6639 | >40 | |
| 103 | N-(6-(2-(4-hydroxybutoxy)-4-pyrimidinyl)-1,3-benzothiazol-2-yl)acetamide | A | 359 | 0.7267 | >40 | |
| 104 | N-(6-(2-(2-hydroxyethoxy)-4-pyrimidinyl)-1,3-benzothiazol-2-yl)acetamide | A | 331 | 0.5399 | >40 | |
| 105 | N-(6-(2-chloro-4-pyrimidinyl)-1,3-benzothiazol-2-yl)acetamide | A | 305 | 1.6974 | 8.2701 | |
| 106 | N-(6-(2-((4-methylbenzyl)oxy)-4-pyrimidinyl)-1,3-benzothiazol-2-yl)acetamide | C | 391 | 0.2197 | 1.2438 | 2.5314 |
| 107 | N-(6-(2-((3-methylbenzyl)oxy)-4-pyrimidinyl)-1,3-benzothiazol-2-yl)acetamide | C | 391 | 0.1814 | 0.8363 | 1.2091 |
| 108 | N-(6-(2-((3-methoxybenzyl)oxy)-4-pyrimidinyl)-1,3-benzothiazol-2-yl)acetamide | C | 407 | 0.0967 | 0.2924 | 0.6820 |
| 109 | N-(6-(2-((3-fluorophenyl)sulfanyl)-4-pyrimidinyl)-1,3-benzothiazol-2-yl)acetamide | C | 397 | 0.1994 | 0.1197 | 1.8370 |
| 110 | N-(6-(6-methyl-5-((phenylsulfonyl)amino)-3-pyridinyl)-1,3-benzothiazol-2-yl)acetamide | I | 439 | 0.0038 | 0.0106 | 0.0314 |
| 111 | N-(6-(5-(((4-fluorophenyl)sulfonyl)amino)-6-methyl-3-pyridinyl)-1,3-benzothiazol-2-yl)acetamide | I | 457 | 0.0041 | 0.0131 | 0.0255 |
| 112 | N-(6-(5-(((2-fluorophenyl)sulfonyl)amino)-6-methyl-3-pyridinyl)-1,3-benzothiazol-2-yl)acetamide | I | 457 | 0.0055 | 0.0091 | 0.0169 |
| 113 | N-(6-(6-methyl-5-(((3-(trifluoromethyl)phenyl)sulfonyl)amino)-3-pyridinyl)-1,3-benzothiazol-2-yl)acetamide | I | 507 | 0.0064 | 0.0130 | 0.0067 |
| 114 | N-(6-(5-(((4-tert-butylphenyl)sulfonyl)amino)-6-methyl-3-pyridinyl)-1,3-benzothiazol-2-yl)acetamide | I | 495 | 0.0070 | 0.0089 | 0.0144 |
| 115 | N-(6-(5-(((3-(difluoromethoxy)phenyl)sulfonyl)amino)-6-methyl-3-pyridinyl)-1,3-benzothiazol-2-yl)acetamide | I | 505 | 0.0071 | 0.0150 | 0.0307 |
| 116 | N-(6-(5-(((4-methoxyphenyl)sulfonyl)amino)-6-methyl-3-pyridinyl)-1,3-benzothiazol-2-yl)acetamide | I | 469 | 0.0075 | 0.0120 | 0.0093 |
| 117 | N-(4-fluoro-6-(5-(((4-(trifluoromethyl)phenyl)sulfonyl)amino)-3-pyridinyl)-1,3-benzothiazol-2-yl)acetamide | J | 511 | 0.0077 | 0.0558 | 0.3014 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 118 | N-(6-(6-(((4-methoxyphenyl)sulfonyl)amino)-2-pyrazinyl)-1,3-benzothiazol-2-yl)acetamide | C | 456 | 0.0084 | 0.0179 | 0.1474 |
| 119 | N-(6-(5-(((4-acetylphenyl)sulfonyl)amino)-6-chloro-3-pyridinyl)-1,3-benzothiazol-2-yl)acetamide | O | 501 | 0.0123 | 0.0135 | 0.0345 |
| 120 | N-(6-(6-((4-methoxyphenyl)sulfonyl)-2-pyrazinyl)-1,3-benzothiazol-2-yl)acetamide | D | 441 | 0.0164 | 1.0656 | 0.3315 |
| 121 | N-(6-(6-((2-fluorophenyl)sulfonyl)-2-pyrazinyl)-1,3-benzothiazol-2-yl)acetamide | D | 429 | 0.0191 | 0.4956 | 0.1897 |
| 122 | N-(6-(2-((2,4-dimethylphenyl)sulfanyl)-4-pyrimidinyl)-1,3-benzothiazol-2-yl)acetamide | C | 407 | 0.0196 | 0.2605 | |
| 123 | N-(6-(2-((2,5-dimethylphenyl)sulfanyl)-4-pyrimidinyl)-1,3-benzothiazol-2-yl)acetamide | C | 407 | 0.0235 | 0.5373 | |
| 124 | N-(6-(5-(dimethylamino)-6-methoxy-3-pyridinyl)-1,3-benzothiazol-2-yl)acetamide | L | 343 | 0.0247 | 0.0908 | 0.0666 |
| 125 | N-(6-(2-((2-chlorophenyl)sulfanyl)-4-pyrimidinyl)-1,3-benzothiazol-2-yl)acetamide | C | 413 | 0.0254 | 0.4251 | 0.5484 |
| 126 | N-(6-(6-(((4-methoxyphenyl)sulfonyl)(methyl)amino)-2-pyrazinyl)-1,3-benzothiazol-2-yl)acetamide | C | 470 | 0.0271 | 0.3213 | 0.0806 |
| 127 | N-(6-(6-(methyl((4-methylphenyl)sulfonyl)amino)-2-pyrazinyl)-1,3-benzothiazol-2-yl)acetamide | C | 454 | 0.0278 | 0.0316 | 0.0581 |
| 128 | N-(6-(2-((3,4-dimethylphenyl)sulfanyl)-4-pyrimidinyl)-1,3-benzothiazol-2-yl)acetamide | C | 407 | 0.0339 | 0.5221 | |
| 129 | N-(6-(2-((2,6-dimethylphenyl)sulfanyl)-4-pyrimidinyl)-1,3-benzothiazol-2-yl)acetamide | C | 407 | 0.0383 | 0.4773 | 0.9783 |
| 130 | N-(6-(6-((2-fluorophenyl)sulfanyl)-2-pyrazinyl)-1,3-benzothiazol-2-yl)acetamide | C | 397 | 0.0390 | 0.0650 | 0.4421 |
| 131 | N-(4-fluoro-6-(2-(((4-methoxyphenyl)sulfonyl)amino)-4-pyrimidinyl)-1,3-benzothiazol-2-yl)acetamide | J, A, C | 474 | 0.0413 | 0.1263 | 1.7996 |
| 132 | N-(6-(6-chloro-5-((1-methylethyl)amino)-3-pyridinyl)-1,3-benzothiazol-2-yl)acetamide | K | 361 | 0.0414 | 0.3790 | 0.3155 |
| 133 | N-(6-(6-((4-methoxyphenyl)sulfanyl)-2-pyrazinyl)-1,3-benzothiazol-2-yl)acetamide | C | 409 | 0.0415 | 0.0754 | 1.2345 |
| 134 | N-(6-(2-((2-bromophenyl)sulfanyl)-4-pyrimidinyl)-1,3-benzothiazol-2-yl)acetamide | C | 457 | 0.0470 | 0.6684 | 1.2248 |
| 135 | N-(6-(6-(benzyloxy)-2-pyrazinyl)-1,3-benzothiazol-2-yl)acetamide | C | 377 | 0.0542 | 0.2187 | 1.9708 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 136 | N-(5-(3-(((4-methylphenyl)sulfonyl)amino)phenyl)[1,3]thiazolo[5,4-b]pyridin-2-yl)acetamide | N | 439 | 0.0586 | 0.1993 | 0.1724 |
| 137 | N-(4-fluoro-6-(6-((2-fluorophenyl)sulfonyl)-2-pyridinyl)-1,3-benzothiazol-2-yl)acetamide | J, D | 446 | 0.0650 | 1.1385 | 0.9014 |
| 138 | N-(6-(2-((4-chlorophenyl)sulfanyl)-4-pyrimidinyl)-1,3-benzothiazol-2-yl)acetamide | C | 413 | 0.0699 | 2.8818 | |
| 139 | N-(6-(2-((4-bromophenyl)sulfanyl)-4-pyrimidinyl)-1,3-benzothiazol-2-yl)acetamide | C | 457 | 0.0807 | 1.0530 | |
| 140 | N-(6-(2-((3-chlorophenyl)sulfanyl)-4-pyrimidinyl)-1,3-benzothiazol-2-yl)acetamide | C | 413 | 0.0836 | 0.1343 | |
| 141 | N-(6-(6-chloro-5-((1-methylethyl)amino)-3-pyridinyl)-1,3-benzothiazol-2-yl)-2-(2-pyridinyl)acetamide | K | 438 | 0.0954 | 0.8458 | 0.8497 |
| 142 | N-(6-(5-amino-6-methyl-3-pyridinyl)-1,3-benzothiazol-2-yl)acetamide | I | 299 | 0.1109 | >40 | |
| 143 | N-(4-fluoro-6-(2-(((4-methoxyphenyl)sulfonyl)(methyl)amino)-4-pyrimidinyl)-1,3-benzothiazol-2-yl)acetamide | J, A, C | 488 | 0.1114 | 0.1086 | 0.3279 |
| 144 | N-(6-(6-chloro-5-((1-methylethyl)amino)-3-pyridinyl)-1,3-benzothiazol-2-yl)-2-methoxyacetamide | K | 391 | 0.1117 | 1.5749 | 0.7226 |
| 145 | N-(6-(6-methoxy-5-((1-methylethyl)amino)-3-pyridinyl)-1,3-benzothiazol-2-yl)acetamide | L | 357 | 0.1137 | 0.4236 | 0.8510 |
| 146 | N-(5-(3-(((4-methoxyphenyl)sulfonyl)amino)phenyl)[1,3]thiazolo[5,4-b]pyridin-2-yl)acetamide | N | 455 | 0.1169 | 0.3587 | 0.3731 |
| 147 | N-(6-(6-(methylamino)-5-((1-methylethyl)amino)-3-pyridinyl)-1,3-benzothiazol-2-yl)acetamide | M | 356 | 0.1491 | 5.6756 | 0.4395 |
| 148 | N-(4-fluoro-6-(6-((4-methoxyphenyl)sulfonyl)-2-pyridinyl)-1,3-benzothiazol-2-yl)acetamide | J, D | 458 | 0.1514 | 1.3565 | 0.8808 |
| 149 | N-(6-(2-((3,5-dimethylphenyl)sulfanyl)-4-pyrimidinyl)-1,3-benzothiazol-2-yl)acetamide | C | 407 | 0.1858 | 0.3873 | |
| 150 | N-(6-(6-chloro-2-pyrazinyl)-1,3-benzothiazol-2-yl)acetamide | A | 305 | 0.1859 | 0.9025 | 0.5032 |
| 151 | N-(6-(6-chloro-5-((1-methylethyl)amino)-3-pyridinyl)-1,3-benzothiazol-2-yl)-2-((2S)-tetrahydro-2-furanyl)acetamide | K | 431 | 0.2297 | 1.6186 | >5 |
| 152 | N-(6-(5-amino-6-(methylamino)-3-pyridinyl)-1,3-benzothiazol-2-yl)acetamide | M | 314 | 0.2750 | 0.8642 | |
| 153 | N-(6-(6-(3-(dimethylamino)propoxy)-5-((1-methylethyl)amino)-3-pyridinyl)-1,3-benzothiazol-2-yl)acetamide | L | 428 | 0.2839 | 1.8394 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 154 | N-(6-(2-((2-(1-methylethyl)phenyl)sulfanyl)-4-pyrimidinyl)-1,3-benzothiazol-2-yl)acetamide | C | 421 | 0.3760 | 1.2071 | |
| 155 | 6-(6-chloro-5-((1-methylethyl)amino)-3-pyridinyl)-1,3-benzothiazol-2-amine | K | 319 | 0.5094 | 1.1532 | 1.9940 |
| 156 | N-(5-(3-aminophenyl)[1,3]thiazolo[5,4-b]pyridin-2-yl)acetamide | N | 285 | 0.6415 | 13.3333 | |
| 157 | N-(6-(2,2,3-trimethyl-2,3-dihydro-1H-imidazo[4,5-b]pyridin-6-yl)-1,3-benzothiazol-2-yl)acetamide | M | 354 | 0.6638 | >40 | |
| 158 | N-(6-(2-((2,5-dimethoxyphenyl)sulfanyl)-4-pyrimidinyl)-1,3-benzothiazol-2-yl)acetamide | C | 439 | 0.8312 | 0.4260 | |
| 159 | N-(6-(6-(2-(dimethylamino)ethoxy)-5-((1-methylethyl)amino)-3-pyridinyl)-1,3-benzothiazol-2-yl)acetamide | L | 414 | 0.9144 | 3.7396 | |
| 160 | N-(6-(2-(4-morpholinyl)-4-pyrimidinyl)-1,3-benzothiazol-2-yl)acetamide | C | 356 | 2.7424 | 18.8718 | |
| 161 | N-(6-(6-chloro-5-(((4-(1-hydroxy-1-methylethyl)phenyl)sulfonyl)amino)-3-pyridinyl)-1,3-benzothiazol-2-yl)acetamide | O | 517 | 0.0137 | 0.0446 | 0.0041 |
| 162 | N-(6-(6-chloro-5-(((4-fluorophenyl)sulfonyl)amino)-3-pyridinyl)-1,3-benzothiazol-2-yl)acetamide | | 477 | 0.0049 | 0.0073 | 0.0104 |
| 163 | N-(6-(6-chloro-5-(((4-methoxyphenyl)sulfonyl)amino)-3-pyridinyl)-1,3-benzothiazol-2-yl)acetamide | | 489 | 0.0030 | 0.0038 | 0.0038 |
| 164 | N-(6-(5-(((4-fluorophenyl)sulfonyl)amino)-1,3,4-oxadiazol-2-yl)-1,3-benzothiazol-2-yl)acetamide | | 434 | 0.0178 | 0.3221 | |
| 165 | N-(5-(2-amino-1,3-benzothiazol-6-yl)-1,3,4-oxadiazol-2-yl)-4-methylbenzenesulfonamide | | 388 | 0.1965 | 0.1705 | |
| 166 | tert-butyl (6-(5-(((4-methylphenyl)sulfonyl)amino)-1,3,4-oxadiazol-2-yl)-1,3-benzothiazol-2-yl)carbamate | | 486 (M − H) | 0.3362 | 2.2026 | 0.2392 |
| 167 | tert-butyl (6-(5-(((4-fluorophenyl)sulfonyl)amino)-1,3,4-oxadiazol-2-yl)-1,3-benzothiazol-2-yl)carbamate | | 490 (M − H) | 0.6634 | 5.8039 | |
| 168 | N-(5-(2-amino-1,3-benzothiazol-6-yl)-1,3,4-oxadiazol-2-yl)-4-fluorobenzenesulfonamide | | 390 (M − H) | 0.6647 | 0.8158 | |
| 169 | tert-butyl (6-(5-(benzylamino)-1,3,4-oxadiazol-2-yl)-1,3-benzothiazol-2-yl)carbamate | | 424 | 4.2439 | 2.6939 | |
| 170 | tert-butyl (6-(5-(benzyl(methylsulfonyl)amino)-1,3,4-oxadiazol-2-yl)-1,3-benzothiazol-2-yl)carbamate | | 502 | 3.9065 | 4.7562 | |
| 171 | N-(6-(6-chloro-5-((cyclohexylsulfonyl)amino)-3-pyridinyl)-1,3-benzothiazol-2-yl)acetamide | P | 465 | 0.0032 | 0.0263 | 0.0433 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 172 | N-(6-(6-chloro-5-(((3-(trifluoromethyl)phenyl)sulfonyl)amino)-3-pyridinyl)-1,3-benzothiazol-2-yl)acetamide | P | 527 | 0.0063 | 0.0069 | 0.0070 |
| 173 | N-(6-(5-(((3-tert-butylphenyl)sulfonyl)amino)-6-chloro-3-pyridinyl)-1,3-benzothiazol-2-yl)acetamide | P | 515 | 0.0061 | 0.0069 | 0.0051 |
| 174 | N-(6-(6-chloro-5-(((4-hydroxyphenyl)sulfonyl)amino)-3-pyridinyl)-1,3-benzothiazol-2-yl)acetamide | P | 475 | 0.0072 | 0.0123 | 0.0155 |
| 175 | N-(6-(6-chloro-5-(((3,5-dichlorophenyl)sulfonyl)amino)-3-pyridinyl)-1,3-benzothiazol-2-yl)acetamide | P | 527 | 0.0032 | 0.0054 | 0.0117 |
| 176 | N-(6-(6-chloro-5-(((3,5-difluorophenyl)sulfonyl)amino)-3-pyridinyl)-1,3-benzothiazol-2-yl)acetamide | P | 495 | 0.0103 | 0.0124 | 0.0182 |
| 177 | N-(6-(6-chloro-5-((propylsulfonyl)amino)-3-pyridinyl)-1,3-benzothiazol-2-yl)acetamide | P | 425 | 0.0154 | 0.0349 | 0.0363 |
| 178 | N-(6-(5-((butylsulfonyl)amino)-6-chloro-3-pyridinyl)-1,3-benzothiazol-2-yl)acetamide | P | 439 | 0.0106 | 0.0199 | 0.0156 |
| 179 | N-(6-(6-chloro-5-(((1-methylethyl)sulfonyl)amino)-3-pyridinyl)-1,3-benzothiazol-2-yl)acetamide | P | 425 | 0.0127 | 0.0307 | 0.0294 |
| 180 | N-(6-(6-chloro-5-(((4-chlorophenyl)sulfonyl)amino)-3-pyridinyl)-1,3-benzothiazol-2-yl)acetamide | Q | 493 | 0.0049 | 0.0087 | 0.0126 |
| 181 | N-(6-(6-chloro-5-((phenylsulfonyl)amino)-3-pyridinyl)-1,3-benzothiazol-2-yl)acetamide | Q | 459 | 0.0127 | 0.0145 | 0.0104 |
| 182 | N-(6-(6-chloro-5-(((4-(difluoromethoxy)phenyl)sulfonyl)amino)-3-pyridinyl)-1,3-benzothiazol-2-yl)acetamide | Q | 525 | 0.0060 | 0.0060 | 0.0249 |
| 183 | N-(6-(6-chloro-5-(((3-fluorophenyl)sulfonyl)amino)-3-pyridinyl)-1,3-benzothiazol-2-yl)acetamide | Q | 477 | 0.0066 | 0.0104 | 0.0169 |
| 184 | N-(6-(6-chloro-5-(((3-(difluoromethoxy)phenyl)sulfonyl)amino)-3-pyridinyl)-1,3-benzothiazol-2-yl)acetamide | Q | 525 | 0.0072 | 0.0122 | 0.0065 |
| 185 | N-(6-(6-chloro-5-(((3-chlorophenyl)sulfonyl)amino)-3-pyridinyl)-1,3-benzothiazol-2-yl)acetamide | Q | 493 | 0.0060 | 0.0081 | 0.0059 |
| 186 | N-(6-(6-chloro-5-((2-thiophenylsulfonyl)amino)-3-pyridinyl)-1,3-benzothiazol-2-yl)acetamide | Q | 465 | 0.0066 | 0.0143 | 0.0156 |
| 187 | N-(6-(6-chloro-5-((3-thiophenylsulfonyl)amino)-3-pyridinyl)-1,3-benzothiazol-2-yl)acetamide | Q | 465 | 0.0211 | 0.0421 | 0.0374 |
| 188 | N-(6-(5-((benzylsulfonyl)amino)-6-chloro-3-pyridinyl)-1,3-benzothiazol-2-yl)acetamide | Q | 473 | 0.0069 | 0.0254 | 0.1096 |
| 189 | N-(6-(6-chloro-5-(((4-methylphenyl)sulfonyl)amino)-3-pyridinyl)-1,3-benzothiazol-2-yl)acetamide | Q | 473 | 0.0064 | 0.0077 | 0.0039 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 190 | N-(6-(6-chloro-5-(((4-(trifluoromethyl)phenyl)sulfonyl)amino)-3-pyridinyl)-1,3-benzothiazol-2-yl)acetamide | Q | 527 | 0.0049 | 0.0074 | 0.0115 |
| 191 | N-(6-(5-(((4-tert-butylphenyl)sulfonyl)amino)-6-chloro-3-pyridinyl)-1,3-benzothiazol-2-yl)acetamide | Q | 515 | 0.0036 | 0.0042 | 0.0026 |
| 192 | N-(5-(2-amino-1,3-benzothiazol-6-yl)-2-chloro-3-pyridinyl)-4-fluorobenzenesulfonamide | Q | 435 | 0.0048 | 0.0116 | 0.1510 |
| 193 | N-(6-(6-chloro-5-(((5-chloro-2-thiophenyl)sulfonyl)amino)-3-pyridinyl)-1,3-benzothiazol-2-yl)acetamide | Q | 499 | 0.0068 | 0.0096 | 0.0168 |
| 194 | N-(6-(5-(((4-methylphenyl)sulfonyl)amino)-3-pyridinyl)-1,3-benzothiazol-2-yl)acetamide | R | 439 | 0.0098 | 0.0255 | 0.0276 |
| 195 | N-(6-(5-(((4-methoxyphenyl)sulfonyl)amino)-3-pyridinyl)-1,3-benzothiazol-2-yl)acetamide | R | 455 | 0.0078 | 0.0217 | 0.0328 |
| 196 | N-(6-(5-(((4-(trifluoromethyl)phenyl)sulfonyl)amino)-3-pyridinyl)-1,3-benzothiazol-2-yl)acetamide | R | 493 | 0.0067 | 0.0157 | 0.1227 |
| 197 | N-(6-(5-(((3-(trifluoromethyl)phenyl)sulfonyl)amino)-3-pyridinyl)-1,3-benzothiazol-2-yl)acetamide | R | 493 | 0.0094 | 0.0119 | 0.0798 |
| 198 | N-(6-(5-(((4-fluorophenyl)sulfonyl)amino)-3-pyridinyl)-1,3-benzothiazol-2-yl)acetamide | R | 443 | 0.0053 | 0.0147 | 0.0404 |
| 199 | N-(6-(5-(((3-fluorophenyl)sulfonyl)amino)-3-pyridinyl)-1,3-benzothiazol-2-yl)acetamide | R | 443 | 0.0038 | 0.0103 | 0.0750 |
| 200 | N-(6-(5-(((3,4-dichlorophenyl)sulfonyl)amino)-3-pyridinyl)-1,3-benzothiazol-2-yl)acetamide | R | 493 | 0.0056 | 0.0098 | 0.0357 |
| 201 | N-(6-(5-(((4-tert-butylphenyl)sulfonyl)amino)-3-pyridinyl)-1,3-benzothiazol-2-yl)acetamide | R | 481 | 0.0065 | 0.0111 | 0.1169 |
| 202 | N-(6-(5-((phenylsulfonyl)amino)-3-pyridinyl)-1,3-benzothiazol-2-yl)acetamide | R | 425 | 0.0056 | 0.0317 | 0.2712 |
| 203 | N-(6-(2-(((4-fluorophenyl)sulfonyl)(methyl)amino)-4-pyrimidinyl)-1,3-benzothiazol-2-yl)acetamide | | 458 | 0.3235 | 0.9297 | |
| 204 | N-(6-(2-(methyl(6-quinolinylsulfonyl)amino)-4-pyrimidinyl)-1,3-benzothiazol-2-yl)acetamide | | 491 | 0.3541 | 0.4043 | |
| 205 | N-(6-(2-(((4-tert-butylphenyl)sulfonyl)(methyl)amino)-4-pyrimidinyl)-1,3-benzothiazol-2-yl)acetamide | | 496 | 0.0295 | 0.0872 | 0.0576 |
| 206 | N-(6-(2-(methyl(2-thiophenylsulfonyl)amino)-4-pyrimidinyl)-1,3-benzothiazol-2-yl)acetamide | | 446 | 0.1766 | 0.1937 | 0.3812 |
| 207 | N-(6-(2-(methyl(1-naphthalenylsulfonyl)amino)-4-pyrimidinyl)-1,3-benzothiazol-2-yl)acetamide | | 490 | 0.1256 | 0.2209 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 208 | N-(6-(2-((5-isoquinolinylsulfonyl)(methyl)amino)-4-pyrimidinyl)-1,3-benzothiazol-2-yl)acetamide | | 491 | 0.4617 | 0.7427 | |
| 209 | N-(6-(2-(methyl(3-thiophenylsulfonyl)amino)-4-pyrimidinyl)-1,3-benzothiazol-2-yl)acetamide | | 446 | 0.1849 | 0.8547 | |
| 210 | N-(6-(2-(((3,4-dimethylphenyl)sulfonyl)(methyl)amino)-4-pyrimidinyl)-1,3-benzothiazol-2-yl)acetamide | | 468 | 0.0147 | 0.0391 | 0.0593 |
| 211 | N-(6-(2-(methyl((1-methyl-1H-imidazol-4-yl)sulfonyl)amino)-4-pyrimidinyl)-1,3-benzothiazol-2-yl)acetamide | | 444 | 0.9289 | 3.9338 | |
| 212 | N-(6-(2-(((2,4-dimethylphenyl)sulfonyl)(methyl)amino)-4-pyrimidinyl)-1,3-benzothiazol-2-yl)acetamide | | 468 | 0.0722 | 0.0603 | 0.2371 |
| 213 | N-(6-(2-(methyl((4-(trifluoromethyl)phenyl)sulfonyl)amino)-4-pyrimidinyl)-1,3-benzothiazol-2-yl)acetamide | | 508 | 0.0913 | 0.1191 | 0.0928 |
| 214 | N-(6-(2-(methyl(2-naphthalenylsulfonyl)amino)-4-pyrimidinyl)-1,3-benzothiazol-2-yl)acetamide | | 490 | 0.0740 | 0.0862 | 0.2559 |
| 215 | N-(6-(2-(methyl((4-methylphenyl)sulfonyl)amino)-4-pyridinyl)-1,3-benzothiazol-2-yl)acetamide | | 453 | 0.4377 | 0.4502 | |
| 216 | N-(6-(2-(((4-methylphenyl)sulfonyl)amino)-4-pyridinyl)-1,3-benzothiazol-2-yl)acetamide | | 439 | 0.0351 | 0.1196 | 0.0794 |
| 217 | N-(6-(2-(((4-methoxyphenyl)sulfonyl)amino)-4-pyridinyl)-1,3-benzothiazol-2-yl)acetamide | | 455 | 0.0671 | 0.1170 | 0.0711 |
| 218 | N-(6-(5-(methyl((4-(trifluoromethyl)phenyl)sulfonyl)amino)-3-pyridinyl)-1,3-benzothiazol-2-yl)acetamide | | 507 | 1.0525 | 8.2691 | |
| 219 | N-(6-(5-(((4-fluorophenyl)sulfonyl)(methyl)amino)-3-pyridinyl)-1,3-benzothiazol-2-yl)acetamide | | 457 | 0.3754 | 2.9314 | |
| 220 | N-(6-(5-(((4-chlorophenyl)sulfonyl)(methyl)amino)-3-pyridinyl)-1,3-benzothiazol-2-yl)acetamide | | 473 | 0.5392 | 3.3292 | |
| 221 | N-(6-(5-(((3,4-dichlorophenyl)sulfonyl)(methyl)amino)-3-pyridinyl)-1,3-benzothiazol-2-yl)acetamide | | 507 | 0.0792 | 2.1006 | 0.3196 |
| 222 | N-(6-(5-(((3,4-difluorophenyl)sulfonyl)(methyl)amino)-3-pyridinyl)-1,3-benzothiazol-2-yl)acetamide | | 475 | 0.3769 | 2.8928 | 2.1816 |
| 223 | N-(6-(5-(((4-tert-butylphenyl)sulfonyl)(methyl)amino)-3-pyridinyl)-1,3-benzothiazol-2-yl)acetamide | | 495 | 0.0535 | 3.8168 | 0.4172 |
| 224 | N-(6-(5-(methyl(phenylsulfonyl)amino)-3-pyridinyl)-1,3-benzothiazol-2-yl)acetamide | | 439 | 0.1110 | 1.4878 | 0.1447 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 225 | N-(6-(6-(methyl((3-methylphenyl)sulfonyl)amino)-2-pyridinyl)-1,3-benzothiazol-2-yl)acetamide | | 453 | 0.0647 | 0.2940 | 0.2440 |
| 226 | N-(6-(6-(((2-fluorophenyl)sulfonyl)(methyl)amino)-2-pyridinyl)-1,3-benzothiazol-2-yl)acetamide | | 457 | 0.1607 | 0.5763 | |
| 227 | N-(6-(6-(tert-butylamino)-2-pyrazinyl)-1,3-benzothiazol-2-yl)acetamide | | 342 | | | 0.3625 |
| 228 | N-(5-(5-(((4-fluorophenyl)sulfonyl)amino)-3-pyridinyl)[1,3]thiazolo[5,4-b]pyridin-2-yl)acetamide | | 444 | 0.0075 | 0.0559 | 0.0549 |
| 229 | N-(6-(5-(2-(2-oxo-1-pyrrolidinyl)ethoxy)-3-pyridinyl)-1,3-benzothiazol-2-yl)acetamide | | 397 | 1.0762 | 14.9687 | |
| 230 | N-(6-(5-(2-(4-morpholinyl)ethoxy)-3-pyridinyl)-1,3-benzothiazol-2-yl)acetamide | | 399 | 2.7949 | 19.2630 | |
| 231 | N-(6-(5-(1-methyl-2-(4-morpholinyl)ethoxy)-3-pyridinyl)-1,3-benzothiazol-2-yl)acetamide | | 413 | 0.6372 | 15.6950 | |
| 232 | N-(6-(5-(2-(2-oxo-1,3-oxazolidin-3-yl)ethoxy)-3-pyridinyl)-1,3-benzothiazol-2-yl)acetamide | | 399 | 0.8368 | 7.4432 | |
| 233 | N-(6-(5-(2-(1-piperidinyl)ethoxy)-3-pyridinyl)-1,3-benzothiazol-2-yl)acetamide | | 397 | 4.1402 | 11.9127 | |
| 234 | N-(6-(5-(2-(1-azepanyl)ethoxy)-3-pyridinyl)-1,3-benzothiazol-2-yl)acetamide | | 411 | 2.4881 | 9.9827 | |
| 235 | N-(6-(6-chloro-5-(tetrahydro-3-furanyloxy)-3-pyridinyl)-1,3-benzothiazol-2-yl)acetamide | | 390 | 0.1687 | 2.8709 | |
| 235 | N-(6-(6-chloro-5-(1-methylethoxy)-3-pyridinyl)-1,3-benzothiazol-2-yl)acetamide | | 362 | 0.0441 | 0.4722 | 0.4523 |
| 236 | N-(6-(6-chloro-5-((3S)-tetrahydro-3-furanyloxy)-3-pyridinyl)-1,3-benzothiazol-2-yl)acetamide | | 390 | 0.1501 | 1.3706 | 0.8283 |
| 237 | N-(6-(6-bromo-5-methoxy-3-pyridinyl)-1,3-benzothiazol-2-yl)acetamide | | 378 | 8.3725 | 13.3333 | >5 |
| 238 | N-(6-(6-chloro-5-fluoro-3-pyridinyl)-1,3-benzothiazol-2-yl)acetamide | | 322 | 0.2505 | 13.3333 | 1.4933 |
| 239 | N-(6-(6-chloro-5-ethoxy-3-pyridinyl)-1,3-benzothiazol-2-yl)acetamide | | 348 | 0.0538 | 3.7911 | 2.9577 |
| 240 | N-(6-(6-chloro-5-methoxy-3-pyridinyl)-1,3-benzothiazol-2-yl)acetamide | | 334 | 0.1551 | 1.2751 | 0.6430 |
| 241 | N-(6-(4-methoxy-3-pyridinyl)-1,3-benzothiazol-2-yl)acetamide | | 300 | 0.0735 | 10.6605 | 0.8162 |
| 242 | N-(6-(6-methoxy-3-pyridinyl)-1,3-benzothiazol-2-yl)acetamide | | 300 | 0.0739 | >40 | 0.6355 |
| 243 | N-(6-(6-ethoxy-3-pyridinyl)-1,3-benzothiazol-2-yl)acetamide | | 314 | 0.1562 | >40 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 244 | N-(6-(6-methoxy-4-methyl-3-pyridinyl)-1,3-benzothiazol-2-yl)acetamide | | 314 | 0.6878 | 2.9942 | |
| 245 | N-(6-(4-methyl-3-pyridinyl)-1,3-benzothiazol-2-yl)acetamide | | 284 | 0.4856 | 42.4633 | |
| 246 | N-(6-(6-chloro-4-methoxy-3-pyridinyl)-1,3-benzothiazol-2-yl)acetamide | | 334 | 0.2558 | 12.3880 | |
| 247 | N-(6-(6-chloro-5-(difluoromethoxy)-3-pyridinyl)-1,3-benzothiazol-2-yl)acetamide | | 370 | 0.0195 | 0.2435 | 0.0939 |
| 248 | N-(6-(4-(difluoromethoxy)-3-pyridinyl)-1,3-benzothiazol-2-yl)acetamide | | 336 | 3.8429 | 17.0800 | |
| 249 | N-(6-(6-(difluoromethoxy)-3-pyridinyl)-1,3-benzothiazol-2-yl)acetamide | | 336 | 0.7167 | 8.1062 | |
| 250 | N-(6-(6-(difluoromethoxy)-4-methyl-3-pyridinyl)-1,3-benzothiazol-2-yl)acetamide | | 350 | 11.8795 | 27.4829 | |
| 251 | N-(6-(4-(hydroxymethyl)-3-pyridinyl)-1,3-benzothiazol-2-yl)acetamide | | 300 | 1.9119 | >40 | |
| 252 | N-(6-(5-(2-(3,3-dimethyl-2-oxo-1-pyrrolidinyl)ethoxy)-3-pyridinyl)-1,3-benzothiazol-2-yl)acetamide | | 425 | 2.9205 | 45.0081 | |
| 253 | N-(6-(5-(2-(3-methyl-2-oxo-1-pyrrolidinyl)ethoxy)-3-pyridinyl)-1,3-benzothiazol-2-yl)acetamide | | 411 | 1.5392 | 45.5773 | |
| 254 | N-(6-(5-(2-(3,3-difluoro-2-oxo-1-pyrrolidinyl)ethoxy)-3-pyridinyl)-1,3-benzothiazol-2-yl)acetamide | | 433 | 1.1798 | 24.1262 | |
| 255 | N-(6-(5-(2-(3-fluoro-2-oxo-1-pyrrolidinyl)ethoxy)-3-pyridinyl)-1,3-benzothiazol-2-yl)acetamide | | 415 | 0.7935 | >40 | |
| 256 | N-(6-(6-chloro-5-(((4-(1-hydroxyethyl)phenyl)sulfonyl)amino)-3-pyridinyl)-1,3-benzothiazol-2-yl)acetamide | | 541 (M + K) | 0.0052 | 0.0073 | 0.0099 |
| 257 | N-(6-(6-chloro-5-(((4-(1-hydroxyethyl)phenyl)sulfonyl)amino)-3-pyridinyl)-1,3-benzothiazol-2-yl)acetamide (enantiomer A) | | 503 | 0.0062 | 0.0072 | 0.0083 |
| 258 | N-(6-(6-chloro-5-(((4-1-hydroxyethyl)phenyl)sulfonyl)amino)-3-pyridinyl)-1,3-benzothiazol-2-yl)acetamide (enantiomer B) | | 503 | 0.0076 | 0.0114 | 0.0488 |
| 259 | N-(6-(5-(((4-(1-hydroxyethyl)phenyl)sulfonyl)amino)-3-pyridinyl)-1,3-benzothiazol-2-yl)acetamide | | 469 | 0.0121 | 0.0322 | 0.3883 |
| 260 | N-(6-(3-(((4-methoxyphenyl)sulfonyl)amino)phenyl)-1,3-benzothiazol-2-yl)acetamide | | 454 | 0.0948 | 0.4134 | |
| 261 | N-(6-(2-(tetrahydro-2H-pyran-4-ylamino)-4-pyrimidinyl)-1,3-benzothiazol-2-yl)acetamide | | 370 | 0.8998 | 13.0507 | 1.7007 |
| 262 | N-(6-(2-((2R)-2-(2-methylphenyl)-1-pyrrolidinyl)-4-pyrimidinyl)-1,3-benzothiazol-2-yl)acetamide | | 430 | 1.5605 | 0.7775 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 263 | N-(6-(2-(1-piperidinyl)-4-pyrimidinyl)-1,3-benzothiazol-2-yl)acetamide | | 354 | 1.9379 | >40 | |
| 264 | N-(6-(2-(2-pyridinylamino)-4-pyrimidinyl)-1,3-benzothiazol-2-yl)acetamide | | 363 | 2.4878 | >40 | |
| 265 | N-(6-(2-(1-piperidinylamino)-4-pyrimidinyl)-1,3-benzothiazol-2-yl)acetamide | | 369 | 2.5981 | 40.7889 | |
| 266 | N-(6-(2-((2R)-2-phenyl-1-pyrrolidinyl)-4-pyrimidinyl)-1,3-benzothiazol-2-yl)acetamide | | 416 | 2.6177 | 1.6099 | |
| 267 | N-(6-(6-cyano-5-(((4-methoxyphenyl)sulfonyl)amino)-3-pyridinyl)-1,3-benzothiazol-2-yl)acetamide | | 478 (M − H) | 0.0145 | 0.0209 | 1.4341 |
| 268 | N-(6-(5-amino-6-cyano-3-pyridinyl)-1,3-benzothiazol-2-yl)acetamide | | 308 (M − H) | 0.2413 | 17.0134 | 0.8418 |
| 269 | N-(6-(6-chloro-5-(dimethylamino)-3-pyridinyl)-1,3-benzothiazol-2-yl)acetamide | | 347 | 0.0199 | 0.2211 | 0.0567 |
| 270 | phenyl (6-(6-chloro-5-(dimethylamino)-3-pyridinyl)-1,3-benzothiazol-2-yl)carbamate | | 425 | 0.0346 | 2.4594 | >5 |
| 271 | N-(6-(6-chloro-5-(dimethylamino)-3-pyridinyl)-1,3-benzothiazol-2-yl)-2-methoxyacetamide | | 377 | 0.0515 | 1.2339 | 0.3124 |
| 272 | N-(6-(6-chloro-5-(dimethylamino)-3-pyridinyl)-1,3-benzothiazol-2-yl)-2-phenoxyacetamide | | 439 | 0.0589 | 1.4503 | >5 |
| 273 | 1-(6-(6-chloro-5-(dimethylamino)-3-pyridinyl)-1,3-benzothiazol-2-yl)-3-(2-(4-morpholinyl)ethyl)urea | | 461 | 0.1149 | 2.0740 | |
| 274 | 6-(6-chloro-5-(dimethylamino)-3-pyridinyl)-1,3-benzothiazol-2-amine | | 305 | 0.1912 | 0.6126 | 0.9854 |
| 275 | N-(6-(6-chloro-5-(dimethylamino)-3-pyridinyl)-1,3-benzothiazol-2-yl)-N~2~,N~2~-dimethylglycinamide | | 390 | 0.3108 | 2.9043 | 0.6162 |
| 276 | N-(6-(6-chloro-5-(dimethylamino)-3-pyridinyl)-1,3-benzothiazol-2-yl)methanesulfonamide | | 383 | 1.7228 | 29.9441 | |
| 277 | di-tert-butyl (5-(2-(acetylamino)-1,3-benzothiazol-6-yl)-2-chloro-3-pyridinyl)imidodicarbonate | | 519 | 2.1872 | 4.8013 | |
| 288 | N-(6-(5-(cyanomethoxy)-3-pyridinyl)-1,3-benzothiazol-2-yl)acetamide | | 325 | 0.0833 | 0.4635 | 0.2355 |
| 289 | N-(6-(5-fluoro-3-pyridinyl)-1,3-benzothiazol-2-yl)acetamide | | 288 | 0.0963 | 3.2089 | 0.4496 |
| 290 | N-(6-(6-chloro-5-(1-cyanoethoxy)-3-pyridinyl)-1,3-benzothiazol-2-yl)acetamide | | 373 | 0.1109 | 0.7469 | |
| 291 | N-(6-(2-chloro-5-(1-cyanoethoxy)-3-pyridinyl)-1,3-benzothiazol-2-yl)acetamide | | 373 | 0.9834 | 3.7894 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 292 | N-(6-(6-chloro-5-((2-methoxyethoxy)methoxy)-3-pyridinyl)-1,3-benzothiazol-2-yl)acetamide | | 408 | 0.1643 | 2.0750 | |
| 293 | N-(6-(5-((2-methoxyethoxy)methoxy)-6-(trifluoromethyl)-3-pyridinyl)-1,3-benzothiazol-2-yl)acetamide | | 442 | 0.2114 | >40 | |
| 294 | N-(6-(5-(((2R)-5-oxo-2-pyrrolidinyl)methoxy)-3-pyridinyl)-1,3-benzothiazol-2-yl)acetamide | | 383 | | | >5 |
| 295 | N-(6-(5-((1-aminocyclopropyl)methoxy)-3-pyridinyl)-1,3-benzothiazol-2-yl)acetamide | | 355 | | | |
| 296 | N-(6-(5-hydroxy-3-pyridinyl)-1,3-benzothiazol-2-yl)acetamide | | 286 | | | 0.4184 |
| 297 | N-(6-(6-chloro-3-pyridinyl)-1,3-benzothiazol-2-yl)acetamide | | 304 | | | 1.1879 |
| 298 | N-(2-((5-(2-(acetylamino)-1,3-benzothiazol-6-yl)-3-pyridinyl)oxy)ethyl)-2-methoxyacetamide | | 401 | | | 1.8278 |
| 300 | N-(6-(6-(3-azabicyclo[322]non-3-yl)-2-pyrazinyl)-1,3-benzothiazol-2-yl)acetamide | | 394 | | | 8.9411 |
| 301 | N-(6-(6-chloro-5-hydroxy-3-pyridinyl)-1,3-benzothiazol-2-yl)acetamide | | 320 | 0.0050 | 0.0941 | 0.1001 |
| 302 | N-(6-(5-hydroxy-6-(trifluoromethyl)-3-pyridinyl)-1,3-benzothiazol-2-yl)acetamide | | 354 | 0.0085 | 0.1592 | 0.1570 |
| 303 | 5-(2-(acetylamino)-1,3-benzothiazol-6-yl)-2-chloro-3-pyridinyl acetate | | 362 | 0.0020 | 0.0122 | 0.0017 |
| 304 | N-(6-(6-chloro-5-(((4-methoxyphenyl)sulfonyl)amino)-3-pyridinyl)-1,3-benzothiazol-2-yl)cyclohexanecarboxamide | | 557 | 0.0163 | 0.0292 | |
| 305 | N-(2-chloro-5-(2-((1-methylethyl)amino)-1,3-benzothiazol-6-yl)-3-pyridinyl)-4-methoxybenzenesulfonamide | | 489 | 0.0589 | 0.2241 | |
| 306 | N-(2-chloro-5-(2-((cyclohexylmethyl)amino)-1,3-benzothiazol-6-yl)-3-pyridinyl)-4-methoxybenzenesulfonamide | | 543 | 0.1039 | 0.4114 | |
| 307 | N-(5-(2-amino-1,3-benzothiazol-6-yl)-2-chloro-3-pyridinyl)-3-(difluoromethoxy)benzenesulfonamide | | 483 | 0.0067 | 0.0173 | 0.1152 |
| 308 | N-(5-(2-amino-1,3-benzothiazol-6-yl)-2-chloro-3-pyridinyl)-2-chloro-4-(trifluoromethyl)benzenesulfonamide | | 519 | 0.0026 | 0.0106 | 0.5006 |
| 309 | N-(5-(2-amino-1,3-benzothiazol-6-yl)-2-chloro-3-pyridinyl)-2-chloro-4-fluorobenzenesulfonamide | | 469 | 0.0149 | 0.0368 | 0.4959 |
| 310 | N-(5-(2-amino-1,3-benzothiazol-6-yl)-2-chloro-3-pyridinyl)-2,4-dichlorobenzenesulfonamide | | 485 | 0.0076 | 0.0174 | 0.4021 |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 311 | N-(5-(2-amino-1,3-benzothiazol-6-yl)-2-chloro-3-pyridinyl)-2,4-difluorobenzenesulfonamide | | 453 | 0.0171 | 0.0491 | 0.2222 |
| 312 | N-(5-(2-amino-1,3-benzothiazol-6-yl)-2-chloro-3-pyridinyl)-4-fluoro-2-methylbenzenesulfonamide | | 449 | 0.0060 | 0.0249 | 0.3483 |
| 313 | N-(5-(2-amino-1,3-benzothiazol-6-yl)-2-chloro-3-pyridinyl)-4-chloro-2-fluorobenzenesulfonamide | | 469 | 0.0136 | 0.0279 | 0.4240 |
| 314 | N-(5-(2-amino-1,3-benzothiazol-6-yl)-2-chloro-3-pyridinyl)-2-(trifluoromethyl)benzenesulfonamide | | 485 | 0.0025 | 0.0127 | 0.2050 |
| 315 | 6-(5-(tert-butylamino)-6-chloro-3-pyridinyl)-1,3-benzothiazol-2-amine | | 333 | 0.9649 | 2.9385 | |
| 316 | N-(6-(6-chloro-5-((1-piperidinylsulfonyl)amino)-3-pyridinyl)-1,3-benzothiazol-2-yl)acetamide | | 466 | 0.0103 | 0.0358 | 0.0070 |
| 317 | N-(2-chloro-5-(2-(methylamino)-1,3-benzothiazol-6-yl)-3-pyridinyl)-4-fluorobenzenesulfonamide | | 449 | 0.0086 | 0.0302 | 0.2457 |
| 318 | 2-chloro-N-(2-chloro-5-(2-(methylamino)-1,3-benzothiazol-6-yl)-3-pyridinyl)-6-methylbenzenesulfonamide | | 479 | 0.0112 | 0.0423 | 0.3288 |
| 319 | 2,6-dichloro-N-(2-chloro-5-(2-(methylamino)-1,3-benzothiazol-6-yl)-3-pyridinyl)benzenesulfonamide | | 499 | 0.0092 | 0.0365 | 0.4744 |
| 320 | N-(2-chloro-5-(2-(methylamino)-1,3-benzothiazol-6-yl)-3-pyridinyl)-2-fluorobenzenesulfonamide | | 449 | 0.0146 | 0.0618 | 0.4478 |
| 321 | 4-acetyl-N-(2-chloro-5-(2-(methylamino)-1,3-benzothiazol-6-yl)-3-pyridinyl)benzenesulfonamide | | 473 | 0.0120 | 0.0222 | 0.6724 |
| 322 | N-(1-(4-((2-chloro-5-(2-(methylamino)-1,3-benzothiazol-6-yl)-3-pyridinyl)sulfamoyl)phenyl)-1-methylethyl)acetamide | | 530 | 0.0108 | 0.0254 | 0.5575 |
| 323 | N-(1-(4-((5-(2-amino-1,3-benzothiazol-6-yl)-2-chloro-3-pyridinyl)sulfamoyl)phenyl)-1-methylethyl)acetamide | | 516 | 0.0196 | 0.0332 | 0.9152 |
| 324 | N-(5-(2-amino-1,3-benzothiazol-6-yl)-2-chloro-3-pyridinyl)-4-(1-hydroxy-1-methylethyl)benzenesulfonamide | | 475 | 0.0109 | 0.0171 | 0.1512 |
| 325 | 4-acetyl-N-(5-(2-amino-1,3-benzothiazol-6-yl)-2-chloro-3-pyridinyl)benzenesulfonamide | | 459 | 0.0180 | 0.0206 | 0.4679 |
| 326 | N-(5-(1,3-benzoxazol-6-yl)-2-chloro-3-pyridinyl)-4-fluorobenzenesulfonamide | | 404 | 0.0223 | 0.0345 | >5 |
| 327 | N-(2-chloro-5-(2-(methylsulfanyl)-1,3-benzothiazol-6-yl)-3-pyridinyl)-4-methoxybenzenesulfonamide | | 478 | 0.2225 | 0.3843 | |
| 334 | 5-(1,3-benzothiazol-6-yl)-2-chloro-3-pyridinol | | 263 | 0.1164 | 1.3488 | |

TABLE I-continued

| Ex. # | IUPAC Name | Synthetic Method | Mass Spec m/z Found (M + H unless designated otherwise) | PI3Kα ATP loss IC$_{50}$ | PI3Kβ ATP loss IC$_{50}$ | HCT 116 pAKT IC$_{50}$ |
|---|---|---|---|---|---|---|
| 335 | 5-(1,3-benzothiazol-6-yl)-2-chloro-3-pyridinyl acetate | | 305 | 0.0156 | 0.1127 | 0.0440 |
| 336 | 1-(5-(1,3-benzothiazol-6-yl)-3-pyridinyl)ethanone | | 255 | 2.5523 | 13.2740 | |
| 341 | 6-fluoro-5-(2-methyl-1,3-benzothiazol-6-yl)-2-(trifluoromethyl)-3-pyridinol | | 329 | 21.7768 | >40 | |

Various experimental methods have been employed to synthesize compounds of the present invention, as more generally described in Schemes 1, 2, 3 and 4 above, and further described in more detail by the representative examples. In Table I, if data is not present for a particular assay, the data was not available.

The following compounds in Tables 2-6 are additional representative examples of compounds of the present invention that may be made by processes analogous to those disclosed herein.

TABLE 2

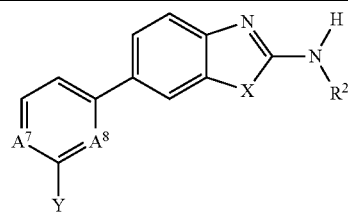

| R$^2$ | A$^7$ | A$^8$ | X | Y |
|---|---|---|---|---|
| —C(O)CH$_3$ | N | N | S | —NHSO$_2$-(3-CF$_3$-phenyl) |
| —C(O)CH$_3$ | N | N | S | —NHSO$_2$-(3-Cl-phenyl) |
| —C(O)C$_2$H$_5$ | N | N | S | —NHSO$_2$-(3-OCH$_3$-phenyl) |
| —C(O)C$_2$H$_5$ | N | N | O | —NHSO$_2$-(2-Cl-phenyl) |
| —C(O)C$_2$H$_5$ | N | N | O | —NHSO$_2$-(2-OH-phenyl) |
| —C(O)CH$_3$ | N— | N | O | —NHSO$_2$-(3-OCF$_3$-phenyl) |
| —C(O)CH$_3$ | N | N | S | —NHSO$_2$-(2-CF$_3$-phenyl) |
| —C(O)C$_2$H$_5$ | CH | N | S | —NHSO$_2$-(2-F-phenyl) |
| —C(O)C$_2$H$_5$ | CH | N | S | —NHSO$_2$-(3-F-phenyl) |
| —C(O)C$_2$H$_5$ | CH | N | O | —NHSO$_2$-(4-CF$_3$-phenyl) |
| —C(O)C$_2$H$_5$ | CH | N | O | —NHSO$_2$-(4-OCH$_3$-phenyl) |
| —C(O)C$_3$H$_7$ | CH | N | O | —NHSO$_2$-(4-Cl-phenyl) |
| —C(O)C$_3$H$_7$ | CH | N | S | —NHSO$_2$-(4-C$_2$H$_5$-phenyl) |
| —CH$_3$ | N | N | S | —NHSO$_2$-(4-CH$_3$-phenyl) |
| —C$_2$H$_5$— | N | N | O | —NHSO$_2$-(4-OH-phenyl) |
| —C(O)C$_2$H$_5$ | N | N | O | —NHSO$_2$-(2-OEt-phenyl) |
| —C(O)CH$_3$ | N— | N | O | —NHSO$_2$-(3-Et-phenyl) |
| —C(O)CH$_3$ | N | N | S | —NHSO$_2$-(4-F-phenyl) |
| —C(O)CH$_3$ | N | N | S | —SO$_2$CH$_2$-(3-CF$_3$-phenyl) |
| —C(O)CH$_3$ | N | N | S | —SO$_2$C(CH$_3$)$_2$-(3-Cl-phenyl) |
| —C(O)C$_2$H$_5$ | N | N | S | —SO$_2$-(3-OCH$_3$-phenyl) |
| —C(O)C$_2$H$_5$ | N | N | O | —SO$_2$CH$_2$-(4-CF$_3$-phenyl) |
| —C(O)C$_2$H$_5$ | N | N | O | —SO$_2$C(CH$_3$)2-(4-Cl-phenyl) |
| —C(O)CH$_3$ | N | N | O | —SO$_2$-(4-OCH$_3$-phenyl) |
| —C(O)CH$_3$ | N | N | S | —SO$_2$-(2-CF$_3$-phenyl) |
| —C(O)C$_2$H$_5$ | CH | N | S | —SO$_2$C(CH$_3$)2-(2-Cl-phenyl) |
| —C(O)C$_2$H$_5$ | CH | N | S | —SO$_2$-(2-OCH$_3$-phenyl) |
| —C(O)C$_2$H$_5$ | CH | N | O | —SO$_2$CH$_2$-(4-F-phenyl) |
| —C(O)C$_2$H$_5$ | CH | N | O | —SO$_2$C(CH$_3$)$_2$-(4-CH$_3$-phenyl) |
| —C(O)C$_3$H$_7$ | CH | N | O | —SO$_2$-(4-CH$_3$-phenyl) |
| —C(O)C$_3$H$_7$ | CH | N | S | —SO$_2$CH$_2$-(3,5-diF-phenyl) |
| —CH$_3$ | N | N | S | —SO$_2$C(CH$_3$)$_2$-(3,4-diF-phenyl) |
| —C$_2$H$_5$ | N | N | O | —SO$_2$-(2-F, 4-OCH$_3$-phenyl) |
| —C(O)C$_2$H$_5$ | N | N | O | —SO$_2$CH$_2$-(3-CF$_3$-phenyl) |

TABLE 2-continued

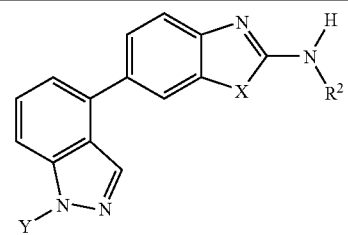

| R$^2$ | A$^7$ | A$^8$ | X | Y |
|---|---|---|---|---|
| —C(O)CH$_3$ | N | N | O | —SO$_2$C(CH$_3$)$_2$-(3-Cl-phenyl) |
| —C(O)CH$_3$ | N | N | S | —SO$_2$-(3-OEt-phenyl) |
| —C(O)CH$_3$ | N | N | S | —NHSO$_2$-(3,5-diF-phenyl) |
| —C(O)CH$_3$ | N | N | S | —NHSO$_2$-(2,4-diOCH$_3$-phenyl) |
| —C(O)CH$_3$ | N | N | S | —NHC(O)-(3-CF$_3$-phenyl) |
| —C(O)CH$_3$ | N | N | S | —NHC(O)-(3-Cl-phenyl) |
| —C(O)C$_2$H$_5$ | N | N | S | —NHC(O)-(3-OCH$_3$-phenyl) |
| —C(O)C$_2$H$_5$ | N | N | O | —NHC(O)-(2-Cl-phenyl) |
| —C(O)C$_2$H$_5$ | N | N | O | —NHC(O)-(2-OH-phenyl) |
| —C(O)CH$_3$ | N | N | O | —C(O)NH-(3-OCF$_3$-phenyl) |
| —C(O)CH$_3$ | N | N | S | —C(O)NH-(2-CF$_3$-phenyl) |
| —C(O)C$_2$H$_5$ | CH | N | S | —C(O)NH-(2-F-phenyl) |
| —C(O)C$_2$H$_5$ | CH | N | S | —C(O)NH-(3-F-phenyl) |
| —C(O)C$_2$H$_5$ | CH | N | O | —SO$_2$NH-(4-CF$_3$-phenyl) |

TABLE 3

| R$^2$ | X | R$^6$ |
|---|---|---|
| —C(O)CH$_3$ | S | —SO$_2$-(3-CF$_3$-phenyl) |
| —C(O)CH$_3$ | S | —SO$_2$-(3-Cl-phenyl) |
| —C(O)C$_2$H$_5$ | S | —SO$_2$-(3-OCH$_3$-phenyl) |
| —C(O)C$_2$H$_5$ | O | —C(CH$_3$)$_2$-(2-Cl-phenyl) |
| —C(O)C$_2$H$_5$ | O | —C(CH$_3$)$_2$-(2-OH-phenyl) |
| —C(O)CH$_3$ | O | —C(CH$_3$)$_2$-(3-OCF$_3$-phenyl) |
| —C(O)CH$_3$ | S | —CH$_2$-(2-CF$_3$-phenyl) |
| —C(O)C$_2$H$_5$ | S | —C(CH$_3$)$_2$-(2-F-phenyl) |
| —C(O)C$_2$H$_5$ | S | —CH$_2$-(3-F-phenyl) |
| —C(O)C$_2$H$_5$ | O | —CH$_2$-(4-CF$_3$-phenyl) |
| —C(O)C$_2$H$_5$ | O | —CH$_2$-(4-OCH$_3$-phenyl) |
| —C(O)C$_3$H$_7$ | O | —CH$_2$-(4-Cl-phenyl) |
| —C(O)C$_3$H$_7$ | S | —CH$_2$-(4-C$_2$H$_5$-phenyl) |
| —CH$_3$ | S | —CH$_2$-(4-CH$_3$-phenyl) |
| —C$_2$H$_5$ | O | —C(CH$_3$)$_2$-(4-OH-phenyl) |

TABLE 3-continued

Structure: indazole fused bicycle connected to benzoxazole/thiazole with NH-R² substituent, Y on indazole N.

| R² | X | R⁶ |
|---|---|---|
| —C(O)CH₃ | O | —C(CH₃)₂-(3-CF₃-phenyl) |
| —C(O)CH₃ | O | —C(CH₃)₂-(3-Cl-phenyl) |
| —C(O)C₂H₅ | S | —SO₂-(3-OCH₃-phenyl) |
| —C(O)C₂H₅ | S | —SO₂-(2-Cl-phenyl) |
| —C(O)C₂H₅ | S | —C(CH₃)₂-(2-OH-phenyl) |
| —C(O)CH₃ | S | —SO₂-(3-OCF₃-phenyl) |
| —C(O)CH₃ | S | —SO₂-(2-CF₃-phenyl) |

TABLE 4

Structure with B¹, B² heterocycle, X, Y substituents.

| R² | B¹ | B² | X | Y |
|---|---|---|---|---|
| —C(O)CH₃ | N | S | S | —NHSO₂-(3-CF₃-phenyl) |
| —C(O)CH₃ | N | S | S | —NHSO₂-(3-Cl-phenyl) |
| —C(O)C₂H₅ | N | S | S | —NHSO₂-(3-OCH₃-phenyl) |
| —C(O)C₂H₅ | N | S | O | —NHSO₂-(2-Cl-phenyl) |
| —C(O)C₂H₅ | N | S | O | —NHSO₂-(2-OH-phenyl) |
| —C(O)CH₃ | N | NH | O | —NHSO₂-(3-OCF₃-phenyl) |
| —C(O)CH₃ | N | NH | S | —NHSO₂-(2-CF₃-phenyl) |
| —C(O)C₂H₅ | CH | NH | S | —NHSO₂-(2-F-phenyl) |
| —C(O)C₂H₅ | CH | NH | S | —NHSO₂-(3-F-phenyl) |
| —C(O)C₂H₅ | CH | O | O | —NHSO₂-(4-CF₃-phenyl) |
| —C(O)C₂H₅ | CH | O | O | —NHSO₂-(4-OCH₃-phenyl) |
| —C(O)C₃H₇ | CH | O | O | —NHSO₂-(4-Cl-phenyl) |
| —C(O)C₃H₇ | CH | O | S | —NHSO₂-(4-C₂H₅-phenyl) |
| —CH₃ | N | O | S | —NHSO₂-(4-CH₃-phenyl) |
| —C₂H₅ | N | O— | O | —NHSO₂-(4-OH-phenyl) |
| —C(O)C₂H₅ | N | O | O | —NHSO₂-(2-Cl-phenyl) |
| —C(O)C₂H₅ | N | O | S | —NHSO₂-(2-OH-phenyl) |
| —C(O)CH₃ | N— | NH | S | —NHSO₂-(3-OCF₃-phenyl) |
| —C(O)CH₃ | N | NH | O | —NHSO₂-(2-CF₃-phenyl) |
| —C(O)CH₃ | N | NH | S | —NHC(O)-(3-OCH₃-phenyl) |

TABLE 5

Structure with A⁷, A⁸ (pyridine), X, Y substituents.

| R² | A⁷ | A⁸ | X | Y |
|---|---|---|---|---|
| —C(O)CH₃ | N | N | S | —NHSO₂-(2-CF₃-phenyl) |
| —C(O)C₂H₅ | CH | N | S | —NHSO₂-(2-F-phenyl) |
| —C(O)C₂H₅ | CH | N | S | —NHSO₂-(3-F-phenyl) |

TABLE 5-continued

| R² | A⁷ | A⁸ | X | Y |
|---|---|---|---|---|
| —C(O)C₂H₅ | CH | N | O | —NHSO₂-(4-CF₃-phenyl) |
| —C(O)C₂H₅ | CH | N | O | —NHSO₂-(4-OCH₃-phenyl) |
| —C(O)C₃H₇ | CH | N | O | —NHSO₂-(4-Cl-phenyl) |
| —C(O)C₃H₇ | CH | N | S | —NHSO₂-(4-C₂H₅-phenyl) |
| —CH₃ | N | N | S | —NHSO₂-(4-CH₃-phenyl) |
| —C₂H₅ | N | N | O | —NHSO₂-(4-OH-phenyl) |
| —C(O)C₂H₅ | N | N | O | —NHSO₂-(2-OEt-phenyl) |
| —C(O)CH₃ | N— | N | O | —NHSO₂-(3-Et-phenyl) |
| —C(O)CH₃ | N | N | S | —NHSO₂-(4-F-phenyl) |
| —C(O)CH₃ | N | N | S | —SO₂CH₂-(3-CF₃-phenyl) |
| —C(O)CH₃ | N | N | S | —SO₂C(CH₃)₂-(3-Cl-phenyl) |
| —C(O)C₂H₅ | N | N | S | —SO₂-(3-OCH₃-phenyl) |
| —C(O)C₂H₅ | N | N | O | —SO₂CH₂-(4-CF₃-phenyl) |
| —C(O)C₂H₅ | N | N | O | —SO₂C(CH₃)₂-(4-Cl-phenyl) |
| —C(O)CH₃ | N | N | O | —SO₂-(4-OCH₃-phenyl) |
| —C(O)CH₃ | N | N | S | —SO₂CH₂-(2-CF₃-phenyl) |
| —C(O)C₂H₅ | CH | N | S | —SO₂C(CH₃)₂-(2-Cl-phenyl) |
| —C(O)C₂H₅ | CH | N | S | —SO₂-(2-OCH₃-phenyl) |
| —C(O)C₂H₅ | CH | N | O | —SO₂CH₂-(4-F-phenyl) |
| —C(O)C₂H₅ | CH | N | O | —SO₂C(CH₃)₂-(4-CH₃-phenyl) |
| —C(O)C₃H₇ | CH | N | O | —SO₂-(4-CH₃-phenyl) |
| —C(O)C₃H₇ | CH | N | S | —SO₂CH₂-(3,5-diF-phenyl) |
| —CH₃ | N | N | S | —SO₂C(CH₃)₂-(3,4-diF-phenyl) |
| —C₂H₅ | N | N | O | —SO₂-(2-F, 4-OCH₃-phenyl) |

TABLE 6

Structure with A⁷, A⁸ (pyridine), X, Y substituents.

| R² | A⁷ | A⁸ | X | Y |
|---|---|---|---|---|
| —C(O)CH₃ | N | N | S | —NHSO₂-(2-CF₃-phenyl) |
| —C(O)C₂H₅ | CH | N | S | —NHSO₂-(2-F-phenyl) |
| —C(O)C₂H₅ | CH | N— | S | —NHSO₂-(3-F-phenyl) |
| —C(O)C₂H₅ | CH | N | O | —NHSO₂-(4-CF₃-phenyl) |
| —C(O)C₂H₅ | CH | N | O | —NHSO₂-(4-OCH₃-phenyl) |
| —C(O)C₃H₇ | CH | N | O | —NHSO₂-(4-Cl-phenyl) |
| —C(O)C₃H₇ | CH | N | S | —NHSO₂-(4-C₂H₅-phenyl) |
| —CH₃ | N | N | S | —NHSO₂-(4-CH₃-phenyl) |
| —C₂H₅ | N | N— | O | —NHSO₂-(4-OH-phenyl) |
| —C(O)C₂H₅ | N | N | O | —NHSO₂-(2-OEt-phenyl) |
| —C(O)CH₃ | N | N | O | —NHSO₂-(3-Et-phenyl) |
| —C(O)CH₃ | N | N | S | —NHSO₂-(4-F-phenyl) |
| —C(O)CH₃ | N | N | S | —SO₂CH₂-(3-CF₃-phenyl) |
| —C(O)CH₃ | N | N | S | —SO₂C(CH₃)₂-(3-Cl-phenyl) |
| —C(O)C₂H₅ | N | N | S | —SO₂-(3-OCH₃-phenyl) |
| —C(O)C₂H₅ | N | N | O | —SO₂CH₂-(4-CF₃-phenyl) |
| —C(O)C₂H₅ | N | N | O | —SO₂C(CH₃)₂-(4-Cl-phenyl) |
| —C(O)CH₃ | N | N | O | —SO₂-(4-OCH₃-phenyl) |
| —C(O)CH₃ | N | N | S | —SO₂CH₂-(2-CF₃-phenyl) |
| —C(O)C₂H₅ | CH | N | S | —SO₂C(CH₃)₂-(2-Cl-phenyl) |
| —C(O)C₂H₅ | CH | N— | S | —SO₂-(2-OCH₃-phenyl) |
| —C(O)C₂H₅ | CH | N | O | —SO₂CH₂-(4-F-phenyl) |
| —C(O)C₂H₅ | CH | N | O | —SO₂C(CH₃)₂-(4-CH₃-phenyl) |
| —C(O)C₃H₇ | CH | N | O | —SO₂-(4-CH₃-phenyl) |

TABLE 6-continued

| R² | A⁷ | A⁸ | X | Y |
|---|---|---|---|---|
| —C(O)C₃H₇ | CH | N | S | —SO₂CH₂-(3,5-diF-phenyl) |
| —CH₃ | N | N | S | —SO₂C(CH₃)₂-(3,4-diF-phenyl) |

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or in a different order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal. It should also be appreciated that the protecting groups should not be present in the end-products. One of ordinary skill in the art knows, or can establish, which protecting groups are suitable with the reactions described herein. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen). For clarity, the substituents may be attached to the same carbon or nitrogen atom. For example, gem-dialkyl substituents are contemplated herein.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labelled reagent for a non-isotopically labelled reagent.

The pharmacological properties of the compounds of this invention may be confirmed by a number of assays. The following assays have been carried out with the compounds according to the invention. Compounds of the invention were found to inhibit the activity of one or more members of the PI3 kinase enzyme family.

Biological Evaluation

The following assays can be employed to determine the degree of activity of individual compounds as PI3 kinase inhibitors. Compounds described herein have been tested in one or more of these assays, and have shown activity thereby demonstrating and confirming the utility of the compounds of the invention as PI3 kinase inhibitors and in the prophylaxis and treatment of PI3 kinase mediated diseases, including, without limitation, cell-proliferative and cell survival disorders and cancer.

Recombinant Expression of PI3K Enzymes

Full length p110 subunits of PI3K α, β and δ, N-terminally labeled with polyHis tag, were co-expressed with p85 in baculovirus expression vectors in sf9 insect cells. P110/p85 heterodimers were purified by sequential Ni-NTA, Q-HP, and Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, was expressed with baculovirus in Hi5 insect cells. The γ isozyme was purified by sequential Ni-NTA, Superdex-200, and Q-HP chromatography. They isozyme was stored frozen at −80° C. in $NaH_2PO_4$, pH 8, 0.2M NaCl, 1% ethylene glycol, 2 mM β-mercaptoethanol.

|  | Alpha | Beta | Delta | Gamma |
| --- | --- | --- | --- | --- |
| 50 mM Tris | pH 8 | pH 7.5 | pH 7.5 | pH 8 |
| $MgCl_2$ | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 hr | 2 hr | 2 hr | 1 hr |
| [Enzyme] | 15 nM | 40 nM | 15 nM | 50 nM |

In Vitro PI3 Kinase Enzyme Assays

PI3K enzyme assays (alpha, beta, delta and gamma) were performed in 25 mL with the above final concentrations of components in white polypropylene plates (Costar catalogue #3355). Phosphatidyl inositol phosphoacceptor, PtdIns(4,5)P2 (eg. P4508) was obtained from Echelon Biosciences. The ATPase activity of the alpha and gamma isozymes was not greatly stimulated by PtdIns(4,5)P2 under these conditions and was therefore omitted from the assay of these isozymes. Test compounds were dissolved in DMSO and diluted with three-fold serial dilutions. The compound in DMSO (1 μL) was added per test well, and the inhibition relative to reactions containing no compound, with and without enzyme was determined. After assay incubation at RT, the reaction was stopped and residual ATP determined by addition of an equal volume of a commercial ATP bioluminescence kit (Perkin Elmer EasyLite) according to the manufacturer's instructions, and detected using an Analyst GT luminometer.

'Activity data for the exemplary compounds tested in the PI3K alpha and beta enzyme assays is provided in Table I.

Cell-Based Phospho-AKT Ser473 Assay

This assay determines the ability of test compounds to inhibit the phosphorylation of Serine 473 in Akt using a MSD based sandwich immunoassay (Meso Scale Detection, catalogue # N411CAB-1). HCT 116 human colon carcinoma cell lines were grown routinely in McCoy's 5A growth medium (GIBCO, catalogue #16600) containing 10% FBS (GIBCO, catalogue #10099-141) and X1 Penicillin-streptomycin-glutamine (GIBCO, catalogue #10378-016). Prior to the assay cells were detached from the culture flask with trypsin, and re-suspended in complete media to give a final concentration of $1.6 \times 10^5$ cells per ml. Aliquots (100 μl) of the HCT116 cell suspension were seeded into each well of a 96 well tissue culture plate (Corning Incorporated COSTAR, catalogue#3595) to give a final density of 16,000 cells per well. Cells were then incubated overnight at 37° C.

The following day the cells were treated with serially diluted test compounds and incubated for 2 hours at 37° C. The culture media on the HCT 116 cells was replaced with 189 μl McCoys media, supplemented with 0.1% BSA (ICN Biomedicals, Inc., Catalogue#160069). Test compounds were prepared as either 10 mM or 0.5 mM stock solutions in DMSO, and serially diluted 3 fold in a 10-point dose-response curve to give final concentrations that were 200-fold greater than the desired final test concentration. Aliquots (1 μl) of serially-diluted tested compounds were transferred to 96 well tissue culture plates containing the HCT 116 cells. As a minimum response control, each plate contained wells having a final concentration of 2.5 μM of a potent PI3K inhibitor which had previously been shown to completely inhibit Akt phosphorylation at this test concentration. As a maximum response control, wells contained 0.5% DMSO in place of test compound. The plates were mixed at 700 rpm for 2 min to ensure even distribution of the test compound and incubated for 2 hours at 37° C. Cells were then stimulated with insulin-like growth factor 1 (Sigma, product #13769) at final concentration of 100 ng/ml for 15 minutes at 37° C. The media was then removed and the cells treated with 80 μl cell-lysis buffer (MSD) containing a cocktail of protease and phosphatase inhibitors for one hour at 4° C.

25 μl Cell-lysate was then transferred to pre-blocked MSD assay plates pre-coated with a capture antibody specific for Akt, and the plates incubated for 2 hours at room temperature. The cell lysates were then removed and plates were then washed four times with 200 μl per well of Tris wash buffer (500 mM Tris, PH 7.5, 1.5M NaCl, 0.2% Tween-20). Subsequently cells were incubated for 1 hour at room temperature with a 25 μl solution containing the detection antibody, anti-phospho Akt (Ser 473) labeled with an electrochemiluminescent compound (MSD SULPHO-TAG™ label). The detection antibody was removed and plates were then washed four times with 200 μl per well of Tris wash buffer. An aliquot of 150 μl of diluted MSD read buffer was then applied to each well, and the electrochemiluminescent signal was measured using a MSD SECTOR™ plate reader. This instrument measures the intensity of emitted light to determine a quantitative measure of phosphorylated Akt in each well. The dose-response data obtained with each compound were analyzed and the $IC_{50}$ inhibition of Akt phosphorylation at Ser473 calculated.

Activity data for the exemplary compounds tested in the PI3K cell based Akt assay is provided in Table I.

The compounds of the present invention may also inhibit mTOR. The assay below can be used to determine if a compound inhibits mTOR. Thus, one aspect of the present invention concerns compounds that inhibit PI3K and mTOR. The present invention also contemplates the use of such compounds for the treatment of the diseases and conditions, such as cancer, disclosed herein.

In Vitro mTOR Assay

The Invitrogen (Carlsbad, Calif.) mammalian target of rapamycin (mTOR) Lanthascreen assay can be used to quantitate mTOR kinase activity in an in vitro setting. Active mTOR phosphorylates eukaryotic translation initiation factor 4E binding protein 1 (4E-BP1) on residue threonine 46. This phosphorylation event can be detected with a phospho-specific terbium (Tb) labeled Ab, in turn bringing the Tb label in close proximity to the GFP tagged 4E-BP1 and allowing for time-resolved fluorescence resonance energy transfer (TR-FRET), which correlates 4E-BP1 phosphorylation levels with mTOR kinase activity.

Enzyme reaction buffer can be prepared in deionized water containing 50 mM HEPES (pH 7.5), 0.01% Polysorbate 20, 1 mM EGTA, and 10 mM $MnCl_2$.

Dilutions of the compound to be tested can be prepared in 96-well polypropylene plates (Fisher Scientific, Waltham, Mass.). One row represents a 10-point dose of compound diluted 1:3 in enzyme reaction buffer and 20% dimethyl sulfoxide (DMSO). The top concentration for all compounds is 36 μM. Wells 6 and 12 can serve as the no compound (DMSO only) and high compound controls.

An mTOR substrate solution can prepared in enzyme reaction buffer containing 1600 nM green fluorescent protein tagged eukaryotic translation initiation factor 4E binding protein 1 (GFP-4E-BPI) (Invitrogen, Carlsbad, Calif.) and 28 uM adenosine triphosphate (ATP) (Calbiochem, Gibbstown, N.J.).

mTOR enzyme (Invitrogen, Carlsbad, Calif.) can be diluted in enzyme reaction buffer to a working concentration of 100 ng/mL.

The enzyme assay can be run in 384 well low volume assay plates (Corning, Corning, N.Y.). 2.5 uL of substrate solution containing GFP-4E-BPI and ATP can be added to appropriate wells in the assay plate followed by 2.5 μL of compound dilutions. 5 μL of appropriately diluted mTOR enzyme can be added and the reaction allowed to proceed for 1 hour at room temperature. Final reagent concentrations in the enzyme assay are 50 ng/mL mTOR, 400 nM GFP-4E-BP1, and 7 μM ATP.

The enzyme assay can be terminated upon the addition of 10 μL of 20 mM EDTA and 4 nM Tb-labeled anti-phospho-4E-BP1 [T46] antibody (Invitrogen, Carlsbad, Calif.). The assay plate can then be incubated at room temperature for 1 hour and results read on a Tecan Safire II plate reader (Tecan, Mannedorf, Switzerland).

Indications

Accordingly, compounds of the invention are useful for, but not limited to, the prevention or treatment of PI3K mediated diseases and disorders including, melanomas, carcinomas, and other cancers, resulting from unregulated PI3K cell signaling pathways. In one embodiment of the invention, there is provided a method of modulating a PI3K enzyme in a subject, the method comprising administering to the subject an effective dosage amount of a compound of the present invention.

PI3K mediated disorders involve various cancers. In one embodiment, the invention provides a method of treating a PI3K mediated condition selected from the group consisting of a melanoma, a solid tumor, ovarian cancer, cervical cancer, breast cancer, colon cancer, endometrial cancer, pancreatic cancer, lung cancer, gastric carcinoma, glioblastoma, hepatocellular carcinoma, prostate carcinoma, rectal cancer, acute lyelogeous leukemia (AML), chronic lyelogenous leukemia (CML), small cell mung cancer, non-small-cell lung cancer, thyroid cancer and a combination thereof in a subject, the method comprising administering to the subject an effective dosage amount of a compound of the present invention.

Cancers which may be treated with compounds of the invention include, without limitation, carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Treatment of PI3K mediated cancers may be accomplished in combination with other oncological therapies. In one embodiment, the invention provides a method wherein administering the effective amount of a compound of the present invention to the subject comprises administering the compound in combination with one or more compounds selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof.

In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Other therapeutic agents such as those described below may be employed with the inventive compounds in the present methods. In the methods of the present invention, such other therapeutic agent(s) may be administered prior to, simultaneously with or following the administration of the compound(s) of the present invention.

The term "subject" as used herein is not intended to be limited to humans. Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutically acceptable salt thereof, or a pharmaceutical composition or medicament comprising the compound, to a subject (i.e., an animal, preferably a mammal, most preferably a human) which may be in need thereof, such as, for example, for pain, inflammation, cancer and the like. Treatment also encompasses prophylactic administration of a compound of the invention, or a pharmaceutical salt thereof, or a pharmaceutical composition or medicament of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. In yet another embodiment, there is provided a method of manufacturing a medicament having therein a compound of Formulas I through VI, comprising combining the compound with a pharmaceutically acceptable excipient.

The pharmaceutical composition, or medicament (used herein synonymously with composition) of the invention may comprise a therapeutically effective amount of a compound of the invention. Thus, a therapeutically effective amount may be administered to the subject in a single dosage form or in multiple dosage forms. Accordingly, another aspect of the invention provides a medicament comprising a therapeutically effective dosage amount of a compound of the invention. A therapeutically effective amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer such as with radiation therapy or with cytostatic or cytotoxic agents.

If formulated as a fixed dose, such combination products employ the compounds of this invention within the accepted dosage ranges. Compounds of the present invention may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or intravenous (IV) administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

The compounds of the present invention may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflomithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; miifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar.

It is noted that the agents recited above may also be administered as pharmaceutically acceptable salts when appropriate.

The compounds of the present invention may also be used in combination with radiation therapy, hormone therapy, surgery and immunotherapy, which therapies are well know to those skilled in the art.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The foregoing description is merely illustrative of the invention and is not intended to limit the invention to the disclosed compounds, compositions and methods. Variations and changes, which are apparent to one skilled in the art, are intended to be within the scope and nature of the invention, as defined in the appended claims. From the foregoing description, one skilled in the art can make various changes and modifications of the invention to adapt it to various usages and conditions. All patents and other publications recited herein are hereby incorporated by reference in their entireties.

What is claimed is:

1. A compound of Formula V

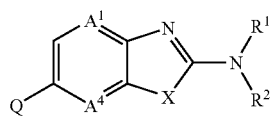

or a pharmaceutically acceptable salt thereof, wherein
Q is

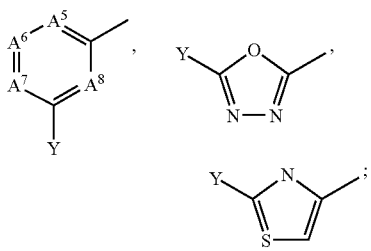

X is S;
$A^1$ is CH or C-halo;
$A^4$ is CH or C-halo;
$A^5$ is $CR^3$ or N;
$A^6$ is $CR^3$ or N;
$A^7$ is $CR^3$ or N;
$A^8$ is $CR^3$ or N; provided that no more than three of $A^5$, $A^6$, $A^7$ and $A^8$ is N;
each $R^3$ is independently H, $C_1$-$C_6$alkyl, halo, —$OC_1$-$C_6$alkyl, -Ohaloalkyl, —CN, or —$CF_3$;
$R^1$ is H;
$R^2$ is H, or $C(O)R^{7a}$,
$R^{7a}$ is $C_1$-$C_6$alkyl , —$(CRR)_nNR^xR^y$, —$(CRR)_n$aryl, —$(CRR)_n$heteroaryl, —$(CRR)_nOR$ —$(CRR)_n$heterocycloalkyl, —$(CRR)_n$Ophenyl, —$NR(CRR)_nR^xR^y$, or —$S(O)_2R$;
each R is independently H or $C_1$-$C_6$ alkyl;
each $R^X$ and $R^Y$ are independently hydrogen, or $C_1$-$C_6$alkyl, or $R^X$ and $R^Y$ together with the nitrogen atom to which they are attached form a 5 to 8 membered ring containing from 1 to 3 heteroatoms independently selected from N, O or S;
each n is independently 0, 1, 2, 3 or 4;
Y is —$NRSO_2(CRR)_n$aryl, —$NRSO_2C_1$-$C_6$alkyl, or —$NRSO_2$heteroaryl;
wherein aryl or heteroaryl can be optionally substituted with from 1 to 4 substitutents selected from halo, $C_1$-$C_6$alkyl, —$CF_3$, —CN, —$OC_1$-$C_6$haloalkyl, —$OC_1$-$C_6$alkyl, or $C(O)C_1$-$C_6$alkyl.

2. A compound of claim 1, or a pharmaceutically acceptable salt thereof, wherein
Q is

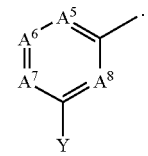

3. A compound of claim 1, or a pharmaceutically acceptable salt thereof, wherein X is S; Y is —$NRSO_2$phenyl; and R is H or $CH_3$, wherein phenyl can be optionally substituted with from 1 to 4 substitutents selected from halo, $C_1$-$C_6$alkyl, —$CF_3$, —CN, —$OC_1$-$C_6$haloalkyl, —$OC_1$-$C_6$alkyl, or $C(O)C_1$-$C_6$alkyl.

4. A compound of claim 1, or a pharmaceutically acceptable salt thereof, wherein Q is

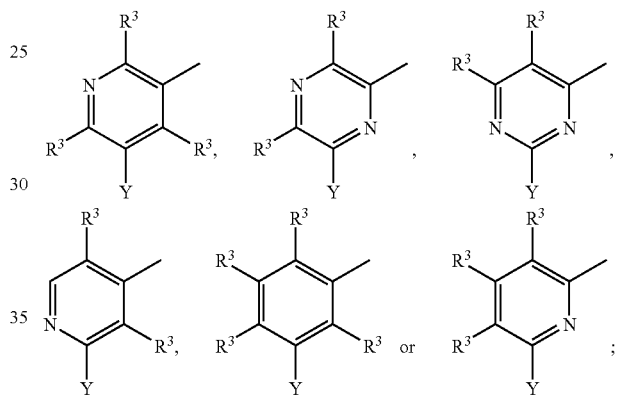

and each $R^3$ is independently H, halo, $C_1$-$C_6$alkyl, —$OC_1$-$C_6$alkyl, —CN or —$CF_3$.

5. A compound of claim 1, or a pharmaceutically acceptable salt thereof, wherein
$R^1$ is H and $R^2$ is $C(O)CH_3$.

6. A compound of claim 1, or a pharmaceutically acceptable salt thereof, wherein $A^4$ is CH N.

7. A compound of claim 1, or a pharmaceutically acceptable salt thereof, wherein Q is

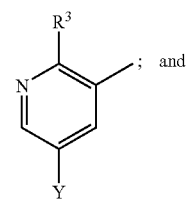

; and $R^3$ is halo, $C_1$-$C_6$alkyl, —$OC_1$-$C_6$alkyl, —CN or —$CF_3$.

8. A compound of claim 1, or a pharmaceutically acceptable salt thereof, wherein
$R^1$ is H;
$R^2$ is $C(O)CH_3$;
$A^1$ and $A^4$ are CH;

Q is

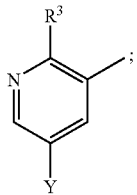

$R^3$ is halo; and
Y is —NHSO$_2$-phenyl, wherein the phenyl is optionally substituted with from 1 to 4 substituents selected from halo, C$_1$-C$_6$ alkyl, —CF$_3$, —CN, —OC$_1$-C$_6$haloalkyl, —OC$_1$-C$_6$alkyl, or C(O)C$_1$-C$_6$alkyl.

9. A compound of Formula IV

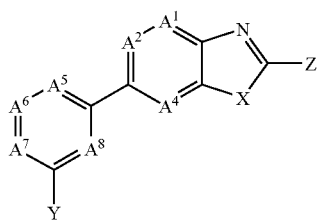

IV or a pharmaceutically acceptable salt thereof, wherein
A$^1$ is CR$^3$;
A$^2$ is CR$^4$;
A$^4$ is CR$^6$;
A$^5$ is CR$^3$ or N;
A$^6$ is CR$^3$ or N;
A$^7$ is CR$^3$ or N;
A$^8$ is CR$^3$ or N; provided that no more than three of A$^5$, A$^6$, A$^7$, and A$^8$ is N;
X is S;
Y is NR$^9$S(O)$_2$R$^8$ or NR$^9$S(O)$_2$R$^9$;
Z is —NR$^1$R$^2$;
R$^1$ is H, C$_{1-6}$-alkyl, C$_{2-6}$-alkenyl, C$_{2-6}$-alkynyl or C$_{3-6}$-cycloalkyl;
R$^2$ is H, C$_{2-6}$-alkenyl-R$^{7a}$, C$_{2-6}$-alkynyl-R$^{7a}$, C$_{3-6}$-cycloalkyl-R$^{7a}$, C(O)R$^{7a}$, C(=O)NHR$^{7a}$, COOR$^{7a}$, S(O)$_2$R$^{7a}$ or a partially or fully saturated or fully unsaturated 5- or 6-membered monocyclic ring formed of carbon atoms and including 1-3 heteroatoms selected from N, O and S, wherein the C$_{1-6}$-alkyl-R$^{7a}$, C$_{2-6}$-alkenyl-R$^{7a}$, C$_{2-6}$-alkynyl-R$^{7a}$ and C$_{3-6}$-cycloalkyl-R$^{7a}$ is optionally substituted with 1-5 subsituents of R$^9$, or R$^1$ and R$^2$ together with the nitrogen atom to which they are attached form a 5 to 8 membered ring containing from 1 to 3 heteroatoms independently selected from N, O or S;
R$^3$ is H, halo, haloalkyl, OH, C$_{1-4}$-alkyl, —O—C$_{1-4}$-alkyl, —S—C$_{1-4}$-alkyl, or C$_{1-4}$-alkyl-OH;
R$^4$ is H, halo, haloalkyl, OH, NH$_2$, C$_{1-6}$-alkyl, —O—C$_{1-6}$-alkyl, —O—C$_{1-8}$-haloalkyl, —C$_{1-6}$-alkyl-O—C$_{1-6}$-alkyl, —S—C$_{1-6}$-alkyl, —C$_{1-6}$-alkyl-S—C$_{1-6}$-alkyl, —NH—C$_{1-6}$-alkyl, —N-di-C$_{1-6}$-alkyl, —C$_{1-6}$-alkyl-NH—C$_{1-6}$-alkyl, C$_{2-8}$-alkenyl, C$_{2-8}$-alkynyl, C$_{3-6}$-cycloalkyl, wherein each of said C$_{1-6}$-alkyl, C$_{2-8}$-alkenyl, C$_{2-8}$-alkynyl is optionally substituted independently with 1-5 substituents of R$^9$;

R$^6$ is H, halo, haloalkyl, OH, NH$_2$, C$_{1-8}$-alkyl, —O—C$_{1-8}$-alkyl, —O—C$_{1-8}$-haloalkyl, —C$_{1-6}$-alkyl-O—C$_{1-6}$-alkyl, —S—C$_{1-8}$-alkyl, —C$_{1-6}$-alkyl-S—C$_{1-6}$-alkyl, —NH—C$_{1-8}$-alkyl, —N-di-C$_{1-8}$-alkyl, —C$_{1-6}$-alkyl-NH—C$_{1-6}$-alkyl, C$_{2-8}$-alkenyl, C$_{2-8}$-alkynyl or C$_{3-6}$-cycloalkyl;

each R$^{7a}$ independently, is H, C$_{1-8}$-alkyl, C$_{2-8}$-alkenyl, C$_{2-8}$-alkynyl, C$_{3-6}$cycloalkyl, C$_{4-8}$-cycloalkenyl, NR$^8$R$^9$, NR$^9$R$^9$, OR$^8$, SR$^8$, OR$^9$, SR$^9$, C(O)R$^8$, OC(O) R$^9$, COOR$^9$, C(O)R$^9$, C(O)NR$^8$R$^9$, NR$^9$C(O)R$^9$, C(O) NR$^9$R$^9$, NR$^9$C(O)NR$^9$R$^9$, S(O)$_2$R$^8$, S(O)$_2$R$^9$, S(O)$_2$NR$^8$R$^9$, S(O)$_2$NR$^9$R$^9$, NR$^9$S(O)$_2$NR$^9$R$^9$, NR$^9$S(O)$_2$R$^8$ or NR$^9$S(O)$_2$R$^9$, each of the C$_{1-8}$-alkyl, C$_{2-8}$-alkenyl, C$_{2-8}$-alkynyl, C$_{3-6}$-cycloalkyl and C$_{4-8}$-cycloalkenyl is optionally substituted with one or more substituents of R$^8$, R$^9$, NR$^8$R$^9$, NR$^9$R$^9$, OR$^8$, SR$^8$, OR$^9$, SR$^9$, C(O)R$^8$, OC(O)R$^9$, COOR$^9$, C(O)R$^9$, C(O)NR$^9$R$^9$, NR$^9$C(O)R$^9$, C(O)NR$^9$R$^9$, NR$^9$C(O)NR$^9$R$^9$, S(O)$_2$R$^8$, S(O)$_2$R$^9$, S(O)$_2$ NR$^9$R$^9$, NR$^9$S(O)$_2$NR$^9$R$^9$, NR$^9$S(O)$_2$R$^8$ or NR$^9$S(O)$_2$R$^9$;

R$^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of R$^9$; and each R$^9$, independently, is H, F, Cl, Br, I, haloalkyl, CN, OH, C$_{1-8}$-alkyl, —O—C$_{1-8}$-alkyl, —C$_{1-6}$-alkyl-O—C$_{1-6}$-alkyl, —S—C$_{1-6}$-alkyl, —C$_{1-6}$-alkyl-S—C$_{1-6}$-alkyl, —C$_{1-6}$-alkyl-NH—C$_{1-6}$-alkyl, C$_{2-8}$-alkenyl, C$_{2-8}$-alkynyl, C$_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said C$_{1-8}$-alkyl, C$_{2-8}$-alkenyl, C$_{2-8}$-alkynyl and ring of said ring system is optionally substituted independently with 1-5 substituents of halo, haloalkyl, CN, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

10. A compound of claim 9, or a pharmaceutically acceptable salt thereof, wherein
A$^1$ is CR$^3$;
A$^2$ is CR$^4$;
A$^4$ is CR$^6$;
A$^5$ is CR$^3$;
A$^6$ is CR$^3$;
A$^7$ is N;
A$^8$ is N;
X is S;
Y is NR$^9$S(O)$_2$R$^8$ or NR$^9$S(O)$_2$R$^9$;
each R$^3$, independently, is H, halo, haloalkyl, OH, C$_{1-4}$-alkyl, —O—C$_{1-4}$-alkyl, —O—C$_{1-4}$-haloalkyl, or —S—C$_{1-4}$-alkyl;
R$^4$ is H, halo, haloalkyl, C$_{1-6}$-alkyl, —O—C$_{1-6}$-alkyl, —O—C$_{1-8}$-haloalkyl-or —S—C$_{1-6}$-alkyl; and
R$^6$ is H, halo, haloalkyl, C$_{1-8}$-alkyl, —O—C$_{1-8}$-alkyl, —O—C$_{1-8}$-haloalkyl-or —S—C$_{1-8}$-alkyl.

11. A compound of Formula II

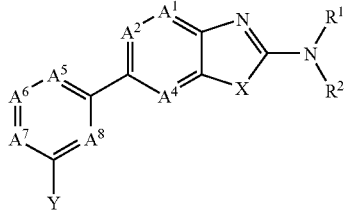

or a pharmaceutically acceptable salt thereof, wherein
$A^1$ is $CR^3$;
$A^2$ is $CR^4$;
$A^4$ is $CR^6$;
$A^5$ is $CR^3$ or N;
$A^6$ is $CR^3$ or N;
$A^7$ is $CR^3$ or N;
$A^8$ is $CR^3$ or N; provided that no more than three of $A^5$, $A^6$, $A^7$, and $A^8$ is N;
X is S;
Y is $NR^9S(O)_2R^8$ or $NR^9S(O)_2R^9$;
$R^1$ is H, $C_{1-6}$-alkyl, $C_{2-6}$-alkenyl, $C_{2-6}$-alkynyl or $C_{3-6}$-cycloalkyl;
$R^2$ is $C_{1-6}$-alkyl-$R^{7a}$, $C_{2-6}$-alkenyl-$R^{7a}$, $C_{2-6}$-alkynyl-$R^{7a}$, $C_{3-6}$-cycloalkyl-$R^{7a}$, $C(O)R^{7a}$, $C(=O)NHR^{7a}$, $COOR^{7a}$, $S(O)_2R^{7a}$ or a partially or fully saturated or fully unsaturated 5- or 6-membered monocyclic ring formed of carbon atoms and including 1-3 heteroatoms selected from N, O and S, wherein the $C_{1-6}$-alkyl-$R^{7a}$, $C_{2-6}$-alkenyl-$R^{7a}$, $C_{2-6}$-alkynyl-$R^{7a}$ and $C_{3-6}$-cycloalkyl-$R^{7a}$ is optionally substituted with 1-5 subsituents of $R^9$;
$R^3$ is H, halo, haloalkyl, OH, $C_{1-4}$-alkyl, —O—$C_{1-4}$-alkyl, —O—$C_{1-4}$-haloalkyl, —S—$C_{1-4}$-alkyl, or —$C_{1-4}$-alkyl-OH;
$R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, wherein each of said $C_{1-6}$-alkyl, $C_{2-8}$-alkenyl, $C_{2-8}$-alkynyl is optionally substituted independently with 1-5 substituents of $R^9$;
$R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl or $C_{3-6}$-cycloalkyl;
each $R^{7a}$ independently, is H, $C_{1-8}$-alkyl, $C_{2-8}$-alkenyl, $C_{2-8}$-alkynyl, $C_{3-6}$cycloalkyl, $C_{4-8}$-cycloalkenyl, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^8R^9$, $NR^9C(O)R^9$, $C(O)NR^9R^9$, $NR^9C(O)NR^9R^9$, $S(O)_2R^8$, $S(O)_2R^9$, $S(O)_2NR^8R^9$, $S(O)_2NR^9R^9$, $NR^9S(O)_2NR^9R^9$, $NR^9S(O)_2R^8$ or $NR^9S(O)_2R^9$, each of the $C_{1-8}$-alkyl, $C_{2-8}$-alkenyl, $C_{2-8}$-alkynyl, $C_{3-6}$-cycloalkyl and $C_{4-8}$-cycloalkenyl is optionally substituted with one or more substituents of $R^8$, $R^9$, $NR^8R^9$, $NR^9R^9$, $OR^8$, $SR^8$, $OR^9$, $SR^9$, $C(O)R^8$, $OC(O)R^9$, $COOR^9$, $C(O)R^9$, $C(O)NR^9R^9$, $NR^9C(O)R^9$, $C(O)NR^9R^9$, $NR^9C(O)NR^9R^9$, $S(O)_2R^8$, $S(O)_2R^9$, $S(O)_2NR^9R^9$, $NR^9S(O)_2NR^9R^9$, $NR^9S(O)_2R^8$ or $NR^9S(O)_2R^9$;

$R^8$ is a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$; and
each $R^9$, independently, is H, F, Cl, Br, I, haloalkyl, CN, OH, $C_{1-8}$-alkyl, —O—$C_{1-8}$-alkyl, —$C_{1-6}$-alkyl-O—$C_{1-6}$-alkyl, —S—$C_{1-6}$-alkyl, —$C_{1-6}$-alkyl-S—$C_{1-6}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{2-8}$-alkenyl, $C_{2-8}$-alkynyl and ring of said ring system is optionally substituted independently with 1-5 substituents of halo, haloalkyl, CN, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

12. A compound of claim 11, or a pharmaceutically acceptable salt thereof, wherein
$A^1$ is $CR^3$;
$A^2$ is $CR^4$;
$A^4$ is $CR^6$;
$A^5$ is $CR^3$;
$A^6$ is $CR^3$;
$A^7$ is N;
$A^8$ is N;
X is S;
each $R^3$, independently, is H, halo, haloalkyl, OH, $C_{1-4}$-alkyl, —O—$C_{1-4}$-alkyl, —O—$C_{1-4}$-haloalkyl, or —S—$C_{1-4}$-alkyl;
$R^4$ is H, halo, haloalkyl, $C_{1-6}$-alkyl, —O—$C_{1-6}$-alkyl, —O—$C_{1-8}$-haloalkyl-or —S—$C_{1-6}$-alkyl; and
$R^6$ is H, halo, haloalkyl, $C_{1-8}$-alkyl, —O—$C_{1-8}$-alkyl, —O—$C_{1-8}$-haloalkyl-or —S—$C_{1-8}$-alkyl.

13. A compound of claim 11, or a pharmaceutically acceptable salt thereof, wherein
$A^2$ is $CR^4$ and $R^4$ is H, halo, haloalkyl, OH, $NH_2$, $C_{1-6}$alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl.

14. A compound of claim 11, or a pharmaceutically acceptable salt thereof, wherein
$A^1$ is $CR^3$ and $R^3$ is H, halo, haloalkyl, OH, $C_{1-4}$-alkyl, —O—$C_{1-4}$-alkyl, —O—$C_{1-4}$-haloalkyl, or —S—$C_{1-4}$-alkyl;
$A^2$ is $CR^4$ and $R^4$ is H, halo, haloalkyl, OH, $NH_2$, $C_{1-6}$-alkyl, —O—$C_{1-6}$-alkyl, —O—$C_{1-8}$-haloalkyl, —$C_{1-6}$-alkyl-O—$C_{1-6}$-alkyl, —S—$C_{1-6}$-alkyl, —$C_{1-6}$-alkyl-S—$C_{1-6}$-alkyl, —NH—$C_{1-6}$-alkyl, —N-di-$C_{1-6}$-alkyl, —$C_{1-6}$-alkyl-NH—$C_{1-6}$-alkyl; and
$A^4$ is $CR^6$ and $R^6$ is H, halo, haloalkyl, OH, $NH_2$, $C_{1-8}$-alkyl, —O—$C_{1-8}$-alkyl, —O—$C_{1-8}$-haloalkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl or —N-di-$C_{1-8}$-alkyl.

15. A compound of claim 11, or a pharmaceutically acceptable salt thereof, wherein $R^1$ is H or $C_{1-6}$-alkyl and $R^2$ is $C_{1-6}$-alkyl-$R^{7a}$, $C(O)R^{7a}$ or $S(O)_2R^{7a}$.

16. A pharmaceutical composition comprising a pharmaceutically acceptable excipient and a compound according to claim 11, 9 or 1.

17. The compound:
- N-(6-(6-(((2-fluorophenyl)sulfonyl)amino)-2-pyridinyl)-1,3-benzothiazol-2-yl)acetamide;
- N-(6-(6-(methyl((4-methylphenyl)sulfonyl)amino)-2-pyridinyl)-1,3-benzothiazol-2-yl)acetamide;
- N-(6-(6-(methyl(phenylsulfonyl)amino)-2-pyridinyl)-1,3-benzothiazol-2-yl)acetamide;
- N-(6-(2-((phenylsulfonyl)amino)-4-pyrimidinyl)-1,3-benzothiazol-2-yl)acetamide;
- N-(6-(2-(((4-methoxyphenyl)sulfonyl)amino)-4-pyrimidinyl)-1,3-benzothiazol-2-yl)acetamide;
- N-(6-(2-((3-pyridinylsulfonyl)amino)-4-pyrimidinyl)-1,3-benzothiazol-2-yl)acetamide;
- N-(6-(2-(((4-fluorophenyl)sulfonyl)amino)-4-pyrimidinyl)-1,3-benzothiazol-2-yl)acetamide;
- N-(6-(2-(((2-fluorophenyl)sulfonyl)amino)-4-pyrimidinyl)-1,3-benzothiazol-2-yl)acetamide;
- N-(6-(2-(((3-fluorophenyl)sulfonyl)amino)-4-pyrimidinyl)-1,3-benzothiazol-2-yl)acetamide;
- N-(6-(2-(((4-methylphenyl)sulfonyl)amino)-4-pyrimidinyl)-1,3-benzothiazol-2-yl)acetamide;
- N-(6-(2-(((4-ethylphenyl)sulfonyl)amino)-4-pyrimidinyl)-1,3-benzothiazol-2-yl)acetamide;
- N-(6-(2-(((3-methoxyphenyl)sulfonyl)amino)-4-pyrimidinyl)-1,3-benzothiazol-2-yl)acetamide;
- N-(6-(2-(((3,4-dimethoxyphenyl)sulfonyl)amino)-4-pyrimidinyl)-1,3-benzothiazol-2-yl)acetamide;
- N-(6-(2-(((4-methoxyphenyl)sulfonyl)(methyl)amino)-4-pyrimidinyl)-1,3-benzothiazol-2-yl)acetamide;
- N-(6-(2-(ethyl((4-methoxyphenyl)sulfonyl)amino)-4-pyrimidinyl)-1,3-benzothiazol-2-yl)acetamide;
- N-(6-(2-(methyl((4-methylphenyl)sulfonyl)amino)-4-pyrimidinyl)-1,3-benzothiazol-2-yl)acetamide;
- N-(6-(2-(methyl(phenylsulfonyl)amino)-4-pyrimidinyl)-1,3-benzothiazol-2-yl)acetamide;
- N-(6-(2-(((2-fluorophenyl)sulfonyl)(methyl)amino)-4-pyrimidinyl)-1,3-benzothiazol-2-yl)acetamide;
- N-(6-(2-(methyl((3-methylphenyl)sulfonyl)amino)-4-pyrimidinyl)-1,3-benzothiazol-2-yl)acetamide;
- N-(6-(6-methyl-5-((phenylsulfonyl)amino)-3-pyridinyl)-1,3-benzothiazol-2-yl)acetamide;
- N-(6-(5-(((4-fluorophenyl)sulfonyl)amino)-6-methyl-3-pyridinyl)-1,3-benzothiazol-2-yl)acetamide;
- N-(6-(5-(((2-fluorophenyl)sulfonyl)amino)-6-methyl-3-pyridinyl)-1,3-benzothiazol-2-yl)acetamide;
- N-(6-(6-methyl-5-(((3-(trifluoromethyl)phenyl)sulfonyl)amino)-3-pyridinyl)-1,3-benzothiazol-2-yl)acetamide;
- N-(6-(5-(((4-tert-butylphenyl)sulfonyl)amino)-6-methyl-3-pyridinyl)-1,3-benzothiazol-2-yl)acetamide;
- N-(6-(5-(((3-(difluoromethoxy)phenyl)sulfonyl)amino)-6-methyl-3-pyridinyl)-1,3-benzothiazol-2-yl)acetamide;
- N-(6-(5-(((4-methoxyphenyl)sulfonyl)amino)-6-methyl-3-pyridinyl)-1,3-benzothiazol-2-yl)acetamide;
- N-(4-fluoro-6-(5-(((4-(trifluoromethyl)phenyl)sulfonyl)amino)-3-pyridinyl)-1,3-benzothiazol-2-yl)acetamide;
- N-(6-(6-(((4-methoxyphenyl)sulfonyl)amino)-2-pyrazinyl)-1,3-benzothiazol-2-yl)acetamide;
- N-(6-(5-(((4-acetylphenyl)sulfonyl)amino)-6-chloro-3-pyridinyl)-1,3-benzothiazol-2-yl)acetamide;
- N-(6-(6-(((4-methoxyphenyl)sulfonyl)(methyl)amino)-2-pyrazinyl)-1,3-benzothiazol-2-yl)acetamide;
- N-(6-(6-(methyl((4-methylphenyl)sulfonyl)amino)-2-pyrazinyl)-1,3-benzothiazol-2-yl)acetamide;
- N-(4-fluoro-6-(2-(((4-methoxyphenyl)sulfonyl)amino)-4-pyrimidinyl)-1,3-benzothiazol-2-yl)acetamide;
- N-(4-fluoro-6-(2-(((4-methoxyphenyl)sulfonyl)(methyl)amino)-4-pyrimidinyl)-1,3-benzothiazol-2-yl)acetamide;
- N-(6-(6-chloro-5-(((4-(1-hydroxy-1-methylethyl)phenyl)sulfonyl)amino)-3-pyridinyl)-1,3-benzothiazol-2-yl)acetamide;
- N-(6-(6-chloro-5-(((4-fluorophenyl)sulfonyl)amino)-3-pyridinyl)-1,3-benzothiazol-2-yl)acetamide;
- N-(6-(6-chloro-5-(((4-methoxyphenyl)sulfonyl)amino)-3-pyridinyl)-1,3-benzothiazol-2-yl)acetamide;
- N-(6-(5-(((4-fluorophenyl)sulfonyl)amino)-1,3,4-oxadiazol-2-yl)-1,3-benzothiazol-2-yl)acetamide;
- tert-butyl (6-(5-(((4-methylphenyl)sulfonyl)amino)-1,3,4-oxadiazol-2-yl)-1,3-benzothiazol-2-yl)carbamate;
- tert-butyl (6-(5-(((4-fluorophenyl)sulfonyl)amino)-1,3,4-oxadiazol-2-yl)-1,3-benzothiazol-2-yl)carbamate;
- tert-butyl (6-(5-(benzyl(methylsulfonyl)amino)-1,3,4-oxadiazol-2-yl)-1,3-benzothiazol-2-yl)carbamate;
- N-(6-(6-chloro-5-((cyclohexylsulfonyl)amino)-3-pyridinyl)-1,3-benzothiazol-2-yl)acetamide;
- N-(6-(6-chloro-5-(((3-(trifluoromethyl)phenyl)sulfonyl)amino)-3-pyridinyl)-1,3-benzothiazol-2-yl)acetamide;
- N-(6-(5-(((3-tert-butylphenyl)sulfonyl)amino)-6-chloro-3-pyridinyl)-1,3-benzothiazol-2-yl)acetamide;
- N-(6-(6-chloro-5-(((4-hydroxyphenyl)sulfonyl)amino)-3-pyridinyl)-1,3-benzothiazol-2-yl)acetamide;
- N-(6-(6-chloro-5-(((3,5-dichlorophenyl)sulfonyl)amino)-3-pyridinyl)-1,3-benzothiazol-2-yl)acetamide;
- N-(6-(6-chloro-5-(((3,5-difluorophenyl)sulfonyl)amino)-3-pyridinyl)-1,3-benzothiazol-2-yl)acetamide;
- N-(6-(6-chloro-5-((propylsulfonyl)amino)-3-pyridinyl)-1,3-benzothiazol-2-yl)acetamide;
- N-(6-(5-((butylsulfonyl)amino)-6-chloro-3-pyridinyl)-1,3-benzothiazol-2-yl)acetamide;
- N-(6-(6-chloro-5-(((1-methylethyl)sulfonyl)amino)-3-pyridinyl)-1,3-benzothiazol-2-yl)acetamide;
- N-(6-(6-chloro-5-(((4-chlorophenyl)sulfonyl)amino)-3-pyridinyl)-1,3-benzothiazol-2-yl)acetamide;
- N-(6-(6-chloro-5-((phenylsulfonyl)amino)-3-pyridinyl)-1,3-benzothiazol-2-yl)acetamide;
- N-(6-(6-chloro-5-(((4-(difluoromethoxy)phenyl)sulfonyl)amino)-3-pyridinyl)-1,3-benzothiazol-2-yl)acetamide;
- N-(6-(6-chloro-5-(((3-fluorophenyl)sulfonyl)amino)-3-pyridinyl)-1,3-benzothiazol-2-yl)acetamide;
- N-(6-(6-chloro-5-(((3-(difluoromethoxy)phenyl)sulfonyl)amino)-3-pyridinyl)-1,3-benzothiazol-2-yl)acetamide;
- N-(6-(6-chloro-5-(((3-chlorophenyl)sulfonyl)amino)-3-pyridinyl)-1,3-benzothiazol-2-yl)acetamide;
- N-(6-(6-chloro-5-((2-thiophenylsulfonyl)amino)-3-pyridinyl)-1,3-benzothiazol-2-yl)acetamide;
- N-(6-(6-chloro-5-((3-thiophenylsulfonyl)amino)-3-pyridinyl)-1,3-benzothiazol-2-yl)acetamide;
- N-(6-(5-((benzylsulfonyl)amino)-6-chloro-3-pyridinyl)-1,3-benzothiazol-2-yl)acetamide;
- N-(6-(6-chloro-5-(((4-methylphenyl)sulfonyl)amino)-3-pyridinyl)-1,3-benzothiazol-2-yl)acetamide;
- N-(6-(6-chloro-5-(((4-trifluoromethyl)phenyl)sulfonyl)amino)-3-pyridinyl)-1,3-benzothiazol-2-yl)acetamide;
- N-(6-(5-(((4-tert-butylphenyl)sulfonyl)amino)-6-chloro-3-pyridinyl)-1,3-benzothiazol-2-yl)acetamide;
- N-(6-(6-chloro-5-(((5-chloro-2-thiophenyl)sulfonyl)amino)-3-pyridinyl)-1,3-benzothiazol-2-yl)acetamide;
- N-(6-(5-(((4-methylphenyl)sulfonyl)amino)-3-pyridinyl)-1,3-benzothiazol-2-yl)acetamide;

N-(6-(5-(((4-methoxyphenyl)sulfonyl)amino)-3-pyridinyl)-1,3-benzothiazol-2-yl)acetamide;
N-(6-(5-(((4-(trifluoromethyl)phenyl)sulfonyl)amino)-3-pyridinyl)-1,3-benzothiazol-2-yl)acetamide;
N-(6-(5-(((3-(trifluoromethyl)phenyl)sulfonyl)amino)-3-pyridinyl)-1,3-benzothiazol-2-yl)acetamide;
N-(6-(5-(((4-fluorophenyl)sulfonyl)amino)-3-pyridinyl)-1,3-benzothiazol-2-yl)acetamide;
N-(6-(5-(((3-fluorophenyl)sulfonyl)amino)-3-pyridinyl)-1,3-benzothiazol-2-yl)acetamide;
N-(6-(5-(((3,4-dichlorophenyl)sulfonyl)amino)-3-pyridinyl)-1,3-benzothiazol-2-yl)acetamide;
N-(6-(5-(((4-tert-butylphenyl)sulfonyl)amino)-3-pyridinyl)-1,3-benzothiazol-2-yl)acetamide;
N-(6-(5-((phenylsulfonyl)amino)-3-pyridinyl)-1,3-benzothiazol-2-yl)acetamide;
N-(6-(2-(((4-fluorophenyl)sulfonyl)(methyl)amino)-4-pyrimidinyl)-1,3-benzothiazol-2-yl)acetamide;
N-(6-(2-(methyl(6-quinolinylsulfonyl)amino)-4-pyrimidinyl)-1,3-benzothiazol-2-yl)acetamide;
N-(6-(2-(((4-tert-butylphenyl)sulfonyl)(methyl)amino)-4-pyrimidinyl)-1,3-benzothiazol-2-yl)acetamide;
N-(6-(2-(methyl(2-thiophenylsulfonyl)amino)-4-pyrimidinyl)-1,3-benzothiazol-2-yl)acetamide;
N-(6-(2-(methyl(1-naphthalenylsulfonyl)amino)-4-pyrimidinyl)-1,3-benzothiazol-2-yl)acetamide;
N-(6-(2-((5-isoquinolinylsulfonyl)(methyl)amino)-4-pyrimidinyl)-1,3-benzothiazol-2-yl)acetamide;
N-(6-(2-(methyl(3-thiophenylsulfonyl)amino)-4-pyrimidinyl)-1,3-benzothiazol-2-yl)acetamide;
N-(6-(2-(((3,4-dimethylphenyl)sulfonyl)(methyl)amino)-4-pyrimidinyl)-1,3-benzothiazol-2-yl)acetamide;
N-(6-(2-(methyl((1-methyl-1H-imidazol-4-yl)sulfonyl)amino)-4-pyrimidinyl)-1,3-benzothiazol-2-yl)acetamide;
N-(6-(2-(((2,4-dimethylphenyl)sulfonyl)(methyl)amino)-4-pyrimidinyl)-1,3-benzothiazol-2-yl)acetamide;
N-(6-(2-(methyl((4-(trifluoromethyl)phenyl)sulfonyl)amino)-4-pyrimidinyl)-1,3-benzothiazol-2-yl)acetamide;
N-(6-(2-(methyl(2-naphthalenylsulfonyl)amino)-4-pyrimidinyl)-1,3-benzothiazol-2-yl)acetamide;
N-(6-(2-(methyl((4-methylphenyl)sulfonyl)amino)-4-pyridinyl)-1,3-benzothiazol-2-yl)acetamide;
N-(6-(2-(((4-methylphenyl)sulfonyl)amino)-4-pyridinyl)-1,3-benzothiazol-2-yl)acetamide;
N-(6-(2-(((4-methoxyphenyl)sulfonyl)amino)-4-pyridinyl)-1,3-benzothiazol-2-yl)acetamide;
N-(6-(5-(methyl((4-(trifluoromethyl)phenyl)sulfonyl)amino)-3-pyridinyl)-1,3-benzothiazol-2-yl)acetamide;
N-(6-(5-(((4-fluorophenyl)sulfonyl)(methyl)amino)-3-pyridinyl)-1,3-benzothiazol-2-yl)acetamide;
N-(6-(5-(((4-chlorophenyl)sulfonyl)(methyl)amino)-3-pyridinyl)-1,3-benzothiazol-2-yl)acetamide;
N-(6-(5-(((3,4-dichlorophenyl)sulfonyl)(methyl)amino)-3-pyridinyl)-1,3-benzothiazol-2-yl)acetamide;
N-(6-(5-(((3,4-difluorophenyl)sulfonyl)(methyl)amino)-3-pyridinyl)-1,3-benzothiazol-2-yl)acetamide;
N-(6-(5-(((4-tert-butylphenyl)sulfonyl)(methyl)amino)-3-pyridinyl)-1,3-benzothiazol-2-yl)acetamide;
N-(6-(5-(methyl(phenylsulfonyl)amino)-3-pyridinyl)-1,3-benzothiazol-2-yl)acetamide;
N-(6-(6-(methyl((3-methylphenyl)sulfonyl)amino)-2-pyridinyl)-1,3-benzothiazol-2-yl)acetamide;
N-(6-(6-(((2-fluorophenyl)sulfonyl)(methyl)amino)-2-pyridinyl)-1,3-benzothiazol-2-yl)acetamide;
N-(6-(6-chloro-5-(((4-(1-hydroxyethyl)phenyl)sulfonyl)amino)-3-pyridinyl)-1,3-benzothiazol-2-yl)acetamide;
N-(6-(6-chloro-5-(((4-(1-hydroxyethyl)phenyl)sulfonyl)amino)-3-pyridinyl)-1,3-benzothiazol-2-yl)acetamide (enantiomer A);
N-(6-(6-chloro-5-(((4-(1-hydroxyethyl)phenyl)sulfonyl)amino)-3-pyridinyl)-1,3-benzothiazol-2-yl)acetamide (enantiomer B);
N-(6-(5-(((4-(1-hydroxyethyl)phenyl)sulfonyl)amino)-3-pyridinyl)-1,3-benzothiazol-2-yl)acetamide;
N-(6-(3-(((4-methoxyphenyl)sulfonyl)amino)phenyl)-1,3-benzothiazol-2-yl)acetamide;
N-(6-(6-cyano-5-(((4-methoxyphenyl)sulfonyl)amino)-3-pyridinyl)-1,3-benzothiazol-2-yl)acetamide;
N-(6-(6-chloro-5-(((4-methoxyphenyl)sulfonyl)amino)-3-pyridinyl)-1,3-benzothiazol-2-yl)cyclohexanecarboxamide;
N-(2-chloro-5-(2-((1-methylethyl)amino)-1,3-benzothiazol-6-yl)-3-pyridinyl)-4-methoxybenzenesulfonamide;
N-(2-chloro-5-(2-((cyclohexylmethyl)amino)-1,3-benzothiazol-6-yl)-3-pyridinyl)-4-methoxybenzenesulfonamide;
N-(5-(2-amino-1,3-benzothiazol-6-yl)-2-chloro-3-pyridinyl)-3-(difluoromethoxy)benzenesulfonamide;
N-(5-(2-amino-1,3-benzothiazol-6-yl)-2-chloro-3-pyridinyl)-2-chloro-4-(trifluoromethyl)benzenesulfonamide;
N-(5-(2-amino-1,3-benzothiazol-6-yl)-2-chloro-3-pyridinyl)-2-chloro-4-fluorobenzenesulfonamide;
N-(5-(2-amino-1,3-benzothiazol-6-yl)-2-chloro-3-pyridinyl)-2,4-dichlorobenzenesulfonamide;
N-(5-(2-amino-1,3-benzothiazol-6-yl)-2-chloro-3-pyridinyl)-2,4-difluorobenzenesulfonamide;
N-(5-(2-amino-1,3-benzothiazol-6-yl)-2-chloro-3-pyridinyl)-4-fluoro-2-methylbenzenesulfonamide;
N-(5-(2-amino-1,3-benzothiazol-6-yl)-2-chloro-3-pyridinyl)-4-chloro-2-fluorobenzenesulfonamide;
N-(5-(2-amino-1,3-benzothiazol-6-yl)-2-chloro-3-pyridinyl)-2-(trifluoromethyl)benzenesulfonamide;
N-(6-(6-chloro-5-((1-piperidinylsulfonyl)amino)-3-pyridinyl)-1,3-benzothiazol-2-yl)acetamide;
N-(2-chloro-5-(2-(methylamino)-1,3-benzothiazol-6-yl)-3-pyridinyl)-4-fluorobenzenesulfonamide;
2-chloro-N-(2-chloro-5-(2-(methylamino)-1,3-benzothiazol-6-yl)-3-pyridinyl)-6-methylbenzenesulfonamide;
2,6-dichloro-N-(2-chloro-5-(2-(methylamino)-1,3-benzothiazol-6-yl)-3-pyridinyl)benzenesulfonamide;
N-(2-chloro-5-(2-(methylamino)-1,3-benzothiazol-6-yl)-3-pyridinyl)-2-fluorobenzenesulfonamide;
4-acetyl-N-(2-chloro-5-(2-(methylamino)-1,3-benzothiazol-6-yl)-3-pyridinyl)benzenesulfonamide;
N-(5-(2-amino-1,3-benzothiazol-6-yl)-2-chloro-3-pyridinyl)-4-(1-hydroxy-1-methylethyl)benzenesulfonamide;
4-acetyl-N-(5-(2-amino-1,3-benzothiazol-6-yl)-2-chloro-3-pyridinyl)benzenesulfonamide; or
N-(2-chloro-5-(2-(methylsulfanyl)-1,3-benzothiazol-6-yl)-3-pyridinyl)-4-methoxybenzenesulfonamide; or a pharmaceutically acceptable salt thereof.

* * * * *